United States Patent
Li

(10) Patent No.: US 11,352,645 B2
(45) Date of Patent: Jun. 7, 2022

(54) COMPOSITIONS AND METHODS FOR TREATING LEBER'S HEREDITARY OPTIC NEUROPATHY

(71) Applicant: WUHAN NEUROPHTH BIOTECHNOLOGY LIMITED COMPANY, Hubei (CN)

(72) Inventor: Bin Li, Hubei (CN)

(73) Assignee: Wuhan Neurophth Biotechnology Limited Company, Hubei (CN)

( * ) Notice: Subject to any disclaimer, the term of this patent is extended or adjusted under 35 U.S.C. 154(b) by 0 days.

(21) Appl. No.: 17/181,849

(22) Filed: Feb. 22, 2021

(65) Prior Publication Data

US 2021/0189429 A1 Jun. 24, 2021

Related U.S. Application Data

(63) Continuation of application No. PCT/CN2019/101538, filed on Aug. 20, 2019.

(30) Foreign Application Priority Data

Aug. 20, 2018 (CN) .......................... 201810948193.1
Sep. 4, 2018 (WO) ................ PCT/CN2018/103937
(Continued)

(51) Int. Cl.
*C12N 15/86* (2006.01)
*A61K 31/56* (2006.01)
(Continued)

(52) U.S. Cl.
CPC .............. *C12N 15/86* (2013.01); *A61K 31/56* (2013.01); *A61K 45/06* (2013.01); *A61K 48/00* (2013.01);
(Continued)

(58) Field of Classification Search
CPC .......... C12N 15/86; C12N 2750/14141; A61P 27/02; A61K 31/56; A61K 45/06;
(Continued)

(56) References Cited

U.S. PATENT DOCUMENTS

| 3,625,214 A | 12/1971 | Higuchi et al. |
| 4,789,734 A | 12/1988 | Pierschbacher et al. |

(Continued)

FOREIGN PATENT DOCUMENTS

| CN | 102517304 A | 6/2012 |
| CN | 102634527 A | 11/2013 |

(Continued)

OTHER PUBLICATIONS

Cwerman-Thibault H, Augustin S, Lechauve C, et al. Nuclear expression of mitochondrial ND4 leads to the protein assembling in complex I and prevents optic atrophy and visual loss. Molecular Therapy—Methods & Clinical Development. Jan. 1, 2015;2:15003.; cited in IDS Aug. 5, 2021 (Year: 2015).*

(Continued)

*Primary Examiner* — Kevin K Hill
*Assistant Examiner* — Anjeanette Roberts
(74) *Attorney, Agent, or Firm* — Cooley LLP

(57) ABSTRACT

Disclosed herein is a recombinant nucleic acid, comprising: a mitochondrial targeting sequence; a mitochondrial protein coding sequence, wherein said mitochondrial protein coding sequence encodes a polypeptide comprising a mitochondrial protein; and a 3'UTR nucleic acid sequence. Also disclosed is a pharmaceutical composition comprising the recombinant nucleic acid and a method of treating Leber's hereditary optic neuropathy (LHON) using the pharmaceutical composition.

27 Claims, 20 Drawing Sheets

Specification includes a Sequence Listing.

(30) Foreign Application Priority Data

| Oct. 19, 2018 | (CN) | 201811221305.X |
|---|---|---|
| Oct. 22, 2018 | (CN) | 201811230856.2 |
| Nov. 2, 2018 | (WO) | PCT/CN2018/113799 |
| Nov. 30, 2018 | (WO) | PCT/CN2018/118662 |
| Jan. 4, 2019 | (WO) | PCT/CN2019/070461 |

(51) Int. Cl.
- *A61K 45/06* (2006.01)
- *A61P 27/02* (2006.01)
- *A61K 48/00* (2006.01)

(52) U.S. Cl.
CPC ........ *A61K 48/005* (2013.01); *A61K 48/0083* (2013.01); *A61P 27/02* (2018.01); *A61K 48/0075* (2013.01); *C12N 2750/14141* (2013.01)

(58) Field of Classification Search
CPC .. A61K 48/00; A61K 48/005; A61K 48/0083; A61K 48/0075
See application file for complete search history.

(56) References Cited

U.S. PATENT DOCUMENTS

| | | | |
|---|---|---|---|
| 4,897,268 A | 1/1990 | Tice et al. | |
| 4,906,474 A | 3/1990 | Langer et al. | |
| 4,925,673 A | 5/1990 | Steiner et al. | |
| 5,075,109 A | 12/1991 | Tice et al. | |
| 5,811,128 A | 9/1998 | Tice et al. | |
| 5,814,344 A | 9/1998 | Tice et al. | |
| 5,820,883 A | 10/1998 | Tice et al. | |
| 5,853,763 A | 12/1998 | Tice et al. | |
| 5,928,647 A | 7/1999 | Rock | |
| 5,942,252 A | 8/1999 | Tice et al. | |
| 6,207,392 B1 | 3/2001 | Weiss et al. | |
| 7,704,721 B2 | 4/2010 | Wright et al. | |
| 8,637,257 B2 * | 1/2014 | Brys | A61K 31/7088 435/7.1 |
| 9,701,961 B2 * | 7/2017 | Feinstein | A61P 25/00 |
| 10,308,987 B2 * | 6/2019 | Parr | C12Q 1/6886 |
| 10,906,931 B2 * | 2/2021 | Moghadam | A61K 38/02 |
| 11,034,954 B2 | 6/2021 | Li | |
| 2008/0166724 A1 * | 7/2008 | Gerber | A61P 9/10 435/6.16 |
| 2009/0306188 A1 | 12/2009 | Corral-Debrinski et al. | |
| 2010/0272688 A1 * | 10/2010 | Acland | A61K 38/51 424/93.2 |
| 2015/0250869 A1 | 9/2015 | Sene et al. | |
| 2016/0206706 A1 | 7/2016 | Wright et al. | |
| 2016/0289674 A1 * | 10/2016 | Bancel | C12N 15/67 |
| 2018/0207293 A1 * | 7/2018 | Shimizu | A61K 31/277 |
| 2020/0263172 A1 | 8/2020 | Li et al. | |
| 2021/0163898 A1 * | 6/2021 | Towheed | C12N 9/0036 |
| 2021/0189429 A1 | 6/2021 | Li | |
| 2021/0353774 A1 | 11/2021 | Li | |

FOREIGN PATENT DOCUMENTS

| | | | |
|---|---|---|---|
| CN | 102634527 B | 11/2013 | |
| CN | 104450747 B | 2/2018 | |
| EP | 2913403 A1 | 9/2015 | |
| WO | WO-9739776 A1 | 10/1997 | |
| WO | WO 2006/117250 A2 | 11/2006 | |
| WO | WO 2008/063802 A2 | 5/2008 | |
| WO | WO 2016/044023 A1 | 3/2016 | |
| WO | WO 2017/011519 A1 | 1/2017 | |
| WO | WO-2019033119 A1 * | 2/2019 | A61P 27/06 |
| WO | WO-2019241206 A1 * | 12/2019 | C12N 9/1085 |
| WO | WO 2020/000641 A1 | 1/2020 | |
| WO | WO 2020/001657 A1 | 1/2020 | |
| WO | WO 2020/010491 A1 | 1/2020 | |
| WO | WO 2020/037938 A1 | 2/2020 | |
| WO | WO 2020/038352 A1 | 2/2020 | |
| WO | WO 2020/077756 A1 | 4/2020 | |
| WO | WO 2020/082417 A1 | 4/2020 | |

OTHER PUBLICATIONS

Newman NJ. Treatment of hereditary optic neuropathies. Nature Reviews Neurology. Oct. 2012;8(10):545-56. (Year: 2012).*

Glerum DM, Tzagoloff A. Isolation of a human cDNA for heme A: farnesyltransferase by functional complementation of a yeast cox10 mutant. Proceedings of the National Academy of Sciences. Aug. 30, 1994;91(18):8452-6. (Year: 1994).*

Guy J, Qi X, Koilkonda RD, Arguello T, Chou TH, Rugged M, Porciatti V, Lewin AS, Hauswirth WW. Efficiency and safety of AAV-mediated gene delivery of the human ND4 complex I subunit in the mouse visual system. Investigative ophthalmology & visual science. Sep. 1, 2009;50(9):4205-14. (Year: 2009).*

Fumoto S, Kawakami S, Hashida M, Nishida K. Targeted gene delivery: importance of administration routes. Novel Gene Therapy Approaches. Feb. 13, 2013:3-1. (Year: 2013).*

Daya S, Berns KI. Gene therapy using adeno-associated virus vectors. Clinical microbiology reviews. Oct. 2008;21(4):583-93. (Year: 2008).*

Mingozzi and High, Immune responses to AAV vectors: overcoming barriers to successful gene therapy, Blood. 2013, 122(1):23-36 (Year: 2013).*

Kattenhorn et al, Adeno-Associated Virus Gene Therapy for Liver Disease, 2016, Human Gene Therapy, vol. 27 No. 12, pp. 947-961 (Year: 2016).*

Perrin S. Preclinical research: Make mouse studies work. Nature News. Mar. 27, 2014;507(7493):423. (Year: 2014).*

Sequence alignment SEQ ID No. 10 of 17181849 and SEQ ID No. 19870 of 15174219; US20160289674A1 Publ: Oct. 6, 2016. Alignment Aug. 2021 (Year: 2016).*

Sequence alignment SEQ ID No. 12 of 17181849 and SEQ ID No. 19864 of 15174219; US20160289674A1 Publ: Oct. 6, 2016. Alignment Aug. 2021 (Year: 2016).*

Bennett J, Anand V, Acland GM, Maguire AM. [50] Cross-species comparison of in vivo reporter gene expression after recombinant adeno-associated virus-mediated retinal transduction. Methods in enzymology. Jan. 1, 2000;316:777-89. (Year: 2000).*

Allocca, et al. "Novel adeno-associated virus serotypes efficiently transduce murine photoreceptors." J Virol. Oct. 2007;81(20):11372-80. doi: 10.1128/JVI.01327-07.

Altschul, et al. "Basic local alignment search tool." J Mol Biol. Oct. 5, 1990;215(3):403-10. doi: 10.1016/S0022-2836(05)80360-2.

Altschul, et al. "A protein alignment scoring system sensitive at all evolutionary distances." J Mol Evol. Mar. 1993;36(3):290-300. doi: 10.1007/BF00160485.

Altschul, et al. "Gapped BLAST and PSI-BLAST: a new generation of protein database search programs." Nucleic Acids Res. Sep. 1, 1997;25(17):3389-402. doi: 10.1093/nar/25.17.3389.

Bainbridge, et al. "Effect of gene therapy on visual function in Leber's congenital amaurosis." N Engl J Med. May 22, 2008;358(21):2231-9, doi: 10.1056/NEJMoa0802268.

Bangham, et al. "Diffusion of univalent ions across the lamellae of swollen phospholipids." J Mol Biol. Aug. 1965;13(1):238-52, doi: 10.1016/s0022-2836(65)80093-6.

Bonnet, et al. "The optimized allotopic expression of ND1 or ND4 genes restores respiratory chain complex I activity in fibroblasts harboring mutations in these genes." Biochimica et Biophysica Acta 2008;10 (1783):1707-1717.

Choi, et al. "AAV hybrid serotypes: improved vectors for gene delivery." Curr Gene Ther. Jun. 2005;5(3):299-310. doi: 10.2174/1566523054064968.

Coura, et al. "The state of the art of adeno-associated virus-based vectors in gene therapy." Virol J. Oct. 16, 2007;4:99. doi: 10.1186/1743-422X-4-99.

Cronin, et al. "Functional Genomics Study of the RdCVF-/-Mouse Model." ARVO Annual Meeting, May 2008, Abstract only.

(56) References Cited

OTHER PUBLICATIONS

Cwerman-Thibault, et al. "Nuclear expression of mitochondrial ND4 leads to the protein assembling in complex I and prevents optic atrophy and visual loss." Molecular Therapy—Methods & Clinical Development. 2015;2(15003):1-15.
Devereux, et al. "A comprehensive set of sequence analysis programs for the VAX." Nucleic Acids Res. Jan. 11, 1984;12(1 Pt 1):387-95. doi: 10.1093/nar/12.1part1.387.
Gao, et al. "Comparison of Immunosuppressive Effects and ND4 Expression among Different Immunosuppressive Strategies following AAV2-ND4 Gene Treatment for Leber Hereditary Optic Neuropathy." Acta Medici nae Universitatis Scientiae et Technologiae Huazchong. 2013;42(2): 187-191.
Guy, et al. "Gene Therapy for Leber Hereditary Optic Neuropathy: Low- and Medium-Dose Visual Results." Ophthalmology. Nov. 2017;124(11):1621-1634. doi: 10.1016/j.ophtha.2017.05.016.
Greenwood, et al. "Current research into brain barriers and the delivery of therapeutics for neurological diseases: a report on CNS barrier congress London, UK, 2017." Fluids Barriers CNS. 2017; 14:31.
Hocquemiller, et al. "Adena-Associated Virus-Based Gene Therapy for CNS Diseases." Hum Gene Ther. Jul. 1, 2016; 27(7): 478-496.
Hudry, et al. "Therapeutic AAV Gene Transfer to the Nervous System: A Clinical Reality." Neuron . Mar. 6, 2019;101(5):839-862.
International Search Report and Written Opinion issued by the International Searching Authority for Application No. PCT/CN2018/095023, dated Apr. 9, 2019, 14 pages including English translation of ISR.
International Search Report and Written Opinion issued by the International Searching Authority for Application No. PCT/CN2018/103937, dated Apr. 3, 2019, 19 pages including English translation of Search Report.
International Search Report and Written Opinion issued by the International Searching Authority for Application No. PCT/CN2018/118662, dated Jul. 18, 2019, 18 pages including English translation of ISR.
International Search Report and Written Opinion issued by the International Searching Authority for Application No. PCT/CN2019/070461, dated May 22, 2019, 13 pages including translation of ISR.
International Search Report and Written Opinion issued by the International Searching Authority for Application No. PCT/CN2019/094136, dated Oct. 10, 2019, 10 pages.
International Search Report and Written Opinion issued by the International Searching Authority for Application No. PCT/CN2019/101538, dated Nov. 29, 2019, 14 pages.
International Search Report and Written Opinion issued by the International Searching Authority for Application No. PCT/CN2018/113799, dated Aug. 5, 2019, 15 pages including English translation of Search Report.
Karlin and Altschul. "Applications and statistics for multiple high-scoring segments in molecular sequences." Proc Natl Acad Sci U S A. Jun. 15, 1993;90(12):5873-7. doi: 10.1073/pnas.90.12.5873.
Kim, et al. "Preparation of multilamellar vesicles of defined size-distribution by solvent-spherule evaporation." Biochim Biophys Acta. Feb. 14, 1985;812(3):793-801. doi: 10.1016/0005-2736(85)90274-3.
Koilkonda, et al. "Safety and Effects of the Vector for the Leber Hereditary Optic Neuropathy Gene Therapy Clinical Trial." JAMA Ophthalmol. 2014;132(4):409-420.
Kushnareva, et al. "Mitochondrial dysfunction in an Opa1Q285STOP mouse model of dominant optic atrophy results from Opa1 haploinsufficiency." Cell Death and Disease Jul. 7, 2016(7):e-2309, 13 pages.
Kraus and Aaronson. "Detection and isolation of novel protein-tyrosine kinase genes employing reduced stringency hybridization." Methods Enzymol. 1991;200:546-56. doi: 10.1016/0076-6879(91)00170-2.
Gregoriadis. "Liposomes." Drug Carriers in Biology and Medicine. Chapter 14: pp. 2.sup. 87-341 (Academic Press, 1979).
Laughlin, et al. "Spliced adenovims-associated virus RNA." Proc Natl Acad Sci U S A. Nov. 1979;76(11):5567-71, doi: 10.1073/pnas.76.11.5567.
Mancuso, et al. "Gene therapy for red-green colour blindness in adult primates." Nature. Oct. 8, 2009;461(7265):784-7. doi: 10.1038/nature08401.
Manfredsson, et al. "AAV9: a potential blood-brain barrier buster."Mol Ther. Mar. 2009; 17(3):403-405.
NCBI Reference Sequence: NC_001829.1, dated Aug. 13, 2018, 3 pages.
NCBI Reference Sequence: NC_002077.1, dated Aug. 13, 2018, 3 pages.
NCBI Reference Sequence: NC_001729.1, dated Aug. 13, 2018, 3 pages.
NCBI Reference Sequence: NC_004828.1 Aug. 13, 2018, 3 pages.
NCBI Reference Sequence: NC_005889.1 Aug. 13, 2018, 3 pages.
NCBI. "Genbank Accession No. KP240659.1" Gen Bank, Dec. 4, 2016 (Dec. 4, 2016), 8 pages.
NCBI. "Genbank Accession No. LX309664.1" Gen Bank, Oct. 28, 2017 (Oct. 28, 2017).
NCBI. "Genbank Accession No. LX309670.1" Gen Bank, Oct. 28, 2017 (Oct. 28, 2017), 2 pages.
NCBI. "Genbank Accession No. MF522909.1" GenBank, Oct. 21, 2017 (Oct. 21, 2017), 8 pages.
NCBI. "Genbank Accession No. YP_003024026.1" GenBank, Oct. 31, 2014 (Oct. 31, 2014), 2 pages.
GenBank LX309670, dated Oct. 28, 2017, 2 pages.
GenBank LX309664, dated Oct. 28, 2017, 2 pages.
GenBank LX309667, dated Oct. 28, 2017, 2 pages.
NCBI Gene ID: 4535. MT-ND1 mitochondrially encoded NADH dehydrogenase 1 [ *Homo sapiens* (human) ]. Updated on Apr. 20, 2021.
NCBI Gene ID: 4538. "MT-ND4 mitochondrially encoded NADH dehydrogenase 4 [ *Homo sapiens* (human) ]." Updated on Apr. 20, 2021.
NCBI Gene ID: 4541. "MT-ND6 mitochondrially encoded NADH dehydrogenase 6 [ *Homo sapiens* (human) ]." Updated on Apr. 20, 2021.
Sun, et al. "Detection of Neutralizing Antibody to Human Adenovirus Type 5 in Marmosets." J. South Med. Univ., 36(4):582-587 (2016).
Szoka, et al. "Procedure for preparation of liposomes with large internal aqueous space and high capture by reverse-phase evaporation." Proc Natl Acad Sci U S A. Sep. 1978;75(9):4194-8. doi: 10.1073/pnas.75.9.4194.
Vignal, et al. "Safety of rAAV2/2-ND4 Gene Therapy for Leber Hereditary Optic Neuropathy." Ophthalmology. Jun. 2018;125(6):945-947, doi: 10.1016/j.ophtha.2017.12.036.
Wan, et al. "Efficacy and Safety of rAAV2-ND4 Treatment for Leber's Hereditary Optic Neuropathy." Sci Rep. Feb. 19, 2016;6:21587. doi: 10.1038/srep21587.
Wu, et al. "Adeno-associated virus serotypes: vector toolkit for human gene therapy." Mol Ther. Sep. 2006;14(3):316-27, doi: 10.1016/j.ymthe.2006.05.009.
Yang, et al. "Long-term outcomes of gene therapy for the treatment of Leber's hereditary optic neuropathy." EBioMedicine. Aug. 2016;10:258-68, doi: 10.1016/j.ebiom.2016.07.002.
Yang, et al. "Study on transfection of adeno associated virus 2-ND4 gene into mitochondria." Zhonghua Shiyan Yanke Zazhi/Chinese Journal of Experimental Ophthalmology. Aug. 2014;32(8):693-695.
Yang, et al. "Chemical and material communication between the optic nerves in rats." Clin Experiment Ophthalmol, 2015;43: 742-748. https://doi.org/10.1111/ceo.12547.
Yang, Y. Codon and Anticodon. Foreign Medical Molecular Biology Fascicule 7(4):156-163 (1985). English Translation Included.
Yu, et al. "Mutant NADH dehydrogenase subunit 4 gene delivery to mitochondria by targeting sequence-modified adeno-associated virus induces visual loss and optic atrophy in mice." Molecular Vision 2012; 18: 1668-1683.
Yu, et al. "Gene delivery to mitochondria by targeting modified adenoassociated virus suppresses Leber's hereditary optic neuropathy in a mouse model." PNAS May 15, 2012 109 (20) E1238-E1247; https://doi.org/10.1073/pnas.1119577109.

(56) References Cited

OTHER PUBLICATIONS

Kotterman et al. "Antibody Neutralization Poses a Barrier to Intravitreal Adena-Associated Viral Vector Gene Delivery to Non-Human Primates."Gene Ther. Feb. 2015; 22(2): 116-126. (Year: 2015).

Ribera et al. "Biochemical, histological and functional correction of mucopolysaccharidosis type 1118 by intra-cerebrospinal fluid gen therapy" Hum Mol Genet Apr. 1, 2015;24(7):2078-95. (Year: 2015).

Cross et al., "Characterization of Adsorption of Adeno-Associated Virus to Commonly Used Catheter Materials: AAV2 vs. AAV1/2", Molecular Therapy, No. 512 (2006).

Croyle et al., "Development of formulations that enhance physical stability of viral vectors for gene therapy," Gene Therapy 8: 1281-1290 (2001).

Guidance on nonclinical safety studies for the conduct of human clinical trials and marketing authorization for pharmaceuticals. ICH/M3 (R2), 26 pages (2009).

Patel et al., "Poloxamers: A pharmaceutical excipients with therapeutic behaviors," International Journal of PharmTech Research 1(2):299-303 (2009).

Entezari et al., "High-dose intravenous methylprednisolone in recent traumatic optic neuropathy; a randomized double-masked placebo-controlled clinical trial." Graefe's Archive for Clinical and Experimental Ophthalmology vol. 245, pp. 1267-1271 (2007) (Year: 2007).

Yuan et al., "Preliminary clinical observation of creatine phosphate sodium treatment for Leber hereditary optic neuropathy." Mar. 2017, Ophthalmology in China 26(2):126-130 (Year: 2017).

\* cited by examiner

COMPOSITIONS AND METHODS FOR TREATING LEBER'S HEREDITARY OPTIC NEUROPATHY

CROSS-REFERENCE TO RELATED APPLICATIONS

This application is a continuation application of PCT Application No. PCT/CN2019/101538, filed on Aug. 20, 2019, which claims the benefit of PCT Application No. PCT/CN2018/103937, filed on Sep. 4, 2018; PCT Application No. PCT/CN2018/113799, filed on Nov. 2, 2018; Chinese Application No. CN201811230856.2, filed on Oct. 22, 2018; PCT Application No. PCT/CN2018/118662, filed on Nov. 30, 2018; Chinese Application No. CN201811221305.X, filed on Oct. 19, 2018; PCT Application No. PCT/CN2019/070461, filed on Jan. 4, 2019; Chinese Application No. CN201810948193.1, filed on Aug. 20, 2018; each of which are incorporated herein by reference in their entirety.

REFERENCE TO SEQUENCE LISTING

The instant application contains a Sequence Listing which has been submitted in ASCII format via EFS-Web and is hereby incorporated by reference in its entirety. Said ASCII copy, created on Feb. 22, 2021, is named WNBT_005_02US_ST25.txt and is 298 kb in size.

BACKGROUND

Leber's hereditary optic neuropathy (LHON) is a mitochondrially inherited (transmitted from mother to offspring) degeneration of retinal ganglion cells (RGCs) and their axons that leads to an acute or subacute loss of central vision; this affects predominantly young adult males. LHON is only transmitted through the mother, as it is primarily due to mutations in the mitochondrial (not nuclear) genome, and only the egg contributes mitochondria to the embryo. LHON is usually due to one of three pathogenic mitochondrial DNA (mtDNA) point mutations. These mutations are at nucleotide positions 11778 G to A (G11778A), 3460 G to A (G3460A) and 14484 T to C (T14484C), respectively in the NADH dehydrogenase subunit-4 protein (ND4), NADH dehydrogenase subunit-1 protein (ND1) and NADH dehydrogenase subunit-6 protein (ND6) subunit genes of complex I of the oxidative phosphorylation chain in mitochondria. Each mutation is believed to have significant risk of permanent loss of vision. It typically progresses within several weeks to several months without pain, until the binocular vision deteriorate to below 0.1, which seriously affects the quality of life of the patient. Two LHON mutants, G3460A and T14484C, results in the reduction of the patient's platelets isolated mitochondrial NADH dehydrogenase activity by 80%. Ninety percent of the Chinese LHON patients carry the G11778A mutation. The G11778A mutation changes an arginine into histidine in the ND4 protein, resulting the dysfunction and optic nerve damage in LHON patients. There is a need for developing compositions and methods for treating LHON with higher transfection efficiency and treatment efficacy.

SUMMARY

Disclosed here recombinant nucleic acids, pharmaceutical compositions, and methods for treating LHON. In one aspect, disclosed herein is a recombinant nucleic acid, comprising: a mitochondrial targeting sequence; a mitochondrial protein coding sequence comprising a sequence that is at least 99% identical to a sequence selected from the group consisting of SEQ ID NO: 7, 8, 10, and 12; and a 3'UTR nucleic acid sequence.

In some cases, the mitochondrial targeting sequence encodes a polypeptide comprising a peptide sequence that is at least 90%, at least 95%, at least 97%, at least 99%, or 100% identical to a sequence selected from the group consisting of SEQ ID NO: 129-159. In some cases, the mitochondrial targeting sequence comprises a sequence that is at least 90%, at least 95%, at least 97%, at least 99%, or 100% identical to a sequence as set forth in SEQ ID NO: 2. In some cases, the mitochondrial targeting sequence comprises a sequence that is at least 90%, at least 95%, at least 97%, at least 99%, or 100% identical to a sequence as set forth in SEQ ID NO: 3. In some cases, the mitochondrial targeting sequence comprises a sequence that is at least 90%, at least 95%, at least 97%, at least 99%, or 100% identical to a sequence as set forth in SEQ ID NO: 4. In some cases, the mitochondrial targeting sequence comprises a sequence that is at least 90%, at least 95%, at least 97%, at least 99%, or 100% identical to a sequence as set forth in SEQ ID NO: 5.

In some cases, the mitochondrial protein coding sequence comprises a sequence that is at least 90%, at least 95%, at least 97%, at least 99%, or 100% identical to a sequence as set forth in SEQ ID NO: 7 or 8. In some cases, the mitochondrial protein coding sequence comprises a sequence that is at least 90%, at least 95%, at least 97%, at least 99%, or 100% identical to a sequence as set forth in SEQ ID NO: 10. In some cases, the mitochondrial protein coding sequence comprises a sequence that is at least 90%, at least 95%, at least 97%, at least 99%, or 100% identical to a sequence as set forth in SEQ ID NO: 12.

In some cases, the 3'UTR nucleic acid sequence comprises a sequence that is at least 90%, at least 95%, at least 97%, at least 99%, or 100% identical to a sequence selected from the group consisting of SEQ ID NO: 111-125. In some cases, the 3'UTR nucleic acid sequence comprises a sequence that is at least 90%, at least 95%, at least 97%, at least 99%, or 100% identical to a sequence as set forth in SEQ ID NO: 13 or SEQ ID NO: 14.

In some cases, the recombinant nucleic acid comprises a sequence that is at least 90%, at least 95%, at least 97%, at least 99%, or 100% identical to a sequence selected from the group consisting of SEQ ID NO: 17-20, 23-24, 27-28, 31-34, 37-38, 41-42, 45-48, 51-52, 55-56, 59-62, 65-66, 69-70, 73-76, 79-80, and 83-84.

In another aspect, disclosed herein is a recombinant nucleic acid, comprising: a mitochondrial targeting sequence comprising a sequence that is at least 90% identical to a sequence selected from the group consisting of SEQ ID NO: 2, 3, 4, and 5; a mitochondrial protein coding sequence, wherein the mitochondrial protein coding sequence encodes a polypeptide comprising a mitochondrial protein; and a 3'UTR nucleic acid sequence.

In some cases, the mitochondrial targeting sequence comprises a sequence that is at least 90%, at least 95%, at least 97%, at least 99%, or 100% identical to a sequence as set forth in SEQ ID NO: 2. In some cases, the mitochondrial targeting sequence comprises a sequence that is at least 90%, at least 95%, at least 97%, at least 99%, or 100% identical to a sequence as set forth in SEQ ID NO: 3. In some cases, the mitochondrial targeting sequence comprises a sequence that is at least 90%, at least 95%, at least 97%, at least 99%, or 100% identical to a sequence as set forth in SEQ ID NO:

4. In some cases, the mitochondrial targeting sequence comprises a sequence that is at least 90%, at least 95%, at least 97%, at least 99%, or 100% identical to a sequence as set forth in SEQ ID NO: 5.

In some cases, the mitochondrial protein is selected from a group consisting of NADH dehydrogenase 4 (ND4), NADH dehydrogenase 6 (ND6), NADH dehydrogenase 1 (ND1), and a variant thereof. In some cases, the mitochondrial protein comprises NADH dehydrogenase 4 (ND4), or a variant thereof. In some cases, the mitochondrial protein comprises a peptide sequence that is at least 90%, at least 95%, at least 97%, at least 99%, or 100% identical to a sequence as set forth in SEQ ID NO: 160. In some cases, the mitochondrial protein coding sequence comprises a sequence that is at least 90%, at least 95%, at least 97%, at least 99%, or 100% identical to a sequence as set forth in SEQ ID NO: 6, 7, or 8. In some cases, the mitochondrial protein comprises NADH dehydrogenase 6 (ND6), or a variant thereof. In some cases, the mitochondrial protein comprises a sequence that is at least 90%, at least 95%, at least 97%, at least 99%, or 100% identical to a sequence as set forth in SEQ ID NO: 161. In some cases, the mitochondrial protein coding sequence comprises a sequence that is at least 90%, at least 95%, at least 97%, at least 99%, or 100% identical to a sequence as set forth in SEQ ID NO: 9 or 10. In some cases, the mitochondrial protein comprises NADH dehydrogenase 1 (ND1), or a variant thereof. In some cases, the mitochondrial protein comprises a sequence that is at least 90%, at least 95%, at least 97%, at least 99%, or 100% identical to a sequence as set forth in SEQ ID NO: 162. In some cases, the mitochondrial protein coding sequence comprises a sequence that is at least 90%, at least 95%, at least 97%, at least 99%, or 100% identical to a sequence as set forth in SEQ ID NO: 11 or 12.

In some cases, the 3'UTR nucleic acid sequence is located at 3' of the mitochondrial targeting sequence. In some cases, the 3'UTR nucleic acid sequence comprises a sequence selected from the group consisting of hsACO2, hsATP5B, hsAK2, hsALDH2, hsCOX10, hsUQCRFS1, hsNDUFV1, hsNDUFV2, hsSOD2, hsCOX6c, hsIRP1, hsMRPS12, hsATP5J2, rnSOD2, and hsOXA1L. In some cases, the 3'UTR nucleic acid sequence comprises a sequence that is at least 90%, at least 95%, at least 97%, at least 99%, or 100% identical to a sequence selected from the group consisting of SEQ ID NO: 111-125. In some cases, the 3'UTR nucleic acid sequence comprises a sequence that is at least 90%, at least 95%, at least 97%, at least 99%, or 100% identical to a sequence as set forth in SEQ ID NO: 13 or SEQ ID NO: 14.

In some cases, the mitochondrial targeting sequence is located at 5' of the 3'UTR nucleic acid sequence. In some cases, the mitochondrial targeting sequence is located at 3' of the mitochondrial targeting sequence.

In some cases, the recombinant nucleic acid comprises a sequence that is at least 90%, at least 95%, at least 97%, at least 99%, or 100% identical to a sequence selected from the group consisting of SEQ ID NO: 29-84.

In another aspect, disclosed herein is a recombinant nucleic acid, comprising: a mitochondrial targeting sequence; a mitochondrial protein coding sequence comprising a sequence that is at least 90%, at least 95%, at least 97%, at least 99%, or 100% identical to a sequence selected from the group consisting of SEQ ID NO: 7, 8, 10, and 12; and a 3'UTR nucleic acid sequence.

In some cases, the mitochondrial targeting sequence comprises a sequence encodes a polypeptide selected from the group consisting of hsCOX10, hsCOX8, scRPM2, lcSirt5, tbNDUS7, ncQCR2, hsATP5G2, hsLACTB, spilv1, gmCOX2, crATP6, hsOPA1, hsSDHD, hsADCK3, osP0644B06.24-2, *Neurospora crassa* ATPS (ncATP9), hsGHITM, hsNDUFAB1, hsATP5G3, crATP6_hsADCK3, ncATP9_ncATP9, zmLOC100282174, ncATP9_zmLOC100282174_spilv1_ncATP9, zmLOC100282174_hsADCK3_crATP6_hsATP5G3, zmLOC100282174_hsADCK3_hsATP5G3, ncATP9_zmLOC100282174, hsADCK3_zmLOC100282174_crATP6_hsATP5G3, crATP6_hsADCK3_zmLOC100282174_hsATP5G3, hsADCK3_zmLOC100282174, hsADCK3_zmLOC100282174_crATP6, ncATP9_zmLOC100282174_spilv1_GNFP_ncATP9, and ncATP9_zmLOC100282174_spilv1_lcSirt5_osP0644B06.24-2_hsATP5G2_ncATP9. In some cases, the mitochondrial targeting sequence encodes a polypeptide comprising a peptide sequence that is at least 90%, at least 95%, at least 97%, at least 99%, or 100% identical to a sequence selected from the group consisting of SEQ ID NO: 129-159. In some cases, the mitochondrial targeting sequence comprises a sequence that is at least 90%, at least 95%, at least 97%, at least 99%, or 100% identical to a sequence as set forth in SEQ ID NO: 2 or 3. In some cases, the mitochondrial targeting sequence comprises a sequence that is at least 90%, at least 95%, at least 97%, at least 99%, or 100% identical to a sequence as set forth in SEQ ID NO: 4. In some cases, the mitochondrial targeting sequence comprises a sequence that is at least 90%, at least 95%, at least 97%, at least 99%, or 100% identical to a sequence as set forth in SEQ ID NO: 5.

In some cases, the mitochondrial protein coding sequence comprises a sequence that is at least 90%, at least 95%, at least 97%, at least 99%, or 100% identical to a sequence as set forth in SEQ ID NO: 7 or 8. In some cases, the mitochondrial protein coding sequence comprises a sequence that is at least 90%, at least 95%, at least 97%, at least 99%, or 100% identical to a sequence as set forth in SEQ ID NO: 10. In some cases, the mitochondrial protein coding sequence comprises a sequence that is at least 90%, at least 95%, at least 97%, at least 99%, or 100% identical to a sequence as set forth in SEQ ID NO: 12.

In some cases, the 3'UTR nucleic acid sequence is located at 3' of the mitochondrial targeting sequence. In some cases, the 3'UTR nucleic acid sequence comprises a sequence selected from the group consisting of hsACO2, hsATP5B, hsAK2, hsALDH2, hsCOX10, hsUQCRFS1, hsNDUFV1, hsNDUFV2, hsSOD2, hsCOX6c, hsIRP1, hsMRPS12, hsATP5J2, rnSOD2, and hsOXA1L. In some cases, the 3'UTR nucleic acid sequence comprises a sequence that is at least 90%, at least 95%, at least 97%, at least 99%, or 100% identical to a sequence selected from the group consisting of SEQ ID NO: 111-125. In some cases, the 3'UTR nucleic acid sequence comprises a sequence that is at least 90%, at least 95%, at least 97%, at least 99%, or 100% identical to a sequence as set forth in SEQ ID NO: 13 or SEQ ID NO: 14.

In some cases, the mitochondrial targeting sequence is located at 5' of the 3'UTR nucleic acid sequence. In some cases, the mitochondrial targeting sequence is located at 3' of the mitochondrial targeting sequence.

In some cases, the recombinant nucleic acid comprises a sequence that is at least 90%, at least 95%, at least 97%, at least 99%, or 100% identical to a sequence selected from the group consisting of SEQ ID NO: 17-20, 23-24, 27-28, 31-34, 37-38, 41-42, 45-48, 51-52, 55-56, 59-62, 65-66, 69-70, 73-76, 79-80, and 83-84.

In another aspect, disclosed herein is a recombinant nucleic acid, comprising a mitochondrial targeting sequence that is at least 90%, at least 95%, at least 97%, at least 99%, or 100% identical to a sequence selected from the group consisting of SEQ ID NO: 2, 3, and 4. In some cases, the mitochondrial targeting sequence comprises a sequence that is at least 90%, at least 95%, at least 97%, at least 99%, or 100% identical to a sequence as set forth in SEQ ID NO: 2. In some cases, the mitochondrial targeting sequence comprises a sequence that is at least 90%, at least 95%, at least 97%, at least 99%, or 100% identical to a sequence as set forth in SEQ ID NO: 3. In some cases, the mitochondrial targeting sequence comprises a sequence that is at least 90%, at least 95%, at least 97%, at least 99%, or 100% identical to a sequence as set forth in SEQ ID NO: 4.

In some cases, the recombinant nucleic acid further comprises a mitochondrial protein coding sequence, wherein the mitochondrial protein coding sequence encodes a polypeptide comprising a mitochondrial protein. In some cases, the mitochondrial protein is selected from a group consisting of NADH dehydrogenase 4 (ND4), NADH dehydrogenase 6 (ND6), NADH dehydrogenase 1 (ND1), and a variant thereof. In some cases, the mitochondrial protein comprises NADH dehydrogenase 4 (ND4), or a variant thereof. In some cases, the mitochondrial protein comprises a peptide sequence that is at least 90%, at least 95%, at least 97%, at least 99%, or 100% identical to a sequence as set forth in SEQ ID NO: 160. In some cases, the mitochondrial protein coding sequence comprises a sequence that is at least 90%, at least 95%, at least 97%, at least 99%, or 100% identical to a sequence as set forth in SEQ ID NO: 6, 7, or 8. In some cases, the mitochondrial protein comprises NADH dehydrogenase 6 (ND6), or a variant thereof. In some cases, the mitochondrial protein comprises a sequence that is at least 90%, at least 95%, at least 97%, at least 99%, or 100% identical to a sequence as set forth in SEQ ID NO: 161. In some cases, the mitochondrial protein coding sequence comprises a sequence that is at least 90%, at least 95%, at least 97%, at least 99%, or 100% identical to a sequence as set forth in SEQ ID NO: 9 or 10. In some cases, the mitochondrial protein comprises NADH dehydrogenase 1 (ND1), or a variant thereof. In some cases, the mitochondrial protein comprises a sequence that is at least 90%, at least 95%, at least 97%, at least 99%, or 100% identical to a sequence as set forth in SEQ ID NO: 162. In some cases, the mitochondrial protein coding sequence comprises a sequence that is at least 90%, at least 95%, at least 97%, at least 99%, or 100% identical to a sequence as set forth in SEQ ID NO: 11 or 12.

In some cases, the recombinant nucleic acid further comprises a 3'UTR nucleic acid sequence. In some cases, the 3'UTR nucleic acid sequence is located at 3' of the mitochondrial targeting sequence. In some cases, the 3'UTR nucleic acid sequence comprises a sequence selected from the group consisting of hsACO2, hsATP5B, hsAK2, hsALDH2, hsCOX10, hsUQCRFS1, hsNDUFV1, hsNDUFV2, hsSOD2, hsCOX6c, hsIRP1, hsMRPS12, hsATP5J2, rnSOD2, and hsOXA1L. In some cases, the 3'UTR nucleic acid sequence comprises a sequence that is at least 90%, at least 95%, at least 97%, at least 99%, or 100% identical to a sequence selected from the group consisting of SEQ ID NO: 111-125. In some cases, the 3'UTR nucleic acid sequence comprises a sequence that is at least 90%, at least 95%, at least 97%, at least 99%, or 100% identical to a sequence as set forth in SEQ ID NO: 13 or SEQ ID NO: 14. In some cases, the mitochondrial targeting sequence is located at 5' of the 3'UTR nucleic acid sequence. In some cases, the mitochondrial targeting sequence is located at 3' of the mitochondrial targeting sequence.

In some cases, the recombinant nucleic acid comprises a sequence that is at least 90%, at least 95%, at least 97%, at least 99%, or 100% identical to a sequence selected from the group consisting of SEQ ID NO: 29-70.

In another aspect, disclosed herein is a recombinant nucleic acid, comprising a mitochondrial protein coding sequence, wherein the mitochondrial protein coding sequence encodes a polypeptide comprising a mitochondrial protein, wherein the mitochondrial protein coding sequence comprises a sequence that is at least 90%, at least 95%, at least 97%, at least 99%, or 100% identical to a sequence selected from the group consisting of SEQ ID NO: 7, 8, 10, and 12.

In some cases, the recombinant nucleic acid further comprises a mitochondrial targeting sequence. In some cases, the mitochondrial targeting sequence comprises a sequence encodes a polypeptide selected from the group consisting of hsCOX10, hsCOX8, scRPM2, lcSirt5, tbNDUS7, ncQCR2, hsATP5G2, hsLACTB, spilv1, gmCOX2, crATP6, hsOPA1, hsSDHD, hsADCK3, osP0644B06.24-2, Neurospora crassa ATPS (ncATP9), hsGHITM, hsNDUFAB1, hsATP5G3, crATP6_hsADCK3, ncATP9_ncATP9, zmLOC100282174, ncATP9_zmLOC100282174_spilv1_ncATP9, zmLOC100282174_hsADCK3_crATP6_hsATP5G3, zmLOC100282174_hsADCK3_hsATP5G3, ncATP9_zmLOC100282174, hsADCK3_zmLOC100282174_crATP6_hsATP5G3, crATP6_hsADCK3_zmLOC100282174_hsATP5G3, hsADCK3_zmLOC100282174, hsADCK3_zmLOC100282174_crATP6, ncATP9_zmLOC100282174_spilv1_GNFP_ncATP9, and ncATP9_zmLOC100282174_spilv1_lcSirt5_osP0644B06.24-2_hsATP5G2_ncATP9. In some cases, the mitochondrial targeting sequence encodes a polypeptide comprising a peptide sequence that is at least 90%, at least 95%, at least 97%, at least 99%, or 100% identical to a sequence selected from the group consisting of SEQ ID NO: 129-159. In some cases, the mitochondrial targeting sequence comprises a sequence that is at least 90%, at least 95%, at least 97%, at least 99%, or 100% identical to a sequence as set forth in SEQ ID NO: 2. In some cases, the mitochondrial targeting sequence comprises a sequence that is at least 90%, at least 95%, at least 97%, at least 99%, or 100% identical to a sequence as set forth in SEQ ID NO: 3. In some cases, the mitochondrial targeting sequence comprises a sequence that is at least 90%, at least 95%, at least 97%, at least 99%, or 100% identical to a sequence as set forth in SEQ ID NO: 4. In some cases, the mitochondrial targeting sequence comprises a sequence that is at least 90%, at least 95%, at least 97%, at least 99%, or 100% identical to a sequence as set forth in SEQ ID NO: 5.

In some cases, the mitochondrial protein coding sequence comprises a sequence that is at least 90%, at least 95%, at least 97%, at least 99%, or 100% identical to a sequence as set forth in SEQ ID NO: 7 or 8. In some cases, the mitochondrial protein coding sequence comprises a sequence that is at least 90%, at least 95%, at least 97%, at least 99%, or 100% identical to a sequence as set forth in SEQ ID NO: 10. In some cases, the mitochondrial protein coding sequence comprises a sequence that is at least 90%, at least 95%, at least 97%, at least 99%, or 100% identical to a sequence as set forth in SEQ ID NO: 12.

In some cases, the recombinant nucleic acid further comprises a3'UTR nucleic acid sequence. In some cases, the 3'UTR nucleic acid sequence is located at 3' of the mitochondrial targeting sequence. In some cases, the 3'UTR nucleic acid sequence comprises a sequence selected from the group consisting of hsACO2, hsATP5B, hsAK2, hsALDH2, hsCOX10, hsUQCRFS1, hsNDUFV1, hsNDUFV2, hsSOD2, hsCOX6c, hsIRP1, hsMRPS12, hsATP5J2, rnSOD2, and hsOXA1L. In some cases, the 3'UTR nucleic acid sequence comprises a sequence that is at least 90%, at least 95%, at least 97%, at least 99%, or 100% identical to a sequence selected from the group consisting of SEQ ID NO: 111-125. In some cases, the 3'UTR nucleic acid sequence comprises a sequence that is at least 90%, at least 95%, at least 97%, at least 99%, or 100% identical to a sequence as set forth in SEQ ID NO: 13 or SEQ ID NO: 14. In some cases, the mitochondrial targeting sequence is located at 5' of the 3'UTR nucleic acid sequence. In some cases, the mitochondrial targeting sequence is located at 3' of the mitochondrial targeting sequence.

In some cases, the recombinant nucleic acid comprises a sequence that is at least 90%, at least 95%, at least 97%, at least 99%, or 100% identical to a sequence selected from the group consisting of SEQ ID NO: 17-20, 23-24, 27-28, 31-34, 37-38, 41-42, 45-48, 51-52, 55-56, 59-62, 65-66, 69-70, 73-76, 79-80, and 83-84.

In another aspect, disclosed herein is a viral vector comprising the recombinant nucleic acid disclosed herein. In some cases, the viral vector is an adeno-associated virus (AAV) vector. In some cases, the AAV vector is selected from the group consisting of AAV1, AAV2, AAV3, AAV4, AAV5, AAV6, AAV7, AAV8, AAV9, AAV10, AAV11, AAV12, AAV13, AAV14, AAV15, and AAV16 vectors. In some cases, the AAV vector is a recombinant AAV (rAAV) vector. In some cases, the rAAV vector is rAAV2 vector.

In another aspect, disclosed herein is a pharmaceutical composition, comprising an adeno-associated virus (AAV) comprising any recombinant nucleic acid disclosed herein. In some cases, the pharmaceutical composition further comprises a pharmaceutically acceptable excipient thereof. Also disclosed is a pharmaceutical composition, comprising the viral vector disclosed herein, and a pharmaceutically acceptable excipient thereof, wherein the viral vector comprises any recombinant nucleic acid disclosed herein. Also disclosed is a pharmaceutical composition, comprising: an adeno-associated virus (AAV) comprising any recombinant nucleic acid disclosed herein, wherein the recombinant nucleic acid comprises a sequence that is at least 90%, at least 95%, at least 97%, at least 99%, or 100% identical to a sequence as set forth in SEQ ID NO: 15; and a pharmaceutically acceptable excipient.

In some cases, the pharmaceutically acceptable excipient comprises phosphate-buffered saline (PBS), α,α-trehalose dehydrate, L-histidine monohydrochloride monohydrate, polysorbate 20, NaCl, $NaH_2PO_4$, $Na_2HPO_4$, $KH_2PO_4$, $K_2HPO_4$, poloxamer 188, or any combination thereof. In some cases, the pharmaceutically acceptable excipient is selected from phosphate-buffered saline (PBS), α,α-trehalose dehydrate, L-histidine monohydrochloride monohydrate, polysorbate 20, NaCl, $NaH_2PO_4$, $Na_2HPO_4$, $KH_2PO_4$, $K_2HPO_4$, poloxamer 188, and any combination thereof. In some cases, the pharmaceutically acceptable excipient comprises poloxamer 188. In some cases, the pharmaceutically acceptable excipient comprises 0.0001%-0.01% poloxamer 188. In some cases, the pharmaceutically acceptable excipient comprises 0.001% poloxamer 188. In some cases, the pharmaceutically acceptable excipient further comprises one or more salts. In some cases, the one or more salts comprises NaCl, $NaH_2PO_4$, $Na_2HPO_4$, and $KH_2PO_4$. In some cases, the one or more salts comprises 80 mM NaCl, 5 mM $NaH_2PO_4$, 40 mM $Na_2HPO_4$, and 5 mM $KH_2PO_4$. In some cases, the one or more salts comprises NaCl, $Na_2HPO_4$, and $KH_2PO_4$. In some cases, the one or more salts comprises 154 mM NaCl, 5.6 mM $Na_2HPO_4$, and 8.4 mM $KH_2PO_4$. In some cases, the pharmaceutical composition has a pH of 6-8. In some cases, the pharmaceutical composition has a pH of 7.2-7.4. In some cases, the pharmaceutical composition has a pH of 7.3. In some cases, the pharmaceutical composition has a viral titer of at least $1.0 \times 10^{10}$ vg/mL. In some cases, the pharmaceutical composition has a viral titer of at least $5.0 \times 10^{10}$ vg/mL.

In some cases, the pharmaceutical composition is subject to five freeze/thaw cycles, the pharmaceutical composition retains at least 60%, 70%, 80%, or 90% of a viral titer as compared to the viral titer prior to the five freeze/thaw cycles. In some cases, the pharmaceutical composition, when administered to a patient with Leber's hereditary optic neuropathy, generates a higher average recovery of vision than a comparable pharmaceutical composition without the recombinant nucleic acid. In some cases, the pharmaceutical composition, when administered to a patient with Leber's hereditary optic neuropathy, generates a higher average recovery of vision than a comparable pharmaceutical composition comprising a recombinant nucleic acid as set forth in SEQ ID NO: 15.

In another aspect, disclosed herein is a method of treating an eye disorder, comprising administering any pharmaceutical composition disclosed herein to a patient in need thereof. In some cases, the eye disorder is Leber's hereditary optic neuropathy (LHON). In some cases, the method comprises administering the pharmaceutical composition to one or both eyes of the patient. In some cases, the pharmaceutical composition is administered via intraocular or intravitreal injection. In some cases, the pharmaceutical composition is administered via intravitreal injection. In some cases, about 0.01-0.1 mL of the pharmaceutical composition is administered via intravitreal injection. In some cases, about 0.05 mL of the pharmaceutical composition is administered via intravitreal injection.

In some cases, the method further comprises administering methylprednisolone to the patient. In some cases, the methylprednisolone is administered prior to the intravitreal injection of the pharmaceutical composition. In some cases, the methylprednisolone is administered orally In some cases, the methylprednisolone is administered daily for at least 1, 2, 3, 4, 5, 6, or 7 days prior to the intravitreal injection of the pharmaceutical composition. In some cases, the methylprednisolone is administered daily. In some cases, the a daily dosage of about 32 mg/60 kg methylprednisolone is administered. In some cases, the methylprednisolone is administered after the intravitreal injection of the pharmaceutical composition. In some cases, the method further comprises administering sodium creatine phosphate to the patient. In some cases, the sodium creatine phosphate is administered intravenously. In some cases, the methylprednisolone is administered intravenously or orally. In some cases, the method comprises administering methylprednisolone intravenously for at least one day, which is followed by administering methylprednisolone orally for at least a week. In some cases, the method comprises administering methylprednisolone intravenously for about 3 days, which is followed by administering methylprednisolone orally for at least about 6 weeks. In some cases, the methylprednisolone is administered intravenously at a daily dose of about 80 mg/60 kg. In some cases, the administering the pharmaceutical composition generates a higher average recovery of vision than a comparable pharmaceutical composition without the recombinant nucleic acid. In some cases, the administering the pharmaceutical composition generates a higher average recovery of vision than a comparable pharmaceutical composition comprising a recombinant nucleic acid as set forth in SEQ ID NO: 15.

In some embodiments, the present disclosure provides a method of treating an eye disorder, comprising administering to a patient in need thereof (a) a first pharmaceutical composition comprising an adeno-associated virus (AAV) comprising a recombinant nucleic acid comprising: (i) a nucleic acid sequence encoding a mitochondrial targeting peptide; (ii) a nucleic acid sequence encoding a mitochondrial protein comprising a nucleic acid sequence that is at least 90%, at least 95%, at least 97%, at least 99%, or 100% identical to a sequence selected from the group consisting of SEQ ID NO: 6-12; and (iii) a 3'UTR nucleic acid sequence; and (b) a second pharmaceutical composition comprising a steroid.

In some embodiments, the nucleic acid sequence encoding the mitochondrial protein encodes a polypeptide comprising an amino acid sequence that is at least 90%, at least 95%, at least 97%, at least 99%, or 100% identical to a sequence selected from the group consisting of SEQ ID NO: 160-162. In some embodiments, the nucleic acid sequence encoding a mitochondrial targeting peptide encodes a polypeptide comprising an amino acid sequence that is at least 90%, at least 95%, at least 97%, at least 99%, or 100% identical to a sequence selected from the group consisting of SEQ ID NO: 126-159. In some embodiments, the nucleic acid sequence encoding a mitochondrial targeting peptide comprises a nucleic acid sequence that is at least 90%, at least 95%, at least 97%, at least 99%, or 100% identical to a sequence selected from the group consisting of SEQ ID NO: 1-5. In some embodiments, the 3'UTR nucleic acid sequence comprises a nucleic sequence that is at least 90%, at least 95%, at least 97%, at least 99%, or 100% identical to a sequence selected from the group consisting of SEQ ID NO: 13, 14, and 111-125.

In some embodiments, the present disclosure provides a method of treating an eye disorder, comprising administering to a patient in need thereof (a) a first pharmaceutical composition comprising an adeno-associated virus (AAV) comprising a recombinant nucleic acid comprising: (i) a nucleic acid sequence encoding a mitochondrial targeting peptide comprising an amino sequence that is at least 90%, at least 95%, at least 97%, at least 99%, or 100% identical to a sequence selected from the group consisting of SEQ ID NO: 126-159; (ii) a nucleic acid sequence encoding a mitochondrial protein; and (iii) a 3'UTR nucleic acid sequence; and (b) a second pharmaceutical composition comprising a steroid.

In some embodiments, said mitochondrial protein is selected from the group consisting of NADH dehydrogenase 4 (ND4), NADH dehydrogenase 6 (ND6), NADH dehydrogenase 1 (ND1), and variants thereof. In some embodiments, the nucleic acid sequence encoding a mitochondrial protein comprises a nucleic acid sequence that is at least 90%, at least 95%, at least 97%, at least 99%, or 100% identical to a nucleic acid sequence selected from the group consisting of SEQ ID NO: 6-12. In some embodiments, the nucleic acid sequence encoding a mitochondrial protein encodes a polypeptide comprising an amino acid sequence that is at least 90%, at least 95%, at least 97%, at least 99%, or 100% identical to a sequence selected from the group consisting of SEQ ID NO: 160-162. In some embodiments, the nucleic acid sequence encoding a mitochondrial targeting peptide comprises a nucleic acid sequence that is at least 90%, at least 95%, at least 97%, at least 99%, or 100% identical to a sequence selected from the group consisting of SEQ ID NO: 1-5. In some embodiments, the 3'UTR nucleic acid sequence comprises a sequence that is at least 90%, at least 95%, at least 97%, at least 99%, or 100% identical to a sequence selected from the group consisting of SEQ ID NO: 13, 14, and 111-125.

In some embodiments, the present disclosure provides a method of treating an eye disorder, comprising administering to a patient in need thereof (a) a first pharmaceutical composition comprising an adeno-associated virus (AAV) comprising a recombinant nucleic acid comprising: (i) a nucleic acid sequence encoding a mitochondrial targeting peptide comprising an amino sequence that is at least 90%, at least 95%, at least 97%, at least 99%, or 100% identical to a sequence selected from the group consisting of SEQ ID NO: 126-159; (ii) a nucleic acid sequence encoding a mitochondrial protein comprising a nucleic acid sequence that is at least 90%, at least 95%, at least 97%, at least 99%, or 100% identical to a sequence selected from the group consisting of SEQ ID NO: 6-12; and (iii) a 3'UTR nucleic acid sequence that is at least 90%, at least 95%, at least 97%, at least 99%, or 100% identical to a sequence selected from the group consisting of SEQ ID NO: 13, 14, and 111-125; and (b) a second pharmaceutical composition comprising a steroid.

In some embodiments, the present disclosure provides a method of treating an eye disorder, comprising administering to a patient in need thereof (a) first pharmaceutical composition comprising an adeno-associated virus (AAV) comprising a recombinant nucleic acid comprising: (i) a nucleic acid sequence encoding a mitochondrial targeting peptide; and (ii) a nucleic acid sequence encoding a mitochondrial protein; and (b) a second pharmaceutical composition comprising a steroid. In some embodiments, the mitochondrial protein is selected from the group consisting of NADH dehydrogenase 4 (ND4), NADH dehydrogenase 6 (ND6), NADH dehydrogenase 1 (ND1), and variants thereof. In some embodiments, the 3'UTR nucleic acid sequence comprises a nucleic sequence that is at least 90%, at least 95%, at least 97%, at least 99%, or 100% identical to a sequence selected from the group consisting of SEQ ID NO: 13, 14, and 111-125.

In some embodiments, the recombinant nucleic acid comprises a sequence that is at least 90%, at least 95%, at least 97%, at least 99%, or 100% identical to a sequence from the group consisting of SEQ ID NO: 15-84. In some embodiments, the recombinant nucleic acid comprises a sequence that is at least 90%, at least 95%, at least 97%, at least 99%, or 100% identical to SEQ ID NO: 15.

In some embodiments, the first pharmaceutical composition is administered via intraocular or intravitreal injection. In some embodiments, about 0.01-0.1 mL of the first pharmaceutical composition is administered via intravitreal injection. In some embodiments, about 0.05 mL of the first pharmaceutical composition is administered via intravitreal injection. In some embodiments, the first pharmaceutical composition is administered to one or both eyes of the patient.

In some embodiments, the steroid selected from the group consisting of alclometasone diproprionate, amcinonide, beclomethasone diproprionate, betamethasone, betamethasone benzoate, betamethasone diproprionate, betamethasone sodium phosphate, betamethasone sodium phosphate and acetate, betamethasone valerate, clobetasol proprionate, clocortolone pivalate, cortisol (hydrocortisone), cortisol (hydrocortisone) acetate, cortisol (hydrocortisone) butyrate, cortisol (hydrocortisone) cypionate, cortisol (hydrocortisone) sodium phosphate, cortisol (hydrocortisone) sodium succinate, cortisol (hydrocortisone) valerate, cortisone acetate, desonide, desoximetasone, dexamethasone, dexamethasone acetate, dexamethasone sodium phosphate, diflorasone diacetate, fludrocortisone acetate, flunisolide, fluocinolone acetonide, fluocinonide, fluorometholone, flurandrenolide, halcinonide, medrysone, methylprednisolone, methylprednisolone acetate, methylprednisolone sodium succinate, mometasone furoate, paramethasone acetate, prednisolone, prednisolone acetate, prednisolone sodium phosphate, prednisolone tebutate, prednisone, triamcinolone, triamcinolone acetonide, triamcinolone diacetate, and triamcinolone hexacetonide or a synthetic analog thereof.

In some embodiments, the steroid is a glucocorticoid. In some embodiments, the glucocorticoid is methylprednisolone or prednisone.

In some embodiments, the methylprednisolone is formulated as a tablet or as a liquid for intravenous administration. In some embodiments, the steroid is administered orally or intravenously.

In some embodiments, the steroid is administered prior to administration of the first pharmaceutical composition. In some embodiments, the steroid is administered daily for at least 1, 2, 3, 4, 5, 6, or 7 days prior to the administration of the first pharmaceutical composition. In some embodiments, the steroid is methylprednisolone and is administered at a daily dosage of about 30 mg/60 kg to about 40 mg/60 kg or about 30 mg to about 40 mg. In some embodiments, the daily dosage of methylprednisolone is about 32 mg/60 kg or 32 mg. In some embodiments, the steroid is prednisone and is administered at a daily dosage of about 50 mg/60 kg to about 70 mg/60 kg. In some embodiments, the daily dosage of prednisone is about 60 mg/60 kg.

In some embodiments, the steroid is administered after the administration of the first pharmaceutical composition. In some embodiments, the steroid is administered daily for at least 1 day, at least 2 days, at least 3 days, at least 4 days, at least 5 days, at least 6 days, at least 7 days, at least 8 days, at least 9 days, at least 10 days, at least 1 week, at least 2 weeks, at least 3 weeks, at least 4 weeks, at least 5 weeks, at least 6 weeks, at least 7 weeks, at least 8 weeks, at least 9 weeks, at least 10 weeks, at least 11 weeks, at least 12 weeks, at least 13 weeks, at least 14 weeks, or at least 15 weeks after the administration of the first pharmaceutical composition.

In some embodiments, the steroid is methylprednisolone and is administered at a daily dosage of between about 70 mg/60 kg and 90 mg/60 kg or between about 70 mg and 90 mg. In some embodiments, the daily dosage of methylprednisolone is about 80 mg/60 kg or 80 mg. In some embodiments, the methylprednisolone is administered for at least two days after the administration of the first pharmaceutical composition. In some embodiments, subsequent doses of methylprednisolone are administered daily for at least 7 weeks after the administration of the first pharmaceutical composition and wherein the dosage of the methylprednisolone is decreased on a weekly basis.

In some embodiments, the steroid is prednisone and is administered at a daily dosage of between about 50 mg/60 kg and 70 mg/60 kg or between about 50 mg and about 70 mg. In some embodiments, the daily dosage of predisone is about 60 mg/60 kg or about 60 mg. In some embodiments, the predisone is administered for at least seven days after the administration of the first pharmaceutical composition. In some embodiments, wherein after seven days, the predisone is administered at a daily dosage of between about 30 mg/60 kg and about 50 mg/60 kg or between about 30 mg and 50 mg. In some embodiments, the daily dosage of predisone is about 40 mg/60 kg or 40 mg. In some embodiments, subsequent doses of predisone are administered daily for at least 4 days and wherein the dosage of the predisone is decreased on a daily basis.

In some embodiments, the steroid is administered prior to and after the administration of the first pharmaceutical compound.

In some embodiments, the steroid is methylprednisolone and is administered daily for at least seven days prior to the administration of the first pharmaceutical compound and daily for at least 7 weeks after administration of the first pharmaceutical compound. In some embodiments, the methylprednisolone is administered prior to the administration of the first pharmaceutical compound at a daily dosage of about 32 mg/60 kg or 32 mg. In some embodiments, the methylprednisolone is administered at a daily dosage of about 80 mg/60 kg or 80 mg for at least 2 days after the administration of the first pharmaceutical compound. In some embodiments, beginning three days after administration of the first pharmaceutical compound, the methylprednisolone is administered at a daily dosage of about 40 mg/60 kg or 40 mg for at least 4 days. In some embodiments, beginning one week after administration of the first pharmaceutical compound, the methylprednisolone is administered at a daily dosage of about 32 mg/60 kg or 32 mg for at least one week. In some embodiments, beginning two weeks after administration of the first pharmaceutical compound, the methylprednisolone is administered at a daily dosage of about 24 mg/60 kg or 24 mg for at least one week. In some embodiments, beginning three weeks after administration of the first pharmaceutical compound, the methylprednisolone is administered at a daily dosage of about 16 mg/60 kg or 16 mg for at least one week. In some embodiments, beginning four weeks after administration of the first pharmaceutical compound, the methylprednisolone is administered at a daily dosage of about 8 mg/60 kg or 8 mg for at least one week. In some embodiments, beginning five weeks after administration of the first pharmaceutical compound, the methylprednisolone is administered at a daily dosage of about 6 mg/60 kg or 6 mg for at least one week. In some embodiments, beginning six weeks after administration of the first pharmaceutical compound, the methylprednisolone is administered at a daily dosage of about 4 mg/60 kg or 4 mg for at least one week.

In some embodiments, the steroid is prednisone and is administered daily for at least two days prior to the administration of the first pharmaceutical compound and daily for at least eleven days after administration of the first pharmaceutical compound. In some embodiments, the prednisone is administered prior to the administration of the first pharmaceutical compound at a daily dosage of about 60 mg/60 kg or 60 mg. In some embodiments, the prednisone is administered at a daily dosage of about 60 mg/60 kg or 60 mg for at least seven days after the administration of the first pharmaceutical compound. In some embodiments, eight days after administration of the first pharmaceutical compound, the prednisone is administered at a daily dosage of about 40 mg/60 kg or 40 mg for at least one day. In some embodiments, nine days after administration of the first pharmaceutical compound, the prednisone is administered at a daily dosage of about 20 mg/60 kg or 20 mg for at least one day. In some embodiments, ten days after administration of the first pharmaceutical compound, the prednisone is administered at a daily dosage of about 10 mg/60 kg or 10 mg for at least one day.

In some embodiments, the methods further comprise administering sodium creatine phosphate to the patient. In some embodiments, the sodium creatine phosphate is administered intravenously prior to and/or after the administration of the first pharmaceutical composition.

In some embodiments, administration of the first and second pharmaceutical compositions generates a higher average recovery of vision than a comparable pharmaceutical composition administered without the second pharmaceutical composition. In some embodiments, administration of the first and second pharmaceutical compositions generates a lower incidence of an adverse event than a comparable pharmaceutical composition administered without the second pharmaceutical composition. In some embodiments, the adverse event is selected from anterior chamber inflammation, vitritis, ocular hypertension, cataract removal, keratitis, vitreous hemorrhage, allergic conjunctivitis, and eye pain. In some embodiments, the higher average recovery of vision and the lower incidence of an adverse event is determined in a population of patients with the eye disorder. In some embodiments, the population of patients are ethnically matched. In some embodiments, the population of patients are Chinese or Argentinian.

In some embodiments, the eye disorder is Leber's hereditary optic neuropathy (LHON). In some embodiments, the AAV is selected from AAV1, AAV2, AAV3, AAV4, AAV5, AAV6, AAV7, AA8, AAV9, and AAV10. In some embodiments, the AAV is AAV2.

In some embodiments, the present disclosure provides a method of screening patients for treatment of an eye disorder, the method comprising: (a) obtaining a serum sample from a patient; (b) culturing a population of target cells with a composition comprising an adeno-associated virus (AAV) comprising a recombinant nucleic acid encoding a detectable label in the presence of the serum sample; and (c) detecting the expression level of the detectable label in the target cell population after the culturing, wherein the patient is selected for the treatment if the expression level of the detectable label in the target cell population is higher than a pre-determined threshold.

In some embodiments, the present disclosure provides a method of screening patients for treatment of an eye disorder, the method comprising: (a) culturing a population of target cells with a composition comprising an adeno-associated virus (AAV) comprising a recombinant nucleic acid encoding a detectable label in the presence of a serum sample from a patient; and (b) detecting the expression level of the detectable label in the target cell population after the culturing, wherein the patient is selected for the treatment if the expression level of the detectable label in the target cell population is higher than a pre-determined threshold.

In some embodiments, the present disclosure provides a method of treating an eye disorder for a patient in need thereof, comprising: (a) obtaining a serum sample from a patient; (b) culturing a population of target cells with a composition comprising a first adeno-associated virus (AAV) comprising a first recombinant nucleic acid encoding a detectable label in the presence of the serum sample; (c) detecting the expression level of the detectable label in the target cell population; and (d) administering to the patient a pharmaceutical composition comprising a second AAV comprising a second recombinant nucleic acid, wherein the expression level of the detectable label in the target cell population is higher than a pre-determined threshold.

In some embodiments, the present disclosure provides a method of treating an eye disorder for a patient in need thereof, comprising: (a) culturing a population of target cells with a composition comprising a first adeno-associated virus (AAV) comprising a first recombinant nucleic acid encoding a detectable label in the presence of a serum sample from a patient; (b) detecting the expression level of the detectable label in the target cell population; and (c) administering to the patient a pharmaceutical composition comprising a second AAV comprising a second recombinant nucleic acid, wherein the expression level of the detectable label in the target cell population is higher than a pre-determined threshold.

In some embodiments, the detectable label is a fluorescent protein. In some embodiments, the fluorescent protein is green fluorescent protein (GFP). In some embodiments, the detectable label is detected by flow cytometry or qPCR. In some embodiments, the culturing step is at least 12 hours, 1 day, 2 days, 3 days, 4 days, 5 days, 6 days, 7 days, or longer.

In some embodiments, the pre-determined threshold is about 40% of cells expressing the detectable label when detected by flow cytometry. In some embodiments, the pre-determined threshold is a relative expression level of the detectable label of about 0.6 when detected by qPCR. In some embodiments, the target cells are HEK-293 T cells.

In some embodiments, the treatment is a recombinant AAV comprising a nucleic acid sequence encoding a mitochondrial protein. In some embodiments, the mitochondrial protein is selected from the group consisting of NADH dehydrogenase 4 (ND4), NADH dehydrogenase 6 (ND6), NADH dehydrogenase 1 (ND1), and variants thereof. In some embodiments, the patient comprises a mutation selected from G11778A in the ND4 gene, G3460A in the ND1 gene, and T14484C in the ND6 gene.

In some embodiments, the present disclosure provides a kit, comprising an adeno-associated virus (AAV) comprising a recombinant nucleic acid encoding a detectable label, a population of target cells, and one or more reagents for detecting the detectable label. In some embodiments, the kit further comprises a transfection reagent for transfecting the population of target cells with the AAV. In some embodiments, the kit further comprises a second AAV comprising a recombinant nucleic acid encoding a mitochondrial protein. In some embodiments, the one or more reagents for detecting the detectable label are selected an antibody that binds to the detectable label and one or more primer oligonucleotides specific for the recombinant nucleic acid encoding the detectable label.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Definitions

Figure 1:
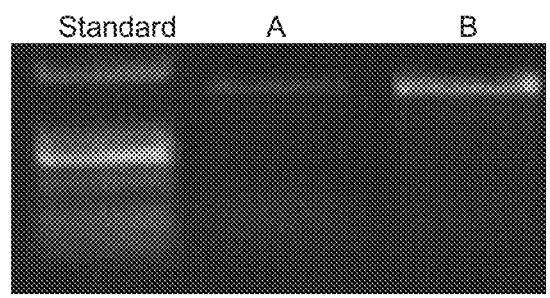
FIG. 1 shows the PCR nucleic acid electrophoresis verification of ND4 (lane A) and optimized ND4 (lane B) gene cloning results.

Unless defined otherwise, all technical and scientific terms used herein have the same meaning as commonly understood by one of the ordinary skill in the art to which this disclosure belongs. Although any methods and materials similar or equivalent to those described herein can be used in the practice or testing of the formulations or unit doses herein, some methods and materials are now described. Unless mentioned otherwise, the techniques employed or contemplated herein are standard methodologies. The materials, methods and examples are illustrative only and not limiting.

As used herein and in the appended claims, the singular forms "a," "and," and "the" include plural referents unless the context clearly dictates otherwise. Thus, for example, reference to "a compound" includes a plurality of such agents, and reference to "the salt" includes reference to one or more salts (or to a plurality of salts) and equivalents thereof known to those skilled in the art, and so forth.

As used herein, unless otherwise indicated, the term "or" can be conjunctive or disjunctive. As used herein, unless otherwise indicated, any embodiment can be combined with any other embodiment.

As used herein, unless otherwise indicated, some inventive embodiments herein contemplate numerical ranges. When ranges are present, the ranges include the range endpoints. Additionally, every subrange and value within the range is present as if explicitly written out.

The term "about" and its grammatical equivalents in relation to a reference numerical value and its grammatical equivalents as used herein can include a range of values plus or minus 10% from that value, such as a range of values plus or minus 10%, 9%, 8%, 7%, 6%, 5%, 4%, 3%, 2%, or 1% from that value. For example, the amount "about 10" includes amounts from 9 to 11.

The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

The term "subject" refers to a mammal that has been or will be the object of treatment, observation or experiment. The term "mammal" is intended to have its standard meaning, and encompasses humans, dogs, cats, sheep, and cows, for example. The methods described herein can be useful in both human therapy and veterinary applications. In some embodiments, the subject is a human.

The term "treating" or "treatment" encompasses administration of at least one compound disclosed herein, or a pharmaceutically acceptable salt thereof, to a mammalian subject, particularly a human subject, in need of such an administration and includes (i) arresting the development of clinical symptoms of the disease, such as cancer, (ii) bringing about a regression in the clinical symptoms of the disease, such as cancer, and/or (iii) prophylactic treatment for preventing the onset of the disease, such as cancer.

The term "therapeutically effective amount" of a chemical entity described herein refers to an amount effective, when administered to a human or non-human subject, to provide a therapeutic benefit such as amelioration of symptoms, slowing of disease progression, or prevention of disease.

As used herein, unless otherwise indicated, the terms "nucleic acid" and "polynucleotide" can be used interchangeably.

As used herein, unless otherwise indicated, a drug dosage of X mg/60 kg refers to X mg of the drug per 60 kg body weight of the patient. For example, a drug dosage of 100 mg/60 kg means a patient with 60 kg body weight is instructed to take 100 mg of the drug, and accordingly, another patient with 30 kg body weight is instructed to take 50 mg of the drug.

Nucleic Acid and Polypeptide Sequences

Table 1 discloses all the nucleic acid and polypeptide sequences disclosed herein. The first column shows the SEQ ID NO of each sequence. The second column describes the nucleic acid or polypeptide construct. For example, the construct COX10-ND6-3'UTR is a nucleic acid combining the nucleic acid sequences of COX10 (SEQ ID NO: 1), ND6 (SEQ ID NO: 9), and 3'UTR (SEQ ID NO: 13) (from 5' to 3' without linker between the nucleic acid sequences.

TABLE 1 nucleic acid and polypeptide sequences and SEQ ID NOs

| SEQ | Description | Sequence |
|---|---|---|
| 1 | COX10 | ATGGCCGCATCTCCGCACACTCTCTCCTCACGCCTCCTGACAGGTTGCGTAGGAGGCTCTGTC<br>TGGTATCTTGAAAGAAGAACT |
| 2 | opt_COX10 | ATGGCCGCCTCTCCACACACACTGAGTAGCAGACTGCTGACCGGCTGTGTTGGCGGCTCTGTG<br>TGGTATCTGGAACGGCGGACA |
| 3 | opt_COX10* | ATGGCCGCCAGCCCCCACACCCTGAGCAGCCGCCTGCTGACCGGCTGCGTGGGCGGCAGCGTG<br>TGGTACCTGGAGCGCCGCACC |
| 4 | COX8 | ATGTCCGTCCTGACGCGCCTGCTGCTGCGGGGCTTGACACGGCTCGGCTCGGCGGCTCCAGTG<br>CGGCGCGCCAGAATCCATTCGTTG |
| 5 | OPA1 | GTGCTGCCCGCCTAGAAAGGGTGAAGTGGTTGTTTCCGTGACGGACTGAGTACGGGTGCCTGT<br>CAGGCTCTTGCGGAAGTCCATGCGCCATTGGGAGGGCCTCGGCCGCGGCTCTGTGCCCTTGCT<br>GCTGAGGGCCACTTCCTGGGTCATTCCTGGACCGGGAGCCGGGCTGGGGCTCACACGGGGGCT<br>CCCGCGTGGCCGTCTCGGCGCCTGCGTGACCTCCCCGCCGGCGGGATGTGGCGACTACGTCGG<br>GCCGCTGTGGCCTG |
| 6 | ND4 | ATGCTAAAACTAATCGTCCCAACAATTATGTTACTACCACTGACATGGCTTTCCAAAAAACAC<br>ATGATTTGGATCAACACAACCACCCACAGCCTAATTATTAGCATCATCCCTCTACTATTTTTT<br>AACCAAATCAACAACAACCTATTTAGCTGTTCCCCAACCTTTTCCTCCGACCCCCTAACAACC<br>CCCCTCCTAATGCTAACTACCTGGCTCCTACCCCTCACAATCATGGCAAGCCAACGCCACTTA<br>TCCAGTGAACCACTATCACGAAAAAAACTCTACCTCTCTATGCTAATCTCCCTACAAATCTCC<br>TTAATTATGACATTCACAGCCACAGAACTAATCATGTTTTATATCTTCTTCGAAACCACACTT<br>ATCCCCACCTTGGCTATCATCACCCGATGGGGCAACCAGCCAGAACGCCTGAACGCAGGCACA<br>TACTTCCTATTCTACACCCTAGTAGGCTCCCTTCCCCTACTCATCGCACTAATTTACACTCAC<br>AACACCCTAGGCTCACTAAACATTCTACTACTCACTCTCACTGCCCAAGAACTATCAAACTCC<br>TGGGCCAACAACTTAATGTGGCTAGCTTACACAATGGCTTTTATGGTAAAGATGCCTCTTTAC<br>GGACTCCACTTATGGCTCCCTAAAGCCCATGTCGAAGCCCCCATCGCTGGGTCAATGGTACTT<br>GCCGCAGTACTCTTAAAACTAGGCGGCTATGGTATGATGCGCCTCACACTCATTCTCAACCCC<br>CTGACAAAACACATGGCCTACCCCTTCCTTGTACTATCCCTATGGGGCATGATTATGACAAGC<br>TCCATCTGCCTACGACAAACAGACCTAAAATCGCTCATTGCATACTCTTCAATCAGCCACATG<br>GCCCTCGTAGTAACAGCCATTCTCATCCAAACCCCCTGGAGCTTCACCGGCGCAGTCATTCTC<br>ATGATCGCCCACGGGCTTACATCCTCATTACTATTCTGCCTAGCAAACTCAAACTACGAACGC<br>ACTCACAGTCGCATCATGATCCTCTCTCAAGGACTTCAAACTCTACTCCCACTAATGGCTTTT<br>TGGTGGCTTCTAGCAAGCCTCGCTAACCTCGCCTTACCCCCCACTATTAACCTACTGGGAGAA<br>CTCTCTGTGCTAGTAACCACGTTCTCCTGGTCAAATATCACTCTCCTACTTACAGGACTCAAC<br>ATGCTAGTCACAGCCCTATACTCCCTCTACATGTTTACCACAACACAATGGGGCTCACTCAC<br>CACCACATTAACAACATGAAACCCTCATTCACACGAGAAAACACCCTCATGTTCATGCACCTA<br>TCCCCCATTCTCCTCCTATCCCTCAACCCCGACATCATTACCGGGTTTTCCTCTTAA |
| 7 | opt_ND4 | ATGCTGAAGCTGATCGTGCCCACCATCATGCTGCTGCCTCTGACCTGGCTGAGCAAGAAACAC<br>ATGATCTGGATCAACACCACCACGCACAGCCTGATCATCAGCATCATCCCTCTGCTGTTCTTC<br>AACCAGATCAACAACAACCTGTTCAGCTGCAGCCCCACCTTCAGCAGCGACCCTCTGACAACA<br>CCTCTGCTGATGCTGACCACCTGGCTGCTGCCCCTCACAATCATGGCCTCTCAGAGACACCTG<br>AGCAGCGAGCCCCTGAGCCGGAAGAAACTGTACCTGAGCATGCTGATCTCCCTGCAGATCTCT<br>CTGATCATGACCTTCACCGCCACCGAGCTGATCATGTTCTACATCTTTTTCGAGACAACGCTG<br>ATCCCCACACTGGCCATCATCACCAGATGGGGCAACCAGCCTGAGAGACTGAACGCCGGCACC<br>TACTTTCTGTTCTACACCCTCGTGGGCAGCCTGCCACTGCTGATTGCCCTGATCTACACCCAC<br>AACACCCTGGGCTCCCTGAACATCCTGCTGCTGACACTGACAGCCCAAGAGCTGAGCAACAGC<br>TGGGCCAACAATCTGATGTGGCTGGCCTACACAATGGCCTTCATGGTCAAGATGCCCCTGTAC<br>GGCCTGCACCTGTGGCTGCCTAAAGCTCATGTGGAAGCCCCTATCGCCGGCTCTATGGTGCTG<br>GCTGCAGTGCTGCTGAAACTCGGCGGCTACGGCATGATGCGGCTGACCCTGATTCTGAATCCC<br>CTGACCAAGCACATGGCCTATCCATTTCTGGTGCTGAGCCTGTGGGCATGATTATGACCAGC<br>AGCATCTGCCTGCGGCAGACCGATCTGAAGTCCCTGATCGCCTACAGCTCCATCAGCCACATG<br>GCCCTGGTGGTCACCGCCATCCTGATTCAGACCCCTGGAGCTTTACAGGCGCCGTGATCCTG<br>ATGATTGCCCACGGCCTGACAAGCAGCCTGCTGTTTTGTCTGGCCAACAGCAACTACGAGCGG<br>ACCCACAGCAGAATCATGATCCTGTCTCAGGGCCTGCAGACCCTCCTGCCTCTTATGGCTTTT<br>TGGTGGCTGCTGGCCTCTCTGGCCAATCTGGCACTGCCTCCTACCATCAATCTGCTGGGCGAA<br>CTGAGCGTGCTGGTCACCACATTCAGCTGGTCCAATATCACCCTGCTGCTCACCGGCCTGAAC<br>ATGCTGGTTACAGCCCTGTACTCCCTGTACATGTTCACCACCACACAGTGGGGAAGCCTGACA<br>CACCACATCAACAATATGAAGCCCAGCTTCACCCGCGAGAACACCCTGATGTTCATGCATCTG<br>AGCCCCATTCTGCTGCTGTCCCTGAATCCTGATATCATCACCGGCTTCTCCAGCTGA |
| 8 | opt_ND4* | ATGCTGAAGCTGATCGTGCCCACCATCATGCTGCTGCCCCTGACCTGGCTGAGCAAGAAGCAC<br>ATGATCTGGATCAACACCACCACCCACAGCCTGATCATCAGCATCATCCCCCTGCTGTTCTTC<br>AACCAGATCAACAACAACCTGTTCAGCTGCAGCCCCACCTTCAGCAGCGACCCCCTGACCACC<br>CCCCTGCTGATGCTGACCACCTGGCTGCTGCCCCTGACCATCATGGCCAGCCAGCGCCACCTG<br>AGCAGCGAGCCCCTGAGCCGCAAGAAGCTGTACCTGAGCATGCTGATCAGCCTGCAGATCAGC<br>CTGATCATGACCTTCACCGCCACCGAGCTGATCATGTTCTACATCTTCTTCGAGACCACCCTG<br>ATCCCCACCCTGGCCATCATCACCCGCTGGGGCAACCAGCCCGAGCGCCTGAACGCCGGCACC<br>TACTTCCTGTTCTACACCCTGGTGGGCAGCCTGCCCCTGCTGATCGCCCTGATCTACACCCAC<br>AACACCCTGGGCAGCCTGAACATCCTGCTGCTGACCCTGACCGCCCAGGAGCTGAGCAACAGC<br>TGGGCCAACAACCTGATGTGGCTGGCCTACACCATGGCCTTCATGGTGAAGATGCCCCTGTAC<br>GGCCTGCACCTGTGGCTGCCCAAGGCCCACGTGGAGGCCCCCATCGCCGGCAGCATGGTGCTG<br>GCCGCCGTGCTGCTGAAGCTGGGCGGCTACGGCATGATGCGCCTGACCCTGATCCTGAACCCC |

TABLE 1-continued nucleic acid and polypeptide sequences and SEQ ID NOs

| SEQ | Description | Sequence |
|---|---|---|
| | | CTGACCAAGCACATGGCCTACCCCTTCCTGGTGCTGAGCCTGTGGGGCATGATCATGACCAGC<br>AGCATCTGCCTGCGCCAGACCGACCTGAAGAGCCTGATCGCCTACAGCAGCATCAGCCACATG<br>GCCCTGGTGGTGACCGCCATCCTGATCCAGACCCCCTGGAGCTTCACCGGCGCCGTGATCCTG<br>ATGATCGCCCACGGCCTGACCAGCAGCCTGCTGTTCTGCCTGGCCAACAGCAACTACGAGCGC<br>ACCCACAGCCGCATCATGATCCTGAGCCAGGGCCTGCAGACCCTGCTGCCCCTGATGGCCTTC<br>TGGTGGCTGCTGGCCAGCCTGGCCAACCTGGCCCTGCCCCCCACCATCAACCTGCTGGGCGAG<br>CTGAGCGTGCTGGTGACCACCTTCAGCTGGAGCAACATCACCCTGCTGCTGACCGGCCTGAAC<br>ATGCTGGTGACCGCCCTGTACAGCCTGTACATGTTCACCACCACCCAGTGGGGCAGCCTGACC<br>CACCACATCAACAACATGAAGCCCAGCTTCACCCGCGAGAACACCCTGATGTTCATGCACCTG<br>AGCCCCATCCTGCTGCTGAGCCTGAACCCCGACATCATCACCGGCTTCAGCAGCTAA |
| 9 | ND6 | ATGATGTATGCTTTGTTTCTGTTGAGTGTGGGTTTAGTAATGGGGTTTGTGGGGTTTTCTTCT<br>AAGCCTTCTCCTATTTATGGGGGTTTAGTATTGATTGTTAGCGGTGTGGTCGGGTGTGTTATT<br>ATTCTGAATTTTGGGGGAGGTTATATGGGTTTAATGGTTTTTTTAATTTATTTAGGGGGAATG<br>ATGGTTGTCTTTGGATATACTACAGCGATGGCTATTGAGGAGTATCCTGAGGCATGGGGGTCA<br>GGGGTTGAGGTCTTGGTGAGTGTTTTAGTGGGGTTAGCGATGGAGGTAGGATTGGTGCTGTGG<br>GTGAAAGAGTATGATGGGGTGGTGGTTGTGGTAAACTTTAATAGTGTAGGAAGCTGGATGATT<br>TATGAAGGAGAGGGGTCAGGGTTGATTCGGGAGGATCCTATTGGTGCGGGGGCTTTGTATGAT<br>TATGGGCGTTGGTTAGTAGTAGTTACTGGTTGGACATTGTTTGTTGGTGTATATATTGTAATT<br>GAGATTGCTCGGGGGAATTAG |
| 10 | opt_ND6 | ATGATGTACGCCCTGTTCCTGCTGAGCGTGGGCCTGGTGATGGGCTTCGTGGGCTTCAGCAGC<br>AAGCCCAGCCCCATCTACGGCGGCCTGGTGCTGATCGTGAGCGGCGTGGTGGGCTGCGTGATC<br>ATCCTGAACTTCGGCGGCGGCTACATGGGCCTGATGGTGTTCCTGATCTACCTGGGCGGCATG<br>ATGGTGGTGTTCGGCTACACCACCGCCATGGCCATCGAGGAGTACCCCGAGGCCTGGGGCAG<br>GGCGTGGAGGTGCTGGTGAGCGTGCTGGTGGGCCTGGCCATGGAGGTGGGCCTGGTGCTGTGG<br>GTGAAGGAGTACGACGGCGTGGTGGTGGTGAACTTCAACAGCGTGGGCAGCTGGATGATC<br>TACGAGGGCGAGGGCAGCGGCCTGATCCGCGAGGACCCCATCGGCGCCGGCGCCCTGTACGAC<br>TACGGCCGCTGGCTGGTGGTGGTGACCGGCTGGACCCTGTTCGTGGGCGTGTACATCGTGATC<br>GAGATCGCCCGCGGCAACTAA |
| 11 | ND1 | ATGGCCAACCTCCTACTCCTCATTGTACCCATTCTAATCGCAATGGCATTCCTAATGCTTACC<br>GAACGAAAAATTCTAGGCTATATGCAACTACGCAAAGGCCCCAACGTTGTAGGCCCCTACGGG<br>CTACTACAACCCTTCGCTGACGCCATAAAAACTCTTCACCAAAGAGCCCCTAAAACCCGCCACA<br>TCTACCATCACCCTCTACATCACCGCCCCGACCTTAGCTCTCACCATCGCTCTTCTACTATGG<br>ACCCCCCTCCCCATGCCCAACCCCCTGGTCAACCTCAACCTAGGCCTCCTATTTATTCTAGCC<br>ACCTCTAGCCTAGCCGTTTACTCAATCCTCTGGTCAGGGTGGGCATCAAACTCAAACTACGCC<br>CTGATCGGCGCACTGCGAGCAGTAGCCCAAACAATCTCATATGAAGTCACCCTAGCCATCATT<br>CTACTATCAACATTACTAATGAGTGGCTCCTTTAACCTCTCCACCCTTATCACAACACAAGAA<br>CACCTCTGGTTACTCCTGCCATCATGGCCCTTGGCCATGATGTGGTTTATCTCCACACTAGCA<br>GAGACCAACCGAACCCCCTTCGACCTTGCCGAAGGGGAGTCCGAACTAGTCTCAGGCTTCAAC<br>ATCGAATACGCCGCAGGCCCCTTCGCCCTATTCTTCATGGCCGAATACACAAACATTATTATG<br>ATGAACACCCTCACCACTACAATCTTCCTAGGAACAACATATGACGCACTCTCCCCTGAACTC<br>TACACAACATATTTTGTCACCAAGACCCTACTTCTAACCTCCCTGTTCTTATGGATTCGAACA<br>GCATACCCCCGATTCCGCTACGACCAACTCATGCACCTCCTATGGAAAAACTTCCTACCACTC<br>ACCCTAGCATTACTTATGTGGTATGTCTCCATGCCCATTACAATCTCCAGCATTCCCCCTCAA<br>ACCTAA |
| 12 | opt_ND1 | ATGGCCAACCTGCTGCTGCTGATCGTGCCCATCCTGATCGCCATGGCCTTCCTGATGCTGACC<br>GAGCGCAAGATCCTGGGCTACATGCAGCTGCGCAAGGGCCCCAACGTGGTGGGCCCCTACGGC<br>CTGCTGCAGCCCTTCGCCGACGCCATCAAGCTGTTCACCAAGGAGCCCCTGAAGCCCGCCACC<br>AGCACCATCACCCTGTACATCACCGCCCCACCCTGGCCCTGACCATCGCCTGCTGCTGTGG<br>ACCCCCCTGCCCATGCCCAACCCCCTGGTGAACCTGAACCTGGGCCTGCTGTTCATCCTGGCC<br>ACCAGCAGCCTGGCCGTGTACAGCATCCTGTGGAGCGGCTGGGCCAGCAACAGCAACTACGCC<br>CTGATCGGCGCCCTGCGCGCCGTGGCCCAGACCATCAGCTACGAGGTGACCCTGGCCATCATC<br>CTGCTGAGCACCCTGCTGATGAGCGGCAGCTTCAACCTGAGCACCCTGATCACCACCCAGGAG<br>CACCTGTGGCTGCTGCTGCCCAGCTGGCCCCTGGCCATGATGTGGTTCATCAGCACCCTGGCC<br>GAGACCAACCGCACCCCCTTCGACCTGGCCGAGGGCGAGAGCGAGCTGGTGAGCGGCTTCAAC<br>ATCGAGTACGCCGCCGGCCCCTTCGCCCTGTTCTTCATGGCCGAGTACACCAACATCATCATG<br>ATGAACACCCTGACCACCACCATCTTCCTGGGCACCACCTACGACGCCCTGAGCCCCGAGCTG<br>TACACCACCTACTTCGTGACCAAGACCCTGCTGCTGACCAGCCTGTTCCTGTGGATCCGCACC<br>GCCTACCCCCGCTTCCGCTACGACCAGCTGATGCACCTGCTGTGGAAGAACTTCCTGCCCCTG<br>ACCCTGGCCCTGCTGATGTGGTACGTGAGCATGCCCATCACCATCAGCAGCATCCCCCCCCAG<br>ACCTAA |
| 13 | 3'UTR | GAGCACTGGGACGCCCACCGCCCCTTTCCCTCCGCTGCCAGGCGAGCATGTTGTGGTAATTCT<br>GGAACACAAGAAGAGAAATTGCTGGGTTTAGAACAAGATTATAAACGAATTCGGTGCTCAGTG<br>ATCACTTGACAGTTTTTTTTTTTTAAATATTACCCAAAATGCTCCCCAAATAAGAAATGCA<br>TCAGCTCAGTCAGTGAATACAAAAAAGGAATTATTTTTCCCTTTGAGGGTCTTTTATACATCT<br>CTCCTCCAACCCCACCCTCTATTCTGTTTCTTCCTCCTCACATGGGGGTACACATACACAGCT<br>TCCTCTTTTGGTTCCATCCTTACCACCACACCACACGCACACTCCACATGCCCAGCAGATGG<br>CACTTGGTGGCCAGAAAGTGTGAGCCTCATGATCTGCTGCTCTGTAGTTCTGTGAGCTCAGGTC<br>CCTCAAAGGCCTCGGAGCACCCCCTTCCTTGTGACTGAGCCAGGGCCTGCATTTTTGGTTTTC<br>CCCACCCCACACATTCTCAACCATAGTCCTTCTAACAATACCAATAGCTAGGACCCGGCTGCT<br>GTGCACTGGGACTGGGGATTCCACATGTTTGCCTTGGGAGTCTCAAGCTGGACTGCCAGCCCC<br>TGTCCTCCCTTCACCCCCATTGCGTATGAGCATTTCAGAACTCCAAGGAGTCACAGGCATCTT |

TABLE 1-continued nucleic acid and polypeptide sequences and SEQ ID NOs

| SEQ | Description | Sequence |
|---|---|---|
| | | TATAGTTCACGTTAACATATAGACACTGTTGGAAGCAGTTCCTTCTAAAAGGGTAGCCCTGGA<br>CTTAATACCAGCCGGATACCTCTGGCCCCCACCCCATTACTGTACCTCTGGAGTCACTACTGT<br>GGGTCGCCACTCCTCTGCTACACAGCACGGCTTTTTCAAGGCTGTATTGAGAAGGGAAGTTAG<br>GAAGAAGGGTGTGCTGGGCTAACCAGCCCACAGAGCTCACATTCCTGTCCCTTGGGTGAAAAA<br>TACATGTCCATCCTGATATCTCCTGAATTCAGAAATTAGCCTCCACATGTGCAATGGCTTTAA<br>GAGCCAGAAGCAGGGTTCTGGGAATTTTGCAAGTTACCTGTGGCCAGGTGTGGTCTCGGTTAC<br>CAAATACGGTTACCTGCAGCTTTTTAGTCCTTTGTGCTCCCACGGGTCTACAGAGTCCCATCT<br>GCCCAAAGGTCTTGAAGCTTGACAGGATGTTTTCGATTACTCAGTCTCCCAGGGCACTACTGG<br>TCCGTAGGATTCGATTGGTCGGGGTAGGAGAGTTAAACAACATTTAAACAGAGTTCTCTCAAA<br>AATGTCTAAAGGGATTGTAGGTAGATAACATCCAATCACTGTTTGCACTTATCTGAAATCTTC<br>CCTCTTGGCTGCCCCCAGGTATTTACTGTGGAGAACATTGCATAGGAATGTCTGGAAAAAGCT<br>TCTACAACTTGTTACAGCCTTCACATTTGTAGAAGCTTT |
| 14 | 3'UTR* | GAGCACTGGGACGCCCACCGCCCCTTTCCCTCCGCTGCCAGGCGAGCATGTTGTGGTAATTCT<br>GGAACACAAGAAGAGAAATTGCTGGGTTTAGAACAAGATTATAAACGAATTCGGTGCTCAGTG<br>ATCACTTGACAGTTTTTTTTTTTTTAAATATTACCCAAATGCTCCCCAAATAAGAAATGCA<br>TCAGCTCAGTCAGTGAATACAAAAAAGGAATTATTTTTCCCTTTGAGGGTCTTTTATACATCT<br>CTCCTCCAACCCCACCCTCTATTCTGTTTCTTCCTCCTCACATGGGGGTACACATACACAGCT<br>TCCTCTTTTGGTTCCATCCTTACCACCACACCACGCACACTCCACATGCCCAGCAGAGTGG<br>CACTTGGTGGCCAGAAAGTGTGAGCCTCATGATCTGCTGTCTGTAGTTCTGTGAGCTCAGGTC<br>CCTCAAAGGCTCGGAGCACCCCCTTCCTTGTGACTGAGCCAGGGCCTGCATTTTTGGTTTTC<br>CCCACCCCACACATTCTCAACCATAGTCCTTCTAACAATACCAATAGCTAGGACCCGGCTGCT<br>GTGCACTGGGACTGGGGATTCCACATGTTTGCCTTGGGAGTCTCAAGCTGGACTGCCA |
| 15 | COX10-<br>ND4-3'UTR | ATGGCCGCATCTCCGCACACTCTCTCCTCACGCCTCCTGACAGGTTGCGTAGGAGGCTCTGTC<br>TGGTATCTTGAAAGAAGAACTATGCTAAAACTAATCGTCCCAACAATTATGTTACTACCACTG<br>ACATGGCTTTCCAAAAAACACATGATTTGGATCAACACAACCACCCACAGCCTAATTATTAGC<br>ATCATCCCTCTACTATTTTTAACCAAATCAACAACAACCTATTTAGCTGTTCCCCAACCTTT<br>TCCTCCGACCCCCTAACAACCCCCTCCTAATGCTAACTACCTGGCTCCTACCCCTCACAATC<br>ATGGCAAGCCAACGCCACTTATCCAGTGAACCACTATCACGAAAAAAACTCTACCTCTCTATG<br>CTAATCTCCCTACAAATCTCCTTAATTATGACATTCACAGCCACAGAACTAATCATGTTTTAT<br>ATCTTCTTCGAAACCACACTTATCCCCACCTTGGCTATCATCACCCGATGGGGCAACCAGCCA<br>GAACGCCTGAACGCAGGCACATACTTCCTATTCTACACCCTAGTAGGCTCCCTTCCCCTACTC<br>ATCGCACTAATTTACACTCACAACACCCTAGGCTCACTAAACATTCTACTACTCACTCTCACT<br>GCCCAAGAACTATCAAACTCCTGGGCCAACAACTTAATGTGGCTAGCTTACACAATGGCTTTT<br>ATGGTAAAGATGCCTCTTTACGGACTCCACTTATGGCTCCCTAAAGCCCATGTCGAAGCCCCC<br>ATCGCTGGGTCAATGGTACTTGCCGCAGTACTCTTAAAACTAGGCGGCTATGGTATGATGCGC<br>CTCACACTCATTCTCAACCCCCTGACAAAACACATGGCCTACCCTTCCTTGTACTATCCCTA<br>TGGGGCATGATTATGACAAGCTCCATCTGCCTACGACAAACAGACCTAAAATCGCTCATTGCA<br>TACTCTTCAATCAGCCACATGGGCCTCGTAGTAACAGCCATTCTCATCCAAACCCCCTGGAGC<br>TTCACCGGCGCAGTCATTCTCATGATCGCCCACGGGCTTACATCCTCATTACTATTCTGCCTA<br>GCAAACTCAAACTACGAACGCACTCACAGTCGCATCATGATCCTCTCTCAAGGACTTCAAACT<br>CTACTCCCACTAATGGCTTTTTGGTGGCTTCTAGCAAGCCTCGCTAACCTCGCCTTACCCCCC<br>ACTATTAACCTACTGGGAGAACTCTCTGTGCTAGTAACCACGTTCTCCTGGTCAAATATCACT<br>CTCCTACTTACAGGACTCAACATGCTAGTCACAGCCCTATACTCCCTCTACATGTTTACCACA<br>ACACAATGGGGCTCACTCACCCACCACATTAACAACATGAAACCCTCATTCACACGAGAAAAC<br>ACCCTCATGTTCATGCACCCTATCCCCCATTCTCCTCCTATCCCTCAACCCCGACATCATTACC<br>GGGTTTTCCTCTTAAGAGCACTGGGACGCCCACCGCCCCTTTCCCTCCGCTGCCAGGCGAGCA<br>TGTTGTGGTAATTCTGGAACACAAGAAGAGAAATTGCTGGGTTTAGAACAAGATTATAAACGA<br>ATTCGGTGCTCAGTGATCACTTGACAGTTTTTTTTTTTTTAAATATTACCCAAATGCTCCC<br>CAAATAAGAAATGCATCAGCTCAGTCAGTGAATACAAAAAAGGAATTATTTTTCCCTTTGAGG<br>GTCTTTTATACATCTCTCCTCCAACCCCACCCTCTATTCTGTTTCTTCCTCCTCACATGGGGG<br>TACACATACACAGCTTCCTCTTTTGGTTCCATCCTTACCACCACACCACGCACACTCCACA<br>TGCCCAGCAGAGTGGCACTTGGTGGCCAGAAAGTGTGAGCCTCATGATCTGCTGTCTGTAGTT<br>CTGTGAGCTCAGGTCCCTCAAAGGCCTCGGAGCACCCCCTTCCTTGTGACTGAGCCAGGGCCT<br>GCATTTTTGGTTTTCCCCACCCCACACATTCTCAACCATAGTCCTTCTAACAATACCAATAGC<br>TAGGACCCGGCTGCTGTGCACTGGGACTGGGGATTCCACATGTTTGCCTTGGGAGTCTCAAGC<br>TGGACTGCCAGCCCCTGTCCTCCCTTCACCCCCATTGCGTATGAGCATTTCAGAACTCCAAGG<br>AGTCACAGGCATCTTTATAGTTCACGTTAACATATAGACACTGTTGGAAGCAGTTCCTTCTAA<br>AAGGGTAGCCCTGGACTTAATACCAGCCGGATACCTCTGGCCCCCACCCCATTACTGTACCTC<br>TGGAGTCACTACTGTGGGTCGCCACTCCTCTGCTACACAGCACGGCTTTTTCAAGGCTGTATT<br>GAGAAGGGAAGTTAGGAAGAAGGGTGTGCTGGGCTAACCAGCCCACAGAGCTCACATTCCTGT<br>CCCTTGGGTGAAAAATACATGTCCATCCTGATATCTCCTGAATTCAGAAATTAGCCTCCACAT<br>GTGCAATGGCTTTAAGAGCCAGAAGCAGGGTTCTGGGAATTTTGCAAGTTACCTGTGGCCAGG<br>TGTGGTCTCGGTTACCAAATACGGTTACCTGCAGCTTTTTAGTCCTTTGTGCTCCCACGGGTC<br>TACAGAGTCCCATCTGCCCAAAGGTCTTGAAGCTTGACAGGATGTTTTCGATTACTCAGTCTC<br>CCAGGGCACTACTGGTCCGTAGGATTCGATTGGTCGGGGTAGGAGAGTTAAACAACATTTAAA<br>CAGAGTTCTCTCAAAAATGTCTAAAGGGATTGTAGGTAGATAACATCCAATCACTGTTTGCAC<br>TTATCTGAAATCTTCCCTCTTGGCTGCCCCCAGGTATTTACTGTGGAGAACATTGCATAGGAA<br>TGTCTGGAAAAAGCTTCTACAACTTGTTACAGCCTTCACATTTGTAGAAGCTTT |
| 16 | COX10-<br>ND4-<br>3'UTR* | ATGGCCGCATCTCCGCACACTCTCTCCTCACGCCTCCTGACAGGTTGCGTAGGAGGCTCTGTC<br>TGGTATCTTGAAAGAAGAACTATGCTAAAACTAATCGTCCCAACAATTATGTTACTACCACTG<br>ACATGGCTTTCCAAAAAACACATGATTTGGATCAACACAACCACCCACAGCCTAATTATTAGC<br>ATCATCCCTCTACTATTTTTAACCAAATCAACAACAACCTATTTAGCTGTTCCCCAACCTTT<br>TCCTCCGACCCCCTAACAACCCCCTCCTAATGCTAACTACCTGGCTCCTACCCCTCACAATC |

TABLE 1-continued nucleic acid and polypeptide sequences and SEQ ID NOs

| SEQ | Description | Sequence |
|---|---|---|
| | | ATGGCAAGCCAACGCCACTTATCCAGTGAACCACTATCACGAAAAAAACTCTACCTCTCTATG
CTAATCTCCCTACAAATCTCCTTAATTATGACATTCACAGCCACAGAACTAATCATGTTTTAT
ATCTTCTTCGAAACCACACTTATCCCCACCTTGGCTATCATCACCCGATGGGGCAACCAGCCA
GAACGCCTGAACGCAGGCACATACTTCCTATTCTACACCCTAGTAGGCTCCCTTCCCCTACTC
ATCGCACTAATTTACACTCACAACACCCTAGGCTCACTAAACATTCTACTACTCACTCTCACT
GCCCAAGAACTATCAAACTCCTGGGCCAACAACTTAATGTGGCTAGCTTACACAATGGCTTTT
ATGGTAAAGATGCCTCTTTACGGACTCCACTTATGGCTCCCTAAAGCCCATGTCGAAGCCCCC
ATCGCTGGGTCAATGGTACTTGCCGCAGTACTCTTAAAACTAGGCGGCTATGGTATGATGCGC
CTCACACTCATTCTCAACCCCCTGACAAAACACATGGCCTACCCCTTCCTTGTACTATCCCTA
TGGGGCATGATTATGACAAGCTCCATCTGCCTACGACAAACAGACCTAAAATCGCTCATTGCA
TACTCTTCAATCAGCCACATGGCCCTCGTAGTAACAGCCATTCTCATCCAAACCCCCTGGAGC
TTCACCGGCGCAGTCATTCTCATGATCGCCCACGGGCTTACATCCTCATTACTATTCTGCCTA
GCAAACTCAAACTACGAACGCACTCACAGTCGCATCATGATCCTCTCTCAAGGACTTCAAACT
CTACTCCCACTAATGGCTTTTTGGTGGCTTCTAGCAAGCCTCGCTAACCTCGCCTTACCCCCC
ACTATTAACCTACTGGGAGAACTCTCTGTGCTAGTAACCACGTTCTCCTGGTCAAATATCACT
CTCCTACTTACAGGACTCAACATGCTAGTCACAGCCCTATACTCCCTCTACATGTTTACCACA
ACACAATGGGGCTCACTCACCCACCACATTAACAACATGAAACCCTCATTCACACGAGAAAAC
ACCCTCATGTTCATGCACCTATCCCCCATTCTCCTCCTATCCCTCAACCCCGACATCATTACC
GGGTTTTCCTCTTAAGAGCACTGGGACGCCCACCGCCCCTTTCCCTCCGCTGCCAGGCGAGCA
TGTTGTGGTAATTCTGGAACACAAGAAGAGAAATTGCTGGGTTTAGAACAAGATTATAAACGA
ATTCGGTGCTCAGTGATCACTTGACAGTTTTTTTTTTTTTAAATATTACCCAAAATGCTCCC
CAAATAAGAAATGCATCAGCTCAGTCAGTGAATACAAAAAAGGAATTATTTTTCCCTTTGAGG
GTCTTTTATACATCTCTCCTCCAACCCCACCCTCTATTCTGTTTCTTCCTCCTCACATGGGGG
TACACATACACAGCTTCCTCTTTTGGTTCCATCCTTACCACCACACCACACGCACACTCCACA
TGCCCAGCAGAGTGGCACTTGGTGGCCAGAAAGTGTGAGCCTCATGATCTGCTGTCTGTAGTT
CTGTGAGCTCAGGTCCCTCAAAGGCCTCGGAGCACCCCCTTCCTTGTGACTGAGCCAGGGCCT
GCATTTTTGGTTTTCCCCACCCCACACATTCTCAACCATAGTCCTTCTAACAATACCAATAGC
TAGGACCCGGCTGCTGTGCACTGGGACTGGGGATTCCACATGTTTGCCTTGGGAGTCTCAAGC
TGGACTGCCA |
| 17 | COX10-opt_ND4-3'UTR | ATGGCCGCATCTCCGCACACTCTCTCCTCACGCCTCCTGACAGGTTGCGTAGGAGGCTCTGTC
TGGTATCTTGAAAGAAGAACTATGCTGAAGCTGATCGTGCCCACCATCATGCTGCTGCCTCTG
ACCTGGCTGAGCAAGAAACACATGATCTGGATCAACACCACCACGCACAGCCTGATCATCAGC
ATCATCCCTCTGCTGTTCTTCAACCAGATCAACAACAACCTGTTCAGCTGCAGCCCCACCTTC
AGCAGCGACCCTCTGACAACACCTCTGCTGATGCTGACCACCTGGCTGCTGCCCCTCACAATC
ATGGCCTCTCAGAGACACCTGAGCAGCGAGCCCTGAGCCGGAAGAAACTGTACCTGAGCATG
CTGATCTCCCTGCAGATCTCTCTGATCATGACCTTCACCGCCACCGAGCTGATCATGTTCTAC
ATCTTTTTCGAGACAACGCTGATCCCCACACTGGCCATCATCACCAGATGGGGCAACCAGCCT
GAGAGACTGAACGCCGGCACCTACTTTCTGTTCTACACCCTCGTGGGCAGCCTGCCACTGCTG
ATTGCCCTGATCTACACCCACAACACCCTGGGCTCCCTGAACATCCTGCTGCTGACACTGACA
GCCCAAGAGCTGAGCAACAGCTGGGCCAACAATCTGATGTGGCTGGCCTACACAATGGCCTTC
ATGGTCAAGATGCCCCTGTACGGCCTGCACCTGTGGCTGCCTAAAGCTCATGTGGAAGCCCCT
ATCGCCGGCTCTATGGTGCTGGCTGCAGTGCTGCTGAAACTCGGCGGCTACGGCATGATGCGG
CTGACCCTGATTCTGAATCCCCTGACCAAGCACATGGCCTATCCATTTCTGGTGCTGAGCCTG
TGGGGCATGATTATGACCAGCAGCATCTGCCTGCGGCAGACCGATCTGAAGTCCCTGATCGCC
TACAGCTCCATCAGCCACATGGCCCTGGTGGTCACCGCCATCCTGATTCAGACCCCTTGGAGC
TTTACAGGCGCCGTGATCCTGATGATTGCCCACGGCCTGACAAGCAGCCTGCTGTTTTGTCTG
GCCAACAGCAACTACGAGCGGACCCACAGCAGAATCATGATCCTGTCTCAGGGCCTGCAGACC
CTCCTGCCTCTTATGGCTTTTTGGTGGCTGCTGGCCTCTCTGGCCAATCTGGCACTGCCTCCT
ACCATCAATCTGCGGGCGAGCTGAGCGTGCTGGTCACCACATTCAGCTGGTCCAATATCACC
CTGCTGCTCACCGGCCTGAACATGCTGGTTACAGCCCTGTACTCCCTGTACATGTTCACCACC
ACACAGTGGGGAAGCCTGACACACCCACATCAACAATATGAAGCCCAGCTTCACCCGCGAGAAC
ACCCTGATGTTCATGCATCTGAGCCCCATTCTGCTGCTGTCCCTGAATCCTGATATCATCACC
GGCTTCTCCAGCTGAGAGCACTGGGACGCCCACCGCCCCTTTCCCTCCGCTGCCAGGCGAGCA
TGTTGTGGTAATTCTGGAACACAAGAAGAGAAATTGCTGGGTTTAGAACAAGATTATAAACGA
ATTCGGTGCTCAGTGATCACTTGACAGTTTTTTTTTTTTTAAATATTACCCAAAATGCTCCC
CAAATAAGAAATGCATCAGCTCAGTCAGTGAATACAAAAAAGGAATTATTTTTCCCTTTGAGG
GTCTTTTATACATCTCTCCTCCAACCCCACCCTCTATTCTGTTTCTTCCTCCTCACATGGGGG
TACACATACACAGCTTCCTCTTTTGGTTCCATCCTTACCACCACACCACACGCACACTCCACA
TGCCCAGCAGAGTGGCACTTGGTGGCCAGAAAGTGTGAGCCTCATGATCTGCTGTCTGTAGTT
CTGTGAGCTCAGGTCCCTCAAAGGCCTCGGAGCACCCCCTTCCTTGTGACTGAGCCAGGGCCT
GCATTTTTGGTTTTCCCCACCCCACACATTCTCAACCATAGTCCTTCTAACAATACCAATAGC
TAGGACCCGGCTGCTGTGCACTGGGACTGGGGATTCCACATGTTTGCCTTGGGAGTCTCAAGC
TGGACTGCCAGCCCCTGTCCTCCCTTCACCCCCATTGCGTATGAGCATTTCAGAACTCCAAGG
AGTCACAGGCATCTTTATAGTTCACGTTAACATATAGACACTGTTGGAAGCAGTTCCTTCTAA
AAGGGTAGCCCTGGACTTAATACCAGCCGGATACCTCTGGCCCCCACCCCATTACTGTACCTC
TGGAGTCACTACTGTGGGTCGCCACTCCTCTGCTACACAGCACGGCTTTTTCAAGGCTGTATT
GAGAAGGGAAGTTAGGAAGAAGGGTGTGCTGGGCTAACCAGCCCACAGAGCTCACATTCCTGT
CCCTTGGGTGAAAAATACATGTCCATCCTGATATCTCCTGAATTCAGAAATTAGCCTCCACAT
GTGCAATGGCTTTAAGAGCCAGAAGCAGGGTTCTGGGAATTTTGCAAGTTACCTGTGGCCAGG
TGTGGTCTCGGTTACCAAATACGGTTACCTGCAGCTTTTTGTCTTTGTGCTCCCACGGCTC
TACAGAGTCCCATCTGCCCAAAGGTCTTGAAGCTTGACAGGATGTTTTCGATTACTCAGTCTC
CCAGGGCACTACTGGTCCGTAGGATTCGATTGGTCGGGGTAGGAGAGTTAAACAACATTTAAA
CAGAGTTCTCTCAAAAATGTCTAAAGGGATTGTAGGTAGATAACATCCAATCACTGTTTGCAC
TTATCTGAAATCTTCCCTCTTGGCTGCCCCCAGGTATTTACTGTGGAGAACATTGCATAGGAA
TGTCTGGAAAAAGCTTCTACAACTTGTTACAGCCTTCACATTTGTAGAAGCTTT |

TABLE 1-continued nucleic acid and polypeptide sequences and SEQ ID NOs

| SEQ | Description | Sequence |
|---|---|---|
| 18 | COX10-opt_ND4-3'UTR* | ATGGCCGCATCTCCGCACACTCTCTCCTCACGCCTCCTGACAGGTTGCGTAGGAGGCTCTGTC<br>TGGTATCTTGAAAGAAGAACTATGCTGAAGCTGATCGTGCCCACCATCATGCTGCTGCCTCTG<br>ACCTGGCTGAGCAAGAAACACATGATCTGGATCAACACCACCACGCACAGCCTGATCATCAGC<br>ATCATCCCTCTGCTGTTCTTCAACCAGATCAACAACAACCTGTTCAGCTGCAGCCCCACCTTC<br>AGCAGCGACCCTCTGACAACACCTCTGCTGATGCTGACCACCTGGCTGCTGCCCCTCACAATC<br>ATGGCCTCTCAGAGACACCTGAGCAGCGAGCCCCTGAGCCGGAAGAAACTGTACCTGAGCATG<br>CTGATCTCCCTGCAGATCTCTCTGATCATGACCTTCACCGCCACCGAGCTGATCATGTTCTAC<br>ATCTTTTTCGAGACAACGCTGATCCCCACACTGGCCATCATCACCAGATGGGGCAACCAGCCT<br>GAGAGACTGAACGCCGGCACCTACTTTCTGTTCTACACCCTCGTGGGCAGCCTGCCACTGCTG<br>ATTGCCCTGATCTACACCCACAACACCCTGGGCTCCCTGAACATCCTGCTGCTGACACTGACA<br>GCCCAAGAGCTGAGCAACAGCTGGGCCAACAATCTGATGTGGCTGGCCTACACAATGGCCTTC<br>ATGGTCAAGATGCCCCTGTACGGCCTGCACCTGTGGCTGCCTAAAGCTCATGTGGAAGCCCCT<br>ATCGCCGGCTCTATGGTGCTGGCTGCAGTGCTGCTGAAACTCGGCGGCTACGGCATGATGCGG<br>CTGACCCTGATTCTGAATCCCCTGACCAAGCACATGGCCTATCCATTTCTGGTGCTGAGCCTG<br>TGGGGCATGATTATGACCAGCAGCATCTGCCTGCGGCAGACCGATCTGAAGTCCCTGATCGCC<br>TACAGCTCCATCAGCCACATGGCCCTGGTGGTCACCGCCATCCTGATTCAGACCCCTTGGAGC<br>TTTACAGGCGCCGTGATCCTGATGATTGCCCACGGCCTGACAAGCAGCCTGCTGTTTTGTCTG<br>GCCAACAGCAACTACGAGCGGACCCACAGCAGAATCATGATCCTGTCTCAGGGCCTGCAGACC<br>CTCCTGCCTCTTATGGCTTTTTGGTGGCTGCTGGCCTCTCTGGCCAATCTGGCACTGCCTCCT<br>ACCATCAATCTGCTGGGCGAGCTGAGCGTGCTGGTCACCACATTCAGCTGGTCCAATATCACC<br>CTGCTGCTCACCGGCCTGAACATGCTGGTTACAGCCCTGTACTCCCTGTACATGTTCACCACC<br>ACACAGTGGGGAAGCCTGACACACCACATCAACAATATGAAGCCCAGCTTCACCCGCGAGAAC<br>ACCCTGATGTTCATGCATCTGAGCCCCATTCTGCTGCTGTCCCTGAATCCTGATATCATCACC<br>GGCTTCTCCAGCTGAGAGCACTGGGACGCCCACCGCCCCTTTCCCTCCGCTGCCAGGCGAGCA<br>TGTTGTGGTAATTCTGGAACACAAGAAGAGAAATTGCTGGGTTTAGAACAAGATTATAAACGA<br>ATTCGGTGCTCAGTGATCACTTGACAGTTTTTTTTTTTTAAATATTACCCAAAATGCTCCC<br>CAAATAAGAAATGCATCAGCTCAGTCAGTGAATACAAAAAAGGAATTATTTTTCCCTTTGAGG<br>GTCTTTTATACATCTCTCCTCCAACCCCACCCTCTATTCTGTTTCTTCCTCCTCACATGGGGG<br>TACACATACACAGCTTCCTCTTTTGGTTCCATCCTTACCACCACACCACACGCACACTCCACA<br>TGCCCAGCAGAGTGGCACTTGGTGGCCAGAAAGTGTGAGCCTCATGATCTGCTGTCTGTAGTT<br>CTGTGAGCTCAGGTCCCTCAAAGGCCTCGGAGCACCCCCTTCCTTGTGACTGAGCCAGGGCCT<br>GCATTTTTGGTTTTCCCCACCCCACACATTCTCAACCATAGTCCTTCTAACAATACCAATAGC<br>TAGGACCCGGCTGCTGTGCACTGGGACTGGGGATTCCACATGTTTGCCTTGGGAGTCTCAAGC<br>TGGACTGCCA |
| 19 | COX10-opt_ND4*-3'UTR | ATGGCCGCATCTCCGCACACTCTCTCCTCACGCCTCCTGACAGGTTGCGTAGGAGGCTCTGTC<br>TGGTATCTTGAAAGAAGAACTATGCTGAAGCTGATCGTGCCCACCATCATGCTGCTGCCCCTG<br>ACCTGGCTGAGCAAGAAGCACATGATCTGGATCAACACCACCCACCACAGCCTGATCATCAGC<br>ATCATCCCCCTGCTGTTCTTCAACCAGATCAACAACAACCTGTTCAGCTGCAGCCCCACCTTC<br>AGCAGCGACCCCCTGACCACCCCCTGCTGATGCTGACCACCTGGCTGCTGCCCCTGACCATC<br>ATGGCCAGCCAGCGCCACCTGAGCAGCGAGCCCCTGAGCCGCAAGAAGCTGTACCTGAGCATG<br>CTGATCAGCCTGCAGATCAGCCTGATCATGACCTTCACCGCCACCGAGCTGATCATGTTCTAC<br>ATCTTCTTCGAGACCACCCTGATCCCCACCCTGGCCATCATCACCCGCTGGGGCAACCAGCCC<br>GAGCGCCTGAACGCCGGCACCTACTTCCTGTTCTACACCCTGGTGGGCAGCCTGCCCCTGCTG<br>ATCGCCCTGATCTACACCCACAACACCCTGGGCAGCCTGAACATCCTGCTGCTGACCCTGACC<br>GCCCAGGAGCTGAGCAACAGCTGGGCCAACAACCTGATGTGGCTGGCCTACACCATGGCCTTC<br>ATGGTGAAGATGCCCCTGTACGCCTGCACCTGTGGCTGCCCAAGGCCCACGTGGAGGCCCCC<br>ATCGCCGGCAGCATGGTGCTGGCCGCCGTGCTGCTGAAGCTGGGCGGCTACGGCATGATGCGC<br>CTGACCCTGATCCTGAACCCCCTGACCAAGCACATGGCCTACCCCTTCCTGGTGCTGAGCCTG<br>TGGGGCATGATCATGACCAGCAGCATCTGCCTGCGCCAGACCGACCTGAAGAGCCTGATCGCC<br>TACAGCAGCATCAGCCACATGGCCCTGGTGGTGACCGCCATCCTGATCCAGACCCCCTGGAGC<br>TTCACCGGCGCCGTGATCCTGATGATCGCCCACGGCCTGACCAGCAGCCTGCTGTTCTGCCTG<br>GCCAACAGCAACTACGAGCGCACCCACAGCCGCATCATGATCCTGAGCCAGGGCCTGCAGACC<br>CTGCTGCCCCTGATGGCCTTCTGGTGGCTGCTGGCCAGCCTGGCCAACCTGGCCCTGCCCCCC<br>ACCATCAACCTGCTGGGCGAGCTGAGCGTGCTGGTGACCACCTTCAGCTGGAGCAACATCACC<br>CTGCTGCTGACCGGCCTGAACATGCTGGTGACCGCCCTGTACAGCCTGTACATGTTCACCACC<br>ACCCAGTGGGGCAGCCTGACCCACCACATCAACAACATGAAGCCCAGCTTCACCCGCGAGAAC<br>ACCCTGATGTTCATGCACCTGAGCCCCATCCTGCTGCTGAGCCTGAACCCCGACATCATCACC<br>GGCTTCAGCAGCTAAGAGCACTGGGACGCCCACCGCCCCTTTCCCTCCGCTGCCAGGCGAGCA<br>TGTTGTGGTAATTCTGGAACACAAGAAGAGAAATTGCTGGGTTTAGAACAAGATTATAAACGA<br>ATTCGGTGCTCAGTGATCACTTGACAGTTTTTTTTTTTTAAATATTACCCAAAATGCTCCC<br>CAAATAAGAAATGCATCAGCTCAGTCAGTGAATACAAAAAAGGAATTATTTTTCCCTTTGAGG<br>GTCTTTTATACATCTCTCCTCCAACCCCACCCTCTATTCTGTTTCTTCCTCCTCACATGGGGG<br>TACACATACACAGCTTCCTCTTTTGGTTCCATCCTTACCACCACACCACACGCACACTCCACA<br>TGCCCAGCAGAGTGGCACTTGGTGGCCAGAAAGTGTGAGCCTCATGATCTGCTGTCTGTAGTT<br>CTGTGAGCTCAGGTCCCTCAAAGGCCTCGGAGCACCCCCTTCCTTGTGACTGAGCCAGGGCCT<br>GCATTTTTGGTTTTCCCCACCCCACACATTCTCAACCATAGTCCTTCTAACAATACCAATAGC<br>TAGGACCCGGCTGCTGTGCACTGGGACTGGGGATTCCACATGTTTGCCTTGGGAGTCTCAAGC<br>TGGACTGCCAGCCCCTGTCCTCCCTTCACCCCATTGCGTATGAGCATTTCAGAACTCCAAGG<br>AGTCACAGGCATCTTTATAGTTCACGTTAACATATAGACACTGTTGAAGCAGTTCCTTCTAA<br>AAGGGTAGCCCTGGACTTAATACCAGCCGGATACCTCTGGCCCCCACCCCATTACTGTACCTC<br>TGGAGTCACTACTGTGGGTCGCCACTCCTCTGCTACACAGCACGGCTTTTTCAAGGCTGTATT<br>GAGAAGGGAAGTTAGGAAGAAGGGTGTGCTGGGCTAACCAGCCCACAGAGCTCACATTCCTGT<br>CCCTTGGGTGAAAATACATGTCCATCCTGATATCTCCTGAATTCAGAAATTAGCCTCCACAT<br>GTGCAATGGCTTTAAGAGCCAGAAGCAGGGTTCTGGGAATTTTGCAAGTTACCTGTGGCCAGG<br>TGTGGTCTCGGTTACCAAATACGGTTACCTGCAGCTTTTTAGTCCTTTGTGCTCCCACGGGTC |

TABLE 1-continued nucleic acid and polypeptide sequences and SEQ ID NOs

| SEQ | Description | Sequence |
|---|---|---|
| | | TACAGAGTCCCATCTGCCCAAAGGTCTTGAAGCTTGACAGGATGTTTTCGATTACTCAGTCTC<br>CCAGGGCACTACTGGTCCGTAGGATTCGATTGGTCGGGGTAGGAGAGTTAAACAACATTTAAA<br>CAGAGTTCTCTCAAAAATGTCTAAAGGGATTGTAGGTAGATAACATCCAATCACTGTTTGCAC<br>TTATCTGAAATCTTCCCTCTTGGCTGCCCCCAGGTATTTACTGTGGAGAACATTGCATAGGAA<br>TGTCTGGAAAAAGCTTCTACAACTTGTTACAGCCTTCACATTTGTAGAAGCTTT |
| 20 | COX10-<br>opt_ND4*-<br>3'UTR* | ATGGCCGCATCTCCGCACACTCTCTCCTCACGCCTCCTGACAGGTTGCGTAGGAGGCTCTGTC<br>TGGTATCTTGAAAGAAGAACTATGCTGAAGCTGATCGTGCCCACCATCATGCTGCTGCCCCTG<br>ACCTGGCTGAGCAAGAAGCACATGATCTGGATCAACACCACCCACCCACAGCCTGATCATCAGC<br>ATCATCCCCCTGCTGTTCTTCAACCAGATCAACAACAACCTGTTCAGCTGCAGCCCCACCTTC<br>AGCAGCGACCCCCTGACCACCCCCCTGCTGATGCTGACCACCTGGCTGCTGCCCCTGACCATC<br>ATGGCCAGCCAGCGCCACCTGAGCAGCGAGCCCCTGAGCCGCAAGAAGCTGTACCTGAGCATG<br>CTGATCAGCCTGCAGATCAGCCTGATCATGACCTTCACCGCCACCGAGCTGATCATGTTCTAC<br>ATCTTCTTCGAGACCACCCTGATCCCCACCCTGGCCATCATCACCCGCTGGGGCAACCAGCCC<br>GAGCGCCTGAACGCCGGCACCTACTTCCTGTTCTACACCCTGGTGGGCAGCCTGCCCCTGCTG<br>ATCGCCCTGATCTACACCCACAACACCCTGGGCAGCCTGAACATCCTGCTGCTGACCCTGACC<br>GCCCAGGAGCTGAGCAACAGCTGGGCCAACAACCTGATGTGGCTGGCCTACACCATGGCCTTC<br>ATGGTGAAGATGCCCCTGTACGGCCTGCACCTGTGGCTGCCCAAGGCCCACGTGGAGGCCCCC<br>ATCGCCGGCAGCATGGTGCTGGCCGCCGTGCTGCTGAAGCTGGGCGGCTACGGCATGATGCGC<br>CTGACCCTGATCCTGAACCCCCTGACCAAGCACATGGCCTACCCCTTCCTGGTGCTGAGCCTG<br>TGGGGCATGATCATGACCAGCAGCATCTGCCTGCGCCAGACCGACCTGAAGAGCTGATCGCC<br>TACAGCAGCATCAGCCACATGGGCCCTGGTGGTGACCGCCATCCTGATCCAGACCCCCTGGAGC<br>TTCACCGGCGCCGTGATCCTGATGATCGCCCACGGCCTGACCAGCAGCTGCTGTTCTGCCTG<br>GCCAACAGCAACTACGAGCGCACCCACAGCCGCATCATGATCCTGAGCCAGGGCCTGCAGACC<br>CTGCTGCCCCTGATGGCCTTCTGGTGGCTGCTGGCCAGCCTGGCCAACCTGGCCCTGCCCCCC<br>ACCATCAACCTGCTGGGCGAGCTGAGCGTGCTGGTGACCACCTTCAGCTGGAGCAACATCACC<br>CTGCTGCTGACCGGCCTGAACATGCTGGTGACCGCCCTGTACAGCCTGTACATGTTCACCACC<br>ACCCAGTGGGGCAGCCTGACCCACCCATCAACAACATGAAGCCCAGCTTCACCCGCGAGAAC<br>ACCCTGATGTTCATGCACCTGAGCCCCCATCCTGCTGCTGAGCCTGAACCCCGACATCATCACC<br>GGCTTCAGCAGCTAAGAGCACTGGGACGCCCACCGCCCCTTTCCCTCCGCTGCCAGGCGAGCA<br>TGTTGTGGTAATTCTGGAACACAAGAAGAGAAATTGCTGGGTTTAGAACAAGATTATAAACGA<br>ATTCGGTGCTCAGTGATCACTTGACAGTTTTTTTTTTTTAAATATTACCCAAAATGCTCCC<br>CAAATAAGAAATGCATCAGCTCAGTCAGTGAATACAAAAAAGGAATTATTTTTCCCTTTGAGG<br>GTCTTTTATACATCTCTCCTCCAACCCCACCCTCTATTCTGTTTCTTCCTCCTCACATGGGGG<br>TACACATACACAGCTTCCTCTTTTGGTTCCATCCTTACCACCACACCACACGCACACTCCACA<br>TGCCCAGCAGAGTGGCACTTGGTGGCCAGAAAGTGTGAGCCTCATGATCTGCTGTCTGTAGTT<br>CTGTGAGCTCAGGTCCCTCAAAGGCCTCGGAGCACCCCTTCCTTGTGACTGAGCCAGGGCCT<br>GCATTTTGGTTTTCCCCACCCCACACATTCTCAACCATAGTCCTTCTAACAATACCAATAGC<br>TAGGACCCGGCTGCTGTGCACTGGGACTGGGGATTCCACATGTTTGCCTTGGGAGTCTCAAGC<br>TGGACTGCCA |
| 21 | COX10-<br>ND6-3'UTR | ATGGCCGCATCTCCGCACACTCTCTCCTCACGCCTCCTGACAGGTTGCGTAGGAGGCTCTGTC<br>TGGTATCTTGAAAGAAGAACTATGATGTATGCTTTGTTTCTGTTGAGTGTGGGTTTAGTAATG<br>GGGTTTGTGGGGTTTTCTTCTAAGCCTTCTCCTATTTATGGGGGTTTAGTATTGATTGTTAGC<br>GGTGTGGTCGGGTGTGTTATTATTCTGAATTTTGGGGGAGGTTATATGGGTTTAATGGTTTTT<br>TTAATTTATTTAGGGGGAATGATGGTTGTCTTTGGATATACTACAGCGATGGCTATTGAGGAG<br>TATCCTGAGGCATGGGGGTCAGGGGTTGAGGTCTTGGTGAGTGTTTTAGTGGGGTTAGCGATG<br>GAGGTAGGATTGGTGCTGTGGGTGAAAGAGTATGATGGGGTGGTGGTTGTGGTAAACTTTAAT<br>AGTGTAGGAAGCTGGATGATTTATGAAGGAGAGGGGTCAGGGTTGATTCGGGAGGATCCTATT<br>GGTGCGGGGGCTTTGTATGATTATGGGCGTTGGTAGTAGTAGTTACTGGTTGGACATTGTTT<br>GTTGGTGTATATATTGTAATTGAGATTGCTCGGGGGAATTAGGAGCACTGGGACGCCCACCGC<br>CCCTTTCCCTCCGCTGCCAGGCGAGCATGTTGTGGTAATTCTGGAACACAAGAAGAGAAATTG<br>CTGGGTTTAGAACAAGATTATAAACGAATTCGGTGCTCAGTGATCACTTGACAGTTTTTTTT<br>TTTTTAAATATTACCCAAAATGCTCCCCAAATAAGAAATGCATCAGCTCAGTCAGTGAATACA<br>AAAAAGGAATTATTTTTCCCTTTGAGGGTCTTTTATACATCTCTCCTCCAACCCCACCCTCTA<br>TTCTGTTTCTTCCTCCTCACATGGGGGTACACATACACAGCTTCCTCTTTTGGTTCCATCCTT<br>ACCACCACACCACACGCACACTCCACATGCCCAGCAGAGTGGCACTTGGTGGCCAGAAAGTGT<br>GAGCCTCATGATCTGCTGTCTGTAGTTCTGTGAGCTCAGGTCCCTCAAAGGCCTCGGAGCACC<br>CCCTTCCTTGTGACTGAGCCAGGGCCTGCATTTTGGTTTTCCCCACCCCACACATTCTCAAC<br>CATAGTCCTTCTAACAATACCAATAGCTAGGACCCGGCTGCTGTGCACTGGGACTGGGGATTC<br>CACATGTTTGCCTTGGGAGTCTCAAGCTGGACTGCCAGCCCCTGTCCTCCCTTCACCCCCATT<br>GCGTATGAGCATTTCAGAACTCCAAGGAGTCACAGGCATCTTTATAGTTCACGTTAACATATA<br>GACACTGTTGGAAGCAGTTCCTTCTAAAAGGGTAGCCCTGGACTTAATACCAGCCGGATACCT<br>CTGGCCCCACCCCATTACTGTACCTCTGGAGTCACTACTGTGGGTCGCCACTCCTCTGCTAC<br>ACAGCACGGCTTTTTCAAGGCTGTATTGAGAAGGGAAGTTAGGAAGAAGGGTGTGCTGGGCTA<br>ACCAGCCCACAGAGCTCACATTCCTGTCCCTTGGGTGAAAAATACATGTCCATCCTGATATCT<br>CCTGAATTCAGAAATTAGCCTCCACATGTGCAATGGCTTTAAGAGCCAGAAGCAGGGTTCTGG<br>GAATTTTGCAAGTTACCTGTGGCCAGGTGTGGTCTCGGTTACCAAATACGGTTACCTGCAGCT<br>TTTTAGTCCTTTGTGCTCCCACGGGTCTACAGAGTCCCATCTGCCCAAAGGTCTTGAAGCTTG<br>ACAGGATGTTTTCGATTACTCAGTCTCCCAGGGCACTACTGGTCCGTAGGATTCGATTGGTCG<br>GGGTAGGAGAGTTAAACAACATTTAAACAGAGTTCTCTCAAAAATGTCTAAAGGGATTGTAGG<br>TAGATAACATCCAATCACTGTTTGCACTTATCTGAAATCTTCCCTCTTGGCTGCCCCCAGGTA<br>TTTACTGTGGAGAACATTGCATAGGAATGTCTGGAAAAAGCTTCTACAACTTGTTACAGCCTT<br>CACATTTGTAGAAGCTTT |

TABLE 1-continued nucleic acid and polypeptide sequences and SEQ ID NOs

| SEQ | Description | Sequence |
|---|---|---|
| 22 | COX10-ND6-3'UTR* | ATGGCCGCATCTCCGCACACTCTCTCCTCACGCCTCCTGACAGGTTGCGTAGGAGGCTCTGTC<br>TGGTATCTTGAAAGAAGAACTATGATGTATGCTTTGTTTCTGTTGAGTGTGGGTTTAGTAATG<br>GGGTTTGTGGGGTTTTCTTCTAAGCCTTCTCCTATTTATGGGGGTTTAGTATTGATTGTTAGC<br>GGTGTGGTCGGGTGTGTTATTATTCTGAATTTTGGGGGAGGTTATATGGGTTTAATGGTTTTT<br>TTAATTTATTTAGGGGGAATGATGGTTGTCTTTGGATATACTACAGCGATGGCTATTGAGGAG<br>TATCCTGAGGCATGGGGGTCAGGGGTTGAGGTCTTGGTGAGTGTTTTAGTGGGGTTAGCGATG<br>GAGGTAGGATTGGTGCTGTGGGTGAAAGAGTATGATGGGGTGGTGGTTGTGGTAAACTTTAAT<br>AGTGTAGGAAGCTGGATGATTTATGAAGGAGAGGGGTCAGGGTTGATTCGGGAGGATCCTATT<br>GGTGCGGGGGCTTTGTATGATTATGGGCGTTGGTTAGTAGTAGTTACTGGTTGGACATTGTTT<br>GTTGGTGTATATATTGTAATTGAGATTGCTCGGGGGAATTAGGAGCACTGGGACGCCCACCGC<br>CCCTTTCCCTCCGCTGCCAGGCGAGCATGTTGTGGTAATTCTGAACACAAGAAGAGAAATTG<br>CTGGGTTTAGAACAAGATTATAAACGAATTCGGTGCTCAGTGATCACTTGACAGTTTTTTTT<br>TTTTTAAATATTACCCAAAATGCTCCCCAAATAAGAAATGCTCAGCTCAGTCAGTGAATACA<br>AAAAAGGAATTATTTTTCCCTTTGAGGGTCTTTTATACATCTCTCCTCCAACCCCACCCTCTA<br>TTCTGTTTCTTCCTCCTCACATGGGGGTACACATACACAGCTTCCTCTTTTGGTTCCATCCTT<br>ACCACCACACCACACGCACACTCCACATGCCCAGCAGAGTGGCACTTGGTGGCCAGAAAGTGT<br>GAGCCTCATGATCTGCTGTCTGTAGTTCTGTGAGCTCAGGTCCCTCAAAGGCCTCGGAGCACC<br>CCCTTCCTTGTGACTGAGCCAGGGCCTGCATTTTTGGTTTTCCCCACCCCACACATTCTCAAC<br>CATAGTCCTTCTAACAATACCAATAGCTAGGACCCGGCTGCTGTGCACTGGGACTGGGGATTC<br>CACATGTTTGCCTTGGGAGTCTCAAGCTGGACTGCCA |
| 23 | COX10-opt_ND6-3'UTR | ATGGCCGCATCTCCGCACACTCTCTCCTCACGCCTCCTGACAGGTTGCGTAGGAGGCTCTGTC<br>TGGTATCTTGAAAGAAGAACTATGATGTACGCCCTGTTCCTGCTGAGCGTGGGCCTGGTGATG<br>GGCTTCGTGGGCTTCAGCAGCAAGCCCAGCCCCATCTACGGCGGCCTGGTGCTGATCGTGAGC<br>GGCGTGGTGGGCTGCGTGATCATCCTGAACTTCGGCGGCGGCTACATGGGCTTCGATGGTGTTC<br>CTGATCTACCTGGGCGGCATGATGGTGGTGTTCGGCTACACCACCGCCATGGCCATCGAGGAG<br>TACCCCGAGGCCTGGGCAGCGGCGTGGAGGTGCTGGTGAGCGTGCTGGTGGGCCTGGCCATG<br>GAGGTGGGCCTGGTGCTGTGGGTGAAGGAGTACGACGGCGTGGTGGTGGTGAACTTCAAC<br>AGCGTGGGCAGCTGGATGATCTACGAGGGCGAGGGCAGCGGCCTGATCCGCGAGGACCCCATC<br>GGCGCCGGCGCCCTGTACGACTACGGCCGCTGGCTGGTGGTGGTGACCGGCTGGACCCTGTTC<br>GTGGGCGTGTACATCGTGATCGAGATCGCCCGCGGCAACTAAGAGCACTGGGACGCCCACCGC<br>CCCTTTCCCTCCGCTGCCAGGCGAGCATGTTGTGGTAATTCTGAACACAAGAAGAGAAATTG<br>CTGGGTTTAGAACAAGATTATAAACGAATTCGGTGCTCAGTGATCACTTGACAGTTTTTTTT<br>TTTTTAAATATTACCCAAAATGCTCCCCAAATAAGAAATGCATCAGCTCAGTCAGTGAATACA<br>AAAAAGGAATTATTTTTCCCTTTGAGGGTCTTTTATACATCTCTCCTCCAACCCCACCCTCTA<br>TTCTGTTTCTTCCTCCTCACATGGGGGTACACATACACAGCTTCCTCTTTTGGTTCCATCCTT<br>ACCACCACACCACACGCACACTCCACATGCCCAGCAGAGTGGCACTTGGTGGCCAGAAAGTGT<br>GAGCCTCATGATCTGCTGTCTGTAGTTCTGTGAGCTCAGGTCCCTCAAAGGCCTCGGAGCACC<br>CCCTTCCTTGTGACTGAGCCAGGGCCTGCATTTTTGGTTTTCCCCACCCCACACATTCTCAAC<br>CATAGTCCTTCTAACAATACCAATAGCTAGGACCCGGCTGCTGTGCACTGGGACTGGGGATTC<br>CACATGTTTGCCTTGGGAGTCTCAAGCTGGACTGCCAGCCCCTGTCCTCCCTTCACCCCCATT<br>GCTATGAGCATTTCAGAACTCCAAGGAGTCACAGGCATCTTTATAGTTCACGTTAACATATA<br>GACACTGTTGGAAGCAGTTCCTTCTAAAAGGGTAGCCCTGGACTTAATACCAGCCGGATACCT<br>CTGGCCCCCACCCCATTACTGTACCTCTGGAGTCACTACTGTGGGTCGCCACTCCTCTGCTAC<br>ACAGCACGGCTTTTTCAAGGCTGTATTGAGAAGGGAAGTTAGGAAGAAGGGTGTGCTGGGCTA<br>ACCAGCCCACAGAGCTCACATTCCTGTCCCTTGGGTGAAAAATACATGTCCATCCTGATATCT<br>CCTGAATTCAGAAATTAGCCTCCACATGTGCAATGGCTTTAAGAGCCAGAAGCAGGGTTCTGG<br>GAATTTTGCAAGTTACCTGTGGCCAGGTGTGGTCTCGGTTACCAAATACGGTTACCTGCAGCT<br>TTTTAGTCCTTTGTGCTCCCACGGGTCTACAGAGTCCCATCTGCCCAAAGGTCTTGAAGCTTG<br>ACAGGATGTTTTCGATTACTCAGTCTCCCAGGGCACTACTGGTCCGTAGGATTCGATTGGTCG<br>GGGTAGGAGAGTTAAACAACATTTTAAACAGAGTTCTCTCAAAAATGTCTAAAGGGATTGTAGG<br>TAGATAACATCCAATCACTGTTTGCACTTATCTGAAATCTTCCCTCTTGGCTGCCCCCAGGTA<br>TTTACTGTGGAGAACATTGCATAGGAATGTCTGGAAAAAGCTTCTACAACTTGTTACAGCCTT<br>CACATTTGTAGAAGCTTT |
| 24 | COX10-opt_ND6-3'UTR* | ATGGCCGCATCTCCGCACACTCTCTCCTCACGCCTCCTGACAGGTTGCGTAGGAGGCTCTGTC<br>TGGTATCTTGAAAGAAGAACTATGATGTACGCCCTGTTCCTGCTGAGCGTGGGCCTGGTGATG<br>GGCTTCGTGGGCTTCAGCAGCAAGCCCAGCCCCATCTACGGCGGCCTGGTGCTGATCGTGAGC<br>GGCGTGGTGGGCTGCGTGATCATCCTGAACTTCGGCGGCGGCTACATGGGCTTCGATGGTGTTC<br>CTGATCTACCTGGGCGGCATGATGGTGGTGTTCGGCTACACCACCGCCATGGCCATCGAGGAG<br>TACCCCGAGGCCTGGGCAGCGGCGTGGAGGTGCTGGTGAGCGTGCTGGTGGGCCTGGCCATG<br>GAGGTGGGCCTGGTGCTGTGGGTGAAGGAGTACGACGGCGTGGTGGTGGTGAACTTCAAC<br>AGCGTGGGCAGCTGGATGATCTACGAGGGCGAGGGCAGCGGCCTGATCCGCGAGGACCCCATC<br>GGCGCCGGCGCCCTGTACGACTACGGCCGCTGGCTGGTGGTGGTGACCGGCTGGACCCTGTTC<br>GTGGGCGTGTACATCGTGATCGAGATCGCCCGCGGCAACTAAGAGCACTGGGACGCCCACCGC<br>CCCTTTCCCTCCGCTGCCAGGCGAGCATGTTGTGGTAATTCTGAACACAAGAAGAGAAATTG<br>CTGGGTTTAGAACAAGATTATAAACGAATTCGGTGCTCAGTGATCACTTGACAGTTTTTTTT<br>TTTTTAAATATTACCCAAAATGCTCCCCAAATAAGAAATGCATCAGCTCAGTCAGTGAATACA<br>AAAAAGGAATTATTTTTCCCTTTGAGGGTCTTTTATACATCTCTCCTCCAACCCCACCCTCTA<br>TTCTGTTTCTTCCTCCTCACATGGGGGTACACATACACAGCTTCCTCTTTTGGTTCCATCCTT<br>ACCACCACACCACACGCACACTCCACATGCCCAGCAGAGTGGCACTTGGTGGCCAGAAAGTGT<br>GAGCCTCATGATCTGCTGTCTGTAGTTCTGTGAGCTCAGGTCCCTCAAAGGCCTCGGAGCACC<br>CCCTTCCTTGTGACTGAGCCAGGGCCTGCATTTTTGGTTTTCCCCACCCCACACATTCTCAAC<br>CATAGTCCTTCTAACAATACCAATAGCTAGGACCCGGCTGCTGTGCACTGGGACTGGGGATTC<br>CACATGTTTGCCTTGGGAGTCTCAAGCTGGACTGCCA |

TABLE 1-continued nucleic acid and polypeptide sequences and SEQ ID NOs

| SEQ | Description | Sequence |
|---|---|---|
| 25 | COX10-<br>ND1-3'UTR | ATGGCCGCATCTCCGCACACTCTCTCCTCACGCCTCCTGACAGGTTGCGTAGGAGGCTCTGTC<br>TGGTATCTTGAAAGAAGAACTATGGCCAACCTCCTACTCCTCATTGTACCCATTCTAATCGCA<br>ATGGCATTCCTAATGCTTACCGAACGAAAAATTCTAGGCTATATGCAACTACGCAAAGGCCCC<br>AACGTTGTAGGCCCCTACGGGCTACTACAACCCTTCGCTGACGCCATAAAACTCTTCACCAAA<br>GAGCCCCTAAAACCCGCCACATCTACCATCACCCTCTACATCACCGCCCCGACCTTAGCTCTC<br>ACCATCGCTCTTCTACTATGGACCCCCCTCCCCATGCCCAACCCCCTGGTCAACCTCAACCTA<br>GGCCTCCTATTTATTCTAGCCACCTCTAGCCTAGCCGTTTACTCAATCCTCTGGTCAGGGTGG<br>GCATCAAACTCAAACTACGCCCTGATCGGCGCACTGCGAGCAGTAGCCCAAACAATCTCATAT<br>GAAGTCACCCTAGCCATCATTCTACTATCAACATTACTAATGAGTGGCTCCTTTAACCTCTCC<br>ACCCTTATCACAACACAAGAACACCTCTGGTTACTCCTGCCATCATGGCCCTTGGCCATGATG<br>TGGTTTATCTCCACACTAGCAGAGACCAACCGAACCCCCTTCGACCTTGCCGAAGGGGAGTCC<br>GAACTAGTCTCAGGCTTCAACATCGAATACGCCGCAGGCCCCTTCGCCCTATTCTTCATGGCC<br>GAATACACAAACATTATTATGATGAACACCCTCACCACTACAATCTTCCTAGGAACAACATAT<br>GACGCACTCTCCCCTGAACTCTACACAACATATTTTGTCACCAAGACCCTACTTCTAACCTCC<br>CTGTTCTTATGGATTCGAACAGCATACCCCCGATTCCGCTACGACCAACTCATGCACCTCCTA<br>TGGAAAAACTTCCTACCACTCACCCTAGCATTACTTATGTGGTATGTCTCCATGCCCATTACA<br>ATCTCCAGCATTCCCCCTCAAACCTAAGAGCACTGGGACGCCCACCGCCCCTTTCCCTCCGCT<br>GCCAGGCGAGCATGTTGTGGTAATTCTGGAACACAAGAAGAGAAATTGCTGGGTTTAGAACAA<br>GATTATAAACGAATTCGGTGCTCAGTGATCACTTGACAGTTTTTTTTTTTTTAAATATTACC<br>CAAAATGCTCCCCAAATAAGAAATGCATCAGCTCAGTCAGTGAATACAAAAAAGGAATTATTT<br>TTCCCTTTGAGGGTCTTTTATACATCTCTCCTCCAACCCCACCCTCTATTCTGTTTCTTCCTC<br>CTCACATGGGGGTACACATACACAGCTTCCTCTTTTGGTTCATCCTTACCACCACACCACAC<br>GCACACTCCACATGCCCAGCAGAGTGGCACTTGGTGGCCAGAAAGTGTGAGCCTCATGATCTG<br>CTGTCTGTAGTTCTGTGAGCTCAGGTCCCTCAAAGGCCTCGGAGCACCCCCTTCCTTGTGACT<br>GAGCCAGGGCCTGCATTTTTGGTTTTCCCCACCCCACACATTCTCAACCATAGTCCTTCTAAC<br>AATACCAATAGCTAGGACCCGGCTGCTGTGCACTGGGACTGGGGATTCCACATGTTTGCCTTG<br>GGAGTCTCAAGCTGGACTGCCAGCCCCTGTCCTCCCTTCACCCCCATTGCGTATGAGCATTTC<br>AGAACTCCAAGGAGTCACAGGCATCTTTATAGTTCACGTTAACATATAGACACTGTTGGAAGC<br>AGTTCCTTCTAAAAGGGTAGCCCTGGACTTAATACCAGCCGGATACCTCTGGCCCCCACCCCA<br>TTACTGTACCTCTGGAGTCACTACTGTGGGTCGCCACTCCTCTGCTACACAGCACGGCTTTTT<br>CAAGGCTGTATTGAGAAGGGAAGTTAGGAAGAAGGGTGTGCTGGGCTAACCAGCCCACAGAGC<br>TCACATTCCTGTCCCTTGGGTGAAAAATACATGTCCATCCTGATATCTCCTGAATTCAGAAAT<br>TAGCCTCCACATGTGCAATGGCTTTAAGAGCCAGAAGCAGGGTTCTGGGAATTTTGCAAGTTA<br>CCTGTGGCCAGGTGTGGTCTCGGTTACCAAATACGGTTACCTGCAGCTTTTTAGTCCTTTGTG<br>CTCCCACGGGTCTACAGAGTCCCATCTGCCCAAAGGTCTTGAAGCTTGACAGGATGTTTTCGA<br>TTACTCAGTCTCCCAGGGCACTACTGGTCCGTAGGATTCGATTGGTCGGGGTAGGAGAGTTAA<br>ACAACATTTAAACAGAGTTCTCTCAAAAATGTCTAAAGGGATTGTAGGTAGATAACATCCAAT<br>CACTGTTTGCACTTATCTGAAATCTTCCCTCTTGGCTGCCCCCAGGTATTTACTGTGGAGAAC<br>ATTGCATAGGAATGTCTGGAAAAAGCTTCTACAACTTGTTACAGCCTTCACATTTGTAGAAGC<br>TTT |
| 26 | COX10-<br>ND1-<br>3'UTR* | ATGGCCGCATCTCCGCACACTCTCTCCTCACGCCTCCTGACAGGTTGCGTAGGAGGCTCTGTC<br>TGGTATCTTGAAAGAAGAACTATGGCCAACCTCCTACTCCTCATTGTACCCATTCTAATCGCA<br>ATGGCATTCCTAATGCTTACCGAACGAAAAATTCTAGGCTATATGCAACTACGCAAAGGCCCC<br>AACGTTGTAGGCCCCTACGGGCTACTACAACCCTTCGCTGACGCCATAAAACTCTTCACCAAA<br>GAGCCCCTAAAACCCGCCACATCTACCATCACCCTCTACATCACCGCCCCGACCTTAGCTCTC<br>ACCATCGCTCTTCTACTATGGACCCCCCTCCCCATGCCCAACCCCCTGGTCAACCTCAACCTA<br>GGCCTCCTATTTATTCTAGCCACCTCTAGCCTAGCCGTTTACTCAATCCTCTGGTCAGGGTGG<br>GCATCAAACTCAAACTACGCCCTGATCGGCGCACTGCGAGCAGTAGCCCAAACAATCTCATAT<br>GAAGTCACCCTAGCCATCATTCTACTATCAACATTACTAATGAGTGGCTCCTTTAACCTCTCC<br>ACCCTTATCACAACACAAGAACACCTCTGGTTACTCCTGCCATCATGGCCCTTGGCCATGATG<br>TGGTTTATCTCCACACTAGCAGAGACCAACCGAACCCCCTTCGACCTTGCCGAAGGGGAGTCC<br>GAACTAGTCTCAGGCTTCAACATCGAATACGCCGCAGGCCCCTTCGCCCTATTCTTCATGGCC<br>GAATACACAAACATTATTATGATGAACACCCTCACCACTACAATCTTCCTAGGAACAACATAT<br>GACGCACTCTCCCCTGAACTCTACACAACATATTTTGTCACCAAGACCCTACTTCTAACCTCC<br>CTGTTCTTATGGATTCGAACAGCATACCCCCGATTCCGCTACGACCAACTCATGCACCTCCTA<br>TGGAAAAACTTCCTACCACTCACCCTAGCATTACTTATGTGGTATGTCTCCATGCCCATTACA<br>ATCTCCAGCATTCCCCCTCAAACCTAAGAGCACTGGGACGCCCACCGCCCCTTTCCCTCCGCT<br>GCCAGGCGAGCATGTTGTGGTAATTCTGGAACACAAGAAGAGAAATTGCTGGGTTTAGAACAA<br>GATTATAAACGAATTCGGTGCTCAGTGATCACTTGACAGTTTTTTTTTTTTTAAATATTACC<br>CAAAATGCTCCCCAAATAAGAAATGCATCAGCTCAGTCAGTGAATACAAAAAAGGAATTATTT<br>TTCCCTTTGAGGGTCTTTTATACATCTCTCCTCCAACCCCACCCTCTATTCTGTTTCTTCCTC<br>CTCACATGGGGGTACACATACACAGCTTCCTCTTTTGGTTCATCCTTACCACCACACCACAC<br>GCACACTCCACATGCCCAGCAGAGTGGCACTTGGTGGCCAGAAAGTGTGAGCCTCATGATCTG<br>CTGTCTGTAGTTCTGTGAGCTCAGGTCCCTCAAAGGCCTCGGAGCACCCCCTTCCTTGTGACT<br>GAGCCAGGGCCTGCATTTTTGGTTTTCCCCACCCCACACATTCTCAACCATAGTCCTTCTAAC<br>AATACCAATAGCTAGGACCCGGCTGCTGTGCACTGGGACTGGGGATTCCACATGTTTGCCTTG<br>GGAGTCTCAAGCTGGACTGCCA |
| 27 | COX10-<br>opt_ND1-<br>3'UTR | ATGGCCGCATCTCCGCACACTCTCTCCTCACGCCTCCTGACAGGTTGCGTAGGAGGCTCTGTC<br>TGGTATCTTGAAAGAAGAACTATGGCCAACCTCCTGCTGCTGATCGTGCCCATCCTGATCGCC<br>ATGGCCTTCCTGATGCTGACCGAGCGCAAGATCCTGGGCTACATGCAGCTGCGCAAGGGCCCC<br>AACGTGGTGGGCCCCTACGGCCTGCTGCAGCCCTTCGCCGACGCCATCAAGCTGTTCACCAAG<br>GAGCCCCTGAAGCCCGCCACCAGCACCATCACCCTGTACATCACCGCCCCCACCCTGGCCCTG<br>ACCATCGCCCTGCTGCTGTGGACCCCCCTGCCCATGCCCAACCCCCTGGTCAACCTGAACCTG<br>GGCCTGCTGTTCATCCTGGCCACCAGCAGCCTGGCCGTGTACAGCATCCTGTGGAGCGGCTGG |

TABLE 1-continued nucleic acid and polypeptide sequences and SEQ ID NOs

| SEQ | Description | Sequence |
|---|---|---|
| | | GCCAGCAACAGCAACTACGCCCTGATCGGCGCCCTGCGCGCCGTGGCCCAGACCATCAGCTAC |
| | | GAGGTGACCCTGGCCATCATCCTGCTGAGCACCCTGCTGATGAGCGGCAGCTTCAACCTGAGC |
| | | ACCCTGATCACCACCCAGGAGCACCTGTGGCTGCTGCTGCCCAGCTGGCCCTGGCCATGATG |
| | | TGGTTCATCAGCACCCTGGCCGAGACCAACCGCACCCCCTTCGACCTGGCCGAGGGCGAGAGC |
| | | GAGCTGGTGAGCGGCTTCAACATCGAGTACGCCGCCGGCCCCTTCGCCCTGTTCTTCATGGCC |
| | | GAGTACACCAACATCATCATGATGAACACCCTGACCACCACCATCTTCCTGGGCACCACCTAC |
| | | GACGCCCTGAGCCCCGAGCTGTACACCACCTACTTCGTGACCAAGACCCTGCTGCTGACCAGC |
| | | CTGTTCCTGTGGATCCGCACCGCCTACCCCCGCTTCCGCTACGACCAGCTGATGCACCTGCTG |
| | | TGGAAGAACTTCCTGCCCCTGACCCTGGCCCTGCTGATGTGGTACGTGAGCATGCCCATCACC |
| | | ATCAGCAGCATCCCCCCCCAGACCTAAGAGCACTGGGACGCCCACCGCCCCTTTCCCTCCGCT |
| | | GCCAGGCGAGCATGTTGTGGTAATTCTGGAACACAAGAAGAGAAATTGCTGGGTTTAGAACAA |
| | | GATTATAAACGAATTCGGTGCTCAGTGATCACTTGACAGTTTTTTTTTTTTAAATATTACC |
| | | CAAAATGCTCCCCAAATAAGAAATGCATCAGCTCAGTCAGTGAATACAAAAAAGGAATTATTT |
| | | TTCCCTTTGAGGGTCTTTTATACATCTCTCCTCCAACCCCACCCTCTATTCTGTTTCTTCCTC |
| | | CTCACATGGGGGTACACATACACAGCTTCCTCTTTTGGTTCCATCCTTACCACCACACCACAC |
| | | GCACACTCCACATGCCCAGCAGAGTGGCACTTGGTGGCCAGAAAGTGTGAGCCTCATGATCTG |
| | | CTGTCTGTAGTTCTGTGAGCTCAGGTCCCTCAAAGGCCTCGGAGCACCCCCTTCTTGTGACT |
| | | GAGCCAGGGCCTGCATTTTTGGTTTTCCCCACCCCACACATTCTCAACCATAGTCCTTCTAAC |
| | | AATACCAATAGCTAGGACCCGGCTGCTGTGCACTGGGACTGGGGATTCCACATGTTTGCCTTG |
| | | GGAGTCTCAAGCTGGACTGCCAGCCCCTGTCCTCCCTTCACCCCCATTGCGTATGAGCATTTC |
| | | AGAACTCCAAGGAGTCACAGGCATCTTTATAGTTCACGTTAACATATAGACACTGTTGGAAGC |
| | | AGTTCCTTCTAAAAGGGTAGCCCTGGACTTAATACCAGCCGGATACCTCTGGCCCCCACCCCA |
| | | TTACTGTACCTCTGGAGTCACTACTGTGGGTCGCCACTCCTCTGCTACACAGCACGGCTTTTT |
| | | CAAGGCTGTATTGAGAAGGGAAGTTAGGAAGAAGGGTGTGCTGGGCTAACCAGCCCACAGAGC |
| | | TCACATTCCTGTCCCTTGGGTGAAAAATACATGTCCATCCTGATATCTCCTGAATTCAGAAAT |
| | | TAGCCTCCACATGTGCAATGGCTTTAAGAGCCAGAAGCAGGGTTCTGGGAATTTTGCAAGTTA |
| | | CCTGTGGCCAGGTGTGGTCTCGGTTACCAAATACGGTTACCTGCAGCTTTTTAGTCCTTTGTG |
| | | CTCCCACGGGTCTACAGAGTCCCATCTGCCCAAAGGTCTTGAAGCTTGACAGGATGTTTTCGA |
| | | TTACTCAGTCTCCCAGGGCACTACTGGTCCGTAGGATTCGATTGGTCGGGGTAGGAGAGTTAA |
| | | ACAACATTTAAACAGAGTTCTCTCAAAAATGTCTAAAGGGATTGTAGGTAGATAACATCCAAT |
| | | CACTGTTTGCACTTATCTGAAATCTTCCCTCTTGGCTGCCCCCAGGTATTTACTGTGGAGAAC |
| | | ATTGCATAGGAATGTCTGGAAAAAGCTTCTACAACTTGTTACAGCCTTCACATTTGTAGAAGC |
| | | TTT |
| 28 | COX10-opt_ND1-3'UTR* | ATGGCCGCATCTCCGCACACTCTCTCCTCACGCCTCCTGACAGGTTGCGTAGGAGGCTCTGTC |
| | | TGGTATCTTGAAAGAAGAACTATGGCCAACCTGCTGCTGCTGATCGTGCCCATCCTGATCGCC |
| | | ATGGCCTTCCTGATGCTGACCGAGCGCAAGATCCTGGGCTACATGCAGCTGCGCAAGGGCCCC |
| | | AACGTGGTGGCCCCCTACGGCTGCTGCAGCCCTTCGCCGACGCCATCAAGCTGTTCACCAAG |
| | | GAGCCCCTGAAGCCCGCCACCAGCACCATCACCCTGTACATCACCGCCCCCACCCTGGCCCTG |
| | | ACCATCGCCCTGCTGCTGTGGACCCCCCTGCCCATGCCCAACCCCCTGGTGAACCTGAACCTG |
| | | GGCCTGCTGTTCATCCTGGCCACCAGCAGCCTGGCCGTGTACAGCATCCTGTGGAGCGGCTGG |
| | | GCCAGCAACAGCAACTACGCCCTGATCGGCGCCCTGCGCGCCGTGGCCCAGACCATCAGCTAC |
| | | GAGGTGACCCTGGCCATCATCCTGCTGAGCACCCTGCTGATGAGCGGCAGCTTCAACCTGAGC |
| | | ACCCTGATCACCACCCAGGAGCACCTGTGGCTGCTGCTGCCCAGCTGGCCCTGGCCATGATG |
| | | TGGTTCATCAGCACCCTGGCCGAGACCAACCGCACCCCCTTCGACCTGGCCGAGGGCGAGAGC |
| | | GAGCTGGTGAGCGGCTTCAACATCGAGTACGCCGCCGGCCCCTTCGCCCTGTTCTTCATGGCC |
| | | GAGTACACCAACATCATCATGATGAACACCCTGACCACCACCATCTTCCTGGGCACCACCTAC |
| | | GACGCCCTGAGCCCCGAGCTGTACACCACCTACTTCGTGACCAAGACCCTGCTGCTGACCAGC |
| | | CTGTTCCTGTGGATCCGCACCGCCTACCCCCGCTTCCGCTACGACCAGCTGATGCACCTGCTG |
| | | TGGAAGAACTTCCTGCCCCTGACCCTGGCCCTGCTGATGTGGTACGTGAGCATGCCCATCACC |
| | | ATCAGCAGCATCCCCCCCCAGACCTAAGAGCACTGGGACGCCCACCGCCCCTTTCCCTCCGCT |
| | | GCCAGGCGAGCATGTTGTGGTAATTCTGGAACACAAGAAGAGAAATTGCTGGGTTTAGAACAA |
| | | GATTATAAACGAATTCGGTGCTCAGTGATCACTTGACAGTTTTTTTTTTTTAAATATTACC |
| | | CAAAATGCTCCCCAAATAAGAAATGCATCAGCTCAGTCAGTGAATACAAAAAAGGAATTATTT |
| | | TTCCCTTTGAGGGTCTTTTATACATCTCTCCTCCAACCCCACCCTCTATTCTGTTTCTTCCTC |
| | | CTCACATGGGGGTACACATACACAGCTTCCTCTTTTGGTTCCATCCTTACCACCACACCACAC |
| | | GCACACTCCACATGCCCAGCAGAGTGGCACTTGGTGGCCAGAAAGTGTGAGCCTCATGATCTG |
| | | CTGTCTGTAGTTCTGTGAGCTCAGGTCCCTCAAAGGCCTCGGAGCACCCCCTTCTTGTGACT |
| | | GAGCCAGGGCCTGCATTTTTGGTTTTCCCCACCCCACACATTCTCAACCATAGTCCTTCTAAC |
| | | AATACCAATAGCTAGGACCCGGCTGCTGTGCACTGGGACTGGGGATTCCACATGTTTGCCTTG |
| | | GGAGTCTCAAGCTGGACTGCCA |
| 29 | opt_COX10-ND4-3'UTR | ATGGCCGCCTCTCCACACACACTGAGTAGCAGACTGCTGACCGGCTGTGTTGGCGGCTCTGTG |
| | | TGGTATCTGGAACGGCGGACAATGCTAAAACTAATCGTCCCAACAATTATGTTACTACCACTG |
| | | ACATGGCTTTCCAAAAAACACATGATTTGGATCAACACAACCACCCACAGCCTAATTATTAGC |
| | | ATCATCCCTCTACTATTTTTAACCAAATCAACAACAACCTATTTAGCTGTTCCCCAACCTTT |
| | | TCCTCCGACCCCCTAACAACCCCCTCCTAATGCTAACTACCTGGCTCCTACCCCTCACAATC |
| | | ATGGCAAGCCAACGCCACTTATCCAGTGAACACTATCACGAAAAAAACTCTACCTCTCTATG |
| | | CTAATCTCCCTACAAATCTCCTTAATTATGACATTCACAGCCACAGAACTAATCATGTTTTAT |
| | | ATCTTCTTCGAAACCACACTTATCCCCACCTTGGCTATCATCACCCGATGGGGCAACCAGCCA |
| | | GAACGCCTGAACGCAGGCACATACTTCCTATTCTACACCCTAGTAGGCTCCCTTCCCCTACTC |
| | | ATCGCACTAATTTACACTCACAACACCCTAGGCTCACTAAACATTCTACTACTCACTCTCACT |
| | | GCCCAAGAACTATCAAACTCCTGGGCCAACAACTTAATGTGGCTAGCTTACACAATGGCTTTT |
| | | ATGGTAAAGATGCCTCTTTACGGACTCCACTTATGGCTCCCTAAAGCCCATGTCGAAGCCCCC |
| | | ATCGCTGGGTCAATGGTACTTGCCGCAGTACTCTTAAAACTAGGCGGCTATGGTATGATGCGC |
| | | CTCACACTCATTCTCAACCCCCTGACAAAACACATGGCCTACCCCTTCCTTGTACTATCCCTA |

TABLE 1-continued nucleic acid and polypeptide sequences and SEQ ID NOs

| SEQ | Description | Sequence |
|---|---|---|
| | | TGGGGCATGATTATGACAAGCTCCATCTGCCTACGACAAACAGACCTAAAATCGCTCATTGCA<br>TACTCTTCAATCAGCCACATGGCCCTCGTAGTAACAGCCATTCTCATCCAAACCCCCTGGAGC<br>TTCACCGGCGCAGTCATTCTCATGATCGCCCACGGGCTTACATCCTCATTACTATTCTGCCTA<br>GCAAACTCAAACTACGAACGCACTCACAGTCGCATCATGATCCTCTCTCAAGGACTTCAAACT<br>CTACTCCCACTAATGGCTTTTTGGTGGCTTCTAGCAAGCCTCGCTAACCTCGCCTTACCCCCC<br>ACTATTAACCTACTGGGAGAACTCTCTGTGCTAGTAACCACGTTCTCCTGGTCAAATATCACT<br>CTCCTACTTACAGGACTCAACATGCTAGTCACAGCCCTATACTCCCTCTACATGTTTACCACA<br>ACACAATGGGGCTCACTCACCCACCACATTAACAACATGAAACCCTCATTCACACGAGAAAAC<br>ACCCTCATGTTCATGCACCTATCCCCCATTCTCCTCCTATCCCTCAACCCCGACATCATTACC<br>GGGTTTTCCTCTTAAGAGCACTGGGACGCCCACCGCCCCTTTCCCTCCGCTGCCAGGCGAGCA<br>TGTTGTGGTAATTCTGGAACACAAGAAGAGAAATTGCTGGGTTTAGAACAAGATTATAAACGA<br>ATTCGGTGCTCAGTGATCACTTGACAGTTTTTTTTTTTTTAAATATTACCCAAAATGCTCCC<br>CAAATAAGAAATGCATCAGCTCAGTCAGTGAATACAAAAAAGGAATTATTTTTCCCTTTGAGG<br>GTCTTTTATACATCTCTCCTCCAACCCCACCCTCTATTCTGTTTCTTCCTCCTCACATGGGGG<br>TACACATACACAGCTTCCTCTTTTGGTTCCATCCTTACCACCACACCACACGCACACTCCACA<br>TGCCCAGCAGAGTGGCACTTGGTGGCCAGAAAGTGTGAGCCTCATGATCTGCTGTCTGTAGTT<br>CTGTGAGCTCAGGTCCCTCAAAGGCCTCGGAGCACCCCCTTCCTTGTGACTGAGCCAGGGCCT<br>GCATTTTTGGTTTTCCCCACCCCACACATTCTCAACCATAGTCCTTCTAACAATACCAATAGC<br>TAGGACCCGGCTGCTGTGCACTGGGACTGGGGATTCCACATGTTTGCCTTGGGAGTCTCAAGC<br>TGGACTGCCAGCCCCTGTCCTCCCTTCACCCCCATTGCGTATGAGCATTTCAGAACTCCAAGG<br>AGTCACAGGCATCTTTATAGTTCACGTTAACATATAGACACTGTTGGAAGCAGTTCCTTCTAA<br>AAGGGTAGCCCTGGACTTAATACCAGCCGGATACCTCTGGCCCCCACCCCATTACTGTACCTC<br>TGGAGTCACTACTGTGGGTCGCCACTCCTCTGCTACACAGCACGGCTTTTTCAAGGCTGTATT<br>GAGAAGGGAAGTTAGGAAGAAGGGTGTGCTGGGCTAACCAGCCCACAGAGCTCACATTCCTGT<br>CCCTTGGGTGAAAAATACATGTCCATCCTGATATCTCCTGAATTCAGAAATTAGCCTCCACAT<br>GTGCAATGGCTTTAAGAGCCAGAAGCAGGGTTCTGGGAATTTTGCAAGTTACCTGTGGCCAGG<br>TGTGGTCTCGGTTACCAAATACGGTTACCTGCAGCTTTTTAGTCCTTTGTGCTCCCACGGGTC<br>TACAGAGTCCCATCTGCCCAAAGGTCTTGAAGCTTGACAGGATGTTTTCGATTACTCAGTCTC<br>CCAGGGCACTACTGGTCCGTAGGATTCGATTGGTCGGGGTAGGAGAGTTAAACAACATTTAAA<br>CAGAGTTCTCTCAAAAATGTCTAAAGGGATTGTAGGTAGATAACATCCAATCACTGTTTGCAC<br>TTATCTGAAATCTTCCCTCTTGGCTGCCCCCAGGTATTTACTGTGGAGAACATTGCATAGGAA<br>TGTCTGGAAAAAGCTTCTACAACTTGTTACAGCCTTCACATTTGTAGAAGCTTT |
| 30 | opt_COX10<br>-ND4-<br>3'UTR* | ATGGCCGCCTCTCCACACACACTGAGTAGCAGACTGCTGACCGGCTGTGTTGGCGGCTCTGTG<br>TGGTATCTGGAACGGCGGACAATGCTAAAACTAATCGTCCCAACAATTATGTTACTACCACTG<br>ACATGGCTTTCCAAAAAACACATGATTTGGATCAACACAACCACCCACAGCCTAATTATTAGC<br>ATCATCCCTCTACTATTTTTTAACCAAATCAACAACAACCTATTTAGCTGTTCCCCAACCTTT<br>TCCTCCGACCCCCTAACAACCCCCCTCCTAATGCTAACTACCTGGCTCCTACCCCTCACAATC<br>ATGGCAAGCCAACGCCACTTATCCAGTGAACCACTATCACGAAAAAAACTCTACCTCTCTATG<br>CTAATCTCCCTACAAATCTCCTTAATTATGACATTCACAGCCACAGAACTAATCATGTTTTAT<br>ATCTTCTTCGAAACCACACTTATCCCCACCTTGGCTATCATCACCCGATGGGGCAACCAGCCA<br>GAACGCCTGAACGCAGGCACATACTTCCTATTCTACACCCTAGTAGGCTCCCTTCCCCTACTC<br>ATCGCACTAATTTACACTCACAACACCCTAGGCTCACTAAACATTCTACTACTCACTCTCACT<br>GCCCAAGAACTATCAAACTCCTGGGCCAACAACTTAATGTGGCTAGCTTACACAATGGCTTTT<br>ATGGTAAAGATGCCTCTTTACGGACTCCACTTATGGCTCCCTAAAGCCCATGTCGAAGCCCCC<br>ATCGCTGGGTCAATGGTACTTGCCGCAGTACTCTTAAAACTAGGCGGCTATGGTATGATGCGC<br>CTCACACTCATTCTCAACCCCCTGACAAAACACATGGCCTACCCCTTCCTTGTACTATCCCTA<br>TGGGGCATGATTATGACAAGCTCCATCTGCCTACGACAAACAGACCTAAAATCGCTCATTGCA<br>TACTCTTCAATCAGCCACATGGCCCTCGTAGTAACAGCCATTCTCATCCAAACCCCCTGGAGC<br>TTCACCGGCGCAGTCATTCTCATGATCGCCCACGGGCTTACATCCTCATTACTATTCTGCCTA<br>GCAAACTCAAACTACGAACGCACTCACAGTCGCATCATGATCCTCTCTCAAGGACTTCAAACT<br>CTACTCCCACTAATGGCTTTTTGGTGGCTTCTAGCAAGCCTCGCTAACCTCGCCTTACCCCCC<br>ACTATTAACCTACTGGGAGAACTCTCTGTGCTAGTAACCACGTTCTCCTGGTCAAATATCACT<br>CTCCTACTTACAGGACTCAACATGCTAGTCACAGCCCTATACTCCCTCTACATGTTTACCACA<br>ACACAATGGGGCTCACTCACCCACCACATTAACAACATGAAACCCTCATTCACACGAGAAAAC<br>ACCCTCATGTTCATGCACCTATCCCCCATTCTCCTCCTATCCCTCAACCCCGACATCATTACC<br>GGGTTTTCCTCTTAAGAGCACTGGGACGCCCACCGCCCCTTTCCCTCCGCTGCCAGGCGAGCA<br>TGTTGTGGTAATTCTGGAACACAAGAAGAGAAATTGCTGGGTTTAGAACAAGATTATAAACGA<br>ATTCGGTGCTCAGTGATCACTTGACAGTTTTTTTTTTTTAAATATTACCCAAAATGCTCCC<br>CAAATAAGAAATGCATCAGCTCAGTCAGTGAATACAAAAAAGGAATTATTTTTCCCTTTGAGG<br>GTCTTTTATACATCTCTCCTCCAACCCCACCCTCTATTCTGTTTCTTCCTCCTCACATGGGGG<br>TACACATACACAGCTTCCTCTTTTGGTTCCATCCTTACCACCACACCACACGCACACTCCACA<br>TGCCCAGCAGAGTGGCACTTGGTGGCCAGAAAGTGTGAGCCTCATGATCTGCTGTCTGTAGTT<br>CTGTGAGCTCAGGTCCCTCAAAGGCCTCGGAGCACCCCCTTCCTTGTGACTGAGCCAGGGCCT<br>GCATTTTTGGTTTTCCCCACCCCACACATTCTCAACCATAGTCCTTCTAACAATACCAATAGC<br>TAGGACCCGGCTGCTGTGCACTGGGACTGGGGATTCCACATGTTTGCCTTGGGAGTCTCAAGC<br>TGGACTGCCA |
| 31 | opt_COX10<br>-opt_ND4-<br>3'UTR | ATGGCCGCCTCTCCACACACACTGAGTAGCAGACTGCTGACCGGCTGTGTTGGCGGCTCTGTG<br>TGGTATCTGGAACGGCGGACAATGCTGAAGCTGATCGTGCCCACCATCATGCTGCTGCCTCTG<br>ACCTGGCTGAGCAAGAAACACATGATCTGGATCACAACACCACGCACAGCCTGATCATCAGC<br>ATCATCCCTCTGCTGTTCTTCAACCAGATCAACAACAACCTGTTCAGCTGCAGCCCCACCTTC<br>AGCAGCGACCCTCTGACAACACCTCTGCTGATGCTGACCACCTGGCTGCTGCCCCTCACAATC<br>ATGGCCTCTCAGAGACACCTGAGCAGCGAGCCCTGAGCCGGAAGAAACTGTACCTGAGCATG<br>CTGATCTCCCTGCAGATCTCTCTGATCATGACCTTCACCGCCACCGAGCTGATCATGTTCTAC<br>ATCTTTTTTCGAGACAACGCTGATCCCCACACTGGCCATCATCACCAGATGGGGCAACCAGCCT |

TABLE 1-continued nucleic acid and polypeptide sequences and SEQ ID NOs

| SEQ | Description | Sequence |
|---|---|---|
| | | GAGAGACTGAACGCCGGCACCTACTTTCTGTTCTACACCCTCGTGGGCAGCCTGCCACTGCTG
ATTGCCCTGATCTACACCCACAACACCCTGGGCTCCCTGAACATCCTGCTGCTGACACTGACA
GCCCAAGAGCTGAGCAACAGCTGGGCCAACAATCTGATGTGGCTGGCCTACACAATGGCCTTC
ATGGTCAAGATGCCCCTGTACGGCCTGCACCTGTGGCTGCCTAAAGCTCATGTGGAAGCCCCT
ATCGCCGGCTCTATGGTGCTGGCTGCAGTGCTGCTGAAACTCGGCGGCTACGGCATGATGCGG
CTGACCCTGATTCTGAATCCCCTGACCAAGCACATGGCCTATCCATTTCTGGTGCTGAGCCTG
TGGGGCATGATTATGACCAGCAGCATCTGCCTGCGGCAGACCGATCTGAAGTCCCTGATCGCC
TACAGCTCCATCAGCCACATGGCCCTGGTGGTCACCGCCATCCTGATTCAGACCCCTTGGAGC
TTTACAGGCGCCGTGATCCTGATGATTGCCCACGGCCTGACAAGCAGCCTGCTGTTTTGTCTG
GCCAACAGCAACTACGAGCGGACCCACAGCAGAATCATGATCCTGTCTCAGGGCCTGCAGACC
CTCCTGCCTCTTATGGCTTTTTGGTGGCTGCTGGCCTCTCTGGCCAATCTGGCACTGCCTCCT
ACCATCAATCTGCTGGGCGAGCTGAGCGTGCTGGTCACCACATTCAGCTGGTCCAATATCACC
CTGCTGCTCACCGGCCTGAACATGCTGGTTACAGCCCTGTACTCCCTGTACATGTTCACCACC
ACACAGTGGGGAAGCCTGACACACCCACATCAACAATATGAAGCCCAGCTTCACCCGCGAGAAC
ACCCTGATGTTCATGCATCTGAGCCCCATTCTGCTGCTGTCCCTGAATCCTGATATCATCACC
GGCTTCTCCAGCTGAGAGCACTGGGACGCCCACCGCCCCTTTCCCTCCGCTGCCAGGCGAGCA
TGTTGTGGTAATTCTGGAACACAAGAAGAGAAATTGCTGGGTTTAGAACAAGATTATAAACGA
ATTCGGTGCTCAGTGATCACTTGACAGTTTTTTTTTTTTTAAATATTACCCAAAATGCTCCC
CAAATAAGAAATGCATCAGCTCAGTCAGTGAATACAAAAAAGGAATTATTTTTCCCTTTGAGG
GTCTTTTATACATCTCTCCTCCAACCCCACCCTCTATTCTGTTTCTTCCTCCTCACATGGGGG
TACACATACACAGCTTCCTCTTTTGGTTCCATCCTTACCACCACACCACACGCACACTCCACA
TGCCCAGCAGAGTGGCACTTGGTGGCCAGAAAGTGTGAGCCTCATGATCTGCTGTCTGTAGTT
CTGTGAGCTCAGGTCCCTCAAAGGCCTCGGAGCACCCCCTTCCTTGTGACTGAGCCAGGGCCT
GCATTTTGGTTTTCCCCACCCCACACATTCTCAACCATAGTCCTTCTAACAATACCAATAGC
TAGGACCCGGCTGCTGTGCACTGGGACTGGGGATTCCACATGTTTGCCTTGGGAGTCTCAAGC
TGGACTGCCAGCCCCTGTCCTCCCTTCACCCCCATTGCGTATGAGCATTTCAGAACTCCAAGG
AGTCACAGGCATCTTTATAGTTCACGTTAACATATAGACACTGTTGGAAGCAGTTCCTTCTAA
AAGGGTAGCCCTGGACTTAATACCAGCCGGATACCTCTGGCCCCCACCCCATTACTGTACCTC
TGGAGTCACTACTGTGGGTCGCCACTCCTCTGCTACACAGCACGGCTTTTTCAAGGCTGTATT
GAGAAGGGAAGTTAGGAAGAAGGGTGTGCTGGGCTAACCAGCCCACAGAGCTCACATTCCTGT
CCCTTGGGTGAAAAATACATGTCCATCCTGATATCTCCTGAATTCAGAAATTAGCCTCCACAT
GTGCAATGGCTTTAAGAGCCAGAAGCAGGGTTCTGGGAATTTTGCAAGTTACCTGTGGCCAGG
TGTGGTCTCGGTTACCAAATACGGTTACCTGCAGCTTTTTAGTCCTTTGTGCTCCCACGGGTC
TACAGAGTCCCATCTGCCCAAAGGTCTTGAAGCTTGACAGGATGTTTTCGATTACTCAGTCTC
CCAGGGCACTACTGGTCCGTAGGATTCGATTGGTCGGGGTAGGAGAGTTAAACAACATTTAAA
CAGAGTTCTCTCAAAAATGTCTAAAGGGATTGTAGGTAGATAACATCCAATCACTGTTTGCAC
TTATCTGAAATCTTCCCTCTTGGCTGCCCCCAGGTATTTACTGTGGAGAACATTGCATAGGAA
TGTCTGGAAAAAGCTTCTACAACTTGTTACAGCCTTCACATTTGTAGAAGCTTT |
| 32 | opt_COX10
-opt_ND4-
3'UTR* | ATGGCCGCCTCTCCACACACACTGAGTAGCAGACTGCTGACCGGCTGTGTTGGCGGCTCTGTG
TGGTATCTGGAACGGCGGACAATGCTGAAGCTGATCGTGCCCACCATCATGCTGCTGCCCCTG
ACCTGGCTGAGCAAGAAACACATGATCTGGATCAACACCACCACGCACAGCCTGATCATCAGC
ATCATCCCTCTGCTGTTCTTCAACCAGATCAACAACAACCTGTTCAGCTGCAGCCCCACCTTC
AGCAGCGACCCTCTGACAACACCTCTGCTGATGCTGACCACCTGGCTGCTGCCCCTCACAATC
ATGGCCTCTCAGAGACACCTGAGCAGCGAGCCCCTGAGCCGGAAGAAACTGTACCTGAGCATG
CTGATCTCCCTGCAGATCTCTCTGATCATGACCTTCACCGCCACCGAGCTGATCATGTTCTAC
ATCTTTTTCGAGACAACGCTGATCCCCACACTGGCCATCATCACCAGATGGGGCAACCAGCCT
GAGAGACTGAACGCCGGCACCTACTTTCTGTTCTACACCCTCGTGGGCAGCCTGCCACTGCTG
ATTGCCCTGATCTACACCCACAACACCCTGGGCTCCCTGAACATCCTGCTGCTGACACTGACA
GCCCAAGAGCTGAGCAACAGCTGGGCCAACAATCTGATGTGGCTGGCCTACACAATGGCCTTC
ATGGTCAAGATGCCCCTGTACGGCCTGCACCTGTGGCTGCCTAAAGCTCATGTGGAAGCCCCT
ATCGCCGGCTCTATGGTGCTGGCTGCAGTGCTGCTGAAACTCGGCGGCTACGGCATGATGCGG
CTGACCCTGATTCTGAATCCCCTGACCAAGCACATGGCCTATCCATTTCTGGTGCTGAGCCTG
TGGGGCATGATTATGACCAGCAGCATCTGCCTGCGGCAGACCGATCTGAAGTCCCTGATCGCC
TACAGCTCCATCAGCCACATGGCCCTGGTGGTCACCGCCATCCTGATTCAGACCCCTTGGAGC
TTTACAGGCGCCGTGATCCTGATGATTGCCCACGGCCTGACAAGCAGCCTGCTGTTTTGTCTG
GCCAACAGCAACTACGAGCGGACCCACAGCAGAATCATGATCCTGTCTCAGGGCCTGCAGACC
CTCCTGCCTCTTATGGCTTTTTGGTGGCTGCTGGCCTCTCTGGCCAATCTGGCACTGCCTCCT
ACCATCAATCTGCTGGGCGAGCTGAGCGTGCTGGTCACCACATTCAGCTGGTCCAATATCACC
CTGCTGCTCACCGGCCTGAACATGCTGGTTACAGCCCTGTACTCCCTGTACATGTTCACCACC
ACACAGTGGGGAAGCCTGACACACCCACATCAACAATATGAAGCCCAGCTTCACCCGCGAGAAC
ACCCTGATGTTCATGCATCTGAGCCCCATTCTGCTGCTGTCCCTGAATCCTGATATCATCACC
GGCTTCTCCAGCTGAGAGCACTGGGACGCCCACCGCCCCTTTCCCTCCGCTGCCAGGCGAGCA
TGTTGTGGTAATTCTGGAACACAAGAAGAGAAATTGCTGGGTTTAGAACAAGATTATAAACGA
ATTCGGTGCTCAGTGATCACTTGACAGTTTTTTTTTTTTTAAATATTACCCAAAATGCTCCC
CAAATAAGAAATGCATCAGCTCAGTCAGTGAATACAAAAAAGGAATTATTTTTCCCTTTGAGG
GTCTTTTATACATCTCTCCTCCAACCCCACCCTCTATTCTGTTTCTTCCTCCTCACATGGGGG
TACACATACACAGCTTCCTCTTTTGGTTCCATCCTTACCACCACACCACACGCACACTCCACA
TGCCCAGCAGAGTGGCACTTGGTGGCCAGAAAGTGTGAGCCTCATGATCTGCTGTCTGTAGTT
CTGTGAGCTCAGGTCCCTCAAAGGCCTCGGAGCACCCCCTTCCTTGTGACTGAGCCAGGGCCT
GCATTTTGGTTTTCCCCACCCCACACATTCTCAACCATAGTCCTTCTAACAATACCAATAGC
TAGGACCCGGCTGCTGTGCACTGGGACTGGGGATTCCACATGTTTGCCTTGGGAGTCTCAAGC
TGGACTGCCA |

TABLE 1-continued nucleic acid and polypeptide sequences and SEQ ID NOs

| SEQ | Description | Sequence |
|---|---|---|
| 33 | opt_COX10<br>-opt_ND4*-<br>3'UTR | ATGGCCGCCTCTCCACACACACTGAGTAGCAGACTGCTGACCGGCTGTGTTGGCGGCTCTGTG<br>TGGTATCTGGAACGGCGGACAATGCTGAAGCTGATCGTGCCCACCATCATGCTGCTGCCCCTG<br>ACCTGGCTGAGCAAGAAGCACATGATCTGGATCAACACCACCACCCACAGCCTGATCATCAGC<br>ATCATCCCCCTGCTGTTCTTCAACCAGATCAACAACAACCTGTTCAGCTGCAGCCCCACCTTC<br>AGCAGCGACCCCCTGACCACCCCCCTGCTGATGCTGACCACCTGGCTGCTGCCCCTGACCATC<br>ATGGCCAGCCAGCGCCACCTGAGCAGCGAGCCCCTGAGCCGCAAGAAGCTGTACCTGAGCATG<br>CTGATCAGCCTGCAGATCAGCCTGATCATGACCTTCACCGCCACCGAGCTGATCATGTTCTAC<br>ATCTTCTTCGAGACCACCCTGATCCCCACCCTGGCCATCATCACCCGCTGGGGCAACCAGCCC<br>GAGCGCCTGAACGCCGGCACCTACTTCCTGTTCTACACCCTGGGCAGCCTGCCCCTGCTG<br>ATCGCCCTGATCTACACCCACAACACCCTGGGCAGCCTGAACATCCTGCTGCTGACCCTGACC<br>GCCCAGGAGCTGAGCAACAGCTGGGCCAACAACCTGATGTGGCTGGCCTACACCATGGCCTTC<br>ATGGTGAAGATGCCCCTGTACGGCCTGCACCTGTGGCTGCCCAAGGCCCACGTGGAGGCCCCC<br>ATCGCCGGCAGCATGGTGCTGGCCGCCGTGCTGCTGAAGCTGGGCGGCTACGGCATGATGCGC<br>CTGACCCTGATCCTGAACCCCCTGACCAAGCACATGGCCTACCCCTTCCTGGTGCTGAGCCTG<br>TGGGGCATGATCATGACCAGCAGCATCTGCCTGCGCCAGACCGACCTGAAGAGCCTGATCGCC<br>TACAGCAGCATCAGCCACATGGCCCTGGTGGTGACCGCCATCCTGATCCAGACCCCCTGGAGC<br>TTCACCGGCGCCGTGATCCTGATGATCGCCCACGGCCTGACCAGCAGCCTGCTGTTCTGCCTG<br>GCCAACAGCAACTACGAGCGCACCCACAGCCGCATCATGATCCTGAGCCAGGGCCTGCAGACC<br>CTGCTGCCCCTGATGGCCTTCTGGTGGCTGCTGGCCAGCCTGGCCAACTGGCCCTGCCCCCC<br>ACCATCAACCTGCTGGGCGAGCTGAGCGTGCTGGTGACCACCTTCAGCTGGAGCAACATCACC<br>CTGCTGCTGACCGGCCTGAACATGCTGGTGACCGCCCTGTACAGCCTGTACATGTTCACCACC<br>ACCCAGTGGGGCAGCCTGACCCACCACATCAACAACATGAAGCCCAGCTTCACCCGCGAGAAC<br>ACCCTGATGTTCATGCACCTGAGCCCCATCCTGCTGCTGAGCCTGAACCCCGACATCATCACC<br>GGCTTCAGCAGCTAAGAGCACTGGGACGCCCACCGCCCCTTTCCCTCCGCTGCCAGGCGAGCA<br>TGTTGTGGTAATTCTGGAACACAAGAAGAGAAATTGCTGGGTTTAGAACAAGATTATAAACGA<br>ATTCGGTGCTCAGTGATCACTTGACAGTTTTTTTTTTTTTAAATATTACCCAAAATGCTCCC<br>CAAATAAGAAATGCATCAGCTCAGTCAGTGAATACAAAAAAGGAATTATTTTTCCCTTTGAGG<br>GTCTTTTATACATCTCTCCTCCAACCCCACCCTCTATTCTGTTTCTTCCTCCTCACATGGGGG<br>TACACATACACAGCTTCCTCTTTTGGTTCCATCCTTACCACCACACCACACGCACACTCCACA<br>TGCCCAGCAGAGTGGCACTTGGTGGCCAGAAAGTGTGAGCCTCATGATCTGCTGTCTGTAGTT<br>CTGTGAGCTCAGGTCCCTCAAAGGCCTCGGAGCACCCCCTTCCTTGTGACTGAGCAGGGCCT<br>GCATTTTTGGTTTTCCCCACCCCACACATTCTCAACCATAGTCCTTCTAACAATACCAATAGC<br>TAGGACCCGGCTGCTGTGCACTGGGACTGGGGATTCCACATGTTTGCCTTGGGAGTCTCAAGC<br>TGGACTGCCAGCCCCTGTCCTCCCTTCACCCCCATTGCGTATGAGCATTTCAGAACTCCAAGG<br>AGTCACAGGCATCTTTATAGTTCACGTTAACATATAGACACTGTTGGAAGCAGTTCCTTCTAA<br>AAGGGTAGCCCTGGACTTAATACCAGCCGGATACCTCTGGCCCCCACCCCATTACTGTACCTC<br>TGGAGTCACTACTGTGGGTCGCCACTCCTCTGCTACACAGCACGGCTTTTTCAAGGCTGTATT<br>GAGAAGGGAAGTTAGGAAGAAGGGTGTGCTGGGCTAACCAGCCCACAGAGCTCACATTCCTGT<br>CCCTTGGGTGAAAAATACATGTCCATCCTGATATCTCCTGAATTCAGAAATTAGCCTCCACAT<br>GTGCAATGGCTTTAAGAGCCAGAAGCAGGGTTCTGGGAATTTTGCAAGTTACCTGTGGCCAGG<br>TGTGGTCTCGGTTACCAAATACGGTTACCTGCAGCTTTTTAGTCCTTTGTGCTCCCACGGGTC<br>TACAGAGTCCCATCTGCCCAAAGGTCTTGAAGCTTGACAGGATGTTTTCGATTACTCAGTCTC<br>CCAGGGCACTACTGGTCCGTAGGATTCGATTGGTCGGGGTAGGAGAGTTAAACAACATTTAAA<br>CAGAGTTCTCTCAAAAATGTCTAAAGGGATTGTAGGTAGATAACATCCAATCACTGTTTGCAC<br>TTATCTGAAATCTTCCCTCTTGGCTGCCCCAGGTATTTACTGTGGAGAACATTGCATAGGAA<br>TGTCTGGAAAAGCTTCTACAACTTGTTACAGCCTTCACATTTGTAGAAGCTTT |
| 34 | opt_COX10<br>-opt_ND4*-<br>3'UTR* | ATGGCCGCCTCTCCACACACACTGAGTAGCAGACTGCTGACCGGCTGTGTTGGCGGCTCTGTG<br>TGGTATCTGGAACGGCGGACAATGCTGAAGCTGATCGTGCCCACCATCATGCTGCTGCCCCTG<br>ACCTGGCTGAGCAAGAAGCACATGATCTGGATCAACACCACCACCCACAGCCTGATCATCAGC<br>ATCATCCCCCTGCTGTTCTTCAACCAGATCAACAACAACCTGTTCAGCTGCAGCCCCACCTTC<br>AGCAGCGACCCCCTGACCACCCCCCTGCTGATGCTGACCACCTGGCTGCTGCCCCTGACCATC<br>ATGGCCAGCCAGCGCCACCTGAGCAGCGAGCCCCTGAGCCGCAAGAAGCTGTACCTGAGCATG<br>CTGATCAGCCTGCAGATCAGCCTGATCATGACCTTCACCGCCACCGAGCTGATCATGTTCTAC<br>ATCTTCTTCGAGACCACCCTGATCCCCACCCTGGCCATCATCACCCGCTGGGGCAACCAGCCC<br>GAGCGCCTGAACGCCGGCACCTACTTCCTGTTCTACACCCTGGGCAGCCTGCCCCTGCTG<br>ATCGCCCTGATCTACACCCACAACACCCTGGGCAGCCTGAACATCCTGCTGCTGACCCTGACC<br>GCCCAGGAGCTGAGCAACAGCTGGGCCAACAACCTGATGTGGCTGGCCTACACCATGGCCTTC<br>ATGGTGAAGATGCCCCTGTACGGCCTGCACCTGTGGCTGCCCAAGGCCCACGTGGAGGCCCCC<br>ATCGCCGGCAGCATGGTGCTGGCCGCCGTGCTGCTGAAGCTGGGCGGCTACGGCATGATGCGC<br>CTGACCCTGATCCTGAACCCCCTGACCAAGCACATGGCCTACCCCTTCCTGGTGCTGAGCCTG<br>TGGGGCATGATCATGACCAGCAGCATCTGCCTGCGCCAGACCGACCTGAAGAGCCTGATCGCC<br>TACAGCAGCATCAGCCACATGGCCCTGGTGGTGACCGCCATCCTGATCCAGACCCCCTGGAGC<br>TTCACCGGCGCCGTGATCCTGATGATCGCCCACGGCCTGACCAGCAGCCTGCTGTTCTGCCTG<br>GCCAACAGCAACTACGAGCGCACCCACAGCCGCATCATGATCCTGAGCCAGGGCCTGCAGACC<br>CTGCTGCCCCTGATGGCCTTCTGGTGGCTGCTGGCCAGCCTGGCCAACTGGCCCTGCCCCCC<br>ACCATCAACCTGCTGGGCGAGCTGAGCGTGCTGGTGACCACCTTCAGCTGGAGCAACATCACC<br>CTGCTGCTGACCGGCCTGAACATGCTGGTGACCGCCCTGTACAGCCTGTACATGTTCACCACC<br>ACCCAGTGGGGCAGCCTGACCCACCACATCAACAACATGAAGCCCAGCTTCACCCGCGAGAAC<br>ACCCTGATGTTCATGCACCTGAGCCCCATCCTGCTGCTGAGCCTGAACCCCGACATCATCACC<br>GGCTTCAGCAGCTAAGAGCACTGGGACGCCCACCGCCCCTTTCCCTCCGCTGCCAGGCGAGCA<br>TGTTGTGGTAATTCTGGAACACAAGAAGAGAAATTGCTGGGTTTAGAACAAGATTATAAACGA<br>ATTCGGTGCTCAGTGATCACTTGACAGTTTTTTTTTTTTAAATATTACCCAAAATGCTCCC<br>CAAATAAGAAATGCATCAGCTCAGTCAGTGAATACAAAAAAGGAATTATTTTTCCCTTTGAGG<br>GTCTTTTATACATCTCTCCTCCAACCCCACCCTCTATTCTGTTTCTTCCTCCTCACATGGGGG<br>TACACATACACAGCTTCCTCTTTTGGTTCCATCCTTACCACCACACCACACGCACACTCCACA |

TABLE 1-continued nucleic acid and polypeptide sequences and SEQ ID NOs

| SEQ | Description | Sequence |
|---|---|---|
| | | TGCCCAGCAGAGTGGCACTTGGTGGCCAGAAAGTGTGAGCCTCATGATCTGCTGTCTGTAGTT<br>CTGTGAGCTCAGGTCCCTCAAAGGCCTCGGAGCACCCCCTTCCTTGTGACTGAGCCAGGGCCT<br>GCATTTTTGGTTTTCCCCACCCCACACATTCTCAACCATAGTCCTTCTAACAATACCAATAGC<br>TAGGACCCGGCTGCTGTGCACTGGGACTGGGGATTCCACATGTTTGCCTTGGGAGTCTCAAGC<br>TGGACTGCCA |
| 35 | opt_COX10<br>-ND6-<br>3'UTR | ATGGCCGCCTCTCCACACACACTGAGTAGCAGACTGCTGACCGGCTGTGTTGGCGGCTCTGTG<br>TGGTATCTGGAACGGCGGACAATGATGTATGCTTTGTTTCTGTTGAGTGTGGGTTTAGTAATG<br>GGGTTTGTGGGGTTTTCTTCTAAGCCTTCTCCTATTTATGGGGGTTTAGTATTGATTGTTAGC<br>GGTGTGGTCGGGTGTGTTATTATTCTGAATTTTGGGGGAGGTTATATGGGTTTAATGGTTTTT<br>TTAATTTATTTAGGGGGAATGATGGTTGTCTTTGGATATACTACAGCGATGGCTATTGAGGAG<br>TATCCTGAGGCATGGGGGTCAGGGGTTGAGGTCTTGGTGAGTGTTTTAGTGGGGTTAGCGATG<br>GAGGTAGGATTGGTGCTGTGGGTGAAAGAGTATGATGGGGTGGTGGTTGTGGTAAACTTTAAT<br>AGTGTAGGAAGCTGGATGATTTATGAAGGAGAGGGGTCAGGGTTGATTCGGGAGGATCCTATT<br>GGTGCGGGGGCTTTGTATGATTATGGGCGTTGGTTAGTAGTAGTTACTGGTTGGACATTGTTT<br>GTTGGTGTATATATTGTAATTGAGATTGCTCGGGGGAATTAGGAGCACTGGGACGCCCACCGC<br>CCCTTTCCCTCCGCTGCCAGGCGAGCATGTTGTGGTAATTCTGGAACACAAGAAGAGAAATTG<br>CTGGGTTTAGAACAAGATTATAAACGAATTCGGTGCTCAGTGATCACTTGACAGTTTTTTTTT<br>TTTTTAAATATTACCCAAAATGCTCCCCAAATAAGAAATGCATCAGCTCAGTCAGTGAATACA<br>AAAAAGGAATTATTTTTCCCTTTGAGGGTCTTTTATACATCTCTCCTCCAACCCCACCCTCTA<br>TTCTGTTTCTTCCTCCTCACATGGGGGTACACATACACAGCTTCCTCTTTTGGTTCCATCCTT<br>ACCACCACACCACACGCACACTCCACATGCCCAGCAGAGTGGCACTTGGTGGCCAGAAAGTGT<br>GAGCCTCATGATCTGCTGTCTGTAGTTCTGTGAGCTCAGGTCCCTCAAAGGCCTCGGAGCACC<br>CCCTTCCTTGTGACTGAGCCAGGGCCTGCATTTTTGGTTTTCCCCACCCCACACATTCTCAAC<br>CATAGTCCTTCTAACAATACCAATAGCTAGGACCCGGCTGCTGTGCACTGGGACTGGGGATTC<br>CACATGTTTGCCTTGGGAGTCTCAAGCTGGACTGCCAGCCCCTGTCCTCCCTTCACCCCCATT<br>GCGTATGAGCATTTCAGAACTCCAAGGAGTCACAGGCATCTTTATAGTTCACGTTAACATATA<br>GACACTGTTGGAAGCAGTTCCTTCTAAAAGGGTAGCCCTGGACTTAATACCAGCCGGATACCT<br>CTGGCCCCCACCCCATTACTGTACCTCTGGAGTCACTACTGTGGGTCGCCACTCCTCTGCTAC<br>ACAGCACGGCTTTTTCAAGGCTGTATTGAGAAGGGAAGTTAGGAAGAAGGGTGTGCTGGGCTA<br>ACCAGCCCACAGAGCTCACATTCCTGTCCCTTGGGTGAAAAATACATGTCCATCCTGATATCT<br>CCTGAATTCAGAAATTAGCCTCCACATGTGCAATGGCTTTAAGAGCCAGAAGCAGGGTTCTGG<br>GAATTTTGCAAGTTACCTGTGGCCAGGTGTGGTCTCGGTTACCAAATACGGTTACCTGCAGCT<br>TTTTAGTCCTTTGTGCTCCCACGGGTCTACAGAGTCCCATCTGCCCAAAGGTCTTGAAGCTTG<br>ACAGGATGTTTTCGATTACTCAGTCTCCCAGGGCACTACTGGTCCGTAGGATTCGATTGGTCG<br>GGGTAGGAGAGTTAAACAACATTTAAACAGAGTTCTCTCAAAAATGTCTAAAGGGATTGTAGG<br>TAGATAACATCCAATCACTGTTTGCACTTATCTGAAATCTTCCCTCTTGGCTGCCCCCAGGTA<br>TTTACTGTGGAGAACATTGCATAGGAATGTCTGGAAAAAGCTTCTACAACTTGTTACAGCCTT<br>CACATTTGTAGAAGCTTT |
| 36 | opt_COX10<br>-ND6-<br>3'UTR* | ATGGCCGCCTCTCCACACACACTGAGTAGCAGACTGCTGACCGGCTGTGTTGGCGGCTCTGTG<br>TGGTATCTGGAACGGCGGACAATGATGTATGCTTTGTTTCTGTTGAGTGTGGGTTTAGTAATG<br>GGGTTTGTGGGGTTTTCTTCTAAGCCTTCTCCTATTTATGGGGGTTTAGTATTGATTGTTAGC<br>GGTGTGGTCGGGTGTGTTATTATTCTGAATTTTGGGGGAGGTTATATGGGTTTAATGGTTTTT<br>TTAATTTATTTAGGGGGAATGATGGTTGTCTTTGGATATACTACAGCGATGGCTATTGAGGAG<br>TATCCTGAGGCATGGGGGTCAGGGGTTGAGGTCTTGGTGAGTGTTTTAGTGGGGTTAGCGATG<br>GAGGTAGGATTGGTGCTGTGGGTGAAAGAGTATGATGGGGTGGTGGTTGTGGTAAACTTTAAT<br>AGTGTAGGAAGCTGGATGATTTATGAAGGAGAGGGGTCAGGGTTGATTCGGGAGGATCCTATT<br>GGTGCGGGGGCTTTGTATGATTATGGGCGTTGGTTAGTAGTAGTTACTGGTTGGACATTGTTT<br>GTTGGTGTATATATTGTAATTGAGATTGCTCGGGGGAATTAGGAGCACTGGGACGCCCACCGC<br>CCCTTTCCCTCCGCTGCCAGGCGAGCATGTTGTGGTAATTCTGGAACACAAGAAGAGAAATTG<br>CTGGGTTTAGAACAAGATTATAAACGAATTCGGTGCTCAGTGATCACTTGACAGTTTTTTTTT<br>TTTTTAAATATTACCCAAAATGCTCCCCAAATAAGAAATGCATCAGCTCAGTCAGTGAATACA<br>AAAAAGGAATTATTTTTCCCTTTGAGGGTCTTTTATACATCTCTCCTCCAACCCCACCCTCTA<br>TTCTGTTTCTTCCTCCTCACATGGGGGTACACATACACAGCTTCCTCTTTTGGTTCCATCCTT<br>ACCACCACACCACACGCACACTCCACATGCCCAGCAGAGTGGCACTTGGTGGCCAGAAAGTGT<br>GAGCCTCATGATCTGCTGTCTGTAGTTCTGTGAGCTCAGGTCCCTCAAAGGCCTCGGAGCACC<br>CCCTTCCTTGTGACTGAGCCAGGGCCTGCATTTTTGGTTTTCCCCACCCCACACATTCTCAAC<br>CATAGTCCTTCTAACAATACCAATAGCTAGGACCCGGCTGCTGTGCACTGGGACTGGGGATTC<br>CACATGTTTGCCTTGGGAGTCTCAAGCTGGACTGCCA |
| 37 | opt_COX10<br>-opt_ND6-<br>3'UTR | ATGGCCGCCTCTCCACACACACTGAGTAGCAGACTGCTGACCGGCTGTGTTGGCGGCTCTGTG<br>TGGTATCTGGAACGGCGGACAATGATGTATGCCCTGTTCCTGCTGAGCGTGGGCCTGGTGATG<br>GGCTTCGTGGGCTTCAGCAGCAAGCCCAGCCCCATCTACGGCGGCCTGGTGCTGATCGTGAGC<br>GGCGTGGTGGGCTGCGTGATCATCCTGAACTTCGGCGGCGGCTACATGGGCCTGATGGTGTTC<br>CTGATCTACCTGGGCGGCATGATGGTGGTGTTCGGCTACACCACCGCCATGGCCATCGAGGAG<br>TACCCCGAGGCCTGGGGCAGCGGCGTGGAGGTGCTGGTGAGCGTGCTGGTGGGCCTGAGCATG<br>GAGGTGGGCCTGGTGCTGTGGGTGAAGGAGTACGACGGCGTGGTGGTGGTGAACTTCAAC<br>AGCGTGGGCAGCTGGATGATCTACGAGGGCGAGGGCAGCGGCCTGATCCGCGAGGACCCCATC<br>GGCGCCGGCGCCCTGTACGACTACGGCCGCTGGCTGGTGGTGGTGACCGGCTGGACCCTGTTC<br>GTGGGCGTGTACATCGTGATCGAGATCGCCCGCGGCAACTAAGAGCACTGGGACGCCCACCGC<br>CCCTTTCCCTCCGCTGCCAGGCGAGCATGTTGTGGTAATTCTGGAACACAAGAAGAGAAATTG<br>CTGGGTTTAGAACAAGATTATAAACGAATTCGGTGCTCAGTGATCACTTGACAGTTTTTTTTT<br>TTTTTAAATATTACCCAAAATGCTCCCCAAATAAGAAATGCATCAGCTCAGTCAGTGAATACA<br>AAAAAGGAATTATTTTTCCCTTTGAGGGTCTTTTATACATCTCTCCTCCAACCCCACCCTCTA<br>TTCTGTTTCTTCCTCCTCACATGGGGTACACATACACAGCTTCCTCTTTTGGTTCCATCCTT |

TABLE 1-continued nucleic acid and polypeptide sequences and SEQ ID NOs

| SEQ | Description | Sequence |
|---|---|---|
| | | ACCACCACACCACACGCACACTCCACATGCCCAGCAGAGTGGCACTTGGTGGCCAGAAAGTGT<br>GAGCCTCATGATCTGCTGTCTGTAGTTCTGTGAGCTCAGGTCCCTCAAAGGCCTCGGAGCACC<br>CCCTTCCTTGTGACTGAGCCAGGGCCTGCATTTTTGGTTTTCCCCACCCCACACATTCTCAAC<br>CATAGTCCTTCTAACAATACCAATAGCTAGGACCCGGCTGCTGTGCACTGGGACTGGGGATTC<br>CACATGTTTGCCTTGGGAGTCTCAAGCTGGACTGCCAGCCCTGTCCTCCCTTCACCCCCATT<br>GCGTATGAGCATTTCAGAACTCCAAGGAGTCACAGGCATCTTTATAGTTCACGTTAACATATA<br>GACACTGTTGGAAGCAGTTCCTTCTAAAAGGGTAGCCCTGGACTTAATACCAGCCGGATACCT<br>CTGGCCCCCACCCCATTACTGTACCTCTGGAGTCACTACTGTGGGTCGCCACTCCTCTGCTAC<br>ACAGCACGGCTTTTTCAAGGCTGTATTGAGAAGGGAAGTTAGGAAGAAGGGTGTGCTGGGCTA<br>ACCAGCCCACAGAGCTCACATTCCTGTCCCTTGGGTGAAAAATACATGTCCATCCTGATATCT<br>CCTGAATTCAGAAATTAGCCTCCACATGTGCAATGGCTTTAAGAGCCAGAAGCAGGGTTCTGG<br>GAATTTTGCAAGTTACCTGTGGCCAGGTGTGGTCTCGGTTACCAAATACGGTTACCTGCAGCT<br>TTTTAGTCCTTTGTGCTCCCACGGGTCTACAGAGTCCCATCTGCCCAAAGGTCTTGAAGCTTG<br>ACAGGATGTTTTCGATTACTCAGTCTCCCAGGGCACTACTGGTCCGTAGGATTCGATTGGTCG<br>GGGTAGGAGAGTTAAACAACATTTAAACAGAGTTCTCTCAAAAATGTCTAAAGGGATTGTAGG<br>TAGATAACATCCAATCACTGTTTGCACTTATCTGAAATCTTCCCTCTTGGCTGCCCCCAGGTA<br>TTTACTGTGGAGAACATTGCATAGGAATGTCTGGAAAAAGCTTCTACAACTTGTTACAGCCTT<br>CACATTTGTAGAAGCTTT |
| 38 | opt_COX10<br>-opt_ND6-<br>3'UTR* | ATGGCCGCCTCTCCACACACACTGAGTAGCAGACTGCTGACCGGCTGTGTTGGCGGCTCTGTG<br>TGGTATCTGGAACGGCGGACAATGATGTACGCCCTGTTCCTGCTGAGCGTGGGCTGGTGATG<br>GGCTTCGTGGGCTTCAGCAGCAAGCCCAGCCCCATCTACGGCGGCCTGGTGCTGATCGTGAGC<br>GGCGTGGTGGGCTGCGTGATCATCCTGAACTTCGGCGGCGGCTACATGGGCCTGATGGTGTTC<br>CTGATCTACCTGGGCGGCATGATGGTGGTGTTCGGCTACACCACCGCCATGGCCATCGAGGAG<br>TACCCCGAGGCTGGGGCAGCGGCGTGGAGGTGCTGGTGAGCGTGCTGGTGGGCCTGGCCATG<br>GAGGTGGGCCTGGTGCTGTGGGTGAAGGAGTACGACGGCGTGGTGGTGGTGAACTTCAAC<br>AGCGTGGGCAGCTGGATGATCTACGAGGGCGAGGGCAGCGGCCTGATCCGCGAGGACCCCATC<br>GGCGCCGGCGCCCTGTACGACTACGGCCGCTGGCTGGTGGTGGTGACCGGCTGGACCCTGTTC<br>GTGGGCGTGTACATCGTGATCGAGATCGCCCGCGGCAACTAAGAGCACTGGGACGCCCACCGC<br>CCCTTTCCCTCCGCTGCCAGGCGAGCATGTTGTGGTAATTCTGGAACACAAGAAGAGAAATTG<br>CTGGGTTTAGAACAAGATTATAAACGAATTCGGTGCTCAGTGATCACTTGACAGTTTTTTTTT<br>TTTTTAAATATTACCCAAAATGCTCCCCAAATAAGAAATGCATCAGCTCAGTCAGTGAATACA<br>AAAAAGGAATTATTTTTCCCTTTGAGGGTCTTTTATACATCTCTCCTCCAACCCCACCCTCTA<br>TTCTGTTTCTTCCTCCTCACATGGGGGTACACATACACAGCTTCCTCTTTTGGTTCCATCCTT<br>ACCACCACACCACACGCACACTCCACATGCCCAGCAGAGTGGCACTTGGTGGCCAGAAAGTGT<br>GAGCCTCATGATCTGCTGTCTGTAGTTCTGTGAGCTCAGGTCCCTCAAAGGCCTCGGAGCACC<br>CCCTTCCTTGTGACTGAGCCAGGGCCTGCATTTTTGGTTTTCCCCACCCCACACATTCTCAAC<br>CATAGTCCTTCTAACAATACCAATAGCTAGGACCCGGCTGCTGTGCACTGGGACTGGGGATTC<br>CACATGTTTGCCTTGGGAGTCTCAAGCTGGACTGCCA |
| 39 | opt_COX10<br>-ND1-<br>3'UTR | ATGGCCGCCTCTCCACACACACTGAGTAGCAGACTGCTGACCGGCTGTGTTGGCGGCTCTGTG<br>TGGTATCTGGAACGGCGGACAATGCCAACCTCCTACTCCTCATTGTACCCATTCTAATCGCA<br>ATGGCATTCCTAATGCTTACCGAACGAAAAATTCTAGGCTATATGCAACTACGCAAAGGCCCC<br>AACGTTGTAGGCCCCTACGGGCTACTACAACCCTTCGCTGACGCCATAAAACTCTTCACCAAA<br>GAGCCCCTAAAACCCGCCACATCTACCATCACCCTCTACATCACCGCCCCGACCTTAGCTCTC<br>ACCATCGCTCTTCTACTATGGACCCCCCTCCCCATGCCCAACCCCCTGGTCAACCTCAACCTA<br>GGCCTCCTATTTATTCTAGCCACCTCTAGCCTAGCCGTTTACTCAATCCTCTGGTCAGGGTGG<br>GCATCAAACTCAAACTACGCCCTGATCGGCGCACTGCGAGCAGTAGCCCAAACAATCTCATAT<br>GAAGTCACCCTAGCCATCATTCTACTATCAACATTACTAATGAGTGGCTCCTTTAACCTCTCC<br>ACCCTTATCACAACACAAGAACACCTCTGGTTACTCCTGCCATCATGGCCCTTGGCATGATG<br>TGGTTTATCTCCACACTAGCAGAGACCAACCGAACCCCCTTCGACCTTGCCGAAGGGGAGTCC<br>GAACTAGTCTCAGGCTTCAACATCGAATACGCCGCAGGCCCCTTCGCCCTATTCTTCATGGCC<br>GAATACACAAACATTATTATGATGAACACCCTCACCACTACAATCTTCCTAGGAACAACATAT<br>GACGCACTCTCCCCTGAACTCTACACAACATATTTTGTCACCAAGACCCTACTTCTAACCTCC<br>CTGTTCTTATGGATTCGAACAGCATACCCCCGATTCCGCTACGACCAACTCATGCACCTCCTA<br>TGGAAAAACTTCCTACCACTCACCCTAGCATTACTTATGTGGTATGTCTCCATGCCCATTACA<br>ATCTCCAGCATTCCCCCTCAAACCTAAGAGCACTGGGACGCCCACCGCCCCTTTCCCTCCGCT<br>GCCAGGCGAGCATGTTGTGGTAATTCTGGAACACAAGAAGAGAAATTGCTGGGTTTAGAACAA<br>GATTATAAACGAATTCGGTGCTCAGTGATCACTTGACAGTTTTTTTTTTTTTAAATATTACC<br>CAAAATGCTCCCCAAATAAGAAATGCATCAGCTCAGTCAGTGAATACAAAAAAGGAATTATTT<br>TTCCCTTTGAGGGTCTTTTATACATCTCTCCTCCAACCCCACCCTCTATTCTGTTTCTTCCTC<br>CTCACATGGGGTACACATACACAGCTTCCTCTTTTGGTTCCATCCTTACCACCACACCACAC<br>GCACACTCCACATGCCCAGCAGAGTGGCACTTGGTGGCCAGAAAGTGTGAGCCTCATGATCTG<br>CTGTCTGTAGTTCTGTGAGCTCAGGTCCCTCAAAGGCCTCGGAGCACCCCCTTCCTTGTGACT<br>GAGCCAGGGCCTGCATTTTTGGTTTTCCCCACCCCACACATTCTCAACCATAGTCCTTCTAAC<br>AATACCAATAGCTAGGACCCGGCTGCTGTGCACTGGGACTGGGGATTCCACATGTTTGCCTTG<br>GGAGTCTCAAGCTGGACTGCCAGCCCTGTCCTCCCTTCACCCCCATTGCGTATGAGCATTTC<br>AGAACTCCAAGGAGTCACAGGCATCTTTATAGTTCACGTTAACATATAGACACTGTTGGAAGC<br>AGTTCCTTCTAAAAGGGTAGCCCTGGACTTAATACCAGCCGGATACCTCTGGCCCCCACCCCA<br>TTACTGTACCTCTGGAGTCACTACTGTGGGTCGCCACTCCTCTGCTACACAGCACGGCTTTTT<br>CAAGGCTGTATTGAGAAGGGAAGTTAGGAAGAAGGGTGTGCTGGGCTAACCAGCCCACAGAGC<br>TCACATTCCTGTCCCTTGGGTGAAAAATACATGTCCATCCTGATATCTCCTGAATTCAGAAAT<br>TAGCCTCCACATGTGCAATGGCTTTAAGAGCCAGAAGCAGGGTTCTGGGAATTTTGCAAGTTA<br>CCTGTGGCCAGGTGTGGTCTCGGTTACCAAATACGGTTACCTGCAGCTTTTTAGTCCTTTGTG<br>CTCCCACGGGTCTACAGAGTCCCATCTGCCCAAAGGTCTTGAAGCTTGACAGGATGTTTTCGA<br>TTACTCAGTCTCCCAGGGCACTACTGGTCCGTAGGATTCGATTGGTCGGGGTAGGAGAGTTAA |

TABLE 1-continued nucleic acid and polypeptide sequences and SEQ ID NOs

| SEQ | Description | Sequence |
|---|---|---|
| | | ACAACATTTAAACAGAGTTCTCTCAAAAATGTCTAAAGGGATTGTAGGTAGATAACATCCAAT CACTGTTTGCACTTATCTGAAATCTTCCCTCTTGGCTGCCCCCAGGTATTTACTGTGGAGAAC ATTGCATAGGAATGTCTGGAAAAAGCTTCTACAACTTGTTACAGCCTTCACATTTGTAGAAGC TTT |
| 40 | opt_COX10 -ND1- 3'UTR* | ATGGCCGCCTCTCCACACACACTGAGTAGCAGACTGCTGACCGGCTGTGTTGGCGGCTCTGTG TGGTATCTGGAACGGCGGACAATGGCCAACCTCCTACTCCTCATTGTACCCATTCTAATCGCA ATGGCATTCCTAATGCTTACCGAACGAAAAATTCTAGGCTATATGCAACTACGCAAAGGCCCC AACGTTGTAGGCCCCTACGGGCTACTACAACCCTTCGCTGACGCCATAAAACTCTTCACCAAA GAGCCCCTAAAACCCGCCACATCTACCATCACCCTCTACATCACCGCCCCGACCTTAGCTCTC ACCATCGCTCTTCTACTATGGACCCCCCTCCCCATGCCCAACCCCTGGTCAACCTCAACCTA GGCCTCCTATTTATTCTAGCCACCTCTAGCCTAGCCGTTTACTCAATCCTCTGGTCAGGGTGG GCATCAAACTCAAACTACGCCTCGATCGGCGCACTGCGAGCAGTAGCCCAAACAATCTCATAT GAAGTCACCCTAGCCATCATTCTACTATCAACATTACTAATGAGTGGCTCCTTTAACCTCTCC ACCCTTATCACAACACAAGAACACCTCTGGTTACTCCTGCCATCATGGGCCCTTGGCCATGATG TGGTTTATCTCCACACTAGCAGAGACCAACCGAACCCCCTTCGACCTTGCCGAAGGGGAGTCC GAACTAGTCTCAGGCTTCAACATCGAATACGCCGCAGGCCCCTTCGCCCTATTCTTCATGGCC GAATACACAAACATTATTATGATGAACACCCTCACCACTACAATCTTCCTAGGAACAACATAT GACGCACTCTCCCCTGAACTCTACACAACATATTTTGTCACCAAGACCCTACTTCTAACCTCC CTGTTCTTATGGATTCGAACAGCATACCCCCGATTCCGCTACGACCAACTCATGCACCTCCTA TGGAAAAACTTCTACCACTCACCCTAGCATTACTTATGTGGTATGTCTCCATGCCCATTACA ATCTCCAGCATTCCCCCTCAAACCTAAGAGCACTGGGACGCCCACCGCCCCTTTCCCTCCGCT GCCAGGCGAGCATGTTGTGGTAATTCTGGAACACAAGAAGAGAAATTGCTGGGTTTAGAACAA GATTATAAACGAATTCGGTGCTCAGTGATCACTTGACAGTTTTTTTTTTTTAAATATTACC CAAAATGCTCCCCAAATAAGAAATGCATCAGCTCAGTCAGTGAATACAAAAAAGGAATTATTT TTCCCTTTGAGGGTCTTTTATACATCTCCTCCAACCCCACCCTCTATTCTGTTTCTTCCTC CTCACATGGGGGTACACATACACAGCTTCCTCTTTTGGTTCCATCCTTACCACCACACCACAC GCACACTCCACATGCCCAGCAGAGTGGCACTTGGTGGCCAGAAAGTGTGAGCCTCATGATCTG CTGTCTGTAGTTCTGTGAGCTCAGGTCCCTCAAAGGCCTCGGAGCACCCCCTTCCTTGTGACT GAGCCAGGGCCTGCATTTTTGGTTTTCCCCACCCCACACATTCTCAACCATAGTCCTTCTAAC AATACCAATAGCTAGGACCCGGCTGCTGTGCACTGGGACTGGGGATTCCACATGTTTGCCTTG GGAGTCTCAAGCTGGACTGCCA |
| 41 | opt_COX10 -opt_ND1- 3'UTR | ATGGCCGCCTCTCCACACACACTGAGTAGCAGACTGCTGACCGGCTGTGTTGGCGGCTCTGTG TGGTATCTGGAACGGCGGACAATGGCCAACCTGCTGCTGCTGATCGTGCCCATCCTGATCGCC ATGGCCTTCCTGATGCTGACCGAGCGCAAGATCCTGGGCTACATGCAGCTGCGCAAGGGCCCC AACGTGGTGGGCCCCTACGGCCTGCTGCAGCCCTTCGCCGACGCCATCAAGCTGTTCACCAAG GAGCCCCTGAAGCCCGCCACCAGCACCATCACCCTGTACATCACCGCCCCCACCCTGGCCCTG ACCATCGCCCTGCTGCTGTGGACCCCCCTGCCCATGCCCAACCCCTGGTCAACCTGAACCTG GGCCTGCTGTTCATCCTGGCCACCAGCAGCCTGGCCGTGTACAGCATCCTGTGGAGCGGCTGG GCCAGCAACAGCAACTACGCCCTGATCGGCGCCTGCGCCGTGGCCCAGACCATCAGCTAC GAGGTGACCCTGGCCATCATCCTGCTGAGCACCCTGCTGATGAGCGGCAGCTTCAACCTGAGC ACCCTGATCACCACCCAGGAGCACCTGTGGCTGCTGCTGCCCAGCTGGCCCCTGGCCATGATG TGGTTCATCAGCACCCTGGCCGAGACCAACCGCACCCCCTTCGACCTGGCCGAGGGCGAGAGC GAGCTGGTGAGCGGCTTCAACATCGAGTACGCCGCCGGCCCCTTCGCCCTGTTCTTCATGGCC GAGTACACCAACATCATCATGATGAACACCCTGACCACCACCATCTTCCTGGGCACCACCTAC GACGCCCTGAGCCCCGAGCTGTACACCACCTACTTCGTGACCAAGACCCTGCTGCTGACCAGC CTGTTCCTGTGGATCCGCACCGCCTACCCCCGCTTCCGCTACGACCAGCTGATGCACCTGCTG TGGAAGAACTTCCTGCCCCTGACCCTGGCCCTGCTGATGTGGTACGTGAGCATGCCCATCACC ATCAGCAGCATCCCCCCCCAGACCTAAGAGCACTGGGACGCCCACCGCCCCTTTCCCTCCGCT GCCAGGCGAGCATGTTGTGGTAATTCTGGAACACAAGAAGAGAAATTGCTGGGTTTAGAACAA GATTATAAACGAATTCGGTGCTCAGTGATCACTTGACAGTTTTTTTTTTTTAAATATTACC CAAAATGCTCCCCAAATAAGAAATGCATCAGCTCAGTCAGTGAATACAAAAAAGGAATTATTT TTCCCTTTGAGGGTCTTTTATACATCTCCTCCAACCCCACCCTCTATTCTGTTTCTTCCTC CTCACATGGGGGTACACATACACAGCTTCCTCTTTTGGTTCCATCCTTACCACCACACCACAC GCACACTCCACATGCCCAGCAGAGTGGCACTTGGTGGCCAGAAAGTGTGAGCCTCATGATCTG CTGTCTGTAGTTCTGTGAGCTCAGGTCCCTCAAAGGCCTCGGAGCACCCCCTTCCTTGTGACT GAGCCAGGGCCTGCATTTTTGGTTTTCCCCACCCCACACATTCTCAACCATAGTCCTTCTAAC AATACCAATAGCTAGGACCCGGCTGCTGTGCACTGGGACTGGGGATTCCACATGTTTGCCTTG GGAGTCTCAAGCTGGACTGCCAGCCCTGTCCTCCCTTCACCCCCATTGCGTATGAGCATTTC AGAACTCCAAGGAGTCACAGGCATCTTTATAGTTCACGTTAACATATAGACACTGTTGGAAGC AGTTCCTTCTAAAAGGGTAGCCCTGGACTTAATACCAGCCGGATACCTCTGGCCCCCACCCCA TTACTGTACCTCTGGAGTCACTACTGTGGGTCGCCACTCCTCTGCTACACAGCACGGCTTTTT CAAGGCTGTATTGAGAAGGGAAGTTAGGAAGAAGGGTGTGCTGGGCTAACCAGCCCACAGAGC TCACATTCCTGTCCCTTGGGTGAAAAATACATGTCCATCCTGATATCTCCTGAATTCAGAAAT TAGCCTCCACATGTGCAATGGCTTTAAGAGCCAGAAGCAGGGTTCTGGGAATTTTGCAAGTTA CCTGTGGCCAGGTGTGGTCTCGGTTACCAAATACGGTTACCTGCAGCTTTTTAGTCCTTTGTG CTCCCACGGGTCTACAGAGTCCCATCTGCCCAAAGGTCTTGAAGCTTGACAGGATGTTTTCGA TTACTCAGTCTCCCAGGGCACTACTGGTCCGTAGGATTCGATTGGTCGGGGTAGGAGAGTTAA ACAACATTTAAACAGAGTTCTCTCAAAAATGTCTAAAGGGATTGTAGGTAGATAACATCCAAT CACTGTTTGCACTTATCTGAAATCTTCCCTCTTGGCTGCCCCCAGGTATTTACTGTGGAGAAC ATTGCATAGGAATGTCTGGAAAAAGCTTCTACAACTTGTTACAGCCTTCACATTTGTAGAAGC TTT |

TABLE 1-continued nucleic acid and polypeptide sequences and SEQ ID NOs

| SEQ | Description | Sequence |
|---|---|---|
| 42 | opt_COX10<br>-opt_ND1-<br>3'UTR* | ATGGCCGCCTCTCCACACACACTGAGTAGCAGACTGCTGACCGGCTGTGTTGGCGGCTCTGTG<br>TGGTATCTGGAACGGCGGACAATGGCCAACCTGCTGCTGCTGATCGTGCCCATCCTGATCGCC<br>ATGGCCTTCCTGATGCTGACCGAGCGCAAGATCCTGGGCTACATGCAGCTGCGCAAGGGCCCC<br>AACGTGGTGGGCCCCTACGGCCTGCTGCAGCCCTTCGCCGACGCCATCAAGCTGTTCACCAAG<br>GAGCCCCTGAAGCCCGCCACCAGCACCATCACCCTGTACATCACCGCCCCCACCCTGGCCCTG<br>ACCATCGCCCTGCTGCTGTGGACCCCCCTGCCCATGCCCAACCCCCTGGTGAACCTGAACCTG<br>GGCCTGCTGTTCATCCTGGCCACCAGCAGCCTGGCCGTGTACAGCATCCTGTGGAGCGGCTGG<br>GCCAGCAACAGCAACTACGCCCTGATCGGCGCCCTGCGCGCCGTGGCCCAGACCATCAGCTAC<br>GAGGTGACCCTGGCCATCATCCTGCTGAGCACCCTGCTGATGAGCGGCAGCTTCAACCTGAGC<br>ACCCTGATCACCACCCAGGAGCACCTGTGGCTGCTGCTGCCCAGCTGGCCCCTGGCCATGATG<br>TGGTTCATCAGCACCCTGGCCGAGACCAACCGCACCCCCTTCGACCTGGCCGAGGGCGAGAGC<br>GAGCTGGTGAGCGGCTTCAACATCGAGTACGCCGCCGGCCCCTTCGCCCTGTTCTTCATGGCC<br>GAGTACACCAACATCATCATGATGAACACCCTGACCACCACCATCTTCCTGGGCACCACCTAC<br>GACGCCCTGAGCCCCGAGCTGTACACCACCTACTTCGTGACCAAGACCCTGCTGCTGACCAGC<br>CTGTTCCTGTGGATCCGCACCGCCTACCCCGCTTCCGCTACGACCAGCTGATGCACCTGCTG<br>TGGAAGAACTTCCTGCCCCTGACCCTGGCCCTGCTGATGTGGTACGTGAGCATGCCCATCACC<br>ATCAGCAGCATCCCCCCCAGACCTAAGAGCACTGGGACGCCCACCGCCCCTTTCCCTCCGCT<br>GCCAGGCGAGCATGTTGTGGTAATTCTGGAACACAAGAAGAGAAATTGCTGGGTTTAGAACAA<br>GATTATAAACGAATTCGGTGCTCAGTGATCACTTGACAGTTTTTTTTTTTTTAAATATTACC<br>CAAAATGCTCCCCAAATAAGAAATGCATCAGCTCAGTCAGTGAATACAAAAAAGGAATTATTT<br>TTCCCTTTGAGGGTCTTTTATACATCTCTCCTCCAACCCCACCCTCTATTCTGTTTCTTCCTC<br>CTCACATGGGGGTACACATACACAGCTTCCTCTTTTGGTTCCATCCTTACCACCACACCCACAC<br>GCACACTCCACATGCCCAGCAGAGTGGCACTTGGTGGCCAGAAAGTGTGAGCCTCATGATCTG<br>CTGTCTGTAGTTCTGTGAGCTCAGGTCCCTCAAAGGCCTCGGAGCACCCCCTTCCTTGTGACT<br>GAGCCAGGGCCTGCATTTTTGGTTTTCCCCACCCCACACATTCTCAACCATAGTCCTTCTAAC<br>AATACCAATAGCTAGGACCCGGCTGCTGTGCACTGGGACTGGGGATTCCACATGTTTGCCTTG<br>GGAGTCTCAAGCTGGACTGCCA |
| 43 | opt_COX10<br>*-ND4-<br>3'UTR | ATGGCCGCCAGCCCCCACACCCTGAGCAGCCGCCTGCTGACCGGCTGCGTGGGCGGCAGCGTG<br>TGGTACCTGGAGCGCCGCACCATGCTAAAACTAATCGTCCCAACAATTATGTTACTACCACTG<br>ACATGGCTTTCCAAAAAACACATGATTTGGATCAACACAACCACCCACAGCCTAATTATTAGC<br>ATCATCCTCTACTATTTTTTAACCAAATCAACAACAACCTATTTAGCTGTTCCCCAACCTTT<br>TCCTCCGACCCCTAACAACCCCCCTCCTAATGCTAACTACCTGGCTCCTACCCCTCACAATC<br>ATGGCAAGCCAACGCCACTTATCCAGTGAACCACTATCACGAAAAAAACTCTACCTCTCTATG<br>CTAATCTCCCTACAAATCTCCTTAATTATGACATTCACAGCCACAGAACTAATCATGTTTTAT<br>ATCTTCTTCGAAACCACACTTATCCCCACCTTGGCTATCATCACCCGATGGGGCAACCAGCCA<br>GAACGCCTGAACGCAGGCACATACTTCCTATTCTACACCCTAGTAGGCTCCCTTCCCCTACTC<br>ATCGCACTAATTTACACTCACAACACCCTAGGCTCACTAAACATTCTACTACTCACTCTCACT<br>GCCCAAGAACTATCAAACTCCTGGGCCAACAACTTAATGTGGCTAGCTTACACAATGGCTTTT<br>ATGGTAAAGATGCCTCTTTACGGACTCCACTTATGGCTCCCTAAAGCCCATGTCGAAGCCCCC<br>ATCGCTGGGTCAATGGTACTTGCCGCAGTACTCTTAAAACTAGGCGGCTATGGTATGATGCGC<br>CTCACACTCATTCTCAACCCCCTGACAAAACACATGGCCTACCCCTTCCTTGTACTATCCCTA<br>TGGGGCATGATTATGACAAGCTCCATCTGCCTACGACAAACAGACCTAAAATCGCTCATTGCA<br>TACTCTTCAATCAGCCACATGGCCCTCGTAGTAACAGCCATTCTCATCCAAACCCCCTGGAGC<br>TTCACCGGCGCAGTCATTCTCATGATCGCCCACGGGCTTACATCCTCATTACTATTCTGCCTA<br>GCAAACTCAAACTACGAACGCACTCACAGTCGCATCATGATCCTCTCTCAAGGACTTCAAACT<br>CTACTCCCACTAATGGCTTTTTGGTGGCTTCTAGCAAGCCTCGCTAACCTCGCCTTACCCCCC<br>ACTATTAACCTACTGGGAGAACTCTCTGTGCTAGTAACCACGTTCTCCTGGTCAAATATCACT<br>CTCCTACTTACAGGACTCAACATGCTAGTCACAGCCCTATACTCCCTCTACATGTTTACCACA<br>ACACAATGGGGCTCACTCACCCACCACATTAACAACATGAAACCCTCATTCACACGAGAAAAC<br>ACCCTCATGTTCATGCACCTATCCCCATTCTCCTCCTATCCCTCAACCCCGACATCATTACC<br>GGGTTTTCCTCTTAAGAGCACTGGGACGCCCACCGCCCCTTTCCCTCCGCTGCCAGGCGAGCA<br>TGTTGTGGTAATTCTGGAACACAAGAAGAGAAATTGCTGGGTTTAGAACAAGATTATAAACGA<br>ATTCGGTGCTCAGTGATCACTTGACAGTTTTTTTTTTTTTAAATATTACCCAAAATGCTCCC<br>CAAATAAGAAATGCATCAGCTCAGTCAGTGAATACAAAAAAGGAATTATTTTTCCCTTTGAGG<br>GTCTTTTATACATCTCTCCTCCAACCCCACCCTCTATTCTGTTTCTTCCTCCTCACATGGGGG<br>TACACATACACAGCTTCCTCTTTTGGTTCCATCCTTACCACCACACCACACGCACACTCCACA<br>TGCCCAGCAGAGTGGCACTTGGTGGCCAGAAAGTGTGAGCCTCATGATCTGCTGTCTGTAGTT<br>CTGTGAGCTCAGGTCCCTCAAAGGCCTCGGAGCACCCCCTTCCTTGTGACTGAGCCAGGGCCT<br>GCATTTTTGGTTTTCCCCACCCCACACATTCTCAACCATAGTCCTTCTAACAATACCAATAGC<br>TAGGACCCGGCTGCTGTGCACTGGGACTGGGGATTCCACATGTTTGCCTTGGGAGTCTCAAGC<br>TGGACTGCCAGCCCCTGTCCTCCCTTCACCCCCATTGCGTATGAGCATTTCAGAACTCCAAGG<br>AGTCACAGGCATCTTTATAGTTCACGTTAACATATAGACACTGTTGGAAGCAGTTCCTTCTAA<br>AAGGGTAGCCCTGGACTTAATACCAGCCGGATACCTCTGGCCCCCACCCCATTACTGTACCTC<br>TGGAGTCACTACTGTGGGTCGCCACTCCTCTGCTACACAGCACGGCTTTTTCAAGGCTGTATT<br>GAGAAGGGAAGTTAGGAAGAAGGGTGTGCTGGGCTAACCAGCCCACAGAGCTCACATTCCTGT<br>CCCTTGGGTGAAAAATACATGTCCATCCTGATATCTCCTGAATTCAGAAATTAGCCTCCACAT<br>GTGCAATGGCTTTAAGAGCCAGAAGCAGGGTTCTGGGAATTTTGCAAGTTACCTGTGGCCAGG<br>TGTGGTCTCGGTTACCAAATACGGTTACCTGCAGCTTTTTAGTCCTTTGTGCTCCCACGGGTC<br>TACAGAGTCCCATCTGCCCAAAGGTCTTGAAGCTTGACAGGATGTTTTCGATTACTCAGTCTC<br>CCAGGGCACTACTGGTCCGTAGGATTCGATTGGTCGGGTAGGAGAGTTAAACAACATTTAAA<br>CAGAGTTCTCTCAAAAATGTCTAAAGGGATTGTAGGTAGATAACATCCAATCACTGTTTGCAC<br>TTATCTGAAATCTTCCCTCTTGGCTGCCCCCAGGTATTTACTGTGGAGAACATTGCATAGGAA<br>TGTCTGGAAAAAGCTTCTACAACTTGTTACAGCCTTCACATTTGTAGAAGCTTT |

TABLE 1-continued nucleic acid and polypeptide sequences and SEQ ID NOs

| SEQ | Description | Sequence |
|---|---|---|
| 44 | opt_COX10<br>*4ND4-<br>3'UTR* | ATGGCCGCCAGCCCCCACACCCTGAGCAGCCGCCTGCTGACCGGCTGCGTGGGCGGCAGCGTG<br>TGGTACCTGGAGCGCCGCACCATGCTAAAACTAATCGTCCCAACAATTATGTTACTACCACTG<br>ACATGGCTTTCCAAAAAACACATGATTTGGATCAACACAACCACCCACAGCCTAATTATTAGC<br>ATCATCCCTCTACTATTTTTTAACCAAATCAACAACAACCTATTTAGCTGTTCCCCAACCTTT<br>TCCTCCGACCCCCTAACAACCCCCCTCCTAATGCTAACTACCTGGCTCCTACCCCTCACAATC<br>ATGGCAAGCCAACGCCACTTATCCAGTGAACCACTATCACGAAAAAAACTCTACCTCTCTATG<br>CTAATCTCCCTACAAATCTCCTTAATTATGACATTCACAGCCACAGAACTAATCATGTTTTAT<br>ATCTTCTTCGAAACCACACTTATCCCCACCTTGGCTATCATCACCCGATGGGGCAACCAGCCA<br>GAACGCCTGAACGCAGGCACATACTTCCTATTCTACACCCTAGTAGGCTCCCTTCCCCTACTC<br>ATCGCACTAATTTACACTCACAACACCCTAGGCTCACTAAACATTCTACTACTCACTCTCACT<br>GCCCAAGAACTATCAAACTCCTGGGCCAACAACTTAATGTGGCTAGCTTACACAATGGCTTTT<br>ATGGTAAAGATGCCTCTTTACGGACTCCACTTATGGCTCCCTAAAGCCCATGTCGAAGCCCCC<br>ATCGCTGGGTCAATGGTACTTGCCGCAGTACTCTTAAAACTAGGCGGCTATGGTATGATGCGC<br>CTCACACTCATTCTCAACCCCCTGACAAAACACATGGCCTACCCCTTCCTTGTACTATCCCTA<br>TGGGGCATGATTATGACAAGCTCCATCTGCCTACGACAAACAGACCTAAATCGCTCATTGCA<br>TACTCTTCAATCAGCCACATGGCCCTCGTAGTAACAGCCATTCTCATCCAAACCCCCTGGAGC<br>TTCACCGGCGCAGTCATTCTCATGATCGCCCACGGGCTTACATCCTCATTACTATTCTGCCTA<br>GCAAACTCAAACTACGAACGCACTCACAGTCGCATCATGATCCTCTCTCAAGGACTTCAAACT<br>CTACTCCCACTAATGGCTTTTTGGTGGCTTCTAGCAAGCCTCGCTAACCTCGCCTTACCCCCC<br>ACTATTAACCTACTGGGAGAACTCTCTGTGCTAGTAACCACGTTCTCCTGGTCAAATATCACT<br>CTCCTACTTACAGGACTCAACATGCTAGTCACAGCCCTATACTCCCTCTACATGTTTACCACA<br>ACACAATGGGGCTCACTCACCCACCACATTAACAACATGAAACCCTCATTCACACGAGAAAAC<br>ACCCTCATGTTCATGCACCTATCCCCCATTCTCCTCCTATCCCTCAACCCCGACATCATTACC<br>GGGTTTTCCTCTTAAGAGCACTGGGACGCCCACCGCCCCTTTCCCTCCGCTGCCAGGCGAGCA<br>TGTTGTGGTAATTCTGGAACACAAGAAGAGAAATTGCTGGGTTTAGAACAAGATTATAAACGA<br>ATTCGGTGCTCAGTGATCACTTGACAGTTTTTTTTTTTTTAAATATTACCCAAAATGCTCCC<br>CAAATAAGAAATGCATCAGCTCAGTCAGTGAATACAAAAAAGGAATTATTTTTCCCTTTGAGG<br>GTCTTTTATACATCTCTCCTCCAACCCCACCCTCTATTCTGTTTCTTCCTCCTCACATGGGGG<br>TACACATACACAGCTTCCTCTTTTGGTTCCATCCTTACCACCACACCACACGCACACTCCACA<br>TGCCCAGCAGAGTGGCACTTGGTGGCCAGAAAGTGTGAGCCTCATGATCTGCTGTCTGTAGTT<br>CTGTGAGCTCAGGTCCCTCAAAGGCCTCGGAGCACCCCCTTCCTTGTGACTGAGCCAGGGCCT<br>GCATTTTTGGTTTTCCCCACCCCACACATTCTCAACCATAGTCCTTCTAACAATACCAATAGC<br>TAGGACCCGGCTGCTGTGCACTGGGACTGGGGATTCCACATGTTTGCCTTGGGAGTCTCAAGC<br>TGGACTGCCA |
| 45 | opt_COX10<br>*-opt_ND4-<br>3'UTR | ATGGCCGCCAGCCCCCACACCCTGAGCAGCCGCCTGCTGACCGGCTGCGTGGGCGGCAGCGTG<br>TGGTACCTGGAGCGCCGCACCATGCTGAAGCTGATCGTGCCCACCATCATGCTGCTGCCTCTG<br>ACCTGGCTGAGCAAGAAACACATGATCTGGATCAACACCACCACGCACAGCCTGATCATCAGC<br>ATCATCCCTCTGCTGTTCTTCAACCAGATCAACAACAACCTGTTCAGCTGCAGCCCCACCTTC<br>AGCAGCGACCCTCTGACAACACCTCTGCTGATGCTGACCACCTGGCTGCTGCCCCTCACAATC<br>ATGGCCTCTCAGAGACACCTGAGCAGCGAGCCCCTGAGCCGGAAGAAACTGTACCTGAGCATG<br>CTGATCTCCCTGCAGATCTCTCTGATCATGACCTTCACCGCCACCGAGCTGATCATGTTCTAC<br>ATCTTTTTTCGAGACAACGCTGATCCCCACACTGGCCATCATCACCAGATGGGGCAACCAGCCT<br>GAGAGACTGAACGCCGGCACCTACTTTCTGTTCTACACCCTCGTGGGCAGCCTGCCACTGCTG<br>ATTGCCCTGATCTACACCCACAACACCCTGGGCTCCCTGAACATCCTGCTGCTGACACTGACA<br>GCCCAAGAGCTGAGCAACAGCTGGGCCAACAATCTGATGTGGCTGGCCTACACAATGGCCTTC<br>ATGGTCAAGATGCCCCTGTACGGCCTGCACCTGTGGCTGCCTAAAGCTCATGTGGAAGCCCCT<br>ATCGCCGGCTCTATGGTGCTGGCTGCAGTGCTGCTGAAACTCGGCGGCTACGGCATGATGCGG<br>CTGACCCTGATTCTGAATCCCCTGACCAAGCACATGGCCTATCCATTTCTGGTGCTGAGCCTG<br>TGGGGCATGATTATGACCAGCAGCATCTGCCTGCGGCAGACCGATCTGAAGTCCCTGATCGCC<br>TACAGCTCCATCAGCCACATGGCCCTGGTGGTCACCGCCATCCTGATTCAGACCCCCTTGGAGC<br>TTTACAGGCGCCGTGATCCTGATGATTGCCCACGGCCTGACAAGCAGCCTGCTGTTTTGTCTG<br>GCCAACAGCAACTACGAGCGGACCCACAGCAGAATCATGATCCTGTCTCAGGGCCTGCAGACC<br>CTCCTGCCTCTTATGGCTTTTTGGTGGCTGCTGCCTCT<br>ACCATCAATCTGCTGGGCGAGCTGAGCGTGCTGGTCACCACATTCAGCTGGTCCAATATCACC<br>CTGCTGCTCACCGGCCTGAACATGCTGGTTACAGCCCTGTACTCCCTGTACATGTTCACCACC<br>ACACAGTGGGGAAGCCTGACACACCCATCAACAATATGAAGCCCAGCTTCACCCGCGAGAAC<br>ACCCTGATGTTCATGCATCTGAGCCCCATTCTGCTGCTGCCCTGAATCCTGATATCATCACC<br>GGCTTCTCCAGCTGAGAGCACTGGGACGCCCACCGCCCCTTTCCCTCCGCTGCCAGGCGAGCA<br>TGTTGTGGTAATTCTGGAACACAAGAAGAGAAATTGCTGGGTTTAGAACAAGATTATAAACGA<br>ATTCGGTGCTCAGTGATCACTTGACAGTTTTTTTTTTTTTAAATATTACCCAAAATGCTCCC<br>CAAATAAGAAATGCATCAGCTCAGTCAGTGAATACAAAAAAGGAATTATTTTTCCCTTTGAGG<br>GTCTTTTATACATCTCTCCTCCAACCCCACCCTCTATTCTGTTTCTTCCTCCTCACATGGGGG<br>TACACATACACAGCTTCCTCTTTTGGTTCCATCCTTACCACCACACCACACGCACACTCCACA<br>TGCCCAGCAGAGTGGCACTTGGTGGCCAGAAAGTGTGAGCCTCATGATCTGCTGTCTGTAGTT<br>CTGTGAGCTCAGGTCCCTCAAAGGCCTCGGAGCACCCCCTTCCTTGTGACTGAGCCAGGGCCT<br>GCATTTTTGGTTTTCCCCACCCCACACATTCTCAACCATAGTCCTTCTAACAATACCAATAGC<br>TAGGACCCGGCTGCTGTGCACTGGGACTGGGGATTCCACATGTTTGCCTTGGGAGTCTCAAGC<br>TGGACTGCCAGCCCCTGTCCTCCCTTCACCCCCATTGCGTATGAGCATTTCAGAACTCCAAGG<br>AGTCACAGGCATCTTTATAGTTCACGTTAACATATAGACACTGTTGGAAGCAGTTCCTTCTAA<br>AAGGGTAGCCCTGGACTTAATACCAGCCGGATACCTCTGGCCCCCACCCCATTACTGTACCTC<br>TGGAGTCACTACTGTGGGTCGCCACTCCTCTGCTACACAGCACGGCTTTTTCAAGGCTGTATT<br>GAGAAGGGAAGTTAGGAAGAAGGGTGTGCTGGGCTAACCAGCCCACAGAGCTCACATTCCTGT<br>CCCTTGGGTGAAAATACATGTCCATCCTGATATCTCCTGAATTCAGAAATTAGCCTCCACAT<br>GTGCAATGGCTTTAAGAGCCAGAAGCAGGGTTCTGGGAATTTTGCAAGTTACCTGTGGCCAGG<br>TGTGGTCTCGGTTACCAAATACGGTTACCTGCAGCTTTTTAGTCCTTTGTGCTCCCACGGGTC |

TABLE 1-continued nucleic acid and polypeptide sequences and SEQ ID NOs

| SEQ | Description | Sequence |
|---|---|---|
| | | TACAGAGTCCCATCTGCCCAAAGGTCTTGAAGCTTGACAGGATGTTTTCGATTACTCAGTCTC<br>CCAGGGCACTACTGGTCCGTAGGATTCGATTGGTCGGGGTAGGAGAGTTAAACAACATTTAAA<br>CAGAGTTCTCTCAAAAATGTCTAAAGGGATTGTAGGTAGATAACATCCAATCACTGTTTGCAC<br>TTATCTGAAATCTTCCCTCTTGGCTGCCCCCAGGTATTTACTGTGGAGAACATTGCATAGGAA<br>TGTCTGGAAAAAGCTTCTACAACTTGTTACAGCCTTCACATTTGTAGAAGCTTT |
| 46 | opt_COX10<br>*-opt_ND4-<br>3'UTR* | ATGGCCGCCAGCCCCCACACCCTGAGCAGCCGCCTGCTGACCGGCTGCGTGGGCGGCAGCGTG<br>TGGTACCTGGAGCGCCGCACCATGCTGAAGCTGATCGTGCCCACCATCATGCTGCTGCCCTCTG<br>ACCTGGCTGAGCAAGAAACACATGATCTGGATCAACACCACCACGCACAGCCTGATCATCAGC<br>ATCATCCCTCTGCTGTTCTTCAACCAGATCAACAACAACCTGTTCAGCTGCAGCCCCACCTTC<br>AGCAGCGACCCTCTGACAACACCTCTGCTGATGCTGACCACCTGGCTGCTGCCCCTCACAATC<br>ATGGCCTCTCAGAGACACCTGAGCAGCGAGCCCCTGAGCCGGAAGAAACTGTACCTGAGCATG<br>CTGATCTCCCTGCAGATCTCTCTGATCATGACCTTCACCGCCACCGAGCTGATCATGTTCTAC<br>ATCTTTTTTCGAGACAACGCTGATCCCCACACTGGCCATCATCACCAGATGGGGCAACCAGCCT<br>GAGAGACTGAACGCCGGCACCTACTTTCTGTTCTACACCCTCGTGGGCAGCCTGCCACTGCTG<br>ATTGCCCTGATCTACACCCACAACACCCTGGGCTCCCTGAACATCCTGCTGCTGACACTGACA<br>GCCCAAGAGCTGAGCAACAGCTGGGCCAACAATCTGATGTGGCTGGCCTACACAATGGCCTTC<br>ATGGTCAAGATGCCCCTGTACGGCCTGCACCTGTGGCTGCCTAAAGCTCATGTGGAAGCCCCT<br>ATCGCCGGCTCTATGGTGCTGGCTGCAGTGCTGCTGAAACTCGGCGGCTACGGCATGATGCGG<br>CTGACCCTGATTCTGAATCCCCTGACCAAGCACATGGCCTATCCATTTCTGGTGCTGAGCCTG<br>TGGGGCATGATTATGACCAGCAGCATCTGCCTGCGGCAGACCGATCTGAAGTCCCTGATCGCC<br>TACAGCTCCATCAGCCACATGGCCCTGGTGGTCACCGCCATCCTGATTCAGACCCCTTGGAGC<br>TTTACAGGCGCCGTGATCCTGATGATTGCCCACGGCCTGACAAGCAGCCTGCTGTTTTGTCTG<br>GCCAACAGCAACTACGAGCGGACCCACAGCAGAATCATGATCCTGTCTCAGGGCCTGCAGACC<br>CTCCTGCCTCTTATGGCTTTTTGGTGGCTGCTGCCTCTCTGGCCAATCTGGCACTGCCTCCT<br>ACCATCAATCTGCTGGGCGAGCTGAGCGTGCTGGTCACCACATTCAGCTGGTCCAATATCACC<br>CTGCTGCTCACCGGCCTGAACATGCTGGTTACAGCCCTGTACTCCCTGTACATGTTCACCACC<br>ACACAGTGGGGAAGCCTGACACACCCACATCAACAATATGAAGCCCAGCTTCACCCGCGAGAAC<br>ACCCTGATGTTCATGCATCTGAGCCCCATTCTGCTGCTGTCCCTGAATCCTGATATCATCACC<br>GGCTTCTCCAGCTGAGAGCACTGGGACGCCCACCGCCCCTTTCCCTCCGCTGCCAGGCGAGCA<br>TGTTGTGGTAATTCTGGAACACAAGAAGAGAAATTGCTGGGTTTAGAACAAGATTATAAACGA<br>ATTCGGTGCTCAGTGATCACTTGACAGTTTTTTTTTTTTTAAATATTACCCAAAATGCTCCC<br>CAAATAAGAAATGCATCAGCTCAGTCAGTGAATACAAAAAAGGAATTATTTTTCCCTTTGAGG<br>GTCTTTTATACATCTCTCCTCCAACCCCACCCTCTATTCTGTTTCTTCCTCCTCACATGGGGG<br>TACACATACACAGCTTCCTCTTTTGGTTCCATCCTTACCACCACACCACACGCACACTCCACA<br>TGCCCAGCAGAGTGGCACTTGGTGGCCAGAAAGTGTGAGCCTCATGATCTGCTGTCTGTAGTT<br>CTGTGAGCTCAGGTCCCTCAAAGGCCTCGGAGCACCCCCTTCCTTGTGACTGAGCCAGGGCCT<br>GCATTTTTGGTTTTCCCCACCCCACACATTCTCAACCATAGTCCTTCTAACAATACCAATAGC<br>TAGGACCCGGCTGCTGTGCACTGGGACTGGGGATTCCACATGTTTGCCTTGGGAGTCTCAAGC<br>TGGACTGCCA |
| 47 | opt_COX10<br>*-<br>opt_ND4*-<br>3'UTR | ATGGCCGCCAGCCCCCACACCCTGAGCAGCCGCCTGCTGACCGGCTGCGTGGGCGGCAGCGTG<br>TGGTACCTGGAGCGCCGCACCATGCTGAAGCTGATCGTGCCCACCATCATGCTGCTGCCCCTG<br>ACCTGGCTGAGCAAGAAGCACATGATCTGGATCAACACCACCACCCACAGCCTGATCATCAGC<br>ATCATCCCCCTGCTGTTCTTCAACCAGATCAACAACAACCTGTTCAGCTGCAGCCCCACCTTC<br>AGCAGCGACCCCCTGACCACCCCCTGCTGATGCTGACCACCTGGCTGCTGCCCCTGACCATC<br>ATGGCCAGCCAGCGCCACCTGAGCAGCGAGCCCCTGAGCCGCAAGAAGCTGTACCTGAGCATG<br>CTGATCAGCCTGCAGATCAGCCTGATCATGACCTTCACCGCCACCGAGCTGATCATGTTCTAC<br>ATCTTCTTCGAGACCACCCTGATCCCCACCCTGGCCATCATCACCCGCTGGGGCAACCAGCCC<br>GAGCGCCTGAACGCCGGCACCTACTTCCTGTTCTACACCCTGGTGGGCAGCCTGCCCCTGCTG<br>ATCGCCCTGATCTACACCCACAACACCCTGGGCAGCCTGAACATCCTGCTGCTGACCCTGACC<br>GCCCAGGAGCTGAGCAACAGCTGGGCCAACAACCTGATGTGGCTGGCCTACACCATGGCCTTC<br>ATGGTGAAGATGCCCCTGTACGGCCTGCACCTGTGGCTGCCCAAGGCCCACGTGGAGGCCCCC<br>ATCGCCGGCAGCATGGTGCTGGCCGCCGTGCTGCTGAAGCTGGGCGGCTACGGCATGATGCGC<br>CTGACCCTGATCCTGAACCCCCTGACCAAGCACATGGCCTACCCCTTCCTGGTGCTGAGCCTG<br>TGGGGCATGATCATGACCAGCAGCATCTGCCTGCGCCAGACCGACCTGAAGAGCCTGATCGCC<br>TACAGCAGCATCAGCCACATGGCCCTGGTGGTGACCGCCATCCTGATCCAGACCCCCTGGAGC<br>TTCACCGGCGCCGTGATCCTGATGATCGCCCACGGCCTGACCAGCAGCCTGCTGTTCTGCCTG<br>GCCAACAGCAACTACGAGCGCACCCACAGCCGCATCATGATCCTGAGCCAGGGCCTGCAGACC<br>CTGCTGCCCCTGATGGCCTTCTGGTGGCTGCTGGCCAGCCTGGCCAACCTGGCCCTGCCCCCC<br>ACCATCAACCTGCTGGGCGAGCTGAGCGTGCTGGTGACCACCTTCAGCTGGAGCAACATCACC<br>CTGCTGCTGACCGGCCTGAACATGCTGGTGACCGCCCTGTACAGCCTGTACATGTTCACCACC<br>ACCCAGTGGGGCAGCCTGACCCACCACATCAACAACATGAAGCCCAGCTTCACCCGCGAGAAC<br>ACCCTGATGTTCATGCACCTGAGCCCCATCCTGCTGCTGAGCCTGAACCCCGACATCATCACC<br>GGCTTCAGCAGCTAAGAGCACTGGGACGCCCACCGCCCCTTTCCCTCCGCTGCCAGGCGAGCA<br>TGTTGTGGTAATTCTGGAACACAAGAAGAGAAATTGCTGGGTTTAGAACAAGATTATAAACGA<br>ATTCGGTGCTCAGTGATCACTTGACAGTTTTTTTTTTTTTAAATATTACCCAAAATGCTCCC<br>CAAATAAGAAATGCATCAGCTCAGTCAGTGAATACAAAAAAGGAATTATTTTTCCCTTTGAGG<br>GTCTTTTATACATCTCTCCTCCAACCCCACCCTCTATTCTGTTTCTTCCTCCTCACATGGGGG<br>TACACATACACAGCTTCCTCTTTTGGTTCCATCCTTACCACCACACCACACGCACACTCCACA<br>TGCCCAGCAGAGTGGCACTTGGTGGCCAGAAAGTGTGAGCCTCATGATCTGCTGTCTGTAGTT<br>CTGTGAGCTCAGGTCCCTCAAAGGCCTCGGAGCACCCCCTTCCTTGTGACTGAGCCAGGGCCT<br>GCATTTTTGGTTTTCCCCACCCCACACATTCTCAACCATAGTCCTTCTAACAATACCAATAGC<br>TAGGACCCGGCTGCTGTGCACTGGGACTGGGGATTCCACATGTTTGCCTTGGGAGTCTCAAGC<br>TGGACTGCCAGCCCCTGTCCTCCCTTCACCCCCATTGCGTATGAGCATTTCAGAACTCCAAGG<br>AGTCACAGGCATCTTTATAGTTCACGTTAACATATAGACACTGTTGGAAGCAGTTCCTTCTAA |

TABLE 1-continued nucleic acid and polypeptide sequences and SEQ ID NOs

| SEQ | Description | Sequence |
|---|---|---|
| | | AAGGGTAGCCCTGGACTTAATACCAGCCGGATACCTCTGGCCCCCACCCCATTACTGTACCTC<br>TGGAGTCACTACTGTGGGTCGCCACTCCTCTGCTACACAGCACGGCTTTTTCAAGGCTGTATT<br>GAGAAGGGAAGTTAGGAAGAAGGGTGTGCTGGGCTAACCAGCCCACAGAGCTCACATTCCTGT<br>CCCTTGGGTGAAAAATACATGTCCATCCTGATATCTCCTGAATTCAGAAATTAGCCTCCACAT<br>GTGCAATGGCTTTAAGAGCCAGAAGCAGGGTTCTGGGAATTTTGCAAGTTACCTGTGGCCAGG<br>TGTGGTCTCGGTTACCAAATACGGTTACCTGCAGCTTTTTAGTCCTTTGTGCTCCCACGGGTC<br>TACAGAGTCCCATCTGCCCAAAGGTCTTGAAGCTTGACAGGATGTTTTCGATTACTCAGTCTC<br>CCAGGGCACTACTGGTCCGTAGGATTCGATTGGTCGGGGTAGGAGAGTTAAACAACATTTAAA<br>CAGAGTTCTCTCAAAAATGTCTAAAGGGATTGTAGGTAGATAACATCCAATCACTGTTTGCAC<br>TTATCTGAAATCTTCCCTCTTGGCTGCCCCCAGGTATTTACTGTGGAGAACATTGCATAGGAA<br>TGTCTGGAAAAAGCTTCTACAACTTGTTACAGCCTTCACATTTGTAGAAGCTTT |
| 48 | opt_COX10<br>*-<br>opt_ND4*-<br>3'UTR* | ATGGCCGCCAGCCCCCACACCCTGAGCAGCCGCCTGCTGACCGGCTGCGTGGGCGGCAGCGTG<br>TGGTACCTGGAGCGCCGCACCATGCTGAAGCTGATCGTGCCCACCATCATGCTGCTGCCCCTG<br>ACCTGGCTGAGCAAGAAGCACATGATCTGGATCAACACCACCACCCACAGCCTGATCATCAGC<br>ATCATCCCCCTGCTGTTCTTCAACCAGATCAACAACAACCTGTTCAGCTGCAGCCCCACCTTC<br>AGCAGCGACCCCCTGACCACCCCCCTGCTGATGCTGACCACTTGGCTGCTGCCCCTGACCATC<br>ATGGCCAGCCAGCGCCACCTGAGCAGCGAGCCCCTGAGCCGCAAGAAGCTGTACCTGAGCATG<br>CTGATCAGCCTGCAGATCAGCCTGATCATGACCTTCACCGCCACCGAGCTGATCATGTTCTAC<br>ATCTTCTTCGAGACCACCCTGATCCCCACCCTGGCCATCATCACCCGCTGGGGCAACCAGCCC<br>GAGCGCCTGAACGCCGGACACCTACTTCCTGTTCTACACCCTGGTGGGCAGCCTGCCCCTGCTG<br>ATCGCCCTGATCTACACCCACAACACCCTGGGCAGCCTGAACATCCTGCTGCTGACCCTGACC<br>GCCCAGGAGCTGAGCAACAGCTGGGCCAACAACCTGATGTGGCTGGCCTACACCATGGCCTTC<br>ATGGTGAAGATGCCCCTGTACGGCCTGCACCTGTGGCTGCCCAAGGCCCACGTGGAGGCCCCC<br>ATCGCCGGCAGCATGGTGCTGGCCGCCGTGCTGCTGAAGCTGGGCGGCTACGGCATGATGCGC<br>CTGACCCTGATCCTGAACCCCCTGACCAAGCACATGGCCTACCCCTTCCTGGTGCTGAGCCTG<br>TGGGGCATGATCATGACCAGCAGCATCTGCCTGCGCCAGACCGACCTGAAGAGCCTGATCGCC<br>TACAGCAGCATCAGCCACATGGCCCTGGTGGTGACCGCCATCCTGATCCAGACCCCCTGGAGC<br>TTCACCGGCGCCGTGATCCTGATGATCGCCCACGGCCTGACCAGCAGCCTGCTGTTCTGCCTG<br>GCCAACAGCAACTACGAGCGCACCCACAGCCGCATCATGATCCTGAGCCAGGGCCTGCAGACC<br>CTGCTGCCCCTGATGGCCTTCTGGTGGCTGCTGGCCAGCCTGGCCAACCTGGCCCTGCCCCCC<br>ACCATCAACCTGCTGGGCGAGCTGAGCGTGCTGGTGACCACCTTCAGCTGGAGCAACATCACC<br>CTGCTGCTGACCGGCCTGAACATGCTGGTGACCGCCCTGTACAGCCTGTACATGTTCACCACC<br>ACCCAGTGGGGCAGCCTGACCCACCACATCAACAACATGAAGCCCAGCTTCACCCGCAGGAAC<br>ACCCTGATGTTCATGCACCTGAGCCCCATCCTGCTGCTGAGCCTGAACCCCGACATCATCACC<br>GGCTTCAGCAGCTAAGAGCACTGGGACGCCCACCGCCCCTTTCCCTCCGCTGCCAGGCGAGCA<br>TGTTGTGGTAATTCTGGAACACAAGAAGAGAAATTGCTGGGTTTAGAACAAGATTATAAACGA<br>ATTCGGTGCTCAGTGATCACTTGACAGTTTTTTTTTTTTTTAAATATTACCCAAAATGCTCCC<br>CAAATAAGAAATGCATCAGCTCAGTCAGTGAATACAAAAAAGGAATTATTTTTCCCTTTGAGG<br>GTCTTTTATACATCTCTCCTCCAACCCCACCCTCTATTCTGTTTCTTCCTCCTCACATGGGGG<br>TACACATACACAGCTTCCTCTTTTGGTTCCATCCTTACCACCACACCACACGCACACTCCACA<br>TGCCCAGCAGAGTGGCACTTGGTGGCCAGAAAGTGTGAGCCTCATGATCTGCTGTCTGTAGTT<br>CTGTGAGCTCAGGTCCCTCAAAGGCCTCGGAGCACCCCCTTCCTTGTGACTGAGCCAGGGCCT<br>GCATTTTTGGTTTTCCCCACCCCACACATTCTCAACCATAGTCCTTCTAACAATACCAATAGC<br>TAGGACCCGGCTGCTGTGCACTGGGACTGGGGATTCCACATGTTTGCCTTGGGAGTCTCAAGC<br>TGGACTGCCA |
| 49 | opt_COX10<br>*-ND6-<br>3'UTR | ATGGCCGCCAGCCCCCACACCCTGAGCAGCCGCCTGCTGACCGGCTGCGTGGGCGGCAGCGTG<br>TGGTACCTGGAGCGCCGCACCATGATGTATGCTTTGTTTCTGTTGAGTGTGGGTTTAGTAATG<br>GGGTTTGTGGGGTTTTCTTCTAAGCCTTCTCCTATTTATGGGGGTTTAGTATTGATTGTTAGC<br>GGTGTGGTCGGGTGTGTTATTATTCTGAATTTTGGGGGAGGTTATATGGGTTTAATGGTTTTT<br>TTAATTTATTTAGGGGGAATGATGGTTGTCTTTGGATATACTACAGCGATGGCTATTGAGGAG<br>TATCCTGAGGCATGGGGGTCAGGGGTTGAGGTCTTGGTGAGTGTTTTAGTGGGGTTAGCGATG<br>GAGGTAGGATTGGTGCTGTGGGTGAAAGAGTATGATGGGGTGGTGGTTGTGGTAAACTTTAAT<br>AGTGTAGGAAGCTGGATGATTTATGAAGGAGAGGGGTCAGGGTTGATTCGGGAGGATCCTATT<br>GGTGCGGGGCTTTGTATGATTATGGGCGTTGGTTAGTAGTAGTTACTGGTTGGACATTGTTT<br>GTTGGTGTATATATTGTAATTGAGATTGCTCGGGGGAATTAGGAGCACTGGGACGCCCACCGC<br>CCCTTTCCCTCCGCTGCCAGGCGAGCATGTTGTGGTAATTCTGGAACACAAGAAGAGAAATTG<br>CTGGGTTTAGAACAAGATTATAAACGAATTCGGTGCTCAGTGATCACTTGACAGTTTTTTTT<br>TTTTTTAAATATTACCCAAAATGCTCCCCAAATAAGAAATGCATCAGCTCAGTCAGTGAATACA<br>AAAAAGGAATTATTTTTCCCTTTGAGGGTCTTTTATACATCTCTCCTCCAACCCCACCCTCTA<br>TTCTGTTTCTTCCTCCTCACATGGGGTACACATACACAGCTTCCTCTTTTGGTTCCATCCTT<br>ACCACCACACCACACGCACACTCCACATGCCCAGCAGAGTGGCACTTGGTGGCCAGAAAGTGT<br>GAGCCTCATGATCTGCTGTCTGTAGTTCTGTGAGCTCAGGTCCCTCAAAGGCCTCGGAGCACC<br>CCCTTCCTTGTGACTGAGCCAGGGCCTGCATTTTTGGTTTTCCCCACCCCACACATTCTCAAC<br>CATAGTCCTTCTAACAATACCAATAGCTAGGACCCGGCTGCTGTGCACTGGGACTGGGGATTC<br>CACATGTTTGCCTTGGGAGTCTCAAGCTGGACTGCCAGCCCCTGTCCTCCCTTCACCCCCATT<br>GCGTATGAGCATTTCAGAACTCCAAGGAGTCACAGGCATCTTTATAGTTCACGTTAACATATA<br>GACACTGTTGGAAGCAGTTCCTTCTAAAAGGGTAGCCCTGGACTTAATACCAGCCGGATACCT<br>CTGGCCCCCACCCCATTACTGTACCTCTGGAGTCACTACTGTGGGTCGCCACTCCTCTGCTAC<br>ACAGCACGGCTTTTTCAAGGCTGTATTGAGAAGGGAAGTTAGGAAGAAGGGTGTGCTGGGCTA<br>ACCAGCCCACAGAGCTCACATTCCTGTCCCTTGGGTGAAAAATACATGTCCATCCTGATATCT<br>CCTGAATTCAGAAATTAGCCTCCACATGTGCAATGGCTTTAAGAGCCAGAAGCAGGGTTCTGG<br>GAATTTTGCAAGTTACCTGTGGCCAGGTGTGGTCTCGGTTACCAAATACGGTTACCTGCAGCT<br>TTTTAGTCCTTTGTGCTCCCACGGGTCTACAGAGTCCCATCTGCCCAAAGGTCTTGAAGCTTG<br>ACAGGATGTTTTCGATTACTCAGTCTCCCAGGGCACTACTGGTCCGTAGGATTCGATTGGTCG |

TABLE 1-continued nucleic acid and polypeptide sequences and SEQ ID NOs

| SEQ | Description | Sequence |
|---|---|---|
| | | GGGTAGGAGAGTTAAACAACATTTAAACAGAGTTCTCTCAAAAATGTCTAAAGGGATTGTAGG<br>TAGATAACATCCAATCACTGTTTGCACTTATCTGAAATCTTCCCTCTTGGCTGCCCCCAGGTA<br>TTTACTGTGGAGAACATTGCATAGGAATGTCTGGAAAAAGCTTCTACAACTTGTTACAGCCTT<br>CACATTTGTAGAAGCTTT |
| 50 | opt_COX10<br>*-ND6-<br>3'UTR* | ATGGCCGCCAGCCCCCACACCCTGAGCAGCCGCCTGCTGACCGGCTGCGTGGGCGGCAGCGTG<br>TGGTACCTGGAGCGCCGCACCATGATGTATGCTTTGTTTCTGTTGAGTGTGGGTTTAGTAATG<br>GGGTTTGTGGGGTTTTCTTCTAAGCCTTCTCCTATTTATGGGGGTTTAGTATTGATTGTTAGC<br>GGTGTGGTCGGGTGTGTTATTATTCTGAATTTTGGGGGAGGTTATATGGGTTTAATGGTTTTT<br>TTAATTTATTTAGGGGGAATGATGGTTGTCTTTGGATATACTACAGCGATGGCTATTGAGGAG<br>TATCCTGAGGCATGGGGGTCAGGGGTTGAGGTCTTGGTGAGTGTTTTAGTGGGGTTAGCGATG<br>GAGGTAGGATTGGTGCTGTGGGTGAAAGAGTATGATGGGGTGGTGGTTGTGGTAAACTTTAAT<br>AGTGTAGGAAGCTGGATGATTTATGAAGGAGAGGGGTCAGGGTTGATTCGGAGGATCCTATT<br>GGTGCGGGGGCTTTGTATGATTATGGGCGTTGGTTAGTAGTAGTTACTGGTTGGACATTGTTT<br>GTTGGTGTATATATTGTAATTGAGATTGCTCGGGGGAATTAGGAGCACTGGGACGCCCACCGC<br>CCCTTTCCCTCCGCTGCCAGGCGAGCATGTTGTGGTAATTCTGGAACACAAGAAGAGAAATTG<br>CTGGGTTTAGAACAAGATTATAAACGAATTCGGTGCTCAGTGATCACTTGACAGTTTTTTTT<br>TTTTTAAATATTACCCAAAATGCTCCCCAAATAAGAAATGCATCAGCTCAGTCAGTGAATACA<br>AAAAGGAATTATTTTTCCCTTTGAGGGTCTTTTATACATCTCTCCTCCAACCCCACCCTCTA<br>TTCTGTTTCTTCCTCCTCACATGGGGGTACACATACACAGCTTCCTCTTTTGGTTCCATCCTT<br>ACCACCACACCACACGCACACTCCACATGCCCAGCAGAGTGGCACTTGGTGGCCAGAAAGTGT<br>GAGCCTCATGATCTGCTGTCTGTAGTTCTGTGAGCTCAGGTCCCTCAAAGGCCTCGGAGCACC<br>CCCTTCCTTGTGACTGAGCCAGGGCCTGCATTTTTGGTTTTCCCCACCCCACACATTCTCAAC<br>CATAGTCCTTCTAACAATACCAATAGCTAGGACCCGGCTGCTGTGCACTGGGACTGGGGATTC<br>CACATGTTTGCCTTGGGAGTCTCAAGCTGGACTGCCA |
| 51 | opt_COX10<br>*-opt_ND6-<br>3'UTR | ATGGCCGCCAGCCCCCACACCCTGAGCAGCCGCCTGCTGACCGGCTGCGTGGGCGGCAGCGTG<br>TGGTACCTGGAGCGCCGCACCATGATGTACGCCCTGTTCCTGCTGAGCGTGGGCCTGGTGATG<br>GGCTTCGTGGGCTTCAGCAGCAAGCCCAGCCCCATCTACGGCGGCCTGGTGCTGATCGTGAGC<br>GGCGTGGTGGGCTGCGTGATCATCCTGAACTTCGGCGGCGGCTACATGGGCCTGATGGTGTTC<br>CTGATCTACCTGGGCGGCATGATGGTGGTGTTCGGCTACACCACCGCCATGGCCATCGAGGAG<br>TACCCCGAGGCCTGGGCAGCGGCGTGGAGGTGCTGGTGAGCGTGCTGGTGGGCCTGGCCATG<br>GAGGTGGGCCTGGTGCTGTGGGTGAAGGAGTACGACGGCGTGGTGGTGGTGAACTTCAAC<br>AGCGTGGGCAGCTGGATGATCTACGAGGGCGAGGGCAGCGGCCTGATCCGCGAGGACCCCATC<br>GGCGCCGGCGCCCTGTACGACTACGGCCGCTGGCTGGTGGTGGTGACCGGCTGGACCCTGTTC<br>GTGGGCGTGTACATCGTGATCGAGATCGCCCGCGGCAACTAAGAGCACTGGGACGCCCACCGC<br>CCCTTTCCCTCCGCTGCCAGGCGAGCATGTTGTGGTAATTCTGGAACACAAGAAGAGAAATTG<br>CTGGGTTTAGAACAAGATTATAAACGAATTCGGTGCTCAGTGATCACTTGACAGTTTTTTTT<br>TTTTTAAATATTACCCAAAATGCTCCCCAAATAAGAAATGCATCAGCTCAGTCAGTGAATACA<br>AAAAGGAATTATTTTTCCCTTTGAGGGTCTTTTATACATCTCTCCTCCAACCCCACCCTCTA<br>TTCTGTTTCTTCCTCCTCACATGGGGGTACACATACACAGCTTCCTCTTTTGGTTCCATCCTT<br>ACCACCACACCACACGCACACTCCACATGCCCAGCAGAGTGGCACTTGGTGGCCAGAAAGTGT<br>GAGCCTCATGATCTGCTGTCTGTAGTTCTGTGAGCTCAGGTCCCTCAAAGGCCTCGGAGCACC<br>CCCTTCCTTGTGACTGAGCCAGGGCCTGCATTTTTGGTTTTCCCCACCCCACACATTCTCAAC<br>CATAGTCCTTCTAACAATACCAATAGCTAGGACCCGGCTGCTGTGCACTGGGACTGGGGATTC<br>CACATGTTTGCCTTGGGAGTCTCAAGCTGGACTGCCAGCCCCTGTCCTCCCTTCACCCCCATT<br>GCGTATGAGCATTTCAGAACTCCAAGGAGTCACAGGCATCTTTATAGTTCACGTTAACATATA<br>GACACTGTTGGAAGCAGTTCCTTCTAAAAGGGTAGCCCTGGACTTAATACCAGCCGGATACCT<br>CTGGCCCCCACCCCATTACTGTACCTCTGGAGTCACTACTGTGGGTCGCCACTCCTCTGCTAC<br>ACAGCACGGCTTTTTCAAGGCTGTATTGAGAAGGGAAGTTAGGAAGAAGGGTGTGCTGGGCTA<br>ACCAGCCCACAGAGCTCACATTCCTGTCCCTTGGGTGAAAAATACATGTCCATCCTGATATCT<br>CCTGAATTCAGAAATTAGCCTCCACATGTGCAATGGCTTTAAGAGCCAGAAGCAGGGTTCTGG<br>GAATTTTGCAAGTTACCTGTGGCCAGGTGTGGTCTCGGTTACCAAATACGGTTACCTGCAGCT<br>TTTTAGTCCTTTGTGCTCCCACGGGTCTACAGAGTCCCATCTGCCCAAAGGTCTTGAAGCTTG<br>ACAGGATGTTTTCGATTACTCAGTCTCCCAGGGCACTACTGGTCCGTAGGATTCGATTGGTCG<br>GGGTAGGAGAGTTAAACAACATTTAAACAGAGTTCTCTCAAAAATGTCTAAAGGGATTGTAGG<br>TAGATAACATCCAATCACTGTTTGCACTTATCTGAAATCTTCCCTCTTGGCTGCCCCCAGGTA<br>TTTACTGTGGAGAACATTGCATAGGAATGTCTGGAAAAAGCTTCTACAACTTGTTACAGCCTT<br>CACATTTGTAGAAGCTTT |
| 52 | opt_COX10<br>*-opt_ND6-<br>3'UTR* | ATGGCCGCCAGCCCCCACACCCTGAGCAGCCGCCTGCTGACCGGCTGCGTGGGCGGCAGCGTG<br>TGGTACCTGGAGCGCCGCACCATGATGTACGCCCTGTTCCTGCTGAGCGTGGGCCTGGTGATG<br>GGCTTCGTGGGCTTCAGCAGCAAGCCCAGCCCCATCTACGGCGGCCTGGTGCTGATCGTGAGC<br>GGCGTGGTGGGCTGCGTGATCATCCTGAACTTCGGCGGCGGCTACATGGGCCTGATGGTGTTC<br>CTGATCTACCTGGGCGGCATGATGGTGGTGTTCGGCTACACCACCGCCATGGCCATCGAGGAG<br>TACCCCGAGGCCTGGGCAGCGGCGTGGAGGTGCTGGTGAGCGTGCTGGTGGGCCTGGCCATG<br>GAGGTGGGCCTGGTGCTGTGGGTGAAGGAGTACGACGGCGTGGTGGTGGTGAACTTCAAC<br>AGCGTGGGCAGCTGGATGATCTACGAGGGCGAGGGCAGCGGCCTGATCCGCGAGGACCCCATC<br>GGCGCCGGCGCCCTGTACGACTACGGCCGCTGGCTGGTGGTGGTGACCGGCTGGACCCTGTTC<br>GTGGGCGTGTACATCGTGATCGAGATCGCCCGCGGCAACTAAGAGCACTGGGACGCCCACCGC<br>CCCTTTCCCTCCGCTGCCAGGCGAGCATGTTGTGGTAATTCTGGAACACAAGAAGAGAAATTG<br>CTGGGTTTAGAACAAGATTATAAACGAATTCGGTGCTCAGTGATCACTTGACAGTTTTTTTT<br>TTTTTAAATATTACCCAAAATGCTCCCCAAATAAGAAATGCATCAGCTCAGTCAGTGAATACA<br>AAAAGGAATTATTTTTCCCTTTGAGGGTCTTTTATACATCTCTCCTCCAACCCCACCCTCTA<br>TTCTGTTTCTTCCTCCTCACATGGGGGTACACATACACAGCTTCCTCTTTTGGTTCCATCCTT<br>ACCACCACACCACACGCACACTCCACATGCCCAGCAGAGTGGCACTTGGTGGCCAGAAAGTGT |

TABLE 1-continued nucleic acid and polypeptide sequences and SEQ ID NOs

| SEQ | Description | Sequence |
|---|---|---|
| | | GAGCCTCATGATCTGCTGTCTGTAGTTCTGTGAGCTCAGGTCCCTCAAAGGCCTCGGAGCACC
CCCTTCCTTGTGACTGAGCCAGGGCCTGCATTTTTGGTTTTCCCCACCCCACACATTCTCAAC
CATAGTCCTTCTAACAATACCAATAGCTAGGACCCGGCTGCTGTGCACTGGGACTGGGGATTC
CACATGTTTGCCTTGGGAGTCTCAAGCTGGACTGCCA |
| 53 | opt_COX10
*-ND1-
3'UTR | ATGGCCGCCAGCCCCCACACCCTGAGCAGCCGCCTGCTGACCGGCTGCGTGGGCGGCAGCGTG
TGGTACCTGGAGCGCCGCACCATGGCCAACCTCCTACTCCTCATTGTACCCATTCTAATCGCA
ATGGCATTCCTAATGCTTACCGAACGAAAAATTCTAGGCTATATGCAACTACGCAAAGGCCCC
AACGTTGTAGGCCCCTACGGGCTACTACAACCCTTCGCTGACGCCATAAAACTCTTCACCAAA
GAGCCCCTAAAACCCGCCACATCTACCATCACCCTCTACATCACCGCCCCGACCTTAGCTCTC
ACCATCGCTCTTCTACTATGGACCCCCCTCCCCATGCCCAACCCCCTGGTCAACCTCAACCTA
GGCCTCCTATTTATTCTAGCCACCTCTAGCCTAGCCGTTTACTCAATCCTCTGGTCAGGGTGG
GCATCAAACTCAAACTACGCCCTGATCGGCGCACTGCGAGCAGTAGCCCAAACAATCTCATAT
GAAGTCACCCTAGCCATCATTCTACTATCAACATTACTAATGAGTGGCTCCTTTAACCTCTCC
ACCCTTATCACAACACAAGAACACCTCTGGTTACTCCTGCCATCATGGCCCTTGGCCATGATG
TGGTTTATCTCCACACTAGCAGAGACCAACCGAACCCCCTTCGACCTTGCCGAAGGGGAGTCC
GAACTAGTCTCAGGCTTCAACATCGAATACGCCGCAGGCCCCTTCGCCCTATTCTTCATGGCC
GAATACACAAACATTATTATGATGAACACCCTCACCACTACAATCTTCCTAGGAACAACATAT
GACGCACTCTCCCCTGAACTCTACACAACATATTTTGTCACCAAGACCCTACTTCTAACCTCC
CTGTTCTTATGGATTCGAACAGCATACCCCCGATTCCGCTACGACCAACTCATGCACCTCCTA
TGGAAAAACTTCCTACCACTCACCCTAGCATTACTTATGTGGTATGTCTCCATGCCCATTACA
ATCTCCAGCATTCCCCCTCAAACCTAAGAGCACTGGGACGCCCACCGCCCCTTTCCCTCCGCT
GCCAGGCGAGCATGTTGTGGTAATTCTGGAACACAAGAAGAGAAATTGCTGGGTTTAGAACAA
GATTATAAACGAATTCGGTGCTCAGTGATCACTTGACAGTTTTTTTTTTTTAAATATTACC
CAAAATGCTCCCCAAATAAGAAATGCATCAGCTCAGTCAGTGAATACAAAAAAGGAATTATTT
TTCCCTTTGAGGGTCTTTTATACATCTCTCCTCCAACCCCACCCTCTATTCTGTTTCTTCCTC
CTCACATGGGGGTACACATACACAGCTTCCTCTTTTGGTTCCATCCTTACCACCACACCACAC
GCACACTCCACATGCCCAGCAGAGTGGCACTTGGTGGCCAGAAAGTGTGAGCCTCATGATCTG
CTGTCTGTAGTTCTGTGAGCTCAGGTCCCTCAAAGGCCTCGGAGCACCCCCTTCCTTGTGACT
GAGCCAGGGCCTGCATTTTTGGTTTTCCCCACCCCACACATTCTCAACCATAGTCCTTCTAAC
AATACCAATAGCTAGGACCCGGCTGCTGTGCACTGGGACTGGGGATTCCACATGTTTGCCTTG
GGAGTCTCAAGCTGGACTGCCAGCCCCTGTCCTCCCTTCACCCCCATTGCGTATGAGCATTTC
AGAACTCCAAGGAGTCACAGGCATCTTTATAGTTCACGTTAACATATAGACACTGTTGGAAGC
AGTTCCTTCTAAAAGGGTAGCCCTGGACTTAATACCAGCCGGATACCTCTGGCCCCCACCCCA
TTACTGTACCTCTGGAGTCACTACTGTGGGTCGCCACTCCTCTGCTACACAGCACGGCTTTTT
CAAGGCTGTATTGAGAAGGGAAGTTAGGAAGAAGGGTGTGCTGGGCTAACCAGCCCACAGAGC
TCACATTCCTGTCCCTTGGGTGAAAAATACATGTCCATCCTGATATCTCCTGAATTCAGAAAT
TAGCCTCCACATGTGCAATGGCTTTAAGAGCCAGAAGCAGGGTTCTGGGAATTTTGCAAGTTA
CCTGTGGCCAGGTGTGGTCTCGGTTACCAAATACGGTTACCTGCAGCTTTTTAGTCCTTTGTG
CTCCCACGGGTCTACAGAGTCCCATCTGCCCAAAGGTCTTGAAGCTTGACAGGATGTTTTCGA
TTACTCAGTCTCCCAGGGCACTACTGGTCCGTAGGATTCGATTGGTCGGGTAGGAGGTTAA
ACAACATTTAAACAGAGTTCTCTCAAAAATGTCTAAAGGGATTGTAGGTAGATAACATCCAAT
CACTGTTTGCACTTATCTGAAATCTTCCCTCTTGGCTGCCCCCAGGTATTTACTGTGGAGAAC
ATTGCATAGGAATGTCTGGAAAAAGCTTCTACAACTTGTTACAGCCTTCACATTTGTAGAAGC
TTT |
| 54 | opt_COX10
*-ND1-
3'UTR* | ATGGCCGCCAGCCCCCACACCCTGAGCAGCCGCCTGCTGACCGGCTGCGTGGGCGGCAGCGTG
TGGTACCTGGAGCGCCGCACCATGGCCAACCTCCTACTCCTCATTGTACCCATTCTAATCGCA
ATGGCATTCCTAATGCTTACCGAACGAAAAATTCTAGGCTATATGCAACTACGCAAAGGCCCC
AACGTTGTAGGCCCCTACGGGCTACTACAACCCTTCGCTGACGCCATAAAACTCTTCACCAAA
GAGCCCCTAAAACCCGCCACATCTACCATCACCCTCTACATCACCGCCCCGACCTTAGCTCTC
ACCATCGCTCTTCTACTATGGACCCCCCTCCCCATGCCCAACCCCCTGGTCAACCTCAACCTA
GGCCTCCTATTTATTCTAGCCACCTCTAGCCTAGCCGTTTACTCAATCCTCTGGTCAGGGTGG
GCATCAAACTCAAACTACGCCCTGATCGGCGCACTGCGAGCAGTAGCCCAAACAATCTCATAT
GAAGTCACCCTAGCCATCATTCTACTATCAACATTACTAATGAGTGGCTCCTTTAACCTCTCC
ACCCTTATCACAACACAAGAACACCTCTGGTTACTCCTGCCATCATGGCCCTTGGCCATGATG
TGGTTTATCTCCACACTAGCAGAGACCAACCGAACCCCCTTCGACCTTGCCGAAGGGGAGTCC
GAACTAGTCTCAGGCTTCAACATCGAATACGCCGCAGGCCCCTTCGCCCTATTCTTCATGGCC
GAATACACAAACATTATTATGATGAACACCCTCACCACTACAATCTTCCTAGGAACAACATAT
GACGCACTCTCCCCTGAACTCTACACAACATATTTTGTCACCAAGACCCTACTTCTAACCTCC
CTGTTCTTATGGATTCGAACAGCATACCCCCGATTCCGCTACGACCAACTCATGCACCTCCTA
TGGAAAAACTTCCTACCACTCACCCTAGCATTACTTATGTGGTATGTCTCCATGCCCATTACA
ATCTCCAGCATTCCCCCTCAAACCTAAGAGCACTGGGACGCCCACCGCCCCTTTCCCTCCGCT
GCCAGGCGAGCATGTTGTGGTAATTCTGGAACACAAGAAGAGAAATTGCTGGGTTTAGAACAA
GATTATAAACGAATTCGGTGCTCAGTGATCACTTGACAGTTTTTTTTTTTTAAATATTACC
CAAAATGCTCCCCAAATAAGAAATGCATCAGCTCAGTCAGTGAATACAAAAAAGGAATTATTT
TTCCCTTTGAGGGTCTTTTATACATCTCTCCTCCAACCCCACCCTCTATTCTGTTTCTTCCTC
CTCACATGGGGGTACACATACACAGCTTCCTCTTTTGGTTCCATCCTTACCACCACACCACAC
GCACACTCCACATGCCCAGCAGAGTGGCACTTGGTGGCCAGAAAGTGTGAGCCTCATGATCTG
CTGTCTGTAGTTCTGTGAGCTCAGGTCCCTCAAAGGCCTCGGAGCACCCCCTTCCTTGTGACT
GAGCCAGGGCCTGCATTTTTGGTTTTCCCCACCCCACACATTCTCAACCATAGTCCTTCTAAC
AATACCAATAGCTAGGACCCGGCTGCTGTGCACTGGGACTGGGGATTCCACATGTTTGCCTTG
GGAGTCTCAAGCTGGACTGCCA |

TABLE 1-continued nucleic acid and polypeptide sequences and SEQ ID NOs

| SEQ | Description | Sequence |
|---|---|---|
| 55 | opt_COX10*-opt_ND1-3'UTR | ATGGCCGCCAGCCCCCACACCCTGAGCAGCCGCCTGCTGACCGGCTGCGTGGGCGGCAGCGTG<br>TGGTACCTGGAGCGCCGCACCATGGCCAACCTGCTGCTGCTGATCGTGCCCATCCTGATCGCC<br>ATGGCCTTCCTGATGCTGACCGAGCGCAAGATCCTGGGCTACATGCAGCTGCGCAAGGGCCCC<br>AACGTGGTGGGCCCCTACGGCCTGCTGCAGCCCTTCGCCGACGCCATCAAGCTGTTCACCAAG<br>GAGCCCCTGAAGCCCGCCACCAGCACCATCACCCTGTACATCACCGCCCCCACCCTGGCCCTG<br>ACCATCGCCCTGCTGCTGTGGACCCCCCTGCCCATGCCCAACCCCCTGGTGAACCTGAACCTG<br>GGCCTGCTGTTCATCCTGGCCACCAGCAGCCTGGCCGTGTACAGCATCCTGTGGAGCGGCTGG<br>GCCAGCAACAGCAACTACGCCCTGATCGGCGCCCTGCGCGCCGTGGCCCAGACCATCAGCTAC<br>GAGGTGACCCTGGCCATCATCCTGCTGAGCACCCTGCTGATGAGCGGCAGCTTCAACCTGAGC<br>ACCCTGATCACCACCCAGGAGCACCTGTGGCTGCTGCTGCCCAGCTGGCCCCTGGCCATGATG<br>TGGTTCATCAGCACCCTGGCCGAGACCAACCGCACCCCCTTCGACCTGGCCGAGGGCGAGAGC<br>GAGCTGGTGAGCGGCTTCAACATCGAGTACGCCGCCGGCCCCTTCGCCCTGTTCTTCATGGCC<br>GAGTACACCAACATCATCATGATGAACACCCTGACCACCACCATCTTCCTGGGCACCACCTAC<br>GACGCCCTGAGCCCCGAGCTGTACACCACCTACTTCGTGACCAAGACCCTGCTGCTGACCAGC<br>CTGTTCCTGTGGATCCGCACCGCCTACCCCGCTTCCGCTACGACCAGCTGATGCACCTGCTG<br>TGGAAGAACTTCCTGCCCCTGACCCTGGCCCTGCTGATGTGGTACGTGAGCATGCCCATCACC<br>ATCAGCAGCATCCCCCCCCAGACCTAAGAGCACTGGGACGCCCACCGCCCCTTTCCCTCCGCT<br>GCCAGGCGAGCATGTTGTGGTAATTCTGGAACACAAGAAGAGAAATTGCTGGGTTTAGAACAA<br>GATTATAAACGAATTCGGTGCTCAGTGATCACTTGACAGTTTTTTTTTTTTAAATATTACC<br>CAAAATGCTCCCCAAATAAGAAATGCATCAGCTCAGTCAGTGAATACAAAAAAGGAATTATTT<br>TTCCCTTTGAGGGTCTTTTATACATCTCTCCTCCAACCCCACCCTCTATTCTGTTTCTTCCTC<br>CTCACATGGGGGTACACATACACAGCTTCCTCTTTTGGTTCCATCCTTACCACCACACCCACAC<br>GCACACTCCACATGCCCAGCAGAGTGGCACTTGGTGGCCAGAAAGTGTGAGCCTCATGATCTG<br>CTGTCTGTAGTTCTGTGAGCTCAGGTCCCTCAAAGGCCTCGGAGCACCCCCTTCCTTGTGACT<br>GAGCCAGGGCCTGCATTTTTGGTTTTCCCCACCCCACACATTCTCAACCATAGTCCTTCTAAC<br>AATACCAATAGCTAGGACCCGGCTGCTGTGCACTGGGACTGGGGATTCCACATGTTTGCCTTG<br>GGAGTCTCAAGCTGGACTGCCAGCCCCTGTCCTCCCTTCACCCCCATTGCGTATGAGCATTTC<br>AGAACTCCAAGGAGTCACAGGCATCTTTATAGTTCACGTTAACATATAGACACTGTTGGAAGC<br>AGTTCCTTCTAAAAGGGTAGCCCTGGACTTAATACCAGCCGGATACCTCTGGCCCCCACCCCA<br>TTACTGTACCTCTGGAGTCACTACTGTGGGTCGCCACTCCTCTGCTACACAGCACGGCTTTTT<br>CAAGGCTGTATTGAGAAGGGAAGTTAGGAAGAAGGGTGTGCTGGGCTAACCAGCCCACAGAGC<br>TCACATTCCTGTCCCTTGGGTGAAAAATACATGTCCATCCTGATATCTCCTGAATTCAGAAAT<br>TAGCCTCCACATGTGCAATGGCTTTAAGAGCCAGAAGCAGGGTTCTGGGAATTTTGCAAGTTA<br>CCTGTGGCCAGGTGTGGTCTCGGTTACCAAATACGGTTACCTGCAGCTTTTTAGTCCTTTGTG<br>CTCCCACGGGTCTACAGAGTCCCATCTGCCCAAAGGTCTTGAAGCTTGACAGGATGTTTTCGA<br>TTACTCAGTCTCCCAGGGCACTACTGGTCCGTAGGATTCGATTGGTCGGGGTAGGAGAGTTAA<br>ACAACATTTAAACAGAGTTCTCTCAAAAATGTCTAAAGGGATTGTAGGTAGATAACATCCAAT<br>CACTGTTTGCACTTATCTGAAATCTTCCCTCTTGGCTGCCCCCAGGTATTTACTGTGGAGAAC<br>ATTGCATAGGAATGTCTGGAAAAAGCTTCTACAACTTGTTACAGCCTTCACATTTGTAGAAGC<br>TTT |
| 56 | opt_COX10*-opt_ND1-3'UTR* | ATGGCCGCCAGCCCCCACACCCTGAGCAGCCGCCTGCTGACCGGCTGCGTGGGCGGCAGCGTG<br>TGGTACCTGGAGCGCCGCACCATGGCCAACCTGCTGCTGCTGATCGTGCCCATCCTGATCGCC<br>ATGGCCTTCCTGATGCTGACCGAGCGCAAGATCCTGGGCTACATGCAGCTGCGCAAGGGCCCC<br>AACGTGGTGGGCCCCTACGGCCTGCTGCAGCCCTTCGCCGACGCCATCAAGCTGTTCACCAAG<br>GAGCCCCTGAAGCCCGCCACCAGCACCATCACCCTGTACATCACCGCCCCCACCCTGGCCCTG<br>ACCATCGCCCTGCTGCTGTGGACCCCCCTGCCCATGCCCAACCCCCTGGTGAACCTGAACCTG<br>GGCCTGCTGTTCATCCTGGCCACCAGCAGCCTGGCCGTGTACAGCATCCTGTGGAGCGGCTGG<br>GCCAGCAACAGCAACTACGCCCTGATCGGCGCCCTGCGCGCCGTGGCCCAGACCATCAGCTAC<br>GAGGTGACCCTGGCCATCATCCTGCTGAGCACCCTGCTGATGAGCGGCAGCTTCAACCTGAGC<br>ACCCTGATCACCACCCAGGAGCACCTGTGGCTGCTGCTGCCCAGCTGGCCCCTGGCCATGATG<br>TGGTTCATCAGCACCCTGGCCGAGACCAACCGCACCCCCTTCGACCTGGCCGAGGGCGAGAGC<br>GAGCTGGTGAGCGGCTTCAACATCGAGTACGCCGCCGGCCCCTTCGCCCTGTTCTTCATGGCC<br>GAGTACACCAACATCATCATGATGAACACCCTGACCACCACCATCTTCCTGGGCACCACCTAC<br>GACGCCCTGAGCCCCGAGCTGTACACCACCTACTTCGTGACCAAGACCCTGCTGCTGACCAGC<br>CTGTTCCTGTGGATCCGCACCGCCTACCCCGCTTCCGCTACGACCAGCTGATGCACCTGCTG<br>TGGAAGAACTTCCTGCCCCTGACCCTGGCCCTGCTGATGTGGTACGTGAGCATGCCCATCACC<br>ATCAGCAGCATCCCCCCCCAGACCTAAGAGCACTGGGACGCCCACCGCCCCTTTCCCTCCGCT<br>GCCAGGCGAGCATGTTGTGGTAATTCTGGAACACAAGAAGAGAAATTGCTGGGTTTAGAACAA<br>GATTATAAACGAATTCGGTGCTCAGTGATCACTTGACAGTTTTTTTTTTTTAAATATTACC<br>CAAAATGCTCCCCAAATAAGAAATGCATCAGCTCAGTCAGTGAATACAAAAAAGGAATTATTT<br>TTCCCTTTGAGGGTCTTTTATACATCTCTCCTCCAACCCCACCCTCTATTCTGTTTCTTCCTC<br>CTCACATGGGGGTACACATACACAGCTTCCTCTTTTGGTTCCATCCTTACCACCACACCCACAC<br>GCACACTCCACATGCCCAGCAGAGTGGCACTTGGTGGCCAGAAAGTGTGAGCCTCATGATCTG<br>CTGTCTGTAGTTCTGTGAGCTCAGGTCCCTCAAAGGCCTCGGAGCACCCCCTTCCTTGTGACT<br>GAGCCAGGGCCTGCATTTTTGGTTTTCCCCACCCCACACATTCTCAACCATAGTCCTTCTAAC<br>AATACCAATAGCTAGGACCCGGCTGCTGTGCACTGGGACTGGGGATTCCACATGTTTGCCTTG<br>GGAGTCTCAAGCTGGACTGCCA |
| 57 | COX8-ND4-3'UTR | ATGTCCGTCCTGACGCGCCTGCTGCTGCGGGGCTTGACACGGCTCGGCTCGGCGGCTCCAGTG<br>CGGCGCGCCAGAATCCATTCGTTGATGCTAAAACTAATCGTCCCAACAATTATGTTACTACCA<br>CTGACATGGCTTTCCAAAAAACACATGATTTGGATCAACACAACCACCCACAGCCTAATTATT<br>AGCATCATCCCTCTACTATTTTTAACCAAATCAACAACAACCTATTTAGCTGTTCCCCAACC<br>TTTTCCTCCGACCCCCTAACAACCCCCCTCCTAATGCTAACTACCTGGCTCCTACCCCTCACA<br>ATCATGGCAAGCCAACGCCACTTATCCAGTGAACCACTATCACGAAAAAAACTCTACCTCTCT<br>ATGCTAATCTCCCTACAAATCTCCTTAATTATGACATTCACAGCCACAGAACTAATCATGTTT |

TABLE 1-continued nucleic acid and polypeptide sequences and SEQ ID NOs

| SEQ | Description | Sequence |
|---|---|---|
| | | TATATCTTCTTCGAAACCACACTTATCCCCACCTTGGCTATCATCACCCGATGGGGCAACCAG<br>CCAGAACGCCTGAACGCAGGCACATACTTCCTATTCTACACCCTAGTAGGCTCCCTTCCCCTA<br>CTCATCGCACTAATTTACACTCACAACACCCTAGGCTCACTAAACATTCTACTACTCACTCTC<br>ACTGCCCAAGAACTATCAAACTCCTGGGCCAACAACTTAATGTGGCTAGCTTACACAATGGCT<br>TTTATGGTAAAGATGCCTCTTTACGGACTCCACTTATGGCTCCCTAAAGCCCATGTCGAAGCC<br>CCCATCGCTGGGTCAATGGTACTTGCCGCAGTACTCTTAAAACTAGGCGGCTATGGTATGATG<br>CGCCTCACACTCATTCTCAACCCCCTGACAAAACACATGGCCTACCCCTTCCTTGTACTATCC<br>CTATGGGGCATGATTATGACAAGCTCCATCTGCCTACGACAAACAGACCTAAAATCGCTCATT<br>GCATACTCTTCAATCAGCCACATGGCCCTCGTAGTAACAGCCATTCTCATCCAAACCCCCTGG<br>AGCTTCACCGGCGCAGTCATTCTCATGATCGCCCACGGGCTTACATCCTCATTACTATTCTGC<br>CTAGCAAACTCAAACTACGAACGCACTCACAGTCGCATCATGATCCTCTCTCAAGGACTTCAA<br>ACTCTACTCCCACTAATGGCTTTTTGGTGGCTTCTAGCAAGCCTCGCTAACCTCGCCTTACCC<br>CCCACTATTAACCTACTGGGAGAACTCTCTGTGCTAGTAACCACGTTCTCCTGGTCAAATATC<br>ACTCTCCTACTTACAGGACTCAACATGCTAGTCACAGCCCTATACTCCCTCTACATGTTTACC<br>ACAACACAATGGGCTCACTCACCCACCACATTAACAACATGAAACCCTCATTCACACGAGAA<br>AACACCCTCATGTTCATGCACCTATCCCCCATTCTCCTCCTATCCCTCAACCCCGACATCATT<br>ACCGGGTTTTCCTCTTAAGAGCACTGGGACGCCCACCGCCCCTTTCCCTCCGCTGCCAGGCGA<br>GCATGTTGTGGTAATTCTGGAACACAAGAAGAGAAATTGCTGGGTTTAGAACAAGATTATAAA<br>CGAATTCGGTGCTCAGTGATCACTTGACAGTTTTTTTTTTTTAAATATTACCCAAAATGCT<br>CCCCAAATAAGAAATGCATCAGCTCAGTCAGTGAATACAAAAAAGGAATTATTTTTCCCTTTG<br>AGGGTCTTTTATACATCTCTCCTCCAACCCCACCCTCTATTCTGTTTCTTCCTCCTCACATGG<br>GGGTACACATACACAGCTTCCTCTTTTGGTTCCATCCTTACCACCACACCACACGCACACTCC<br>ACATGCCCAGCAGAGTGGCACTTGGTGGCCAGAAAGTGTGAGCCTCATGATCTGCTGTCTGTA<br>GTTCTGTGAGCTCAGGTCCCTCAAAGGCTCGGAGCACCCCCTTCCTTGTGACTGAGCCAGGG<br>CCTGCATTTTTGGTTTTCCCCACCCCACACATTCTCAACCATAGTCCTTCTAACAATACCAAT<br>AGCTAGGACCCGGCTGCTGTGCACTGGGACTGGGGATTCCACATGTTTGCCTTGGGAGTCTCA<br>AGCTGGACTGCCAGCCCCTGTCCTCCCTTCACCCCCATTGCGTATGAGCATTTCAGAACTCCA<br>AGGAGTCACAGGCATCTTTATAGTTCACGTTAACATATAGACACTGTTGGAAGCAGTTCCTTC<br>TAAAAGGGTAGCCCTGGACTTAATACCAGCGGATACCTCTGGCCCCCACCCCATTACTGTAC<br>CTCTGGAGTCACTACTGTGGGTCGCCACTCCTCTGCTACACAGCACGGCTTTTTCAAGGCTGT<br>ATTGAGAAGGGAAGTTAGGAAGAAGGGTGTGCTGGGCTAACCAGCCCACAGAGCTCACATTCC<br>TGTCCCTTGGGTGAAAAATACATGTCCATCCTGATATCTCCTGAATTCAGAAATTAGCCTCCA<br>CATGTGCAATGGCTTTAAGAGCCAGAAGCAGGGTTCTGGGAATTTTGCAAGTTACCTGTGGCC<br>AGGTGTGGTCCGGTTACCAAATACGGTTACCTGCAGCTTTTTAGTCCTTTGTGCTCCCACGG<br>GTCTACAGAGTCCCATCTGCCCAAAGGTCTTGAAGCTTGACAGGATGTTTTCGATTACTCAGT<br>CTCCCAGGGCACTACTGGTCCGTAGGATTCGATTGGTCGGGTAGGAGAGTTAAACAACATTT<br>AAACAGAGTTCTCTCAAAAATGTCTAAAGGGATTGTAGGTAGATAACATCCAATCACTGTTTG<br>CACTTATCTGAAATCTTCCCTCTTGGCTGCCCCCAGGTATTTACTGTGGAGAACATTGCATAG<br>GAATGTCTGGAAAAAGCTTCTACAACTTGTTACAGCCTTCACATTTGTAGAAGCTTT |
| 58 | COX8-<br>ND4-<br>3'UTR* | ATGTCCGTCCTGACGCGCCTGCTGCTGCGGGGCTTGACACGGCTCGGCTCGGCGGCTCCAGTG<br>CGGCGCGCCAGAATCCATTCGTTGATGCTAAAACTAATCGTCCCAACAATTATGTTACTACCA<br>CTGACATGGCTTTCCAAAAAACACATGATTTGGATCAACAACAACCACCCACAGCCTAATTATT<br>AGCATCATCCCTCTACTATTTTTTAACCAAATCAACAACAACCTATTTAGCTGTTCCCCAACC<br>TTTTCCTCCGACCCCCTAACAACCCCCCTCCTAATGCTAACTACCTGGCTCCTACCCCTCACA<br>ATCATGGCAAGCCAACGCCACTTATCCAGTGAACCACTATCACGAAAAAAACTCTACCTCTCT<br>ATGCTAATCTCCCTACAAATCTCCTTAATTATGACATTCACAGCCACAGAACTAATCATGTTT<br>TATATCTTCTTCGAAACCACACTTATCCCCACCTTGGCTATCATCACCCGATGGGGCAACCAG<br>CCAGAACGCCTGAACGCAGGCACATACTTCCTATTCTACACCCTAGTAGGCTCCCTTCCCCTA<br>CTCATCGCACTAATTTACACTCACAACACCCTAGGCTCACTAAACATTCTACTACTCACTCTC<br>ACTGCCCAAGAACTATCAAACTCCTGGGCCAACAACTTAATGTGGCTAGCTTACACAATGGCT<br>TTTATGGTAAAGATGCCTCTTTACGGACTCCACTTATGGCTCCCTAAAGCCCATGTCGAAGCC<br>CCCATCGCTGGGTCAATGGTACTTGCCGCAGTACTCTTAAAACTAGGCGGCTATGGTATGATG<br>CGCCTCACACTCATTCTCAACCCCCTGACAAAACACATGGCCTACCCCTTCCTTGTACTATCC<br>CTATGGGGCATGATTATGACAAGCTCCATCTGCCTACGACAAACAGACCTAAAATCGCTCATT<br>GCATACTCTTCAATCAGCCACATGGCCCTCGTAGTAACAGCCATTCTCATCCAAACCCCCTGG<br>AGCTTCACCGGCGCAGTCATTCTCATGATCGCCCACGGGCTTACATCCTCATTACTATTCTGC<br>CTAGCAAACTCAAACTACGAACGCACTCACAGTCGCATCATGATCCTCTCTCAAGGACTTCAA<br>ACTCTACTCCCACTAATGGCTTTTTGGTGGCTTCTAGCAAGCCTCGCTAACCTCGCCTTACCC<br>CCCACTATTAACCTACTGGGAGAACTCTCTGTGCTAGTAACCACGTTCTCCTGGTCAAATATC<br>ACTCTCCTACTTACAGGACTCAACATGCTAGTCACAGCCCTATACTCCCTCTACATGTTTACC<br>ACAACACAATGGGCTCACTCACCCACCACATTAACAACATGAAACCCTCATTCACACGAGAA<br>AACACCCTCATGTTCATGCACCTATCCCCCATTCTCCTCCTATCCCTCAACCCCGACATCATT<br>ACCGGGTTTTCCTCTTAAGAGCACTGGGACGCCCACCGCCCCTTTCCCTCCGCTGCCAGGCGA<br>GCATGTTGTGGTAATTCTGGAACACAAGAAGAGAAATTGCTGGGTTTAGAACAAGATTATAAA<br>CGAATTCGGTGCTCAGTGATCACTTGACAGTTTTTTTTTTTTAAATATTACCCAAAATGCT<br>CCCCAAATAAGAAATGCATCAGCTCAGTCAGTGAATACAAAAAAGGAATTATTTTTCCCTTTG<br>AGGGTCTTTTATACATCTCTCCTCCAACCCCACCCTCTATTCTGTTTCTTCCTCCTCACATGG<br>GGGTACACATACACAGCTTCCTCTTTTGGTTCCATCCTTACCACCACACCACACGCACACTCC<br>ACATGCCCAGCAGAGTGGCACTTGGTGGCCAGAAAGTGTGAGCCTCATGATCTGCTGTCTGTA<br>GTTCTGTGAGCTCAGGTCCCTCAAAGGCTCGGAGCACCCCCTTCCTTGTGACTGAGCCAGGG<br>CCTGCATTTTTGGTTTTCCCCACCCCACACATTCTCAACCATAGTCCTTCTAACAATACCAAT<br>AGCTAGGACCCGGCTGCTGTGCACTGGGACTGGGGATTCCACATGTTTGCCTTGGGAGTCTCA<br>AGCTGGACTGCCA |

TABLE 1-continued nucleic acid and polypeptide sequences and SEQ ID NOs

| SEQ | Description | Sequence |
|---|---|---|
| 59 | COX8-opt_ND4-3'UTR | ATGTCCGTCCTGACGCGCCTGCTGCTGCGGGGCTTGACACGGCTCGGCTCGGCGGCTCCAGTG<br>CGGCGCGCCAGAATCCATTCGTTGATGCTGAAGCTGATCGTGCCCACCATCATGCTGCTGCCT<br>CTGACCTGGCTGAGCAAGAAACACATGATCTGGATCAACACCACCACGCACAGCCTGATCATC<br>AGCATCATCCCTCTGCTGTTCTTCAACCAGATCAACAACAACCTGTTCAGCTGCAGCCCCACC<br>TTCAGCAGCGACCCTCTGACAACACCTCTGCTGATGCTGACCACCTGGCTGCTGCCCCTCACA<br>ATCATGGCCTCTCAGAGACACCTGAGCAGCGAGCCCTGAGCCGGAAGAAACTGTACCTGAGC<br>ATGCTGATCTCCCTGCAGATCTCTCTGATCATGACCTTCACCGCCACCGAGCTGATCATGTTC<br>TACATCTTTTTCGAGACAACGCTGATCCCCACACTGGCCATCATCACCAGATGGGGCAACCAG<br>CCTGAGAGACTGAACGCCGGCACCTACTTTCTGTTCTACACCCTCGTGGGCAGCCTGCCACTG<br>CTGATTGCCCTGATCTACACCCACAACACCCTGGGCTCCCTGAACATCCTGCTGCTGACACTG<br>ACAGCCCAAGAGCTGAGCAACAGCTGGGCCAACAATCTGATGTGGCTGGCCTACACAATGGCC<br>TTCATGGTCAAGATGCCCCTGTACGGCCTGCACCTGTGGCTGCCTAAAGCTCATGTGGAAGCC<br>CCTATCGCCGGCTCTATGGTGCTGGCTGCAGTGCTGCTGAAACTCGGCGGCTACGGCATGATG<br>CGGCTGACCCTGATTCTGAATCCCCTGACCAAGCACATGGCCTATCCATTTCTGGTGCTGAGC<br>CTGTGGGGCATGATTATGACCAGCAGCATCTGCCTGCGGCAGACCGATCTGAAGTCCCTGATC<br>GCCTACAGCTCCATCAGCCACATGGCCCTGGTGGTCACCGCCATCCTGATTCAGACCCCTTGG<br>AGCTTTACAGGCGCCGTGATCCTGATGATTGCCCACGGCCTGACAAGCAGCCTGCTGTTTTGT<br>CTGGCCAACAGCAACTACGAGCGGACCCACAGCAGAATCATGATCCTGTCTCAGGGCCTGCAG<br>ACCCTCCTGCCTCTTATGGCTTTTTGGTGGCTGCTGGCCTCTCTGGCCAATCTGGCACTGCCT<br>CCTACCATCAATCTGCTGGGCGAGCTGAGCGTGCTGGTCACCACATTCAGCTGGTCCAATATC<br>ACCCTGCTGCTCACCGGCCTGAACATGCTGGTTACAGCCCTGTACTCCCTGTACATGTTCACC<br>ACCACACAGTGGGGAAGCCTGACACACCACATCAACAATATGAAGCCCAGCTTCACCCGCGAG<br>AACACCCTGATGTTCATGCATCTGAGCCCCATTCTGCTGCTGTCCCTGAATCCTGATATCATC<br>ACCGGCTTCTCCAGCTGAGAGCACTGGGACGCCCACCGCCCCTTTCCCTCCGCTGCCAGGCGA<br>GCATGTTGTGGTAATTCTGGAACACAAGAAGAGAAATTGCTGGGTTTAGAACAAGATTATAAA<br>CGAATTCGGTGCTCAGTGATCACTTGACAGTTTTTTTTTTTTAAATATTACCCAAAATGCT<br>CCCCAAATAAGAAATGCATCAGCTCAGTCAGTGAATACAAAAAAGGAATTATTTTTCCCTTTG<br>AGGGTCTTTTATACATCTCTCCTCCAACCCCACCCTCTATTCTGTTTCTTCCTCCTCACATGG<br>GGGTACACATACACAGCTTCCTCTTTTGGTTCCATCCTTACCACCACACCACACGCACACTCC<br>ACATGCCCAGCAGAGTGGCACTTGGTGGCCAGAAAGTGTGAGCCTCATGATCTGCTGTCTGTA<br>GTTCTGTGAGCTCAGGTCCCTCAAAGGCCTCGGAGCACCCCCTTCCTTGTGACTGAGCCAGGG<br>CCTGCATTTTTGGTTTTCCCCACCCCACACATTCTCAACCATAGTCCTTCTAACAATACCAAT<br>AGCTAGGACCCGGCTGCTGTGCACTGGGACTGGGGATTCCACATGTTTGCCTTGGGAGTCTCA<br>AGCTGGACTGCCAGCCCCTGTCCTCCCTTCACCCCCATTGCGTATGAGCATTTCAGAACTCCA<br>AGGAGTCACAGGCATCTTTATAGTTCACGTTAACATATAGACACTGTTGGAAGCAGTTCCTTC<br>TAAAAGGGTAGCCCTGGACTTAATACCAGCCGGATACCTCTGGCCCCCACCCCATTACTGTAC<br>CTCTGGAGTCACTACTGTGGGTCGCCACTCCTCTGCTACACAGCACGGCTTTTTCAAGGCTGT<br>ATTGAGAAGGGAAGTTAGGAAGAAGGGTGTGCTGGGCTAACCAGCCCACAGAGCTCACATTCC<br>TGTCCCTTGGGTGAAAAATACATGTCCATCCTGATATCTCCTGAATTCAGAAATTAGCCTCCA<br>CATGTGCAATGGCTTTAAGAGCCAGAAGCAGGGTTCTGGGAATTTTGCAAGTTACCTGTGGCC<br>AGGTGTGGTCTCGGTTACCAAATACGGTTACCTGCAGCTTTTTAGTCCTTTGTGCTCCCACGG<br>GTCTACAGAGTCCCATCTGCCCAAAGGTCTTGAAGCTTGACAGGATGTTTTCGATTACTCAGT<br>CTCCCAGGGCACTACTGGTCCGTAGGATTCGATTGGTCGGGTAGGAGAGTTAAACAACATTT<br>AAACAGAGTTCTCTCAAAAATGTCTAAAGGGATTGTAGGTAGATAACATCCAATCACTGTTTG<br>CACTTATCTGAAATCTTCCCTCTTGGCTGCCCCCAGGTATTTACTGTGGAGAACATTGCATAG<br>GAATGTCTGGAAAAAGCTTCTACAACTTGTTACAGCCTTCACATTTGTAGAAGCTTT |
| 60 | COX8-opt_ND4-3'UTR* | ATGTCCGTCCTGACGCGCCTGCTGCTGCGGGGCTTGACACGGCTCGGCTCGGCGGCTCCAGTG<br>CGGCGCGCCAGAATCCATTCGTTGATGCTGAAGCTGATCGTGCCCACCATCATGCTGCTGCCT<br>CTGACCTGGCTGAGCAAGAAACACATGATCTGGATCAACACCACCACGCACAGCCTGATCATC<br>AGCATCATCCCTCTGCTGTTCTTCAACCAGATCAACAACAACCTGTTCAGCTGCAGCCCCACC<br>TTCAGCAGCGACCCTCTGACAACACCTCTGCTGATGCTGACCACCTGGCTGCTGCCCCTCACA<br>ATCATGGCCTCTCAGAGACACCTGAGCAGCGAGCCCTGAGCCGGAAGAAACTGTACCTGAGC<br>ATGCTGATCTCCCTGCAGATCTCTCTGATCATGACCTTCACCGCCACCGAGCTGATCATGTTC<br>TACATCTTTTTCGAGACAACGCTGATCCCCACACTGGCCATCATCACCAGATGGGGCAACCAG<br>CCTGAGAGACTGAACGCCGGCACCTACTTTCTGTTCTACACCCTCGTGGGCAGCCTGCCACTG<br>CTGATTGCCCTGATCTACACCCACAACACCCTGGGCTCCCTGAACATCCTGCTGCTGACACTG<br>ACAGCCCAAGAGCTGAGCAACAGCTGGGCCAACAATCTGATGTGGCTGGCCTACACAATGGCC<br>TTCATGGTCAAGATGCCCCTGTACGGCCTGCACCTGTGGCTGCCTAAAGCTCATGTGGAAGCC<br>CCTATCGCCGGCTCTATGGTGCTGGCTGCAGTGCTGCTGAAACTCGGCGGCTACGGCATGATG<br>CGGCTGACCCTGATTCTGAATCCCCTGACCAAGCACATGGCCTATCCATTTCTGGTGCTGAGC<br>CTGTGGGGCATGATTATGACCAGCAGCATCTGCCTGCGGCAGACCGATCTGAAGTCCCTGATC<br>GCCTACAGCTCCATCAGCCACATGGCCCTGGTGGTCACCGCCATCCTGATTCAGACCCCTTGG<br>AGCTTTACAGGCGCCGTGATCCTGATGATTGCCCACGGCCTGACAAGCAGCCTGCTGTTTTGT<br>CTGGCCAACAGCAACTACGAGCGGACCCACAGCAGAATCATGATCCTGTCTCAGGGCCTGCAG<br>ACCCTCCTGCCTCTTATGGCTTTTTGGTGGCTGCTGGCCTCTCTGGCCAATCTGGCACTGCCT<br>CCTACCATCAATCTGCTGGGCGAGCTGAGCGTGCTGGTCACCACATTCAGCTGGTCCAATATC<br>ACCCTGCTGCTCACCGGCCTGAACATGCTGGTTACAGCCCTGTACTCCCTGTACATGTTCACC<br>ACCACACAGTGGGGAAGCCTGACACACCACATCAACAATATGAAGCCCAGCTTCACCCGCGAG<br>AACACCCTGATGTTCATGCATCTGAGCCCCATTCTGCTGCTGTCCCTGAATCCTGATATCATC<br>ACCGGCTTCTCCAGCTGAGAGCACTGGGACGCCCACCGCCCCTTTCCCTCCGCTGCCAGGCGA<br>GCATGTTGTGGTAATTCTGGAACACAAGAAGAGAAATTGCTGGGTTTAGAACAAGATTATAAA<br>CGAATTCGGTGCTCAGTGATCACTTGACAGTTTTTTTTTTTTAAATATTACCCAAAATGCT<br>CCCCAAATAAGAAATGCATCAGCTCAGTCAGTGAATACAAAAAAGGAATTATTTTTCCCTTTG<br>AGGGTCTTTTATACATCTCTCCTCCAACCCCACCCTCTATTCTGTTTCTTCCTCCTCACATGG<br>GGGTACACATACACAGCTTCCTCTTTTGGTTCCATCCTTACCACCACACCACACGCACACTCC |

TABLE 1-continued nucleic acid and polypeptide sequences and SEQ ID NOs

| SEQ | Description | Sequence |
|---|---|---|
| | | ACATGCCCAGCAGAGTGGCACTTGGTGGCCAGAAAGTGTGAGCCTCATGATCTGCTGTCTGTA<br>GTTCTGTGAGCTCAGGTCCCTCAAAGGCCTCGGAGCACCCCCTTCCTTGTGACTGAGCCAGGG<br>CCTGCATTTTTGGTTTTCCCCACCCCACACATTCTCAACCATAGTCCTTCTAACAATACCAAT<br>AGCTAGGACCCGGCTGCTGTGCACTGGGACTGGGGATTCCACATGTTTGCCTTGGGAGTCTCA<br>AGCTGGACTGCCA |
| 61 | COX8-<br>opt_ND4*-<br>3'UTR | ATGTCCGTCCTGACGCGCCTGCTGCTGCGGGGCTTGACACGGCTCGGCTCGGCGGCTCCAGTG<br>CGGCGCGCCAGAATCCATTCGTTGATGCTGAAGCTGATCGTGCCCACCATCATGCTGCTGCCC<br>CTGACCTGGCTGAGCAAGAAGCACATGATCTGGATCAACACCACCACCCACAGCCTGATCATC<br>AGCATCATCCCCCTGCTGTTCTTCAACCAGATCAACAACAACCTGTTCAGCTGCAGCCCCACC<br>TTCAGCAGCGACCCCCTGACCACCCCCCTGCTGATGCTGACCACCTGGCTGCTGCCCCTGACC<br>ATCATGGCCAGCCAGCGCCACCTGAGCAGCGAGCCCCTGAGCCGCAAGAAGCTGTACCTGAGC<br>ATGCTGATCAGCCTGCAGATCAGCCTGATCATGACCTTCACCGCCACCGAGCTGATCATGTTC<br>TACATCTTCTTCGAGACCACCCTGATCCCCACCCTGGCCATCATCACCCGCTGGGGCAACCAG<br>CCCGAGCGCCTGAACGCCGGCACCTACTTCCTGTTCTACACCCTGGTGGGCAGCCTGCCCCTG<br>CTGATCGCCCTGATCTACACCCACAACACCCTGGGCAGCCTGAACATCCTGCTGCTGACCCTG<br>ACCGCCCAGGAGCTGAGCAACAGCTGGGCCAACAACCTGATGTGGCTGGCCTACACCATGGCC<br>TTCATGGTGAAGATGCCCCTGTACGGCCTGCACCTGTGGCTGCCCAAGGCCCACGTGGAGGCC<br>CCCATCGCCGGCAGCATGGTGCTGGCCGCCGTGCTGCTGAAGCTGGGCGGCTACGGCATGATG<br>CGCCTGACCCTGATCCTGAACCCCCTGACCAAGCACATGGCCTACCCCTTCCTGGTGCTGAGC<br>CTGTGGGGCATGATCATGACCAGCAGCATCTGCCTGCGCCAGACCGACCTGAAGAGCCTGATC<br>GCCTACAGCAGCATCAGCCACATGGCCCTGGTGGTGACCGCCATCCTGATCCAGACCCCCTGG<br>AGCTTCACCGGCGCCGTGATCCTGATGATCGCCCACGGCCTGACCAGCAGCCTGCTGTTCTGC<br>CTGGCCAACAGCAACTACGAGCGCACCCACAGCCGCATCATGATCCTGAGCCAGGGCCTGCAG<br>ACCCTGCTGCCCCTGATGGCCTTCTGGTGGCTGCTGGCCAGCCTGGCCAACCTGGCCCTGCCC<br>CCCACCATCAACCTGCTGGGCGAGCTGAGCGTGCTGGTGACCACCTTCAGCTGGAGCAACATC<br>ACCCTGCTGCTGACCGGCCTGAACATGCTGGTGACCGCCCTGTACAGCCTGTACATGTTCACC<br>ACCACCCAGTGGGGCAGCCTGACCCACCACATCAACAACATGAAGCCCAGCTTCACCCGCGAG<br>AACACCCTGATGTTCATGCACCTGAGCCCCATCCTGCTGCTGAGCCTGAACCCCGACATCATC<br>ACCGGCTTCAGCAGCTAAGAGCACTGGGACGCCCACCGCCCCTTTCCCTCCGCTGCCAGGCGA<br>GCATGTTGTGGTAATTCTGGAACACAAGAAGAGAAATTGCTGGGTTTAGAACAAGATTATAAA<br>CGAATTCGGTGCTCAGTGATCACTTGACAGTTTTTTTTTTTTTAAATATTACCCAAAATGCT<br>CCCCAAATAAGAAATGCATCAGCTCAGTCAGTGAATACAAAAAAGGAATTATTTTTCCCTTTG<br>AGGGTCTTTTATACATCTCTCCTCCAACCCCACCCTCTATTCTGTTTCTTCCTCCTCACATGG<br>GGGTACACATACACAGCTTCCTCTTTTGGTTCCATCCTTACCACCACACCACACGCACACTCC<br>ACATGCCCAGCAGAGTGGCACTTGGTGGCCAGAAAGTGTGAGCCTCATGATCTGCTGTCTGTA<br>GTTCTGTGAGCTCAGGTCCCTCAAAGGCCTCGGAGCACCCCCTTCCTTGTGACTGAGCCAGGG<br>CCTGCATTTTTGGTTTTCCCCACCCCACACATTCTCAACCATAGTCCTTCTAACAATACCAAT<br>AGCTAGGACCCGGCTGCTGTGCACTGGGACTGGGGATTCCACATGTTTGCCTTGGGAGTCTCA<br>AGCTGGACTGCCAGCCCCTGTCCTCCCTTCACCCCCATTGCGTATGAGCATTTCAGAACTCCA<br>AGGAGTCACAGGCATCTTTATAGTTCACGTTAACATATAGACACTGTTGGAAGCAGTTCCTTC<br>TAAAAGGGTAGCCCTGGACTTAATACCAGCCGGATACCTCTGGCCCCCACCCCATTACTGTAC<br>CTCTGGAGTCACTACTGTGGGTCGCCACTCCTCTGCTACACAGCACGGCTTTTTCAAGGCTGT<br>ATTGAGAAGGGAAGTTAGGAAGAGGGTGTGCTGGGCTAACAGCCCACAGAGCTCACATTCC<br>TGTCCCTTGGGTGAAAAATACATGTCCATCCTGATATCTCCTGAATTCAGAAATTAGCCTCCA<br>CATGTGCAATGGCTTTAAGAGCCAGAAGCAGGGTTCTGGGAATTTTGCAAGTTACCTGTGGCC<br>AGGTGTGGTCTCGGTTACCAAATACGGTTACCTGCAGCTTTTTAGTCCTTTGTGCTCCCACGG<br>GTCTACAGAGTCCCATCTGCCCAAAGGTCTTGAAGCTTGACAGGATGTTTTCGATTACTCAGT<br>CTCCCAGGGCACTACTGGTCCGTAGGATTCGATTGGTCGGGTAGGAGAGTTAAACAACATTT<br>AAACAGAGTTCTCTCAAAAATGTCTAAAGGGATTGTAGGTAGATAACATCCAATCACTGTTTG<br>CACTTATCTGAAATCTTCCCTCTTGGCTGCCCCCAGGTATTTACTGTGGAGAACATTGCATAG<br>GAATGTCTGGAAAAAGCTTCTACAACTTGTTACAGCCTTCACATTTGTAGAAGCTTT |
| 62 | COX8-<br>opt_ND4*-<br>3'UTR* | ATGTCCGTCCTGACGCGCCTGCTGCTGCGGGGCTTGACACGGCTCGGCTCGGCGGCTCCAGTG<br>CGGCGCGCCAGAATCCATTCGTTGATGCTGAAGCTGATCGTGCCCACCATCATGCTGCTGCCC<br>CTGACCTGGCTGAGCAAGAAGCACATGATCTGGATCAACACCACCACCCACAGCCTGATCATC<br>AGCATCATCCCCCTGCTGTTCTTCAACCAGATCAACAACAACCTGTTCAGCTGCAGCCCCACC<br>TTCAGCAGCGACCCCCTGACCACCCCCCTGCTGATGCTGACCACCTGGCTGCTGCCCCTGACC<br>ATCATGGCCAGCCAGCGCCACCTGAGCAGCGAGCCCCTGAGCCGCAAGAAGCTGTACCTGAGC<br>ATGCTGATCAGCCTGCAGATCAGCCTGATCATGACCTTCACCGCCACCGAGCTGATCATGTTC<br>TACATCTTCTTCGAGACCACCCTGATCCCCACCCTGGCCATCATCACCCGCTGGGGCAACCAG<br>CCCGAGCGCCTGAACGCCGGCACCTACTTCCTGTTCTACACCCTGGTGGGCAGCCTGCCCCTG<br>CTGATCGCCCTGATCTACACCCACAACACCCTGGGCAGCCTGAACATCCTGCTGCTGACCCTG<br>ACCGCCCAGGAGCTGAGCAACAGCTGGGCCAACAACCTGATGTGGCTGGCCTACACCATGGCC<br>TTCATGGTGAAGATGCCCCTGTACGGCCTGCACCTGTGGCTGCCCAAGGCCCACGTGGAGGCC<br>CCCATCGCCGGCAGCATGGTGCTGGCCGCCGTGCTGCTGAAGCTGGGCGGCTACGGCATGATG<br>CGCCTGACCCTGATCCTGAACCCCCTGACCAAGCACATGGCCTACCCCTTCCTGGTGCTGAGC<br>CTGTGGGGCATGATCATGACCAGCAGCATCTGCCTGCGCCAGACCGACCTGAAGAGCCTGATC<br>GCCTACAGCAGCATCAGCCACATGGCCCTGGTGGTGACCGCCATCCTGATCCAGACCCCCTGG<br>AGCTTCACCGGCGCCGTGATCCTGATGATCGCCCACGGCCTGACCAGCAGCCTGCTGTTCTGC<br>CTGGCCAACAGCAACTACGAGCGCACCCACAGCCGCATCATGATCCTGAGCCAGGGCCTGCAG<br>ACCCTGCTGCCCCTGATGGCCTTCTGGTGGCTGCTGGCCAGCCTGGCCAACCTGGCCCTGCCC<br>CCCACCATCAACCTGCTGGGCGAGCTGAGCGTGCTGGTGACCACCTTCAGCTGGAGCAACATC<br>ACCCTGCTGCTGACCGGCCTGAACATGCTGGTGACCGCCCTGTACAGCCTGTACATGTTCACC<br>ACCACCCAGTGGGGCAGCCTGACCCACCACATCAACAACATGAAGCCCAGCTTCACCCGCGAG<br>AACACCCTGATGTTCATGCACCTGAGCCCCATCCTGCTGCTGAGCCTGAACCCCGACATCATC |

TABLE 1-continued nucleic acid and polypeptide sequences and SEQ ID NOs

| SEQ | Description | Sequence |
|---|---|---|
| | | ACCGGCTTCAGCAGCTAAGAGCACTGGGACGCCCACCGCCCCTTTCCCTCCGCTGCCAGGCGA<br>GCATGTTGTGGTAATTCTGGAACACAAGAAGAGAAATTGCTGGGTTTAGAACAAGATTATAAA<br>CGAATTCGGTGCTCAGTGATCACTTGACAGTTTTTTTTTTTTAAATATTACCCAAAATGCT<br>CCCCAAATAAGAAATGCATCAGCTCAGTCAGTGAATACAAAAAAGGAATTATTTTTCCCTTTG<br>AGGGTCTTTTATACATCTCTCCTCCAACCCCACCCTCTATTCTGTTTCTTCCTCCTCACATGG<br>GGGTACACATACACAGCTTCCTCTTTTGGTTCCATCCTTACCACCACACCACACGCACACTCC<br>ACATGCCCAGCAGAGTGGCACTTGGTGGCCAGAAAGTGTGAGCCTCATGATCTGCTGTCTGTA<br>GTTCTGTGAGCTCAGGTCCCTCAAAGGCCTGGAGCACCCCCTTCCTTGTGACTGAGCCAGGG<br>CCTGCATTTTTGGTTTTCCCCACCCCACACATTCTCAACCATAGTCCTTCTAACAATACCAAT<br>AGCTAGGACCCGGCTGCTGTGCACTGGGACTGGGGATTCCACATGTTTGCCTTGGGAGTCTCA<br>AGCTGGACTGCCA |
| 63 | COX8-<br>ND6-3'UTR | ATGTCCGTCCTGACGCGCCTGCTGCTGCGGGGCTTGACACGGCTCGGCTCGGCGGCTCCAGTG<br>CGGCGCGCCAGAATCCATTCGTTGATGATGTATGCTTTGTTTCTGTTGAGTGTGGGTTTAGTA<br>ATGGGGTTTGTGGGGTTTTCTTCTAAGCCTTCTCCTATTTATGGGGGTTTAGTATTGATTGTT<br>AGCGGTGTGGTCGGGTGTGTTATTATTCTGAATTTTGGGGGAGGTTATATGGGTTTAATGGTT<br>TTTTTAATTTATTTAGGGGGAATGATGGTTGTCTTTGGATATACTACAGCGATGGCTATTGAG<br>GAGTATCCTGAGGCATGGGGGTCAGGGGTTGAGGTCTTGGTGAGTGTTTTAGTGGGGTTAGCG<br>ATGGAGGTAGGATTGGTGCTGTGGGTGAAAGAGTATGATGGGGTGGTGGTTGTGGTAAACTTT<br>AATAGTGTAGGAAGCTGGATGATTTATGAAGGAGAGGGGTCAGGGTTGATTCGGGAGGATCCT<br>ATTGGTGCGGGGCTTTGTATGATTATGGGCGTTGGTTAGTAGTAGTTACTGGTTGGACATTG<br>TTTGTTGGTGTATATATTGTAATTGAGATTGCTCGGGGGAATTAGGAGCACTGGGACGCCCAC<br>CGCCCCTTTCCCTCCGCTGCCAGGCGAGCATGTTGTGGTAATTCTGGAACACAAGAAGAGAAA<br>TTGCTGGGTTTAGAACAAGATTATAAACGAATTCGGTGCTCAGTGATCACTTGACAGTTTTTT<br>TTTTTTTTAAATATTACCCAAAATGCTCCCCAAATAAGAAATGCATCAGCTCAGTCAGTGAAT<br>ACAAAAAAGGAATTATTTTTCCCTTTGAGGGTCTTTTATACATCTCTCCTCCAACCCCACCCT<br>CTATTCTGTTTCTTCCTCCTCACATGGGGGTACACATACACAGCTTCCTCTTTTGGTTCCATC<br>CTTACCACCACACCACACGCACACTCCACATGCCCAGCAGAGTGGCACTTGGTGGCCAGAAAG<br>TGTGAGCCTCATGATCTGCTGTCTGTAGTTCTGTGAGCTCAGGTCCCTCAAAGGCCTGGAGC<br>ACCCCCTTCCTTGTGACTGAGCCAGGGCCTGCATTTTTGGTTTTCCCCACCCCACACATTCTC<br>AACCATAGTCCTTCTAACAATACCAATAGCTAGGACCCGGCTGCTGTGCACTGGGACTGGGGA<br>TTCCACATGTTTGCCTTGGGAGTCTCAAGCTGGACTGCCAGCCCCTGTCCTCCCTTCACCCCC<br>ATTGCGTATGAGCATTTCAGAACTCCAAGGAGTCACAGGCATCTTTATAGTTCACGTTAACAT<br>ATAGACACTGTTGGAAGCAGTTCCTTCTAAAAGGGGTAGCCTGGACTTAATACCAGCCGGATA<br>CCTCTGGCCCCCACCCCATTACTGTACCTCTGGAGTCACTACTGTGGGTCGCCACTCCTCTGC<br>TACACAGCACGGCTTTTTCAAGGCTGTATTGAGAAGGGAAGTTAGGAAGAAGGGTGTGCTGGG<br>CTAACCAGCCCACAGAGCTCACATTCCTGTCCCTTGGGTGAAAAATACATGTCCATCCTGATA<br>TCTCCTGAATTCAGAAATTAGCCTCCACATGTGCAATGGCTTTAAGAGCCAGAAGCAGGGTTC<br>TGGGAATTTTGCAAGTTACCTGTGGCCAGGTGTGGTCTCGGTTACCAAATACGGTTACCTGCA<br>GCTTTTTAGTCCTTTGTGCTCCCACGGGTCTACAGAGTCCCATCTGCCCAAAGGTCTTGAAGC<br>TTGACAGGATGTTTTCGATTACTCAGTCTCCCAGGGCACTACTGGTCCGTAGGATTCGATTGG<br>TCGGGGTAGGAGAGTTAAACAACATTTAAACAGAGTTCTCTCAAAAATGTCTAAAGGGATTGT<br>AGGTAGATAACATCCAATCACTGTTTGCACTTATCTGAAATCTTCCCTCTTGGCTGCCCCCAG<br>GTATTTACTGTGGAGAACATTGCATAGGAATGTCTGGAAAAAGCTTCTACAACTTGTTACAGC<br>CTTCACATTTGTAGAAGCTTT |
| 64 | COX8-<br>ND6-<br>3'UTR* | ATGTCCGTCCTGACGCGCCTGCTGCTGCGGGGCTTGACACGGCTCGGCTCGGCGGCTCCAGTG<br>CGGCGCGCCAGAATCCATTCGTTGATGATGTATGCTTTGTTTCTGTTGAGTGTGGGTTTAGTA<br>ATGGGGTTTGTGGGGTTTTCTTCTAAGCCTTCTCCTATTTATGGGGTTTAGTATTGATTGTT<br>AGCGGTGTGGTCGGGTGTGTTATTATTCTGAATTTTGGGGGAGGTTATATGGGTTTAATGGTT<br>TTTTTAATTTATTTAGGGGGAATGATGGTTGTCTTTGGATATACTACAGCGATGGCTATTGAG<br>GAGTATCCTGAGGCATGGGGGTCAGGGGTTGAGGTCTTGGTGAGTGTTTTAGTGGGGTTAGCG<br>ATGGAGGTAGGATTGGTGCTGTGGGTGAAAGAGTATGATGGGGTGGTGGTTGTGGTAAACTTT<br>AATAGTGTAGGAAGCTGGATGATTTATGAAGGAGAGGGGTCAGGGTTGATTCGGGAGGATCCT<br>ATTGGTGCGGGGCTTTGTATGATTATGGGCGTTGGTTAGTAGTAGTTACTGGTTGGACATTG<br>TTTGTTGGTGTATATATTGTAATTGAGATTGCTCGGGGGAATTAGGAGCACTGGGACGCCCAC<br>CGCCCCTTTCCCTCCGCTGCCAGGCGAGCATGTTGTGGTAATTCTGGAACACAAGAAGAGAAA<br>TTGCTGGGTTTAGAACAAGATTATAAACGAATTCGGTGCTCAGTGATCACTTGACAGTTTTTT<br>TTTTTTTTAAATATTACCCAAAATGCTCCCCAAATAAGAAATGCATCAGCTCAGTCAGTGAAT<br>ACAAAAAAGGAATTATTTTTCCCTTTGAGGGTCTTTTATACATCTCTCCTCCAACCCCACCCT<br>CTATTCTGTTTCTTCCTCCTCACATGGGGGTACACATACACAGCTTCCTCTTTTGGTTCCATC<br>CTTACCACCACACCACACGCACACTCCACATGCCCAGCAGAGTGGCACTTGGTGGCCAGAAAG<br>TGTGAGCCTCATGATCTGCTGTCTGTAGTTCTGTGAGCTCAGGTCCCTCAAAGGCCTGGAGC<br>ACCCCCTTCCTTGTGACTGAGCCAGGGCCTGCATTTTTGGTTTTCCCCACCCCACACATTCTC<br>AACCATAGTCCTTCTAACAATACCAATAGCTAGGACCCGGCTGCTGTGCACTGGGACTGGGGA<br>TTCCACATGTTTGCCTTGGGAGTCTCAAGCTGGACTGCCA |
| 65 | COX8-<br>opt_ND6-<br>3'UTR | ATGTCCGTCCTGACGCGCCTGCTGCTGCGGGGCTTGACACGGCTCGGCTCGGCGGCTCCAGTG<br>CGGCGCGCCAGAATCCATTCGTTGATGATGTACGCCCTGTTCCTGCTGAGCGTGGGCCTGGTG<br>ATGGGCTTCGTGGGCTTCAGCAGCAAGCCCAGCCCCATCTACGGCGGCCTGGTGCTGATCGTG<br>AGCGGCGTGGTGGGCTGCGTGATCATCCTGAACTTCGGCGGCGGCTACACCGGCCATGCCATCGAG<br>TTCCTGATCTACCTGGGCGGCATGATGGTGGTGTTCGGCTACACCACCGCCATGGCCATCGAG<br>GAGTACCCCGAGGCCTGGGCAGCGGCGGAGGTGCTGGTGAGCGTGCTGGTGGGCCTGGCC<br>ATGGAGGTGGGCCTGGTGCTGTGGGTGAAGGAGTACGACGGCGTGGTGGTGGTGGTGAACTTC<br>AACAGCGTGGGCAGCTGGATGATCTACGAGGGCGAGGGCAGCGGCCTGATCCGCGAGGACCCC<br>ATCGGCGCCGGCGCCCTGTACGACTACGGCCGCTGGCTGGTGGTGGTGACCGGCTGGACCCTG |

TABLE 1-continued nucleic acid and polypeptide sequences and SEQ ID NOs

| SEQ | Description | Sequence |
|---|---|---|
| | | TTCGTGGGCGTGTACATCGTGATCGAGATCGCCCGCGGCAACTAAGAGCACTGGGACGCCCAC<br>CGCCCCTTTCCCTCCGCTGCCAGGCGAGCATGTTGTGGTAATTCTGGAACACAAGAAGAGAAA<br>TTGCTGGGTTTAGAACAAGATTATAAACGAATTCGGTGCTCAGTGATCACTTGACAGTTTTTT<br>TTTTTTTTAAATATTACCCAAAATGCTCCCCAAATAAGAAATGCATCAGCTCAGTCAGTGAAT<br>ACAAAAAAGGAATTATTTTTCCCTTTGAGGGTCTTTTATACATCTCTCCTCCAACCCCACCCT<br>CTATTCTGTTTCTTCCTCCTCACATGGGGGTACACATACACAGCTTCCTCTTTTGGTTCCATC<br>CTTACCACCACACCACACGCACACTCCACATGCCCAGCAGAGTGGCACTTGGTGGCCAGAAAG<br>TGTGAGCCTCATGATCTGCTGTCTGTAGTTCTGTGAGCTCAGGTCCCTCAAAGGCCTCGGAGC<br>ACCCCCTTCCTTGTGACTGAGCCAGGGCCTGCATTTTTGGTTTTCCCCACCCCACACATTCTC<br>AACCATAGTCCTTCTAACAATACCAATAGCTAGGACCCGGCTGCTGTGCACTGGGACTGGGGA<br>TTCCACATGTTTGCCTTGGGAGTCTCAAGCTGGACTGCCAGCCCCTGTCCTCCCTTCACCCCC<br>ATTGCGTATGAGCATTTCAGAACTCCAAGGAGTCACAGGCATCTTTATAGTTCACGTTAACAT<br>ATAGACACTGTTGGAAGCAGTTCCTTCTAAAAGGGTAGCCCTGGACTTAATACCAGCCGGATA<br>CCTCTGGCCCCCACCCCATTACTGTACCTCTGGAGTCACTACTGTGGGTCGCCACTCCTCTGC<br>TACACAGCACGGCTTTTTCAAGGCTGTATTGAGAAGGGAAGTTAGGAAGAAGGGTGTGCTGGG<br>CTAACCAGCCCACAGAGCTCACATTCCTGTCCCTTGGGTGAAAAATACATGTCCATCCTGATA<br>TCTCCTGAATTCAGAAATTAGCCTCCACATGTGCAATGGCTTTAAGAGCCAGAAGCAGGGTTC<br>TGGGAATTTTGCAAGTTACCTGTGGCCAGGTGTGGTCTCGGTTACCAAATACGGTTACCTGCA<br>GCTTTTTAGTCCTTTGTGCTCCCACGGGTCTACAGAGTCCCATCTGCCCAAAGGTCTTGAAGC<br>TTGACAGGATGTTTTCGATTACTCAGTCTCCCAGGGCACTACTGGTCCGTAGGATTCGATTGG<br>TCGGGGTAGGAGAGTTAAACAACATTTAAACAGAGTTCTCTCAAAAATGTCTAAAGGGATTGT<br>AGGTAGATAACATCCAATCACTGTTTGCACTTATCTGAAATCTTCCCTCTTGGCTGCCCCCAG<br>GTATTTACTGTGGAGAACATTGCATAGGAATGTCTGGAAAAAGCTTCTACAACTTGTTACAGC<br>CTTCACATTTGTAGAAGCTTT |
| 66 | COX8-<br>opt_ND6-<br>3'UTR* | ATGTCCGTCCTGACGCGCCTGCTGCTGCGGGGCTTGACACGGCTCGGCTCGGCGGCTCCAGTG<br>CGGCGCGCCAGAATCCATTCGTTGATGATGTACGCCCTGTTCCTGCTGAGCGTGGGCCTGGTG<br>ATGGGCTTCGTGGGCTTCAGCAGCAAGCCCAGCCCCATCTACGGCGGCCTGGTGCTGATCGTG<br>AGCGGCGTGGTGGGCTGCGTGATCATCCTGAACTTCGGCGGCGGCTACATGGGCCTGATGGTG<br>TTCCTGATCTACCTGGGCGGCATGATGGTGGTGTTCGGCTACACCACCGCCATGGCCATCGAG<br>GAGTACCCCGAGGCCTGGGGCAGCGGCGTGGAGGTGCTGGTGAGCGTGCTGGTGGGCCTGGCC<br>ATGGAGGTGGGCCTGGTGCTGTGGGTGAAGGAGTACGACGGCGTGGTGGTGGTGGTGAACTTC<br>AACAGCGTGGGCAGCTGGATGATCTACGAGGGCGAGGGCAGCGGCCTGATCCGCGAGGACCCC<br>ATCGGCGCCGGCGCCCTGTACGACTACGGCCGCTGGCTGGTGGTGGTGACCGGCTGGACCCTG<br>TTCGTGGGCGTGTACATCGTGATCGAGATCGCCCGCGGCAACTAAGAGCACTGGGACGCCCAC<br>CGCCCCTTTCCCTCCGCTGCCAGGCGAGCATGTTGTGGTAATTCTGGAACACAAGAAGAGAAA<br>TTGCTGGGTTTAGAACAAGATTATAAACGAATTCGGTGCTCAGTGATCACTTGACAGTTTTTT<br>TTTTTTTTAAATATTACCCAAAATGCTCCCCAAATAAGAAATGCATCAGCTCAGTCAGTGAAT<br>ACAAAAAAGGAATTATTTTTCCCTTTGAGGGTCTTTTATACATCTCTCCTCCAACCCCACCCT<br>CTATTCTGTTTCTTCCTCCTCACATGGGGGTACACATACACAGCTTCCTCTTTTGGTTCCATC<br>CTTACCACCACACCACACGCACACTCCACATGCCCAGCAGAGTGGCACTTGGTGGCCAGAAAG<br>TGTGAGCCTCATGATCTGCTGTCTGTAGTTCTGTGAGCTCAGGTCCCTCAAAGGCCTCGGAGC<br>ACCCCCTTCCTTGTGACTGAGCCAGGGCCTGCATTTTTGGTTTTCCCCACCCCACACATTCTC<br>AACCATAGTCCTTCTAACAATACCAATAGCTAGGACCCGGCTGCTGTGCACTGGGACTGGGGA<br>TTCCACATGTTTGCCTTGGGAGTCTCAAGCTGGACTGCCA |
| 67 | COX8-<br>ND1-3'UTR | ATGTCCGTCCTGACGCGCCTGCTGCTGCGGGGCTTGACACGGCTCGGCTCGGCGGCTCCAGTG<br>CGGCGCGCCAGAATCCATTCGTTGATGGCCAACCTCCTACTCCTCATTGTACCCATTCTAATC<br>GCAATGGCATTCCTAATGCTTACCGAACGAAAAATTCTAGGCTATATGCAACTACGCAAAGGC<br>CCCAACGTTGTAGGCCCCTACGGGCTACTACAACCCTTCGCTGACGCCATAAAACTCTTCACC<br>AAAGAGCCCCTAAAACCCGCCACATCTACCATCACCCTCTACATCACCGCCCCGACCTTAGCT<br>CTCACCATCGCTCTTCTACTATGGACCCCCCTCCCCATGCCCAACCCCGTGGTCAACCTCAAC<br>CTAGGCCTCCTATTTATTCTAGCCACCTCTAGCCTAGCCGTTTACTCAATCCTCTGGTCAGGG<br>TGGGCATCAAACTCAAACTAGGCCCCTGATCGGCGCACTGCGAGCAGTAGCCCAAACAATCTCA<br>TATGAAGTCACCCCTAGCCATCATTCTACTATCAACATTACTAATGAGTGGCTCCTTTAACCTC<br>TCCACCCTTATCACAACAAGAACACCTCTGGTTACTCCTGCCATCATGGCCCTTGGCCATG<br>ATGTGGTTTATCTCCACACTAGCAGAGACCAACCGAACCCCCTTCGACCTTGCCGAAGGGGAG<br>TCCGAACTAGTCTCAGGCTTCAACATCGAATACGCCGCAGGCCCCTTCGCCCTATTCTTCATG<br>GCCGAATACACAAACATTATTATGATGAACACCCTCACCACTACAATCTTCCTAGGAACAACA<br>TATGACGCACTCTCCCCTGAACTCTACACAACATATTTTGTCACCAAGACCCTACTTCTAACC<br>TCCCTGTTCTTATGGATTCGAACAGCATACCCCCGATTCCGCTACGACCAACTCATGCACCTC<br>CTATGGAAAAACTTCCTACCACTCACCCTAGCATTACTTATGTGGTATGTCTCCATGCCCATT<br>ACAATCTCCAGCATTCCCCCTCAAACCTAAGAGCACTGGGACGCCCACCGCCCCTTCCCTCC<br>GCTGCCAGGCGAGCATGTTGTGGTAATTCTGGAACACAAGAAGAGAAATTGCTGGGTTTAGAA<br>CAAGATTATAAACGAATTCGGTGCTCAGTGATCACTTGACAGTTTTTTTTTTTTTTAAATATT<br>ACCCAAAATGCTCCCCAAATAAGAAATGCATCAGCTCAGTCAGTGAATACAAAAAAGGAATTA<br>TTTTTCCCTTTGAGGGTCTTTTATACATCTCTCCTCCAACCCCACCCTCTATTCTGTTTCTTC<br>CTCCTCACATGGGGGTACACATACACAGCTTCCTCTTTTGGTTCCATCCTTACCACCACACCA<br>CACGCACACTCCACATGCCCAGCAGAGTGGCACTTGGTGGCCAGAAAGTGTGAGCCTCATGAT<br>CTGCTGTCTGTAGTTCTGTGAGCTCAGGTCCCTCAAAGGCCTCGGAGCACCCCCTTCCTTGTG<br>ACTGAGCCAGGGCCTGCATTTTTGGTTTTCCCCACCCCACACATTCTCAACCATAGTCCTTCT<br>AACAATACCAATAGCTAGGACCCGGCTGCTGTGCACTGGGACTGGGGATTCCACATGTTTGCC<br>TTGGGAGTCTCAAGCTGGACTGCCAGCCCCTGTCCTCCCTTCACCCCCATTGCGTATGAGCAT<br>TTCAGAACTCCAAGGAGTCACAGGCATCTTTATAGTTCACGTTAACATATAGACACTGTTGGA<br>AGCAGTTCCTTCTAAAAGGGTAGCCCTGGACTTAATACCAGCCGGATACCTCTGGCCCCCACC<br>CCATTACTGTACCTCTGGAGTCACTACTGTGGGTCGCCACTCCTCTGCTACACAGCACGGCTT |

TABLE 1-continued nucleic acid and polypeptide sequences and SEQ ID NOs

| SEQ | Description | Sequence |
|---|---|---|
| | | TTTCAAGGCTGTATTGAGAAGGGAAGTTAGGAAGAAGGGTGTGCTGGGCTAACCAGCCCACAG AGCTCACATTCCTGTCCCTTGGGTGAAAAATACATGTCCATCCTGATATCTCCTGAATTCAGA AATTAGCCTCCACATGTGCAATGGCTTTAAGAGCCAGAAGCAGGGTTCTGGGAATTTTGCAAG TTACCTGTGGCCAGGTGTGGTCTCGGTTACCAAATACGGTTACCTGCAGCTTTTTAGTCCTTT GTGCTCCCACGGGTCTACAGAGTCCCATCTGCCCAAAGGTCTTGAAGCTTGACAGGATGTTTT CGATTACTCAGTCTCCCAGGGCACTACTGGTCCGTAGGATTCGATTGGTCGGGGTAGGAGAGT TAAACAACATTTAAACAGAGTTCTCTCAAAAATGTCTAAAGGGATTGTAGGTAGATAACATCC AATCACTGTTTGCACTTATCTGAAATCTTCCCTCTTGGCTGCCCCCAGGTATTTACTGTGGAG AACATTGCATAGGAATGTCTGGAAAAAGCTTCTACAACTTGTTACAGCCTTCACATTTGTAGA AGCTTT |
| 68 | COX8-ND1-3'UTR* | ATGTCCGTCCTGACGCGCCTGCTGCTGCGGGGCTTGACACGGCTCGGCTCGGCGGCTCCAGTG CGGCGCGCCAGAATCCATTCGTTGATGGCCAACCTCCTACTCCTCATTGTACCCATTCTAATC GCAATGGCATTCCTAATGCTTACCGAACGAAAAATTCTAGGCTATATGCAACTACGCAAAGGC CCCAACGTTGTAGGCCCCTACGGGCTACTACAACCCTTCGCTGACGCCATAAAACTCTTCACC AAAGAGCCCCTAAAACCCGCCACATCTACCATCACCCTCTACATCACCGCCCCGACCTTAGCT CTCACCATCGCTCTTCTACTATGGACCCCCCTCCCCATGCCCAACCCCCTGGTCAACCTCAAC CTAGGCCTCCTATTTATTCTAGCCACCTCTAGCCTAGCCGTTTACTCAATCCTCTGGTCAGGG TGGGCATCAAACTCAAACTACGCCCTGATCGGCGCACTGCGAGCAGTAGCCCAAACAATCTCA TATGAAGTCACCCTAGCCATCATTCTACTATCAACATTACTAATGAGTGGCTCCTTTAACCTC TCCACCCTTATCACAACACAAGAACACCTCTGGTTACTCCTGCCATCATGGCCCTTGGCCATG ATGTGGTTTATCTCCACACTAGCAGAGACCAACCGAACCCCCTTCGACCTTGCCGAAGGGGAG TCCGAACTAGTCTCAGGCTTCAACATCGAATACGCCGCAGGCCCCTTCGCCCTATTCTTCATG GCCGAATACACAAACATTATTATGATGAACACCCTCACCACTACAATCTTCCTAGGAACAACA TATGACGCACTCTCCCCTGAACTCTACACAACATATTTTGTCACCAAGACCCTACTTCTAACC TCCCTGTTCTTATGGATTCGAACAGCATACCCCGATTCCGCTACGACCAACTCATGCACCTC CTATGGAAAAACTTCCTACCACTCACCCTAGCATTACTTATGTGGTATGTCTCCATGCCCATT ACAATCTCCAGCATTCCCCCTCAAACCTAAGAGCACTGGGACGCCCACCGCCCCTTTCCCTCC GCTGCCAGGCGAGCATGTTGTGGTAATTCTGGAACACAAGAAGAGAAATTGCTGGGTTTAGAA CAAGATTATAAACGAATTCGGTGCTCAGTGATCACTTGACAGTTTTTTTTTTTTTAAATATT ACCCAAAATGCTCCCCAAATAAGAAATGCATCAGCTCAGTCAGTGAATACAAAAAAGGAATTA TTTTTCCCTTTGAGGGTCTTTTATACATCTCTCCTCCAACCCCACCCTCTATTCTGTTTCTTC CTCCTCACATGGGGGTACACATACACAGCTTCCTCTTTTGGTTCCATCCTTACCACCACACCA CACGCACACTCCACATGCCCAGCAGAGTGGCACTTGGTGGCCAGAAAGTGTGAGCCTCATGAT CTGCTGTCTGTAGTTCTGTGAGCTCAGGTCCCTCAAAGGCCTCGGAGCACCCCCTTCCTTGTG ACTGAGCCAGGGCCTGCATTTTTGGTTTTCCCCACCCCACACATTCTCAACCATAGTCCTTCT AACAATACCAATAGCTAGGACCCGGCTGCTGTGCACTGGGACTGGGGATTCCACATGTTTGCC TTGGGAGTCTCAAGCTGGACTGCCA |
| 69 | COX8-opt_ND1-3'UTR | ATGTCCGTCCTGACGCGCCTGCTGCTGCGGGGCTTGACACGGCTCGGCTCGGCGGCTCCAGTG CGGCGCGCCAGAATCCATTCGTTGATGGCCAACCTGCTGCTGCTGATCGTGCCCATCCTGATC GCCATGGCCTTCCTGATGCTGACCGAGCGCAAGATCCTGGGCTACATGCAGCTGCGCAAGGGC CCCAACGTGGTGGGCCCCTACGGCCTGCTGCAGCCCTTCGCCGACGCCATCAAGCTGTTCACC AAGGAGCCCCTGAAGCCCGCCACCAGCACCATCACCCTGTACATCACCGCCCCCACCCTGGCC CTGACCATCGCCCTGCTGCTGTGGACCCCCCTGCCCATGCCCAACCCCCTGGTGAACCTGAAC CTGGGCCTGCTGTTCATCCTGGCCACCAGCAGCCTGGCCGTGTACAGCATCCTGTGGAGCGGC TGGGCCAGCAACAGCAACTACGCCCTGATCGGCGCCCTGCGCGCCGTGGCCCAGACCATCAGC TACGAGGTGACCCTGGCCATCATCCTGCTGAGCACCCTGCTGATGAGCGGCAGCTTCAACCTG AGCACCCTGATCACCACCCAGGAGCACCTGTGGCTGCTGCTGCCCAGCTGGCCCCTGGCCATG ATGTGGTTCATCAGCACCCTGGCCGAGACCAACCGCACCCCCTTCGACCTGGCCGAGGGCGAG AGCGAGCTGGTGAGCGGCTTCAACATCGAGTACGCCGCCGGCCCCTTCGCCCTGTTCTTCATG GCCGAGTACACCAACATCATCATGATGAACACCCTGACCACCACCATCTTCCTGGGCACCACC TACGACGCCCTGAGCCCCGAGCTGTACACCACCTACTTCGTGACCAAGACCCTGCTGCTGACC AGCCTGTTCCTGTGGATCCGCACCGCCTACCCCCGCTTCCGCTACGACCAGCTGATGCACCTG CTGTGGAAGAACTTCCTGCCCCTGACCCTGGCCCTGCTGATGTGGTACGTGAGCATGCCCATC ACCATCAGCAGCATCCCCCCCCAGACCTAAGAGCACTGGGACGCCCACCGCCCCTTTCCCTCC GCTGCCAGGCGAGCATGTTGTGGTAATTCTGGAACACAAGAAGAGAAATTGCTGGGTTTAGAA CAAGATTATAAACGAATTCGGTGCTCAGTGATCACTTGACAGTTTTTTTTTTTTTAAATATT ACCCAAAATGCTCCCCAAATAAGAAATGCATCAGCTCAGTCAGTGAATACAAAAAAGGAATTA TTTTTCCCTTTGAGGGTCTTTTATACATCTCTCCTCCAACCCCACCCTCTATTCTGTTTCTTC CTCCTCACATGGGGGTACACATACACAGCTTCCTCTTTTGGTTCCATCCTTACCACCACACCA CACGCACACTCCACATGCCCAGCAGAGTGGCACTTGGTGGCCAGAAAGTGTGAGCCTCATGAT CTGCTGTCTGTAGTTCTGTGAGCTCAGGTCCCTCAAAGGCCTCGGAGCACCCCCTTCCTTGTG ACTGAGCCAGGGCCTGCATTTTTGGTTTTCCCCACCCCACACATTCTCAACCATAGTCCTTCT AACAATACCAATAGCTAGGACCCGGCTGCTGTGCACTGGGACTGGGGATTCCACATGTTTGCC TTGGGAGTCTCAAGCTGGACTGCCAGCCCCTGTCCTCCCTTCACCCCCATTGCGTATGAGCAT TTCAGAACTCCAAGGAGTCACAGGCATCTTTATAGTTCACGTTAACATATAGACACTGTTGGA AGCAGTTCCTTCTAAAAGGGTAGCCCTGGACTTAATACCAGCCGGATACCTCTGGCCCCCACC CCATTACTGTACCTCTGGAGTCACTACTGTGGGTCGCCACTCCTCTGCTACACAGCACGGCTT TTTCAAGGCTGTATTGAGAAGGGAAGTTAGGAAGAAGGGTGTGCTGGGCTAACCAGCCCACAG AGCTCACATTCCTGTCCCTTGGGTGAAAAATACATGTCCATCCTGATATCTCCTGAATTCAGA AATTAGCCTCCACATGTGCAATGGCTTTAAGAGCCAGAAGCAGGGTTCTGGGAATTTTGCAAG TTACCTGTGGCCAGGTGTGGTCTCGGTTACCAAATACGGTTACCTGCAGCTTTTTAGTCCTTT GTGCTCCCACGGGTCTACAGAGTCCCATCTGCCCAAAGGTCTTGAAGCTTGACAGGATGTTTT CGATTACTCAGTCTCCCAGGGCACTACTGGTCCGTAGGATTCGATTGGTCGGGGTAGGAGAGT TAAACAACATTTAAACAGAGTTCTCTCAAAAATGTCTAAAGGGATTGTAGGTAGATAACATCC |

TABLE 1-continued nucleic acid and polypeptide sequences and SEQ ID NOs

| SEQ | Description | Sequence |
|---|---|---|
| | | AATCACTGTTTGCACTTATCTGAAATCTTCCCTCTTGGCTGCCCCCAGGTATTTACTGTGGAG<br>AACATTGCATAGGAATGTCTGGAAAAAGCTTCTACAACTTGTTACAGCCTTCACATTTGTAGA<br>AGCTTT |
| 70 | COX8-<br>opt_ND1-<br>3'UTR* | ATGTCCGTCCTGACGCGCCTGCTGCTGCGGGGCTTGACACGGCTCGGCTCGGCGGCTCCAGTG<br>CGGCGCGCCAGAATCCATTCGTTGATGGCCAACCTGCTGCTGCTGATCGTGCCCATCCTGATC<br>GCCATGGCCTTCCTGATGCTGACCGAGCGCAAGATCCTGGGCTACATGCAGCTGCGCAAGGGC<br>CCCAACGTGGTGGGCCCCTACGGCCTGCTGCAGCCCTTCGCCGACGCCATCAAGCTGTTCACC<br>AAGGAGCCCCTGAAGCCCGCCACCAGCACCATCACCCTGTACATCACCGCCCCCACCCTGGCC<br>CTGACCATCGCCCTGCTGCTGTGGACCCCCCTGCCCATGCCCAACCCCCTGGTGAACCTGAAC<br>CTGGGCCTGCTGTTCATCCTGGCCACCAGCAGCCTGGCCGTGTACAGCATCCTGTGGAGCGGC<br>TGGGCCAGCAACAGCAACTACGCCCTGATCGGCGCCCTGCGCGCCGTGGCCCAGACCATCAGC<br>TACGAGGTGACCCTGGCCATCATCCTGCTGAGCACCCTGCTGATGAGCGGCAGCTTCAACCTG<br>AGCACCCTGATCACCACCCAGGAGCACCTGTGGCTGCTGCTGCCCAGCTGGCCCCTGGCCATG<br>ATGTGGTTCATCAGCACCCTGGCCGAGACCAACCGCACCCCCTTCGACCTGGCCGAGGGCGAG<br>AGCGAGCTGGTGAGCGGCTTCAACATCGAGTACGCCGCCGGCCCCTTCGCCCTGTTCTTCATG<br>GCCGAGTACACCAACATCATCATGATGAACACCCTGACCACCACCATCTTCCTGGGCACCACC<br>TACGACGCCCTGAGCCCCGAGCTGTACACCACCTACTTCGTGACCAAGACCCTGCTGCTGACC<br>AGCCTGTTCCTGTGGATCCGCACCGCCTACCCCGCTTCCGCTACGACCAGCTGATGCACCTG<br>CTGTGGAAGAACTTCCTGCCCCTGACCCTGGCCCTGCTGATGTGGTACGTGAGCATGCCCATC<br>ACCATCAGCAGCATCCCCCCAGACCTAAGAGCACTGGGACGCCCACCGCCCCTTTCCCTCC<br>GCTGCCAGGCGAGCATGTTGTGGTAATTCTGGAACACAAGAAGAGAAATTGCTGGGTTTAGAA<br>CAAGATTATAAACGAATTCGGTGCTCAGTGATCACTTGACAGTTTTTTTTTTTTTAAATATT<br>ACCCAAAATGCTCCCCAAATAAGAAATGCATCAGCTCAGTCAGTGAATACAAAAAAGGAATTA<br>TTTTTCCCTTTGAGGGTCTTTTATACATCTCTCCTCCAACCCCACCCTCTATTCTGTTTCTTC<br>CTCCTCACATGGGGGTACACATACACAGCTTCCTCTTTTGGTTCCATCCTTACCACCACACCA<br>CACGCACACTCCACATGCCCAGCAGAGTGGCACTTGGTGGCCAGAAAGTGTGAGCCTCATGAT<br>CTGCTGTCTGTAGTTCTGTGAGCTCAGGTCCCTCAAAGGCCTCGGAGCACCCCCTTCCTTGTG<br>ACTGAGCCAGGGCCTGCATTTTTGGTTTTCCCCACCCCACACATTCTCAACCATAGTCCTTCT<br>AACAATACCAATAGCTAGGACCCGGCTGCTGTGCACTGGGACTGGGGATTCCACATGTTTGCC<br>TTGGGAGTCTCAAGCTGGACTGCCA |
| 71 | OPA1-ND4-<br>3'UTR | GTGCTGCCCGCCTAGAAAGGGTGAAGTGGTTGTTTCCGTGACGGACTGAGTACGGGTGCCTGT<br>CAGGCTCTTGCGGAAGTCCATGCGCCATTGGGAGGGCCTCGGCCGCGGCTCTGTGCCCTTGCT<br>GCTGAGGGCCACTTCCTGGGTCATTCCTGGACCGGGAGCCGGGCTGGGGCTCACACGGGGGCT<br>CCCGCGTGGCCGTCTCGGCGCCTGCGTGACCTCCCCGCCGGCGGGATGTGGCGACTACGTCGG<br>GCCGCTGTGGCCTGATGCTAAAACTAATCGTCCCAACAATTATGTTACTACCACTGACATGGC<br>TTTCCAAAAAACACATGATTTGGATCAACAACAACCACCCACAGCCTAATTATTAGCATCATC<br>CTCTACTATTTTTTAACCAAATCAACAACAACCTATTTAGCTGTTCCCCAACCTTTTCCTCCG<br>ACCCCCTAACAACCCCCCTCCTAATGCTAACTACCTGGCTCCTACCCCTCACAATCATGGCAA<br>GCCAACGCCACTTATCCAGTGAACCACTATCACGAAAAAAACTCTACCTCTCTATGCTAATCT<br>CCCTACAAATCTCCTTAATTATGACATTCACAGCCACAGAACTAATCATGTTTTATATCTTCT<br>TCGAAACCACACTTATCCCCACCTTGGCTATCATCACCCGATGGGGCAACCAGCCAGAACGCC<br>TGAACGCAGGCACATACTTCCTATTCTACACCCTAGTAGGCTCCCTTCCCCTACTCATCGCAC<br>TAATTTACACTCACAACACCCTAGGCTCACTAAACATTCTACTACTCACTCTCACTGCCCAAG<br>AACTATCAAACTCCTGGGCCAACAACTTAATGTGGCTAGCTTACACAATGGCTTTTATGGTAA<br>AGATGCCTCTTTACGGACTCCACTTATGGCTCCCTAAAGCCCATGTCGAAGCCCCCATCGCTG<br>GGTCAATGGTACTTGCCGCAGTACTCTTAAAACTAGGCGGCTATGGTATGATGCGCCTCACAC<br>TCATTCTCAACCCCCTGACAAAACACATGGCCTACCCCTTCCTTGTACTATCCCTATGGGGCA<br>TGATTATGACAAGCTCCATCTGCCTACGACAAACAGACCTAAAATCGCTCATTGCATACTCTT<br>CAATCAGCCACATGGCCCTCGTAGTAACAGCCATTCTCATCCAAACCCCCTGGAGCTTCACCG<br>GCGCAGTCATTCTCATGATCGCCCACGGGCTTACATCCTCATTACTATTCTGCCTAGCAAACT<br>CAAACTACGAACGCACTCACAGTCGCATCATGATCCTCTCTCAAGGACTTCAAACTCTACTCC<br>CACTAATGGCTTTTTGGTGGCTTCTAGCAAGCCTCGCTAACCTCGCCTTACCCCCCACTATTA<br>ACCTACTGGGAGAACTCTCTGTGCTAGTAACCACGTTCTCCTGGTCAAATATCACTCTCCTAC<br>TTACAGGACTCAACATGCTAGTCACAGCCCTATACTCCCTCTACATGTTTACCACAACACAAT<br>GGGGCTCACTCACCCACCACATTAACAACATGAAACCCTCATTCACACGAGAAAACACCCTCA<br>TGTTCATGCACCTATCCCCCATTCTCCTCCTATCCCTCAACCCCGACATCATTACCGGGTTTT<br>CCTCTTAAGAGCACTGGGACGCCCACCGCCCCTTTCCCTCCGCTGCCAGGCGAGCATGTTGTG<br>GTAATTCTGGAACACAAGAAGAGAAATTGCTGGGTTTAGAACAAGATTATAAACGAATTCGGT<br>GCTCAGTGATCACTTGACAGTTTTTTTTTTTAAATATTACCCAAAATGCTCCCCAAATAA<br>GAAATGCATCAGCTCAGTCAGTGAATACAAAAAAGGAATTATTTTTCCCTTTGAGGGTCTTTT<br>ATACATCTCTCCTCCAACCCCACCCTCTATTCTGTTTCTTCCTCCTCACATGGGGTACACAT<br>ACACAGCTTCCTCTTTTGGTTCCATCCTTACCACCACACCACACGCACACTCCACATGCCCAG<br>CAGAGTGGCACTTGGTGGCCAGAAAGTGTGAGCCTCATGATCTGCTGTCTGTAGTTCTGTGAG<br>CTCAGGTCCCTCAAAGGCCTCGGAGCACCCCCTTCCTTGTGACTGAGCCAGGGCCTGCATTTT<br>TGGTTTTCCCCACCCCACACATTCTCAACCATAGTCCTTCTAACAATACCAATAGCTAGGACC<br>CGGCTGCTGTGCACTGGGACTGGGGATTCCACATGTTTGCCTTGGGAGTCTCAAGCTGGACTG<br>CCAGCCCCTGTCCTCCCTTCACCCCCATTGCGTATGAGCATTTCAGAACTCCAAGGAGTCACA<br>GGCATCTTTATAGTTCACGTTAACATATAGACACTGTTGGAAGCAGTTCCTTCTAAAAGGGTA<br>GCCCTGGACTTAATACCAGCCGGATACCTCTGGCCCCACCCCATTACTGACTCTGGAGTC<br>ACTACTGTGGGTCGCCACTCCTCTGCTACACAGCACGGCTTTTTCAAGGCTGTATTGAGAAGG<br>GAAGTTAGGAAGAAGGGTGTGCTGGGCTAACCAGCCCACAGAGCTCACATTCCTGTCCCTTGG<br>GTGAAAAATACATGTCCATCCTGATATCTCCTGAATTCAGAAATTAGCCTCCACATGTGCAAT<br>GGCTTTAAGAGCCAGAAGCAGGGTTCTGGGAATTTTGCAAGTTACCTGTGGCCAGGTGTGGTC<br>TCGGTTACCAAATACGGTTACCTGCAGCTTTTTAGTCCTTTGTGCTCCCACGGGTCTACAGAG |

TABLE 1-continued nucleic acid and polypeptide sequences and SEQ ID NOs

| SEQ | Description | Sequence |
|---|---|---|
| | | TCCCATCTGCCCAAAGGTCTTGAAGCTTGACAGGATGTTTTCGATTACTCAGTCTCCCAGGGC<br>ACTACTGGTCCGTAGGATTCGATTGGTCGGGGTAGGAGAGTTAAACAACATTTAAACAGAGTT<br>CTCTCAAAAATGTCTAAAGGGATTGTAGGTAGATAACATCCAATCACTGTTTGCACTTATCTG<br>AAATCTTCCCTCTTGGCTGCCCCAGGTATTTACTGTGGAGAACATTGCATAGGAATGTCTGG<br>AAAAAGCTTCTACAACTTGTTACAGCCTTCACATTTGTAGAAGCTTT |
| 72 | OPA1-ND4-<br>3'UTR* | GTGCTGCCCGCCTAGAAAGGGTGAAGTGGTTGTTTCCGTGACGGACTGAGTACGGGTGCCTGT<br>CAGGCTCTTGCGGAAGTCCATGCGCCATTGGGAGGGCCTCGGCCGCGGCTCTGTGCCCTTGCT<br>GCTGAGGGCCACTTCCTGGGTCATTCCTGGACCGGGAGCCGGGCTGGGGCTCACACGGGGGCT<br>CCCGCGTGGCCGTCTCGGCGCCTGCGTGACCTCCCCGCCGGCGGGATGTGGCGACTACGTCGG<br>GCCGCTGTGGCCTGATGCTAAAACTAATCGTCCCAACAATTATGTTACTACCACTGACATGGC<br>TTTCCAAAAAACACATGATTTGGATCAACACAACCACCCACAGCCTAATTATTAGCATCATCC<br>CTCTACTATTTTTTAACCAAATCAACAACAACCTATTTAGCTGTTCCCCAACCTTTTCCTCCG<br>ACCCCCTAACAACCCCCCTCCTAATGCTAACTACCTGGCTCCTACCCCTCACAATCATGGCAA<br>GCCAACGCCACTTATCCAGTGAACCACTATCACGAAAAAAACTCTACCTCTCTATGCTAATCT<br>CCCTACAAATCTCCTTAATTATGACATTCACAGCCACAGAACTAATCATGTTTTATATCTTCT<br>TCGAAACCACACTTATCCCCACCTTGGCTATCATCACCCGATGGGGCAACCAGCCAGAACGCC<br>TGAACGCAGGCACATACTTCCTATTCTACACCCTAGTAGGCTCCCTTCCCCTACTCATCGCAC<br>TAATTTACACTCACAACACCCTAGGCTCACTAAACATTCTACTACTCACTCTCACTGCCCAAG<br>AACTATCAAACTCCTGGGCCAACAACTTAATGTGGCTAGCTTACACAATGGCTTTTATGGTAA<br>AGATGCCTCTTTACGGACTCCACTTATGGCTCCCTAAAGCCATGTCGAAGCCCCCATCGCTG<br>GGTCAATGGTACTTGCCGCAGTACTCTTAAAACTAGGCGGCTATGGTATGATGCGCCTCACAC<br>TCATTCTCAACCCCCTGACAAAACACATGGCCTACCCCTTCCTTGTACTATCCCTATGGGGCA<br>TGATTATGACAAGCTCCATCGCCTACGACAAACAGACCTAAAATCGCTCATTGCATACTCTT<br>CAATCAGCCACATGGCCCTCGTAGTAACAGCCATTCTCATCCAAACCCCCTGGAGCTTCACCG<br>GCGCAGTCATTCTCATGATCGCCCACGGGCTTACATCCTCATTACTATTCTGCCTAGCAAACT<br>CAAACTACGAACGCACTCACAGTCGCATCATGATCCTCTCTCAAGGACTTCAAACTCTACTCC<br>CACTAATGGCTTTTTGGTGGCTTCTAGCAAGCCTCGCTAACCTCGCCTTACCCCCCACTATTA<br>ACCTACTGGGAGAACTCTCTGTGCTAGTAACCACGTTCTCCTGGTCAAATATCACTCTCCTAC<br>TTACAGGACTCAACATGCTAGTCACAGCCCTATACTCCCTCTACATGTTTACCACAACACAAT<br>GGGGCTCACTCACCCACCACATTAACAACATGAAACCCTCATTCACACGAGAAAACACCCTCA<br>TGTTCATGCACCTATCCCCCATTCTCCTCCTATCCCTCAACCCCGACATCATTACCGGGTTTT<br>CCTCTTAAGAGCACTGGGACGCCCACCGCCCCTTTCCCTCCGCTGCCAGGCGAGCATGTTGTG<br>GTAATTCTGGAACACAAGAAGAGAAATTGCTGGGTTTAGAACAAGATTATAAACGAATTCGGT<br>GCTCAGTGATCACTTGACAGTTTTTTTTTTTTTAAATATTACCCAAAATGCTCCCCAAATAA<br>GAAATGCATCAGCTCAGTCAGTGAATACAAAAAAGGAATTATTTTTCCCTTTGAGGGTCTTTT<br>ATACATCTCTCCTCCAACCCCACCCTCTATTCTGTTTCTTCCTCCTCACATGGGGGTACACAT<br>ACACAGCTTCCTCTTTTGGTTCCATCCTTACCACCACACCACACGCACACTCCACATGCCCAG<br>CAGAGTGGCACTTGGTGGCCAGAAAGTGTGAGCCTCATGATCTGCTGTCTGTAGTTCTGTGAG<br>CTCAGGTCCCTCAAAGGCCTCGGAGCACCCCCTTCCTTGTGACTGAGCCAGGGCCTGCATTTT<br>TGGTTTTCCCCACCCCACACATTCTCAACCATAGTCCTTCTAACAATACCAATAGCTAGGACC<br>CGGCTGCTGTGCACTGGGACTGGGGATTCCACATGTTTGCCTTGGGAGTCTCAAGCTGGACTG<br>CCA |
| 73 | OPA1-<br>opt_ND4-<br>3'UTR | GTGCTGCCCGCCTAGAAAGGGTGAAGTGGTTGTTTCCGTGACGGACTGAGTACGGGTGCCTGT<br>CAGGCTCTTGCGGAAGTCCATGCGCCATTGGGAGGGCCTCGGCCGCGGCTCTGTGCCCTTGCT<br>GCTGAGGGCCACTTCCTGGGTCATTCCTGGACCGGGAGCCGGGCTGGGGCTCACACGGGGGCT<br>CCCGCGTGGCCGTCTCGGCGCCTGCGTGACCTCCCCGCCGGCGGGATGTGGCGACTACGTCGG<br>GCCGCTGTGGCCTGATGCTGAAGCTGATCGTGCCCACCATCATGCTGCTGCCTCTGACCTGGC<br>TGAGCAAGAAACACATGATCTGGATCAACACAACCACACGCACAGCCTGATCATCAGCATCATCC<br>CTCTGCTGTTCTTCAACCAGATCAACAACAACCTGTTCAGCTGCAGCCCCACCTTCAGCAGCG<br>ACCCTCTGACAACACCTCTGCTGATGCTGACCACCTGGCTGCTGCCCCTCACAATCATGGCCT<br>CTCAGAGACACCTGAGCAGCGAGCCCCTGAGCCGGAAGAAACTGTACCTGAGCATGCTGATCT<br>CCCTGCAGATCTCTCTGATCATGACCTTCACCGCCACCGAGCTGATCATGTTCTACATCTTTT<br>TCGAGACAACGCTGATCCCCACACTGGCCATCATCACCAGATGGGGCAACCAGCCTGAGAGAC<br>TGAACGCCGGCACCTACTTTCTGTTCTACACCCTCGTGGGCAGCCTGCCACTGCTGATTGCCC<br>TGATCTACACCCACAACACCCTGGGCTCCCTGAACATCCTGCTGCTGACACTGACAGCCCAAG<br>AGCTGAGCAACAGCTGGGCCAACAATCTGATGTGGCTGGCCTACACAATGGCCTTCATGGTCA<br>AGATGCCCCTGTACGGCCTGCACCTGTGGCTGCCTAAAGCTCATGTGGAAGCCCCTATCGCTG<br>GCTCTATGGTGCTGGCTGCAGTGCTGCTGAAACTCGGCGGCTACGGCATGATGCGGCTGACCC<br>TGATTCTGAATCCCCTGACCAAGCACATGGCCTATCATTTCTGGTGCTGAGCCTGTGGGGCA<br>TGATTATGACCAGCAGCATCTGCCTGCGCAGACCGATCTGAAGTCCCTGATCGCCTACAGCT<br>CCATCAGCCACATGGCCCTGGTGGTCACCGCCATCCTGATTCAGACCCCTTGGAGCTTCACAG<br>GCGCCGTGATCCTGATGATTGCCCACGGCCTGACAAGCAGCTGCTGTTTTGTCTGGCCAACA<br>GCAACTACGAGCGGACCCACAGCAGAATCATGATCCTGTCTCAGGGCCTGCAGACCCTCCTGC<br>CTCTTATGGCTTTTTGGTGGCTGCTGGCCTCTCTGGCCAATCTGGCACTGCCTCCTACCATCA<br>ATCTGCTGGGCGAGCTGAGCGTGCTGGTCACCACATTCAGCTGGTCCAATATCACTCTGCTGC<br>TCACCGGCCTGAACATGCTGGTTACAGCCCTGTACTCCCTGTACATGTTCACCACCACACAGT<br>GGGGAAGCCTGACACACCACATCAACAATATGAAGCCCAGCTTCACCCGCGAGAACACCCTGA<br>TGTTCATGCATCTGAGCCCCATTCTGCTGCTGTCCCTGAATCCTGATATCATCACCGGCTTCT<br>CCAGCTGAGAGCACTGGGACGCCCACCGCCCCTTTCCCTCCGCTGCCAGGCGAGCATGTTGTG<br>GTAATTCTGGAACACAAGAAGAGAAATTGCTGGGTTTAGAACAAGATTATAAACGAATTCGGT<br>GCTCAGTGATCACTTGACAGTTTTTTTTTTTTTAAATATTACCCAAAATGCTCCCCAAATAA<br>GAAATGCATCAGCTCAGTCAGTGAATACAAAAAAGGAATTATTTTTCCCTTTGAGGGTCTTTT<br>ATACATCTCTCCTCCAACCCCACCCTCTATTCTGTTTCTTCCTCCTCACATGGGGGTACACAT<br>ACACAGCTTCCTCTTTTGGTTCCATCCTTACCACCACACCACACGCACACTCCACATGCCCAG |

TABLE 1-continued nucleic acid and polypeptide sequences and SEQ ID NOs

| SEQ | Description | Sequence |
|---|---|---|
| | | CAGAGTGGCACTTGGTGGCCAGAAAGTGTGAGCCTCATGATCTGCTGTCTGTAGTTCTGTGAG<br>CTCAGGTCCCTCAAAGGCCTCGGAGCACCCCCTTCCTTGTGACTGAGCCAGGGCCTGCATTTT<br>TGGTTTTCCCCACCCCACACATTCTCAACCATAGTCCTTCTAACAATACCAATAGCTAGGACC<br>CGGCTGCTGTGCACTGGGACTGGGGATTCCACATGTTTGCCTTGGGAGTCTCAAGCTGGACTG<br>CCAGCCCCTGTCCTCCCTTCACCCCCATTGCGTATGAGCATTTCAGAACTCCAAGGAGTCACA<br>GGCATCTTTATAGTTCACGTTAACATATAGACACTGTTGGAAGCAGTTCCTTCTAAAAGGGTA<br>GCCCTGGACTTAATACCAGCCGGATACCTCTGGCCCCCACCCCATTACTGTACCTCTGGAGTC<br>ACTACTGTGGGTCGCCACTCCTCTGCTACACAGCACGGCTTTTTCAAGGCTGTATTGAGAAGG<br>GAAGTTAGGAAGAAGGGTGTGCTGGGCTAACCAGCCCACAGAGCTCACATTCCTGTCCCTTGG<br>GTGAAAAATACATGTCCATCCTGATATCTCCTGAATTCAGAAATTAGCCTCCACATGTGCAAT<br>GGCTTTAAGAGCCAGAAGCAGGGTTCTGGGAATTTTGCAAGTTACCTGTGGCCAGGTGTGGTC<br>TCGGTTACCAAATACGGTTACCTGCAGCTTTTTAGTCCTTTGTGCTCCCACGGGTCTACAGAG<br>TCCCATCTGCCCAAAGGTCTTGAAGCTTGACAGGATGTTTTCGATTACTCAGTCTCCCAGGGC<br>ACTACTGGTCCGTAGGATTCGATTGGTCGGGGTAGGAGAGTTAAACAACATTTAAACAGAGTT<br>CTCTCAAAAATGTCTAAAGGGATTGTAGGTAGATAACATCCAATCACTGTTTGCACTTATCTG<br>AAATCTTCCCTCTTGGCTGCCCCCAGGTATTTACTGTGGAGAACATTGCATAGGAATGTCTGG<br>AAAAAGCTTCTACAACTTGTTACAGCCTTCACATTTGTAGAAGCTTT |
| 74 | OPA1-<br>opt_ND4-<br>3'UTR* | GTGCTGCCCGCCTAGAAAGGGTGAAGTGGTTGTTTCCGTGACGGACTGAGTACGGGTGCCTGT<br>CAGGCTCTTGCGGAAGTCCATGCGCCATTGGGAGGGCCTCGGCCGCGGCTCTGTGCCCTTGCT<br>GCTGAGGGCCACTTCCTGGGTCATTCCTGGACCGGGAGCCGGGCTGGGGCTCACACGGGGGCT<br>CCCGCGTGGCCGTCTCGGCGCCTGCGTGACCTCCCCGCCGGCGGGATGTGGCGACTACGTCGG<br>GCCGCTGTGGCCTGATGCTGAAGCTGATCGTGCCCACCATCATGCTGCTGCCTCTGACCTGGC<br>TGAGCAAGAAACACATGATCTGGATCAACACCACCACGCACAGCCTGATCATCAGCATCATCC<br>CTCTGCTGTTCTTCAACCAGATCAACAACAACCTTGTTCAGCTGCAGCCCCACCTTCAGCAGCG<br>ACCCTCTGACAACACCTCTGCTGATGCTGACCACCTGGCTGCTGCCCCTCACAATCATGGCCT<br>CTCAGAGACACCTGAGCAGCGAGCCCTGAGCCGGAAGAAACTGTACCTGAGCATGCTGATCT<br>CCCTGCAGATCTCTCTGATCATGACCTTCACCGCCACCGAGCTGATCATGTTCTACATCTTTT<br>TCGAGACAACGCTGATCCCCACACTGGCCATCATCACCAGATGGGGCAACCAGCCTGAGAGAC<br>TGAACGCCGGCACCTACTTTCTGTTCTACACCCTCGTGGGCAGCCTGCCACTGCTGATTGCCC<br>TGATCTACACCCACAACACCCTGGGCTCCCTGAACATCCTGCTGCTGACACTGACAGCCCAAG<br>AGCTGAGCAACAGCTGGGCCAACAATCTGATGTGGCTGGCCTACACAATGGCCTTCATGGTCA<br>AGATGCCCCTGTACGGCCTGCACCTGTGGCTGCCTAAAGCTCATGTGGAAGCCCCTATCGCCG<br>GCTCTATGGTGCTGGCTGCAGTGCTGCTGAAACTCGGCGGCTACGGCATGATGCGGCTGACCC<br>TGATTCTGAATCCCCTGACCAAGCACATGGCCTATCCATTTCTGGTGCTGAGCCTGTGGGGCA<br>TGATTATGACCAGCAGCATCTGCCTGCGGCAGACCGATCTGAAGTCCCTGATCGCCTACAGCT<br>CCATCAGCCACATGGCCCTGGTGGTCACCGCCATCCTGATTCAGACCCCTTGGAGCTTTACAG<br>GCGCCGTGATCCTGATGATTGCCCACGGCCTGACAAGCAGCCTGCTGTTTTGTCTGGCCAACA<br>GCAACTACGAGCGGACCCACAGCAGAATCATGATCCGTCTCAGGGCCTGCAGACCCTCCTGC<br>CTCTTATGGCTTTTTGGTGGCTGCTGGCCTCTCTGGCCAATCTGGCACTGCCTCCTACCATCA<br>ATCTGCTGGGCGAGCTGAGCGTGCTGGTCACCACATTCAGCTGGTCCAATATCACCCTGCTGC<br>TCACCGGCCTGAACATGCTGGTTACAGCCCTGTACTCCCTGACATGTTCACCACCACACAGT<br>GGGGAAGCCTGACACACCCACATCAACAATATGAAGCCCAGCTTCACCCGCGAGAACACCCTGA<br>TGTTCATGCATCTGAGCCCCATTCTGCTGCTGTCCCTGAATCCTGATATCATCACCGGCTTCT<br>CCAGCTGAGAGCACTGGGACGCCCACCGCCCCTTTCCCTCCGCTGCCAGGCGAGCATGTTGTG<br>GTAATTCTGGAACACAAGAAGAGAAATTGCTGGGTTTAGAACAAGATTATAAACGAATTCGGT<br>GCTCAGTGATCACTTGACAGTTTTTTTTTTTTTAAATATTACCCAAAATGCTCCCCAAATAA<br>GAAATGCATCAGCTCAGTCAGTGAATACAAAAAAGGAATTATTTTTCCCTTTGAGGGTCTTTT<br>ATACATCTCTCCTCCAACCCCACCCTCTATTCTGTTTCTTCCTCCTCACATGGGGGTACACAT<br>ACACAGCTTCCTCTTTTGGTTCCATCCTTACCACCACACCCACACGCACACTCCACATGCCCAG<br>CAGAGTGGCACTTGGTGGCCAGAAAGTGTGAGCCTCATGATCTGCTGTCTGTAGTTCTGTGAG<br>CTCAGGTCCCTCAAAGGCCTCGGAGCACCCCCTTCCTTGTGACTGAGCCAGGGCCTGCATTTT<br>TGGTTTTCCCCACCCCACACATTCTCAACCATAGTCCTTCTAACAATACCAATAGCTAGGACC<br>CGGCTGCTGTGCACTGGGACTGGGGATTCCACATGTTTGCCTTGGGAGTCTCAAGCTGGACTG<br>CCA |
| 75 | OPA1-<br>opt_ND4*-<br>3'UTR | GTGCTGCCCGCCTAGAAAGGGTGAAGTGGTTGTTTCCGTGACGGACTGAGTACGGGTGCCTGT<br>CAGGCTCTTGCGGAAGTCCATGCGCCATTGGGAGGGCCTCGGCCGCGGCTCTGTGCCCTTGCT<br>GCTGAGGGCCACTTCCTGGGTCATTCCTGGACCGGGAGCCGGGCTGGGGCTCACACGGGGGCT<br>CCCGCGTGGCCGTCTCGGCGCCTGCGTGACCTCCCCGCCGGCGGGATGTGGCGACTACGTCGG<br>GCCGCTGTGGCCTGATGCTGAAGCTGATCGTGCCCACCATCATGCTGCTGCCCCTGACCTGGC<br>TGAGCAAGAAGCACATGATCTGGATCAACACCACCACCCACAGCCTGATCATCAGCATCATCC<br>CCTGCTGTTCTTCAACCAGATCAACAACAACCTTGTTCAGCTGCAGCCCCACCTTCAGCAGCG<br>ACCCCCTGACCACCCCCCTGCTGATGCTGACCACCTGGCTGCTGCCCCTGACCATCATGGCCA<br>GCCAGCGCCACCTGAGCAGCGAGCCCTGAGCCGCAAGAAGTGTACCTGAGCATGCTGATCA<br>GCCTGCAGATCAGCCTGATCATGACCTTCACCGCCACCGAGCTGATCATGTTCTACATCTTCT<br>TCGAGACCACCCTGATCCCCACCCTGGCCATCATCACCGCTGGGGCAACCAGCCCGAGCGCC<br>TGAACGCCGGCACCTACTTCCTGTTCTACACCCTGGTGGGCAGCCTGCCCCTGCTGATCGCCC<br>TGATCTACACCCACAACACCCTGGGCAGCCTGAACATCCTGCTGCTGACCCTGACCGCCCAGG<br>AGCTGAGCAACAGCTGGGCCAACAACCTGATGTGGCTGGCCTACACCATGGCCTTCATGGTGA<br>AGATGCCCCTGTACGGCCTGCACCTGTGGCTGCCCAAGGCCCACGTGGAGGCCCCCATCGCCG<br>GCAGCATGGTGCTGGCCGCCGTGCTGCTGAAGCTGGGCGGCTACGGCATGATGCGCCTGACCC<br>TGATCCTGAACCCCCTGACCAAGCACATGGCCTACCCCTTCCTGGTGCTGAGCCTGTGGGGCA<br>TGATCATGACCAGCAGCATCTGCCTGCGCCAGACCGACCTGAAGAGCCTGATCGCCTACAGCA<br>GCATCAGCCACATGGCCCTGGTGGTGACCGCCATCCTGATCCAGACCCCCTGGAGCTTCACCG<br>GCGCCGTGATCCTGATGATCGCCCACGGCCTGACCAGCAGCCTGCTGTTCTGCCTGGCCAACA |

TABLE 1-continued nucleic acid and polypeptide sequences and SEQ ID NOs

| SEQ | Description | Sequence |
|---|---|---|
| | | GCAACTACGAGCGCACCCACAGCCGCATCATGATCCTGAGCCAGGGCCTGCAGACCCTGCTGC<br>CCCTGATGGCCTTCTGGTGGCTGCTGGCCAGCCTGGCCAACCTGGCCCTGCCCCCCACCATCA<br>ACCTGCTGGGCGAGCTGAGCGTGCTGGTGACCACCTTCAGCTGGAGCAACATCACCCTGCTGC<br>TGACCGGCCTGAACATGCTGGTGACCGCCCTGTACAGCCTGTACATGTTCACCACCACCCAGT<br>GGGGCAGCCTGACCCACCACATCAACAACATGAAGCCCAGCTTCACCCGCGAGAACACCCTGA<br>TGTTCATGCACCTGAGCCCCATCCTGCTGCTGAGCCTGAACCCCGACATCATCACCGGCTTCA<br>GCAGCTAAGAGCACTGGGACGCCCACCGCCCCTTTCCCTCCGCTGCCAGGCGAGCATGTTGTG<br>GTAATTCTGGAACACAAGAAGAGAAATTGCTGGGTTTAGAACAAGATTATAAACGAATTCGGT<br>GCTCAGTGATCACTTGACAGTTTTTTTTTTTTTAAATATTACCCAAAATGCTCCCCAAATAA<br>GAAATGCATCAGCTCAGTCAGTGAATACAAAAAAGGAATTATTTTTCCCTTTGAGGGTCTTTT<br>ATACATCTCTCCTCCAACCCCACCCTCTATTCTGTTTCTTCCTCCTCACATGGGGGTACACAT<br>ACACAGCTTCCTCTTTTGGTTCCATCCTTACCACCACACCACACGCACACTCCACATGCCCAG<br>CAGAGTGGCACTTGGTGGCCAGAAAGTGTGAGCCTCATGATCTGCTGTCTGTAGTTCTGTGAG<br>CTCAGGTCCCTCAAAGGCCTCGGAGCACCCCCTTCCTTGTGACTGAGCCAGGGCCTGCATTTT<br>TGGTTTTCCCCACCCCACACATTCTCAACCATAGTCCTTCTAACAATACCAATAGCTAGGACC<br>CGGCTGCTGTGCACTGGGACTGGGGATTCCACATGTTTGCCTTGGGAGTCTCAAGCTGGACTG<br>CCAGCCCCTGTCCTCCCTTCACCCCCATTGCGTATGAGCATTTCAGAACTCCAAGGAGTCACA<br>GGCATCTTTATAGTTCACGTTAACATATAGACACTGTTGGAAGCAGTTCCTTCTAAAAGGGTA<br>GCCCTGGACTTAATACCAGCCGGATACCTCTGGCCCCCACCCCATTACTGTACCTCTGGAGTC<br>ACTACTGTGGGTCGCCACTCCTCTGCTACACAGCACGGCTTTTTCAAGGCTGTATTGAGAAGG<br>GAAGTTAGGAAGAAGGGTGTGCTGGGCTAACCAGCCCACAGAGCTCACATTCCTGTCCCTTGG<br>GTGAAAAATACATGTCCATCCTGATATCTCCTGAATTCAGAAATTAGCCTCCACATGTGCAAT<br>GGCTTTAAGAGCCAGAAGCAGGGTTCTGGGAATTTTGCAAGTTACCTGTGGCCAGGTGTGGTC<br>TCGGTTACCAAATACGGTTACCTGCAGCTTTTTAGTCCTTTGTGCTCCCACGGGTCTACAGAG<br>TCCCATCTGCCCAAAGGTCTTGAAGCTTGACAGGATGTTTTCGATTACTCAGTCTCCCAGGGC<br>ACTACTGGTCCGTAGGATTCGATTGGTCGGGGTAGGAGAGTTAAACAACATTTAAACAGAGTT<br>CTCTCAAAAATGTCTAAAGGGATTGTAGGTAGATAACATCCAATCACTGTTTGCACTTATCTG<br>AAATCTTCCCTCTTGGCTGCCCCCAGGTATTTACTGTGGAGAACATTGCATAGGAATGTCTGG<br>AAAAAGCTTCTACAACTTGTTACAGCCTTCACATTTGTAGAAGCTTT |
| 76 | OPA1-<br>opt_ND4*-<br>3'UTR* | GTGCTGCCCGCCTAGAAAGGGTGAAGTGGTTGTTTCCGTGACGGACTGAGTACGGGTGCCTGT<br>CAGGCTCTTGCGGAAGTCCATGCGCCATTGGGAGGGCCTCGGCCGCGGCTCTGTGCCCTTGCT<br>GCTGAGGGCCCACTTCCTGGGTCATTCCTGGACCGGGAGCCGGGCTGGGGCTCACACGGGGGCT<br>CCCGCGTGGCCGTCTCGGCGCCTGCGTGACCTCCCCGCCGGCGGGATGTGGCGACTACGTCGG<br>GCCGCTGTGGCCTGATGCTGAAGCTGATCGTGCCCACCATCATGCTGCTGCCCCCTGACCTGGC<br>TGAGCAAGAAGCACATGATCTGGATCAACACCACCACCCACAGCCTGATCATCAGCATCATCC<br>CCCTGCTGTTCTTCAACCAGATCAACAACAACCTGTTCAGCTGCAGCCCCACCTTCAGCAGCG<br>ACCCCCTGACCACCCCCCTGCTGATGCTGACCACCTGGCTGCTGCCCCTGACCATCATGGCCA<br>GCCAGCGCCACCTGAGCAGCGAGCCCCTGAGCCGCAAGAAGCTGTACCTGAGCATGCTGATCA<br>GCCTGCAGATCAGCCTGATCATGACCTTCACCGCCACCGAGCTGATCATGTTCTACATCTTCT<br>TCGAGACCACCCTGATCCCCACCCTGGCCATCATCACCCGCTGGGGCAACCAGCCCGAGCGCC<br>TGAACGCCGGCACCTACTTCCTGTTCTACACCCTGGTGGGCAGCCTGCCCCTGCTGATCGCCC<br>TGATCTACACCCCACAACACCCTGGGCAGCCTGAACATCCTGCTGCTGACCCTGACCGCCCAGG<br>AGCTGAGCAACAGCTGGGCCAACAACCTGATGTGGCTGGCCTACACCATGGCCTTCATGGTGA<br>AGATGCCCCTGTACGGCCTGCACCTGTGGCTGCCCAAGGCCCACGTGGAGGCCCCCATCGCCG<br>GCAGCATGGTGCTGGCCGCCGTGCTGCTGAAGCTGGGCGGCTACGGCATGATGCGCCTGACCC<br>TGATCCTGAACCCCCTGACCAAGCACATGGCCTACCCCTTCCTGGTGCTGAGCCTGTGGGGCA<br>TGATCATGACCAGCAGCATCTGCCTGCGCCAGACCGACCTGAAGAGCCTGATCGCCTACAGCA<br>GCATCAGCCACATGGGCCTGGTGGTGACCGCCATCCTGATCCAGACCCCCTGGAGCTTCACCG<br>GCGCCGTGATCCTGATGATCGCCCACGGCCTGACCAGCAGCCTGCTGTTCTGCCTGGCCAACA<br>GCAACTACGAGCGCACCCACAGCCGCATCATGATCCTGAGCCAGGGCCTGCAGACCCTGCTGC<br>CCCTGATGGCCTTCTGGTGGCTGCTGGCCAGCCTGGCCAACCTGGCCCTGCCCCCCACCATCA<br>ACCTGCTGGGCGAGCTGAGCGTGCTGGTGACCACCTTCAGCTGGAGCAACATCACCCTGCTGC<br>TGACCGGCCTGAACATGCTGGTGACCGCCCTGTACAGCCTGTACATGTTCACCACCACCCAGT<br>GGGGCAGCCTGACCCACCACATCAACAACATGAAGCCCAGCTTCACCCGCGAGAACACCCTGA<br>TGTTCATGCACCTGAGCCCCATCCTGCTGCTGAGCCTGAACCCCGACATCATCACCGGCTTCA<br>GCAGCTAAGAGCACTGGGACGCCCACCGCCCCTTTCCCTCCGCTGCCAGGCGAGCATGTTGTG<br>GTAATTCTGGAACACAAGAAGAGAAATTGCTGGGTTTAGAACAAGATTATAAACGAATTCGGT<br>GCTCAGTGATCACTTGACAGTTTTTTTTTTTTTAAATATTACCCAAAATGCTCCCCAAATAA<br>GAAATGCATCAGCTCAGTCAGTGAATACAAAAAAGGAATTATTTTTCCCTTTGAGGGTCTTTT<br>ATACATCTCTCCTCCAACCCCACCCTCTATTCTGTTTCTTCCTCCTCACATGGGGGTACACAT<br>ACACAGCTTCCTCTTTTGGTTCCATCCTTACCACCACACCACACGCACACTCCACATGCCCAG<br>CAGAGTGGCACTTGGTGGCCAGAAAGTGTGAGCCTCATGATCTGCTGTCTGTAGTTCTGTGAG<br>CTCAGGTCCCTCAAAGGCCTCGGAGCACCCCCTTCCTTGTGACTGAGCCAGGGCCTGCATTTT<br>TGGTTTTCCCCACCCCACACATTCTCAACCATAGTCCTTCTAACAATACCAATAGCTAGGACC<br>CGGCTGCTGTGCACTGGGACTGGGGATTCCACATGTTTGCCTTGGGAGTCTCAAGCTGGACTG<br>CCA |
| 77 | OPA1-ND6-<br>3'UTR | GTGCTGCCCGCCTAGAAAGGGTGAAGTGGTTGTTTCCGTGACGGACTGAGTACGGGTGCCTGT<br>CAGGCTCTTGCGGAAGTCCATGCGCCATTGGGAGGGCCTCGGCCGCGGCTCTGTGCCCTTGCT<br>GCTGAGGGCCCACTTCCTGGGTCATTCCTGGACCGGGAGCCGGGCTGGGGCTCACACGGGGCT<br>CCCGCGTGGCCGTCTCGGCGCCTGCGTGACCTCCCCGCCGGCGGGATGTGGCGACTACGTCGG<br>GCCGCTGTGGCCTGATGATGTATGCTTTGTTTCTGTTGAGTGTGGGTTTAGTAATGGGGTTTG<br>TGGGGTTTTCTTCTAAGCCTTCTCCTATTTATGGGGGTTTAGTATTGATTGTTAGCGGTGTGG<br>TCGGGTGTGTTATTATTCTGAATTTTGGGGGAGGTTATATGGGTTTAATGGTTTTTTTAATTT<br>ATTTAGGGGGAATGATGGTTGTCTTTGGATATACTACAGCGATGGCTATTGAGGAGTATCCTG |

TABLE 1-continued nucleic acid and polypeptide sequences and SEQ ID NOs

| SEQ | Description | Sequence |
|---|---|---|
| | | AGGCATGGGGGTCAGGGGTTGAGGTCTTGGTGAGTGTTTTAGTGGGGTTAGCGATGGAGGTAG
GATTGGTGCTGTGGGTGAAAGAGTATGATGGGGTGGTGGTTGTGGTAAACTTTAATAGTGTAG
GAAGCTGGATGATTTATGAAGGAGAGGGGTCAGGGTTGATTCGGGAGGATCCTATTGGTGCGG
GGGCTTTGTATGATTATGGGCGTTGGTTAGTAGTAGTTACTGGTTGGACATTGTTTGTTGGTG
TATATATTGTAATTGAGATTGCTCGGGGGAATTAGGAGCACTGGGACGCCCACCGCCCCTTTC
CCTCCGCTGCCAGGCGAGCATGTTGTGGTAATTCTGGAACACAAGAAGAGAAATTGCTGGGTT
TAGAACAAGATTATAAACGAATTCGGTGCTCAGTGATCACTTGACAGTTTTTTTTTTTTTAA
ATATTACCCAAAATGCTCCCCAAATAAGAAATGCATCAGCTCAGTCAGTGAATACAAAAAAGG
AATTATTTTTCCCTTTGAGGGTCTTTTATACATCTCTCCTCCAACCCCACCCTCTATTCTGTT
TCTTCCTCCTCACATGGGGGTACACATACACAGCTTCCTCTTTTGGTTCCATCCTTACCACCA
CACCACACGCACACTCCACATGCCCAGCAGAGTGGCACTTGGTGGCCAGAAAGTGTGAGCCTC
ATGATCTGCTGTCTGTAGTTCTGTGAGCTCAGGTCCCTCAAAGGCCTCGGAGCACCCCCTTCC
TTGTGACTGAGCCAGGGCCTGCATTTTTGGTTTTCCCCACCCCACACATTCTCAACCATAGTC
CTTCTAACAATACCAATAGCTAGGACCCGGCTGCTGTGCACTGGGACTGGGGATTCCACATGT
TTGCCTTGGGAGTCTCAAGCTGGACTGCCAGCCCCTGTCCTCCCTTCACCCCCATTGCGTATG
AGCATTTCAGAACTCCAAGGAGTCACAGGCATCTTTATAGTTCACGTTAACATATAGACACTG
TTGGAAGCAGTTCCTTCTAAAAGGGTAGCCCTGGACTTAATACCAGCCGGATACCTCTGGCCC
CCACCCCATTACTGTACCTCTGGAGTCACTACTGTGGGTCGCCACTCCTCTGCTACACAGCAC
GGCTTTTTCAAGGCTGTATTGAGAAGGGAAGTTAGGAAGAAGGGTGTGCTGGGCTAACCAGCC
CACAGAGCTCACATTCCTGTCCCTTGGGTGAAAAATACATGTCCATCCTGATATCTCCTGAAT
TCAGAAATTAGCCTCCACATGTGCAATGGCTTTAAGAGCCAGAAGCAGGGTTCTGGGAATTTT
GCAAGTTACCTGTGGCCAGGTGTGGTCTCGGTTACCAAATACGGTTACCTGCAGCTTTTTAGT
CCTTTGTGCTCCCACGGGTCTACAGAGTCCCATCTGCCCAAAGGTCTTGAAGCTTGACAGGAT
GTTTTCGATTACTCAGTCTCCCAGGGCACTACTGGTCCGTAGGATTCGATTGGTCGGGGTAGG
AGAGTTAAACAACATTTAAACAGAGTTCTCTCAAAAATGTCTAAAGGGATTGTAGGTAGATAA
CATCCAATCACTGTTTGCACTTATCTGAAATCTTCCCTCTTGGCTGCCCCCAGGTATTTACTG
TGGAGAACATTGCATAGGAATGTCTGGAAAAAGCTTCTACAACTTGTTACAGCCTTCACATTT
GTAGAAGCTTT |
| 78 | OPA1-ND6-3'UTR* | GTGCTGCCCGCCTAGAAAGGGTGAAGTGGTTGTTTCCGTGACGGACTGAGTACGGGTGCCTGT
CAGGCTCTTGCGGAAGTCCATGCGCCATTGGGAGGGCCTCGGCCGCGGCTCTGTGCCCTTGCT
GCTGAGGGCCACTTCCTGGGTCATTCCTGGACCGGGAGCCGGGCTGGGGCTCACACGGGGGCT
CCCGCGTGGCCGTCTCGGCGCCTGCGTGACCTCCCCGCCGGCGGGATGTGGCGACTACGTCGG
GCCGCTGTGGCCTGATGATGTATGCTTTGTTTCTGTTGAGTGTGGGTTTAGTAATGGGGTTTG
TGGGGTTTTCTTCTAAGCCTTCTCCTATTTATGGGGGTTTAGTATTGATTGTTAGCGGTGTGG
TCGGGTGTGTTATTATTCTGAATTTTGGGGGAGGTTATATGGGTTTAATGGTTTTTTTAATTT
ATTTAGGGGGAATGATGGTTGTCTTTGGATATACTACAGCGATGGCTATTGAGGAGTATCCTG
AGGCATGGGGGTCAGGGGTTGAGGTCTTGGTGAGTGTTTTAGTGGGGTTAGCGATGGAGGTAG
GATTGGTGCTGTGGGTGAAAGAGTATGATGGGGTGGTGGTTGTGGTAAACTTTAATAGTGTAG
GAAGCTGGATGATTTATGAAGGAGAGGGGTCAGGGTTGATTCGGGAGGATCCTATTGGTGCGG
GGGCTTTGTATGATTATGGGCGTTGGTTAGTAGTAGTTACTGGTTGGACATTGTTTGTTGGTG
TATATATTGTAATTGAGATTGCTCGGGGGAATTAGGAGCACTGGGACGCCCACCGCCCCTTTC
CCTCCGCTGCCAGGCGAGCATGTTGTGGTAATTCTGGAACACAAGAAGAGAAATTGCTGGGTT
TAGAACAAGATTATAAACGAATTCGGTGCTCAGTGATCACTTGACAGTTTTTTTTTTTTTAA
ATATTACCCAAAATGCTCCCCAAATAAGAAATGCATCAGCTCAGTCAGTGAATACAAAAAAGG
AATTATTTTTCCCTTTGAGGGTCTTTTATACATCTCTCCTCCAACCCCACCCTCTATTCTGTT
TCTTCCTCCTCACATGGGGGTACACATACACAGCTTCCTCTTTTGGTTCCATCCTTACCACCA
CACCACACGCACACTCCACATGCCCAGCAGAGTGGCACTTGGTGGCCAGAAAGTGTGAGCCTC
ATGATCTGCTGTCTGTAGTTCTGTGAGCTCAGGTCCCTCAAAGGCCTCGGAGCACCCCCTTCC
TTGTGACTGAGCCAGGGCCTGCATTTTTGGTTTTCCCCACCCCACACATTCTCAACCATAGTC
CTTCTAACAATACCAATAGCTAGGACCCGGCTGCTGTGCACTGGGACTGGGGATTCCACATGT
TTGCCTTGGGAGTCTCAAGCTGGACTGCCA |
| 79 | OPA1-opt_ND6-3'UTR | GTGCTGCCCGCCTAGAAAGGGTGAAGTGGTTGTTTCCGTGACGGACTGAGTACGGGTGCCTGT
CAGGCTCTTGCGGAAGTCCATGCGCCATTGGGAGGGCCTCGGCCGCGGCTCTGTGCCCTTGCT
GCTGAGGGCCACTTCCTGGGTCATTCCTGGACCGGGAGCCGGGCTGGGGCTCACACGGGGGCT
CCCGCGTGGCCGTCTCGGCGCCTGCGTGACCTCCCCGCCGGCGGGATGTGGCGACTACGTCGG
GCCGCTGTGGCCTGATGATGTACGCCCTGTTCCTGCTGAGCGTGGGCCTGGTGATGGGCTTCG
TGGGCTTCAGCAGCAAGCCCAGCCCCATCTACGGCGGCCTGGTGCTGATCGTGAGCGGCGTGG
TGGGCTGCGTGATCATCCTGAACTTCGGCGGCGGCTACATGGGCCTGATGGTGTTCCTGATCT
ACCTGGGCGGCATGATGGTGGTGTTCGGCTACACCACCGCCATGGCCATCGAGGAGTACCCCG
AGGCCTGGGGCAGCGGCGTGGAGGTGCTGGTGAGCGTGCTGGTGGGCCTGGCCATGGAGGTGG
GCCTGGTGCTGTGGGTGAAGGAGTACGACGGCGTGGTGGTGGTGAACTTCAACAGCGTGG
GCAGCTGGATGATCTACGAGGGCGAGGGCAGCGGCCTGATCCGCGAGGACCCCATCGGCGCCG
GCGCCCTGTACGACTACGCCGCTGGCTGGTGGTGGTGACCGGCTGGACCCTGTTCGTGGGCG
TGTACATCGTGATCGAGATCGCCCGCGGCAACTAAGAGCACTGGGACGCCCACCGCCCCTTTC
CCTCCGCTGCCAGGCGAGCATGTTGTGGTAATTCTGGAACACAAGAAGAGAAATTGCTGGGTT
TAGAACAAGATTATAAACGAATTCGGTGCTCAGTGATCACTTGACAGTTTTTTTTTTTTTAA
ATATTACCCAAAATGCTCCCCAAATAAGAAATGCATCAGCTCAGTCAGTGAATACAAAAAAGG
AATTATTTTTCCCTTTGAGGGTCTTTTATACATCTCTCCTCCAACCCCACCCTCTATTCTGTT
TCTTCCTCCTCACATGGGGGTACACATACACAGCTTCCTCTTTTGGTTCCATCCTTACCACCA
CACCACACGCACACTCCACATGCCCAGCAGAGTGGCACTTGGTGGCCAGAAAGTGTGAGCCTC
ATGATCTGCTGTCTGTAGTTCTGTGAGCTCAGGTCCCTCAAAGGCCTCGGAGCACCCCCTTCC
TTGTGACTGAGCCAGGGCCTGCATTTTTGGTTTTCCCCACCCCACACATTCTCAACCATAGTC
CTTCTAACAATACCAATAGCTAGGACCCGGCTGCTGTGCACTGGGACTGGGGATTCCACATGT
TTGCCTTGGGAGTCTCAAGCTGGACTGCCAGCCCCTGTCCTCCCTTCACCCCCATTGCGTATG |

TABLE 1-continued nucleic acid and polypeptide sequences and SEQ ID NOs

| SEQ | Description | Sequence |
|---|---|---|
| | | AGCATTTCAGAACTCCAAGGAGTCACAGGCATCTTTATAGTTCACGTTAACATATAGACACTG<br>TTGGAAGCAGTTCCTTCTAAAAGGGTAGCCCTGGACTTAATACCAGCCGGATACCTCTGGCCC<br>CCACCCCATTACTGTACCTCTGGAGTCACTACTGTGGGTCGCCACTCCTCTGCTACACAGCAC<br>GGCTTTTTCAAGGCTGTATTGAGAAGGGAAGTTAGGAAGAAGGGTGTGCTGGGCTAACCAGCC<br>CACAGAGCTCACATTCCTGTCCCTTGGGTGAAAAATACATGTCCATCCTGATATCTCCTGAAT<br>TCAGAAATTAGCCTCCACATGTGCAATGGCTTTAAGAGCCAGAAGCAGGGTTCTGGGAATTTT<br>GCAAGTTACCTGTGGCCAGGTGTGGTCTCGGTTACCAAATACGGTTACCTGCAGCTTTTTAGT<br>CCTTTGTGCTCCCACGGGTCTACAGAGTCCCATCTGCCCAAAGGTCTTGAAGCTTGACAGGAT<br>GTTTTCGATTACTCAGTCTCCCAGGGCACTACTGGTCCGTAGGATTCGATTGGTCGGGGTAGG<br>AGAGTTAAACAACATTTAAACAGAGTTCTCTCAAAAATGTCTAAAGGGATTGTAGGTAGATAA<br>CATCCAATCACTGTTTGCACTTATCTGAAATCTTCCCTCTTGGCTGCCCCCAGGTATTTACTG<br>TGGAGAACATTGCATAGGAATGTCTGGAAAAAGCTTCTACAACTTGTTACAGCCTTCACATTT<br>GTAGAAGCTTT |
| 80 | OPA1-<br>opt_ND6-<br>3'UTR* | GTGCTGCCCGCCTAGAAAGGGTGAAGTGGTTGTTTCCGTGACGGACTGAGTACGGGTGCCTGT<br>CAGGCTCTTGCGGAAGTCCATGCGCCATTGGGAGGGCCTCGGCCGCGGCTCTGTGCCCTTGCT<br>GCTGAGGGCCACTTCCTGGGTCATTCCTGGACCGGGAGCCGGGCTGGGGCTCACACGGGGCT<br>CCCGCGTGGCCGTCTCGGCGCCTGCGTGACCTCCCCGCCGGCGGGATGTGGCGACTACGTCGG<br>GCCGCTGTGGCCTGATGATGTACGCCCTGTTCCTGCTGAGCGTGGGCCTGGTGATGGGCTTCG<br>TGGGCTTCAGCAGCAAGCCCAGCCCCATCTACGGCGGCCTGGTGCTGATCGTGAGCGGCGTGG<br>TGGGCTGCGTGATCATCCTGAACTTCGGCGGCGGCTACATGGGCCTGATGGTGTTCCTGATCT<br>ACCTGGGCGGCATGATGGTGGTGTTCGGCTACACCACCGCCATGGCCATCGAGGAGTACCCCG<br>AGGCCTGGGGCAGCGGCGTGGAGGTGCTGGTGAGCGTGCTGGTGGGCCTGGCCATGGAGGTGG<br>GCCTGGTGCTGTGGGTGAAGGAGTACGACGGCGTGGTGGTGGTGAACTTCAACAGCGTGG<br>GCAGCTGGATGATCTACGAGGGCGAGGGCCTGATCCGCGAGGACCCCATCGGCGCCG<br>GCGCCCTGTACGACTACGGCCGCTGGCTGGTGGTGGTGACCGGCTGGACCCTGTTCGTGGGCG<br>TGTACATCGTGATCGAGATCGCCCGCGGCAACTAAGAGCACTGGGACGCCCACCGCCCCTTTC<br>CCTCCGCTGCCAGGCGAGCATGTTGTGGTAATTCTGGAACACAAGAAGAGAAATTGCTGGGTT<br>TAGAACAAGATTATAAACGAATTCGGTGCTCAGTGATCACTTGACAGTTTTTTTTTTTTTAA<br>ATATTACCCAAAATGCTCCCCAAATAAGAAATGCATCAGCTCAGTCAGTGAATACAAAAAAGG<br>AATTATTTTTCCCTTTGAGGGTCTTTTATACATCTCTCCTCCAACCCCACCCTCTATTCTGTT<br>TCTTCCTCCTCACATGGGGGTACACATACACAGCTTCCTCTTTTGGTTCCATCCTTACCACCA<br>CACCACACGCACACTCCACATGCCCAGCAGAGTGGCACTTGGTGGCCAGAAAGTGTGAGCCTC<br>ATGATCTGCTGTCTGTAGTTCTGTGAGCTCAGGTCCCTCAAAGGCCTCGGAGCACCCCCTTCC<br>TTGTGACTGAGCCAGGGCCTGCATTTTTGGTTTTCCCCACCCCACACATTCTCAACCATAGTC<br>CTTCTAACAATACCAATAGCTAGGACCCGGCTGCTGTGCACTGGGACTGGGGATTCCACATGT<br>TTGCCTTGGGAGTCTCAAGCTGGACTGCCA |
| 81 | OPA1-ND1-<br>3'UTR | GTGCTGCCCGCCTAGAAAGGGTGAAGTGGTTGTTTCCGTGACGGACTGAGTACGGGTGCCTGT<br>CAGGCTCTTGCGGAAGTCCATGCGCCATTGGGAGGGCCTCGGCCGCGGCTCTGTGCCCTTGCT<br>GCTGAGGGCCACTTCCTGGGTCATTCCTGGACCGGGAGCCGGGCTGGGGCTCACACGGGGCT<br>CCCGCGTGGCCGTCTCGGCGCCTGCGTGACCTCCCCGCCGGCGGGATGTGGCGACTACGTCGG<br>GCCGCTGTGGCCTGATGGCCAACCTCCTACTCCTCATTGTACCCATTCTAATCGCAATGGCAT<br>TCCTAATGCTTACCGAACGAAAAATTCTAGGCTATATGCAACTACGCAAAGGCCCCAACGTTG<br>TAGGCCCCTACGGGCTACTACAACCCTTCGCTGACGCCATAAAACTCTTCACCAAAGAGCCCC<br>TAAAACCCGCCACATCTACCATCACCCTCTACATCATCGCCCCGACCTTAGCTCTCACCATCG<br>CTCTTCTACTATGGACCCCCCTCCCCATGCCCAACCCCGTGGTCAACCTCAACCTAGGCCTCC<br>TATTTATTCTAGCCACCTCTAGCCTAGCCGTTTACTCAATCCTCTGGTCAGGGTGGGCATCAA<br>ACTCAAACTACGCCCTGATCGGCGCACTGCGAGCAGTAGCCCAAACAATCTCATATGAAGTCA<br>CCCTAGCCATCATTCTACTATCAACATTACTAATGAGTGGCTCCTTTAACCTCTCCACCCTTA<br>TCACAACACAAGAACACCTCTGGTTACTCCTGCCATCATGGCCCTTGGCCATGATGTGGTTTA<br>TCTCCACACTAGCAGAGACCAACCGAACCCCCTTCGACCTTGCCGAAGGGGAGTCCGAACTAG<br>TCTCAGGCTTCAACATCGAATACGCCGCAGGCCCCTTCGCCCTATTCTTCATGGCCGAATACA<br>CAAACATTATTATGATGAACACCCTCACCACTACAATCTTCCTAGGAACAACATATGACGCAC<br>TCTCCCCTGAACTCTACACAACATATTTTGTCACCAAGACCCTACTTCTAACCTCCCTGTTCT<br>TATGGATTCGAACAGCATACCCCCGATTCCGCTACGACCAACTCATGCACCTCCTATGGAAAA<br>ACTTCCTACCACTCACCCTAGCATTACTTATGTGGTATGTCTCCATGCCCATTACAATCTCCA<br>GCATTCCCCCTCAAACCTAAGGACACTGGGACGCCCACCGCCCCTTTCCCTCCGCTGCCAGGC<br>GAGCATGTTGTGGTAATTCTGGAACACAAGAAGAGAAATTGCTGGGTTTAGAACAAGATTATA<br>AACGAATTCGGTGCTCAGTGATCACTTGACAGTTTTTTTTTTTTAAATATTACCCAAAATG<br>CTCCCCAAATAAGAAATGCATCAGCTCAGTCAGTGAATACAAAAAAGGAATTATTTTTCCCTT<br>TGAGGGTCTTTTATACATCTCTCCTCCAACCCCACCCTCTATTCTGTTTCTTCCTCCTCACAT<br>GGGGGTACACATACACAGCTTCCTCTTTTGGTTCCATCCTTACCACCACACCACACGCACACT<br>CCACATGCCCAGCAGAGTGGCACTTGGTGGCCAGAAAGTGTGAGCCTCATGATCTGCTGTCTG<br>TAGTTCTGTGAGCTCAGGTCCCTCAAAGGCCTCGGAGCACCCCCTTCCTTGTGACTGAGCCAG<br>GGCCTGCATTTTTGGTTTTCCCCACCCCACACATTCTCAACCATAGTCCTTCTAACAATACCA<br>ATAGCTAGGACCCGGCTGCTGTGCACTGGGACTGGGGATTCCACATGTTTGCCTTGGGAGTCTC<br>CAAGCTGGACTGCCAGCCCCTGTCCTCCCTTCACCCCCATTGCGTATGAGCATTTCAGAACTC<br>CAAGGAGTCACAGGCATCTTTATAGTTCACGTTAACATATAGACACTGTTGGAAGCAGTTCCT<br>TCTAAAAGGGTAGCCCTGGACTTAATACCAGCCGGATACCTCTGGCCCCCACCCCATTACTGT<br>ACCTCTGGAGTCACTACTGTGGGTCGCCACTCCTCTGCTACACAGCACGGCTTTTTCAAGGCT<br>GTATTGAGAAGGGAAGTTAGGAAGAAGGGTGTGCTGGGCTAACCAGCCCACAGAGCTCACATT<br>CCTGTCCCTTGGGTGAAAAATACATGTCCATCCTGATATCTCCTGAATTCAGAAATTAGCCTC<br>CACATGTGCAATGGCTTTAAGAGCCAGAAGCAGGGTTCTGGGAATTTTGCAAGTTACCTGTGG<br>CCAGGTGTGGTCTCGGTTACCAAATACGGTTACCTGCAGCTTTTTAGTCCTTTGTGCTCCCAC<br>GGGTCTACAGAGTCCCATCTGCCCAAAGGTCTTGAAGCTTGACAGGATGTTTTCGATTACTCA |

TABLE 1-continued nucleic acid and polypeptide sequences and SEQ ID NOs

| SEQ | Description | Sequence |
|---|---|---|
| | | GTCTCCCAGGGCACTACTGGTCCGTAGGATTCGATTGGTCGGGGTAGGAGAGTTAAACAACAT<br>TTAAACAGAGTTCTCTCAAAAATGTCTAAAGGGATTGTAGGTAGATAACATCCAATCACTGTT<br>TGCACTTATCTGAAATCTTCCCTCTTGGCTGCCCCCAGGTATTTACTGTGGAGAACATTGCAT<br>AGGAATGTCTGGAAAAAGCTTCTACAACTTGTTACAGCCTTCACATTTGTAGAAGCTTT |
| 82 | OPA1-ND1-<br>3'UTR* | GTGCTGCCCGCCTAGAAAGGGTGAAGTGGTTGTTTCCGTGACGGACTGAGTACGGGTGCCTGT<br>CAGGCTCTTGCGGAAGTCCATGCGCCATTGGGAGGGCCTCGGCCGCGGCTCTGTGCCCTTGCT<br>GCTGAGGGCCACTTCCTGGGTCATTCCTGGACCGGGAGCCGGGCTGGGGCTCACACGGGGGCT<br>CCCGCGTGGCCGTCTCGGCGCCTGCGTGACCTCCCCGCCGGCGGGATGTGGCGACTACGTCGG<br>GCCGCTGTGGCCTGATGGCCAACCTCCTACTCCTCATTGTACCCATTCTAATCGCAATGGCAT<br>TCCTAATGCTTACCGAACGAAAAATTCTAGGCTATATGCAACTACGCAAAGGCCCCAACGTTG<br>TAGGCCCCTACGGGCTACTACAACCCTTCGCTGACGCCATAAAACTCTTCACCAAAGAGCCCC<br>TAAAACCCGCCACATCTACCATCACCCTCTACATCATCGCCCCGACCTTAGCTCTCACCATCG<br>CTCTTCTACTATGGACCCCCCTCCCCATGCCCAACCCCCTGGTCAACCTCAACCTAGGCCTCC<br>TATTTATTCTAGCCACCTCTAGCCTAGCCGTTTACTCAATCCTCTGGTCAGGGTGGGCATCAA<br>ACTCAAACTACGCCCTGATCGGCGCACTGCGAGCAGTAGCCCAAACAATCTCATATGAAGTCA<br>CCCTAGCCATCATTCTACTATCAACATTACTAATGAGTGGCTCCTTTAACCTCTCCACCCTTA<br>TCACAACACAAGAACACCTCTGGTTACTCCTGCCATCATGGCCCTTGGCCATGATGTGGTTTA<br>TCTCCACACTAGCAGAGACCAACCGAACCCCCTTCGACCTTGCCGAAGGGGAGTCCGAACTAG<br>TCTCAGGCTTCAACATCGAATACGCCGCAGGCCCCTTCGCCCTATTCTTCATGGCCGAATACA<br>CAAACATTATTATGATGAACACCCTCACCACTACAATCTTCCTAGGAACAACATATGACGCAC<br>TCTCCCCTGAACTCTACACAACATATTTTGTCACCAAGACCCTACTTCTAACCTCCCTGTTCT<br>TATGGATTCGAACAGCATACCCCGATTCCGCTACGACCAACTCATGCACCTCCTATGGAAAA<br>ACTTCCTACCACTCACCCTAGCATTACTTATGTGGTATGTCTCCATGCCCATTACAATCTCCA<br>GCATTCCCCCTCAAACCTAAGAGCACTGGGACGCCCACCGCCCTTCCCTCCGCTGCCAGGC<br>GAGCATGTTGTGGTAATTCTGGAACACAAGAAGAGAAATTGCTGGGTTTAGAACAAGATTATA<br>AACGAATTCGGTGCTCAGTGATCACTTGACAGTTTTTTTTTTTTAAATATTACCCAAAATG<br>CTCCCCAAATAAGAAATGCATCAGCTCAGTCAGTGAATACAAAAAAGGAATTATTTTTCCCTT<br>TGAGGGTCTTTTATACATCTCTCCTCCAACCCCACCCTCTATTCTGTTTCTTCCTCCTCACAT<br>GGGGGTACACATACACAGCTTCCTCTTTTGGTTCCATCCTTACCACCACACCACACGCACACT<br>CCACATGCCCAGCAGAGTGGCACTTGGTGGCAGAAAGTGTGAGCCTCATGATCTGCTGTCTG<br>TAGTTCTGTGAGCTCAGGTCCCTCAAAGGCCTCGGAGCACCCCCTTCCTTGTGACTGAGCCAG<br>GGCCTGCATTTTTGGTTTTCCCCACCCCACACATTCTCAACCATAGTCCTTCTAACAATACCA<br>ATAGCTAGGACCCGGCTGCTGTGCACTGGGACTGGGGATTCCACATGTTTGCCTTGGGAGTCT<br>CAAGCTGGACTGCCA |
| 83 | OPA1-<br>opt_ND1-<br>3'UTR | GTGCTGCCCGCCTAGAAAGGGTGAAGTGGTTGTTTCCGTGACGGACTGAGTACGGGTGCCTGT<br>CAGGCTCTTGCGGAAGTCCATGCGCCATTGGGAGGGCCTCGGCCGCGGCTCTGTGCCCTTGCT<br>GCTGAGGGCCACTTCCTGGGTCATTCCTGGACCGGGAGCCGGGCTGGGGCTCACACGGGGGCT<br>CCCGCGTGGCCGTCTCGGCGCCTGCGTGACCTCCCCGCCGGCGGGATGTGGCGACTACGTCGG<br>GCCGCTGTGGCCTGATGGCCAACCTGCTGCTGCTGATCGTGCCCATCCTGATCGCCATGGCCT<br>TCCTGATGCTGACCGAGCGCAAGATCCTGGGCTACATGCAGCTGCGCAAGGGCCCCAACGTGG<br>TGGGCCCCTACGGCCTGCTGCAGCCCTTCGCCGACGCCATCAAGCTGTTCACCAAGGAGCCCC<br>TGAAGCCCGCCACCAGCACCATCACCCTGTACATCACCGCCCCCACCCTGGCCCTGACCATCG<br>CCCTGCTGCTGTGGACCCCCCTGCCCATGCCCAACCCCCTGGTGAACCTGAACCTGGGCCTGC<br>TGTTCATCCTGGCCACCAGCAGCCTGGCCGTGTACAGCATCCTGTGGAGCGGCTGGGCCAGCA<br>ACAGCAACTACGCCCTGATCGGCGCCCTGCGCGCCGTGGCCCAGACCATCAGCTACGAGGTGA<br>CCCTGGCCATCATCCTGCTGAGCACCCTGCTGATGAGCGGCAGCTTCAACCTGAGCACCCTGA<br>TCACCACCCAGGAGCACCTGTGGCTGCTGCTGCCCAGCTGGCCCCTGGCCATGATGTGGTTCA<br>TCAGCACCCTGGCCGAGACCAACCGCACCCCCTTCGACCTGCCCGAGGGCGAGGGCGAGCTGG<br>TGAGCGGCTTCAACATCGAGTACGCCGCCGGCCCCTTCGCCCTGTTCTTCATGGCCGAGTACA<br>CCAACATCATCATGATGAACACCCTGACCACCACCATCTTCCTGGGCACCACCTACGACGCCC<br>TGAGCCCCGAGCTGTACACCACCTACTTCGTGACCAAGACCCTGCTGCTGACCAGCCTGTTCC<br>TGTGGATCCGCACCGCCTACCCCCGCTTCCGCTACGACCAGCTGATGCACCTGCTGTGGAAGA<br>ACTTCCTGCCCCTGACCCTGGCCCTGCTGATGTGGTACGTGAGCATGCCCATCACCATCAGCA<br>GCATCCCCCCCAGACCTAAGAGCACTGGGACGCCCACCGCCCTTCCCTCCGCTGCCAGGC<br>GAGCATGTTGTGGTAATTCTGGAACACAAGAAGAGAAATTGCTGGGTTTAGAACAAGATTATA<br>AACGAATTCGGTGCTCAGTGATCACTTGACAGTTTTTTTTTTTTAAATATTACCCAAAATG<br>CTCCCCAAATAAGAAATGCATCAGCTCAGTCAGTGAATACAAAAAAGGAATTATTTTTCCCTT<br>TGAGGGTCTTTTATACATCTCTCCTCCAACCCCACCCTCTATTCTGTTTCTTCCTCCTCACAT<br>GGGGGTACACATACACAGCTTCCTCTTTTGGTTCCATCCTTACCACCACACCACACGCACACT<br>CCACATGCCCAGCAGAGTGGCACTTGGTGGCAGAAAGTGTGAGCCTCATGATCTGCTGTCTG<br>TAGTTCTGTGAGCTCAGGTCCCTCAAAGGCCTCGGAGCACCCCCTTCCTTGTGACTGAGCCAG<br>GGCCTGCATTTTTGGTTTTCCCCACCCCACACATTCTCAACCATAGTCCTTCTAACAATACCA<br>ATAGCTAGGACCCGGCTGCTGTGCACTGGGACTGGGGATTCCACATGTTTGCCTTGGGAGTCT<br>CAAGCTGGACTGCCAGCCCCTGTCCTCCCTTCACCCCATTGCGTATGAGCATTTCAGAACTC<br>CAAGGAGTCACAGGCATCTTTATAGTTCACGTTAACATATAGACACTGTTGGAAGCAGTTCCT<br>TCTAAAAGGGTAGCCCTGGACTTAATACCAGCCGGATACCTCTGGCCCCCACCCCATTACTGT<br>ACCTCTGGAGTCACTACTGTGGGTCGCCACTCCTCTGCTACACAGCACGGCTTTTTCAAGGCT<br>GTATTGAGAAGGGAAGTTAGGAAGAAGGGTGTGCTGGGCTAACCAGCCCACAGAGCTCACATT<br>CCTGTCCCTTGGGTGAAAAATACATGTCCATCCTGATATCTCCTGAATTCAGAAATTAGCCTC<br>CACATGTGCAATGCTTTAAGAGCCAGAAGCAGGGTTCTGGGAATTTTGCAAGTTACCTGTGG<br>CCAGGTGTGGTCTCGGTTACCAAATACGGTTACCTGCAGCTTTTTAGTCCTTTGTGCTCCCAC<br>GGGTCTACAGAGTCCCATCTGCCCAAAGGTCTTGAAGCTTGACAGGATGTTTTCGATTACTCA<br>GTCTCCCAGGGCACTACTGGTCCGTAGGATTCGATTGGTCGGGGTAGGAGAGTTAAACAACAT |

TABLE 1-continued nucleic acid and polypeptide sequences and SEQ ID NOs

| SEQ | Description | Sequence |
|---|---|---|
|  |  | TTAAACAGAGTTCTCTCAAAAATGTCTAAAGGGATTGTAGGTAGATAACATCCAATCACTGTT<br>TGCACTTATCTGAAATCTTCCCTCTTGGCTGCCCCCAGGTATTTACTGTGGAGAACATTGCAT<br>AGGAATGTCTGGAAAAAGCTTCTACAACTTGTTACAGCCTTCACATTTGTAGAAGCTTT |
| 84 | OPA1-<br>opt_ND1-<br>3'UTR* | GTGCTGCCCGCCTAGAAAGGGTGAAGTGGTTGTTTCCGTGACGGACTGAGTACGGGTGCCTGT<br>CAGGCTCTTGCGGAAGTCCATGCGCCATTGGGAGGGCCTCGGCCGCGGCTCTGTGCCCTTGCT<br>GCTGAGGGCCACTTCCTGGGTCATTCCTGGACCGGGAGCCGGGCTGGGGCTCACACGGGGGCT<br>CCCGCGTGGCCGTCTCGGCGCCTGCGTGACCTCCCCGCCGGCGGGATGTGGCGACTACGTCGG<br>GCCGCTGTGGCCTGATGGCCAACCTGCTGCTGCTGATCGTGCCCATCCTGATCGCCATGGCCT<br>TCCTGATGCTGACCGAGCGCAAGATCCTGGGCTACATGCAGCTGCGCAAGGGCCCCAACGTGG<br>TGGGCCCCTACGGCCTGCTGCAGCCCTTCGCCGACGCCATCAAGCTGTTCACCAAGGAGCCCC<br>TGAAGCCCGCCACCAGCACCATCACCCTGTACATCACCGCCCCCACCCTGGCCCTGACCATCG<br>CCCTGCTGCTGTGGACCCCCCTGCCCATGCCCAACCCCCTGGTGAACCTGAACCTGGGCCTGC<br>TGTTCATCCTGGCCACCAGCAGCCTGGCCGTGTACAGCATCCTGTGGAGCGGCTGGGCCAGCA<br>ACAGCAACTACGCCCTGATCGGCGCCCTGCGCGCCGTGGCCCAGACCATCAGCTACGAGGTGA<br>CCCTGGCCATCATCCTGCTGAGCACCCTGCTGATGAGCGGCAGCTTCAACCTGAGCACCCTGA<br>TCACCACCCAGGAGCACCTGTGGCTGCTGCTGCCCAGCTGGCCCCTGGCCATGATGTGGTTCA<br>TCAGCACCCTGGCCGAGACCAACCGCACCCCCTTCGACCTGGCCGAGGGCGAGAGCGAGCTGG<br>TGAGCGGCTTCAACATCGAGTACGCCGCCGGCCCCTTCGCCCTGTTCTTCATGGCCGAGTACA<br>CCAACATCATCATGATGAACACCCTGACCACCACCATCTTCCTGGGCACCACCTACGACGCCC<br>TGAGCCCCGAGCTGTACACCACCTACTTCGTGACCAAGACCCTGCTGCTGACCAGCCTGTTCC<br>TGTGGATCCGCACCGCCTACCCCGCTTCCGCTACGACCAGCTGATGCACCTGCTGTGGAAGA<br>ACTTCCTGCCCCTGACCCTGGCCCTGCTGATGTGGTACGTGAGCATGCCCATCACCATCAGCA<br>GCATCCCCCCCAGACCTAAGAGCACTGGGACGCCCACCGCCCCTTCCCTCCGCTGCCAGGC<br>GAGCATGTTGTGGTAATTCTGGAACACAAGAAGAGAAATTGCTGGGTTTAGAACAAGATTATA<br>AACGAATTCGGTGCTCAGTGATCACTTGACAGTTTTTTTTTTTTAAATATTACCCAAAATG<br>CTCCCCAAATAAGAAATGCATCAGCTCAGTCAGTGAATACAAAAAAGGAATTATTTTTCCCTT<br>TGAGGGTCTTTTATACATCTCTCCTCCAACCCCACCCTCTATTCTGTTTCTTCCTCCTCACAT<br>GGGGGTACACATACACAGCTTCCTCTTTTGGTTCCATCCTTACCACCACACCACACGCACACT<br>CCACATGCCCAGCAGAGTGGCACTTGGTGGCCAGAAAGTGTGAGCCTCATGATCTGCTGTCTG<br>TAGTTCTGTGAGCTCAGGTCCCTCAAAGGCCTCGGAGCACCCCCTTCCTTGTGACTGAGCCAG<br>GGCCTGCATTTTTGGTTTTCCCCACCCCACACATTCTCAACCATAGTCCTTCTAACAATACCA<br>ATAGCTAGGACCCGGCTGCTGTGCACTGGGACTGGGGATTCCACATGTTTGCCTTGGGAGTCT<br>CAAGCTGGACTGCCA |
| 85 | β-actin-S primer | CGAGATCGTGCGGGACAT |
| 86 | β-actin-A primer | CAGGAAGGAGGGCTGGAAC |
| 87 | ND4-S primer | CTGCCTACGACAAACAGAC |
| 88 | ND4-A primer | AGTGCGTTCGTAGTTTGAG |
| 89 | ND6-F primer | ATGATGTATGCTTTGTTTCTG |
| 90 | ND6-R primer | CTAATTCCCCCGAGCAATCTC |
| 91 | ND6-S primer | AGTGTGGGTTTAGTAATG |
| 92 | ND6-A primer | TGCCTCAGGATACTCCTC |
| 93 | β-actin-F primer | CTCCATCCTGGCCTCGCTGT |
| 94 | β-actin-R primer | GCTGTCACCTTCACCGTTCC |
| 95 | ND6-F primer | GGGTTTTCTTCTAAGCCTTCTCC |
| 96 | ND6-R primer | CCATCATACTCTTTCACCCACAG |
| 97 | opt_ND6-F primer | CGCCTGCTGACCGGCTGCGT |
| 98 | opt_ND6-R | CCAGGCCTCGGGGTACTCCT |

TABLE 1-continued nucleic acid and polypeptide sequences and SEQ ID NOs

| SEQ | Description | Sequence |
|---|---|---|
| 99 | ND1-F primer | ATGGCCGCATCTCCGCACACT |
| 100 | ND1-R primer | TTAGGTTTGAGGGGGAATGCT |
| 101 | ND1-F primer | AACCTCAACCTAGGCCTCCTA |
| 102 | ND1-R primer | TGGCAGGAGTAACCAGAGGTG |
| 103 | ND1-F primer | AGGAGGCTCTGTCTGGTATCTTG |
| 104 | ND1-R primer | TTTTAGGGGCTCTTTGGTGAA |
| 105 | opt-ND1-F primer | GCCGCCTGCTGACCGGCTGCGT |
| 106 | opt-ND1-R primer | TGATGTACAGGGTGATGGTGCTGG |
| 107 | ND4-S primer | GCCAACAGCAACTACGAGC |
| 108 | ND4-A primer | TGATGTTGCTCCAGCTGAAG |
| 109 | opt-ND4-S primer | GCCTGACCCTGATCCTGAAC |
| 110 | opt-ND4-A primer | GTGCGCTCGTAGTTGCTGTT |
| 111 | hsACO2 | GGGCAGTGCCTCCCCGCCCCGCCGCTGGCGTCAAGTTCAGCTCCACGTGTGCCATCAGTGGAT CCGATCCGTCCAGCCATGGCTTCCTATTCCAAGATGGTGTGACCAGACATGCTTCCTGCTCCC CGCTTAGCCCACGGAGTGACTGTGGTTGTGGTGGGGGGGTTCTTAAAATAACTTTTTAGCCCC CGTCTTCCTATTTTGAGTTTGGTTCAGATCTTAAGCAGCTCCATGCAACTGTATTTATTTTTG ATGACAAGACTCCCATCTAAAGTTTTTCTCCTGCCTGATCATTTCATTGGTGGCTGAAGGATT CTAGAGAACCTTTTGTTCTTGCAAGGAAAACAAGAATCCAAAACCAGTGACTGTTCTGTGA |
| 112 | hsATP5B | GGGGTCTTTGTCCTCTGTACTGTCTCTCTCCTTGCCCCTAACCCAAAAAGCTTCATTTTTCTG TGTAGGCTGCACAAGAGCCTTGATTGAAGATATATTCTTTCTGAACAGTATTTAAGGTTTCCA ATAAAATGTACACCCCTCAG |
| 113 | hsAK2 | TGTTGGGTCCAAGAAGGAATTTCTTTCCATCCCTGTGAGGCAATGGGTGGGAATGATAGGACA GGCAAAGAGAAGCTTCCTCAGGCTAGCAAAAATATCATTTGATGTATTGATTAAAAAAGCACT TGCTTGATGTATCTTTGGCGTGTGTGCTACTCTCATCTGTGTGTATGTGTGTTGTGTGTGT GTGTGTGCATGCACATATGTGTTCACTCTGCTACTTTGTAAGTTTTAGGCTAGGTTGCTTTAC CAGCTGTTTACTTCTTTTTTTGTTGTTGTTTGAGACAAGGTTTCGCTCTGCCACCCTGGCTGG AGTGCAGTGGCGTGATCTTGGCTCACGGCAACCTCTGCCTCCTGGGGCTCAAGCAATTATCCC ACCTCAGCCTCCTGAGCAGCTGGGACTACAGGTGCATGCCACAACACCTGGCTGATATTTGTA TTTTTTTGTAGAGACAGGATTTTGCCAAGTTGCCCAGGCTGGTCTTGAACTCCTAGGCTTAAGC AATCCACCCACCTTGGCCTCCTGAAGTGCCAGGATCACAGACGTGAGCCACTACACCCAGCCC AGCTGTTTACTTCTTTAACCATACTTTTGATTTTATTTTTTGACCAAAATGAACTAACCCAGG TAATCTTCCAGGGACCGCAATTCCAGAACCTCATAGTATTTCTTCCATTTCAGCAGCTGATT AGAAGTCCAGGATCATGTGAAGTCAGGCAGGGTCACAGTTCCTGATGGCACATTATGGACAGA GAATTCCATTTTGTTTTCTAACCCATGATGAAAACCCACGTGAGTCAGTGTGTGAACAGGGAT CATTAATTTTTTCCCCTAGGTGGAAGGAAAAAGGCACTTACTTTGCAGGTTACAGAAATTAC TGGGAGAGGATATCGTCATAAAAAGAGCCAGGCCAAATTGGAATATTTTTGTGATCTGCATCA TGATGCTGAAAATAGCAATTATTTGGGAATTGGGTTTGAAAACTGAATTGTTGCCAGAGAATT AAACCAGGTGAAAGGTCCTTTTGAATTCAGATTGTCTTCTGAACATCCAGGCTGATCATCTGA GAGCAGTCAAATCTACTTCCCCAAAAAGAGACCAGGGTAGGTTTATTTGCTTTATTTTTAAT GTTTGCCTGTGTTTCCAAGTGTGAACAAAACAGTGTGTGATCTATTCTTGGATTCATTTTGAT CAGTATTTATTCAAACCCAGTCTCTCTCCAGGACATAAAACTGAAATCAGATATGTTCTTTTT AAGCCCAAACCCTCTCCTTTCTAGATCCAACCCTTCACCCCTAATTTTATGATGGCTATAGCC ATGGACTTCCCCAAGAAAAGATCACCCAGAAATAAGACCACCTGTGACAGTTACCAGCTTTTA TTCATAACCTTAGCTTCCCAACTATTGAGCATTTTCTAAGGTCCCTGCTGTCTTTTGGTCTCT GGTTTGATTTGTGGCAAACAGATGAAGTAACAGCTGCTATGAAGGACCACAAAAACGGCAGC CTCTGGAAAAACCATTAGAAAGTCAGTGGCAGATCCAGTAAATAATATCGCCAGCCTCAGCAT AATCTGCTGCTGACTCGATTCAGTGGACTCTAAAGTGCCCAGCCTCCTGACCTGAGCTCTCCT GCCATCTGTGAGACTACCAGAGGTCTTATCTGCTGTCCACATGGCAACTGGGCATGAGTACCT GGCCACCTTGCTTCCCTCTTTGCCTGGTCCAAGTGAGTGTCTGCTGCCTCTGTCCTGCCTTGT TTTCCTGGCTCTAAACCAACTCCACCCACTCTTAATGGAAACTCAGTCTGGCTTTGTGTGTTT |

TABLE 1-continued nucleic acid and polypeptide sequences and SEQ ID NOs

| SEQ | Description | Sequence |
|---|---|---|
| | | CTGGGAAGCACATGACTTCTGGGAATGGGCAAGGAAGAGGAGTGAAACAAAAACTGTCAGCTA TGTGTGCCTGGTCTGGGATCCTTCTCTGGGTGACAGTGGCATCATGAATCTTAGAATCAGCTC CCC |
| 114 | hsALDH2 | GAATCATGCAAGCTTCCTCCCTCAGCCATTGATGGAAAGTTCAGCAAGATCAGCAACAAAACC AAGAAAAATGATCCTTGCGTGCTGAATATCTGAAAAGAGAAATTTTTCCTACAAAATCTCTTG GGTCAAGAAAGTTCTAGAATTTGAATTGATAAACATGGTGGGTTGGCTGAGGGTAAGAGTATA TGAGGAACCTTTTAAACGACAACAATACTGCTAGCTTTCAGGATGATTTTTAAAAAATAGATT CAAATGTGTTATCCTCTCTCTGAAACGCTTCCTATAACTCGAGTTTATAGGGGAAGAAAAAGC TATTGTTTACAATTATATCACCATTAAGGCAACTGCTACACCCTGCTTTGTATTCTGGGCTAA GATTCATTAAAAACTAGCTGCTCTTAACTTACA |
| 115 | hsCOX10 | GAGCACTGGGACGCCCACCGCCCCTTTCCCTCCGCTGCCAGGCGAGCATGTTGTGGTAATTCT GGAACACAAGAAGAGAAATTGCTGGGTTTAGAACAAGATTATAAACGAATTCGGTGCTCAGTG ATCACTTGACAGTTTTTTTTTTTTTAAATATTACCCAAAATGCTCCCCAAATAAGAAATGCA TCAGCTCAGTCAGTGAATACAAAAAAGGAATTATTTTTCCCTTTGAGGGTCTTTATACATCTC TCCTCCAACCCCACCCTCTATTCTGTTTCTTCCTCCTCACATGGGGTACACATACACAGCTT CCTCTTTTGGTTCCATCCTTACCACCACACCACACGCACACTCCACATGCCCAGCAGAGTGGC ACTTGGTGGCCAGAAAGTGTGAGCCTCATGATCTGCTGTCTGTAGTTCTGTGAGCTCAGGTCC CTCAAAGGCCTCGGAGCACCCCCTTCCTGGTGACTGAGCCAGGGCCTGCATTTTTGGTTTTCC CCACCCCACACATTCTCAACCATAGTCCTTCTAACAATACCAATAGCTAGGACCCGGCTGCTG TGCACTGGGACTGGGGATTCCACATGTTTGCCTTGGGAGTCTCAAGCTGGACTGCCAGCCCCT GTCCTCCCTTCACCCCCATTGCGTATGAGCATTTCAGAACTCCAAGGAGTCACAGGCATCTTT ATAGTTCACGTTAACATATAGACACTGTTGGAAGCAGTTCCTTCTAAAAGGGTAGCCCTGGAC TTAATACCAGCCGGATACCTCTGGCCCCCACCCCATTACTGTACCTCTGGAGTCACTACTGTG GGTCGCCACTCCTCTGCTACACAGCACGGCTTTTTCAAGGCTGTATTGAGAAGGGAAGTTAGG AAGAAGGGTGTGCTGGGCTAACCAGCCCACAGAGCTCACATTCCTGTCCCTTGGGTGAAAAAT ACATGTCCATCCTGATATCTCCTGAATTCAGAAATTAGCCTCCACATGTGCAATGGCTTTAAG AGCCAGAAGCAGGGTTCTGGGAATTTTGCAAGTTATCCTGTGGCCAGGTGTGGTCTCGGTTAC CAAATACGGTTACCTGCAGCTTTTTAGTCCTTTGTGCTCCCACGGGTCTGCAGAGTCCCATCT GCCCAAAGGTCTTGAAGCTTGACAGGATGTTTTCATTACTCAGTCTCCCAGGGCACTGCTGGT CCGTAGGGATTCATTGGTCGGGTGGGAGAGTTAAACAACATTTAAACAGAGTTCTCTCAAAA ATGTCTAAAGGGATTGTAGGTAGATAACATCCAATCACTGTTTGCACTTATCTGAAATCTTCC CTCTTGGCTGCCCCCAGGTATTTACTGTGGAGAAACATTGCATAGGAATGTCTGGAAAAAGCCT CTACAACTTGTTACAGCCTTCACATTTGTACAATTCATTGATTCTCTTTTCCTTCCACAATAA AATGGTATACAAGAAC |
| 116 | hsUQCRFS 1 | GAGACTTGGACTCAAGTCATAGGCTTCTTTCAGTCTTTATGTCACCTCAGGAGACTTATTTGA GAGGAAGCCTTCTGTACTTGAAGTTGATTTGAAATATGTAAGAATTGATGATGTATTTGCAAA CATTAATGTGAAATAAATTGAATTTAATGTTGAATACTTTCAGGCATTCACTTAATAAAGACA CTGTTAAGCACTGTTATGCTCAGTCATACACGCGAAAGGTACAATGTCTTTTAGCTAATTCTA ATTAAAAATTACAGACTGGTGTACAAGATACTTGTG |
| 117 | hsNDUFV1 | CCCACCACCCTGGCCTGCTGTCCTGCGTCTATCCATGTGGAATGCTGGACAATAAAGCGAGTG CTGCCCACCCTCCAGCTGCC |
| 118 | hsNDUFV2 | TTTATATTGAACTGTAAATATGTCACTAGAGAAATAAAATATGGACTTCCAATCTACGTAAAC TTA |
| 119 | hsSOD2 | ACCACGATCGTTATGCTGAGTATGTTAAGCTCTTTATGACTGTTTTTGTAGTGGTATAGAGTA CTGCAGAATACAGTAAGCTGCTCTATTGTAGCATTTCTTGATGTTGCTTAGTCACTTATTTCA TAAACAACTTAATGTTCTGAATAATTTCTTACTAAACATTTTGTTATTGGGCAAGTGATTGAA AATAGTAAATGCTTTGTGTGATTGA |
| 120 | hsCOX6c | TCTTGGAATATAAAGAATTTCTTCAGGTTGAATTACCTAGAAGTTTGTCACTGACTTGTGTTC CTGAACTATGACACATGAATATGTGGGTAAGAAATAGTTCCTCTTGATAAATAAACAATTAA CAAATACTTTGGACAGTAAGTCTTTCTCAGTTCTTAATGATAATGCAGGGCACTTACTAGCAT AAGAATTGGTTTGGGATTTAACTGTTTATGAAGCTAACTTGATTTCCGTGTTTTGTTAAAATT TCATTGTTCTAGCACATCTTTAACTGTGATAGTT |
| 121 | hsIRP1 | GAGACGTGCACTTGGTCGTGCGCCCAGGGAGGAAGCCGCACCACCAGCCAGCGCAGGCCCTGG TGGAGAGGCCTCCCTGGCTGCCTCTGGGAGGGGTGCTGCCTTGTAGATGGAGCAAGTGAGCAC TGAGGGTCTGGTGCCAATCCTGTAGGCACAAAACCAGAAGTTTCTACATTCTCTATTTTTGTT AATCATCTTCTCTTTTTCCAGAATTTGGAAGCTAGAATGGTGGGAATGTCAGTAGTGCCAGAA AGAGAGAACCAAGCTTGTCTTTAAAGTTACTGATCACAGGACGTTGCTTTTTCACTGTTTCCT ATTAATCTTCAGCTGAACACAAGCAAACCTTCTCAGGAGGTGTCTCCTACCCTCTTATTGTTC CTCTTACGCTCTGCTCAATGAAACCTTCCTCTTGAGGGTCATTTTCCTTTCTGTATTAATTAT ACCAGTGTTAAGTGACATAGATAAGAACTTTGCACACTTCAAATCAGAGCAGTGATTCTCTCT TCTCTCCCCTTTTCCTTCAGAGTGAATCATCCAGACTCCTCATGGATAGGTCGGGTGTTAAAG TTGTTTTGATTATGTACCTTTTGATAGATCCACATAAAAAGAAATGTGAAGTTTTCTTTTACT ATCTTTTCATTTATCAAGCAGAGACCTTTGTTGGGAGGCGGTTTGGGAGAACACATTTCTAAT TTGAATGAAATGAAATCTATTTTCAGTG |
| 122 | hsMRPS12 | CAGAAGAAGTGACGGCTGGGGGCACAGTGGGCTGGGCGCCCCTGCAGAACATGAACCTTCCGC TCCTGGCTGCCACAGGGTCCTCCGATGCTGGCCTTTGCGCCTCTAGAGGCAGCCACTCATGGA TTCAAGTCCTGGCTCCGCCTCTTCCATCAGGACCACT |

TABLE 1-continued nucleic acid and polypeptide sequences and SEQ ID NOs

| SEQ | Description | Sequence |
|---|---|---|
| 123 | hsATP5J2 | AGAGGACACACTCTGCACCCCCCCACCCCACGACCTTGGCCCCGAGCCCCTCCGTGAGGAA |
| 124 | rnSOD2 | AGCCCTTCCGCCAGGCTGTGTGTCAGGCCCGTGGTGGGTGTTTTGTAGTAGTGTAGAGCATTGCA |
| 125 | hsOXA1L | CTTATGTTCTGTGCGCATTCTGGCAGGAATTCTGTCTCTTCAGAGACTCATCCTCAAAACAAGACTTGACACTGTGTCCTTGCCCCAGTCCTAGGAACTGTGGCACACAGAGATGTTCATTTTAAAACGGATTTCATGAAACACTCTTGTACTTATGTTTATAAGAGAGCACTGGGTAGCCAAGTGATCTTCCCATTCACAGAGTTAGTAAACCTCTGTACTACATGCTG |
| 126 | MTS-COX10 | MAASPHTLSSRLLTGCVGGSVWYLERRT |
| 127 | MIS-COX8 | MSVLTRLLLRGLTRLGSAAPVRRARIHSL |
| 128 | MTS-OPA1 | MWRLRRAAVA |
| 129 | hsCOX10 | MAASPHTLSSRLLTGCVGGSVWYLERRT |
| 130 | scRPM2 | MAFKSFIYSKGYHRSAAQKKTATSFFDSSYQYLRQNQGLVNSDPVLHASHLHPHPVVVANVNYNNVDDILHPHDLDSSINNTNNPLTHEELLYNQNVSLRSLKQQQSTNYVNNNNNNQHRYY |
| 131 | lcSirt5 | MRKRSLRCHLWSANASLSPRKDEVTSRKESENLVKGKKNKKSHLHLLLFTASKIGTDSVFDVQKSKECCKELGLLFTSLIHSIGSFPFDEEPKAAAVFLPGSLPQLTVLVLAPGSGSCPTGKSTPHLAASGRNAELLRPQNSMIVRQFTCRGTISSHLCAHLRKPHDSRNMARP |
| 132 | tbNDUS7 | MLRRTSFNFTGRAMISRGSPEWSHRLDLKKGKKTTMMHKLGTSKPNNALQYAQMTL |
| 133 | ncQCR2 | MISRSALSRGSQLALRRPAAAKTAQRGFAAAAASPAASYEPTTIAG |
| 134 | hsATP5G2 | MPELILYVAITLSVAERLVGPGHACAEPSFRSSRCSAPLCLLCSGSSSPATAPHPLKMFACSKFVSTPSLVKSTQLLSRPLSAVVLKRPEILTDESLSSLAVSCPLTSLVSSRSFQTSAISRDIDTA |
| 135 | hsLACTB | MYRLMSAVTARAAAPGGLASSCGRRGVHQRAGLPPLGHGWVGGLGLGLGLALGVKLAGGLRGAAPAQSPAAPDPEASPLAEPPQEQSLAPWSPQTPAPPCSRCFARAIESSRDLL |
| 136 | spilv 1 | MTVLAPLRRLHTRAAFSSYGREIALQKRFLNLNSCSAVRRYGTGFSNNLRIKKLKNAFGVVRANSTKSTSTVTTASPIKYDSSFVGKTGGEIFHDMMLKHNVKHVFGYPGGAILPVFDAIYRSPHFEFILPRHEQAAGHA |
| 137 | gmCOX2 | MILCPLEAFIVQHILTISVMGLLSCFRSTVLRKCSKGSSGMSRFLYTNNFQRNLISSGGNESYYGYFNRRSYTSLYMGTGTVGGITSARIRVPNVGCEGFMCSSHLSITQRNSRLIHSTSKIVPN |
| 138 | crATP6 | MALQQAAPRVFGLLGRAPVALGQSGILTGSSGFKNQGFNGSLQSVENHVYAQAFSTSSQEEQAAPSIQGASGMKLPGMAGSMLLGKSRSGLRTGSMVPFAAQQAMNM |
| 139 | hsOPA1 | MWRLRRAAVACEVCQSLVKHSSGIKGSLPLQKLHLVSRSIYHSHHPTLKLQRPQLRTSFQQFSSLTNLPLRKLKFSPIKYGYQPRRN |
| 140 | hsSDHD | MAVLWRLSAVCGALGGRALLLRTPVVRPAHISAFLQDRPIPEWCGVQHIHLSPSHH |
| 141 | hsADCK3 | MAAILGDTIMVAKGLVKLTQAAVETHLQHLGIGGELIMAARALQSTAVEQIGMFLGKVQGQDKHEEYFAENFGGPEGEFHFSVPHAAGASTDFSSASAPDQSAPPSLGHAHSEGPAPAYVASGPFREAGFPGQASSPLGRANGRLFANPRDSFSAMGFQRRF |
| 142 | osP0644B06.24-2 | MALLLRHSPKLRRAHAILGCERGTVVRHFSSSTCSSLVKEDTVSSSNLHPEYAKKIGGSDFSHDRQSGKELQNFKVSPQEASRASNFMRASKYGMPITANGVHSLFSCGQVVPSRCF |
| 143 | Neurospora crassa ATP9 (ncATP9) | MASTRVLASRLASQMAASAKVARPAVRVAQVSKRTIQTGSPLQTLKRTQMTSIVNATTRQAFQKRA |
| 144 | hsGHITM | MLAARLVCLRTLPSRVFHPAFTKASPVVKNSITKNQWLLTPSRE |
| 145 | hsNDUFAB1 | MASRVLSAYVSRLPAAFAPLPRVRMLAVARPLSTALCSAGTQTRLGTLQPALVLAQVPGRVTQLCRQY |
| 146 | hsATP5G3 | MFACAKLACTPSLIRAGSRVAYRPISASVLSRPEASRTGEGSTVFNGAQNGVSQLIQREFQTSAISR |
| 147 | crATP6_hsADCK3 | MALQQAAPRVFGLLGRAPVALGQSGILTGSSGFKNQGFNGSLQSVENHVYAQAFSTSSQEEQAAPSIQGASGMKLPGMAGSMLLGKSRSGLRTGSMVPFAAQQAMNMGGMAAILGDTIMVAKGLVKLTQAAVETHLQHLGIGGELIMAARALQSTAVEQIGMFLGKVQGQDKHEEYFAENFGGPEGEFHFSVPHAAGASTDFSSASAPDQSAPPSLGHAHSEGPAPAYVASGPFREAGFPGQASSPLGRANGRLFANPRDSFSAMGFQRRFGG |

TABLE 1-continued nucleic acid and polypeptide sequences and SEQ ID NOs

| SEQ | Description | Sequence |
|---|---|---|
| 148 | ncATP9_nc ATP9 | MASTRVLASRLASQMAASAKVARPAVRVAQVSKRTIQTGSPLQTLKRTQMTSIVNATTRQAFQ KRAMASTRVLASRLASQMAASAKVARPAVRVAQVSKRTIQTGSPLQTLKRTQMTSIVNATTRQ AFQKRA |
| 149 | zmLOC100 282174 | MALLRAAVSELRRRGRGALTPLPALSSLLSSLSPRSPASTRPEPNNPHADRRHVIALRRCPPL PASAVLAPELLHARGLLPRHWSHASPLSTSSSSSRPADKAQLTWVDKWIPEAARPY |
| 150 | ncATP9_zm LOC100282 174_spilv1_ ncATP9 | MASTRVLASRLASQMAASAKVARPAVRVAQVSKRTIQTGSPLQTLKRTQMTSIVNATTRQAFQ KRAMALLRAAVSELRRRGRGALTPLPALSSLLSSLSPRSPASTRPEPNNPHADRRHVIALRRC PPLPASAVLAPELLHARGLLPRHWSHASPLSTSSSSSRPADKAQLTWVDKWIPEAARPYMTVL APLRRLHTRAAFSSYGREIALQKRFLNLNSCSAVRRYGTGFSNNLRIKKLKNAFGVVRANSTK STSTVTTASPIKYDSSFVGKTGGEIFHDMMLKHNVKHVFGYPGGAILPVFDAIYRSPHFEFIL PRHEQAAGHAMASTRVLASRLASQMAASAKVARPAVRVAQVSKRTIQTGSPLQTLKRTQMTSI VNATTRQAFQKRA |
| 151 | zmLOC100 282174_hsA DCK3_crA TP6_hsATP5G3 | MALLRAAVSELRRRGRGALTPLPALSSLLSSLSPRSPASTRPEPNNPHADRRHVIALRRCPPL PASAVLAPELLHARGLLPRHWSHASPLSTSSSSSRPADKAQLTWVDKWIPEAARPYMAAILGD TIMVAKGLVKLTQAAVETHLQHLGIGGELIMAARALQSTAVEQIGMFLGKVQGQDKHEEYFAE NFGGPEGEFHFSVPHAAGASTDFSSASAPDQSAPPSLGHAHSEGPAPAYVASGPFREAGFPGQ ASSPLGRANGRLFANPRDSFSAMGFQRRFMALQQAAPRVFGLLGRAPVALGQSGILTGSSGFK NQGFNGSLQSVENHVYAQAFSTSSQEEQAAPSIQGASGMKLPGMAGSMLLGKSRSGLRTGSMV PFAAQQAMNMMFACAKLACTPSLIRAGSRVAYRPISASVLSRPEASRTGEGSTVFNGAQNGVS QLIQREFQTSAISR |
| 152 | zmLOC100 282174_hsA DCK3_hsA TP5G3 | MALLRAAVSELRRRGRGALTPLPALSSLLSSLSPRSPASTRPEPNNPHADRRHVIALRRCPPL PASAVLAPELLHARGLLPRHWSHASPLSTSSSSSRPADKAQLTWVDKWIPEAARPYMAAILGD TIMVAKGLVKLTQAAVETHLQHLGIGGELIMAARALQSTAVEQIGMFLGKVQGQDKHEEYFAE NFGGPEGEFHFSVPHAAGASTDFSSASAPDQSAPPSLGHAHSEGPAPAYVASGPFREAGFPGQ ASSPLGRANGRLFANPRDSFSAMGFQRRFMFACAKLACTPSLIRAGSRVAYRPISASVLSRPE ASRTGEGSTVFNGAQNGVSQLIQREFQTSAISR |
| 153 | ncATP9_zm LOC100282 174 | MASTRVLASRLASQMAASAKVARPAVRVAQVSKRTIQTGSPLQTLKRTQMTSIVNATTRQAFQ KRAMALLRAAVSELRRRGRGALTPLPALSSLLSSLSPRSPASTRPEPNNPHADRRHVIALRRC PPLPASAVLAPELLHARGLLPRHWSHASPLSTSSSSSRPADKAQLTWVDKWIPEAARPY |
| 154 | hsADCK3_z mLOC1002 82174_crAT P6_hsATP5G3 | MAAILGDTIMVAKGLVKLTQAAVETHLQHLGIGGELIMAARALQSTAVEQIGMFLGKVQGQDK HEEYFAENFGGPEGEFHFSVPHAAGASTDFSSASAPDQSAPPSLGHAHSEGPAPAYVASGPFR EAGFPGQASSPLGRANGRLFANPRDSFSAMGFQRRFMALLRAAVSELRRRGRGALTPLPALSS LLSSLSPRSPASTRPEPNNPHADRRHVIALRRCPPLPASAVLAPELLHARGLLPRHWSHASPL STSSSSSRPADKAQLTWVDKWIPEAARPYMALQQAAPRVFGLLGRAPVALGQSGILTGSSGFK NQGFNGSLQSVENHVYAQAFSTSSQEEQAAPSIQGASGMKLPGMAGSMLLGKSRSGLRTGSMV PFAAQQAMNMMFACAKLACTPSLIRAGSRVAYRPISASVLSRPEASRTGEGSTVFNGAQNGVS QLIQREFQTSAISR |
| 155 | crATP6_hsADCK3_zmLOC10 0282174_hs ATP5G3 | MALQQAAPRVFGLLGRAPVALGQSGILTGSSGFKNQGFNGSLQSVENHVYAQAFSTSSQEEQA APSIQGASGMKLPGMAGSMLLGKSRSGLRTGSMVPFAAQQAMNMMAAILGDTIMVAKGLVKLT QAAVETHLQHLGIGGELIMAARALQSTAVEQIGMFLGKVQGQDKHEEYFAENFGGPEGEFHFS VPHAAGASTDFSSASAPDQSAPPSLGHAHSEGPAPAYVASGPFREAGFPGQASSPLGRANGRL FANPRDSFSAMGFQRRFMALLRAAVSELRRRGRGALTPLPALSSLLSSLSPRSPASTRPEPNN PHADRRHVIALRRCPPLPASAVLAPELLHARGLLPRHWSHASPLSTSSSSSRPADKAQLTWVD KWIPEAARPYMFACAKLACTPSLIRAGSRVAYRPISASVLSRPEASRTGEGSTVFNGAQNGVS QLIQREFQTSAISR |
| 156 | hsADCK3_z mLOC1002 82174 | MAAILGDTIMVAKGLVKLTQAAVETHLQHLGIGGELIMAARALQSTAVEQIGMFLGKVQGQDK HEEYFAENFGGPEGEFHFSVPHAAGASTDFSSASAPDQSAPPSLGHAHSEGPAPAYVASGPFR EAGFPGQASSPLGRANGRLFANPRDSFSAMGFQRRFGGMALLRAAVSELRRRGRGALTPLPAL SSLLSSLSPRSPASTRPEPNNPHADRRHVIALRRCPPLPASAVLAPELLHARGLLPRHWSHAS PLSTSSSSSRPADKAQLTWVDKWIPEAARPYGG |
| 157 | hsADCK3_z mLOC1002 82174_crAT P6 | MAAILGDTIMVAKGLVKLTQAAVETHLQHLGIGGELIMAARALQSTAVEQIGMFLGKVQGQDK HEEYFAENFGGPEGEFHFSVPHAAGASTDFSSASAPDQSAPPSLGHAHSEGPAPAYVASGPFR EAGFPGQASSPLGRANGRLFANPRDSFSAMGFQRRFGGMALLRAAVSELRRRGRGALTPLPAL SSLLSSLSPRSPASTRPEPNNPHADRRHVIALRRCPPLPASAVLAPELLHARGLLPRHWSHAS PLSTSSSSSRPADKAQLTWVDKWIPEAARPYGGMALQQAAPRVFGLLGRAPVALGQSGILTGS SGFKNQGFNGSLQSVENHVYAQAFSTSSQEEQAAPSIQGASGMKLPGMAGSMLLGKSRSGLRT GSMVPFAAQQAMNMGG |
| 158 | ncATP9_zm LOC100282 174_spilv1_ GNFP_ncA TP9 | MASTRVLASRLASQMAASAKVARPAVRVAQVSKRTIQTGSPLQTLKRTQMTSIVNATTRQAFQ KRAMALLRAAVSELRRRGRGALTPLPALSSLLSSLSPRSPASTRPEPNNPHADRRHVIALRRC PPLPASAVLAPELLHARGLLPRHWSHASPLSTSSSSSRPADKAQLTWVDKWIPEAARPYMTVL APLRRLHTRAAFSSYGREIALQKRFLNLNSCSAVRRYGTGFSNNLRIKKLKNAFGVVRANSTK STSTVTTASPIKYDSSFVGKTGGEIFHDMMLKHNVKHVFGYPGGAILPVFDAIYRSPHFEFIL PRHEQAAGHAVSGEGDATYGKLTLKFICTTGKLPVPWPTLVTTLTYGVQCFSRYPDHMKQHDF FKSAMPEGYVQERTIFFKDDGNYKTRAEVKFEGDTLVNRIELKGIDFKEDGNILGHKLEYNYN |

TABLE 1-continued nucleic acid and polypeptide sequences and SEQ ID NOs

| SEQ | Description | Sequence |
|---|---|---|
| | | SHNVYIMADKQKNGIKVNFKIRHNIEDGSVQLADHYQQNTPIGDGPVLLPDNHYLSTQSALSK DPNEMASTRVLASRLASQMAASAKVARPAVRVAQVSKRTIQTGSPLQTLKRTQMTSIVNATTR QAFQKRA |
| 159 | ncATP9_zm LOC100282 174_spilv1_ lcSirt5_osP0 644B06.24- 2_hsATP5G 2_ncATP9 | MASTRVLASRLASQMAASAKVARPAVRVAQVSKRTIQTGSPLQTLKRTQMTSIVNATTRQAFQ KRAMALLRAAVSELRRRGRGALTPLPALSSLLSSLSPRSPASTRPEPNNPHADRRHVIALRRC PPLPASAVLAPELLHARGLLPRHWSHASPLSTSSSSSRPADKAQLTWVDKWIPEAARPYMTVL APLRRLHTRAAFSSYGREIALQKRFLNLNSCSAVRRYGTGFSNNLRIKKLKNAFGVVRANSTK STSTVTTASPIKYDSSFVGKTGGEIFHDMMLKHNVKHVFGYPGGAILPVFDAIYRSPHFEFIL PRHEQAAGHAMRKRSLRCHLWSANASLSPRKDEVTSRKESENLVKGKKNKKSHLHLLLFTASK IGTDSVFDVQKSKECCKELGLLFTSLIHSIGSFPFDEEPKAAAVFLPGSLPQLTVLVLAPGSG SCPTGKSTPHLAASGRNAELLRPQNSMIVRQFTCRGTISSHLCAHLRKPHDSRNMARPMALLL RHSPKLRRAHAILGCERGTVVRHFSSSTCSSLVKEDTVSSSNLHPEYAKKIGGSDFSHDRQSG KELQNFKVSPQEASRASNFMRASKYGMPITANGVHSLFSCGQVVPSRCFMPELILYVAITLSV AERLVGPGHACAEPSFRSSRCSAPLCLLCSGSSSPATAPHPLKMFACSKFVSTPSLVKSTSQL LSRPLSAVVLKRPEILTDESLSSLAVSCPLTSLVSSRSFQTSAISRDIDTAMASTRVLASRLA SQMAASAKVARPAVRVAQVSKRTIQTGSPLQTLKRTQMTSIVNATTRQAFQKRA |
| 160 | ND4 | MLKLIVPTIMLLPLTWLSKKHMIWINTTTHSLIISIIPLLFFNQINNNLFSCSPTFSSDPLTT PLLMLTTWLLPLTIMASQRHLSSEPLSRKKLYLSMLISLQISLIMTFTATELIMFYIFFETTL IPTLAIITRWGNQPERLNAGTYFLFYTLVGSLPLLIALIYTHNTLGSLNILLLTLTAQELSNS WANNLMWLAYTMAFMVKMPLYGLHLWLPKAHVEAPIAGSMVLAAVLLKLGGYGMMRLTLILNP LTKHMAYPFLVLSLWGMIMTSSICLRQTDLKSLIAYSSISHMALVVTAILIQTPWSFTGAVIL MIAHGLTSSLLFCLANSNYERTHSRIMILSQGLQTLLPLMAFWWLLASLANLALPPTINLLGE LSVLVTTFSWSNITLLLTGLNMLVTALYSLYMFTTTQWGSLTHHINNMKPSFTRENTLMFMHL SPILLLSLNPDIITGFSS |
| 161 | ND6 | MMYALFLLSVGLVMGFVGFSSKPSPIYGGLVLIVSGVVGCVIILNFGGGYMGLMVFLIYLGGM MVVFGYTTAMAIEEYPEAWGSGVEVLVSVLVGLAMEVGLVLWVKEYDGVVVVVNFNSVGSWMI YEGEGSGLIREDPIGAGALYDYGRWLVVVTGWTLFVGVYIVIEIARGN |
| 162 | ND1 | MANLLLLIVPILIAMAFLMLTERKILGYMQLRKGPNVVGPYGLLQPFADAIKLFTKEPLKPAT STITLYITAPTLALTIALLLWTPLPMPNPLVNLNLGLLFILATSSLAVYSILWSGWASNSNYA LIGALRAVAQTISYEVTLAIILLSTLLMSGSFNLSTLITTQEHLWLLLPSWPLAMMWFISTLA ETNRTPFDLAEGESELVSGFNIEYAAGPFALFFMAEYTNIIMMNTLTTTIFLGTTYDALSPEL YTTYFVTKTLLLTSLFLWIRTAYPRFRYDQLMHLLWKNFLPLTLALLMWYVSMPITISSIPPQ T |
| 163 | GFP-F | ACAAGTTCAGCGTGTCCG |
| 164 | GFP-R | CTCGTTGGGGTCTTTGCT |
| 165 | ND4-F | ATCTCCGCACACTCTCTCCTCA |
| 166 | ND4-R | TAGGTTGTTGTTGATTTGGTT |
| 167 | B-actin-F2 | CCTAGAAGCATTTGCGGT |
| 168 | B-actin-R2 | GAGCTACGAGCTGCCTGA |

Adeno-Associated Virus (AAV)

Adeno-associated virus (AAV) is a small virus that infects humans and some other primate species. The compositions disclosed herein comprises firstly an adeno-associated virus (AAV) genome or a derivative thereof.

An AAV genome is a polynucleotide sequence which encodes functions needed for production of an AAV viral particle. These functions include those operating in the replication and packaging cycle for AAV in a host cell, including encapsidation of the AAV genome into an AAV viral particle. Naturally occurring AAV viruses are replication-deficient and rely on the provision of helper functions in trans for completion of a replication and packaging cycle. Accordingly, the AAV genome of the vector of the invention is typically replication-deficient.

The AAV genome can be in single-stranded form, either positive or negative-sense, or alternatively in double-stranded form. The use of a double-stranded form allows bypass of the DNA replication step in the target cell and so can accelerate transgene expression.

The AAV genome may be from any naturally derived serotype or isolate or Glade of AAV. Thus, the AAV genome may be the full genome of a naturally occurring AAV virus. As is known to the skilled person, AAV viruses occurring in nature may be classified according to various biological systems.

Commonly, AAV viruses are referred to in terms of their serotype. A serotype corresponds to a variant subspecies of AAV which owing to its profile of expression of capsid surface antigens has a distinctive reactivity which can be used to distinguish it from other variant subspecies. Typically, a virus having a particular AAV serotype does not efficiently cross-react with neutralising antibodies specific for any other AAV serotype. AAV serotypes include AAV1, AAV2, AAV3, AAV4, AAV5, AAV6, AAV7, AAV8, AAV9, AAV10, AAV11, AAV12, AAV13, AAV14, AAV15, and AAV16, also recombinant serotypes, such as Rec2 and Rec3, recently identified from primate brain.

A preferred serotype of AAV for use in the invention is AAV2. Other serotypes of particular interest for use in the invention include AAV4, AAV5 and AAV8 which efficiently transduce tissue in the eye, such as the retinal pigmented epithelium. The serotype of AAV which is used can be an AAV serotype which is not AAV4. Reviews of AAV serotypes may be found in Choi et al (Curr Gene Ther. 2005; 5(3); 299-310) and Wu et al (Molecular Therapy. 2006; 14(3), 316-327). The sequences of AAV genomes or of elements of AAV genomes including ITR sequences, rep or cap genes for use in the invention may be derived from the following accession numbers for AAV whole genome sequences: Adeno-associated virus 1 NC_002077, AF063497; Adeno-associated virus 2 NC_001401; Adeno-associated virus 3 NC_001729; Adeno-associated virus 3B NC_001863; Adeno-associated virus 4 NC_001829; Adeno-associated virus 5 Y18065, AF085716; Adeno-associated virus 6 NC_001862; Avian AAV ATCC VR-865 AY186198, AY629583, NC_004828; Avian AAV strain DA-1 NC_006263, AY629583; Bovine AAV NC_005889, AY388617.

AAV viruses may also be referred to in terms of clades or clones. This refers to the phylogenetic relationship of naturally derived AAV viruses, and typically to a phylogenetic group of AAV viruses which can be traced back to a common ancestor, and includes all descendants thereof. Additionally, AAV viruses may be referred to in terms of a specific isolate, i.e. a genetic isolate of a specific AAV virus found in nature. The term genetic isolate describes a population of AAV viruses which has undergone limited genetic mixing with other naturally occurring AAV viruses, thereby defining a recognizably distinct population at a genetic level.

Examples of clades and isolates of AAV that may be used in the invention include: Clade A: AAV1 NC_002077, AF063497, AAV6 NC_001862, Hu. 48 AY530611, Hu 43 AY530606, Hu 44 AY530607, Hu 46 AY530609; Clade B: Hu. 19 AY530584, Hu. 20 AY530586, Hu 23 AY530589, Hu22 AY530588, Hu24 AY530590, Hu21 AY530587, Hu27 AY530592, Hu28 AY530593, Hu 29 AY530594, Hu63 AY530624, Hu64 AY530625, Hu13 AY530578, Hu56 AY530618, Hu57 AY530619, Hu49 AY530612, Hu58 AY530620, Hu34 AY530598, Hu35 AY530599, AAV2 NC_001401, Hu45 AY530608, Hu47 AY530610, Hu51 AY530613, Hu52 AY530614, Hu T41 AY695378, Hu S17 AY695376, Hu T88 AY695375, Hu T71 AY695374, Hu T70 AY695373, Hu T40 AY695372, Hu T32 AY695371, Hu T17 AY695370, Hu LG15 AY695377; Clade C: Hu9 AY530629, Hu10 AY530576, Hu11 AY530577, Hu53 AY530615, Hu55 AY530617, Hu54 AY530616, Hu7 AY530628, Hu18 AY530583, Hu15 AY530580, Hu16 AY530581, Hu25 AY530591, Hu60 AY530622, Ch5 AY243021, Hu3 AY530595, Hu1 AY530575, Hu4 AY530602 Hu2, AY530585, Hu61 AY530623; Clade D: Rh62 AY530573, Rh48 AY530561, Rh54 AY530567, Rh55 AY530568, Cy2 AY243020, AAV7 AF513851, Rh35 AY243000, Rh37 AY242998, Rh36 AY242999, Cy6 AY243016, Cy4 AY243018, Cy3 AY243019, Cy5 AY243017, Rh13 AY243013; Clade E: Rh38 AY530558, Hu66 AY530626, Hu42 AY530605, Hu67 AY530627, Hu40 AY530603, Hu41 AY530604, Hu37 AY530600, Rh40 AY530559, Rh2 AY243007, Bb1 AY243023, Bb2 AY243022, Rh10 AY243015, Hu17 AY530582, Hu6 AY530621, Rh25 AY530557, Pi2 AY530554, Pi1 AY530553, Pi3 AY530555, Rh57 AY530569, Rh50 AY530563, Rh49 AY530562, Hu39 AY530601, Rh58 AY530570, Rh61 AY530572, Rh52 AY530565, Rh53 AY530566, Rh51 AY530564, Rh64 AY530574, Rh43 AY530560, AAV8 AF513852, Rh8 AY242997, Rh1 AY530556; Clade F: Hu14 (AAV9) AY530579, Hu31 AY530596, Hu32 AY530597, Clonal Isolate AAV5 Y18065, AF085716, AAV 3 NC_001729, AAV 3B NC_001863, AAV4 NC_001829, Rh34 AY243001, Rh33 AY243002, Rh32 AY243003.

The skilled person can select an appropriate serotype, Glade, clone or isolate of AAV for use in the present invention on the basis of their common general knowledge. For instance, the AAV5 capsid has been shown to transduce primate cone photoreceptors efficiently as evidenced by the successful correction of an inherited color vision defect (Mancuso et al., Nature 2009, 461:784-7).

It should be understood however that the invention also encompasses use of an AAV genome of other serotypes that may not yet have been identified or characterized. The AAV serotype determines the tissue specificity of infection (or tropism) of an AAV virus. Accordingly, preferred AAV serotypes for use in AAV viruses administered to patients in accordance with the invention are those which have natural tropism for or a high efficiency of infection of target cells within eye in LHON. Thus, AAV serotypes for use in AAV viruses administered to patients can be ones which infect cells of the neurosensory retina and retinal pigment epithelium.

Typically, the AAV genome of a naturally derived serotype or isolate or Glade of AAV comprises at least one inverted terminal repeat sequence (ITR). An ITR sequence acts in cis to provide a functional origin of replication, and allows for integration and excision of the vector from the genome of a cell. In preferred embodiments, one or more ITR sequences flank the polynucleotide sequence encoding ND4, ND6, or ND1 or a variant thereof. Preferred ITR sequences are those of AAV2, and variants thereof. The AAV genome typically also comprises packaging genes, such as rep and/or cap genes which encode packaging functions for an AAV viral particle. The rep gene encodes one or more of the proteins Rep78, Rep68, Rep52 and Rep40 or variants thereof. The cap gene encodes one or more capsid proteins such as VP1, VP2 and VP3 or variants thereof. These proteins make up the capsid of an AAV viral particle. Capsid variants are discussed below.

A promoter will be operably linked to each of the packaging genes. Specific examples of such promoters include the p5, p19 and p40 promoters (Laughlin et al., 1979, PNAS, 76:5567-5571). For example, the p5 and p19 promoters are generally used to express the rep gene, while the p40 promoter is generally used to express the cap gene.

As discussed above, the AAV genome used in the vector of the invention may therefore be the full genome of a naturally occurring AAV virus. For example, a vector comprising a full AAV genome may be used to prepare AAV virus in vitro. However, while such a vector may in principle be administered to patients, this will be done rarely in practice. Preferably the AAV genome will be derivatized for the purpose of administration to patients. Such derivatization is standard in the art and the present invention encompasses the use of any known derivative of an AAV genome, and derivatives which could be generated by applying techniques known in the art. Derivatization of the AAV genome and of the AAV capsid are reviewed in Coura and Nardi (Virology Journal, 2007, 4:99), and in Choi et al and Wu et al, referenced above.

Derivatives of an AAV genome include any truncated or modified forms of an AAV genome which allow for expression of a ND4, ND6, or ND1 transgene from a vector of the invention in vivo. Typically, it is possible to truncate the AAV genome significantly to include minimal viral sequence yet retain the above function. This is preferred for safety reasons to reduce the risk of recombination of the vector with wild-type virus, and also to avoid triggering a cellular immune response by the presence of viral gene proteins in the target cell.

Typically, a derivative will include at least one inverted terminal repeat sequence (ITR), preferably more than one ITR, such as two ITRs or more. One or more of the ITRs may be derived from AAV genomes having different serotypes, or may be a chimeric or mutant ITR. A preferred mutant ITR is one having a deletion of a trs (terminal resolution site). This deletion allows for continued replication of the genome to generate a single-stranded genome which contains both coding and complementary sequences i.e. a self-complementary AAV genome. This allows for bypass of DNA replication in the target cell, and so enables accelerated transgene expression.

The one or more ITRs will preferably flank the polynucleotide sequence encoding ND4, ND6, ND1, or a variant thereof at either end. The inclusion of one or more ITRs is preferred to aid concatamer formation of the vector of the invention in the nucleus of a host cell, for example following the conversion of single-stranded vector DNA into double-stranded DNA by the action of host cell DNA polymerases. The formation of such episomal concatamers protects the vector construct during the life of the host cell, thereby allowing for prolonged expression of the transgene in vivo.

In preferred embodiments, ITR elements will be the only sequences retained from the native AAV genome in the derivative. Thus, a derivative will preferably not include the rep and/or cap genes of the native genome and any other sequences of the native genome. This is preferred for the reasons described above, and also to reduce the possibility of integration of the vector into the host cell genome. Additionally, reducing the size of the AAV genome allows for increased flexibility in incorporating other sequence elements (such as regulatory elements) within the vector in addition to the transgene.

With reference to the AAV2 genome, the following portions could therefore be removed in a derivative of the invention: One inverted terminal repeat (ITR) sequence, the replication (rep) and capsid (cap) genes (NB: the rep gene in the wild type AAV genome should not to be confused with ND4, ND6, or ND1, the human gene affected in LHON). However, in some embodiments, including in vitro embodiments, derivatives may additionally include one or more rep and/or cap genes or other viral sequences of an AAV genome. Naturally occurring AAV virus integrates with a high frequency at a specific site on human chromosome 19, and shows a negligible frequency of random integration, such that retention of an integrative capacity in the vector may be tolerated in a therapeutic setting.

Where a derivative genome comprises genes encoding capsid proteins i.e. VP1, VP2 and/or VP3, the derivative may be a chimeric, shuffled or capsid-modified derivative of one or more naturally occurring AAV viruses. In particular, the invention encompasses the provision of capsid protein sequences from different serotypes, clades, clones, or isolates of AAV within the same vector i.e. pseudotyping.

Chimeric, shuffled or capsid-modified derivatives will be typically selected to provide one or more desired functionalities for the viral vector. Thus, these derivatives may display increased efficiency of gene delivery, decreased immunogenicity (humoral or cellular), an altered tropism range and/or improved targeting of a particular cell type compared to an AAV viral vector comprising a naturally occurring AAV genome, such as that of AAV2. Increased efficiency of gene delivery may be effected by improved receptor or co-receptor binding at the cell surface, improved internalization, improved trafficking within the cell and into the nucleus, improved uncoating of the viral particle and improved conversion of a single-stranded genome to double-stranded form. Increased efficiency may also relate to an altered tropism range or targeting of a specific cell population, such that the vector dose is not diluted by administration to tissues where it is not needed.

Chimeric capsid proteins include those generated by recombination between two or more capsid coding sequences of naturally occurring AAV serotypes. This may be performed for example by a marker rescue approach in which non-infectious capsid sequences of one serotype are co-transfected with capsid sequences of a different serotype, and directed selection is used to select for capsid sequences having desired properties. The capsid sequences of the different serotypes can be altered by homologous recombination within the cell to produce novel chimeric capsid proteins.

Chimeric capsid proteins also include those generated by engineering of capsid protein sequences to transfer specific capsid protein domains, surface loops or specific amino acid residues between two or more capsid proteins, for example between two or more capsid proteins of different serotypes.

Shuffled or chimeric capsid proteins may also be generated by DNA shuffling or by error-prone PCR. Hybrid AAV capsid genes can be created by randomly fragmenting the sequences of related AAV genes e.g. those encoding capsid proteins of multiple different serotypes and then subsequently reassembling the fragments in a self-priming polymerase reaction, which may also cause crossovers in regions of sequence homology. A library of hybrid AAV genes created in this way by shuffling the capsid genes of several serotypes can be screened to identify viral clones having a desired functionality. Similarly, error prone PCR may be used to randomly mutate AAV capsid genes to create a diverse library of variants which may then be selected for a desired property.

The sequences of the capsid genes may also be genetically modified to introduce specific deletions, substitutions or insertions with respect to the native wild-type sequence. In particular, capsid genes may be modified by the insertion of a sequence of an unrelated protein or peptide within an open reading frame of a capsid coding sequence, or at the N- and/or C-terminus of a capsid coding sequence.

The unrelated protein or peptide may advantageously be one which acts as a ligand for a particular cell type, thereby conferring improved binding to a target cell or improving the specificity of targeting of the vector to a particular cell population. An example might include the use of RGD peptide to block uptake in the retinal pigment epithelium and thereby enhance transduction of surrounding retinal tissues (Cronin et al., 2008 ARVO Abstract: D1048). The unrelated protein may also be one which assists purification of the viral particle as part of the production process i.e. an epitope or affinity tag. The site of insertion will typically be selected so as not to interfere with other functions of the viral particle e.g. internalization, trafficking of the viral particle. The skilled person can identify suitable sites for insertion based on their common general knowledge. Particular sites are disclosed in Choi et al, referenced above.

The invention additionally encompasses the provision of sequences of an AAV genome in a different order and configuration to that of a native AAV genome. The invention also encompasses the replacement of one or more AAV sequences or genes with sequences from another virus or with chimeric genes composed of sequences from more than one virus. Such chimeric genes may be composed of sequences from two or more related viral proteins of different viral species.

The vector of the invention takes the form of a polynucleotide sequence comprising an AAV genome or derivative thereof and a sequence encoding ND4, ND6, ND1 or a variant thereof.

For the avoidance of doubt, the invention also provides an AAV viral particle comprising a vector of the invention. The AAV particles of the invention include trans-capsidated forms wherein an AAV genome or derivative having an ITR of one serotype is packaged in the capsid of a different serotype. The AAV particles of the invention also include mosaic forms wherein a mixture of unmodified capsid proteins from two or more different serotypes makes up the viral envelope. The AAV particle also includes chemically modified forms bearing ligands adsorbed to the capsid surface. For example, such ligands may include antibodies for targeting a particular cell surface receptor.

The invention additionally provides a host cell comprising a vector or AAV viral particle of the invention.

Recombinant Nucleic Acid Sequences

Also disclosed herein are recombinant nucleic acid sequences comprising a polynucleotide sequence encoding a NADH dehydrogenase subunit-4 (ND4), NADH dehydrogenase subunit-1 (ND1) and NADH dehydrogenase subunit-6 (ND6) polypeptide or a variant thereof.

The polynucleotide sequence for ND4 is shown in SEQ ID NO: 6 and encodes the protein shown in SEQ ID NO: 160. Further nucleic acid sequences for ND4 are SEQ ID NO: 7 and 8. The polynucleotide sequence for ND6 is shown in SEQ ID NO: 9 and encodes the protein shown in SEQ ID NO: 161. A further nucleic acid sequence for ND6 is SEQ ID NO: 10. The polynucleotide sequence for ND1 is shown in SEQ ID NO: 11 and encodes the protein shown in SEQ ID NO: 162. A further nucleic acid sequence for ND1 is SEQ ID NO: 12.

A variant of any one of SEQ ID NO: 160, 161, or 162 may comprise truncations, mutants or homologues thereof, and any transcript variants thereof which encode a functional ND4, ND6, or ND1 polypeptide. Any homologues mentioned herein are typically at least 70% homologous to a relevant region of ND4, ND6, or ND1, and can functionally compensate for the polypeptide deficiency.

Homology can be measured using known methods. For example the UWGCG Package provides the BESTFIT program which can be used to calculate homology (for example used on its default settings) (Devereux et at (1984) Nucleic Acids Research 12, 387-395). The PILEUP and BLAST algorithms can be used to calculate homology or line up sequences (typically on their default settings), for example as described in Altschul S. F. (1993) J Mol Evol 36:290-300; Altschul, S, F et at (1990) J Mol Biol 215:403-10. Software for performing BLAST analyses is publicly available through the National Center for Biotechnology Information (http://www.ncbi.nlm.nih.gov/).

In preferred embodiments, a recombinant nucleic acid sequence may encode a polypeptide which is at least 55%, 65%, 70%, 75%, 80%, 85%, 90% and more preferably at least 95%, 97%, 99%, 99.5%, or 100% homologous to a relevant region of ND4, ND6, or ND1 (SEQ ID NO: 160, 161, or 162) over at least 20, preferably at least 30, for instance at least 40, 60, 100, 200, 300, 400 or more contiguous amino acids, or even over the entire sequence of the recombinant nucleic acid. The relevant region will be one which provides for functional activity of ND4, ND6, or ND1.

Alternatively, and preferably the recombinant nucleic acid sequence may encode a polypeptide having at least 70%, 75%, 80%, 85%, 90% and more preferably at least 95%, 97%, 99%, 99.5%, or 100% homologous to full-length ND4, ND6, or ND1 (SEQ ID NO: 160, 161, or 162) over its entire sequence. Typically the recombinant nucleic acid sequence differs from the relevant region of ND4, ND6, or ND1 (SEQ ID NO: 160, 161, or 162) by at least, or less than, 2, 5, 10, 20, 40, 50 or 60 mutations (each of which can be substitutions, insertions or deletions).

A recombinant nucleic acid ND4, ND6, or ND1 polypeptide may have a percentage identity with a particular region of SEQ ID NO: 160, 161, or 162 which is the same as any of the specific percentage homology values (i.e. it may have at least 70%, 80% or 90% and more preferably at least 95%, 97%, 99% identity) across any of the lengths of sequence mentioned above.

Variants of ND4, ND6, or ND1 (SEQ ID NO: 160, 161, or 162) also include truncations. Any truncation may be used so long as the variant is still functional. Truncations will typically be made to remove sequences that are non-essential for the protein activity and/or do not affect conformation of the folded protein, in particular folding of the active site. Appropriate truncations can routinely be identified by systematic truncation of sequences of varying length from the N- or C-terminus. Preferred truncations are N-terminal and may remove all other sequences except for the catalytic domain.

Variants of ND4, ND6, or ND1 (SEQ ID NO: 160, 161, or 162) further include mutants which have one or more, for example, 2, 3, 4, 5 to 10, 10 to 20, 20 to 40 or more, amino acid insertions, substitutions or deletions with respect to a particular region of ND4, ND6, or ND1 (SEQ ID NO: 160, 161, or 162). Deletions and insertions are made preferably outside of the catalytic domain as described below. Substitutions are also typically made in regions that are non-essential for protease activity and/or do not affect conformation of the folded protein.

Substitutions preferably introduce one or more conservative changes, which replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative change may introduce another amino acid that is aromatic or aliphatic in the place of a pre-existing aromatic or aliphatic amino acid. Conservative amino acid changes are well known in the art and may be selected in accordance with the properties of the amino acids.

Similarly, preferred variants of the polynucleotide sequence of ND4, ND6, or ND1 (SEQ ID NO: 6, 9, or 11) include polynucleotides having at least 70%, 75%, 80%, 85%, 90% and more preferably at least 95%, 96%, 97%, 98%, 99%, or 99.5% homologous to a relevant region of ND4, ND6, or ND1 (SEQ ID NO: 6, 9, or 11). Preferably the variant displays these levels of homology to full-length ND4, ND6, or ND1 (SEQ ID NO: 6, 9, or 11) over its entire sequence.

Mitochondrial targeting sequences (MTSs) and three prime untranslated regions (3'UTRs) can be used to target proteins or mRNA to the mitochondria. The charge, length, and structure of the MTS can be important for protein import into the mitochondria. Particular 3'UTRs may drive mRNA localization to the mitochondrial surface and thus facilitate co-translational protein import into the mitochondria.

The polynucleotide sequence for a mitochondrial targeting sequence can encode a polypeptide selected from hsCOX10, hsCOX8, scRPM2, lcSirt5, tbNDUS7, ncQCR2, hsATP5G2, hsLACTB, spilv1, gmCOX2, crATP6, hsOPA1, hsSDHD, hsADCK3, osP0644B06.24-2, *Neurospora crassa* ATPS (ncATP9), hsGHITM, hsNDUFAB1, hsATP5G3, crATP6_hsADCK3, ncATP9_ncATP9, zmLOC100282174, ncATP9_zmLOC100282174_spilv1_ncATP9, zmLOC100282174_hsADCK3_crATP6_hsATP5G3, zmLOC100282174_hsADCK3_hsATP5G3, ncATP9_zmLOC100282174, hsADCK3_zmLOC100282174_crATP6_hsATP5G3, crATP6_hsADCK3_zmLOC100282174_hsATP5G3, hsADCK3_zmLOC100282174, hsADCK3_zmLOC100282174_crATP6, ncATP9_zmLOC100282174_spilv1_GNFP_ncATP9, and ncATP9_zmLOC100282174_spilv1_lcSirt5_osP0644B06.24-2_hsATP5G2_ncATP9 (see Table 1 for SEQ ID NO). In one example, the polynucleotide sequences, COX10 (SEQ ID NO: 1, 2, or 3) can encode the mitochondrial targeting sequence, MTS-COX10 (SEQ ID NO: 126). In another example, the polynucleotide sequences, COX8 (SEQ ID NO: 4) can encode the mitochondrial targeting sequence, MTS-COX8 (SEQ ID NO: 127). In another example, the polynucleotide sequences, OPA1 (SEQ ID NO: 5) can encode the mitochondrial targeting sequence, MTS-OPA1 (SEQ ID NO: 128).

The 3'UTR nucleic acid sequence can be selected from hsACO2 (SEQ ID NO: 111), hsATP5B (SEQ ID NO: 112), hsAK2 (SEQ ID NO: 113), hsALDH2 (SEQ ID NO: 114), hsCOX10 (SEQ ID NO: 115), hsUQCRFS1 (SEQ ID NO: 116), hsNDUFV1 (SEQ ID NO: 117), hsNDUFV2 (SEQ ID NO: 118), hsSOD2 (SEQ ID NO: 119), hsCOX6c (SEQ ID NO: 120), hsIRP1 (SEQ ID NO: 121), hsMRPS12 (SEQ ID NO: 122), hsATP5J2 (SEQ ID NO: 123), rnSOD2 (SEQ ID NO: 124), and hsOXA1L (SEQ ID NO: 125). The 3'UTR nucleic acid sequence can also be a variant having at least 70%, 75%, 80%, 85%, 90% and more preferably at least 95%, 96%, 97%, 98%, 99%, 99.5%, or 100% homologous to any 3'UTR nucleic acid sequence listed here. For example, the 3'UTR nucleic acid sequence can be SEQ ID NO: 13 or 14.

Also disclosed herein are recombinant nucleic acid sequences comprising a mitochondrial targeting sequence, a mitochondrial protein coding sequence, and a 3'UTR nucleic acid sequence. For example, the recombinant nucleic acid sequence can be selected from SEQ ID NO: 15-84. The recombinant nucleic acid sequence can also be a variant having at least 70%, 75%, 80%, 85%, 90% and more preferably at least 95%, 96%, 97%, 98%, 99%, 99.5%, or 100% homologous to any recombinant nucleic acid sequence listed here.

Promoters and Regulatory Sequences

The vector of the invention also includes elements allowing for the expression of the disclosed transgene in vitro or in vivo. Thus, the vector typically comprises a promoter sequence operably linked to the polynucleotide sequence encoding the ND4, ND6, or ND1 transgene or a variant thereof.

Any suitable promoter may be used. The promoter sequence may be constitutively active i.e. operational in any host cell background, or alternatively may be active only in a specific host cell environment, thus allowing for targeted expression of the transgene in a particular cell type. The promoter may show inducible expression in response to presence of another factor, for example a factor present in a host cell. In any event, where the vector is administered for therapy, the promoter must be functional in a retinal cell background.

In some embodiments, it is preferred that the promoter shows retinal-cell specific expression in order to allow for the transgene to only be expressed in retinal cell populations. Thus, expression from the promoter may be retinal-cell specific, for example confined only to cells of the neurosensory retina and retinal pigment epithelium.

Preferred promoters for the ND4, ND6, or ND1 transgene include the chicken beta-actin (CBA) promoter, optionally in combination with a cytomegalovirus (CME) enhancer element. In some cases, the preferred promoters for the ND4, ND6, or ND1 transgene comprises the CAG promoter. A particularly preferred promoter is a hybrid CBA/CAG promoter, for example the promoter used in the rAVE expression cassette. Examples of promoters based on human sequences that would induce retina specific gene expression include rhodospin kinase for rods and cones (Allocca et al., 2007, J Viol 81:11372-80), PR2.1 for cones only (Mancuso et al. 2009, Nature) and/or RPE65 for the retinal pigment epithelium (Bainbridge et al., 2008, N Eng J Med).

The vector of the invention may also comprise one or more additional regulatory sequences with may act pre- or post-transcriptionally. The regulatory sequence may be part of the native ND4, ND6, or ND1 gene locus or may be a heterologous regulatory sequence. The vector of the invention may comprise portions of the 5'UTR or 3'UTR from the native ND4, ND6, or ND1 transcript.

Regulatory sequences are any sequences which facilitate expression of the transgene i.e. act to increase expression of a transcript, improve nuclear export of mRNA or enhance its stability. Such regulatory sequences include for example enhancer elements, postregulatory elements and polyadenylation sites. A preferred polyadenylation site is the Bovine Growth Hormone poly-A signal. In the context of the vector of the invention such regulatory sequences will be cis-acting. However, the invention also encompasses the use of trans-acting regulatory sequences located on additional genetic constructs.

A preferred postregulatory element for use in a vector of the invention is the woodchuck hepatitis postregulatory element (WPRE) or a variant thereof. Another regulatory sequence which may be used in a vector of the present invention is a scaffold-attachment region (SAR). Additional regulatory sequences may be selected by the skilled person on the basis of their common general knowledge.

Preparation of Vector

The vector of the invention may be prepared by standard means known in the art for provision of vectors for gene therapy. Thus, well established public domain transfection, packaging and purification methods can be used to prepare a suitable vector preparation.

As discussed above, a vector of the invention may comprise the full genome of a naturally occurring AAV virus in addition to a polynucleotide sequence encoding ND4, ND6, or ND1 or a variant thereof. However, commonly a derivatised genome will be used, for instance a derivative which has at least one inverted terminal repeat sequence (ITR), but which may lack any AAV genes such as rep or cap.

In such embodiments, in order to provide for assembly of the derivatised genome into an AAV viral particle, additional genetic constructs providing AAV and/or helper virus functions will be provided in a host cell in combination with the derivatised genome. These additional constructs will typically contain genes encoding structural AAV capsid proteins i.e. cap, VP1, VP2, VP3, and genes encoding other functions required for the AAV life cycle, such as rep. The selection of structural capsid proteins provided on the additional construct will determine the serotype of the packaged viral vector.

A particularly preferred packaged viral vector for use in the invention comprises a derivatised genome of AAV2 in combination with AAV5 or AAV8 capsid proteins. This packaged viral vector typically comprises one or more AAV2 ITRs.

As mentioned above, AAV viruses are replication incompetent and so helper virus functions, preferably adenovirus helper functions will typically also be provided on one or more additional constructs to allow for AAV replication.

All of the above additional constructs may be provided as plasmids or other episomal elements in the host cell, or alternatively one or more constructs may be integrated into the genome of the host cell.

In these aspects, the invention provides a method for production of a vector of the invention. The method comprises providing a vector which comprises an adeno-associated virus (AAV) genome or a derivative thereof and a polynucleotide sequence encoding ND4, ND6, or ND1 or a variant thereof in a host cell, and providing means for replication and assembly of the vector into an AAV viral particle. Preferably, the method comprises providing a vector comprising a derivative of an AAV genome and a polynucleotide sequence encoding ND4, ND6, or ND1 or a variant thereof, together with one or more additional genetic constructs encoding AAV and/or helper virus functions. Typically, the derivative of an AAV genome comprises at least one ITR. Optionally, the method further comprises a step of purifying the assembled viral particles. Additionally, the method may comprise a step of formulating the viral particles for therapeutic use.

Methods of Therapy and Medical Uses

As discussed above, the present inventors have surprisingly demonstrated that a vector of the invention may be used to address the cellular dysfunction underlying LHON. In particular, they have shown that use of the vector can correct the defect associated with LHON. This provides a means whereby the degenerative process of the disease can be treated, arrested, palliated or prevented.

The invention therefore provides a method of treating or preventing LHON in a patient in need thereof, comprising administering a therapeutically effective amount of a vector encoding a mitochondrial protein described herein to the patient by direct retinal, subretinal or intravitreal injection. In some embodiments, the methods further comprise administration of a steroid prior to, during, and/or after the administration of the vector encoding the mitochondrial protein. Accordingly, LHON is thereby treated or prevented in the patient.

Vectors suitable for use in the present methods include those described herein, comparable vectors encoding a mitochondrial protein, and biosimilars thereof. Comparable vectors encoding a mitochondrial protein suitable for use according to the present methods include those described in the art, for example, those described in Guy et al., Ophthalmology 2017; 124:1621-1634 and Vignal et al., Ophthalmology 2018; 6:945-947, each of which are incorporated by reference in their entireties. A biosimilar is a biological product that is highly similar to and has no clinically meaningful differences from an existing FDA-approved reference product ("reference product"). "Highly similar" products are products with similar purity, chemical identity, and bioactivity to a reference product. However, minor differences between the clinically inactive components of the reference product and the proposed biosimilar product in are acceptable. For example, these could include minor differences in the stabilizer or buffer compared to what is used in the reference product and slight differences (i.e., acceptable within-product variations) are expected during the manufacturing process. Any differences between the proposed biosimilar product and the reference product are carefully evaluated by FDA to ensure the biosimilar meets FDA's high approval standards. "No clinically meaningful differences" means that the biosimilar product has no clinically meaningful differences from the reference product in terms of safety, purity, and potency (safety and effectiveness), generally demonstrated through human pharmacokinetic (exposure) and pharmacodynamic (response) studies, an assessment of clinical immunogenicity, and, if needed, additional clinical studies.

In some embodiments, the patient in need of treatment according to the methods provided herein has one or more mitochondrial DNA (mtDNA) point mutations. In some embodiments, the patient has a point mutation in a gene encoding a protein of complex I in the oxidative phosphorylation chain of the mitochondria. For example, patients may have one or more point mutations in the MT-ND4 gene (also known as ND4, NCBI Gene ID: 4538) encoding the NADH dehydrogenase subunit-4 protein (ND4), the MT-ND1 gene (also known as ND1, NCBI Gene ID: 4535) encoding the NADH dehydrogenase subunit-1 protein (ND1), or the MT-ND6 gene (also known as ND6, NCBI Gene ID: 4541) encoding the NADH dehydrogenase subunit-6 protein (ND6). In some embodiments, the patient has a point mutation at nucleotide position 11778 in the ND4 gene. In some embodiments, the point mutation is G11778A in the ND4 gene. In some embodiments, the patient has a point mutation at nucleotide position 3460 in the ND1 gene. In some embodiments, the point mutation is G3460A in the ND1 gene. In some embodiments, the patient has a point mutation at nucleotide position 14484 in the ND6 gene. In some embodiments, the point mutation is T14484C in the ND6 gene. In some embodiments, the patient in need of treatment according to the methods provided herein has one or more of point mutations selected from G11778A in the ND4 gene, G3460A in the ND1 gene, and T14484C in the ND6 gene and is of Chinese and/or Argentinean descent.

In some embodiments, the patient in need of treatment according to the methods provided herein has one or more of point mutations selected from G11778A in the ND4 gene, G3460A in the ND1 gene, and T14484C in the ND6 gene and is of Argentinean descent. In some embodiments, the patient in need of treatment according to the methods provided herein has one or more of point mutations selected from G11778A in the ND4 gene, G3460A in the ND1 gene, and T14484C in the ND6 gene and is of Chinese descent. In particular embodiments, the patient in need of treatment according to the methods provided herein has one or more of point mutations selected from G11778A in the ND4 gene and is of Chinese descent.

In a related aspect, the invention provides for use of a vector of the invention in a method of treating or preventing LHON by administering said vector to a patient by direct retinal, subretinal or intravitreal injection. Additionally, the invention provides the use of a vector of the invention in the manufacture of a medicament for treating or preventing LHON by direct retinal, subretinal or intravitreal injection.

In all these embodiments, the vector of the invention may be administered in order to prevent the onset of one or more symptoms of LHON. The patient may be asymptomatic. The subject may have a predisposition to the disease. The method or use may comprise a step of identifying whether or not a subject is at risk of developing, or has, LHON. A prophylactically effective amount of the vector is administered to such a subject. A prophylactically effective amount is an amount which prevents the onset of one or more symptoms of the disease.

Alternatively, the vector may be administered once the symptoms of the disease have appeared in a subject i.e. to cure existing symptoms of the disease. A therapeutically effective amount of the antagonist is administered to such a subject. A therapeutically effective amount is an amount which is effective to ameliorate one or more symptoms of the disease. Such an amount may also arrest, slow or reverse some loss of peripheral vision associated with LHON. Such an amount may also arrest, slow or reverse onset of LHON.

A typical single dose is between $10^{10}$ and $10^{12}$ genome particles, depending on the amount of remaining retinal tissue that requires transduction. A genome particle is defined herein as an AAV capsid that contains a single stranded DNA molecule that can be quantified with a sequence specific method (such as real-time PCR). That dose may be provided as a single dose, but may be repeated for the fellow eye or in cases where vector may not have targeted the correct region of retina for whatever reason (such as surgical complication). The treatment is preferably a single permanent treatment for each eye, but repeat injections, for example in future years and/or with different AAV serotypes may be considered.

The invention also provides a method of monitoring treatment or prevention of LHON in a patient comprising measuring activity ex vivo in retinal cells obtained from said patient following administration of the AAV vector of the invention by direct retinal, subretinal or intravitreal injection. This method can allow for determination of the efficacy of treatment.

In some embodiments, the present disclosure provides a method of treating an eye disorder (e.g., LHON) comprising administering a therapeutically effective amount of a vector described herein and a steroid. Exemplary steroids include, but are not limited to, alclometasone diproprionate, amcinonide, beclomethasone diproprionate, betamethasone, betamethasone benzoate, betamethasone diproprionate, betamethasone sodium phosphate, betamethasone sodium phosphate and acetate, betamethasone valerate, clobetasol proprionate, clocortolone pivalate, cortisol (hydrocortisone), cortisol (hydrocortisone) acetate, cortisol (hydrocortisone) butyrate, cortisol (hydrocortisone) cypionate, cortisol (hydrocortisone) sodium phosphate, cortisol (hydrocortisone) sodium succinate, cortisol (hydrocortisone) valerate, cortisone acetate, desonide, desoximetasone, dexamethasone, dexamethasone acetate, dexamethasone sodium phosphate, diflorasone diacetate, fludrocortisone acetate, flunisolide, fluocinolone acetonide, fluocinonide, fluorometholone, flurandrenolide, halcinonide, medrysone, methylprednisolone, methylprednisolone acetate, methylprednisolone sodium succinate, mometasone furoate, paramethasone acetate, prednisolone, prednisolone acetate, prednisolone sodium phosphate, prednisolone tebutate, prednisone, triamcinolone, triamcinolone acetonide, triamcinolone diacetate, and triamcinolone hexacetonide or a synthetic analog thereof, or a combination thereof. In some embodiments, the steroid is a glucocorticoid. In some embodiments, the steroid is selected from prednisone, methylprednisolone, and methylprednisolone sodium succinate.

In some embodiments, the steroid is methylprednisolone. In some embodiments, the methylprednisolone is formulated as a tablet for oral administration, e.g., MEDROL® tablets. For example, in some embodiments, the methylprednisolone is formulated as a tablet with one or more inactive ingredients such as calcium sterate, corn starch, erythrosine sodium, lactose, mineral oil, sorbic acid, sucrose, or FD&C Yellow No. 6. In some embodiments, the methylprednisolone is formulated is a liquid for administration by injection, e.g., SOLU-MEDROL®. For example, in some embodiments, methylprednisolone sodium succinate is formulated as a liquid with one or more inactive ingredients such as monobasic sodium phosphate anhydrous, dried dibasic sodium phosphate, or lactose hydrous, optionally formulated with a preservative such as benzyl alcohol. In some embodiments, the steroid is MEDROL® or SOLU-MEDROL®, including generic versions thereof.

In some embodiments, the patient receives one or more steroid doses of between about 1 mg/60 kg to about 100 mg/60 kg, about 1 mg/60 kg to about 80 mg/60 kg, about 1 mg/60 kg to about 60 mg/60 kg, about 1 mg/60 kg to about 40 mg/60 kg, about 1 mg/60 kg to about 20 mg/60 kg, about 20 mg/60 kg to about 100 mg/60 kg, about 20 mg/60 kg to about 80 mg/60 kg, about 20 mg/60 kg to about 60 mg/60 kg, about 20 mg/60 kg to about 40 mg/60 kg, about 40 mg/60 kg to about 100 mg/60 kg, about 40 mg/60 kg to about 80 mg/60 kg, about 40 mg/60 kg to about 60 mg/60 kg, about 60 mg/60 kg to about 100 mg/60 kg, about 60 mg/60 kg to about 80 mg/60 kg, or about 80 mg/60 kg to about 100 mg/60 kg. In some embodiments, the patient receives one or more steroid doses of about 4 mg/60 kg, 6 mg/60 kg, 8 mg/60 kg, 10 mg/60 kg, 16 mg/60 kg, 20 mg/60 kg, 24 mg/60 kg, 32 mg/60 kg, 40 mg/60 kg, 48 mg/60 kg, 60 mg/60 kg, or 80 mg/60 kg. In some embodiments, the patient receives one or more steroid doses of about 1 mg to about 96 mg. In some embodiments, the patient receives one or more steroid doses of at least about 1 mg. In some embodiments, the patient receives one or more steroid doses of at most about 96 mg. In some embodiments, the patient receives one or more steroid doses of about 1 mg to about 2 mg, about 1 mg to about 4 mg, about 1 mg to about 8 mg, about 1 mg to about 16 mg, about 1 mg to about 32 mg, about 1 mg to about 64 mg, about 1 mg to about 96 mg, about 2 mg to about 4 mg, about 2 mg to about 8 mg, about 2 mg to about 16 mg, about 2 mg to about 32 mg, about 2 mg to about 64 mg, about 2 mg to about 96 mg, about 4 mg to about 8 mg, about 4 mg to about 16 mg, about 4 mg to about 32 mg, about 4 mg to about 64 mg, about 4 mg to about 96 mg, about 8 mg to about 16 mg, about 8 mg to about 32 mg, about 8 mg to about 64 mg, about 8 mg to about 96 mg, about 16 mg to about 32 mg, about 16 mg to about 64 mg, about 16 mg to about 96 mg, about 32 mg to about 64 mg, about 32 mg to about 96 mg, or about 64 mg to about 96 mg. In some embodiments, the patient receives one or more steroid doses of about 1 mg, about 2 mg, about 4 mg, about 8 mg, about 16 mg, about 32 mg, about 64 mg, or about 96 mg. In some embodiments, the steroid is methylprednisolone (e.g., MEDROL®). In some embodiments, the steroid is prednisone.

In some embodiments, one or more doses of the steroid are administered prior to administration of the therapeutic vector (i.e., one or more pre-operative steroid doses). In some embodiments, a daily dose of a steroid is delivered for at least 1 day, 2 days, 3 days, 4 days, 5 days, 6 days, 7 days, 8 days, 9 days, or at least 10 days before administration of the therapeutic vector. In some embodiments, the patient receives one or more pre-operative steroid doses of about 1 mg/60 kg to about 100 mg/60 kg, about 1 mg/60 kg to about 80 mg/60 kg, about 1 mg/60 kg to about 60 mg/60 kg, about 1 mg/60 kg to about 40 mg/60 kg, about 1 mg/60 kg to about 20 mg/60 kg, about 20 mg/60 kg to about 100 mg/60 kg, about 20 mg/60 kg to about 80 mg/60 kg, about 20 mg/60 kg to about 60 mg/60 kg, about 20 mg/60 kg to about 40 mg/60 kg, about 40 mg/60 kg to about 100 mg/60 kg, about 40 mg/60 kg to about 80 mg/60 kg, about 40 mg/60 kg to about 60 mg/60 kg, about 60 mg/60 kg to about 100 mg/60 kg, about 60 mg/60 kg to about 80 mg/60 kg, or about 80 mg/60 kg to about 100 mg/60 kg. In some embodiments, the patient receives one or more pre-operative steroid doses of about 4 mg/60 kg, 6 mg/60 kg, 8 mg/60 kg, 10 mg/60 kg, 16 mg/60 kg, 20 mg/60 kg, 24 mg/60 kg, 32 mg/60 kg, 40 mg/60 kg, 48 mg/60 kg, 60 mg/60 kg, or 80 mg/60 kg. In some embodiments, the patient receives one or more pre-operative steroid doses of about 1 mg to about 96 mg. In some embodiments, the patient receives one or more pre-operative steroid doses of at least about 1 mg. In some embodiments, the patient receives one or more pre-operative steroid doses of at most about 96 mg. In some embodiments, the patient receives one or more pre-operative steroid doses of about 1 mg to about 2 mg, about 1 mg to about 4 mg, about 1 mg to about 8 mg, about 1 mg to about 16 mg, about 1 mg to about 32 mg, about 1 mg to about 64 mg, about 1 mg to about 96 mg, about 2 mg to about 4 mg, about 2 mg to about 8 mg, about 2 mg to about 16 mg, about 2 mg to about 32 mg, about 2 mg to about 64 mg, about 2 mg to about 96 mg, about 4 mg to about 8 mg, about 4 mg to about 16 mg, about 4 mg to about 32 mg, about 4 mg to about 64 mg, about 4 mg to about 96 mg, about 8 mg to about 16 mg, about 8 mg to about 32 mg, about 8 mg to about 64 mg, about 8 mg to about 96 mg, about 16 mg to about 32 mg, about 16 mg to about 64 mg, about 16 mg to about 96 mg, about 32 mg to about 64 mg, about 32 mg to about 96 mg, or about 64 mg to about 96 mg. In some embodiments, the patient receives one or more pre-operative steroid doses of about 1 mg, about 2 mg, about 4 mg, about 8 mg, about 16 mg, about 32 mg, about 64 mg, or about 96 mg. In some embodiments, the steroid is methylprednisolone (e.g., MEDROL®). In some embodiments, the steroid is prednisone.

In some embodiments, the patient receives one or more pre-operative steroid doses of between about 20 mg/60 kg to about 45 mg/60 kg, about 25 mg/60 kg to about 45 mg/60 kg, about 30 mg/60 kg to about 45 mg/60 kg, about 35 mg/60 kg to about 45 mg/60 kg, about 40 mg/60 kg to about 45 mg/60 kg, about 20 mg/60 kg to about 40 mg/60 kg, about 25 mg/60 kg to about 40 mg/60 kg, about 30 mg/60 kg to about 40 mg/60 kg, about 35 mg/60 kg to about 40 mg/60 kg, about 20 mg/60 kg to about 35 mg/60 kg, about 25 mg/60 kg to about 35 mg/60 kg, about 30 mg/60 kg to about 35 mg/60 kg, about 20 mg/60 kg to about 30 mg/60 kg, about 25 mg/60 kg to about 30 mg/60 kg, or about 20 mg/60 kg to about 25 mg/60 kg. In some embodiments, the patient receives one or more pre-operative steroid doses of about 25 mg/60 kg, about 26 mg/60 kg, about 27 mg/60 kg, about 28 mg/60 kg, about 29 mg/60 kg, about 30 mg/60 kg, about 31 mg/60 kg, about 32 mg/60 kg, about 33 mg/60 kg, about 34 mg/60 kg, or about 35 mg/60 kg. In some embodiments, the steroid is methylprednisolone (e.g., MEDROL®). In some embodiments, a daily dose of methylprednisolone (e.g., MEDROL®) between about 25 mg/60 kg and about 45 mg/60 kg is delivered for at least 1 day, 2 days, 3 days, 4 days, 5 days, 6 days, 7 days, 8 days, 9 days, or at least 10 days before administration of the therapeutic vector. In some embodiments, a daily dose of methylprednisolone (e.g., MEDROL®) of about 32 mg/60 kg is delivered for at least 1 day, 2 days, 3 days, 4 days, 5 days, 6 days, 7 days, 8 days, 9 days, or at least 10 days before administration of the therapeutic vector.

In some embodiments, the patient receives one or more pre-operative steroid doses of between about 50 mg/60 kg to about 70 mg/60 kg, about 55 mg/60 kg to about 70 mg/60 kg, about 60 mg/60 kg to about 70 mg/60 kg, about 65 mg/60 kg to about 70 mg/60 kg, about 50 mg/60 kg to about 65 mg/60 kg, about 55 mg/60 kg to about 65 mg/60 kg, about 60 mg/60 kg to about 65 mg/60 kg, about 50 mg/60 kg to about 60 mg/60 kg, about 55 mg/60 kg to about 60 mg/60 kg, or about 50 mg/60 kg to about 55 mg/60 kg. In some embodiments, the patient receives one or more pre-operative doses of about 55 mg/60 kg, about 56 mg/60 kg, about 57 mg/60 kg, about 58 mg/60 kg, about 59 mg/60 kg, about 60 mg/k, about 61 mg/60 kg, about 62 mg/60 kg, about 63 mg/60 kg, about 64 mg/60 kg, or about 65 mg/60 kg. In some embodiments, the steroid is prednisone. In some embodiments, a daily dose of prednisone between about 50 mg/60 kg and about 70 mg/60 kg is delivered for at least 1 day, 2 days, 3 days, 4 days, 5 days, 6 days, 7 days, 8 days, 9 days, or at least 10 days before administration of the therapeutic vector. In some embodiments, a daily dose of prednisone of about 60 mg/60 kg is delivered for at least 1 day, 2 days, 3 days, 4 days, 5 days, 6 days, 7 days, 8 days, 9 days, or at least 10 days before administration of the therapeutic vector.

In some embodiments, one or more doses of the steroid are administered after the administration of the therapeutic vector (i.e., one or more post-operative steroid doses). In some embodiments, a daily dose of a steroid is delivered for at least 1 day, 2 days, 3 days, 4 days, 5 days, 6 days, 7 days, 8 days, 9 days, or at least 10 days after administration of the therapeutic vector. In some embodiments, a daily dose of a steroid is delivered for at least 1 week, 2 weeks, 3 weeks, 4 weeks, 5 days, 6 weeks, 7 weeks, 8 weeks, 9 weeks, 10 weeks, 11 weeks, 12 weeks, 13 weeks, 14 weeks, or at least 15 weeks after administration of the therapeutic vector. In some embodiments, the patient receives one or more post-operative steroid doses of about 1 mg/60 kg to about 100 mg/60 kg, about 1 mg/60 kg to about 80 mg/60 kg, about 1 mg/60 kg to about 60 mg/60 kg, about 1 mg/60 kg to about 40 mg/60 kg, about 1 mg/60 kg to about 20 mg/60 kg, about 20 mg/60 kg to about 100 mg/60 kg, about 20 mg/60 kg to about 80 mg/60 kg, about 20 mg/60 kg to about 60 mg/60 kg, about 20 mg/60 kg to about 40 mg/60 kg, about 40 mg/60 kg to about 100 mg/60 kg, about 40 mg/60 kg to about 80 mg/60 kg, about 40 mg/60 kg to about 60 mg/60 kg, about 60 mg to about 100 mg/60 kg, about 60 mg/60 kg to about 80 mg/60 kg and about 80 mg/60 kg to about 100 mg/60 kg. In some embodiments, the patient receives one or more post-operative steroid doses of about 1 mg to about 96 mg. In some embodiments, the patient receives one or more post-operative steroid doses of at least about 1 mg. In some embodiments, the patient receives one or more post-operative steroid doses of at most about 96 mg. In some embodiments, the patient receives one or more post-operative steroid doses of about 1 mg to about 2 mg, about 1 mg to about 4 mg, about 1 mg to about 8 mg, about 1 mg to about 16 mg, about 1 mg to about 32 mg, about 1 mg to about 64 mg, about 1 mg to about 96 mg, about 2 mg to about 4 mg, about 2 mg to about 8 mg, about 2 mg to about 16 mg, about 2 mg to about 32 mg, about 2 mg to about 64 mg, about 2 mg to about 96 mg, about 4 mg to about 8 mg, about 4 mg to about 16 mg, about 4 mg to about 32 mg, about 4 mg to about 64 mg, about 4 mg to about 96 mg, about 8 mg to about 16 mg, about 8 mg to about 32 mg, about 8 mg to about 64 mg, about 8 mg to about 96 mg, about 16 mg to about 32 mg, about 16 mg to about 64 mg, about 16 mg to about 96 mg, about 32 mg to about 64 mg, about 32 mg to about 96 mg, or about 64 mg to about 96 mg. In some embodiments, the patient receives one or more post-operative steroid doses of about 1 mg, about 2 mg, about 4 mg, about 8 mg, about 16 mg, about 32 mg, about 64 mg, or about 96 mg. In some embodiments, the steroid is methylprednisolone (e.g., MEDROL®). In some embodiments, the steroid is prednisone.

In some embodiments, the patient receives one or more post-operative steroid doses of about 70 mg/60 kg to about 90 mg/60 kg, 75 mg/60 kg to about 90 mg/60 kg, about 80 mg/60 kg to about 90 mg/60 kg, about 85 mg/60 kg to about 90 mg/60 kg, about 70 mg/60 kg to about 85 mg/60 kg, about 75 mg/60 kg to about 85 mg/60 kg, about 80 mg/60 kg to about 85 mg/60 kg, about 70 mg/60 kg to about 80 mg/60 kg, about 75 mg/60 kg to about 80 mg/60 kg, or about 70 mg/60 kg to about 75 mg/60 kg. In some embodiments, the patient receives one or more post-operative steroid doses of about 75 mg/60 kg, about 76 mg/60 kg, about 77 mg/60 kg, about 78 mg/60 kg, about 79 mg/60 kg, about 80 mg/60 kg, about 81 mg/60 kg, about 82 mg/60 kg, about 83 mg/60 kg, about 84 mg/60 kg, or about 85 mg/60 kg. In some embodiments, the steroid is methylprednisolone sodium succinate (e.g., SOLU-MEDROL®). In some embodiments, a daily dose of methylprednisolone sodium succinate (e.g., SOLU-MEDROL®) between about 70 mg and about 90 mg/60 kg is delivered for at least 1 day, 2 days, 3 days, 4 days, 5 days, 6 days, 7 days, 8 days, 9 days, or at least 10 days after administration of the therapeutic vector. In some embodiments, a daily dose of methylprednisolone sodium succinate (e.g., SOLU-MEDROL®) of about 80 mg/60 kg is delivered for at least 1 day, 2 days, 3 days, 4 days, 5 days, 6 days, 7 days, 8 days, 9 days, or at least 10 days after administration of the therapeutic vector.

In some embodiments, the patient receives one or more post-operative steroid doses of about 30 mg/60 kg to about 50 mg/60 kg, 35 mg/60 kg to about 50 mg/60 kg, about 40 mg/60 kg to about 50 mg/60 kg, about 45 mg/60 kg to about 50 mg/60 kg, about 30 mg/60 kg to about 45 mg/60 kg, about 35 mg/60 kg to about 45 mg/60 kg, about 40 mg/60 kg to about 45 mg/60 kg, about 30 mg/60 kg to about 40 mg/60 kg, about 35 mg/60 kg to about 40 mg/60 kg, or about 30 mg/60 kg to about 35 mg/60 kg. In some embodiments, the patient receives one or more post-operative steroid doses of about 35 mg/60 kg, about 36 mg/60 kg, about 37 mg/60 kg, about 38 mg/60 kg, about 39 mg/60 kg, about 40 mg/60 kg, about 41 mg/60 kg, about 42 mg/60 kg, about 43 mg/60 kg, about 44 mg/60 kg, or about 45 mg/60 kg. In some embodiments, the steroid is methylprednisolone (e.g., MEDROL®). In some embodiments, a daily dose of methylprednisolone (e.g., MEDROL®) between about 30 mg/60 kg and about 50 mg/60 kg is delivered for at least 1 day, 2 days, 3 days, 4 days, 5 days, 6 days, 7 days, 8 days, 9 days, or at least 10 days after administration of the therapeutic vector. In some embodiments, a daily dose of methylprednisolone (e.g., MEDROL®) of about 40 mg/60 kg is delivered for at least 1 day, 2 days, 3 days, 4 days, 5 days, 6 days, 7 days, 8 days, 9 days, or at least 10 days after administration of the therapeutic vector.

In some embodiments, the patient receives one or more post-operative steroid doses of about 20 mg/60 kg to about 45 mg/60 kg, 25 mg/60 kg to about 45 mg/60 kg, about 30 mg/60 kg to about 45 mg/60 kg, about 35 mg/60 kg to about 45 mg/60 kg, about 40 mg/60 kg to about 45 mg/60 kg, about 20 mg/60 kg to about 40 mg/60 kg, about 25 mg/60 kg to about 40 mg/60 kg, about 30 mg/60 kg to about 40 mg/60 kg, about 35 mg/60 kg to about 40 mg/60 kg, about 20 mg/60 kg to about 35 mg/60 kg, about 25 mg/60 kg to about 35 mg/60 kg, about 30 mg/60 kg to about 35 mg/60 kg, about 20 mg/60 kg to about 30 mg/60 kg, about 25 mg/60 kg to about 30 mg/60 kg, or about 20 mg/60 kg to about 25 mg/60 kg. In some embodiments, the patient receives one or more post-operative steroid doses of about 25 mg/60 kg, about 26 mg/60 kg, about 27 mg/60 kg, about 28 mg/60 kg, about 29 mg/60 k, about 30 mg/60 kg, about 31 mg/60 kg, about 32 mg/60 kg, about 33 mg/60 kg, about 34 mg/60 kg, or about 35 mg/60 kg. In some embodiments, the steroid is methylprednisolone (e.g., MEDROL®). In some embodiments, a daily dose of methylprednisolone (e.g., MEDROL®) between about 20 mg/60 kg and about 45 mg/60 kg is delivered for at least 1 day, 2 days, 3 days, 4 days, 5 days, 6 days, 7 days, 8 days, 9 days, or at least 10 days after administration of the therapeutic vector. In some embodiments, a daily dose of methylprednisolone (e.g., MEDROL®) of about 32 mg/60 kg is delivered for at least 1 day, 2 days, 3 days, 4 days, 5 days, 6 days, 7 days, 8 days, 9 days, or at least 10 days after administration of the therapeutic vector.

In some embodiments, the patient receives one or more post-operative steroid doses of about 15 mg/60 kg to about 35 mg/60 kg, 20 mg/60 kg to about 35 mg/60 kg, about 25 mg/60 kg to about 35 mg/60 kg, about 30 mg/60 kg to about 35 mg/60 kg, about 15 mg/60 kg to about 30 mg/60 kg, about 20 mg/60 kg to about 30 mg/60 kg, about 25 mg/60 kg to about 30 mg/60 kg, about 15 mg/60 kg to about 25 mg/60 kg, about 20 mg/60 kg to about 25 mg/60 kg, about 15 mg/60 kg to about 20 mg/60 kg. In some embodiments, the patient receives one or more post-operative steroid doses of about 20 mg/60 kg, about 21 mg/60 kg, about 22 mg/60 kg, about 23 mg/60 kg, about 24 mg/60 kg, about 25 mg/60 kg, about 26 mg/60 kg, about 27 mg/60 kg, about 28 mg/60 kg, about 29 mg/60 kg, or about 30 mg/60 kg. In some embodiments, the steroid is methylprednisolone (e.g., MEDROL®). In some embodiments, a daily dose of methylprednisolone (e.g., MEDROL®) between about 15 mg/60 kg and about 35 mg/60 kg is delivered for at least 1 day, 2 days, 3 days, 4 days, 5 days, 6 days, 7 days, 8 days, 9 days, or at least 10 days after administration of the therapeutic vector. In some embodiments, a daily dose of methylprednisolone (e.g., MEDROL®) of about 24 mg/60 kg is delivered for at least 1 day, 2 days, 3 days, 4 days, 5 days, 6 days, 7 days, 8 days, 9 days, or at least 10 days after administration of the therapeutic vector.

In some embodiments, the patient receives one or more post-operative steroid doses of about 5 mg/60 kg to about 25 mg/60 kg, 10 mg/60 kg to about 25 mg/60 kg, about 15 mg/60 kg to about 25 mg/60 kg, about 20 mg/60 kg to about 25 mg/60 kg, about 5 mg/60 kg to about 20 mg/60 kg, about 10 mg/60 kg to about 20 mg/60 kg, about 15 mg/60 kg to about 20 mg/60 kg, about 5 mg/60 kg to about 15 mg/60 kg, about 10 mg/60 kg to about 15 mg/60 kg, or about 5 mg/60 kg to about 10 mg/60 kg. In some embodiments, the patient receives one or more post-operative steroid doses of about 10 mg/60 kg, about 11 mg/60 kg, about 12 mg/60 kg, about 13 mg/60 kg, about 14 mg/60 kg, about 15 mg/60 kg, about 16 mg/60 kg, about 17 mg/60 kg, about 18 mg/60 kg, about 19 mg/60 kg, or about 20 mg/60 kg. In some embodiments, the steroid is methylprednisolone (e.g., MEDROL®). In some embodiments, a daily dose of methylprednisolone (e.g., MEDROL®) between about 5 mg/60 kg and about 25 mg/60 kg is delivered for at least 1 day, 2 days, 3 days, 4 days, 5 days, 6 days, 7 days, 8 days, 9 days, or at least 10 days after administration of the therapeutic vector. In some embodiments, a daily dose of methylprednisolone (e.g., MEDROL®) of about 16 mg/60 kg is delivered for at least 1 day, 2 days, 3 days, 4 days, 5 days, 6 days, 7 days, 8 days, 9 days, or at least 10 days after administration of the therapeutic vector.

In some embodiments, the patient receives one or more post-operative steroid doses of about 1 mg/60 kg to about 20 mg/60 kg, 5 mg/60 kg to about 20 mg/60 kg, about 10 mg/60 kg to about 20 mg/60 kg, about 15 mg/60 kg to about 20 mg/60 kg, about 1 mg/60 kg to about 15 mg/60 kg, about 5 mg/60 kg to about 15 mg/60 kg, about 10 mg/60 kg to about 15 mg/60 kg, about 1 mg/60 kg to about 10 mg/60 kg, about 5 mg/60 kg to about 10 mg/60 kg, or about 1 mg/60 kg to about 5 mg/60 kg. In some embodiments, the patient receives one or more post-operative steroid doses of about 1 mg/60 kg, about 2 mg/60 kg, about 3 mg/60 kg, about 4 mg/60 kg, about 5 mg/60 kg, about 6 mg/60 kg, about 7 mg/60 kg, about 8 mg/60 kg, about 9 mg/60 kg, about 10 mg/60 kg, about 11 mg/60 kg, about 12 mg/60 kg, about 13 mg/60 kg, about 14 mg/60 kg, or about 15 mg/60 kg. In some embodiments, the steroid is methylprednisolone (e.g., MEDROL®). In some embodiments, a daily dose of methylprednisolone (e.g., MEDROL®) between about 1 mg/60 kg and about 20 mg/60 kg is delivered for at least 1 day, 2 days, 3 days, 4 days, 5 days, 6 days, 7 days, 8 days, 9 days, or at least 10 days after administration of the therapeutic vector. In some embodiments, a daily dose of methylprednisolone (e.g., MEDROL®) of about 8 mg/60 kg is delivered for at least 1 day, 2 days, 3 days, 4 days, 5 days, 6 days, 7 days, 8 days, 9 days, or at least 10 days after administration of the therapeutic vector. In some embodiments, a daily dose of methylprednisolone (e.g., MEDROL®) of about 6 mg/60 kg is delivered for at least 1 day, 2 days, 3 days, 4 days, 5 days, 6 days, 7 days, 8 days, 9 days, or at least 10 days after administration of the therapeutic vector. In some embodiments, a daily dose of methylprednisolone (e.g., MEDROL®) of about 4 mg/60 kg is delivered for at least 1 day, 2 days, 3 days, 4 days, 5 days, 6 days, 7 days, 8 days, 9 days, or at least 10 days after administration of the therapeutic vector.

In some embodiments, the patient receives one or more post-operative steroid doses of about 30 mg/60 kg to about 50 mg/60 kg, 35 mg/60 kg to about 50 mg/60 kg, about 40 mg/60 kg to about 50 mg/60 kg, about 45 mg/60 kg to about 50 mg/60 kg, about 30 mg/60 kg to about 45 mg/60 kg, about 35 mg/60 kg to about 45 mg/60 kg, about 40 mg/60 kg to about 45 mg/60 kg, about 30 mg/60 kg to about 40 mg/60 kg, about 35 mg/60 kg to about 40 mg/60 kg, or about 30 mg/60 kg to about 35 mg/60 kg. In some embodiments, the patient receives one or more post-operative steroid doses of about 35 mg/60 kg, about 36 mg/60 kg, about 37 mg/60 kg, about 38 mg/60 kg, about 39 mg/60 kg, about 40 mg/60 kg, about 41 mg/60 kg, about 42 mg/60 kg, about 43 mg/60 kg, about 44 mg/60 kg, or about 45 mg/60 kg. In some embodiments, the steroid is prednisone. In some embodiments, a daily dose of prednisone between about 30 mg/60 kg and about 50 mg/60 kg is delivered for at least 1 day, 2 days, 3 days, 4 days, 5 days, 6 days, 7 days, 8 days, 9 days, or at least 10 days after administration of the therapeutic vector. In some embodiments, a daily dose of prednisone of about 40 mg/60 kg is delivered for at least 1 day, 2 days, 3 days, 4 days, 5 days, 6 days, 7 days, 8 days, 9 days, or at least 10 days after administration of the therapeutic vector.

In some embodiments, the patient receives one or more post-operative steroid doses of about 10 mg/60 kg to about 30 mg/60 kg, 15 mg/60 kg to about 30 mg/60 kg, about 20 mg/60 kg to about 30 mg/60 kg, about 25 mg/60 kg to about 30 mg/60 kg, about 10 mg/60 kg to about 25 mg/60 kg, about 15 mg/60 kg to about 25 mg/60 kg, about 20 mg/60 kg to about 25 mg/60 kg, about 10 mg/60 kg to about 20 mg/60 kg, about 15 mg/60 kg to about 20 mg/60 kg, or about 10 mg/60 kg to about 15 mg/60 kg. In some embodiments, the patient receives one or more post-operative steroid doses of about 15 mg/60 kg, about 16 mg/60 kg, about 17 mg/60 kg, about 18 mg/60 kg, about 19 mg/60 kg, about 20 mg/60 kg, about 21 mg/60 kg, about 22 mg/60 kg, about 23 mg/60 kg, about 24 mg/60 kg, or about 25 mg/60 kg. In some embodiments, the steroid is prednisone. In some embodiments, a daily dose of prednisone between about 10 mg/60 kg and about 30 mg/60 kg is delivered for at least 1 day, 2 days, 3 days, 4 days, 5 days, 6 days, 7 days, 8 days, 9 days, or at least 10 days after administration of the therapeutic vector. In some embodiments, a daily dose of prednisone of about 20 mg/60 kg is delivered for at least 1 day, 2 days, 3 days, 4 days, 5 days, 6 days, 7 days, 8 days, 9 days, or at least 10 days after administration of the therapeutic vector.

In some embodiments, the patient receives one or more post-operative steroid doses of about 1 mg/60 kg to about 20 mg/60 kg, 5 mg/60 kg to about 20 mg/60 kg, about 10 mg/60 kg to about 20 mg/60 kg, about 15 mg/60 kg to about 20 mg/60 kg, about 1 mg/60 kg to about 15 mg/60 kg, about 5 mg/60 kg to about 15 mg/60 kg, about 10 mg/60 kg to about 15 mg/60 kg, about 1 mg/60 kg to about 10 mg/60 kg, about 5 mg/60 kg to about 10 mg/60 kg, or about 1 mg/60 kg to about 5 mg/60 kg. In some embodiments, the patient receives one or more post-operative steroid doses of about 1 mg/60 kg, about 2 mg/60 kg, about 3 mg/60 kg, about 4 mg/60 kg, about 5 mg/60 kg, about 6 mg/60 kg, about 7 mg/60 kg, about 8 mg/60 kg, about 9 mg/60 kg, about 10 mg/60 kg, about 11 mg/60 kg, about 12 mg/60 kg, about 13 mg/60 kg, about 14 mg/60 kg, or about 15 mg/60 kg. In some embodiments, the steroid is prednisone. In some embodiments, a daily dose of prednisone between about 1 mg/60 kg and about 20 mg/60 kg is delivered for at least 1 day, 2 days, 3 days, 4 days, 5 days, 6 days, 7 days, 8 days, 9 days, or at least 10 days after administration of the therapeutic vector. In some embodiments, a daily dose of prednisone of about 10 mg/60 kg is delivered for at least 1 day, 2 days, 3 days, 4 days, 5 days, 6 days, 7 days, 8 days, 9 days, or at least 10 days after administration of the therapeutic vector.

In some embodiments, the patient receives one or more post-operative steroid doses of about 1 g/60 kg to about 15 g/60 kg, about 5 g/60 kg to about 15 g/60 kg, about 10 g/60 kg to about 15 g/60 kg, about 1 g/60 kg to about 10 g/60 kg, about 5 g/60 kg to about 10 g/60 kg, or about 1 g/60 kg to about 5 g/60 kg. In some embodiments, the patient receives one or more post-operative steroid doses of about 1 g/60 kg, about 2 g/60 kg, about 3 g/60 kg, about 4 g/60 kg, about 5 g/60 kg, about 6 g/60 kg, about 7 g/60 kg, about 8 g/60 kg, about 9 g/60 kg, about 10 g/60 kg, about 11 g/60 kg, about 12 g/60 kg, about 13 g/60 kg, about 14 g/60 kg, or about 15 g/60 kg. In some embodiments, the steroid is sodium creatine phosphate. In some embodiments, a daily dose of sodium creatine phosphate between about 1 g/60 kg and about 15 g/60 kg is delivered for at least 1 day, 2 days, 3 days, 4 days, 5 days, 6 days, 7 days, 8 days, 9 days, or at least 10 days after administration of the therapeutic vector. In some embodiments, a daily dose of sodium creatine phosphate of about 2 g/60 kg is delivered for at least 1 day, 2 days, 3 days, 4 days, 5 days, 6 days, 7 days, 8 days, 9 days, or at least 10 days after administration of the therapeutic vector.

In some embodiments, the patient receives an intravenous dose of sodium creatine phosphate (2 g/60 kg) and an intravenous dose of methylprednisolone sodium succinate (e.g., SOL-MEDROL®, 80 mg/60 kg) on the same day as administration of the therapeutic AAV vector and daily for 3 days following administration of the therapeutic AAV vector. On day 3 following administration of the therapeutic AAV vector, the patient is administered methylprednisolone (e.g., MEDROL®) tablets at a dose of 40 mg/60 kg for 4 days. On day 7 following administration of the therapeutic AAV vector, the patient is administered methylprednisolone (e.g., MEDROL®) tablets at a dose of 32 mg/60 kg for 7 days. On day 14 following administration of the therapeutic AAV vector, the patient is administered methylprednisolone (e.g., MEDROL®) tablets at a dose of 24 mg/60 kg for 7 days. On day 21 following administration of the therapeutic AAV vector, the patient is administered methylprednisolone (e.g., MEDROL®) tablets at a dose of 16 mg/60 kg for 7 days. On day 28 following administration of the therapeutic AAV vector, the patient is administered methylprednisolone (e.g., MEDROL®) tablets at a dose of 8 mg/60 kg for 7 days. On day 35 following administration of the therapeutic AAV vector, the patient is administered methylprednisolone (e.g., MEDROL®) tablets at a dose of 6 mg/60 kg for 7 days. On day 42 following administration of the therapeutic AAV vector, the patient is administered methylprednisolone (e.g., MEDROL®) tablets at a dose of 4 mg/60 kg for 7 days. See FIG. 19 for a schematic of an exemplary treatment regimen for LHON gene therapy.

In some embodiments, the patient receives methylprednisolone (e.g., MEDROL®) tablets at a dose of 32 mg/60 kg 7 days prior to administration of the therapeutic AAV vector. On the day of administration of the therapeutic AAV vector, the patient receives an intravenous dose of methylprednisolone sodium succinate (e.g., SOL-MEDROL® (80 mg/60 kg), which is administered daily for 3 days. On day 3 following administration of the therapeutic AAV vector, the patient is administered methylprednisolone (e.g., MEDROL®) tablets at a dose of 40 mg/60 kg for 4 days. On day 7 following administration of the therapeutic AAV vector, the patient is administered methylprednisolone (e.g., MEDROL®) tablets at a dose of 32 mg/60 kg for 7 days. On day 14 following administration of the therapeutic AAV vector, the patient is administered methylprednisolone (e.g., MEDROL®) tablets at a dose of 24 mg/60 kg for 7 days. On day 21 following administration of the therapeutic AAV vector, the patient is administered methylprednisolone (e.g., MEDROL®) tablets at a dose of 16 mg/60 kg for 7 days. On day 28 following administration of the therapeutic AAV vector, the patient is administered methylprednisolone (e.g., MEDROL®) tablets at a dose of 8 mg/60 kg for 7 days. On day 35 following administration of the therapeutic AAV vector, the patient is administered methylprednisolone (e.g., MEDROL®) tablets at a dose of 6 mg/60 kg for 7 days. On day 42 following administration of the therapeutic AAV vector, the patient is administered methylprednisolone (e.g., MEDROL®) tablets at a dose of 4 mg/60 kg for 7 days. See FIG. 19 for an exemplary schematic of the treatment regimen for LHON gene therapy.

In some embodiments, the patient receives prednisone tablets at a dose of 60 mg/60 kg prior to administration of the therapeutic AAV vector and daily for 7 days following administration of the therapeutic AAV vector. On day 8 following administration of the therapeutic AAV vector, the patient is administered prednisone tablets at a dose of 40 mg/kg for one day. On day 9 following administration of the therapeutic AAV vector, the patient is administered prednisone tablets at a dose of 20 mg/kg for one day. On day 10 following administration of the therapeutic AAV vector, the patient is administered prednisone tablets at a dose of 10 mg/kg for one day. See FIG. 20 for an exemplary schematic of the treatment regimen for LHON gene therapy.

Dosage amount and interval can be adjusted individually to be sufficient to maintain therapeutic effect. Skilled artisans will be able to optimize effective local dosages without undue experimentation.

In some embodiments, administration of a steroid prior to, during, and/or after administration of the therapeutic AAV vector described herein results in a higher average recovery of vision than is achieved with administration of a comparable therapeutic AAV vector without the steroid, for example, in a population of at least 10 patients. In some embodiments, administration of a steroid prior to, during, and/or after administration of the therapeutic AAV vector results in a lower incidence of an adverse event than is achieved with administration of a comparable therapeutic AAV vector without the steroid, for example, in a population of at least 10 patients. In some embodiments, the adverse event is selected from anterior chamber inflammation, vitritis, ocular hypertension, cataract removal, keratitis, vitreous hemorrhage, allergic conjunctivitis, and eye pain (See e.g., Example 15).

In some embodiments, the higher average recovery of vision and the lower incidence of an adverse event achieved according to the present methods are determined by comparison to a population of patients with the eye disorder treated with a therapeutic AAV vector without administration of a steroid prior to, during, and/or after administration of the therapeutic AAV vector. In some embodiments, the population of patients treated according to the methods of the present disclosure and the population of patients treated with a comparable therapeutic AAV vector are ethnically matched. In some embodiments, the populations of patients are Chinese or Argentinian.

Diagnostic Methods and Kits

In some embodiments, the present disclosure provides methods of screening patients for treatment of an eye disorder. In such embodiments, the methods comprise culturing a population of target cells with a composition comprising an AAV comprising a recombinant nucleic acid sequence encoding a detectable label in the presence of a serum sample obtained from a patient, and detecting the expression level of the detectable label in the target cells after the culturing, wherein the patient is selected for the treatment if the expression level of the detectable label in the target cells is higher than a pre-determined threshold. In some embodiments, the methods further comprise administering to the patient a pharmaceutical composition comprising an AAV comprising a recombinant nucleic acid sequence encoding a mitochondrial protein.

The methods of screening patients for treatment of an eye disorder described herein utilizes patient-derived serum samples to assess the immune response of particular patient against a recombinant viral vector used to deliver a therapeutic protein. Soluble factors present in patient serum, e.g., antibodies, can prevent viral infection of target cells, thereby reducing the delivery of the therapeutic protein and/or reducing the efficacy of the pharmaceutical composition. Methods of the present disclosure utilize an AAV encoding a detectable label, such that the level of infectivity of target cells can be measured by detection of the label. In some embodiments, the present disclosure provides methods for identifying patients that demonstrate low immune reactivity to an AAV composition and selecting those patients for treatment with the therapeutic AAV vectors described herein. In some embodiments, the present disclosure provides methods for identifying patients that demonstrate high immune reactivity to an AAV composition and excluding those patients from future treatment with the therapeutic AAV vectors described herein.

In some embodiments, the expression level of the detectable label in the target cells correlates with the patient's immune response against the AAV vector. For example, serum from a patient demonstrating high immune reactivity to the AAV contains soluble factors preventing the AAV encoding the detectable label from infecting the target cells and preventing expression of the detectable label in the target cells. In such instances, the expression level of the detectable label in target cells cultured in the presence of the patient serum is reduced relative to the expression level of the detectable label in target cells cultured in the absence of the patient serum. Alternatively, serum from a patient demonstrating low immune reactivity to the AAV contains fewer, or an absence of, soluble factors that prevent the AAV encoding the detectable label from infecting the target cells. In such instances, the expression level of the detectable label in target cells cultured in the presence of the patient serum is the same, or is not significantly reduced, relative to the expression level of the detectable label in target cells cultured in the absence of the patient serum.

The detectable label can be any protein or nucleic acid molecule that is not endogenously expressed by the target cell and/or the AAV vector. Examples of detectable labels include but are not limited to, FLAG tags, poly-histidine tags (e.g. 6×His), SNAP tags, Halo tags, cMyc tags, glutathione-S-transferase tags, avidin, enzymes, fluorescent proteins, luminescent proteins, chemiluminescent proteins, bioluminescent proteins, and phosphorescent proteins. In some embodiments the fluorescent protein is selected from the group consisting of blue/UV proteins (such as BFP, TagBFP, mTagBFP2, Azurite, EBFP2, mKalama1, Sirius, Sapphire, and T-Sapphire); cyan proteins (such as CFP, eCFP, Cerulean, SCFP3A, mTurquoise, mTurquoise2, monomeric Midoriishi-Cyan, TagCFP, and mTFP1); green proteins (such as: GFP, eGFP, meGFP (A208K mutation), Emerald, Superfolder GFP, Monomeric Azami Green, TagGFP2, mUKG, mWasabi, Clover, and mNeonGreen); yellow proteins (such as YFP, eYFP, Citrine, Venus, SYFP2, and TagYFP); orange proteins (such as Monomeric Kusabira-Orange, mKOK, mKO2, mOrange, and mOrange2); red proteins (such as RFP, mRaspberry, mCherry, mStrawberry, mTangerine, tdTomato, TagRFP, TagRFP-T, mApple, mRuby, and mRuby2); far-red proteins (such as mPlum, HcRed-Tandem, mKate2, mNeptune, and NirFP); near-infrared proteins (such as TagRFP657, IFP1.4, and iRFP); long stokes shift proteins (such as mKeima Red, LSS-mKate1, LSS-mKate2, and mBeRFP); photoactivatible proteins (such as PA-GFP, PAmCherry1, and PATagRFP); photoconvertible proteins (such as Kaede (green), Kaede (red), KikGR1 (green), KikGR1 (red), PS-CFP2, PS-CFP2, mEos2 (green), mEos2 (red), mEos3.2 (green), mEos3.2 (red), PSmOrange, and PSmOrange); and photoswitchable proteins (such as Dronpa). In some embodiments, the detectable tag can be selected from AmCyan, AsRed, DsRed2, DsRed Express, E2-Crimson, HcRed, ZsGreen, ZsYellow, mCherry, mStrawberry, mOrange, mBanana, mPlum, mRasberry, tdTomato, DsRed Monomer, and/or AcGFP, all of which are available from Clontech. In particular embodiments, the detectable label is GFP.

The detectable label can be detected by means commonly known in the art including, but not limited to, flow cytometry, qPCR, Western blot, ELISA, and immunohistochemistry. In particular embodiments, the detection method is a high throughput detection method such as flow cytometry or qPCR, such that multiple patient samples can be analyzed simultaneously. In some embodiments, the detection method is flow cytometry. In some embodiments, the detection method is qPCR.

In some embodiments, a pre-determined threshold for the expression level of the detectable label is set for the screening of patients for treatment of an eye disorder. In some embodiments, patients that meet or exceed this threshold are selected for treatment with a therapeutic AAV vector described herein. In some embodiments, patients that do not meet this threshold are excluded from future treatment with a therapeutic AAV vector described herein or must undergo an immunosuppression regiment prior to beginning treatment with a therapeutic AAV vector described herein.

In some embodiments, the pre-determined threshold can be expressed as an absolute expression level of the detectable label in a test sample, above which patient is characterized as suitable for gene therapy and/or below which the patient is characterized as not suitable for gene therapy. For example, in some embodiments where the detectable label is detected by qPCR, the pre-determined threshold is an absolute expression level of greater than or equal to 0.2. In such embodiments, a patient is characterized as suitable for gene therapy if the absolute expression level of the detectable label is greater than or equal to 0.2 and characterized as not suitable for gene therapy if the absolute expression level of the detectable label is less than 0.2. In some embodiments, the pre-determined threshold is an absolute expression level of greater than or equal to 0.6. In such embodiments, a patient is characterized as suitable for gene therapy if the absolute expression level of the detectable label is greater than or equal to 0.6 and characterized as not suitable for gene therapy if the absolute expression level of the detectable label is less than 0.6.

In some embodiments, where the detectable label is detected by flow cytometry, the pre-determined threshold is an absolute expression level of greater than or equal to 20% label-positive target cells in the test sample (e.g., % GFP+ cells ≥20%). In such embodiments, a patient is characterized as suitable for gene therapy if the absolute expression level of the detectable label is greater than or equal to 20% label-positive target cells and characterized as not suitable for gene therapy if the absolute expression level of the detectable label is less than 20% label-positive target cells. In some embodiments, the pre-determined threshold is an absolute expression level of greater than or equal to 40% label-positive target cells in the test sample (e.g., % GFP+ cells ≥40%). In such embodiments, a patient is characterized as suitable for gene therapy if the absolute expression level of the detectable label is greater than or equal to 40% label-positive target cells and characterized as not suitable for gene therapy if the absolute expression level of the detectable label is less than 40% label-positive target cells.

In some embodiments, the pre-determined threshold can be expressed as a relative expression level of the detectable label in a test sample (i.e., expression of the detectable label in a test sample relative to a control sample), above which patient is characterized as suitable for gene therapy and/or below which the patient is characterized as not suitable for gene therapy. In some embodiments, where the detectable label is detected by flow cytometry, the pre-determined threshold is a relative expression level of greater than or equal to 40% label-positive target cells in the test sample (e.g., % GFP+ cells ≥40%). In such embodiments, a patient is characterized as suitable for gene therapy if the absolute expression level of the detectable label is greater than or equal to 40% label-positive target cells and characterized as not suitable for gene therapy if the absolute expression level of the detectable label is less than 40% label-positive target cells. In some embodiments, where the detectable label is detected by flow cytometry, the pre-determined threshold is a relative expression level of greater than or equal to 80% label-positive target cells in the test sample (e.g., % GFP+ cells ≥80%). In such embodiments, a patient is characterized as suitable for gene therapy if the absolute expression level of the detectable label is greater than or equal to 80% label-positive target cells and characterized as not suitable for gene therapy if the absolute expression level of the detectable label is less than 80% label-positive target cells In some embodiments, the patients screened for and/or selected for treatment according to the methods described herein have one or more mtDNA point mutations. In some embodiments, the patients have a point mutation in a gene encoding a protein of complex I in the oxidative phosphorylation chain of the mitochondria. For example, patients may have one or more point mutations in the ND4 gene, the ND1 gene, or the ND6 gene. In some embodiments, the patients have a point mutation at nucleotide position 11778 in the ND4 gene. In some embodiments, the point mutation is G11778A in the ND4 gene. In some embodiments, the patients have a point mutation at nucleotide position 3460 in the ND1 gene. In some embodiments, the point mutation is G3460A in the ND1 gene. In some embodiments, the patients have a point mutation at nucleotide position 14484 in the ND6 gene. In some embodiments, the point mutation is T14484C in the ND6 gene. In some embodiments, patients screened for and/or selected for treatment according to the methods described herein have one or more of point mutations selected from G11778A in the ND4 gene, G3460A in the ND1 gene, and T14484C in the ND6 gene and are of Chinese and/or Argentinean descent.

In some embodiments, the patients screened for and/or selected for treatment according to the methods described herein have one or more of point mutations selected from G11778A in the ND4 gene, G3460A in the ND1 gene, and T14484C in the ND6 gene and are of Argentinean descent. In some embodiments, the patients screened for and/or selected for treatment according to the methods described herein have one or more of point mutations selected from G11778A in the ND4 gene, G3460A in the ND1 gene, and T14484C in the ND6 gene and are of Chinese descent. In particular embodiments, the patients screened for and/or selected for treatment according to the methods described herein have one or more of point mutations selected from G11778A in the ND4 gene and is of Chinese descent.

In some embodiments, the present disclosure provides kits for use in screening patients for treatment of an eye disorder and/or use in the election of a patient for treatment of an eye disorder. In such embodiments, the kits comprise AAV comprising a recombinant nucleic acid encoding a detectable label and one or more reagents for detecting the detectable label. In some embodiments, the one or more reagents for detecting the detectable label are selected an antibody that binds to the detectable label and one or more primer oligonucleotides specific for the recombinant nucleic acid encoding the detectable label.

In some embodiments, the kit further comprises one or more reagents for reconstituting and/or diluting the AAV vector and/or detection reagent components. In some embodiments, the kit further comprises one or more additional reagents, such as a buffer for introducing the AAV vector to a cell, a wash buffer, and/or a cell culture media. Components of a kit can be in separate containers or can be combined in a single container.

In addition to above-mentioned components, in some embodiments a kit further comprises instructions for using the components of the kit to practice the methods of the present disclosure. The instructions for practicing the methods are generally recorded on a suitable recording medium. For example, the instructions may be printed on a substrate, such as paper or plastic, etc. As such, the instructions may be present in the kits as a package insert or in the labeling of the container of the kit or components thereof (i.e., associated with the packaging or sub-packaging). In other embodiments, the instructions are present as an electronic storage data file present on a suitable computer readable storage medium, e.g. CD-ROM, diskette, flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Pharmaceutical Compositions

The vector of the invention can be formulated into pharmaceutical compositions. These compositions may comprise, in addition to the vector, a pharmaceutically acceptable excipient, carrier, buffer, stabilizer or other materials well known to those skilled in the art. Such materials should be non-toxic and should not interfere with the efficacy of the active ingredient. The precise nature of the carrier or other material may be determined by the skilled person according to the route of administration, i.e. here direct retinal, subretinal or intravitreal injection.

The pharmaceutical composition is typically in liquid form. Liquid pharmaceutical compositions generally include a liquid carrier such as water, petroleum, animal or vegetable oils, mineral oil or synthetic oil. Physiological saline solution, magnesium chloride, dextrose or other saccharide solution or glycols such as ethylene glycol, propylene glycol or polyethylene glycol may be included. In some cases, a surfactant, such as pluronic acid (PF68) 0.001% may be used.

For injection at the site of affliction, the active ingredient will be in the form of an aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

For delayed release, the vector may be included in a pharmaceutical composition which is formulated for slow release, such as in microcapsules formed from biocompatible polymers or in liposomal carrier systems according to methods known in the art.

Samples

Samples that are suitable for use in the methods described herein can be nucleic acid samples from a subject. A "nucleic acid sample" as used herein can include RNA or DNA, or a combination thereof. In another embodiment, a "polypeptide sample" (e.g., peptides or proteins, or fragments therefrom) can be used to ascertain information that an amino acid change has occurred, which is the result of a genetic variant. Nucleic acids and polypeptides can be extracted from one or more samples including but not limited to, blood, saliva, urine, mucosal scrapings of the lining of the mouth, expectorant, serum, tears, skin, tissue, or hair. A nucleic acid sample can be assayed for nucleic acid information. "Nucleic acid information," as used herein, includes a nucleic acid sequence itself, the presence/absence of genetic variation in the nucleic acid sequence, a physical property which varies depending on the nucleic acid sequence (e.g., Tm), and the amount of the nucleic acid (e.g., number of mRNA copies). A "nucleic acid" means any one of DNA, RNA, DNA including artificial nucleotides, or RNA including artificial nucleotides. As used herein, a "purified nucleic acid" includes cDNAs, fragments of genomic nucleic acids, nucleic acids produced using the polymerase chain reaction (PCR), nucleic acids formed by restriction enzyme treatment of genomic nucleic acids, recombinant nucleic acids, and chemically synthesized nucleic acid molecules. A "recombinant" nucleic acid molecule includes a nucleic acid molecule made by an artificial combination of two otherwise separated segments of sequence, e.g., by chemical synthesis or by the manipulation of isolated segments of nucleic acids by genetic engineering techniques. As used herein, a "polypeptide" includes proteins, fragments of proteins, and peptides, whether isolated from natural sources, produced by recombinant techniques, or chemically synthesized. A polypeptide may have one or more modifications, such as a post-translational modification (e.g., glycosylation, phosphorylation, etc.) or any other modification (e.g., pegylation, etc.). The polypeptide may contain one or more non-naturally-occurring amino acids (e.g., such as an amino acid with a side chain modification).

In some embodiments, the nucleic acid sample can comprise cells or tissue, for example, cell lines. Exemplary cell types from which nucleic acids can be obtained using the methods described herein include, but are not limited to, the following: a blood cell such as a B lymphocyte, T lymphocyte, leukocyte, erythrocyte, macrophage, or neutrophil; a muscle cell such as a skeletal cell, smooth muscle cell or cardiac muscle cell; a germ cell, such as a sperm or egg; an epithelial cell; a connective tissue cell, such as an adipocyte, chondrocyte; fibroblast or osteoblast; a neuron; an astrocyte; a stromal cell; an organ specific cell, such as a kidney cell, pancreatic cell, liver cell, or a keratinocyte; a stem cell; or any cell that develops therefrom. A cell from which nucleic acids can be obtained can be a blood cell or a particular type of blood cell including, for example, a hematopoietic stem cell or a cell that arises from a hematopoietic stem cell such as a red blood cell, B lymphocyte, T lymphocyte, natural killer cell, neutrophil, basophil, eosinophil, monocyte, macrophage, or platelet. Generally, any type of stem cell can be used including, without limitation, an embryonic stem cell, adult stem cell, or pluripotent stem cell.

In some embodiments, a nucleic acid sample can be processed for RNA or DNA isolation, for example, RNA or DNA in a cell or tissue sample can be separated from other components of the nucleic acid sample. Cells can be harvested from a nucleic acid sample using standard techniques, for example, by centrifuging a cell sample and resuspending the pelleted cells, for example, in a buffered solution, for example, phosphate-buffered saline (PBS). In some embodiments, after centrifuging the cell suspension to obtain a cell pellet, the cells can be lysed to extract DNA. In some embodiments, the nucleic acid sample can be concentrated and/or purified to isolate DNA. All nucleic acid samples obtained from a subject, including those subjected to any sort of further processing, are considered to be obtained from the subject. In some embodiments, standard techniques and kits known in the art can be used to extract RNA or DNA from a nucleic acid sample, including, for example, phenol extraction, a QIAAMP® Tissue Kit (Qiagen, Chatsworth, Calif.), a WIZARD® Genomic DNA purification kit (Promega), or a Qiagen Autopure method using Puregene chemistry, which can enable purification of highly stable DNA well-suited for archiving.

In some embodiments, determining the identity of an allele or determining copy number can, but need not, include obtaining a nucleic acid sample comprising RNA and/or DNA from a subject, and/or assessing the identity, copy number, presence or absence of one or more genetic variations and their chromosomal locations within the genomic DNA (i.e. subject's genome) derived from the nucleic acid sample.

The individual or organization that performs the determination need not actually carry out the physical analysis of a nucleic acid sample from a subject. In some embodiments, the methods can include using information obtained by analysis of the nucleic acid sample by a third party. In some embodiments, the methods can include steps that occur at more than one site. For example, a nucleic acid sample can be obtained from a subject at a first site, such as at a health care provider or at the subject's home in the case of a self-testing kit. The nucleic acid sample can be analyzed at the same or a second site, for example, at a laboratory or other testing facility.

Nucleic Acids

The nucleic acids and polypeptides described herein can be used in methods and kits of the present disclosure. In some embodiments, aptamers that specifically bind the nucleic acids and polypeptides described herein can be used in methods and kits of the present disclosure. As used herein, a nucleic acid can comprise a deoxyribonucleotide (DNA) or ribonucleotide (RNA), whether singular or in polymers, naturally occurring or non-naturally occurring, double-stranded or single-stranded, coding, for example a translated gene, or non-coding, for example a regulatory region, or any fragments, derivatives, mimetics or complements thereof. In some embodiments, nucleic acids can comprise oligonucleotides, nucleotides, polynucleotides, nucleic acid sequences, genomic sequences, complementary DNA (cDNA), anti-sense nucleic acids, DNA regions, probes, primers, genes, regulatory regions, introns, exons, open-reading frames, binding sites, target nucleic acids and allele-specific nucleic acids.

A "probe," as used herein, includes a nucleic acid fragment for examining a nucleic acid in a specimen using the hybridization reaction based on the complementarity of nucleic acid.

A "hybrid" as used herein, includes a double strand formed between any one of the abovementioned nucleic acid, within the same type, or across different types, including DNA-DNA, DNA-RNA, RNA-RNA or the like.

"Isolated" nucleic acids, as used herein, are separated from nucleic acids that normally flank the gene or nucleotide sequence (as in genomic sequences) and/or has been completely or partially purified from other transcribed sequences (e.g., as in an RNA library). For example, isolated nucleic acids of the disclosure can be substantially isolated with respect to the complex cellular milieu in which it naturally occurs, or culture medium when produced by recombinant techniques, or chemical precursors or other chemicals when chemically synthesized. In some instances, the isolated material can form part of a composition, for example, a crude extract containing other substances, buffer system or reagent mix. In some embodiments, the material can be purified to essential homogeneity using methods known in the art, for example, by polyacrylamide gel electrophoresis (PAGE) or column chromatography (e.g., HPLC). With regard to genomic DNA (gDNA), the term "isolated" also can refer to nucleic acids that are separated from the chromosome with which the genomic DNA is naturally associated. For example, the isolated nucleic acid molecule can contain less than about 250 kb, 200 kb, 150 kb, 100 kb, 75 kb, 50 kb, 25 kb, 10 kb, 5 kb, 4 kb, 3 kb, 2 kb, 1 kb, 0.5 kb or 0.1 kb of the nucleotides that flank the nucleic acid molecule in the gDNA of the cell from which the nucleic acid molecule is derived.

Nucleic acids can be fused to other coding or regulatory sequences can be considered isolated. For example, recombinant DNA contained in a vector is included in the definition of "isolated" as used herein. In some embodiments, isolated nucleic acids can include recombinant DNA molecules in heterologous host cells or heterologous organisms, as well as partially or substantially purified DNA molecules in solution. Isolated nucleic acids also encompass in vivo and in vitro RNA transcripts of the DNA molecules of the present disclosure. An isolated nucleic acid molecule or nucleotide sequence can be synthesized chemically or by recombinant means. Such isolated nucleotide sequences can be useful, for example, in the manufacture of the encoded polypeptide, as probes for isolating homologous sequences (e.g., from other mammalian species), for gene mapping (e.g., by in situ hybridization with chromosomes), or for detecting expression of the gene, in tissue (e.g., human tissue), such as by Northern blot analysis or other hybridization techniques disclosed herein. The disclosure also pertains to nucleic acid sequences that hybridize under high stringency hybridization conditions, such as for selective hybridization, to a nucleotide sequence described herein Such nucleic acid sequences can be detected and/or isolated by allele- or sequence-specific hybridization (e.g., under high stringency conditions). Stringency conditions and methods for nucleic acid hybridizations are well known to the skilled person (see, e.g., Current Protocols in Molecular Biology, Ausubel, F. et al., John Wiley & Sons, (1998), and Kraus, M. and Aaronson, S., Methods Enzymol., 200:546-556 (1991), the entire teachings of which are incorporated by reference herein.

Calculations of "identity" or "percent identity" between two or more nucleotide or amino acid sequences can be determined by aligning the sequences for optimal comparison purposes (e.g., gaps can be introduced in the sequence of a first sequence). The nucleotides at corresponding positions are then compared, and the percent identity between the two sequences is a function of the number of identical positions shared by the sequences (i.e. % identity=# of identical positions/total # of positions×100). For example, a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

In some embodiments, the length of a sequence aligned for comparison purposes is at least 30%, at least 40%, at least 50%, at least 60%, at least 70%, at least 80%, at least 90%, or at least 95%, of the length of the reference sequence. The actual comparison of the two sequences can be accomplished by well-known methods, for example, using a mathematical algorithm. A non-limiting example of such a mathematical algorithm is described in Karlin, S. and Altschul, S., Proc. Natl. Acad. Sci. USA, 90-5873-5877 (1993). Such an algorithm is incorporated into the NBLAST and XBLAST programs (version 2.0), as described in Altschul, S. et al., Nucleic Acids Res., 25:3389-3402 (1997). When utilizing BLAST and Gapped BLAST programs, any relevant parameters of the respective programs (e.g., NBLAST) can be used. For example, parameters for sequence comparison can be set at score=100, word length=12, or can be varied (e.g., W=5 or W=20). Other examples include the algorithm of Myers and Miller, CABIOS (1989), ADVANCE, ADAM, BLAT, and FASTA. In some embodiments, the percent identity between two amino acid sequences can be accomplished using, for example, the GAP program in the GCG software package (Accelrys, Cambridge, UK).

"Probes" or "primers" can be oligonucleotides that hybridize in a base-specific manner to a complementary strand of a nucleic acid molecule. Probes can include primers, which can be a single-stranded oligonucleotide probe that can act as a point of initiation of template-directed DNA synthesis using methods including but not limited to, polymerase chain reaction (PCR) and ligase chain reaction (LCR) for amplification of a target sequence. Oligonucleotides, as described herein, can include segments or fragments of nucleic acid sequences, or their complements. In some embodiments, DNA segments can be between 5 and 10,000 contiguous bases, and can range from 5, 10, 12, 15, 20, or 25 nucleotides to 10, 15, 20, 25, 30, 40, 50, 100, 200, 500, 1000 or 10,000 nucleotides. In addition to DNA and RNA, probes and primers can include polypeptide nucleic acids (PNA), as described in Nielsen, P. et al., Science 254: 1497-1500 (1991). A probe or primer can comprise a region of nucleotide sequence that hybridizes to at least about 15, typically about 20-25, and in certain embodiments about 40, 50, 60 or 75, consecutive nucleotides of a nucleic acid molecule.

The present disclosure also provides isolated nucleic acids, for example, probes or primers, that contain a fragment or portion that can selectively hybridize to a nucleic acid that comprises, or consists of, a nucleotide sequence, wherein the nucleotide sequence can comprise at least one polymorphism or polymorphic allele contained in the genetic variations described herein or the wild-type nucleotide that is located at the same position, or the complements thereof. In some embodiments, the probe or primer can be at least 70% identical, at least 80% identical, at least 85% identical, at least 90% identical, or at least 95% identical, to the contiguous nucleotide sequence or to the complement of the contiguous nucleotide sequence.

In some embodiments, a nucleic acid probe can be an oligonucleotide capable of hybridizing with a complementary region of a gene associated with a condition (e.g., LHON) containing a genetic variation described herein. The nucleic acid fragments of the disclosure can be used as probes or primers in assays such as those described herein.

The nucleic acids of the disclosure, such as those described above, can be identified and isolated using standard molecular biology techniques well known to the skilled person. In some embodiments, DNA can be amplified and/or can be labeled (e.g., radiolabeled, fluorescently labeled) and used as a probe for screening, for example, a cDNA library derived from an organism. cDNA can be derived from mRNA and can be contained in a suitable vector. For example, corresponding clones can be isolated, DNA obtained fallowing in vivo excision, and the cloned insert can be sequenced in either or both orientations by art-recognized methods to identify the correct reading frame encoding a polypeptide of the appropriate molecular weight. Using these or similar methods, the polypeptide and the DNA encoding the polypeptide can be isolated, sequenced and further characterized.

In some embodiments, nucleic acid can comprise one or more polymorphisms, variations, or mutations, for example, single nucleotide polymorphisms (SNPs), single nucleotide variations (SNVs), copy number variations (CNVs), for example, insertions, deletions, inversions, and translocations. In some embodiments, nucleic acids can comprise analogs, for example, phosphorothioates, phosphoramidates, methyl phosphonate, chiralmethyl phosphonates, 2-O-methyl ribonucleotides, or modified nucleic acids, for example, modified backbone residues or linkages, or nucleic acids combined with carbohydrates, lipids, polypeptide or other materials, or peptide nucleic acids (PNAs), for example, chromatin, ribosomes, and transcriptosomes. In some embodiments nucleic acids can comprise nucleic acids in various structures, for example, A DNA, B DNA, Z-form DNA, siRNA, tRNA, and ribozymes. In some embodiments, the nucleic acid may be naturally or non-naturally polymorphic, for example, having one or more sequence differences, for example, additions, deletions and/or substitutions, as compared to a reference sequence. In some embodiments, a reference sequence can be based on publicly available information, for example, the U.C. Santa Cruz Human Genome Browser Gateway (genome.ucsc.edu/cgi-bin/hg-Gateway) or the NCBI website (www.ncbi.nlm.nih.gov). In some embodiments, a reference sequence can be determined by a practitioner of the present disclosure using methods well known in the art, for example, by sequencing a reference nucleic acid.

In some embodiments, a probe can hybridize to an allele, SNP, SNV, or CNV as described herein. In some embodiments, the probe can bind to another marker sequence associated with LHON as described herein.

One of skill in the art would know how to design a probe so that sequence specific hybridization can occur only if a particular allele is present in a genomic sequence from a test nucleic acid sample. The disclosure can also be reduced to practice using any convenient genotyping method, including commercially available technologies and methods for genotyping particular genetic variations Control probes can also be used, for example, a probe that binds a less variable sequence, for example, a repetitive DNA associated with a centromere of a chromosome, can be used as a control. In some embodiments, probes can be obtained from commercial sources. In some embodiments, probes can be synthesized, for example, chemically or in vitro, or made from chromosomal or genomic DNA through standard techniques. In some embodiments sources of DNA that can be used include genomic DNA, cloned DNA sequences, somatic cell hybrids that contain one, or a part of one, human chromosome along with the normal chromosome complement of the host, and chromosomes purified by flow cytometry or microdissection. The region of interest can be isolated through cloning, or by site-specific amplification using PCR.

One or more nucleic acids for example, a probe or primer, can also be labeled, for example, by direct labeling, to comprise a detectable label. A detectable label can comprise any label capable of detection by a physical, chemical, or a biological process for example, a radioactive label, such as 32P or 3H, a fluorescent label, such as FITC, a chromophore label, an affinity-ligand label, an enzyme label, such as alkaline phosphatase, horseradish peroxidase, or 12 galactosidase, an enzyme cofactor label, a hapten conjugate label, such as digoxigenin or dinitrophenyl, a Raman signal generating label, a magnetic label, a spin label, an epitope label, such as the FLAG or HA epitope, a luminescent label, a heavy atom label, a nanoparticle label, an electrochemical label, a light scattering label, a spherical shell label, semiconductor nanocrystal label, such as quantum dots (described in U.S. Pat. No. 6,207,392), and probes labeled with any other signal generating label known to those of skill in the art, wherein a label can allow the probe to be visualized with or without a secondary detection molecule. A nucleotide can be directly incorporated into a probe with standard techniques, for example, nick translation, random priming, and PCR labeling. A "signal," as used herein, include a signal suitably detectable and measurable by appropriate means, including fluorescence, radioactivity, chemiluminescence, and the like.

Non-limiting examples of label moieties useful for detection include, without limitation, suitable enzymes such as horseradish peroxidase, alkaline phosphatase, beta-galactosidase, or acetylcholinesterase; members of a binding pair that are capable of forming complexes such as streptavidin/biotin, avidin/biotin or an antigen/antibody complex including, for example, rabbit IgG and anti-rabbit IgG; fluorophores such as umbelliferone, fluorescein, fluorescein isothiocyanate, rhodamine, tetramethyl rhodamine, eosin, green fluorescent protein, erythrosin, coumarin, methyl coumarin, pyrene, malachite green, stilbene, lucifer yellow, Cascade Blue, Texas Red, dichlorotriazinylamine fluorescein, dansyl chloride, phycoerythrin, fluorescent lanthanide complexes such as those including Europium and Terbium, cyanine dye family members, such as Cy3 and Cy5, molecular beacons and fluorescent derivatives thereof, as well as others known in the art as described, for example, in Principles of Fluorescence Spectroscopy, Joseph R. Lakowicz (Editor), Plenum Pub Corp, 2nd edition (July 1999) and the 6th Edition of the Molecular Probes Handbook by Richard P. Hoagland; a luminescent material such as luminol; light scattering or plasmon resonant materials such as gold or silver particles or quantum dots; or radioactive material include 14C, 123I, 124I, 125I, Tc99m, 32P, 33P, 35S or 3H.

Other labels can also be used in the methods of the present disclosure, for example, backbone labels. Backbone labels comprise nucleic acid stains that bind nucleic acids in a sequence independent manner. Non-limiting examples include intercalating dyes such as phenanthridines and acridines (e.g., ethidium bromide, propidium iodide, hexidium iodide, dihydroethidium, ethidium homodimer-1 and -2, ethidium monoazide, and ACMA); some minor grove binders such as indoles and imidazoles (e.g., Hoechst 33258, Hoechst 33342, Hoechst 34580 and DAPI); and miscellaneous nucleic acid stains such as acridine orange (also capable of intercalating), 7-AAD, actinomycin D, LDS751, and hydroxystilbamidine. All of the aforementioned nucleic acid stains are commercially available from suppliers such as Molecular Probes, Inc. Still other examples of nucleic acid stains include the following dyes from Molecular Probes: cyanine dyes such as SYTOX Blue, SYTOX Green, SYTOX Orange, POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO-3, PicoGreen, OliGreen, RiboGreen, SYBR Gold, SYBR Green I, SYBR Green II, SYBR DX, SYTO-40, -41, -42, -43, -44, -45 (blue), SYTO-13, -16, -24, -21, -23, -12, -11, -20, -22, -15, -14, -25 (green), SYTO-81, -80, -82, -83, -84, -85 (orange), SYTO-64, -17, -59, -61, -62, -60, -63 (red).

In some embodiments, fluorophores of different colors can be chosen, for example, 7-amino-4-methylcoumarin-3-acetic acid (AMCA), 5-(and-6)-carboxy-X-rhodamine, lissamine rhodamine B, 5-(and-6)-carboxyfluorescein, fluorescein-5-isothiocyanate (FITC), 7-diethylaminocoumarin-3-carboxylic acid, tetramethylrhodamine-5-(and-6)-isothiocyanate, 5-(and-6)-carboxytetramethylrhodamine, 7-hydroxycoumarin-3-carboxylic acid, 6-[fluorescein 5-(and-6)-carboxamido]hexanoic acid, N-(4,4-difluoro-5,7-dimethyl-4-bora-3a,4a diaza-3-indacenepropionic acid, eosin-5-isothiocyanate, erythrosin-5-isothiocyanate, TRITC, rhodamine, tetramethylrhodamine, R-phycoerythrin, Cy-3, Cy-5, Cy-7, Texas Red, Phar-Red, allophycocyanin (APC), and CASCADE™ blue acetylazide, such that each probe in or not in a set can be distinctly visualized. In some embodiments, fluorescently labeled probes can be viewed with a fluorescence microscope and an appropriate filter for each fluorophore, or by using dual or triple bandpass filter sets to observe multiple fluorophores. In some embodiments, techniques such as flow cytometry can be used to examine the hybridization pattern of the probes.

In other embodiments, the probes can be indirectly labeled, for example, with biotin or digoxygenin, or labeled with radioactive isotopes such as 32P and/or 3H. As a non-limiting example, a probe indirectly labeled with biotin can be detected by avidin conjugated to a detectable marker. For example, avidin can be conjugated to an enzymatic marker such as alkaline phosphatase or horseradish peroxidase. In some embodiments, enzymatic markers can be detected using colorimetric reactions using a substrate and/or a catalyst for the enzyme. In some embodiments, catalysts for alkaline phosphatase can be used, for example, 5-bromo-4-chloro-3-indolylphosphate and nitro blue tetrazolium. In some embodiments, a catalyst can be used for horseradish peroxidase, for example, diaminobenzoate.

Formulations, Routes of Administration, and Effective Doses

Yet another aspect of the present disclosure relates to formulations, routes of administration and effective doses for pharmaceutical compositions comprising an agent or combination of agents of the instant disclosure. Such pharmaceutical compositions can be used to treat a condition (e.g., LHON) as described above.

Compounds of the disclosure can be administered as pharmaceutical formulations including those suitable for oral (including buccal and sub-lingual), rectal, nasal, topical, transdermal patch, pulmonary, vaginal, suppository, or parenteral (including intraocular, intravitreal, intramuscular, intraarterial, intrathecal, intradermal, intraperitoneal, subcutaneous and intravenous) administration or in a form suitable for administration by aerosolization, inhalation or insufflation. General information on drug delivery systems can be found in Ansel et al., Pharmaceutical Dosage Forms and Drug Delivery Systems (Lippencott Williams & Wilkins, Baltimore Md. (1999).

In various embodiments, the pharmaceutical composition includes carriers and excipients (including but not limited to buffers, carbohydrates, mannitol, polypeptides, amino acids, antioxidants, bacteriostats, chelating agents, suspending agents, thickening agents and/or preservatives), water, oils including those of petroleum, animal, vegetable or synthetic origin, such as peanut oil, soybean oil, mineral oil, sesame oil and the like, saline solutions, aqueous dextrose and glycerol solutions, flavoring agents, coloring agents, detackifiers and other acceptable additives, adjuvants, or binders, other pharmaceutically acceptable auxiliary substances to approximate physiological conditions, such as pH buffering agents, tonicity adjusting agents, emulsifying agents, wetting agents and the like. Examples of excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. In some embodiments, the pharmaceutical preparation is substantially free of preservatives. In other embodiments, the pharmaceutical preparation can contain at least one preservative. General methodology on pharmaceutical dosage forms is found in Ansel et al., Pharmaceutical Dosage Forms and Drug Delivery Systems (Lippencott, Williams, & Wilkins, Baltimore Md. (1999)). It can be recognized that, while any suitable carrier known to those of ordinary skill in the art can be employed to administer the compositions of this disclosure, the type of carrier can vary depending on the mode of administration.

Compounds can also be encapsulated within liposomes using well-known technology. Biodegradable microspheres can also be employed as carriers for the pharmaceutical compositions of this disclosure. Suitable biodegradable microspheres are disclosed, for example, in U.S. Pat. Nos. 4,897,268, 5,075,109, 5,928,647, 5,811,128, 5,820,883, 5,853,763, 5,814,344 and 5,942,252.

The compound can be administered in liposomes or microspheres (or microparticles). Methods for preparing liposomes and microspheres for administration to a subject are well known to those of skill in the art. U.S. Pat. No. 4,789,734, the contents of which are hereby incorporated by reference, describes methods for encapsulating biological materials in liposomes. Essentially, the material is dissolved in an aqueous solution, the appropriate phospholipids and lipids added, and along with surfactants if required, and the material dialyzed or sonicated, as necessary. A review of known methods is provided by G. Gregoriadis, Chapter 14, "Liposomes," Drug Carriers in Biology and Medicine, pp. 2.sup.87-341 (Academic Press, 1979).

Microspheres formed of polymers or polypeptides are well known to those skilled in the art, and can be tailored for passage through the gastrointestinal tract directly into the blood stream. Alternatively, the compound can be incorporated and the microspheres, or composite of microspheres, implanted for slow release over a period of time ranging from days to months. See, for example, U.S. Pat. Nos. 4,906,474, 4,925,673 and 3,625,214, and Jein, TIPS 19:155-157 (1998), the contents of which are hereby incorporated by reference.

The concentration of drug can be adjusted, the pH of the solution buffered and the isotonicity adjusted to be compatible with intraocular or intravitreal injection.

The compounds of the disclosure can be formulated as a sterile solution or suspension, in suitable vehicles. The pharmaceutical compositions can be sterilized by conventional, well-known sterilization techniques, or can be sterile filtered. The resulting aqueous solutions can be packaged for use as is, or lyophilized, the lyophilized preparation being combined with a sterile solution prior to administration. Suitable formulations and additional carriers are described in Remington "The Science and Practice of Pharmacy" (20th Ed., Lippincott Williams & Wilkins, Baltimore Md.), the teachings of which are incorporated by reference in their entirety herein.

The agents or their pharmaceutically acceptable salts can be provided alone or in combination with one or more other agents or with one or more other forms. For example, a formulation can comprise one or more agents in particular proportions, depending on the relative potencies of each agent and the intended indication. For example, in compositions for targeting two different host targets, and where potencies are similar, about a 1:1 ratio of agents can be used. The two forms can be formulated together, in the same dosage unit e.g., in one cream, suppository, tablet, capsule, aerosol spray, or packet of powder to be dissolved in a beverage; or each form can be formulated in a separate unit, e.g., two creams, two suppositories, two tablets, two capsules, a tablet and a liquid for dissolving the tablet, two aerosol sprays, or a packet of powder and a liquid for dissolving the powder, etc.

The term "pharmaceutically acceptable salt" means those salts which retain the biological effectiveness and properties of the agents used in the present disclosure, and which are not biologically or otherwise undesirable.

Typical salts are those of the inorganic ions, such as, for example, sodium, potassium, calcium, magnesium ions, and the like. Such salts include salts with inorganic or organic acids, such as hydrochloric acid, hydrobromic acid, phosphoric acid, nitric acid, sulfuric acid, methanesulfonic acid, p toluenesulfonic acid, acetic acid, fumaric acid, succinic acid, lactic acid, mandelic acid, malic acid, citric acid, tartaric acid or maleic acid. In addition, if the agent(s) contain a carboxyl group or other acidic group, it can be converted into a pharmaceutically acceptable addition salt with inorganic or organic bases. Examples of suitable bases include sodium hydroxide, potassium hydroxide, ammonia, cyclohexylamine, dicyclohexyl-amine, ethanolamine, diethanolamine, triethanolamine, and the like.

A pharmaceutically acceptable ester or amide refers to those which retain biological effectiveness and properties of the agents used in the present disclosure, and which are not biologically or otherwise undesirable. Typical esters include ethyl, methyl, isobutyl, ethylene glycol, and the like. Typical amides include unsubstituted amides, alkyl amides, dialkyl amides, and the like.

In some embodiments, an agent can be administered in combination with one or more other compounds, forms, and/or agents, e.g., as described above. Pharmaceutical compositions with one or more other active agents can be formulated to comprise certain molar ratios. For example, molar ratios of about 99:1 to about 1:99 of a first active agent to the other active agent can be used. In some subset of the embodiments, the range of molar ratios of a first active agent: other active agents are selected from about 80:20 to about 20:80; about 75:25 to about 25:75, about 70:30 to about 30:70, about 66:33 to about 33:66, about 60:40 to about 40:60; about 50:50; and about 90:10 to about 10:90. The molar ratio of a first active:other active agents can be about 1:9, and in some embodiments can be about 1:1. The two agents, forms and/or compounds can be formulated together, in the same dosage unit e.g., in one cream, suppository, tablet, capsule, or packet of powder to be dissolved in a beverage; or each agent, form, and/or compound can be formulated in separate units, e.g., two creams, suppositories, tablets, two capsules, a tablet and a liquid for dissolving the tablet, an aerosol spray a packet of powder and a liquid for dissolving the powder, etc.

If necessary or desirable, the agents and/or combinations of agents can be administered with still other agents. The choice of agents that can be co-administered with the agents and/or combinations of agents of the instant disclosure can depend, at least in part, on the condition being treated.

The agent(s) (or pharmaceutically acceptable salts, esters or amides thereof) can be administered per se or in the form of a pharmaceutical composition wherein the active agent(s) is in an admixture or mixture with one or more pharmaceutically acceptable carriers. A pharmaceutical composition, as used herein, can be any composition prepared for administration to a subject. Pharmaceutical compositions for use in accordance with the present disclosure can be formulated in conventional manner using one or more physiologically acceptable carriers, comprising excipients, diluents, and/or auxiliaries, e.g., which facilitate processing of the active agents into preparations that can be administered. Proper formulation can depend at least in part upon the route of administration chosen. The agent(s) useful in the present disclosure, or pharmaceutically acceptable salts, esters, or amides thereof, can be delivered to a subject using a number of routes or modes of administration, including oral, buccal, topical, rectal, transdermal, transmucosal, subcutaneous, intravenous, intraocular, intravitreal, and intramuscular applications, as well as by inhalation.

In some embodiments, oils or non-aqueous solvents can be used to bring the agents into solution, due to, for example, the presence of large lipophilic moieties. Alternatively, emulsions, suspensions, or other preparations, for example, liposomal preparations, can be used. With respect to liposomal preparations, any known methods for preparing liposomes for treatment of a condition can be used. See, for example, Bangham et al., J. Mol. Biol. 23: 238-252 (1965) and Szoka et al., Proc. Natl Acad. Sci. USA 75: 4194-4198 (1978), incorporated herein by reference. Ligands can also be attached to the liposomes to direct these compositions to particular sites of action. Agents of this disclosure can also be integrated into foodstuffs, e.g., cream cheese, butter, salad dressing, or ice cream to facilitate solubilization, administration, and/or compliance in certain subject populations.

The compounds of the disclosure can be formulated for parenteral administration (e.g., by injection, for example, intraocular or intravitreal injection) and can be presented in unit dose form in ampoules, pre-filled syringes, small volume infusion or in multi-dose containers with an added preservative. The compositions can take such forms as suspensions, solutions, or emulsions in oily or aqueous vehicles, for example, solutions in aqueous polyethylene glycol.

For injectable formulations, the vehicle can be chosen from those known in art to be suitable, including aqueous solutions or oil suspensions, or emulsions, with sesame oil, corn oil, cottonseed oil, or peanut oil, as well as elixirs, mannitol, dextrose, or a sterile aqueous solution, and similar pharmaceutical vehicles. The formulation can also comprise polymer compositions which are biocompatible, biodegradable, such as poly(lactic-co-glycolic)acid. These materials can be made into micro or nanospheres, loaded with drug and further coated or derivatized to provide superior sustained release performance. Vehicles suitable for periocular or intraocular injection include, for example, suspensions of therapeutic agent in injection grade water, liposomes and vehicles suitable for lipophilic substances. Other vehicles for periocular or intraocular injection are well known in the art.

In some embodiments, the composition is formulated in accordance with routine procedures as a pharmaceutical composition adapted for intravenous administration to human beings. Typically, compositions for intravenous administration are solutions in sterile isotonic aqueous buffer. Where necessary, the composition can also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

When administration is by injection, the active compound can be formulated in aqueous solutions, specifically in physiologically compatible buffers such as Hanks solution, Ringer's solution, or physiological saline buffer. The solution can contain formulatory agents such as suspending, stabilizing and/or dispersing agents. Alternatively, the active compound can be in powder form for constitution with a suitable vehicle, e.g., sterile pyrogen-free water, before use. In some embodiments, the pharmaceutical composition does not comprise an adjuvant or any other substance added to enhance the immune response stimulated by the peptide. In some embodiments, the pharmaceutical composition comprises a substance that inhibits an immune response to the peptide. Methods of formulation are known in the art, for example, as disclosed in Remington's Pharmaceutical Sciences, latest edition, Mack Publishing Co., Easton P.

In some embodiments, eye disorders can be effectively treated with ophthalmic solutions, suspensions, ointments or inserts comprising an agent or combination of agents of the present disclosure. Eye drops can be prepared by dissolving the active ingredient in a sterile aqueous solution such as physiological saline, buffering solution, etc., or by combining powder compositions to be dissolved before use. Other vehicles can be chosen, as is known in the art, including but not limited to: balance salt solution, saline solution, water soluble polyethers such as polyethyene glycol, polyvinyls, such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate. If desired, additives ordinarily used in the eye drops can be added. Such additives include isotonizing agents (e.g., sodium chloride, etc.), buffer agent (e.g., boric acid, sodium monohydrogen phosphate, sodium dihydrogen phosphate, etc.), preservatives (e.g., benzalkonium chloride, benzethonium chloride, chlorobutanol, etc.), thickeners (e.g., saccharide such as lactose, mannitol, maltose, etc.; e.g., hyaluronic acid or its salt such as sodium hyaluronate, potassium hyaluronate, etc.; e.g., mucopolysaccharide such as chondroitin sulfate, etc.; e.g., sodium polyacrylate, carboxyvinyl polymer, cross-linked polyacrylate, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents known to those skilled in the art).

The solubility of the components of the present compositions can be enhanced by a surfactant or other appropriate co-solvent in the composition. Such cosolvents include polysorbate 20, 60, and 80, Pluronic F68, F-84 and P-103, cyclodextrin, or other agents known to those skilled in the art. Such co-solvents can be employed at a level of from about 0.01% to 2% by weight.

The compositions of the disclosure can be packaged in multidose form. Preservatives can be preferred to prevent microbial contamination during use. Suitable preservatives include: benzalkonium chloride, thimerosal, chlorobutanol, methyl paraben, propyl paraben, phenylethyl alcohol, edetate disodium, sorbic acid, Onamer M, or other agents known to those skilled in the art. In the prior art ophthalmic products, such preservatives can be employed at a level of from 0.004% to 0.02%. In the compositions of the present application the preservative, preferably benzalkonium chloride, can be employed at a level of from 0.001% to less than 0.01%, e.g., from 0.001% to 0.008%, preferably about 0.005% by weight. It has been found that a concentration of benzalkonium chloride of 0.005% can be sufficient to preserve the compositions of the present disclosure from microbial attack.

In some embodiments, the agents of the present disclosure are delivered in soluble rather than suspension form, which allows for more rapid and quantitative absorption to the sites of action. In general, formulations such as jellies, creams, lotions, suppositories and ointments can provide an area with more extended exposure to the agents of the present disclosure, while formulations in solution, e.g., sprays, provide more immediate, short-term exposure.

It is envisioned additionally, that the compounds of the disclosure can be attached releasably to biocompatible polymers for use in sustained release formulations on, in or attached to inserts for topical, intraocular, periocular, or systemic administration. The controlled release from a biocompatible polymer can be utilized with a water soluble polymer to form an instillable formulation, as well. The controlled release from a biocompatible polymer, such as for example, PLGA microspheres or nanospheres, can be utilized in a formulation suitable for intra ocular implantation or injection for sustained release administration, as well any suitable biodegradable and biocompatible polymer can be used.

EXAMPLES

The following exemplary embodiments further describe the present invention. It should be understood that these examples are only intended to illustrate the invention, but not to limit the scope of the present invention. Unless otherwise indicated, the methods and conditions disclosed in e.g., sambrook et al, molecular cloning: a laboratory manual (New York: cold spring harbor laboratory press, 1989) or the conditions recommended by the manufacturer can be used in the examples below.

Example 1—ND4 Plasmid and Virus Preparation 1.1 Plasmid Preparation

The nucleotide sequence for human ND4 (SEQ ID NO: 6) was obtained based on US National Center for Biotechnology Information reference sequence yp_003024035.1. The sequences for the non-optimized mitochondrial targeting sequence COX10 is SEQ ID NO: 1. The optimized sequences for the mitochondrial targeting sequence COX10 (opt_COX10, SEQ ID NO: 2) and the coding sequence of human ND4 (opt_ND4, SEQ ID NO: 7) were designed to improve the transcription efficiency and the translation efficiency. The optimized COX10-ND4 sequence, which is about 75.89% homology to the non-optimized COX10-ND4, was followed by a three prime untranslated region (i.e., 3'UTR, SEQ ID NO: 13) to a recombinant nucleic acid, opt_COX10-opt_ND4-3'UTR (as shown in SEQ ID NO: 31).

The synthesized recombinant nucleic acid, opt_COX10-opt_ND4-3'UTR, was incorporated into an adeno-associated virus (AAV) vector by PCR amplification (FIG. 1). The opt_COX10-opt_ND4-3'UTR was cut by the EcoRI/SalI restriction enzymes to form cohesive ends, and then embedded into an AAV vector with EcoRI/SalI restriction sites, such as the pSNaV vector, to generate the pSNaV/rAAV2/2-ND4 plasmid (i.e., the pAAV2-optimized ND4 plasmid). The pAAV2-opt_ND4 plasmid was compared to the non-optimized pAAV2-ND4 plasmid.

The recon screening and identifying steps were similar to the CN102634527B: the plasmid was cultured at 37° C. in a LB plate. Blue colonies and white colonies were appeared, where white colonies were recombinant clones. The white colonies were picked, added to 100 mg/L ampicillin-containing LB culture medium, cultured at 37° C., 200 rpm for 8 hours and then the plasmid were extracted from the cultured bacterial medium based on the Biomiga plasmid extraction protocol. The identification of the plasmid was confirmed using the EcoRI/SalI restriction enzymes.

1.2 Cell Transfection

One day before transfection, HEK293 cells were inoculated to 225 cm$^2$ cell culture bottle: at the inoculation density of $3.0 \times 10^7$ cells/ml, the culture medium was the Dulbecco's Modified Eagle Medium (DMEM) with 10% bovine serum, at 37° C. in a 5% $CO_2$ incubator overnight. The culture medium were replaced with fresh DMEM with 10% bovine serum on the day of transfection.

After the cells grow to 80-90%, discard the culture medium and transfect the cells with the pAAV2-ND4 and pAAV2-opt_ND4 plasmid, using the PlasmidTrans (VGTC) transfection kit. The detailed transfection protocol was described in CN102634527B example 1. The cells were collected 48 h after the transfection.

1.3 Collection, Concentration and Purification of the Recombinant Adeno-Associated Virus Virus collection: 1) dry ice ethanol bath (or liquid nitrogen) and a 37° C. water bath were prepared; 2) the transfected cells along with media were collected in a 15 ml centrifuge tube; 3) the cells were centrifuged for 3 minutes at 1000 rpm/min; the cells and supernatant were separated; the supernatant were stored separately; and the cells were re-suspended in 1 ml of PBS; 4) the cell suspension were transferred between the dry ice-ethanol bath and 37° C. water bath repeatedly, freeze thawing for four times for 10 minutes each, slightly shaking after each thawing.

Virus concentration: 1) cell debris were removed with 10,000 g centrifugation; the centrifugal supernatant was transferred to a new centrifuge tube; 2) impurities were removed by filtering with a 0.45 μm filter; 3) each ½ volume of 1M NaCl and 10% PEG 8000 solution were added in the sample, uniformly mixed, and stored at 4° C. overnight; 4) supernatant was discarded after 12,000 rpm centrifugation for 2 h; after the virus precipitate was completely dissolving in an appropriate amount of PBS solution, sterilizing the sample with a 0.22 μm filter; 5) adding benzonase nuclease was added to remove residual plasmid DNA (final concentration at 50 U/ml). The tube was inverted several times to mix thoroughly and then incubated at 37° C. for 30 minutes; 6) the sample was filtered with a 0.45 μm filtration head; the filtrate is the concentrated rAAV2 virus.

Virus purification: 1) CsCl was added to the concentrated virus solution until a density of 1.41 g/ml (refraction index at 1.372); 2) the sample was added to in the ultracentrifuge tube and filled the tube with pre-prepared 1.41 g/ml CsCl solution; 3) centrifuged at 175,000 g for 24 hours to form a density gradient. Sequential collection of different densities of the sample was performed. The enriched rAAV2 particles were collected; 4) repeating the process one more time. The virus was loaded to a 100 kDa dialysis bag and dialyzed/desalted at 4° C. overnight. The concentrated and purified recombinant adeno-associated virus were rAAV2-ND4 and rAAV2-optimized ND4.

Similarly, other mitochondrial targeting sequences (MTS), such as OPA1 (SEQ ID NO: 5) can be used to replace COX10 in the above example and create AAV with recombinant plasmids.

Example 2—Intravitreal Injection of rAAV2 in Rabbit Eyes

Twelve rabbits were divided into 2 group: rAAV2-ND4 and rAAV2-optimized ND4. Virus solution ($1 \times 10^{10}$ vg/0.05 mL) was punctured into the vitreous cavity from 3 mm outside the corneal limbus at the pars plana. After the intravitreal injection, the eyes were examined using slit lamp exam and fundus photography inspection. Injection for 30 days. RT-PCR detection and immunoblotting were carried out in each group respectively.

Example 3—Real-Time PCR for the Expression of ND4

The RNAs from the transfected rAAV2-ND4 and rAAV2-optimized ND4 rabbit optic nerve cells were extracted using the TRIZOL total RNA extraction kit. cDNA templates were synthesized by reverse transcription of the extracted RNA.

The NCBI conserved structural domain analysis software were used to analyze the conservative structure of ND4, ensuring that the designed primers amplified fragments were located at non-conserved region; then primers were designed according to the fluorescent quantitative PCR primer design principle:

```
                                       (SEQ ID NO: 85)
(a) β-actin-S: CGAGATCGTGCGGGACAT;

(SEQ ID NO: 86)
(b) β-actin-A: CAGGAAGGAGGGCTGGAAC;

(SEQ ID NO: 87)
(c) ND4-S: CTGCCTACGACAAACAGAC;

(SEQ ID NO: 88)
(d) ND4-A: AGTGCGTTCGTAGTTTGAG;
```

The fluorescent quantitative PCR reaction and protocol: fluorescence quantitative PCR were measured in a real-time PCR detection system. In a 0.2 ml PCR reaction tube, SYBR green mix 12.5 μl, ddH$_2$O 8 μl, 1 μl of each primer, and the cDNA sample 2.5 μl, were added to an overall volume of 25 μl. Each sample was used for amplification of the target gene and amplifying the reference gene β-actin, and each amplification were repeated three times. The common reagents were added together and then divided separately to minimize handling variation. The fluorescent quantitative PCR were carried out: pre-denaturation at 95° C. for 1 s, denaturation at 94° C. for 15 s, annealing at 55° C. for 15 sec, extension at 72° C. for 45 s. A total of 40 cycles of amplification reaction were performed and fluorescence signal acquisition was done at the extension phase of each cycle. After the reaction, a 94° C. to 55° C. melting curve analysis was done.

By adopting a relative quantitative method research of gene expression level difference to beta-actin was used as an internal reference gene.

Figure 2:
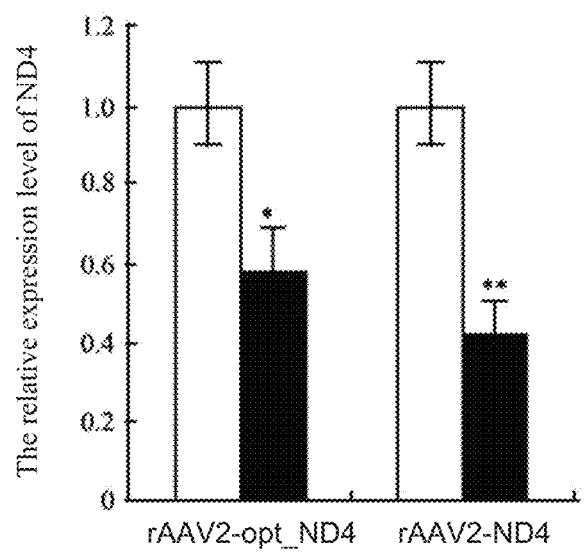
FIG. 2 shows the relative expression level comparison using qPCR between the rAAV2-opt_ND4 (left black column) and rAAV2-ND4 (right black column). β-actin is the internal reference gene (white column).

As shown in FIG. 2, the relative expression level (mRNA level) of the rAAV2-ND4 and rAAV2-optimized ND4 were 0.42±0.23 and 0.57±0.62, respectively (p<0.05, FIG. 2). The results unexpectedly show that the optimized ND4 (opt_ND4, SEQ ID NO: 7) coding nucleic acid sequence and the corresponding recombinant nucleic acid (opt_COX10-opt_ND4-3'UTR, SEQ ID NO: 31) surprisingly increased the transcription efficiency, increasing the expression of the rAAV2-optimized ND4 by about 36%. The results showed that the transcription efficiency of the rAAV2-optimized ND4 is significantly higher.

Example 4—Immunoblotting Detection of ND4 Expression

The ND4 protein was purified from the rabbit nerve cells transfected by rAAV2-optimized ND4 and rAAV2-ND4, respectively. After a 10% polyacrylamide gel electrophoresis, and transferred to a polyvinylidene difluoride membrane (Bio-Rad, HER-hercules, CA, USA) for immune detection. β-actin was used as an internal reference gene. The film strip was observed on an automatic image analysis instrument (Li-Cor; Lincoln, Nebr., USA) and analyzed using the integrated optical density of the protein band with integral normalization method, so as to obtain the same sample corresponding optical density value. The statistical analysis software SPSS 19.0 was used for the data analysis.

Figure 3:
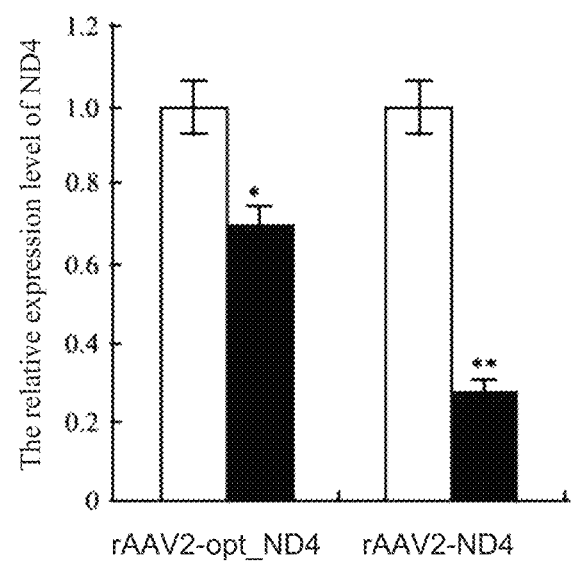
FIG. 3 shows the relative expression level comparison using immunoblotting between the rAAV2-opt_ND4 (left black column) and rAAV2-ND4 (right black column). β-actin is the internal reference gene (white column).

The results was shown in FIG. 3. The average relative protein expression level of ND4 for rAAV2-optimized ND4 (left black column) and rAAV2-ND4 was 0.32±0.11 and 0.68±0.20, respectively (p<0.01, FIG. 3). The results unexpectedly show that the optimized ND4 coding nucleic acid sequence (opt_ND4, SEQ ID NO: 7) and the corresponding recombinant nucleic acid (opt_COX10-opt_ND4-3'UTR, SEQ ID NO: 31) surprisingly increased the translation efficiency, increasing the expression of the rAAV2-optimized ND4 by about 112%. The results showed that the translation efficiency of the rAAV2-optimized ND4 is also significantly higher.

Example 5—Rabbits Intraocular Pressure and Eye-Ground Photography

Slit lamp examination and intraocular pressure measurement was performed on both groups of rabbits at 1, 3, 7, and 30 days after the surgery. No obviously abnormality, conjunctival congestion, secretions, or endophthalmitis were observed and the intraocular pressure were not elevated in all the rabbits.

Figure 4:
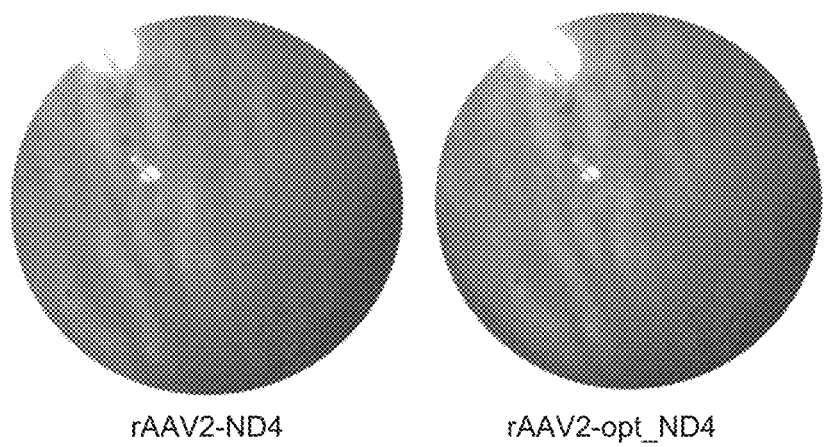
FIG. 4 shows the fundus photographic results for rabbits injected with rAAV2-opt_ND4 (right) and rAAV2-ND4 (left), respectively.

The fundus photographic results were shown in FIG. 4. No obvious damage or complication to the optic nerve and retinal vascular of the rabbits, indicating the standard intravitreal injection is safe without noticeable inflammation reaction or other complications.

Example 6—Human Clinical Trial

Two groups of patients were tested: 1) between 2011 and 2012, 9 patients received intravitreal injection of $1\times10^{10}$ vg/0.05 mL rAAV2-ND4 in a single eye, as a control group; and 2) between 2017 and January 2018, 20 patients received intravitreal injection of $1\times10^{10}$ vg/0.05 mL rAAV2-optimized ND4 in a single eye, as an experimental group. The results of the clinical trial were analyzed using the statistical analysis SPSS 19.0.

Figure 5:
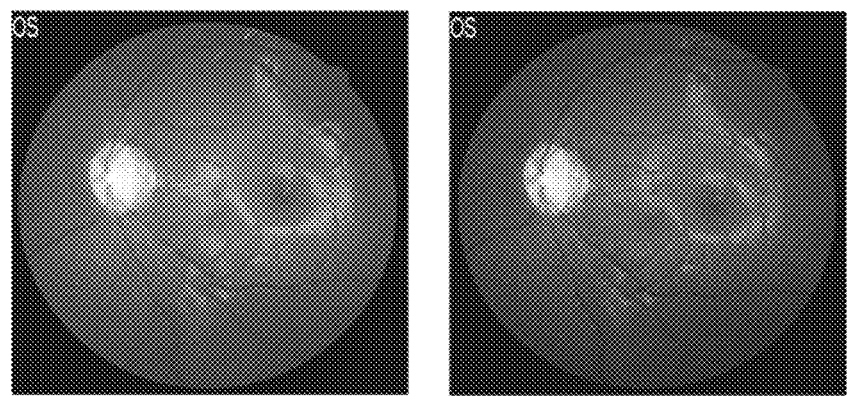
FIG. 5 shows the fundus photographic results for a patient before (left) and after (right) the injection with rAAV2-optimized ND4.

The comparison of the two groups is shown in Table 2. The fastest eyesight improving time was 1 month in the experimental group, which was significantly faster than the control group at 3 months (p<0.01); the optimal recovery of vision for the experimental group was 1.0, which was obviously higher than the control group at 0.8 (p<0.01); the average recovery of vision in the experimental group was 0.582±0.086, which was obviously higher than the control group at 0.344±0.062 (p<0.01). The fundus photographic results were shown in FIG. 5. No obvious damage or complication to the optic nerve and retinal vascular of the patients in the experimental and control groups, indicating the safety of the intravitreal injection of rAAV2-optimized ND4 and rAAV2-ND4.

TABLE 2

The comparison of rAAV2-optimized ND4 and rAAV2-ND4 in LHON gene therapy

| group | Patient number | Fastest eyesight improving time (month) | Number of patients with improved vision | optimal recovery of vision | average recovery of vision |
|---|---|---|---|---|---|
| control | 9 | 3 | 6 (67%) | 0.8 | 0.344 ± 0.062 |
| experimental | 20 | 1 | 15 (75%) | 1.0 | 0.582 ± 0.086 |
| P value | | <0.01 | <0.01 | <0.01 | <0.01 |

Example 7—OPA1 as the Mitochondrial Targeting Sequences

The COX10 and 3'UTR sequences in the recombinant nucleic acid (opt_COX10-opt_ND4-3'UTR, SEQ ID NO: 31) in examples 1-6 were replaced with another mitochondrial targeted sequence, OPA1 (SEQ ID NO: 5) and another 3'UTR sequence, 3'UTR* (SEQ ID NO: 14) respectively, to generate a new recombinant nucleic acid, OPA1-opt_ND4-3'UTR* (SEQ ID NO: 74).

Experimental methods were the same as examples 1-6, where the recombinant nucleic acid opt_COX10-opt_ND4-3'UTR (SEQ ID NO: 31) was replaced by OPA1-opt_ND4-3'UTR* (SEQ ID NO: 74). It was found that, the optimized ND4 sequence has significantly improved transcription and translation efficiencies, expression levels, as well as higher efficacy and safety in treating LHON when compared to non-optimized ND4 (COX10-ND4-3'UTR, SEQ ID NO: 15).

Example 8—Optimized ND4 Sequence Opt_ND4*

Similar experimental methods in examples 1-6 were followed using the nucleic acid, opt_COX10*-opt_ND4*-3'UTR (SEQ ID NO: 47). Follow the similar procedures as in example 1, virus tagged with a fluorescent protein, EGFP, was prepared as rAAV2-ND4-EGFP and rAAV2-opt_ND4*-EGFP.

Figure 6:
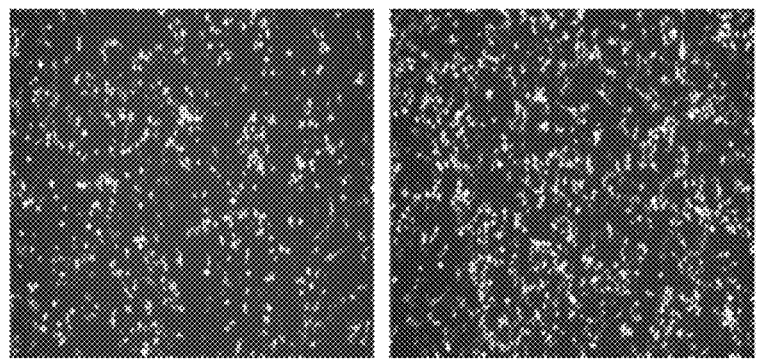
FIG. 6 shows EGFP expression levels of rAAV2-ND4 (left) and rAAV2-opt_ND4* (right).

The frozen 293T cell was resuscitated and allowed to grow in a T75 flask to about 90%. The cells were precipitated and resuspended in DMEM complete medium to a cell density of $5\times10^4$ cells/mL. The cells were resuspended. About 100 µl of the cell suspension (about 5000 cells) were added in each well of a 96 well plate. The cells were cultured and grown to 50% under 37° C. and 5% $CO_2$. About 0.02 µl PBS was mixed with $2\times10^{10}$ vg/0.02 µl of the virus rAAV2-ND4-EGFP and rAAV2-opt_ND4*-EGFP, respectively. After 48 hours, fluorescence microscopy and RT-PCR detection and immunoblotting experiments were performed. As shown in FIG. 6, EGFP was successfully expressed, indicating that rAAV carrying the EGFP gene was successfully transfected in the 293T cells and rAAV2-ND4-EGFP and rAAV2-opt_ND4*-EGFP were successfully expressed.

Real-time PCR tests similar to example 3 was following using the following primers:

```
                                        (SEQ ID NO: 85)
(a) β-actin-S: CGAGATCGTGCGGGACAT;

(SEQ ID NO: 86)
(b) β-actin-A: CAGGAAGGAGGGCTGGAAC;

(SEQ ID NO: 107)
(c) ND4-S: GCCAACAGCAACTACGAGC;

(SEQ ID NO: 108)
(d) ND4-A: TGATGTTGCTCCAGCTGAAG;
```

The results unexpectedly show that the optimized ND4* (opt_ND4, SEQ ID NO: 8) coding nucleic acid sequence and the corresponding recombinant nucleic acid (opt_COX10*-opt_ND4*-3'UTR, SEQ ID NO: 47) surprisingly increased the transcription efficiency, increasing the expression of the rAAV2-opt_ND4 by about 20%. The results showed that the transcription efficiency of the rAAV2-opt_ND4 is significantly higher.

Figure 7:
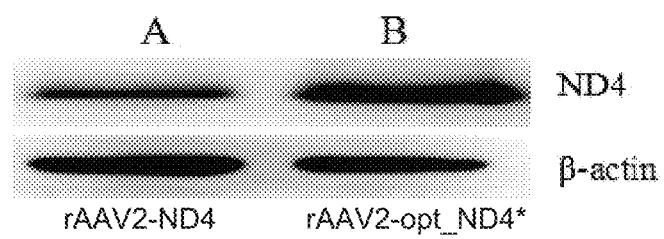
FIG. 7 shows the ND4 expression in 293T cells: rAAV2-ND4 (left) and rAAV2-opt_ND4* (right).
Figure 8:
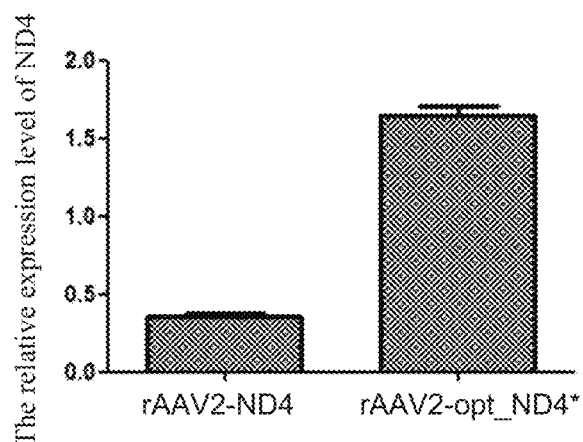
FIG. 8 shows the relative ND4 expression in 293T cells: rAAV2-ND4 (left) and rAAV2-opt_ND4* (right).

FIG. 7 shows the ND4 expression in 293T cells. The average expression of ND4 protein for rAAV2-ND4 is 0.36, while the average expression of ND4 protein for rAAV2-opt_ND4* is 1.65, which is about 4.6 times higher than the rAAV2-ND4 group (p<0.01) (see FIG. 8).

Figure 9:
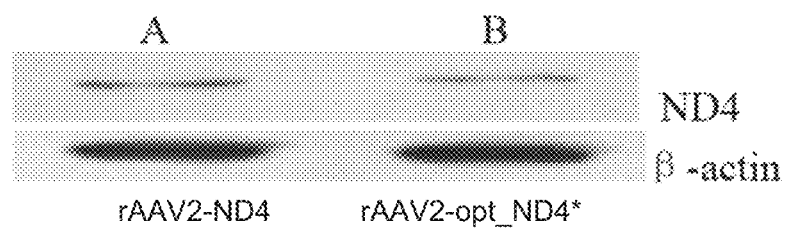
FIG. 9 shows the ND4 expression in rabbit optic nerve cells: rAAV2-ND4 (left) and rAAV2-opt_ND4* (right).
Figure 10:
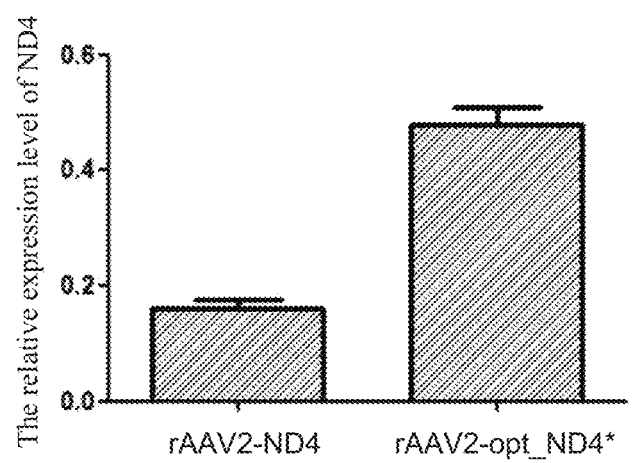
FIG. 10 shows the relative ND4 expression in rabbit optic nerve cells: rAAV2-ND4 (left) and rAAV2-opt_ND4* (right).

FIG. 9 shows the ND4 expression in rabbit optic nerve cells. The average expression of ND4 protein for rAAV2-ND4 is 0.16, while the average expression of ND4 protein for rAAV2-opt_ND4* is 0.48, which is about 3 times higher than the rAAV2-ND4 group (p<0.01) (see FIG. 10).

Similar to example 5, slit lamp examination and intraocular pressure measurement was performed on both groups of rabbits at 1, 3, 7, and 30 days after the surgery. No obviously abnormality, conjunctival congestion, secretions, or endophthalmitis were observed and the intraocular pressure were not elevated in all the rabbits.

Figure 11:
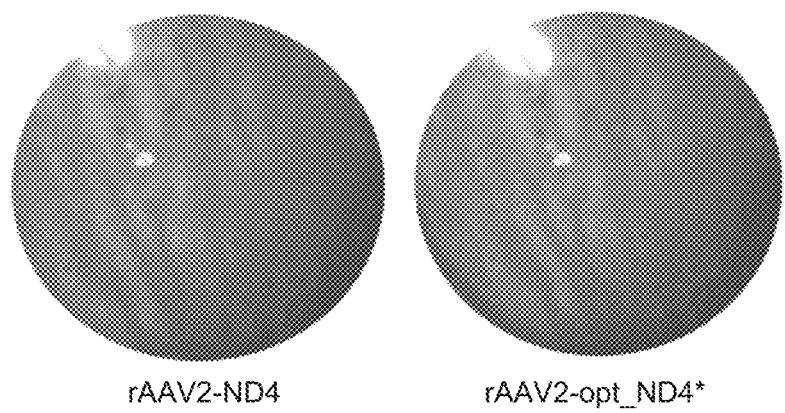
FIG. 11 shows the fundus photographic results for rAAV2-ND4 (left) and rAAV2-opt_ND4* (right).

The fundus photographic results for rAAV2-ND4 and rAAV2-opt_ND4* were shown in FIG. 11. No obvious damage or complication to the optic nerve and retinal vascular of the rabbits, indicating the standard intravitreal injection is safe without noticeable inflammation reaction or other complications.

Figure 12:
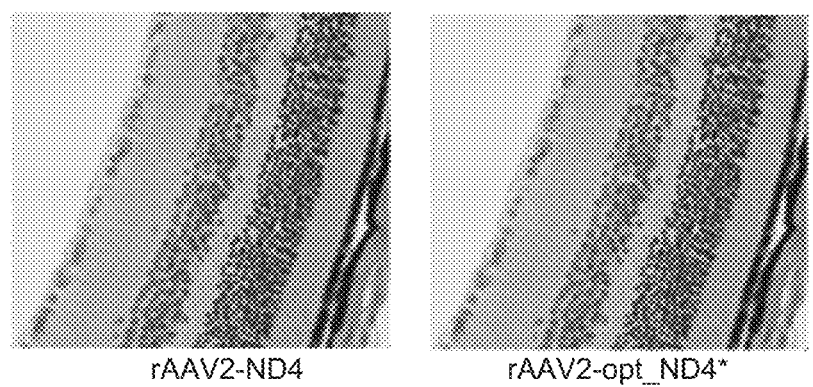
FIG. 12 shows the microscope inspection (HE staining) results for rAAV2-ND4 (left) and rAAV2-opt_ND4* (right).

Eye balls from both rabbit groups were removed after the slit lamp examination and intraocular pressure measurement. Eye balls were fixed, and dehydrated using paraffin. Tissues were pathologically sectioned along the direction of optic nerves. After further dehydration, the tissue sample was dyed using hematoxylin and eosin. The microscope inspection result is referred to FIG. 12. As shown in the HE staining results, the rabbit retinal ganglion fiber layer was not damaged and the number of ganglion cells was not reduced, indicating the intravitreal injection did not produce retinal toxicity or nerve damage, and can be used safely.

Experimental methods were the same as example 8, where the recombinant nucleic acid opt_COX10*-opt_ND4*-3'UTR (SEQ ID NO: 47) was replaced by OPA1-opt_ND4*-3'UTR* (SEQ ID NO: 76). It was found that, the optimized ND4 sequence has significantly improved transcription and translation efficiencies, expression levels, as well as higher efficacy and safety in treating LHON when compared to non-optimized ND4 (COX10-ND4-3'UTR, SEQ ID NO: 15).

Example 9—ND6 Sequence

Similar experimental methods in examples 1-6 were followed using the nucleic acid, COX10-ND6-3'UTR (SEQ ID NO: 21), which is the combination (5' to 3') of COX10 (SEQ ID NO: 1), ND6 (SEQ ID NO: 9), and 3'UTR (SEQ ID NO: 13).

The plasmid screening for COX10-ND6-3'UTR (SEQ ID NO: 21) used the following primers:

```
                                        (SEQ ID NO: 89)
(a) ND6-F: ATGATGTATGCTTTGTTTCTG;

(SEQ ID NO: 90)
(b) ND6-R: CTAATTCCCCCGAGCAATCTC.
```

Figure 13:
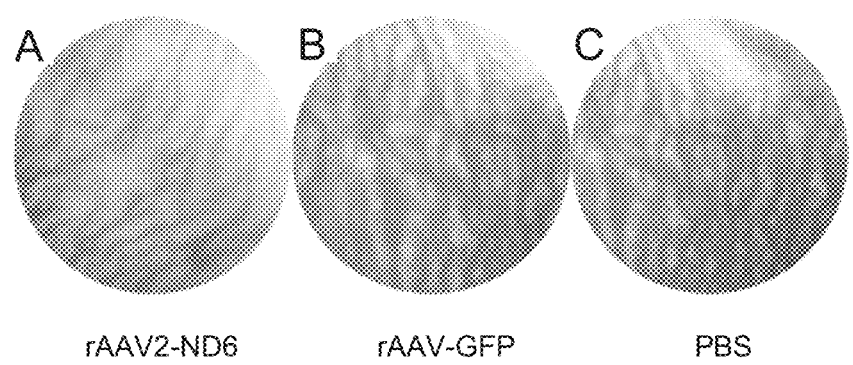
FIG. 13 shows the fundus photographic results for rabbits injected with rAAV2-ND6 (A), rAAV-GFP (B) and PBS, respectively.

The transfected and screened virus rAAV2-ND6 had a viral titer of $2.0 \times 10^{11}$ vg/mL. Similar to example 5, slit lamp examination and intraocular pressure measurement was performed on three groups of rabbits (A: rAAV2-ND6; B: rAAV-GFP; C: PBS) at 1, 7, and 30 days after the surgery (FIG. 13). No obviously abnormality, conjunctival congestion, secretions, or endophthalmitis were observed and the intraocular pressure were not elevated in all the rabbits.

Real-time PCR tests similar to example 3 was following using the following primers:

```
                                        (SEQ ID NO: 85)
(a) β-actin-S: CGAGATCGTGCGGGACAT;

(SEQ ID NO: 86)
(b) β-actin-A: CAGGAAGGAGGGCTGGAAC;

(SEQ ID NO: 91)
(c) ND6-S: AGTGTGGGTTTAGTAATG;

(SEQ ID NO: 92)
(d) ND4-A: TGCCTCAGGATACTCCTC.
```

The results show that the expression of ND6 for rAAV2-ND6 and control (PBS) was 0.59±0.06 and 0.41±0.03, respectively. The results showed that the transcription efficiency of the rAAV2-ND6 is higher than the control group (p<0.01).

Example 10—Optimized Opt_ND6 Sequence

Similar experimental methods in examples 1-6 were followed using the nucleic acid, opt_COX10*-opt_ND6-3'UTR (SEQ ID NO: 51), which is the combination (5' to 3') of opt_COX10* (SEQ ID NO: 3), opt_ND6 (SEQ ID NO: 10), and 3'UTR (SEQ ID NO: 13).

Figure 14:
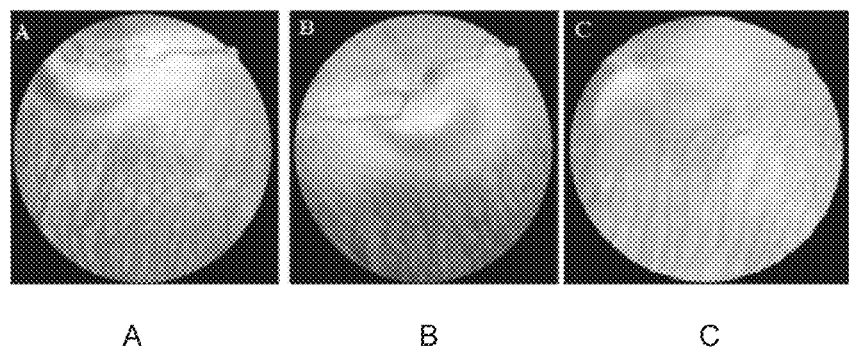
FIG. 14 shows the fundus photographic results for rabbits injected with rAAV2-opt_ND6 (A), rAAV2-ND6 (B), rAAV-EGFP (C), respectively.

Three groups of rabbits were injected: A: $10^{10}$ vg/50 µl of rAAV2-opt_ND6, B: $10^{10}$ vg/50 µl of rAAV2-ND6 (example 9), and C: $10^{10}$ vg/50 µl of rAAV2-EGFP. FIG. 14 shows the fundus photographic results for rabbits injected with rAAV2-opt_ND6 (A), rAAV2-ND6 (B), rAAV-EGFP (C), respectively. No obviously abnormality, conjunctival congestion, secretions, or endophthalmitis were observed and the intraocular pressure were not elevated in all the rabbits.

Real-time PCR tests similar to example 3 was following using the following primers:

```
                                        (SEQ ID NO: 93)
(a) β-actin-F: CTCCATCCTGGCCTCGCTGT;

(SEQ ID NO: 94)
(b) β-actin-R: GCTGTCACCTTCACCGTTCC;
```

-continued (c) ND6-F: GGGTTTTCTTCTAAGCCTTCTCC;  (SEQ ID NO: 95)

(d) ND6-R: CCATCATACTCTTTCACCCACAG;  (SEQ ID NO: 96)

(e) opt_ND6-F: CGCCTGCTGACCGGCTGCGT;  (SEQ ID NO: 97)

(f) opt_ND6-R: CCAGGCCTCGGGGTACTCCT.  (SEQ ID NO: 98)

Figure 15:
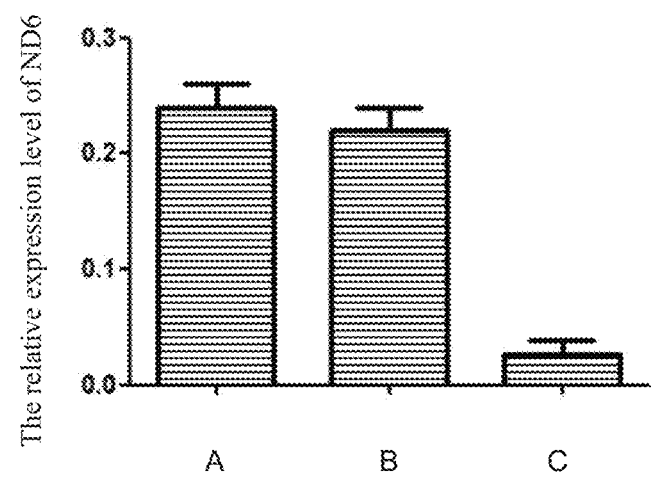
FIG. 15 shows the relative ND6 expression in rabbit optic nerve cells: rAAV2-opt_ND6 (A), rAAV2-ND6 (B), and rAAV-EGFP (C).
Figure 16:
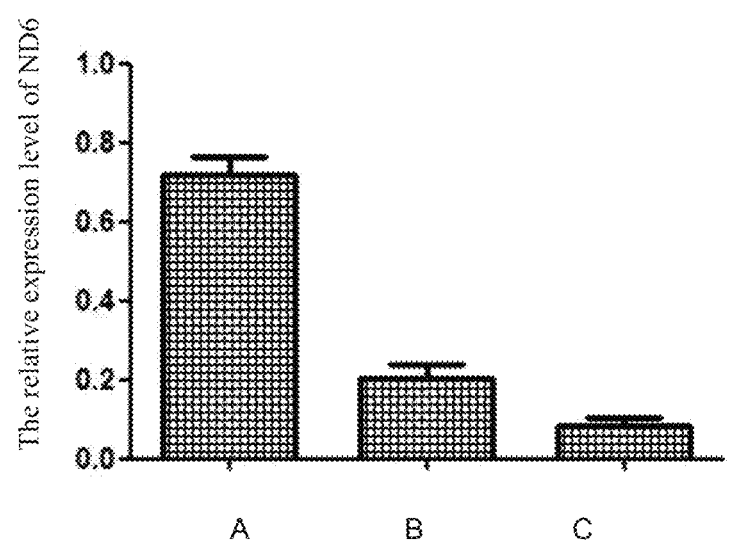
FIG. 16 shows the relative ND6 expression by western blot: rAAV2-opt_ND6 (A), rAAV2-ND6 (B), and rAAV-EGFP (C).

As shown in FIG. 15, rAAV2-opt_ND6 (A) and rAAV2-ND6 (B) both had higher (p<0.05) relative ND6 expression levels than the control group (C). rAAV2-opt_ND6 (A) had a little higher relative ND6 expression levels than rAAV2-ND6 (B). As shown in the western blot in FIG. 16, rAAV2-opt_ND6 (A) had more than 3 times higher relative ND6 expression levels than rAAV2-ND6 (B).

Experimental methods were the same as example 8, where the recombinant nucleic acids, COX10-ND6-3'UTR (SEQ ID NO: 21) and opt_COX10*-opt_ND6-3'UTR (SEQ ID NO: 51), were replaced by OPA1-ND6-3'UTR (SEQ ID NO: 77) and OPA1-opt_ND6-3'UTR (SEQ ID NO: 79). It was found that, the optimized ND6 sequence has significantly improved transcription and translation efficiencies, expression levels, as well as higher efficacy and safety in treating LHON.

Example 11—ND1 and Opt_ND1 Sequences

Similar experimental methods in examples 1-6 were followed using rAAV2-ND1, COX10-ND1-3'UTR (SEQ ID NO: 25), which is the combination (5' to 3') of COX10 (SEQ ID NO: 1), ND1 (SEQ ID NO: 11), and 3'UTR (SEQ ID NO: 13); and rAAV2-opt_ND1, opt_COX10*-opt_ND1-3'UTR (SEQ ID NO: 55), which is the combination (5' to 3') of opt_COX10* (SEQ ID NO: 3), opt_ND1 (SEQ ID NO: 12), and 3'UTR (SEQ ID NO: 13).

The plasmid screening for COX10-ND1-3'UTR (SEQ ID NO: 25) used the following primers:

(a) ND1-F: ATGGCCGCATCTCCGCACACT,  (SEQ ID NO: 99)

(b) ND1-R: TTAGGTTTGAGGGGGAATGCT,  (SEQ ID NO: 100)

The plasmid screening for opt_COX10*-opt_ND1-3'UTR (SEQ ID NO: 55) used the following primers:

(a) ND1-F: AACCTCAACCTAGGCCTCCTA,  (SEQ ID NO: 101)

(b) ND1-R: TGGCAGGAGTAACCAGAGGTG,  (SEQ ID NO: 102)

Three groups of rabbits were injected: A: $10^{10}$ vg/50 µl of rAAV2-opt_ND1, B: $10^{10}$ vg/50 µl of rAAV2-ND1 (example 9), and C: $10^{10}$ vg/50 µl of rAAV2-EGFP. No obviously abnormality, conjunctival congestion, secretions, or endophthalmitis were observed and the intraocular pressure were not elevated in all the rabbits.

Real-time PCR tests similar to example 3 was following using the following primers:

(a) ND1-F: AGGAGGCTCTGTCTGGTATCTTG;  (SEQ ID NO: 103)

(b) ND1-R: TTTTAGGGGCTCTTTGGTGAA;  (SEQ ID NO: 104)

(c) opt_ND1-F: GCCGCCTGCTGACCGGCTGCGT;  (SEQ ID NO: 105)

(d) opt_ND1-R: TGATGTACAGGGTGATGGTGCTGG;  (SEQ ID NO: 106)

Figure 17:
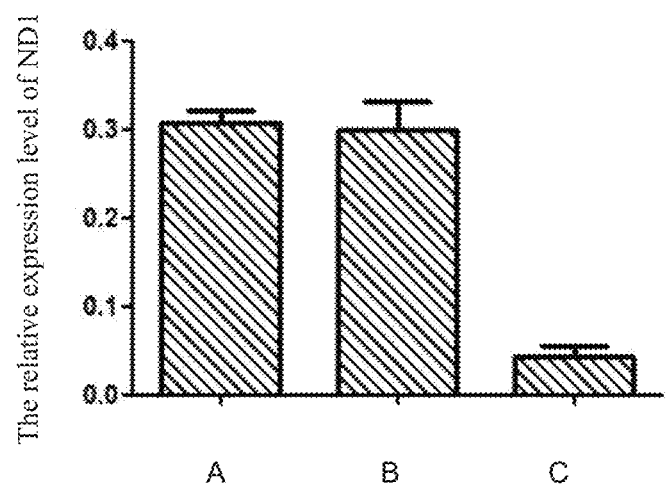
FIG. 17 shows the relative ND1 expression in rabbit optic nerve cells: rAAV2-opt_ND1 (A), rAAV2-ND1 (B), and rAAV-EGFP (C).
Figure 18:
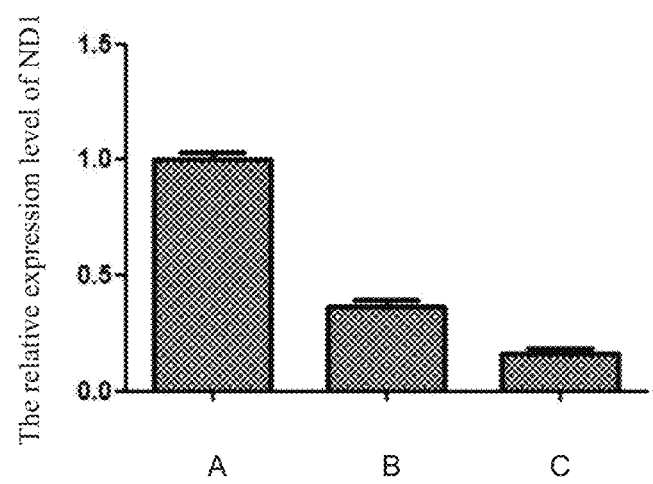
FIG. 18 shows the relative ND1 expression by western blot: rAAV2-opt_ND1 (A), rAAV2-ND1 (B), and rAAV-EGFP (C).

As shown in FIG. 17, rAAV2-opt_ND1 (A) and rAAV2-ND1 (B) both had higher (p<0.05) relative ND1 expression levels than the control group (C). As shown in the western blot in FIG. 18, rAAV2-opt_ND1 (A) had more than 2 times higher relative ND6 expression levels than rAAV2-ND1 (B).

Experimental methods were the same as example 8, where the recombinant nucleic acids, COX10-ND1-3'UTR (SEQ ID NO: 25) and opt_COX10*-opt_ND1-3'UTR (SEQ ID NO: 55), were replaced by OPA1-ND1-3'UTR (SEQ ID NO: 81) and OPA1-opt_ND1-3'UTR (SEQ ID NO: 83). It was found that, the optimized ND1 sequence has significantly improved transcription and translation efficiencies, expression levels, as well as higher efficacy and safety in treating LHON.

Example 12—Other Fusion Proteins

Similar experimental methods in examples 1-6 can be followed using other fusion proteins as set forth in SEQ ID NO: 15-84. And similar results are expected to be achieved.

Example 13—Formulation Development

AAV2 virus samples were used to screen different AAV formulations. The stability of the different AAV formulations were evaluated using the StepOnePlus real-time PCR system. The viral titer of each formulation under a freeze/thaw cycle condition was measured.

First, three different formulations were tested under 1, 2, 3, 4, and 5 freeze/thaw cycles and the viral titers were measured and summarized in Table 3. The three formulations tested were: A: phosphate-buffered saline (PBS); B: 1% α,α-trehalose dehydrate, 1% L-histidine monohydrochloride monohydrate, and 1% polysorbate 20; and C: 180 mM NaCl, 10 mM $NaH_2PO_4$/$Na_2HPO_4$, and 0.001% poloxamer 188, pH 7.3. As shown in Table 3, formulation C has the lowest relative standard deviation (RSD) after 5 freeze/thaw cycles, indicating superior stability as an AAV formulation.

TABLE 3

| Viral titers of formulations A, B, and C | | | | | | | |
|---|---|---|---|---|---|---|---|
| | 0 cycle | 1 cycle | 2 cycles | 3 cycles | 4 cycles | 5 cycles | RSD |
| Formulation A | 1.15E+11 | 9.48E+10 | 6.16E+10 | 2.90E+10 | 1.56E+10 | 5.26E+09 | 83.18 |
| Formulation B | 4.25E+11 | 5.12E+11 | 6.66E+11 | 4.30E+11 | 4.77E+11 | 4.20E+11 | 19.30 |
| Formulation C | 4.96E+11 | 6.91E+11 | 7.69E+11 | 6.82E+11 | 6.83E+11 | 7.27E+11 | 13.90 |

As shown in Table 3, formulation C has the lowest relative standard deviation (RSD) after 5 freeze/thaw cycles, indicating superior stability as an AAV formulation.

Second, another group of three different formulations were tested under 1, 2, 3, 4, and 5 freeze/thaw cycles and the viral titers were measured and summarized in Table 4. The three formulations tested were: D: phosphate-buffered saline (PBS), pH 7.2-7.4; E: PBS and 0.001% poloxamer 188, pH 7.2-7.4; and F: 80 mM NaCl, 5 mM $NaH_2PO_4$, 40 mM $Na_2HPO_4$, 5 mM $KH_2PO_4$ and 0.001% poloxamer 188, 7.2-7.4.

TABLE 4

Viral titers of Formulations of D, E, and F

|  | 0 cycle | 1 cycle | 2 cycles | 3 cycles | 4 cycles | 5 cycles | RSD |
|---|---|---|---|---|---|---|---|
| Formulation D | 1.13E+10 | 4.62E+09 | 2.25E+09 | 1.25E+09 | 1.01E+09 | 9.48E+08 | 113.25 |
| Formulation E | 4.72E+10 | 5.48E+10 | 5.33E+10 | 5.33E+10 | 4.94E+10 | 4.08E+10 | 10.53 |
| Formulation F | 6.61E+10 | 6.08E+10 | 6.47E+10 | 6.84E+10 | 6.52E+10 | 6.05E+10 | 4.81 |

As shown in Table 4, formulation F has the lowest relative standard deviation (RSD) after 5 freeze/thaw cycles, indicating superior stability as an AAV formulation. Overall, formulation F also has the lowest RSD among all tested formulations and can be used as the AAV formulation for future development.

A third group of formulations were tested under 1, 2, 3, and 4 freeze/thaw cycles and the viral titers were determined using qRT-PCR. In addition to formulation F, the two other formulations tested were: G: 8.4 mM $KH_2PO_4$, 5.6 mM $Na_2HPO_4$ and 154 mM NaCl; H: 8.4 mM $KH_2PO_4$, 5.6 mM $Na_2HPO_4$, 0.15 M NaCl and 0.001% poloxamer 188, pH 7.2-7.4.

HEK293 Cell Culture and rAAV2 Transduction:

A cryotube containing HEK293 cells was thawed and dispensed into a cell culture flask containing high-glucose DMEM media supplemented with 10% fetal bovine serum. HEK293 cells were incubated for 24 hours at 37° C. in 5% $CO_2$. HEK293 cells were seeded into 24 well plates and transduced with the AAV2 formulation F, G, or H at a MOI of 20000. The control group was incubated with PBS alone.

RNA Extraction:

Total RNA was isolated from transduced HEK293 cells using TRIZOL and cDNA was synthesized by reverse transcription. Primers for RT-PCR analysis were as follows:

```
                                       (SEQ ID NO: 93)
(a) β-actin-F: CTCCATCCTGGCCTCGCTGT (SEQ ID NO: 94)
(b) β-actin-R: GCTGTCACCTTCACCGTTCC (SEQ ID NO: 165)
(c) ND4-F: ATCTCCGCACACTCTCTCCTCA (SEQ ID NO: 166)
(d) ND4-R: TAGGTTGTTGTTGATTTGGTT
``` qRT-PCR: A reaction mix was prepared containing 10 μL of TB Green, 0.3 μL of forward and reverse primers, 0.4 μL ROX Reference Dye, 4.3 μL EASY Dilution and 5 μL of cDNA. Quantitative RT-PCR was performed by pre-denaturation at 95° C. for 10 minutes followed by 40 cycles of 95° C. for 15 seconds and 60° C. for 1 minute. The fluorescence signals were collected during the extension phase of each cycle. The ND4 expression level (relative quantification) can be calculated as $2^{-(Ct(ND4,sample)-Ct(\beta-actin,sample)-Ct(ND4,control)-Ct(\beta-actin,control))}$.

TABLE 17

ND4 Expression normalized to PBS control

|  | original | 1 cycle | 2 cycles | 3 cycles | 4 cycles | average | RSD |
|---|---|---|---|---|---|---|---|
| Formulation G | 13.21 | 11.27 | 12.77 | 14.95 | 13.37 | 13.05 | 10.11% |

TABLE 17-continued

ND4 Expression normalized to PBS control

|  | original | 1 cycle | 2 cycles | 3 cycles | 4 cycles | average | RSD |
|---|---|---|---|---|---|---|---|
| Formulation H | 105.39 | 104.60 | 71.80 | 102.28 | 107.29 | 96.0175 | 15.53% |
| Formulation F | 122.45 | 35.19 | 89.60 | 78.85 | 30.93 | 81.5225 | 47.28% |

As shown in Table 17, formulations F and H showed higher relative expression of ND4 after 4 freeze/thaw cycles, especially formulation H, which indicated superior stability and transduction efficiency as an AAV formulation.

Example 14—Preparation of Recombinant Adeno-Associated Virus

A recombinant adeno-associated virus rAAV2/2-ND4 was prepared according to the methods described in Example 1.

Plasmid preparation: The fusion nucleic acid according to SEQ ID NO: 6 was synthesized by Chengdu Qingke Yuxi Biotechnology Co., Ltd. The full-length gene was amplified by PCR, and the sticky terminus was formed on the fusion gene by EcoRI/SalI digestion. The fusion gene was inserted into the adeno-associated virus carrier pSNaV with the EcoRI/SalI restriction site, that is, pSNaV/rAAV2/2-ND4 (hereinafter referred to as pAAV2-ND4). Briefly, after incubation at 37° C., the LB plate showed blue colonies and white colonies, wherein the white colonies were recombinant clones. White colonies were picked and added to LB liquid medium containing ampicillin (100 mg/L), and cultured at 37° C. at 200 rpm for 8 hours. After culturing, the bacterial solution was obtained and the plasmid was extracted. In the plasmid extraction step, EcoRI/SalI enzyme digestion was used with reference to Biomega instructions.

Cell transfection: HEK293 cells were seeded in 225 $cm^2$ cell culture flasks at a density of $3.0×10^7$ cells/mL in DMEM containing 10% bovine serum and incubated overnight at 37° C. and 5% $CO_2$. When the cells reached 80-90% confluency, the medium was discarded and the cells were transfected with pAAV2-ND4 (for specific transfection steps, see Example 1) using the PlasmidTrans II (VGTC) transfection kit. The cells were harvested 48 hours following transfection.

Collection and concentration of virus: The transduced cells were collected with medium into a 15 mL centrifuge tube and centrifuged at 1000 rpm for 3 minutes. The cells and supernatant were separated, the supernatant was additionally stored, and the cells were resuspended in 1 mL of PBS. The cell suspension was repeatedly frozen in a dry ice ethanol bath or liquid nitrogen bath and thawed in a 37° C. water bath four times for 10 minutes each, and slightly vortexed after each melting. The supernatants were centrifuged at 10,000×g to remove cell debris, transferred to a new centrifuge tube and filtered using a 0.45 μm filter to remove impurities. A half volume of 1M NaCl 10% PEG8000 solution was added to the supernatant, thoroughly mixed, and kept overnight at 4° C. The following day, the virus was centrifuged at 12,000 rpm for 2 h, the supernatant was discarded, and the precipitated virus was resuspended in an appropriate amount of PBS solution and filtered using a 0.22 μm filter for sterilization. The remaining plasmid DNA was removed by digestion with Benzonase Nuclease (50 U/mL) at 37° C. for 30 minutes and refiltered with a 0.45 μm filter head to obtain concentrated rAAV2 virus.

Purification of virus: Solid CsCl was added to the concentrated virus to a density of 1.41 g/mL (refractive index was 1.372). The sample was placed in an ultracentrifuge tube and the remaining space of the centrifuge tube was filled with pre-formulated 1.41 g/mL CsCl solution. The sample was centrifuged at 175,000×g for 24 hours to form a density gradient to collect samples of different densities. The viral titer of the samples was determined and components enriched with rAAV2 particles were collected. This process was repeated, loading the virus into a 100 kDa dialysis bag and stored overnight at 4° C. for dialysis.

Example 15—Gene Therapy for Treatment of Leber's Hereditary Optic Neuropathy A multicenter prospective clinical trial was performed to assess the efficacy of rAAV-ND4 in patients meeting the diagnostic criteria for LHON.
Study Design
Research Site:
This study was a clinical trial, and the genetic diagnosis was performed at the Genetic Diagnosis Center at Tongji Hospital. Ophthalmic examination was completed in the ophthalmology examination room of Tongji Hospital. The whole body examination (partial) was performed by designated personnel and standard equipment in the laboratory.

Patient recruitment guidelines: Patients were required to be diagnosed as LHON by genetic testing for the 11778 site mutation. The subjects were age 10-65 years old, male or female. Patients were observed at least three months for an improvement in vision. Patients were excluded from the study if they had a terminal disease, previous ocular disease history, allergies to essential drugs used during the treatment, or demonstrated positive results in an AAV2 humoral response test. Patients were required to sign the Informed Consent Form for Leber's Gene Therapy and Informed Consent for Vitreous Injection.
Pre-Operative Guidelines:
Medical staff were advised to disinfect the operating room and medical supplies before surgery, and prepare for consumables during the operation and to strictly abide by the surgical grading system and aseptic operation principles.

Pre-Operative Examination:
Patients underwent a whole body examination prior to surgery including blood analysis, urine analysis, liver and kidney function, blood coagulation function, infectious disease screening, immune analysis (cell immunity: CD3, CD4, CD8; humoral immunity: IgA, IgM, IgG); electrocardiogram and chest fluoroscopy. Patients additionally underwent pre-operative ophthalmologic examinations including visual acuity, intraocular pressure, slit lamp examination, fundus examination, fundus photography, anterior segment photography, optic nerve OCT, visual field examination, and VEP. These series of examinations were performed not less than three times within 6 months. Patients were screened for the mtDNA base pair mutation G11778A in Leber's disease. That is, the arginine of the NADH dehydrogenase subunit 4 protein was converted into histidine, resulting in a loss-of-function disorder, an optic nerve injury, and Leber hereditary optic nerve lesion, which has a high incidence and a poor prognosis (see Chinese Patent CN 102634527 B). An AAV2 humoral immunological assay (described below in Examples 16) was also performed prior to treatment.

Pre-Operative Treatment:
Patients receiving LHON gene therapy were administered a daily 32 mg/60 kg dose of the oral steroid, MEDROL®, once a day starting 7 days before surgery. An AAV2 humoral immunological examination using patient serum was performed to determine if the pre-treatment rAAV2 immunity of the patient was low before beginning rAAV2 treatment. Antibiotic eye drops and eye ointment were applied on the day before surgery to wash the lacrimal conjunctival sac.
Intravitreal Injection:
The clinical grade rAAV2-ND4 dosage form (State Key Laboratory of Biotherapy of Sichuan University) was used as an injection. The recombinant adeno-associated virus rAAV2-ND4 (SEQ ID NO: 6) was prepared as described in Example 14. The dose was $1 \times 10^{10}$ vg/0.05 mL. The amount of drug for intravitreal injection under local anesthesia was 0.05 mL. A single dose of the drug was administered by intraluminal injection under local anesthesia. Disinfection measures and surgical consumables were prepared in a laminar flow operation room. Routine disinfection of the towel, face, and eye was performed before surgery, and the eye was marked for injection.

Gene drugs were managed by designated personnel. Before the drug was administered, the information of the patient was checked to make sure that the drug packaging was complete and non-polluted, and the drug packaging was strictly sterilized. When the drug was extracted from the vial, the operation was slow and smooth, and the drug was pumped once, and the bottle wall was not repeatedly sucked and touched to avoid drug contamination. After the drug was extracted from the vial, the injection was completed within half an hour. After the injection was completed, the drug package and the remaining drug were retained and stored at −20° C. for reference. Absolute aseptic operation was required during the drug extraction process. If the drug fell to the ground, or the suction needle touched the contaminated area, the drug was discarded. Any drug with a risk of contamination was not injected into the patient's vitreous cavity.

Specific operating guidelines for vitreous cavity injection: preparation of instruments and drugs before injection, and assistants to perform routine vitreous cavity injection operations such as disinfection and drape. The drug was removed from dry ice and held tightly by hand for 2-3 minutes until the drug thawed into liquid. The bottle cap and bottle were wiped with gauze containing iodophor twice for sterilization, then dry gauze was used to wipe the bottle and the bottle cap. It should be noted that the wiping was clockwise to prevent the bottle mouth from opening and iodophor infiltration. After completing the disinfection, the bottle cap was opened, and the operator took the drug with an insulin needle, and the volume was adjusted to 0.05 mL. At the same time, the assistant prepared for anesthesia injection, disinfection, reclamation, etc., and washed the conjunctival sac with 0.5% povidone iodine 3 times, and injected the vitreous cavity according to the vitreous cavity injection guidelines. Immediately after withdrawal of the needle, the injection site was pressed with a cotton swab and massaged for 10 seconds to prevent drug leakage.

After injecting the drug, an antibiotic eye ointment was applied to the injected eye and the eye was covered with a cotton swab. The patient laid flat for 20 min and then returned to the ward. The patient was told not to rub their eyes. After completing the injection, attention was paid to the recovery of the patient following gene therapy.

Post-Operative Medication:

Systemic Medication:

(a) MEDROL® tablet, 32 mg/60 kg, for 7 days prior to the surgery;

(b) Sodium creatine phosphate iv drip, 2 g/60 kg, for 3 days after the surgery (including the day of surgery);

(c) SOLU-MEDROL® iv drip, 80 mg/60 kg, for 3 days after the surgery (including the day of surgery);

(d) On the third day after surgery, SOLU-MEDROL® was changed to MEDROL®, po, 40 mg/60 kg; once a day for 4 days;

(e) In the second week after surgery, MEDROL® was reduced, po, 32 mg/60 kg; once a day for 7 days;

(f) In the third week after surgery, MEDROL® was reduced, po, 24 mg/60 kg; once a day for 7 days;

(g) In the fourth week after surgery, MEDROL® was reduced, po, 16 mg/60 kg; once a day for 7 days;

(h) In the fifth week after surgery, MEDROL® was reduced, po, 8 mg/60 kg; once a day for 7 days;

(i) In the sixth week after surgery, MEDROL® was reduced, po, 6 mg/60 kg; once a day for 7 days;

(j) In the seventh week after surgery, MEDROL® was reduced, po, 4 mg/60 kg; once a day for 7 days.

Topical Medications:

(a) tobramycin dexamethasone: eye drops, once a day for 7 days;

(b) tobramycin dexamethasone eye ointment: eye drops, once a day for 7 days.

Figure 19:
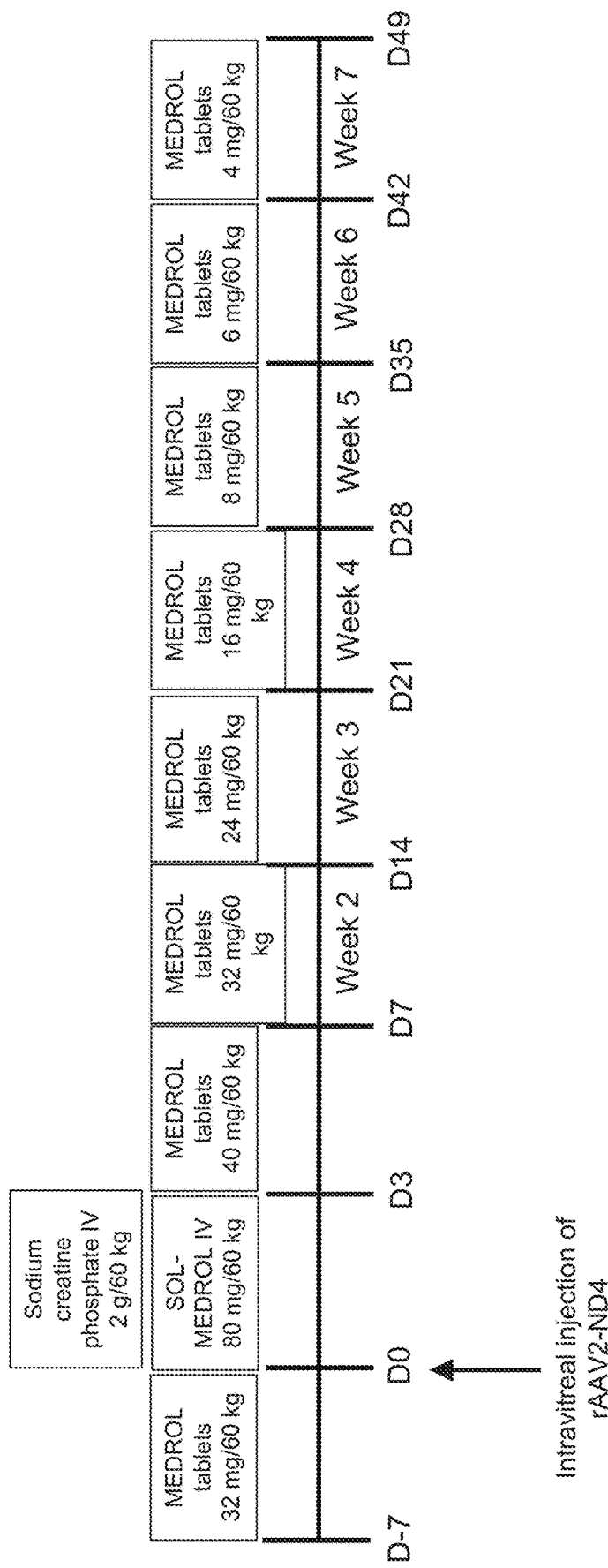
FIG. 19 shows a first exemplary steroid dosing schedule.

A schematic showing the medication dosing schedule is provided in FIG. 19.

Post-Operative Examination and Review

The first day after surgery, patients underwent post-operative ophthalmic examination including visual acuity, intraocular pressure, slit lamp examination, fundus examination anterior segment photography and fundus photography. The second day after surgery, patients underwent testing for visual acuity, intraocular pressure, and slit lamp and fundus examination. The third day after surgery, patients underwent testing for visual acuity, intraocular pressure, and slit lamp and fundus examination.

Patients receiving LHON eye gene therapy were informed to go to the hospital for consultation at a time reserved with the physician or if they felt any discomfort. Post-operative examinations were performed by professionals. All inspection reports were reviewed and signed by medical personnel. It was forbidden for non-professionals or medical personnel who were not familiar with the field to check the patient or answer the patient's condition without authorization.

Before all inspections, alcohol was used to wipe the contact area between the instrument and the patient. After the examination was completed, antibiotic eye drops were given. It was forbidden to drop contaminated eye drops and eye drops into the conjunctival sac.

Results

Efficacy Evaluation:

The International Standard Guide for Improving Vision provides that a visual acuity improvement by 0.3 log MAR (15 letters) is considered a significant improvement and an improvement of 0.2 log MAR (10 letters) is considered an improvement. An improvement below 0.1 log MAR (5 letters) signifies no improvement. A treatment resulting in a vision improvement of 0.2 log MAR is considered effective.

In a first phase of the study, a total of 145 patients were treated. Within one day of treatment, 24 cases (16.55%) showed a significant improvement of 0.3 log MAR and 6 cases (4.14%) showed an improvement of 0.2 log MAR. The total efficacy one day after treatment was 20.69%, with vision loss occurring in 2 cases (1.38%). Within 2 days of treatment, 35 cases (24.14%) showed a significant improvement of 0.3 log MAR, 12 cases (8.22%) showed an improvement of 0.2 log MAR, and the total efficacy was 32.41%. Within 3 days of treatment, 42 cases (28.96%) showed a significant improvement of 0.3 log MAR, 11 cases (7.59%) showed an improvement of 0.2 log MAR, and the total efficacy was 36.55%. These results are summarized below in Table 5.

TABLE 5

Treatment efficacy 3 days post-surgery

| | Increase 0.3 logMAR | Increase 0.2 logMAR | Vision loss | Total efficiency (%) |
|---|---|---|---|---|
| First day | 24 cases (16.55%) | 6 cases (4.14%) | 2 cases (1.38%) | 20.69 |
| Second day | 35 cases (24.14%) | 12 cases (8.22%) | None | 32.41 |
| Third day | 42 cases (28.96%) | 13 cases (7.59%) | None | 42.63 |

129 patients completed the review one month after surgery. Of these patients, 55 patients (42.66%) had a significant improvement of 0.3 log MAR in vision, and 16 (12.40%) had an improvement of 0.2 log MAR in vision. The one month review indicated that the total effective rate of improved vision was 55.04%. The vision of 9 patients (6.98%) decreased. 67 patients completed the review after three months after surgery. Of these patients, 37 patients (55.22%) had a significant improvement of 0.3 log MAR in vision and 8 patients (11.94%) had an improvement of 0.2 log MAR in vision. The three month review indicated that the total effective rate of improved vision was 67.16%. The vision of 4 patients (5.97%) decreased. More recently, a total of 159 were treated: 64.66% of the patients had a significant improvement of 0.3 log MAR in vision, and 6.89% of the patients had an improvement of 0.2 log MAR in vision. Efficacy of treatment is shown below in Table 6.

TABLE 6

Treatment efficacy 1 and 3 months post-surgery

| | Increase 0.3 logMAR | Increase 0.2 logMAR | Vision loss | Total efficiency (%) |
|---|---|---|---|---|
| One month review (n = 129) | 55 cases (42.66%) | 13 cases (11.02%) | 9 cases (6.98%) | 55.04 |

TABLE 6-continued

Treatment efficacy 1 and 3 months post-surgery

|  | Increase 0.3 logMAR | Increase 0.2 logMAR | Vision loss | Total efficiency (%) |
|---|---|---|---|---|
| Three month review (n = 67) | 37 cases (55.22%) | 8 cases (11.94%) | 4 cases (5.97%) | 67.16 |
| Six month review | 64.66% | 6.89% | n.a. | 71.55% |

Safety results: A total of 143 patients were treated in an early phase of the study, including 7 Argentine international patients. The onset time was divided into two years and two years or more, and safety tests were performed regularly. We examined ocular adverse reactions three days, one month and three months after surgery. There were 21 patients with mild ocular hypertension three days after surgery, which was a mild complication and recovered spontaneously without other serious complications. There were 17 patients with ocular hypertension one month after surgery, and only 5 patients with ocular hypertension three months after surgery. There were no other adverse reactions. Adverse reactions are summarized in Table 7.

TABLE 7

Complications of gene therapy for LHON

|  | 3 days post-surgery (n = 141) | 1 month post-surgery (n = 102) | 3 months post-surgery (n = 41) |
|---|---|---|---|
| Anterior chamber inflammation | 0 | 0 | 0 |
| Vitritis | 0 | 0 | 0 |
| Ocular hypertension | 21 | 17 | 5 |
| Cataract removal | 0 | 0 | 0 |
| Keratitis | 0 | 0 | 0 |
| Vitreous hemorrhage | 0 | 0 | 0 |
| Allergic conjunctivitis | 0 | 0 | 0 |
| Eye pain | 0 | 0 | 0 |

A total of 10 Argentine patients were treated. A safety examination conducted on day 3 after the surgery showed that there was no safety issue. Another safety examination conduct on day 10 showed that one subject had mild ocular hypertension, which returned to normal following drug treatment within one month. An efficacy examination was also conducted on day 3 after the surgery. The improvement of 0.3 log MAR and 0.2 log MAR in vision among these Argentine patients were 50% and 10%, respectively. The improvement of 0.3 log MAR in vision at one-month, three-month, and six-month were 60%, 90%, and 100%, respectively.

A similar study was conducted by GenSight Biologics: 15 subjects with the ND4-G11778A mutation received a single intravitreal injection of rAAV2/2-ND4 in the worse-seeing eye. The study design included an initial follow-up period of 48 weeks, followed by a long-term period of an additional 4 years. Patients were divided into two groups: 6 months and 6 to 12 months at the time of onset. In general, patients with shorter onset time had less optic nerve cell damage and the best prognosis for gene therapy. As onset time increased, the prognosis was worse. In the 15 patients treated, there were 10 cases of ocular hypertension, 2 patients with selective cataract removal, 2 patients with severe anterior chamber inflammation and vitritis events, and many other adverse reactions such as keratitis, vitreous hemorrhage, allergic conjunctivitis and eye pain (see Table 7). See Vignal et al., Ophthalmology 2018; 6:945-947.

In a separate study by Guy et al., 14 patients with LHON received a single intravitreal injection of AAV2(Y444,500,730F)-P1ND4v2 with 18 months of follow-up. The patients were separated into two groups, one for onset time of more than 12 months and the other for onset time of less than 12 months. Similar to GenSight Biologics, patients with an onset of less than 12 months had a better prognosis for gene therapy. Two cases of uveitis, 1 case of keratitis, 1 case of eye pain and 1 case of ocular hypertension was observed. See Guy et al., Ophthalmology 2017; 124:1621-1634. As shown in Table 8 below, the methods of the present disclosure resulted in fewer post-surgical complication than the methods of either GenSight Biologics or Guy et al.

TABLE 8

Comparison of complications of Leber's disease gene therapy

|  | 3 days after surgery (n = 141) | 1 mth after surgery (n = 102) | 3 mths after surgery (n = 41) | GenSight Biologics (n = 15) | Guy et al. (n = 14) |
|---|---|---|---|---|---|
| Cataract removal | 0 | 0 | 0 | 2 | No statistics |
| Uveitis | 0 | 0 | 0 | 0 | 2 |
| Vitritis | 0 | 0 | 0 | 13 | No statistics |
| Keratitis | 0 | 0 | 0 | 7 | 1 |
| Anterior chamber inflammation | 0 | 0 | 0 | 14 | No statistics |
| Vitreous hemorrhage | 0 | 0 | 0 | 2 | No statistics |
| Eye pain* | 0 | 0 | 0 | 2 | 1 |
| Allergic conjunctivitis* | 0 | 0 | 0 | 3 | No statistics |
| Ocular hypertension* | 21 | 17 | 5 | 10 | 1 |

*Mild complications (could be self-recovered)

Notably, the methods of the present disclosure did not result in any post-surgical cases of uvetis. Uvetis is considered a serious complication and many types of uveitis require treatment with hormones and immunosuppressive agents. In the West, about a quarter of uveitis patients require treatment of hormones and immunosuppressive agents, and even then, 35% of patients have vision disability. Ocular hypertension is considered a mild complication and is the most common complication in ophthalmic surgery. Under normal circumstances, patients self-recover and the intraocular pressure returns to normal levels.

In summary, the methods of the present disclosure provided a safe and effective treatment for LHON, and no severe complications were observed.

Similar experiments are performed to assess the efficacy of rAAV2 comprising the nucleic acid sequence of SEQ ID NO: 7. These results are expected to show that administration of rAAV2-SEQ5 is a safe and effective treatment for ocular diseases.

Example 16—Diagnostic Assay for LHON Gene Therapy

In the present example, green fluorescent protein was used as a reporter gene in the rAAV2 vector (rAAV2-GFP).

HEK293T cells were cultured with serum from different patients and were transduced with rAAV2-GFP. Transduction efficiency of rAAV2 was determined using RT-PCR or flow cytometry in order to determine the ability of the rAAV2 vector to infect cells in the presence of patient serum. The method of the present disclosure can be used to screen patients prior to treatment with the rAAV2 vector to identify those patients with low immune responses to the rAAV2 vector (i.e., high rAAV2 vector transduction) and high immune responses to the rAAV2 vector (i.e., low rAAV2 vector transduction). In this example, patients with low immune responses to the rAAV2 vector were categorized as patients suitable for treatment with the rAAV2 vector.

Preparation of rAAV2-GFP Virus

HEK293T cells were seeded at a density of $3.0\times10^7$ cells/mL in 225 cm$^2$ cell culture flasks in DMEM containing 10% bovine serum and cultured overnight in a 37° C. incubator containing 5% $CO_2$. When the HEK293T cells reached 80-90% confluency, the culture medium was discarded and cells were transfected with rAAV2-GFP using the Plasmid Trans II (VGTC) transfection kit. Two days following transfection, HEK293T cells were harvested, and the collected cells were re-suspended in PBS, frozen and thawed 3 times, then separated, concentrated and purified to obtain recombinant adeno-associated virus rAAV2-GFP. The titer was measured and the product was customized by Guangzhou Paizhen Biotechnology Co., Ltd.

Isolation of Patient Serum 2 mL of whole blood was collected from patients and centrifuged to isolate serum. The serum was separately added into two tubes and stored at −20° C. or −80° C. for later use. The remaining whole blood was placed in a test tube. Patient information was recorded.

HEK293T Cell Culture

Sterilization:

High temperature sterilization and UV disinfection of tips (1 mL, 5 mL, 0 mL) and EP tubes was carried out for a minimum of 30 minutes before usage. After sterilization, the tips and EP tubes were stored up to 12 hours, which did not result in cell contamination.

Cell Culture Media Preparation:

1:9 media preparation or 1:4 media preparation, kept at 4° C., wherein 1:9 media preparation: 5 mL fetal calf serum, 45 mL DMEM high glucose cell culture medium, and 0.5 mL or 1 mL penicillin (10000 U/mL) and streptomycin (10000/mL) were added to 50 mL centrifuge tube and mixed; 1:4 dosing: 10 mL fetal calf serum, 40 mL DMEM high glucose cell culture medium and 0.5 mL or 1 mL penicillin (10000 U/mL) and streptomycin (10000/mL) were added to a 50 mL centrifuge tube and mixed.

Passage and Seeding of HEK293T Cells

A cryotube containing HEK293T cells was removed from liquid nitrogen and rapidly transferred to a 37° C. water bath for 1-2 min. After thawing, the outer part of the cryotube was wiped with alcohol and placed in an ice bath at 4° C. The cryotube was occasionally shaken in the water bath to ensure even heat distribution.

After disinfection, the HEK293T cells were transferred to a centrifuge tube and 10 times the volume of high glucose DMEM was added to the cells. The suspension was then centrifuged at 1000 rpm for 5 min, the supernatant was discarded, and the HEK293T cells were resuspended in culture medium. The cell suspension was then transferred to a 4 mL culture medium vial and the vial was transferred to the incubator to allow the HEK293T cells to adhere to the wall of the vial. After the cells adhered, the medium was carefully removed and 5 mL of fresh medium was added to continue the culture. After HEK293T cells were incubated for 24 h, the culture medium was replaced and the cells were grown until a monolayer formed, which was then used for cell passage. The tissue culture media was replaced every 2 to 3 days by removing old media, rinsing the cells with PBS 3 times, and adding newly-prepared medium to the cells.

Cell Passage in Flasks:

Once the cells reached confluency and had a round shape, the media was removed from the flask using a 10 mL pipette and the HEK293T cells were washed three times with 5 mL of PBS. After washing, 5 mL of EDTA was added to the cells, incubated for 3 min, and then 20 mL of media was rapidly added to the flask. Air was repeatedly blown into the culture using a 10 mL pipette until the cells were evenly resuspended. Half of the cell suspension was transferred to another flask and culture medium was added to a volume of 20 mL for both flasks.

Cell Passage in 24-Well Plate:

Once the cells reached confluency and had a round shape, the media was removed from the flask using a 10 mL pipette and the HEK293T cells were washed three times with 5 mL of PBS. After washing, 5 mL of EDTA was added to the cells, incubated for 3 min, and then 50 mL of media was rapidly added to the flask. Air was repeatedly blown into the culture using a 10 mL pipette until the cells were evenly resuspended. Two mLs of the cell suspension was distributed into each well of the 24-well plate, the flask was fixed to a total volume of 20 mL, and both the flask and 24-well plate were placed in the incubator to continue the culture. Once the HEK293T cells in the 24-well plate reached confluency (2-3 days later), the cells received 1.7 mL of fresh media and were transduced with rAAV2-GFP virus as described below.

Transduction of rAAV2-GFP in HEK293T Cells in the Presence of Patient Serum

Viral dilution: 1 μL of rAAV2-GFP was diluted to 40 μL of PBS and was added to 1960 μL of high glucose DMEM in a 4 mL EP tube. After the rAAV2-GFP dilution was prepared, the EP tube seal was kept at 4° C.

Patient serum and diluted rAAV2-GFP was prepared as follows:

(a) 1:20 group: 300 μL patient serum+300 μL culture medium+300 μL of the virus dilution (1:3 working dilution);

(b) 1:60 group: 100 μL patient serum+500 μL culture medium+300 μL of the virus dilution (1:9 working dilution);

(c) Control group: 600 μL culture medium (or 300 μL PBS+300 μL culture medium)+300 μL of the virus dilution.

rAAV2-GFP transduction: 300 μL of patient serum/rAAV2-GFP from the 1:20 group, 1:60 group, and the control groups was added to each well of HEK293T cells and incubated for 48 hours following transduction. The experiment was performed in triplicate for each group.

Example 17—RT-PCR Analysis of rAAV2-GFP Expression

Total RNA was isolated from transduced HEK293T cells using TRIZOL, and cDNA was synthesized by reverse transcription. Primers for RT-PCR analysis were designed using Primer Premier 5 and are as follows:

(a) β-actin-F: CCTAGAAGCATTTGCGGT (SEQ ID NO: 167)

(b) β-actin-R: GAGCTACGAGCTGCCTGA (SEQ ID NO: 168)

```
(c) GFP-F: ACAAGTTCAGCGTGTCCG
                                          (SEQ ID NO: 163)

(d) GFP-R: CTCGTTGGGGTCTTTGCT
                                          (SEQ ID NO: 164)
```

For qRT-PCR analysis, a reaction mix was prepared containing 5 μL of SYBR Green, 8 μL of ddH$_2$O, 1 μL each of forward and reverse primers, and 2.5 μL of cDNA. The reaction mix was added to a 0.2 mL PCR reaction tube at a total volume of 25 μL. Each sample was analyzed in triplicate. In order to reduce error, the reagents were mixed in each PCR reaction tube and then dispensed. After the sample was added, quantitative RT-PCR was performed by pre-denaturation at 95° C. for 1 s, denaturation at 94° C. for 15 s, annealing at 55° C. for 15 s, and extension at 72° C. for 45 s for a total of 40 cycles on a RT-PCR detection system. The fluorescence signals were collected during the extension phase of each cycle. After each cycle, the melting curve analysis of 94° C.-55° C. was performed.

The relative expression value=GFP expression level/β-actin, and the expression level of GFP and the expression level of the internal reference gene was 1. The screening criteria of GFP expression level was as follows:

Low expression=relative expression value<0.2     (a)

Moderate expression=0.2≤relative expression
    value<0.6                                    (b)

High expression=0.6≤relative expression value;   (c)

High and moderate expression of GFP indicated that the serum of the patient did not contain anti-rAAV2 antibodies that prevented infection of HEK293T cells and that the probability of an immune response against the virus was low. These patients were identified as those suitable for gene therapy. Low GFP expression indicated that the serum of the patient contained anti-rAAV2 antibodies that prevented infection of HEK293T cells and that rAAV gene therapy may cause an immune response, requiring the patient to undergo immunotherapy before gene therapy treatment. Results are shown in Table 9 below.

TABLE 9

GFP expression by qPCR in HEK293T cells + Patient serum

| | GFP/β-actin relative expression value | | |
|---|---|---|---|
| | 1:20 | 1:60 | Control group |
| Patient A | 0.33 | 0.55 | 0.78 |
| Patient B | 0.35 | 0.52 | 0.79 |
| Patient C | 0.29 | 0.56 | 0.78 |
| Patient D | 0.61 | 0.68 | 0.77 |
| Patient E | 0.12 | 0.18 | 0.79 |

Example 18—GFP Expression in HEK293T Cells by Flow Cytometry

HEK293T cells transduced with rAAV2-GFP were resuspended in the well and transferred to a flow cytometry tube. GFP expression in HEK293T cells was determined using the Beckman Coulter Cyto FLEX S.

Untransduced cells (no drug) were used as a negative control for GFP expression (data not shown). Cells transduced with the rAAV2-GFP vector in the absence of patient serum were used as positive controls for GFP expression (control group described in Example 16). The infection efficiency of the control group was set to 50%. GFP expression in HEK293T cells after incubation with serum dilutions from Patient A is shown in Table 10, GFP expression in HEK293T cells after incubation with serum dilutions from Patient B is shown in Table 11, GFP expression in HEK293T cells after incubation with serum dilutions from Patient C is shown in Table 12, GFP expression in HEK293T cells after incubation with serum dilutions from Patient D is shown in Table 13, GFP expression in HEK293T cells after incubation with serum dilutions from Patient E is shown in Table 14.

TABLE 10

% GFP expression in HEK293T cells + Patient A serum

| Replicate | 1:20 | 1:60 | Control group |
|---|---|---|---|
| 1 | 25.80 | 37.63 | 48.56 |
| 2 | 25.03 | 36.21 | 52.09 |
| 3 | 25.51 | 40.32 | 50.07 |
| Mean % GFP+ cells | 25.45 | 38.05 | 50.24 |

TABLE 11

% GFP expression in HEK293T cells + Patient B serum

| Replicate | 1:20 | 1:60 | Control group |
|---|---|---|---|
| 1 | 33.90 | 36.59 | 48.26 |
| 2 | 29.05 | 33.84 | 53.88 |
| 3 | 31.35 | 33.86 | 51.37 |
| Mean % GFP+ cells | 31.43 | 34.76 | 51.17 |

TABLE 12

% GFP expression in HEK293T cells + Patient C serum

| Replicate | 1:20 | 1:60 | Control group |
|---|---|---|---|
| 1 | 31.45 | 38.16 | 51.56 |
| 2 | 28.92 | 33.60 | 50.09 |
| 3 | 30.41 | 36.58 | 50.33 |
| Mean % GFP+ cells | 30.26 | 36.11 | 50.66 |

TABLE 13

% GFP expression in HEK293T cells + Patient D serum

| Replicate | 1:20 | 1:60 | Control group |
|---|---|---|---|
| 1 | 41.11 | 45.15 | 51.56 |
| 2 | 40.33 | 43.12 | 52.17 |
| 3 | 43.93 | 46.04 | 50.28 |
| Mean % GFP+ cells | 41.79 | 44.77 | 51.34 |

TABLE 14

% GFP expression in HEK293T cells + Patient E serum

| Replicate | 1:20 | 1:60 | Control group |
|---|---|---|---|
| 1 | 12.07 | 15.85 | 49.00 |
| 2 | 16.27 | 16.94 | 53.88 |
| 3 | 13.70 | 14.07 | 50.37 |
| Mean % GFP+ cells | 14.01 | 15.62 | 51.08 |

GFP expression (i.e., the percentage of cells that are GFP+ by flow cytometry) can be expressed as absolute fluorescence (percentage of GFP+ cells in a test sample; as shown in Tables 10-14) or as relative fluorescence ([percentage of GFP+ cells in a test sample/percentage of GFP+ cells in a control sample]*100; as shown in the "Relative GFP fluorescence" column in Table 15). The criteria for screening patients by relative GFP expression is as follows:

Low expression=% GFP+cells<20%    (a)

Moderate expression=20%≤% GFP+cells<40%    (b)

High expression=40%≤% GFP+cells    (c)

High and moderate GFP expression indicated that the serum of the patient did not contain anti-rAAV2 antibodies that prevented infection of target cells and gene therapy could be performed. Low GFP expression indicated that the serum of the patient contained anti-rAAV2 antibodies that prevented infection of target cells and that gene therapy with rAAV may cause an immune response, and immunotherapy should be performed before proceeding with gene therapy.

GFP expression of patients A, B, C, and D were all higher than 20% (as shown in Tables 10-14, indicating that patient serum did not contain anti-rAAV2 antibodies that prevented infection of target cells and that the gene therapy could be directly performed. In particular, the GFP expression level of patient D was higher than 40%, indicating that the patient was in ideal condition for gene therapy (Table 13). The GFP expression level tested for patient E was less than 20% (Table 14), indicating that gene therapy with rAAV2 may cause an immune response and that immunotherapy was needed before starting treatment.

Example 19—Efficiency of Gene Therapy in Patients with Low Immunity to rAAV2

The relationship between GFP expression and gene therapy was first discovered by the inventors. There were no relevant reports in the prior art, and no standard for the relationship between specific expression level and the effect of gene therapy had been established in the art.

In the clinic, the inventors unexpectedly found that subjects with GFP expression levels below 20% experienced an immune response to rAAV2 gene therapy, and for safety reasons, were not further included in the study. Subjects with an expression level higher than 50% were rare, so the purpose of this example was to verify subjects with expression levels between 20% and 50%.

Candidates for gene therapy were screened for an immune response to recombinant adeno-associated virus as described above (Examples 16-18). The patient recruiting guidelines and pre- and post-operative examination procedures are described in Example 15. The dose for intravitreal injection under local anesthesia was $1\times10^{10}$ vg/0.05 mL. A single administration was performed. Clinical observation lasted for 3 months and vision acuity was observed over time.

Subjects were grouped according to % GFP+ cells: Group A=high GFP expression (40%≤% GFP+ cells≤50%) and Group B=moderate GFP expression (20%≤% GFP+ cells< 40%). Target cells were transduced with rAAV2-GFP such that approximately 50% of the cells in the control group were transduced with the vector. In the 20-50% GFP+ range, the inventors found a relationship between expression level and the effect of gene therapy. In subjects with % GFP+ cells below 40% gene therapy was slightly less effective than in subjects with % GFP+ cells greater than or equal to 40%. Therefore, the above criteria for low expression, moderate expression, and high expression was established.

The results are shown in Table 15. The gene therapy was significantly more efficacious in group A (high expression) than in group B (moderate expression) (P<0.05). Guidelines for evaluation of efficiency and visual acuity are described in Example 15.

TABLE 15

Comparison of efficacy between group A and group B

| Group | Number of cases | Efficiency | |
|---|---|---|---|
| Group A | 66 | 47 (71.21%) | P < 0.05 |
| Group B | 39 | 20 (51.28%) | |

Example 20—Screening Patients for LHON Gene Therapy

The effectiveness of the diagnostic assays described above were further verified in additional patients. Serum from 37 patient was diluted as described above in Example 16 and evaluated in the qPCR and flow cytometry assays described above in Example 17 and 18. Testing of each sample was repeated 3 times (n=3) and an average value was obtained (i.e., mean % GFP+ cells). Relative % GFP+ cells for the 1:20 and 1:60 dilutions was calculated relative to the mean % GFP+ cells of the control sample, and subjects were classified as suitable or not suitable for therapy with the rAAV2 vector based on the relative % GFP+ cells (suitable for therapy=relative % GFP+ cells ≥40%; not suitable for therapy=relative % GFP+ cells <40%). Using the methods described herein, 28 patients were classified as suitable and 9 patients were classified as unsuitable for therapy. The results for 37 subjects are shown in Table 16.

TABLE 16

| % GFP+ HEK293T cells + Patient serum | | | | | | |
|---|---|---|---|---|---|---|
| | Mean % GFP+ cells | | | % GFP+ Test/% GFP+ Control | | |
| Case No. | 1:20 | 1:60 | Control | 1:20 | 1:60 | Classification |
| A1 | 52.25 | 83.66 | 55.13 | 94.8% | 151.7% | Suitable for therapy |
| A2 | 41.32 | 80.20 | 55.13 | 74.9% | 145.5% | Suitable for therapy |
| A3 | 32.43 | 78.86 | 55.13 | 58.8% | 143.0% | Suitable for therapy |
| A4 | 52.79 | 53.8 | 49.58 | 106.5% | 108.5% | Suitable for therapy |
| A5 | 55.7 | 61.79 | 49.58 | 112.3% | 124.6% | Suitable for therapy |
| A6 | 53.69 | 64.51 | 49.58 | 108.3% | 130.1% | Suitable for therapy |
| A7 | 54.31 | 58.85 | 49.58 | 109.5% | 118.7% | Suitable for therapy |
| A8 | 50.43 | 57.24 | 49.58 | 101.7% | 115.4% | Suitable for therapy |
| A9 | 47.87 | 57.21 | 49.58 | 96.6% | 115.4% | Suitable for therapy |
| A10 | 49.27 | 55.43 | 54.19 | 90.9% | 102.3% | Suitable for therapy |
| A11 | 30.26 | 36.11 | 51.37 | 58.9% | 70.3% | Suitable for therapy |

TABLE 16-continued

% GFP+ HEK293T cells + Patient serum

| Case No. | Mean % GFP+ cells | | | % GFP+ Test/% GFP+ Control | | Classification |
|---|---|---|---|---|---|---|
| | 1:20 | 1:60 | Control | 1:20 | 1:60 | |
| A12 | 31.43 | 34.76 | 51.37 | 61.2% | 67.7% | Suitable for therapy |
| A13 | 25.86 | 32.03 | 51.37 | 50.3% | 62.4% | Suitable for therapy |
| A14 | 25.45 | 38.05 | 51.37 | 49.5% | 74.1% | Suitable for therapy |
| A15 | 33.82 | 37.84 | 51.37 | 65.8% | 73.7% | Suitable for therapy |
| A16 | 39.34 | 39.08 | 51.37 | 76.6% | 76.1% | Suitable for therapy |
| A17 | 35.39 | 43.65 | 51.37 | 68.9% | 85.0% | Suitable for therapy |
| A18 | 41.08 | 43.74 | 51.37 | 80.0% | 85.1% | Suitable for therapy |
| A19 | 34.55 | 50.39 | 51.37 | 67.3% | 98.1% | Suitable for therapy |
| A20 | 58.96 | 52.91 | 57.84 | 101.9% | 91.5% | Suitable for therapy |
| A21 | 49.09 | 64.89 | 57.84 | 84.9% | 112.2% | Suitable for therapy |
| A22 | 55.13 | 71.83 | 57.84 | 95.3% | 124.2% | Suitable for therapy |
| A23 | 50.39 | 59.43 | 57.84 | 87.1% | 102.7% | Suitable for therapy |
| A24 | 68.34 | 78.68 | 57.84 | 118.2% | 136.0% | Suitable for therapy |
| A25 | 54.38 | 84.02 | 57.84 | 94.0% | 145.3% | Suitable for therapy |
| A26 | 60.39 | 64.2 | 57.84 | 104.4% | 111.0% | Suitable for therapy |
| A27 | 49.62 | 47.91 | 57.84 | 85.8% | 82.8% | Suitable for therapy |
| A28 | 58.59 | 62.54 | 57.84 | 101.3% | 108.1% | Suitable for therapy |
| B1 | 15.26 | 17.32 | 63.19 | 24.1% | 27.4% | Not suitable for therapy |
| B2 | 3.59 | 2.15 | 12.32 | 29.1% | 17.5% | Not suitable for therapy |
| B3 | 12 | 9.81 | 35.4 | 33.9% | 27.7% | Not suitable for therapy |
| B4 | 0.72 | 1.35 | 12.32 | 5.8% | 11.0% | Not suitable for therapy |
| B5 | 2.96 | 2.43 | 12.32 | 24.0% | 19.7% | Not suitable for therapy |
| B6 | 4.38 | 24.4 | 63.03 | 6.9% | 38.7% | Not suitable for therapy |
| B7 | 1.58 | 2.85 | 63.19 | 2.5% | 4.5% | Not suitable for therapy |
| B8 | 13.92 | 7.92 | 51.34 | 27.1% | 15.4% | Not suitable for therapy |
| B9 | 4.78 | 9.06 | 51.08 | 9.4% | 17.7% | Not suitable for therapy |

The 28 patients classified as suitable for therapy received the rAAV2 gene therapy vector. Of the 28 patients that received therapy, the therapy was effective in 20 patients (efficacy rate of 71.43% (20/28)). Of the 9 patients classified as not suitable for therapy, 6 patients still wanted to receive gene therapy. However, the therapy was only effective in one patient classified as not suitable for therapy (efficacy rate of 16.67% (1/6)).

Example 21—Prednisone Treatment Regimen for LHON Gene Therapy

This study will be conducted following the patient recruitment guidelines, surgery and examination procedures as described in Example 15.

Patients undergoing gene therapy for LHON will receive the following treatment regimen:

(a) 2 days before surgery: prednisone tablets, 60 mg/60 kg, once per day for 10 days;

(b) 8 days after surgery: prednisone tablets, 40 mg/60 kg, once per day for 1 day;

(c) 9 days after surgery: prednisone tablets, 20 mg/60 kg, once per day for 1 day;

(d) 10 days after surgery: prednisone tablets, 10 mg/60 kg, once per day for 1 day;

(e) 11 days after surgery: stop steroid treatment.

Figure 20:
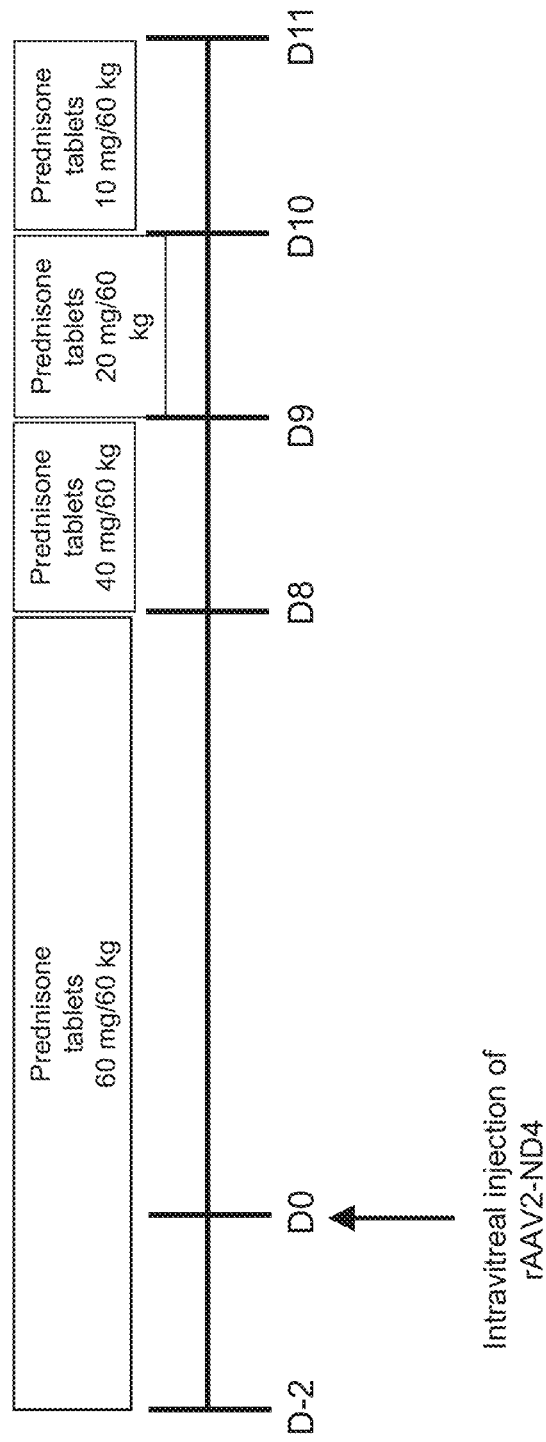
FIG. 20 shows a second exemplary steroid dosing schedule.

A schematic showing the medication dosing schedule is provided in FIG. 20. Patients will be monitored for 3 months following surgery and will be advised to consult a physician if they felt any discomfort or pain throughout the study.

Results are expected to show an improvement in visual acuity with minimal side effects in LHON patients following intravitreal administration of AAV2-ND4 and the treatment regimen described above.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

FURTHER NUMBERED EMBODIMENTS

Further embodiments of the instant invention are provided in the numbered embodiments below:

Embodiment 1

A recombinant nucleic acid, comprising: a mitochondrial targeting sequence; a mitochondrial protein coding sequence comprising a sequence that is at least 99% identical to a sequence selected from the group consisting of SEQ ID NO: 7, 8, 10, and 12; and a 3'UTR nucleic acid sequence.

Embodiment 2

The recombinant nucleic acid of Embodiment 1, wherein said mitochondrial targeting sequence encodes a polypeptide comprising a peptide sequence that is at least 90%, at least 95%, at least 97%, at least 99%, or 100% identical to a sequence selected from the group consisting of SEQ ID NO: 129-159.

Embodiment 3

The recombinant nucleic acid of Embodiment 1, wherein said mitochondrial targeting sequence comprises a sequence that is at least 90%, at least 95%, at least 97%, at least 99%, or 100% identical to a sequence as set forth in SEQ ID NO: 2.

Embodiment 4

The recombinant nucleic acid of Embodiment 1, wherein said mitochondrial targeting sequence comprises a sequence that is at least 90%, at least 95%, at least 97%, at least 99%, or 100% identical to a sequence as set forth in SEQ ID NO: 3.

Embodiment 5

The recombinant nucleic acid of Embodiment 1, wherein said mitochondrial targeting sequence comprises a sequence that is at least 90%, at least 95%, at least 97%, at least 99%, or 100% identical to a sequence as set forth in SEQ ID NO: 4.

Embodiment 6

The recombinant nucleic acid of Embodiment 1, wherein said mitochondrial targeting sequence comprises a sequence that is at least 90%, at least 95%, at least 97%, at least 99%, or 100% identical to a sequence as set forth in SEQ ID NO: 5.

Embodiment 7

The recombinant nucleic acid of Embodiment 1, wherein said mitochondrial protein coding sequence comprises a sequence that is at least 90%, at least 95%, at least 97%, at least 99%, or 100% identical to a sequence as set forth in SEQ ID NO: 7 or 8.

Embodiment 8

The recombinant nucleic acid of Embodiment 1, wherein said mitochondrial protein coding sequence comprises a sequence that is at least 90%, at least 95%, at least 97%, at least 99%, or 100% identical to a sequence as set forth in SEQ ID NO: 10.

Embodiment 9

The recombinant nucleic acid of cl Embodiment aim 1, wherein said mitochondrial protein coding sequence comprises a sequence that is at least 90%, at least 95%, at least 97%, at least 99%, or 100% identical to a sequence as set forth in SEQ ID NO: 12.

Embodiment 10

The recombinant nucleic acid of Embodiment 1, wherein said 3'UTR nucleic acid sequence comprises a sequence that is at least 90%, at least 95%, at least 97%, at least 99%, or 100% identical to a sequence selected from the group consisting of SEQ ID NO: 111-125.

Embodiment 11

The recombinant nucleic acid of Embodiment 1, wherein said 3'UTR nucleic acid sequence comprises a sequence that is at least 90%, at least 95%, at least 97%, at least 99%, or 100% identical to a sequence as set forth in SEQ ID NO: 13 or SEQ ID NO: 14.

Embodiment 12

The recombinant nucleic acid of Embodiment 1, wherein said recombinant nucleic acid comprises a sequence that is at least 90%, at least 95%, at least 97%, at least 99%, or 100% identical to a sequence selected from the group consisting of SEQ ID NO: 17-20, 23-24, 27-28, 31-34, 37-38, 41-42, 45-48, 51-52, 55-56, 59-62, 65-66, 69-70, 73-76, 79-80, and 83-84.

Embodiment 13

A recombinant nucleic acid, comprising: a mitochondrial targeting sequence comprising a sequence that is at least 90% identical to a sequence selected from the group consisting of SEQ ID NO: 2, 3, 4, and 5; a mitochondrial protein coding sequence, wherein said mitochondrial protein coding sequence encodes a polypeptide comprising a mitochondrial protein; and a 3'UTR nucleic acid sequence.

Embodiment 14

The recombinant nucleic acid of Embodiment 13, wherein said mitochondrial targeting sequence comprises a sequence that is at least 90%, at least 95%, at least 97%, at least 99%, or 100% identical to a sequence as set forth in SEQ ID NO: 2.

Embodiment 15

The recombinant nucleic acid of any one of Embodiments 13-14, wherein said mitochondrial targeting sequence comprises a sequence that is at least 90%, at least 95%, at least 97%, at least 99%, or 100% identical to a sequence as set forth in SEQ ID NO: 3.

Embodiment 16

The recombinant nucleic acid of any one of Embodiments 13-15, wherein said mitochondrial targeting sequence comprises a sequence that is at least 90%, at least 95%, at least 97%, at least 99%, or 100% identical to a sequence as set forth in SEQ ID NO: 4.

Embodiment 17

The recombinant nucleic acid of any one of Embodiments 13-16, wherein said mitochondrial targeting sequence comprises a sequence that is at least 90%, at least 95%, at least 97%, at least 99%, or 100% identical to a sequence as set forth in SEQ ID NO: 5.

Embodiment 18

The recombinant nucleic acid of any one of Embodiments 13-17, wherein said mitochondrial protein is selected from a group consisting of NADH dehydrogenase 4 (ND4), NADH dehydrogenase 6 (ND6), NADH dehydrogenase 1 (ND1), and a variant thereof.

Embodiment 19

The recombinant nucleic acid of Embodiment 18, wherein said mitochondrial protein comprises NADH dehydrogenase 4 (ND4), or a variant thereof.

Embodiment 20

The recombinant nucleic acid of any one of Embodiments 13-19, wherein said mitochondrial protein comprises a peptide sequence that is at least 90%, at least 95%, at least 97%, at least 99%, or 100% identical to a sequence as set forth in SEQ ID NO: 160.

Embodiment 21

The recombinant nucleic acid of any one of Embodiments 13-20, wherein said mitochondrial protein coding sequence comprises a sequence that is at least 90%, at least 95%, at least 97%, at least 99%, or 100% identical to a sequence as set forth in SEQ ID NO: 6, 7, or 8.

Embodiment 22

The recombinant nucleic acid of Embodiment 18, wherein said mitochondrial protein comprises NADH dehydrogenase 6 (ND6), or a variant thereof.

Embodiment 23

The recombinant nucleic acid of any one of Embodiments 13-22, wherein said mitochondrial protein comprises a sequence that is at least 90%, at least 95%, at least 97%, at least 99%, or 100% identical to a sequence as set forth in SEQ ID NO: 161.

Embodiment 24

The recombinant nucleic acid of any one of Embodiments 13-23, wherein said mitochondrial protein coding sequence comprises a sequence that is at least 90%, at least 95%, at least 97%, at least 99%, or 100% identical to a sequence as set forth in SEQ ID NO: 9 or 10.

Embodiment 25

The recombinant nucleic acid of any one of Embodiments 13-24, wherein said mitochondrial protein comprises NADH dehydrogenase 1 (ND1), or a variant thereof.

Embodiment 26

The recombinant nucleic acid of any one of Embodiments 13-25, wherein said mitochondrial protein comprises a sequence that is at least 90%, at least 95%, at least 97%, at least 99%, or 100% identical to a sequence as set forth in SEQ ID NO: 162.

Embodiment 27

The recombinant nucleic acid of any one of Embodiments 13-26, wherein said mitochondrial protein coding sequence comprises a sequence that is at least 90%, at least 95%, at least 97%, at least 99%, or 100% identical to a sequence as set forth in SEQ ID NO: 11 or 12.

Embodiment 28

The recombinant nucleic acid of any one of Embodiments 13-27, wherein said 3'UTR nucleic acid sequence is located at 3' of said mitochondrial targeting sequence.

Embodiment 29

The recombinant nucleic acid of any one of Embodiments 13-28, wherein said 3'UTR nucleic acid sequence comprises a sequence selected from the group consisting of hsACO2, hsATP5B, hsAK2, hsALDH2, hsCOX10, hsUQCRFS1, hsNDUFV1, hsNDUFV2, hsSOD2, hsCOX6c, hsIRP1, hsMRPS12, hsATP5J2, rnSOD2, and hsOXA1L.

Embodiment 30

The recombinant nucleic acid of any one of Embodiments 13-29, wherein said 3'UTR nucleic acid sequence comprises a sequence that is at least 90%, at least 95%, at least 97%, at least 99%, or 100% identical to a sequence selected from the group consisting of SEQ ID NO: 111-125.

Embodiment 31

The recombinant nucleic acid of any one of Embodiments 13-29, wherein said 3'UTR nucleic acid sequence comprises a sequence that is at least 90%, at least 95%, at least 97%, at least 99%, or 100% identical to a sequence as set forth in SEQ ID NO: 13 or SEQ ID NO: 14.

Embodiment 32

The recombinant nucleic acid of any one of Embodiments 13-31, wherein said mitochondrial targeting sequence is located at 5' of said 3'UTR nucleic acid sequence.

Embodiment 33

The recombinant nucleic acid of any one of Embodiments 13-32, wherein said mitochondrial targeting sequence is located at 3' of said mitochondrial targeting sequence.

Embodiment 34

The recombinant nucleic acid of any one of Embodiments 13-33, wherein said recombinant nucleic acid comprises a sequence that is at least 90%, at least 95%, at least 97%, at least 99%, or 100% identical to a sequence selected from the group consisting of SEQ ID NO: 29-84.

Embodiment 35

A recombinant nucleic acid, comprising: a mitochondrial targeting sequence; a mitochondrial protein coding sequence comprising a sequence that is at least 90%, at least 95%, at least 97%, at least 99%, or 100% identical to a sequence selected from the group consisting of SEQ ID NO: 7, 8, 10, and 12; and a 3'UTR nucleic acid sequence.

Embodiment 36

The recombinant nucleic acid of Embodiment 35, wherein said mitochondrial targeting sequence comprises a sequence encodes a polypeptide selected from the group consisting of hsCOX10, hsCOX8, scRPM2, lcSirt5, tbNDUS7, ncQCR2, hsATP5G2, hsLACTB, spilv1, gmCOX2, crATP6, hsOPA1, hsSDHD, hsADCK3, osP0644B06.24-2, Neurospora crassa ATP9 (ncATP9), hsGHITM, hsNDUFAB1, hsATP5G3, crATP6_hsADCK3, ncATP9_ncATP9, zmLOC100282174, ncATP9_zmLOC100282174_spilv1_ncATP9, zmLOC100282174_hsADCK3_crATP6_hsATP5G3, zmLOC100282174_hsADCK3_hsATP5G3, ncATP9_zmLOC100282174, hsADCK3_zmLOC100282174_crATP6_hsATP5G3, crATP6_hsADCK3_zmLOC100282174_hsATP5G3, hsADCK3_zmLOC100282174, hsADCK3_zmLOC100282174_crATP6, ncATP9_zmLOC100282174_spilv1_GNFP_ncATP9, and ncATP9_zmLOC100282174_spilv1_lcSirt5_osP0644B06.24-2_hsATP5G2_ncATP9.

Embodiment 37

The recombinant nucleic acid of any one of Embodiments 35-36, wherein said mitochondrial targeting sequence encodes a polypeptide comprising a peptide sequence that is at least 90%, at least 95%, at least 97%, at least 99%, or 100% identical to a sequence selected from the group consisting of SEQ ID NO: 129-159.

Embodiment 38

The recombinant nucleic acid of any one of Embodiments 35-37, wherein said mitochondrial targeting sequence comprises a sequence that is at least 90%, at least 95%, at least 97%, at least 99%, or 100% identical to a sequence as set forth in SEQ ID NO: 2 or 3.

Embodiment 39

The recombinant nucleic acid of any one of Embodiments 35-38, wherein said mitochondrial targeting sequence comprises a sequence that is at least 90%, at least 95%, at least 97%, at least 99%, or 100% identical to a sequence as set forth in SEQ ID NO: 4.

Embodiment 40

The recombinant nucleic acid of any one of Embodiments 35-39, wherein said mitochondrial targeting sequence comprises a sequence that is at least 90%, at least 95%, at least 97%, at least 99%, or 100% identical to a sequence as set forth in SEQ ID NO: 5.

Embodiment 41

The recombinant nucleic acid of any one of Embodiments 35-40, wherein said mitochondrial protein coding sequence comprises a sequence that is at least 90%, at least 95%, at least 97%, at least 99%, or 100% identical to a sequence as set forth in SEQ ID NO: 7 or 8.

Embodiment 42

The recombinant nucleic acid of any one of Embodiments 35-41, wherein said mitochondrial protein coding sequence comprises a sequence that is at least 90%, at least 95%, at least 97%, at least 99%, or 100% identical to a sequence as set forth in SEQ ID NO: 10.

Embodiment 43

The recombinant nucleic acid of any one of Embodiments 35-42, wherein said mitochondrial protein coding sequence comprises a sequence that is at least 90%, at least 95%, at least 97%, at least 99%, or 100% identical to a sequence as set forth in SEQ ID NO: 12.

Embodiment 44

The recombinant nucleic acid of any one of Embodiments 35-43, wherein said 3'UTR nucleic acid sequence is located at 3' of said mitochondrial targeting sequence.

Embodiment 45

The recombinant nucleic acid of any one of Embodiments 35-44, wherein said 3'UTR nucleic acid sequence comprises a sequence selected from the group consisting of hsACO2, hsATP5B, hsAK2, hsALDH2, hsCOX10, hsUQCRFS1, hsNDUFV1, hsNDUFV2, hsSOD2, hsCOX6c, hsIRP1, hsMRPS12, hsATP5J2, rnSOD2, and hsOXA1L.

Embodiment 46

The recombinant nucleic acid of any one of Embodiments 35-45, wherein said 3'UTR nucleic acid sequence comprises a sequence that is at least 90%, at least 95%, at least 97%, at least 99%, or 100% identical to a sequence selected from the group consisting of SEQ ID NO: 111-125.

Embodiment 47

The recombinant nucleic acid of any one of Embodiments 35-46, wherein said 3'UTR nucleic acid sequence comprises a sequence that is at least 90%, at least 95%, at least 97%, at least 99%, or 100% identical to a sequence as set forth in SEQ ID NO: 13 or SEQ ID NO: 14.

Embodiment 48

The recombinant nucleic acid of any one of Embodiments 35-47, wherein said mitochondrial targeting sequence is located at 5' of said 3'UTR nucleic acid sequence.

Embodiment 49

The recombinant nucleic acid of any one of Embodiments 35-48, wherein said mitochondrial targeting sequence is located at 3' of said mitochondrial targeting sequence.

Embodiment 50

The recombinant nucleic acid of any one of Embodiments 35-49, wherein said recombinant nucleic acid comprises a sequence that is at least 90%, at least 95%, at least 97%, at least 99%, or 100% identical to a sequence selected from the group consisting of SEQ ID NO: 17-20, 23-24, 27-28, 31-34, 37-38, 41-42, 45-48, 51-52, 55-56, 59-62, 65-66, 69-70, 73-76, 79-80, and 83-84.

Embodiment 51

A recombinant nucleic acid, comprising a mitochondrial targeting sequence that is at least 90%, at least 95%, at least 97%, at least 99%, or 100% identical to a sequence selected from the group consisting of SEQ ID NO: 2, 3, and 4.

Embodiment 52

The recombinant nucleic acid of Embodiment 51, wherein said mitochondrial targeting sequence comprises a sequence that is at least 90%, at least 95%, at least 97%, at least 99%, or 100% identical to a sequence as set forth in SEQ ID NO: 2.

Embodiment 53

The recombinant nucleic acid of any one of Embodiments 51-52, wherein said mitochondrial targeting sequence comprises a sequence that is at least 90%, at least 95%, at least 97%, at least 99%, or 100% identical to a sequence as set forth in SEQ ID NO: 3.

Embodiment 54

The recombinant nucleic acid of any one of Embodiments 51-53, wherein said mitochondrial targeting sequence comprises a sequence that is at least 90%, at least 95%, at least 97%, at least 99%, or 100% identical to a sequence as set forth in SEQ ID NO: 4.

Embodiment 55

The recombinant nucleic acid of any one of Embodiments 51-54, further comprising a mitochondrial protein coding sequence, wherein said mitochondrial protein coding sequence encodes a polypeptide comprising a mitochondrial protein.

Embodiment 56

The recombinant nucleic acid of any one of Embodiments 51-55, wherein said mitochondrial protein is selected from a group consisting of NADH dehydrogenase 4 (ND4), NADH dehydrogenase 6 (ND6), NADH dehydrogenase 1 (ND1), and a variant thereof.

Embodiment 57

The recombinant nucleic acid of any one of Embodiments 51-56, wherein said mitochondrial protein comprises NADH dehydrogenase 4 (ND4), or a variant thereof.

Embodiment 58

The recombinant nucleic acid of any one of Embodiments 51-57, wherein said mitochondrial protein comprises a peptide sequence that is at least 90%, at least 95%, at least 97%, at least 99%, or 100% identical to a sequence as set forth in SEQ ID NO: 160.

Embodiment 59

The recombinant nucleic acid of any one of Embodiments 51-58, wherein said mitochondrial protein coding sequence comprises a sequence that is at least 90%, at least 95%, at least 97%, at least 99%, or 100% identical to a sequence as set forth in SEQ ID NO: 6, 7, or 8.

Embodiment 60

The recombinant nucleic acid of any one of Embodiments 51-59, wherein said mitochondrial protein comprises NADH dehydrogenase 6 (ND6), or a variant thereof.

Embodiment 61

The recombinant nucleic acid of any one of Embodiments 51-60, wherein said mitochondrial protein comprises a sequence that is at least 90%, at least 95%, at least 97%, at least 99%, or 100% identical to a sequence as set forth in SEQ ID NO: 161.

Embodiment 62

The recombinant nucleic acid of any one of Embodiments 51-61, wherein said mitochondrial protein coding sequence comprises a sequence that is at least 90%, at least 95%, at least 97%, at least 99%, or 100% identical to a sequence as set forth in SEQ ID NO: 9 or 10.

Embodiment 63

The recombinant nucleic acid of any one of Embodiments 51-62, wherein said mitochondrial protein comprises NADH dehydrogenase 1 (ND1), or a variant thereof.

Embodiment 64

The recombinant nucleic acid of any one of Embodiments 51-63, wherein said mitochondrial protein comprises a sequence that is at least 90%, at least 95%, at least 97%, at least 99%, or 100% identical to a sequence as set forth in SEQ ID NO: 162.

Embodiment 65

The recombinant nucleic acid of any one of Embodiments 51-64, wherein said mitochondrial protein coding sequence comprises a sequence that is at least 90%, at least 95%, at least 97%, at least 99%, or 100% identical to a sequence as set forth in SEQ ID NO: 11 or 12.

Embodiment 66

The recombinant nucleic acid of any one of Embodiments 51-65, further comprising a 3'UTR nucleic acid sequence.

Embodiment 67

The recombinant nucleic acid of any one of Embodiments 51-66, wherein said 3'UTR nucleic acid sequence is located at 3' of said mitochondrial targeting sequence.

Embodiment 68

The recombinant nucleic acid of any one of Embodiments 51-67, wherein said 3'UTR nucleic acid sequence comprises a sequence selected from the group consisting of hsACO2, hsATP5B, hsAK2, hsALDH2, hsCOX10, hsUQCRFS1, hsNDUFV1, hsNDUFV2, hsSOD2, hsCOX6c, hsIRP1, hsMRPS12, hsATP5J2, rnSOD2, and hsOXA1L.

Embodiment 69

The recombinant nucleic acid of any one of Embodiments 51-68, wherein said 3'UTR nucleic acid sequence comprises a sequence that is at least 90%, at least 95%, at least 97%, at least 99%, or 100% identical to a sequence selected from the group consisting of SEQ ID NO: 111-125.

Embodiment 70

The recombinant nucleic acid of any one of Embodiments 51-69, wherein said 3'UTR nucleic acid sequence comprises a sequence that is at least 90%, at least 95%, at least 97%, at least 99%, or 100% identical to a sequence as set forth in SEQ ID NO: 13 or SEQ ID NO: 14.

Embodiment 71

The recombinant nucleic acid of any one of Embodiments 51-70, wherein said mitochondrial targeting sequence is located at 5' of said 3'UTR nucleic acid sequence.

Embodiment 72

The recombinant nucleic acid of any one of Embodiments 51-71, wherein said mitochondrial targeting sequence is located at 3' of said mitochondrial targeting sequence.

Embodiment 73

The recombinant nucleic acid of any one of Embodiments 51-72, wherein said recombinant nucleic acid comprises a sequence that is at least 90%, at least 95%, at least 97%, at least 99%, or 100% identical to a sequence selected from the group consisting of SEQ ID NO: 29-70.

Embodiment 74

A recombinant nucleic acid, comprising a mitochondrial protein coding sequence, wherein said mitochondrial protein coding sequence encodes a polypeptide comprising a mitochondrial protein, wherein said mitochondrial protein coding sequence comprises a sequence that is at least 90%, at least 95%, at least 97%, at least 99%, or 100% identical to a sequence selected from the group consisting of SEQ ID NO: 7, 8, 10, and 12.

Embodiment 75

The recombinant nucleic acid of Embodiment 74, further comprising a mitochondrial targeting sequence.

Embodiment 76

The recombinant nucleic acid of any one of Embodiments 74-75, wherein said mitochondrial targeting sequence comprises a sequence encodes a polypeptide selected from the group consisting of hsCOX10, hsCOX8, scRPM2, lcSirt5, tbNDUS7, ncQCR2, hsATP5G2, hsLACTB, spilv1, gmCOX2, crATP6, hsOPA1, hsSDHD, hsADCK3, osP0644B06.24-2, *Neurospora crassa* ATPS (ncATP9), hsGHITM, hsNDUFAB1, hsATP5G3, crATP6_hsADCK3, ncATP9_ncATP9, zmLOC100282174, ncATP9_zmLOC100282174_spilv1_ncATP9, zmLOC100282174_hsADCK3_crATP6_hsATP5G3, zmLOC100282174_hsADCK3_hsATP5G3, ncATP9_zmLOC100282174, hsADCK3_zmLOC100282174_crATP6_hsATP5G3, crATP6_hsADCK3_zmLOC100282174_hsATP5G3, hsADCK3_zmLOC100282174, hsADCK3_zmLOC100282174_crATP6, ncATP9_zmLOC100282174_spilv1_GNFP_ncATP9, and ncATP9_zmLOC100282174_spilv1_lcSirt5_osP0644B06.24-2_hsATP5G2_ncATP9.

Embodiment 77

The recombinant nucleic acid of any one of Embodiments 74-76, wherein said mitochondrial targeting sequence encodes a polypeptide comprising a peptide sequence that is at least 90%, at least 95%, at least 97%, at least 99%, or 100% identical to a sequence selected from the group consisting of SEQ ID NO: 129-159.

Embodiment 78

The recombinant nucleic acid of any one of Embodiments 74-77, wherein said mitochondrial targeting sequence comprises a sequence that is at least 90%, at least 95%, at least 97%, at least 99%, or 100% identical to a sequence as set forth in SEQ ID NO: 2.

Embodiment 79

The recombinant nucleic acid of any one of Embodiments 74-78, wherein said mitochondrial targeting sequence comprises a sequence that is at least 90%, at least 95%, at least 97%, at least 99%, or 100% identical to a sequence as set forth in SEQ ID NO: 3.

Embodiment 80

The recombinant nucleic acid of any one of Embodiments 74-79, wherein said mitochondrial targeting sequence comprises a sequence that is at least 90%, at least 95%, at least 97%, at least 99%, or 100% identical to a sequence as set forth in SEQ ID NO: 4.

Embodiment 81

The recombinant nucleic acid of any one of Embodiments 74-80, wherein said mitochondrial targeting sequence comprises a sequence that is at least 90%, at least 95%, at least 97%, at least 99%, or 100% identical to a sequence as set forth in SEQ ID NO: 5.

Embodiment 82

The recombinant nucleic acid of any one of Embodiments 74-81, wherein said mitochondrial protein coding sequence comprises a sequence that is at least 90%, at least 95%, at least 97%, at least 99%, or 100% identical to a sequence as set forth in SEQ ID NO: 7 or 8.

Embodiment 83

The recombinant nucleic acid of any one of Embodiments 74-80, wherein said mitochondrial protein coding sequence comprises a sequence that is at least 90%, at least 95%, at least 97%, at least 99%, or 100% identical to a sequence as set forth in SEQ ID NO: 10.

Embodiment 84

The recombinant nucleic acid of any one of Embodiments 74-83, wherein said mitochondrial protein coding sequence comprises a sequence that is at least 90%, at least 95%, at least 97%, at least 99%, or 100% identical to a sequence as set forth in SEQ ID NO: 12.

Embodiment 85

The recombinant nucleic acid of any one of Embodiments 74-84, further comprising a 3'UTR nucleic acid sequence.

Embodiment 86

The recombinant nucleic acid of any one of Embodiments 74-85, wherein said 3'UTR nucleic acid sequence is located at 3' of said mitochondrial targeting sequence.

Embodiment 87

The recombinant nucleic acid of any one of Embodiments 74-86, wherein said 3'UTR nucleic acid sequence comprises a sequence selected from the group consisting of hsACO2, hsATP5B, hsAK2, hsALDH2, hsCOX10, hsUQCRFS1, hsNDUFV1, hsNDUFV2, hsSOD2, hsCOX6c, hsIRP1, hsMRPS12, hsATP5J2, mSOD2, and hsOXA1L.

Embodiment 88

The recombinant nucleic acid of any one of Embodiments 74-87, wherein said 3'UTR nucleic acid sequence comprises a sequence that is at least 90%, at least 95%, at least 97%, at least 99%, or 100% identical to a sequence selected from the group consisting of SEQ ID NO: 111-125.|

Embodiment 89

The recombinant nucleic acid of any one of Embodiments 74-88, wherein said 3'UTR nucleic acid sequence comprises a sequence that is at least 90%, at least 95%, at least 97%, at least 99%, or 100% identical to a sequence as set forth in SEQ ID NO: 13 or SEQ ID NO: 14.

Embodiment 90

The recombinant nucleic acid of any one of Embodiments 74-89, wherein said mitochondrial targeting sequence is located at 5' of said 3'UTR nucleic acid sequence.

Embodiment 91

The recombinant nucleic acid of any one of Embodiments 74-90, wherein said mitochondrial targeting sequence is located at 3' of said mitochondrial targeting sequence.

Embodiment 92

The recombinant nucleic acid of any one of Embodiments 74-91, wherein said recombinant nucleic acid comprises a sequence that is at least 90%, at least 95%, at least 97%, at least 99%, or 100% identical to a sequence selected from the group consisting of SEQ ID NO: 17-20, 23-24, 27-28, 31-34, 37-38, 41-42, 45-48, 51-52, 55-56, 59-62, 65-66, 69-70, 73-76, 79-80, and 83-84.

Embodiment 93

A viral vector comprising said recombinant nucleic acid of any one of Embodiments 1-92.|

Embodiment 94

The viral vector of Embodiment 93, wherein said viral vector is an adeno-associated virus (AAV) vector.

Embodiment 95

The viral vector of Embodiment 94, wherein said AAV vector is selected from the group consisting of AAV1, AAV2, AAV3, AAV4, AAV5, AAV6, AAV7, AAV8, AAV9, AAV10, AAV11, AAV12, AAV13, AAV14, AAV15, and AAV16 vectors.

Embodiment 96

The viral vector of any one of Embodiments 93-95, wherein said AAV vector is a recombinant AAV (rAAV) vector.

Embodiment 97

The viral vector of Embodiment 96, wherein said rAAV vector is rAAV2 vector.

Embodiment 98

A pharmaceutical composition, comprising an adeno-associated virus (AAV) comprising said recombinant nucleic acid of any one of Embodiments 1-92.

Embodiment 99

The pharmaceutical composition of Embodiment 98, further comprising a pharmaceutically acceptable excipient thereof.

Embodiment 100

A pharmaceutical composition, comprising said viral vector of any one of Embodiments 93-97, and a pharmaceutically acceptable excipient thereof, wherein said viral vector comprises said recombinant nucleic acid of any one of Embodiments 1-92.|

Embodiment 101

A pharmaceutical composition, comprising: an adeno-associated virus (AAV) comprising a recombinant nucleic acid of any one of Embodiments 1-92, wherein said recombinant nucleic acid comprises a sequence that is at least 90%, at least 95%, at least 97%, at least 99%, or 100% identical to a sequence as set forth in SEQ ID NO: 15; and a pharmaceutically acceptable excipient.

Embodiment 102

The pharmaceutical composition of any one of Embodiments 98-101, wherein said pharmaceutically acceptable excipient comprises phosphate-buffered saline (PBS), α,α-trehalose dehydrate, L-histidine monohydrochloride monohydrate, polysorbate 20, NaCl, $NaH_2PO_4$, $Na_2HPO_4$, $KH_2PO_4$, $K_2HPO_4$, poloxamer 188, or any combination thereof.

Embodiment 103

The pharmaceutical composition of any one of Embodiments 98-102, wherein said pharmaceutically acceptable excipient is selected from phosphate-buffered saline (PBS), α,α-trehalose dehydrate, L-histidine monohydrochloride monohydrate, polysorbate 20, NaCl, $NaH_2PO_4$, $Na_2HPO_4$, $KH_2PO_4$, $K_2HPO_4$, poloxamer 188, and any combination thereof.

Embodiment 104

The pharmaceutical composition of Embodiment 102, wherein said pharmaceutically acceptable excipient comprises poloxamer 188.

Embodiment 105

The pharmaceutical composition of Embodiment 104, wherein said pharmaceutically acceptable excipient comprises 0.0001%-0.01% poloxamer 188.

Embodiment 106

The pharmaceutical composition of Embodiment 105, wherein said pharmaceutically acceptable excipient comprises 0.001% poloxamer 188.

Embodiment 107

The pharmaceutical composition of any one of Embodiments 98-106, wherein said pharmaceutically acceptable excipient further comprises one or more salts.

Embodiment 108

The pharmaceutical composition of Embodiment 107, wherein said one or more salts comprises NaCl, $NaH_2PO_4$, $Na_2HPO_4$, and $KH_2PO_4$.

Embodiment 109

The pharmaceutical composition of Embodiment 107, wherein said one or more salts comprises 80 mM NaCl, 5 mM $NaH_2PO_4$, 40 mM $Na_2HPO_4$, and 5 mM $KH_2PO_4$.

Embodiment 109.1

The pharmaceutical composition of Embodiment 107, wherein said one or more salts comprises NaCl, $Na_2HPO_4$, and $KH_2PO_4$.

Embodiment 109.2

The pharmaceutical composition of Embodiment 107, wherein said one or more salts comprises 154 mM NaCl, 5.6 mM $Na_2HPO_4$, and 8.4 mM $KH_2PO_4$.

Embodiment 110

The pharmaceutical composition of any one of Embodiments 98-109, wherein said pharmaceutical composition has a pH of 6-8.

Embodiment 111

The pharmaceutical composition of Embodiment 110, wherein said pharmaceutical composition has a pH of 7.2-7.4.

Embodiment 112

The pharmaceutical composition of Embodiment 111, wherein said pharmaceutical composition has a pH of 7.3.

Embodiment 113

The pharmaceutical composition of any one of Embodiments 98-112, wherein said pharmaceutical composition has a viral titer of at least $1.0 \times 10^{10}$ vg/mL.

Embodiment 114

The pharmaceutical composition of Embodiment 113, wherein said pharmaceutical composition has a viral titer of at least $5.0 \times 10^{10}$ vg/mL.

Embodiment 115

The pharmaceutical composition of any one of Embodiment 98-114, when said pharmaceutical composition is subject to five freeze/thaw cycles, said pharmaceutical composition retains at least 60%, 70%, 80%, or 90% of a viral titer as compared to the viral titer prior to the five freeze/thaw cycles.

Embodiment 116

The pharmaceutical composition of any one of Embodiment 98-115, wherein said pharmaceutical composition, when administered to a patient with Leber's hereditary optic neuropathy, generates a higher average recovery of vision than a comparable pharmaceutical composition without said recombinant nucleic acid.

Embodiment 117

The pharmaceutical composition of any one of Embodiment 98-116, wherein said pharmaceutical composition, when administered to a patient with Leber's hereditary optic neuropathy, generates a higher average recovery of vision than a comparable pharmaceutical composition comprising a recombinant nucleic acid as set forth in SEQ ID NO: 15.

Embodiment 118

A method of treating an eye disorder, comprising administering said pharmaceutical composition of any one of Embodiments 98-117 to a patient in need thereof.

Embodiment 119

The method of Embodiment 118, wherein said eye disorder is Leber's hereditary optic neuropathy (LHON).

Embodiment 120

The method of Embodiment 118 or 119, comprising administering said pharmaceutical composition to one or both eyes of said patient.

Embodiment 121

The method of any one of Embodiments 118-120, wherein said pharmaceutical composition is administered via intraocular or intravitreal injection.

Embodiment 122

The method of Embodiment 121, wherein said pharmaceutical composition is administered via intravitreal injection.

Embodiment 123

The method of Embodiment 122, wherein about 0.01-0.1 mL of said pharmaceutical composition is administered via intravitreal injection.

Embodiment 124

The method of Embodiment 123, wherein about 0.05 mL of said pharmaceutical composition is administered via intravitreal injection.

Embodiment 125

The method of any one of Embodiments 118-124, further comprising administering methylprednisolone to said patient.

Embodiment 126

The method of Embodiment 125, wherein said methylprednisolone is administered prior to said intravitreal injection of said pharmaceutical composition.

Embodiment 127

The method of any one of Embodiments 125-126, wherein said methylprednisolone is administered orally.

Embodiment 128

The method of any one of Embodiments 125-127, wherein said methylprednisolone is administered daily for at least 1, 2, 3, 4, 5, 6, or 7 days prior to said intravitreal injection of said pharmaceutical composition.

Embodiment 129

The method of any one of Embodiments 125-128, wherein said methylprednisolone is administered daily.

Embodiment 130

The method of any one of Embodiments 125-129, wherein a daily dosage of about 32 mg/60 kg methylprednisolone is administered.

Embodiment 131

The method of any one of Embodiments 125-130, wherein said methylprednisolone is administered after said intravitreal injection of said pharmaceutical composition.

Embodiment 132

The method of any one of Embodiments 125-131, further comprising administering sodium creatine phosphate to said patient.

Embodiment 133

The method of Embodiment 132, wherein said sodium creatine phosphate is administered intravenously.

Embodiment 134

The method of any one of Embodiments 125-133, wherein said methylprednisolone is administered intravenously or orally.

Embodiment 135

The method of any one of Embodiments 125-134, comprising administering methylprednisolone intravenously for at least one day, which is followed by administering methylprednisolone orally for at least a week.

Embodiment 136

The method of Embodiment 135, comprising administering methylprednisolone intravenously for about 3 days, which is followed by administering methylprednisolone orally for at least about 6 weeks.

Embodiment 137

The method of any one of Embodiments 125-136, wherein said methylprednisolone is administered intravenously at a daily dose of about 80 mg/60 kg.

Embodiment 138

The method of any one of Embodiments 125-137, wherein said administering said pharmaceutical composition generates a higher average recovery of vision than a comparable pharmaceutical composition without said recombinant nucleic acid.

Embodiment 139

The method of any one of Embodiments 125-138, wherein said administering said pharmaceutical composition generates a higher average recovery of vision than a comparable pharmaceutical composition comprising a recombinant nucleic acid as set forth in SEQ ID NO: 15.

Embodiment 140

A method of treating an eye disorder, comprising administering to a patient in need thereof (a) a first pharmaceutical composition comprising an adeno-associated virus (AAV) comprising a recombinant nucleic acid comprising: (i) a nucleic acid sequence encoding a mitochondrial targeting peptide; (ii) a nucleic acid sequence encoding a mitochondrial protein comprising a nucleic acid sequence that is at least 90%, at least 95%, at least 97%, at least 99%, or 100% identical to a sequence selected from the group consisting of SEQ ID NO: 6-12; and (iii) a 3'UTR nucleic acid sequence; and (b) a second pharmaceutical composition comprising a steroid.

Embodiment 141

The method of Embodiment 140, wherein the nucleic acid sequence encoding the mitochondrial protein encodes a polypeptide comprising an amino acid sequence that is at least 90%, at least 95%, at least 97%, at least 99%, or 100% identical to a sequence selected from the group consisting of SEQ ID NO: 160-162.

Embodiment 142

The method of Embodiment 140 or Embodiment 141, wherein the nucleic acid sequence encoding a mitochondrial targeting peptide encodes a polypeptide comprising an amino acid sequence that is at least 90%, at least 95%, at least 97%, at least 99%, or 100% identical to a sequence selected from the group consisting of SEQ ID NO: 126-159.

Embodiment 143

The method of any one of Embodiments 140-142, wherein the nucleic acid sequence encoding a mitochondrial targeting peptide comprises a nucleic acid sequence that is at least 90%, at least 95%, at least 97%, at least 99%, or 100% identical to a sequence selected from the group consisting of SEQ ID NO: 1-5.

Embodiment 144

The method of any one of Embodiments 140-143, wherein the 3'UTR nucleic acid sequence comprises a nucleic sequence that is at least 90%, at least 95%, at least 97%, at least 99%, or 100% identical to a sequence selected from the group consisting of SEQ ID NO: 13, 14, and 111-125.

Embodiment 145

A method of treating an eye disorder, comprising administering to a patient in need thereof (a) a first pharmaceutical composition comprising an adeno-associated virus (AAV) comprising a recombinant nucleic acid comprising: (i) a nucleic acid sequence encoding a mitochondrial targeting peptide comprising an amino sequence that is at least 90%, at least 95%, at least 97%, at least 99%, or 100% identical to a sequence selected from the group consisting of SEQ ID NO: 126-159; (ii) a nucleic acid sequence encoding a mitochondrial protein; and (iii) a 3'UTR nucleic acid sequence; and (b) a second pharmaceutical composition comprising a steroid.

Embodiment 146

The method of Embodiment 145, wherein said mitochondrial protein is selected from the group consisting of NADH dehydrogenase 4 (ND4), NADH dehydrogenase 6 (ND6), NADH dehydrogenase 1 (ND1), and variants thereof.

Embodiment 147

The method of Embodiment 146, wherein the nucleic acid sequence encoding a mitochondrial protein comprises a nucleic acid sequence that is at least 90%, at least 95%, at least 97%, at least 99%, or 100% identical to a nucleic acid sequence selected from the group consisting of SEQ ID NO: 6-12.

Embodiment 148

The method of Embodiment 146 or 147, wherein nucleic acid sequence encoding a mitochondrial protein encodes a polypeptide comprising an amino acid sequence that is at least 90%, at least 95%, at least 97%, at least 99%, or 100% identical to a sequence selected from the group consisting of SEQ ID NO: 160-162.

Embodiment 149

The method of any one of Embodiments 146-148, wherein the nucleic acid sequence encoding a mitochondrial targeting peptide comprises a nucleic acid sequence that is at least 90%, at least 95%, at least 97%, at least 99%, or 100% identical to a sequence selected from the group consisting of SEQ ID NO: 1-5.

Embodiment 150

The method of any one of Embodiments 146-149, wherein the 3'UTR nucleic acid sequence comprises a sequence that is at least 90%, at least 95%, at least 97%, at least 99%, or 100% identical to a sequence selected from the group consisting of SEQ ID NO: 13, 14, and 111-125.

Embodiment 151

A method of treating an eye disorder, comprising administering to a patient in need thereof (a) a first pharmaceutical composition comprising an adeno-associated virus (AAV) comprising a recombinant nucleic acid comprising: (i) a nucleic acid sequence encoding a mitochondrial targeting peptide comprising an amino sequence that is at least 90%, at least 95%, at least 97%, at least 99%, or 100% identical to a sequence selected from the group consisting of SEQ ID NO: 126-159; (ii) a nucleic acid sequence encoding a mitochondrial protein comprising a nucleic acid sequence that is at least 90%, at least 95%, at least 97%, at least 99%, or 100% identical to a sequence selected from the group consisting of SEQ ID NO: 6-12; and (iii) a 3'UTR nucleic acid sequence that is at least 90%, at least 95%, at least 97%, at least 99%, or 100% identical to a sequence selected from the group consisting of SEQ ID NO: 13, 14, and 111-125; and (b) a second pharmaceutical composition comprising a steroid.

Embodiment 152

A method of treating an eye disorder, comprising administering to a patient in need thereof (a) a first pharmaceutical composition comprising an adeno-associated virus (AAV) comprising a recombinant nucleic acid comprising: (i) a nucleic acid sequence encoding a mitochondrial targeting peptide; and (ii) a nucleic acid sequence encoding a mitochondrial protein; and (iii) a second pharmaceutical composition comprising a steroid.

Embodiment 153

The method of Embodiment 152, wherein the mitochondrial protein is selected from the group consisting of NADH dehydrogenase 4 (ND4), NADH dehydrogenase 6 (ND6), NADH dehydrogenase 1 (ND1), and variants thereof.

Embodiment 154

The method of Embodiment 152 or 153, wherein the 3'UTR nucleic acid sequence comprises a nucleic sequence that is at least 90%, at least 95%, at least 97%, at least 99%, or 100% identical to a sequence selected from the group consisting of SEQ ID NO: 13, 14, and 111-125.

Embodiment 155

The method of any one of Embodiments 140-154, wherein the recombinant nucleic acid comprises a sequence that is at least 90%, at least 95%, at least 97%, at least 99%, or 100% identical to a sequence selected from the group consisting of SEQ ID NO: 15-84.

Embodiment 156

The method of any one of Embodiments 140-155, wherein the recombinant nucleic acid comprises a sequence that is at least 90%, at least 95%, at least 97%, at least 99%, or 100% identical to SEQ ID NO: 15.

Embodiment 157

The method of any one of Embodiments 140-156, wherein the first pharmaceutical composition is administered via intraocular or intravitreal injection.

Embodiment 158

The method of any one of Embodiments 140-157, wherein about 0.01-0.1 mL of the first pharmaceutical composition is administered via intravitreal injection.

Embodiment 159

The method of any one of Embodiments 140-158, wherein about 0.05 mL of the first pharmaceutical composition is administered via intravitreal injection.

Embodiment 160

The method of any one of Embodiments 140-159, wherein the first pharmaceutical composition is administered to one or both eyes of the patient.

Embodiment 161

The method of any one of Embodiments 140-160, wherein the steroid is selected from the group consisting of alclometasone dipropionate, amcinonide, beclomethasone dipropionate, betamethasone, betamethasone benzoate, betamethasone dipropionate, betamethasone sodium phosphate, betamethasone sodium phosphate and acetate, betamethasone valerate, clobetasol proprionate, clocortolone pivalate, cortisol (hydrocortisone), cortisol (hydrocortisone) acetate, cortisol (hydrocortisone) butyrate, cortisol (hydrocortisone) cypionate, cortisol (hydrocortisone) sodium phosphate, cortisol (hydrocortisone) sodium succinate, cortisol (hydrocortisone) valerate, cortisone acetate, desonide, desoximetasone, dexamethasone, dexamethasone acetate, dexamethasone sodium phosphate, diflorasone diacetate, fludrocortisone acetate, flunisolide, fluocinolone acetonide, fluocinonide, fluorometholone, flurandrenolide, halcinonide, medrysone, methylprednisolone, methylprednisolone acetate, methylprednisolone sodium succinate, mometasone furoate, paramethasone acetate, prednisolone, prednisolone acetate, prednisolone sodium phosphate, prednisolone tebutate, prednisone, triamcinolone, triamcinolone acetonide, triamcinolone diacetate, and triamcinolone hexacetonide or a synthetic analog thereof.

Embodiment 162

The method of Embodiments 140-161, wherein the steroid is a glucocorticoid.

Embodiment 163

The method of Embodiment 162, wherein the glucocorticoid is methylprednisolone or prednisone.

Embodiment 164

The method of Embodiment 163, wherein the methylprednisolone is formulated as a tablet or as a liquid for intravenous administration.

Embodiment 165

The method of any one of Embodiments 140-164, wherein the steroid is administered orally or intravenously.

Embodiment 166

The method of any one of Embodiments 140-165, wherein the steroid is administered prior to administration of the first pharmaceutical composition.

Embodiment 167

The method of Embodiment 166, wherein the steroid is administered daily for at least 1, 2, 3, 4, 5, 6, or 7 days prior to the administration of the first pharmaceutical composition.

Embodiment 168

The method of Embodiment 167, wherein the steroid is methylprednisolone and is administered at a daily dosage of about 30 mg/60 kg to about 40 mg/60 kg or about 30 mg to about 40 mg.

Embodiment 169

The method of Embodiment 168, wherein the daily dosage of methylprednisolone is about 32 mg/60 kg or 32 mg.

Embodiment 170

The method of Embodiment 168, wherein the steroid is prednisone and is administered at a daily dosage of about 50 mg/60 kg to about 70 mg/60 kg.

Embodiment 171

The method of Embodiment 170, wherein the daily dosage of prednisone is about 60 mg/60 kg.

Embodiment 172

The method of any one of Embodiments 140-171, wherein the steroid is administered after the administration of the first pharmaceutical composition.

Embodiment 173

The method of Embodiment 172, wherein the steroid is administered daily for at least 1 day, at least 2 days, at least 3 days, at least 4 days, at least 5 days, at least 6 days, at least 7 days, at least 8 days, at least 9 days, at least 10 days, at least 1 week, at least 2 weeks, at least 3 weeks, at least 4 weeks, at least 5 weeks, at least 6 weeks, at least 7 weeks, at least 8 weeks, at least 9 weeks, at least 10 weeks, at least 11 weeks, at least 12 weeks, at least 13 weeks, at least 14 weeks, or at least 15 weeks after the administration of the first pharmaceutical composition.

Embodiment 174

The method of Embodiment 173, wherein the steroid is methylprednisolone and is administered at a daily dosage of between about 70 mg/60 kg and 90 mg/60 kg or between about 70 mg and 90 mg.

Embodiment 175

The method of Embodiment 174, wherein the daily dosage of methylprednisolone is about 80 mg/60 kg or 80 mg.

Embodiment 176

The method of Embodiment 174 or 175, wherein the methylprednisolone is administered for at least two days after the administration of the first pharmaceutical composition.

Embodiment 177

The method of Embodiment 176, wherein subsequent doses of methylprednisolone are administered daily for at least 7 weeks after the administration of the first pharmaceutical composition and wherein the dosage of the methylprednisolone is decreased on a weekly basis.

Embodiment 178

The method of Embodiment 173, the steroid is predisone and is administered at a daily dosage of between about 50 mg/60 kg and 70 mg/60 kg or between about 50 mg and about 70 mg.

Embodiment 179

The method of Embodiment 178, wherein the daily dosage of predisone is about 60 mg/60 kg or about 60 mg.

Embodiment 180

The method of Embodiment 178 or 179, wherein the predisone is administered for at least seven days after the administration of the first pharmaceutical composition.

Embodiment 181

The method of Embodiment 180, wherein after seven days, the predisone is administered at a daily dosage of between about 30 mg/60 kg and about 50 mg/60 kg or between about 30 mg and 50 mg.

Embodiment 182

The method of Embodiment 181, wherein the daily dosage of predisone is about 40 mg/60 kg or 40 mg.

Embodiment 183

The method of Embodiment 182, wherein subsequent doses of predisone are administered daily for at least 4 days and wherein the dosage of the predisone is decreased on a daily basis.

Embodiment 184

The method of any one of Embodiments 140-183, wherein the steroid is administered prior to and after the administration of the first pharmaceutical compound.

Embodiment 185

The method of Embodiment 184, wherein the steroid is methylprednisolone and is administered daily for at least seven days prior to the administration of the first pharmaceutical compound and daily for at least 7 weeks after administration of the first pharmaceutical compound.

Embodiment 186

The method of Embodiment 185, wherein the methylprednisolone is administered prior to the administration of the first pharmaceutical compound at a daily dosage of about 32 mg/60 kg or 32 mg.

Embodiment 187

The method of Embodiment 185 or 186, wherein the methylprednisolone is administered at a daily dosage of about 80 mg/60 kg or 80 mg for at least 2 days after the administration of the first pharmaceutical compound.

Embodiment 188

The method of Embodiment 187, wherein beginning three days after administration of the first pharmaceutical compound, the methylprednisolone is administered at a daily dosage of about 40 mg/60 kg or 40 mg for at least 4 days.

Embodiment 189

The method of Embodiment 188, wherein beginning one week after administration of the first pharmaceutical compound, the methylprednisolone is administered at a daily dosage of about 32 mg/60 kg or 32 mg for at least one week.

Embodiment 190

The method of Embodiment 189, wherein beginning two weeks after administration of the first pharmaceutical compound, the methylprednisolone is administered at a daily dosage of about 24 mg/60 kg or 24 mg for at least one week.

Embodiment 191

The method of Embodiment 190, wherein beginning three weeks after administration of the first pharmaceutical compound, the methylprednisolone is administered at a daily dosage of about 16 mg/60 kg or 16 mg for at least one week.

Embodiment 192

The method of Embodiment 191, wherein beginning four weeks after administration of the first pharmaceutical compound, the methylprednisolone is administered at a daily dosage of about 8 mg/60 kg or 8 mg for at least one week.

Embodiment 193

The method of Embodiment 192, wherein beginning five weeks after administration of the first pharmaceutical compound, the methylprednisolone is administered at a daily dosage of about 6 mg/60 kg or 6 mg for at least one week.

Embodiment 194

The method of Embodiment 193, wherein beginning six weeks after administration of the first pharmaceutical compound, the methylprednisolone is administered at a daily dosage of about 4 mg/60 kg or 4 mg for at least one week.

Embodiment 195

The method of Embodiment 194, wherein the steroid is prednisone and is administered daily for at least two days prior to the administration of the first pharmaceutical compound and daily for at least eleven days after administration of the first pharmaceutical compound.

Embodiment 196

The method of Embodiment 195, wherein the prednisone is administered prior to the administration of the first pharmaceutical compound at a daily dosage of about 60 mg/60 kg or 60 mg.

Embodiment 197

The method of Embodiment 195 or 196, wherein the prednisone is administered at a daily dosage of about 60 mg/60 kg or 60 mg for at least seven days after the administration of the first pharmaceutical compound.

Embodiment 198

The method of Embodiment 197, wherein eight days after administration of the first pharmaceutical compound, the prednisone is administered at a daily dosage of about 40 mg/60 kg or 40 mg for at least one day.

Embodiment 199

The method of Embodiment 198, wherein nine days after administration of the first pharmaceutical compound, the prednisone is administered at a daily dosage of about 20 mg/60 kg or 20 mg for at least one day.

Embodiment 200

The method of Embodiment 199, wherein ten days after administration of the first pharmaceutical compound, the prednisone is administered at a daily dosage of about 10 mg/60 kg or 10 mg for at least one day.

Embodiment 201

The method of any one of Embodiments 140-200, further comprising administering sodium creatine phosphate to the patient.

Embodiment 202

The method of Embodiment 201, wherein said sodium creatine phosphate is administered intravenously prior to and/or after the administration of the first pharmaceutical composition.

Embodiment 203

The method of any one of Embodiments 140-202, wherein administration of the first and second pharmaceutical compositions generates a higher average recovery of vision than a comparable pharmaceutical composition administered without the second pharmaceutical composition.

Embodiment 204

The method of any one of Embodiments 140-203, wherein administration of the first and second pharmaceutical compositions generates a lower incidence of an adverse event than a comparable pharmaceutical composition administered without the second pharmaceutical composition.

Embodiment 205

The method of Embodiment 204, wherein the adverse event is selected from anterior chamber inflammation, vitritis, ocular hypertension, cataract removal, keratitis, vitreous hemorrhage, allergic conjunctivitis, and eye pain.

Embodiment 206

The method of any one of Embodiments 203-205, wherein the higher average recovery of vision and the lower incidence of an adverse event is determined in a population of patients with the eye disorder.

Embodiment 207

The method of Embodiment 206, wherein the population of patients are ethnically matched.

Embodiment 208

The method of Embodiment 207, wherein the population of patients are Chinese or Argentinian.

Embodiment 209

The method of any one of Embodiments 140-208, wherein the eye disorder is Leber's hereditary optic neuropathy (LHON).

Embodiment 210

The method of any one of Embodiments 140-209, wherein the AAV is selected from AAV1, AAV2, AAV3, AAV4, AAV5, AAV6, AAV7, AA8, AAV9, and AAV10.

Embodiment 211

The method of any one of Embodiments 140-210, wherein the AAV is AAV2.

Embodiment 212

A method of screening patients for treatment of an eye disorder, the method comprising: (a) obtaining a serum sample from a patient; (b) culturing a population of target cells with a composition comprising an adeno-associated virus (AAV) comprising a recombinant nucleic acid encoding a detectable label in the presence of the serum sample; and (c) detecting the expression level of the detectable label in the target cell population after the culturing, wherein the patient is selected for the treatment if the expression level of the detectable label in the target cell population is higher than a pre-determined threshold.

Embodiment 213

A method of treating an eye disorder for a patient in need thereof, comprising: (a) obtaining a serum sample from a patient; (b) culturing a population of target cells with a composition comprising a first adeno-associated virus (AAV) comprising a first recombinant nucleic acid encoding a detectable label in the presence of the serum sample; (c)

detecting the expression level of the detectable label in the target cell population; and (d) administering to the patient a pharmaceutical composition comprising a second AAV comprising a second recombinant nucleic acid, wherein the expression level of the detectable label in the target cell population is higher than a pre-determined threshold.

Embodiment 214

The method of Embodiment 212 or 213, wherein the detectable label is a fluorescent protein.

Embodiment 215

The method of Embodiment 214, wherein the fluorescent protein is green fluorescent protein (GFP).

Embodiment 216

The method of any one of Embodiments 212-215, wherein the detectable label is detected by flow cytometry or qPCR.

Embodiment 217

The method of any one of Embodiments 212-216, wherein the pre-determined threshold is about 40% of cells expressing the detectable label when detected by flow cytometry.

Embodiment 218

The method of any one of Embodiments 212-216, wherein the pre-determined threshold is a relative expression level of the detectable label of about 0.6 when detected by qPCR.

Embodiment 219

The method of any one of Embodiments 212-218, wherein the target cells are HEK-293 T cells.

Embodiment 220

The method of any one of Embodiments 212-219, wherein the treatment is a recombinant AAV comprising a nucleic acid sequence encoding a mitochondrial protein.

Embodiment 221

The method of Embodiment 220, wherein the mitochondrial protein is selected from the group consisting of NADH dehydrogenase 4 (ND4), NADH dehydrogenase 6 (ND6), NADH dehydrogenase 1 (ND1), and variants thereof.

Embodiment 222

The method of any one of Embodiments 212-221, wherein the patient comprises a mutation selected from G11778A in the ND4 gene, G3460A in the ND1 gene, and T14484C in the ND6 gene.

Embodiment 223

The method of any one of Embodiments 212-222, wherein the culturing step is at least 12 hours, 1 day, 2 days, 3 days, 4 days, 5 days, 6 days, 7 days, or longer.

Embodiment 224

A kit, comprising an adeno-associated virus (AAV) comprising a recombinant nucleic acid encoding a detectable label, a population of target cells, and one or more reagents for detecting the detectable label.

Embodiment 225

The kit of Embodiment 224, further comprising a transfection reagent for transfecting the population of target cells with the AAV.

Embodiment 225

The kit of Embodiment 224 or 225, further comprising a second AAV comprising a recombinant nucleic acid encoding a mitochondrial protein.

Embodiment 225

The kit of Embodiment 224, wherein the one or more reagents for detecting the detectable label are selected an antibody that binds to the detectable label and one or more primer oligonucleotides specific for the recombinant nucleic acid encoding the detectable label.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as, an acknowledgment or any form of suggestion that they constitute valid prior art or form part of the common general knowledge in any country in the world.

What is claimed is:

1. A method of treating an eye disorder, comprising
a) administering intravitreally or intraocularly to a patient in need thereof a first pharmaceutical composition comprising a therapeutically effective amount of an adeno-associated virus (AAV) comprising a promoter operably linked to a recombinant nucleic acid comprising:
i) a nucleic acid sequence encoding a mitochondrial targeting peptide;
ii) a nucleic acid sequence encoding a mitochondrial protein comprising a nucleic acid sequence that is:
1) 100% identical to SEQ ID NO: 6;
2) at least 99% identical to SEQ ID NO: 9; or
3) at least 99% identical to SEQ ID NO: 11;
iii) a 3'UTR nucleic acid sequence; and
b) administering to the patient a second pharmaceutical composition comprising a steroid.

2. The method of claim 1, wherein the nucleic acid sequence encoding the mitochondrial protein encodes a polypeptide comprising an amino acid sequence that is at least 90%, at least 95%, at least 97%, at least 99%, or 100% identical to a sequence selected from the group consisting of SEQ ID NO: 160-162.

3. The method of claim 1, wherein the nucleic acid sequence encoding a mitochondrial targeting peptide encodes a polypeptide comprising an amino acid sequence that is at least 90%, at least 95%, at least 97%, at least 99%, or 100% identical to a sequence selected from the group consisting of SEQ ID NO: 126-159.

4. The method of claim 1, wherein the nucleic acid sequence encoding a mitochondrial targeting peptide comprises a nucleic acid sequence that is at least 90%, at least 95%, at least 97%, at least 99%, or 100% identical to a sequence selected from the group consisting of SEQ ID NO: 2-4.

5. The method of claim 1, wherein the 3'UTR nucleic acid sequence comprises a nucleic sequence that is at least 90%, at least 95%, at least 97%, at least 99%, or 100% identical to a sequence selected from the group consisting of SEQ ID NO: 13, 14, and 111-125.

6. The method of claim 1, wherein the recombinant nucleic acid comprises a sequence that is at least 90%, at least 95%, at least 97%, at least 99%, or 100% identical to a sequence selected from the group consisting of SEQ ID NO: 15-16, 21-22, 25-26, 29-30, 35-36, 39-40, 43-44, 49-50, 53-54, 57-58, 63-64, 67-68, 71-72, 77-78, and 81-82.

7. The method of claim 1, wherein about 0.01-0.1 mL of the first pharmaceutical composition is administered via intravitreal injection.

8. The method of claim 1, wherein the steroid selected from the group consisting of alclometasone diproprionate, amcinonide, beclomethasone diproprionate, betamethasone, betamethasone benzoate, betamethasone diproprionate, betamethasone sodium phosphate, betamethasone sodium phosphate and acetate, betamethasone valerate, clobetasol proprionate, clocortolone pivalate, cortisol (hydrocortisone), cortisol (hydrocortisone) acetate, cortisol (hydrocortisone) butyrate, cortisol (hydrocortisone) cypionate, cortisol (hydrocortisone) sodium phosphate, cortisol (hydrocortisone) sodium succinate, cortisol (hydrocortisone) valerate, cortisone acetate, desonide, desoximetasone, dexamethasone, dexamethasone acetate, dexamethasone sodium phosphate, diflorasone diacetate, fludrocortisone acetate, flunisolide, fluocinolone acetonide, fluocinonide, fluorometholone, flurandrenolide, halcinonide, medrysone, methylprednisolone, methylprednisolone acetate, methylprednisolone sodium succinate, mometasone furoate, paramethasone acetate, prednisolone, prednisolone acetate, prednisolone sodium phosphate, prednisolone tebutate, prednisone, triamcinolone, triamcinolone acetonide, triamcinolone diacetate, and triamcinolone hexacetonide or a synthetic analog thereof.

9. The method of claim 1, wherein the steroid is a glucocorticoid.

10. The method of claim 9, wherein the glucocorticoid is methylprednisolone or prednisone.

11. The method of claim 1, wherein the steroid is administered prior to administration of the first pharmaceutical composition.

12. The method of claim 11, wherein the steroid is methylprednisolone and is administered at a daily dosage of about 30 mg/60 kg to about 40 mg/60 kg or about 30 mg to about 40 mg.

13. The method of claim 11, wherein the steroid is prednisone and is administered at a daily dosage of about 50 mg/60 kg to about 70 mg/60 kg.

14. The method of claim 1, wherein the steroid is administered after the administration of the first pharmaceutical composition.

15. The method of claim 14, wherein the steroid is methylprednisolone and is administered at a daily dosage of between about 70 mg/60 kg and 90 mg/60 kg or between about 70 mg and 90 mg.

16. The method of claim 14, wherein the steroid is methylprednisolone and is administered for at least two days after the administration of the first pharmaceutical composition, and wherein subsequent doses of methylprednisolone are administered daily for at least 7 weeks after the administration of the first pharmaceutical composition and wherein the dosage of the methylprednisolone is decreased on a weekly basis.

17. The method of claim 14, wherein the steroid is prednisone and is administered at a daily dosage of between about 50 mg/60 kg and 70 mg/60 kg or between about 50 mg and about 70 mg.

18. The method of claim 17, wherein the prednisone is administered for at least seven days after the administration of the first pharmaceutical composition.

19. The method of claim 18, wherein after seven days, the prednisone is administered at a daily dosage of between about 30 mg/60 kg and about 50 mg/60 kg or between about 30 mg and 50 mg.

20. The method of claim 18, wherein subsequent doses of the prednisone are administered daily for at least 4 days and wherein the dosage of the prednisone is decreased on a daily basis.

21. The method of claim 1, wherein the steroid is administered prior to and after the administration of the first pharmaceutical composition.

22. The method of claim 21, wherein the steroid is methylprednisolone and is administered daily for at least seven days prior to the administration of the first pharmaceutical composition and daily for at least 7 weeks after administration of the first pharmaceutical composition.

23. The method of claim 21, wherein the steroid is prednisone and is administered daily for at least two days prior to the administration of the first pharmaceutical composition and daily for at least eleven days after administration of the first pharmaceutical composition.

24. The method of claim 1, further comprising administering sodium creatine phosphate to the patient.

25. The method of claim 1, wherein the eye disorder is Leber's hereditary optic neuropathy (LHON).

26. The method of claim 1, wherein the AAV is AAV2.

27. A method of treating Leber's hereditary optic neuropathy (LHON), comprising:
- (a) administering intravitreally or intraocularly to a patient in need thereof a first pharmaceutical composition comprising a therapeutically effective amount of an adeno-associated virus (AAV) comprising a promoter operably linked to a recombinant nucleic acid comprising:
  - i) a nucleic acid sequence encoding a mitochondrial targeting peptide, wherein the nucleic acid sequence is at least 90%, at least 95%, at least 97%, at least 99%, or 100% identical to a sequence selected from the group consisting of SEQ ID NO: 1-5, or wherein the mitochondrial targeting peptide comprises an amino sequence that is at least 90%, at least 95%, at least 97%, at least 99%, or 100% identical to a sequence selected from the group consisting of SEQ ID NO: 126-159;
  - ii) a nucleic acid sequence encoding a mitochondrial protein comprising a nucleic acid sequence that is:
    - 1) 100% identical to SEQ ID NO: 6;
    - 2) at least 99% identical to SEQ ID NO: 9; or
    - 3) at least 99% identical to SEQ ID NO: 11; and
  - iii) a 3'UTR nucleic acid sequence that is at least 90%, at least 95%, at least 97%, at least 99%, or 100% identical to a sequence selected from the group consisting of SEQ ID NO: 13, 14, and 111-125; and
- (b) administering to the patient a second pharmaceutical composition comprising methylprednisolone or prednisone.

* * * * *

SEQUENCE LISTING

```
<160> NUMBER OF SEQ ID NOS: 168

<210> SEQ ID NO 1
<211> LENGTH: 84
<212> TYPE: DNA
<213> ORGANISM: Homo sapiens

<400> SEQUENCE: 1
atggccgcat ctccgcacac tctctcctca cgcctcctga caggttgcgt aggaggctct      60
gtctggtatc ttgaaagaag aact                                            84
```

-continued

```
<210> SEQ ID NO 2
<211> LENGTH: 84
<212> TYPE: DNA
<213> ORGANISM: Artificial Sequence
<220> FEATURE:
<223> OTHER INFORMATION: opt_COX10

<400> SEQUENCE: 2
atggccgcct ctccacacac actgagtagc agactgctga ccggctgtgt tggcggctct    60
gtgtggtatc tggaacggcg gaca                                           84

<210> SEQ ID NO 3
<211> LENGTH: 84
<212> TYPE: DNA
<213> ORGANISM: Artificial Sequence
<220> FEATURE:
<223> OTHER INFORMATION: opt_COX10*

<400> SEQUENCE: 3
atggccgcca gccccacac cctgagcagc cgcctgctga ccggctgcgt gggcggcagc     60
gtgtggtacc tggagcgccg cacc                                           84

<210> SEQ ID NO 4
<211> LENGTH: 87
<212> TYPE: DNA
<213> ORGANISM: Artificial Sequence
<220> FEATURE:
<223> OTHER INFORMATION: COX8

<400> SEQUENCE: 4
atgtccgtcc tgacgcgcct gctgctgcgg ggcttgacac ggctcggctc ggcggctcca    60
gtgcggcgcg ccagaatcca ttcgttg                                        87

<210> SEQ ID NO 5
<211> LENGTH: 266
<212> TYPE: DNA
<213> ORGANISM: Homo sapiens

<400> SEQUENCE: 5
gtgctgcccg cctagaaagg gtgaagtggt tgtttccgtg acggactgag tacgggtgcc    60
tgtcaggctc ttgcggaagt ccatgcgcca ttgggagggc ctcggccgcg gctctgtgcc   120
cttgctgctg agggccactt cctgggtcat tcctggaccg ggagccgggc tggggctcac   180 acggggctc ccgcgtggcc gtctcggcgc ctgcgtgacc tccccgccgg cgggatgtgg    240
cgactacgtc gggccgctgt ggcctg                                        266

<210> SEQ ID NO 6
<211> LENGTH: 1380
<212> TYPE: DNA
<213> ORGANISM: Homo sapiens

<400> SEQUENCE: 6
atgctaaaac taatcgtccc aacaattatg ttactaccac tgacatggct ttccaaaaaa    60
cacatgattt ggatcaacac aaccacccac agcctaatta ttagcatcat ccctctacta   120 tttttaacc aaatcaacaa caacctattt agctgttccc caacctttc ctccgacccc     180 ctaacaaccc ccctcctaat gctaactacc tggctcctac ccctcacaat catggcaagc    240
caacgccact atccagtga accactatca cgaaaaaaac tctacctctc tatgctaatc    300
tccctacaaa tctccttaat tatgacattc acagccacag aactaatcat gttttatatc    360
```

```
ttcttcgaaa ccacacttat ccccaccttg gctatcatca cccgatgggg caaccagcca      420
gaacgcctga acgcaggcac atacttccta ttctacaccc tagtaggctc ccttcccta      480 ctcatcgcac taatttacac tcacaacacc ctaggctcac taaacattct actactcact      540
ctcactgccc aagaactatc aaactcctgg gccaacaact taatgtggct agcttacaca      600
atggctttta tggtaaagat gcctctttac ggactccact tatggctccc taaagcccat      660
gtcgaagccc ccatcgctgg gtcaatggta cttgccgcag tactcttaaa actaggcggc      720
tatggtatga tgcgcctcac actcattctc aaccccctga caaaacacat ggcctacccc      780
ttccttgtac tatccctatg ggcatgatt atgacaagct ccatctgcct acgacaaaca      840
gacctaaaat cgctcattgc atactcttca atcagccaca tggccctcgt agtaacagcc      900
attctcatcc aaaccccctg gagcttcacc ggcgcagtca ttctcatgat cgcccacggg      960
cttacatcct cattactatt ctgcctagca aactcaaact acgaacgcac tcacagtcgc     1020
atcatgatcc tctctcaagg acttcaaact ctactcccac taatggcttt ttggtggctt     1080
ctagcaagcc tcgctaacct cgccttaccc cccactatta acctactggg agaactctct     1140
gtgctagtaa ccacgttctc ctggtcaaat atcactctcc tacttacagg actcaacatg     1200
ctagtcacag ccctatactc cctctacatg tttaccacaa cacaatgggg ctcactcacc     1260
caccacatta acaacatgaa accctcattc acacgagaaa acaccctcat gttcatgcac     1320
ctatccccca ttctcctcct atccctcaac cccgacatca ttaccgggtt ttcctcttaa     1380
```

<210> SEQ ID NO 7
<211> LENGTH: 1380
<212> TYPE: DNA
<213> ORGANISM: Artificial Sequence
<220> FEATURE:
<223> OTHER INFORMATION: opt_ND4

<400> SEQUENCE: 7

```
atgctgaagc tgatcgtgcc caccatcatg ctgctgcctc tgacctggct gagcaagaaa       60
cacatgatct ggatcaacac caccacgcac agcctgatca tcagcatcat ccctctgctg      120
ttcttcaacc agatcaacaa caacctgttc agctgcagcc ccaccttcag cagcgacccct     180 ctgacaacac ctctgctgat gctgaccacc tggctgctgc ccctcacaat catggcctct      240
cagagacacc tgagcagcga gcccctgagc cggaagaaac tgtacctgag catgctgatc      300
tccctgcaga tctctctgat catgaccttc accgccaccg agctgatcat gttctacatc      360
tttttcgaga caacgctgat ccccacactg gccatcatca ccagatgggg caaccagcct      420
gagagactga acgccggcac ctactttctg ttctacaccc tcgtgggcag cctgccactg      480
ctgattgccc tgatctacac ccacaacacc ctgggctccc tgaacatcct gctgctgaca      540
ctgacagccc aagagctgag caacagctgg gccaacaatc tgatgtggct ggcctacaca      600
atggccttca tggtcaagat gcccctgtac ggcctgcacc tgtggctgcc taaagctcat      660
gtggaagccc ctatcgccgg ctctatggtg ctggctgcag tgctgctgaa actcggcggc      720
tacggcatga tgcggctgac cctgattctg aatcccctga ccaagcacat ggcctatcca      780
tttctggtgc tgagcctgtg gggcatgatt atgaccagca gcatctgcct gcggcagacc      840
gatctgaagt ccctgatcgc ctacagctcc atcagccaca tggccctggt ggtcaccgcc      900
atcctgattc agaccccttg gagctttaca ggcgccgtga tcctgatgat tgcccacggc      960
ctgacaagca gcctgctgtt tgtctctgcc aacagcaact acgagcggac ccacagcaga     1020
atcatgatcc tgtctcaggg cctgcagacc ctcctgcctc ttatggcttt ttggtggctg     1080
```

```
ctggcctctc tggccaatct ggcactgcct cctaccatca atctgctggg cgagctgagc    1140
gtgctggtca ccacattcag ctggtccaat atcaccctgc tgctcaccgg cctgaacatg    1200
ctggttacag ccctgtactc cctgtacatg ttcaccacca cacagtgggg aagcctgaca    1260
caccacatca acaatatgaa gcccagcttc acccgcgaga acaccctgat gttcatgcat    1320
ctgagcccca ttctgctgct gtccctgaat cctgatatca tcaccggctt ctccagctga    1380
```

```
<210> SEQ ID NO 8
<211> LENGTH: 1380
<212> TYPE: DNA
<213> ORGANISM: Artificial Sequence
<220> FEATURE:
<223> OTHER INFORMATION: opt_ND4*

<400> SEQUENCE: 8
```

```
atgctgaagc tgatcgtgcc caccatcatg ctgctgcccc tgacctggct gagcaagaag     60
cacatgatct ggatcaacac caccacccac agcctgatca tcagcatcat ccccctgctg    120
ttcttcaacc agatcaacaa caacctgttc agctgcagcc ccaccttcag cagcgacccc    180
ctgaccaccc ccctgctgat gctgaccacc tggctgctgc ccctgaccat catggccagc    240
cagcgccacc tgagcagcga gcccctgagc cgcaagaagc tgtacctgag catgctgatc    300
agcctgcaga tcagcctgat catgaccttc accgccaccg agctgatcat gttctacatc    360
ttcttcgaga ccacccctgat ccccaccctg gccatcatca cccgctgggg caaccagccc    420
gagcgcctga cgccggcac ctacttcctg ttctacaccc tggtgggcag cctgcccctg    480
ctgatcgccc tgatctacac ccacaacacc ctgggcagcc tgaacatcct gctgctgacc    540
ctgaccgccc aggagctgag caacagctgg gccaacaacc tgatgtggct ggcctacacc    600
atggccttca tggtgaagat gccccctgtac ggcctgcacc tgtggctgcc caaggcccac    660
gtggaggccc ccatcgccgg cagcatggtg ctggccgccg tgctgctgaa gctgggcggc    720
tacggcatga tgcgcctgac cctgatcctg aaccccctga ccaagcacat ggcctacccc    780
ttcctggtgc tgagcctgtg gggcatgatc atgaccagca gcatctgcct gcgccagacc    840
gacctgaaga gcctgatcgc ctacagcagc atcagccaca tggccctggt ggtgaccgcc    900
atcctgatcc agaccccctg gagcttcacc ggcgccgtga tcctgatgat cgcccacggc    960
ctgaccagca gcctgctgtt ctgcctggcc aacagcaact acgagcgcac ccacagccgc   1020
atcatgatcc tgagccaggg cctgcagacc ctgctgcccc tgatggcctt ctggtggctg   1080
ctggccagcc tggccaacct ggccctgccc ccaccatca acctgctggg cgagctgagc   1140
gtgctggtga ccaccttcag ctggagcaac atcaccctgc tgctgaccgg cctgaacatg   1200
ctggtgaccg ccctgtacag cctgtacatg ttcaccacca cccagtgggg cagcctgacc   1260
caccacatca acaacatgaa gcccagcttc acccgcgaga acaccctgat gttcatgcac   1320
ctgagcccca tcctgctgct gagcctgaac cccgacatca tcaccggctt cagcagctaa   1380
```

```
<210> SEQ ID NO 9
<211> LENGTH: 525
<212> TYPE: DNA
<213> ORGANISM: Homo sapiens

<400> SEQUENCE: 9
```

```
atgatgtatg ctttgtttct gttgagtgtg ggtttagtaa tggggtttgt ggggttttct     60
tctaagcctt ctcctatttta tggggggttta gtattgattg ttagcggtgt ggtcgggtgt    120
```

| | | |
|---|---|---|
| gttattattc tgaattttgg gggaggttat atgggtttaa tggttttttt aatttattta | 180 | |
| ggggaatga tggttgtctt tggatatact acagcgatgg ctattgagga gtatcctgag | 240 | |
| gcatggggt caggggttga ggtcttggtg agtgttttag tggggttagc gatggaggta | 300 | |
| ggattggtgc tgtgggtgaa agagtatgat ggggtggtgg ttgtggtaaa ctttaatagt | 360 | |
| gtaggaagct ggatgattta tgaaggagag gggtcagggt tgattcggga ggatcctatt | 420 | |
| ggtgcggggg ctttgtatga ttatgggcgt tggttagtag tagttactgg ttggacattg | 480 | |
| tttgttggtg tatatattgt aattgagatt gctcggggga attag | 525 | |

<210> SEQ ID NO 10
<211> LENGTH: 525
<212> TYPE: DNA
<213> ORGANISM: Artificial Sequence
<220> FEATURE:
<223> OTHER INFORMATION: opt_ND6

<400> SEQUENCE: 10

| | | |
|---|---|---|
| atgatgtacg ccctgttcct gctgagcgtg ggcctggtga tgggcttcgt gggcttcagc | 60 | |
| agcaagccca gccccatcta cggcggcctg gtgctgatcg tgagcggcgt ggtgggctgc | 120 | |
| gtgatcatcc tgaacttcgg cggcggctac atgggcctga tggtgttcct gatctacctg | 180 | |
| ggcggcatga tggtggtgtt cggctacacc accgccatgg ccatcgagga gtaccccgag | 240 | |
| gcctggggca gcggcgtgga ggtgctggtg agcgtgctgg tgggcctggc catggaggtg | 300 | |
| ggcctggtgc tgtgggtgaa ggagtacgac ggcgtggtgg tggtggtgaa cttcaacagc | 360 | |
| gtgggcagct ggatgatcta cgagggcgag ggcagcggcc tgatccgcga ggaccccatc | 420 | |
| ggcgccggcg ccctgtacga ctacggccgc tggctggtgg tggtgaccgg ctggaccctg | 480 | |
| ttcgtgggcg tgtacatcgt gatcgagatc gcccgcggca actaa | 525 | |

<210> SEQ ID NO 11
<211> LENGTH: 951
<212> TYPE: DNA
<213> ORGANISM: Homo sapiens

<400> SEQUENCE: 11

| | | |
|---|---|---|
| atggccaacc tcctactcct cattgtaccc attctaatcg caatggcatt cctaatgctt | 60 | |
| accgaacgaa aaattctagg ctatatgcaa ctacgcaaag cccccaacgt tgtaggcccc | 120 | |
| tacgggctac tacaacccttt cgctgacgcc ataaaactct tcaccaaaga gcccctaaaa | 180 | |
| cccgccacat ctaccatcac cctctacatc accgccccga ccttagctct caccatcgct | 240 | |
| cttctactat ggacccccct ccccatgccc aaccccctgg tcaacctcaa cctaggcctc | 300 | |
| ctatttattc tagccacctc tagcctagcc gtttactcaa tcctctggtc agggtgggca | 360 | |
| tcaaactcaa actacgccct gatcggcgca ctgcgagcag tagcccaaac aatctcatat | 420 | |
| gaagtcaccc tagccatcat tctactatca acattactaa tgagtggctc ctttaacctc | 480 | |
| tccaccctta tcacaacaca agaacacctc tggttactcc tgccatcatg gcccttggcc | 540 | |
| atgatgtggt ttatctccac actagcagag accaaccgaa cccccttcga ccttgccgaa | 600 | |
| ggggagtccg aactagtctc aggcttcaac atcgaatacg ccgcaggccc cttcgcccta | 660 | |
| ttcttcatgg ccgaatacac aaacattatt atgatgaaca ccctcaccac tacaatcttc | 720 | |
| ctaggaacaa catatgacgc actctcccct gaactctaca aacatatttt tgtcaccaag | 780 | |
| accctacttc taacctccct gttcttatgg attcgaacag catacccccg attccgctac | 840 | |
| gaccaactca tgcacctcct atggaaaaac ttcctaccac tcaccctagc attacttatg | 900 | |

```
tggtatgtct ccatgcccat tacaatctcc agcattcccc ctcaaaccta a        951
```

<210> SEQ ID NO 12
<211> LENGTH: 951
<212> TYPE: DNA
<213> ORGANISM: Artificial Sequence
<220> FEATURE:
<223> OTHER INFORMATION: opt_ND1

<400> SEQUENCE: 12

```
atggccaacc tgctgctgct gatcgtgccc atcctgatcg ccatggcctt cctgatgctg     60
accgagcgca agatcctggg ctacatgcag ctgcgcaagg cccccaacgt ggtgggcccc    120
tacggcctgc tgcagcccct cgccgacgcc atcaagctgt tcaccaagga gcccctgaag    180
cccgccacca gcaccatcac cctgtacatc accgccccca ccctggccct gaccatcgcc    240
ctgctgctgt ggacccccct gcccatgccc aaccccctgg tgaacctgaa cctgggcctg    300
ctgttcatcc tggccaccag cagcctggcc gtgtacagca tcctgtggag cggctgggcc    360
agcaacagca actacgccct gatcggcgcc ctgcgcgccg tggcccagac catcagctac    420
gaggtgaccc tggccatcat cctgctgagc accctgctga tgagcggcag cttcaacctg    480
agcaccctga tcaccaccca ggagcacctg tggctgctgc tgcccagctg gcccctggcc    540
atgatgtggt tcatcagcac cctggccgag accaaccgca ccccttcga cctggccgag    600
ggcgagagcg agctggtgag cggcttcaac atcgagtacg ccgccggccc cttcgccctg    660
ttcttcatgg ccgagtacac caacatcatc atgatgaaca ccctgaccac caccatcttc    720
ctgggcacca cctacgacgc cctgagcccc gagctgtaca ccacctactt cgtgaccaag    780
accctgctgc tgaccagcct gttcctgtgg atccgcaccg cctaccccg cttccgctac    840
gaccagctga tgcacctgct gtggaagaac ttcctgcccc tgaccctggc cctgctgatg    900
tggtacgtga gcatgcccat caccatcagc agcatccccc cccagaccta a             951
```

<210> SEQ ID NO 13
<211> LENGTH: 1425
<212> TYPE: DNA
<213> ORGANISM: Homo sapiens

<400> SEQUENCE: 13

```
gagcactggg acgccaccg ccccctttccc tccgctgcca ggcgagcatg ttgtggtaat     60
tctggaacac aagaagagaa attgctgggt ttagaacaag attataaacg aattcggtgc    120
tcagtgatca cttgacagtt ttttttttttt taaatatta cccaaaatgc tccccaaata    180
agaaatgcat cagctcagtc agtgaataca aaaaggaat tattttttccc tttgagggtc    240
ttttatacat ctctcctcca acccaccct ctattctgtt tcttcctcct cacatggggg    300
tacacataca cagcttcctc ttttggttcc atccttacca ccacaccaca cgcacactcc    360
acatgcccag cagagtggca cttggtggcc agaaagtgtg agcctcatga tctgctgtct    420
gtagttctgt gagctcaggt ccctcaaagg cctcggagca ccccttcct tgtgactgag    480
ccagggcctg catttttggt tttcccacc ccacacattc tcaaccatag tccttctaac    540
aataccaata gctaggaccc ggctgctgtg cactgggact ggggattcca catgtttgcc    600
ttgggagtct caagctggac tgccagcccc tgtcctccct tcaccccat tgcgtatgag    660
catttcagaa ctccaaggag tcacaggcat ctttatagtt cacgttaaca tatagacact    720
gttggaagca gttccttcta aaagggtagc cctggactta ataccagccg gatacctctg    780
```

| | |
|---|---|
| gcccccaccc cattactgta cctctggagt cactactgtg ggtcgccact cctctgctac | 840 |
| acagcacggc tttttcaagg ctgtattgag aagggaagtt aggaagaagg gtgtgctggg | 900 |
| ctaaccagcc cacagagctc acattcctgt cccttgggtg aaaaatacat gtccatcctg | 960 |
| atatctcctg aattcagaaa ttagcctcca catgtgcaat ggctttaaga gccagaagca | 1020 |
| gggttctggg aattttgcaa gttacctgtg gccaggtgtg gtctcggtta ccaaatacgg | 1080 |
| ttacctgcag cttttagtc ctttgtgctc ccacgggtct acagagtccc atctgcccaa | 1140 |
| aggtcttgaa gcttgacagg atgttttcga ttactcagtc cccagggca ctactggtcc | 1200 |
| gtaggattcg attggtcggg gtaggagagt taaacaacat taaacagag ttctctcaaa | 1260 |
| aatgtctaaa gggattgtag gtagataaca tccaatcact gtttgcactt atctgaaatc | 1320 |
| ttccctcttg gctgccccca ggtatttact gtggagaaca ttgcatagga atgtctggaa | 1380 |
| aaagcttcta caacttgtta cagccttcac atttgtagaa gcttt | 1425 |

<210> SEQ ID NO 14
<211> LENGTH: 625
<212> TYPE: DNA
<213> ORGANISM: Homo sapiens

<400> SEQUENCE: 14

| | |
|---|---|
| gagcactggg acgcccaccg cccctttccc tccgctgcca ggcgagcatg ttgtggtaat | 60 |
| tctggaacac aagaagagaa attgctgggt ttagaacaag attataaacg aattcggtgc | 120 |
| tcagtgatca cttgacagtt tttttttttt ttaaatatta cccaaaatgc tccccaaata | 180 |
| agaaatgcat cagctcagtc agtgaataca aaaaggaat tattttttccc tttgagggtc | 240 |
| ttttatacat ctctcctcca accccaccct ctattctgtt tcttcctcct cacatggggg | 300 |
| tacacataca cagcttcctc ttttggttcc atccttacca ccacaccaca cgcacactcc | 360 |
| acatgcccag cagagtggca cttggtggcc agaaagtgtg agcctcatga tctgctgtct | 420 |
| gtagttctgt gagctcaggt ccctcaaagg cctcggagca cccccttcct tgtgactgag | 480 |
| ccagggcctg cattttggt tttccccacc ccacacattc tcaaccatag tccttctaac | 540 |
| aataccaata gctaggaccc ggctgctgtg cactgggact ggggattcca catgtttgcc | 600 |
| ttgggagtct caagctggac tgcca | 625 |

<210> SEQ ID NO 15
<211> LENGTH: 2889
<212> TYPE: DNA
<213> ORGANISM: Artificial Sequence
<220> FEATURE:
<223> OTHER INFORMATION: COX10-ND4-3'UTR

<400> SEQUENCE: 15

| | |
|---|---|
| atggccgcat ctccgcacac tctctcctca cgcctcctga caggttgcgt aggaggctct | 60 |
| gtctggtatc ttgaaagaag aactatgcta aaactaatcg tcccaacaat tatgttacta | 120 |
| ccactgacat ggctttccaa aaaacacatg atttggatca acacaaccac ccacagccta | 180 |
| attattagca tcatccctct actatttttt aaccaaatca caacaaccct atttagctgt | 240 |
| tccccaacct tttcctccga ccccctaaca accccctcc taatgctaac tacctggctc | 300 |
| ctaccctca caatcatggc aagccaacgc acttatcca gtgaaccact atcacgaaaa | 360 |
| aaactctacc tctctatgct aatctcccta caaatctcct taattatgac attcacagcc | 420 |
| acagaactaa tcatgtttta tatcttcttc gaaaccacac ttatccccac cttggctatc | 480 |
| atcacccgat ggggcaacca gccagaacgc ctgaacgcag gcacatactt cctattctac | 540 |

```
acccctagtag gctcccttcc cctactcatc gcactaattt acactcacaa caccctaggc    600
tcactaaaca ttctactact cactctcact gcccaagaac tatcaaactc ctgggccaac    660
aacttaatgt ggctagctta cacaatggct tttatggtaa agatgcctct ttacggactc    720
cacttatggc tccctaaagc ccatgtcgaa gcccccatcg ctgggtcaat ggtacttgcc    780
gcagtactct taaaactagg cggctatggt atgatgcgcc tcacactcat tctcaacccc    840
ctgacaaaac acatggccta ccccttcctt gtactatccc tatggggcat gattatgaca    900
agctccatct gcctacgaca aacagaccta aaatcgctca ttgcatactc ttcaatcagc    960
cacatggccc tcgtagtaac agccattctc atccaaaccc cctggagctt caccggcgca   1020
gtcattctca tgatcgccca cgggcttaca tcctcattac tattctgcct agcaaactca   1080
aactacgaac gcactcacag tcgcatcatg atcctctctc aaggacttca aactctactc   1140
ccactaatgg cttttggtg gcttctagca agcctcgcta acctcgcctt accccccact   1200
attaacctac tgggagaact ctctgtgcta gtaaccacgt tctcctggtc aaatatcact   1260
ctcctactta caggactcaa catgctagtc acagccctat actccctcta catgtttacc   1320
acaacacaat ggggctcact cacccaccac attaacaaca tgaaaccctc attcacacga   1380
gaaaacaccc tcatgttcat gcacctatcc cccattctcc tcctatccct caaccccgac   1440
atcattaccg gtttttcctc ttaagagcac tgggacgccc accgccctt tccctccgct   1500 gccaggcgag catgttgtgg taattctgga acacaagaag agaaattgct gggtttagaa   1560
caagattata aacgaattcg gtgctcagtg atcacttgac agttttttttt tttttaaat   1620 attacccaaa atgctcccca ataagaaat gcatcagctc agtcagtgaa tacaaaaaag   1680
gaattatttt tccctttgag ggtcttttat acatctctcc tccaaccca ccctctattc   1740 tgtttcttcc tcctcacatg ggggtacaca tacacagctt cctcttttgg ttccatcctt   1800
accaccacac cacacgcaca ctccacatgc ccagcagagt ggcacttggt ggccagaaag   1860
tgtgagcctc atgatctgct gtctgtagtt ctgtgagctc aggtccctca aaggcctcgg   1920 agcacccct tccttgtgac tgagccaggg cctgcatttt tggttttccc cacccacac   1980 attctcaacc atagtccttc taacaatacc aatagctagg accggctgc tgtgcactgg   2040 gactggggat tccacatgtt tgccttggga gtctcaagct ggactgccag ccctgtcct    2100 cccttcaccc ccattgcgta tgagcatttc agaactccaa ggagtcacag gcatctttat   2160
agttcacgtt aacatataga cactgttgga agcagttcct tctaaaggg tagccctgga   2220 cttaatacca gccggatacc tctggccccc accccattac tgtacctctg gagtcactac   2280
tgtgggtcgc cactcctctg ctacacagca cggcttttc aaggctgtat tgagaaggga   2340
agttaggaag aagggtgtgc tgggctaacc agcccacaga gctcacattc ctgtcccttg   2400
ggtgaaaaat acatgtccat cctgatatct cctgaattca gaaattagcc tccacatgtg   2460
caatggcttt aagagccaga agcagggttc tgggaatttt gcaagttacc tgtggccagg   2520
tgtggtctcg gttaccaaat acggttacct gcagcttttt agtcctttgt gctcccacgg   2580
gtctacagag tcccatctgc ccaaaggtct tgaagcttga caggatgttt tcgattactc   2640
agtctcccag ggcactactg gtccgtagga ttcgattggt cggggtagga gagttaaaca   2700
acatttaaac agagttctct caaaaatgtc taaagggatt gtaggtagat aacatccaat   2760
cactgtttgc acttatctga aatcttccct cttggctgcc cccaggtatt tactgtggag   2820
aacattgcat aggaatgtct ggaaaaagct tctacaactt gttacagcct tcacatttgt   2880
```

```
agaagcttt                                                              2889
```

<210> SEQ ID NO 16
<211> LENGTH: 2089
<212> TYPE: DNA
<213> ORGANISM: Artificial Sequence
<220> FEATURE:
<223> OTHER INFORMATION: COX10-ND4-3'UTR*

<400> SEQUENCE: 16

```
atggccgcat ctccgcacac tctctcctca cgcctcctga caggttgcgt aggaggctct      60
gtctggtatc ttgaaagaag aactatgcta aaactaatcg tcccaacaat tatgttacta     120
ccactgacat ggcttttcaa aaaacacatg atttggatca cacaaccac ccacagccta      180
attattagca tcatccctct actattttt aaccaaatca caacaacct atttagctgt       240
tccccaacct tttcctccga cccctaaca acccccctcc taatgctaac tacctggctc      300
ctacccctca caatcatggc aagccaacgc acttatcca gtgaaccact atcacgaaaa      360
aaactctacc tctctatgct aatctcccta caaatctcct taattatgac attcacagcc     420
acagaactaa tcatgtttta tatcttcttc gaaaccacac ttatccccac cttggctatc    480
atcacccgat ggggcaacca gccagaacgc ctgaacgcag gcatacttt cctattctac    540
accctagtag ctcccttcc cctactcatc gcactaattt acactcacaa cccctaggc       600
tcactaaaca ttctactact cactctcact gcccaagaac tatcaaactc ctgggccaac     660
aacttaatgt ggctagctta cacaatggct tttatggtaa agatgcctct ttacggactc     720
cacttatggc tccctaaagc ccatgtcgaa gcccccatcg ctgggtcaat ggtacttgcc     780
gcagtactct taaaactagg cggctatggt atgatgcgcc tcacactcat tctcaacccc    840
ctgacaaaac acatggccta ccccttcctt gtactatccc tatggggcat gattatgaca    900
agctccatct gcctacgaca aacagaccta aaatcgctca ttgcatactc ttcaatcagc    960
cacatggccc tcgtagtaac agccattctc atccaaaccc cctggagctt caccggcgca   1020
gtcattctca tgatcgccca cgggcttaca tcctcattac tattctgcct agcaaactca   1080
aactacgaac gcactcacag tcgcatcatg atcctctctc aaggacttca aactctactc   1140
ccactaatgg cttttggtg gcttctagca agcctcgcta acctcgcctt accccccact    1200
attaacctac tgggagaact ctctgtgcta gtaaccacgt tctcctggtc aaatatcact    1260
ctcctactta caggactcaa catgctagtc acagccctat actccctcta catgtttacc    1320
acaacacaat ggggctcact cacccaccac attaacaaca tgaaaccctc attcacacga    1380
gaaaacaccc tcatgttcat gcacctatcc cccattctcc tcctatccct caaccccgac    1440
atcattaccg ggtttttcctc ttaagagcac tgggacgccc accgcccctt ccctccgct    1500
gccaggcgag catgttgtgg taattctgga acacaagaag agaaattgct gggtttagaa    1560
caagattata aacgaattcg gtgctcagtg atcacttgac agtttttttt tttttaaat     1620
attacccaaa atgctcccca ataagaaat gcatcagctc agtcagtgaa tacaaaaaag    1680
gaattatttt tcccttttgag ggtctttat acatctctcc tccaaccca cctctattc     1740
tgtttcttcc tcctcacatg ggggtacaca tacacagctt cctcttttgg ttccatcctt    1800
accaccacac cacacgcaca ctccacatgc ccagcagagt ggcacttggt ggccagaaag    1860
tgtgagcctc atgatctgct gtctgtagtt ctgtgagctc aggtccctca aaggcctcgg    1920
agcacccct tccttgtgac tgagccaggg cctgcatttt tggttttccc cacccacac     1980
attctcaacc atagtccttc taacaatacc aatagctagg accggctgc tgtgcactgg   2040
```

```
gactggggat tccacatgtt tgccttggga gtctcaagct ggactgcca           2089
```

<210> SEQ ID NO 17
<211> LENGTH: 2889
<212> TYPE: DNA
<213> ORGANISM: Artificial Sequence
<220> FEATURE:
<223> OTHER INFORMATION: COX10-opt_ND4-3'UTR

<400> SEQUENCE: 17

```
atggccgcat ctccgcacac tctctcctca cgcctcctga caggttgcgt aggaggctct    60
gtctggtatc ttgaaagaag aactatgctg aagctgatcg tgcccaccat catgctgctg   120
cctctgacct ggctgagcaa gaaacacatg atctggatca acaccaccac gcacagcctg   180
atcatcagca tcatccctct gctgttcttc aaccagatca caacaaccct gttcagctgc   240
agccccacct tcagcagcga ccctctgaca cacctctgc tgatgctgac cacctggctg   300
ctgcccctca caatcatggc ctctcagaga cacctgagca gcgagcccct gagccggaag   360
aaactgtacc tgagcatgct gatctccctg cagatctctc tgatcatgac cttcaccgcc   420
accgagctga tcatgttcta catcttttc gagacaacgc tgatccccac actggccatc   480
atcaccagat ggggcaacca gcctgagaga ctgaacgccg gcacctactt tctgttctac   540
accctcgtgg gcagcctgcc actgctgatt gccctgatct acacccacaa cccctgggc   600
tccctgaaca tcctgctgct gacactgaca gcccaagagc tgagcaacag ctgggccaac   660
aatctgatgt ggctggccta cacaatggcc ttcatggtca agatgcccct gtacggcctg   720
cacctgtggc tgcctaaagc tcatgtggaa gcccctatcg ccggctctat ggtgctggct   780
gcagtgctgc tgaaactcgg cggctacggc atgatgcggc tgaccctgat tctgaatccc   840
ctgaccaagc acatggccta tccatttctg gtgctgagcc tgtggggcat gattatgacc   900
agcagcatct gcctgcggca gaccgatctg aagtccctga tcgcctacag ctccatcagc   960
cacatggccc tggtggtcac cgccatcctg attcagaccc cttggagctt tacaggcgcc  1020
gtgatcctga tgattgccca cggcctgaca agcagcctgc tgtttttgtct ggccaacagc  1080
aactacgagc ggacccacag cagaatcatg atcctgtctc agggcctgca gaccctcctg  1140
cctcttatgg cttttggtg gctgctggcc tctctggcca atctggcact gcctcctacc  1200
atcaatctgc tgggcgagct gagcgtgctg gtcaccacat tcagctggtc caatatcacc  1260
ctgctgctca ccggcctgaa catgctggtt acagccctgt actccctgta catgttcacc  1320
accacacagt ggggaagcct gacacaccac atcaacaata tgaagcccag cttcacccgc  1380
gagaacaccc tgatgttcat gcatctgagc ccattctgc tgctgtccct gaatcctgat  1440
atcatcaccg gcttctccag ctgagagcac tgggacgccc accgcccctt ccctccgct  1500
gccaggcgag catgttgtgg taattctgga acacaagaag agaaattgct gggtttagaa  1560
caagattata acgaattcg gtgctcagtg atcacttgac agtttttttt tttttttaat  1620
attcccaaa atgctcccca ataagaaat gcatcagctc agtcagtgaa tacaaaaaag  1680
gaattatttt tccctttgag ggtctttta catctctcc tccaaccca ccctctattc  1740
tgtttcttcc tcctcacatg gggtacaca tacacagctt cctcttttgg ttccatcctt  1800
accaccacac cacacgcaca ctccacatgc ccagcagagt ggcacttggt ggccagaaag  1860
tgtgagcctc atgatctgct gtctgtagtt ctgtgagctc aggtccctca aaggcctcgg  1920
agcacccct tccttgtgac tgagccaggg cctgcatttt tggttttccc caccccacac  1980
```

| | |
|---|---|
| attctcaacc atagtccttc taacaatacc aatagctagg acccggctgc tgtgcactgg | 2040 |
| gactggggat ccacatgtt tgccttggga gtctcaagct ggactgccag cccctgtcct | 2100 |
| cccttcaccc ccattgcgta tgagcatttc agaactccaa ggagtcacag gcatctttat | 2160 |
| agttcacgtt aacatataga cactgttgga agcagttcct tctaaaaggg tagccctgga | 2220 |
| cttaatacca gccggatacc tctggccccc accccattac tgtacctctg gagtcactac | 2280 |
| tgtgggtcgc cactcctctg ctacacagca cggcttttc aaggctgtat tgagaaggga | 2340 |
| agttaggaag aagggtgtgc tgggctaacc agcccacaga gctcacattc ctgtcccttg | 2400 |
| ggtgaaaaat acatgtccat cctgatatct cctgaattca gaaattagcc tccacatgtg | 2460 |
| caatggcttt aagagccaga agcagggttc tgggaatttt gcaagttacc tgtggccagg | 2520 |
| tgtggtctcg gttaccaaat acggttacct gcagcttttt agtcctttgt gctcccacgg | 2580 |
| gtctacagag tcccatctgc ccaaaggtct tgaagcttga caggatgttt tcgattactc | 2640 |
| agtctcccag ggcactactg gtccgtagga ttcgattggt cggggtagga gagttaaaca | 2700 |
| acatttaaac agagttctct caaaaatgtc taaagggatt gtaggtagat aacatccaat | 2760 |
| cactgtttgc acttatctga aatcttccct cttggctgcc cccaggtatt tactgtggag | 2820 |
| aacattgcat aggaatgtct ggaaaaagct tctacaactt gttacagcct tcacatttgt | 2880 |
| agaagcttt | 2889 |

<210> SEQ ID NO 18
<211> LENGTH: 2089
<212> TYPE: DNA
<213> ORGANISM: Artificial Sequence
<220> FEATURE:
<223> OTHER INFORMATION: COX10-opt_ND4-3'UTR*

<400> SEQUENCE: 18

| | |
|---|---|
| atggccgcat ctccgcacac tctctcctca cgcctcctga caggttgcgt aggaggctct | 60 |
| gtctggtatc ttgaaagaag aactatgctg aagctgatcg tgcccaccat catgctgctg | 120 |
| cctctgacct ggctgagcaa gaaacacatg atctggatca acaccaccac gcacagcctg | 180 |
| atcatcagca tcatccctct gctgttcttc aaccagatca caacaaccct gttcagctgc | 240 |
| agccccacct tcagcagcga ccctctgaca acacctctgc tgatgctgac cacctggctg | 300 |
| ctgcccctca caatcatggc ctctcagaga cacctgagca gcgagcccct gagcggaag | 360 |
| aaactgtacc tgagcatgct gatctccctg cagatctctc tgatcatgac cttcaccgcc | 420 |
| accgagctga tcatgttcta catcttttc gagacaacgc tgatcccac actggccatc | 480 |
| atcaccagat ggggcaacca gcctgagaga ctgaacgccg gcacctactt tctgttctac | 540 |
| accctcgtgg gcagcctgcc actgctgatt gccctgatct acacccacaa cccctgggc | 600 |
| tccctgaaca tcctgctgct gacactgaca gcccaagagc tgagcaacag ctgggccaac | 660 |
| aatctgatgt ggctggccta cacaatggcc ttcatggtca agatgcccct gtacggcctg | 720 |
| cacctgtggc tgcctaaagc tcatgtggaa gcccctatcg ccggctctat ggtgctggct | 780 |
| gcagtgctgc tgaaactcgg cggctacggc atgatgcggc tgaccctgat tctgaatccc | 840 |
| ctgaccaagc acatggccta tccatttctg tgctgagcc tgtggggcat gattatgacc | 900 |
| agcagcatct gcctgcggca gaccgatctg aagtccctga tcgcctacag ctccatcagc | 960 |
| cacatggccc tggtggtcac cgccatcctg attcagaccc cttggagctt acaggcgcc | 1020 |
| gtgatcctga tgattgccca cggcctgaca agcagcctgc tgttttgtct ggccaacagc | 1080 |
| aactacgagc ggacccacag cagaatcatg atcctgtctc agggcctgca gacccttctg | 1140 |

```
cctcttatgg cttttggtg gctgctggcc tctctggcca atctggcact gcctcctacc      1200
atcaatctgc tgggcgagct gagcgtgctg gtcaccacat tcagctggtc caatatcacc      1260
ctgctgctca ccggcctgaa catgctggtt acagccctgt actccctgta catgttcacc      1320
accacacagt ggggaagcct gacacaccac atcaacaata tgaagcccag cttcacccgc      1380
gagaacaccc tgatgttcat gcatctgagc ccattctgc tgctgtccct gaatcctgat       1440
atcatcaccg gcttctccag ctgagagcac tgggacgccc accgcccctt tccctccgct      1500
gccaggcgag catgttgtgg taattctgga acacaagaag agaaattgct gggtttagaa      1560
caagattata aacgaattcg gtgctcagtg atcacttgac agtttttttt tttttttaaat     1620 attacccaaa atgctcccca aataagaaat gcatcagctc agtcagtgaa tacaaaaaag     1680
gaattatttt tccctttgag ggtcttttat acatctctcc tccaacccca ccctctattc      1740
tgtttcttcc tcctcacatg ggggtacaca tacacagctt cctcttttgg ttccatcctt     1800
accaccacac cacacgcaca ctccacatgc ccagcagagt ggcacttggt ggccagaaag      1860
tgtgagcctc atgatctgct gtctgtagtt ctgtgagctc aggtccctca aaggcctcgg      1920
agcaccccct tccttgtgac tgagccaggg cctgcatttt tggttttccc cacccccacac    1980 attctcaacc atagtccttc taacaatacc aatagctagg accggctgc tgtgcactgg       2040 gactggggat tccacatgtt tgccttggga gtctcaagct ggactgcca                  2089
```

<210> SEQ ID NO 19
<211> LENGTH: 2889
<212> TYPE: DNA
<213> ORGANISM: Artificial Sequence
<220> FEATURE:
<223> OTHER INFORMATION: COX10-opt_ND4*-3'UTR

<400> SEQUENCE: 19

```
atggccgcat ctccgcacac tctctcctca cgcctcctga caggttgcgt aggaggctct        60
gtctggtatc ttgaaagaag aactatgctg aagctgatcg tgcccaccat catgctgctg       120
cccctgacct ggctgagcaa gaagcacatg atctggatca caccaccac ccacagcctg        180 atcatcagca tcatccccct gctgttcttc aaccagatca caacaacct gttcagctgc        240 agccccacct tcagcagcga cccccctgacc accccctgc tgatgctgac cacctggctg       300
ctgcccctga ccatcatggc cagccagcgc cacctgagca gcgagcccct gagccgcaag       360
aagctgtacc tgagcatgct gatcagcctg cagatcagcc tgatcatgac cttcaccgcc      420
accgagctga tcatgttcta catcttcttc gagaccaccc tgatcccac cctggccatc        480 atcacccgct ggggcaacca gcccgagcgc ctgaacgccg gcacctactt cctgttctac      540
accctggtgg gcagcctgcc cctgctgatc gccctgatct acacccacaa cccctgggc       600 agcctgaaca tcctgctgct gaccctgacc gcccaggagc tgagcaacag ctgggccaac     660
aacctgatgt ggctggccta caccatggcc ttcatggtga agatgcccct gtacggcctg     720
cacctgtggc tgcccaaggc ccacgtggag gcccccatcg ccggcagcat ggtgctggcc    780
gccgtgctgc tgaagctggg cggctacggc atgatgcgcc tgaccctgat cctgaacccc    840
ctgaccaagc acatggccta cccccttcctg gtgctgagcc tgtggggcat gatcatgacc     900
agcagcatct gcctgcgcca gaccgacctg aagagcctga tcgcctacag cagcatcagc     960
cacatggccc tggtggtgac cgccatcctg atccagaccc cctggagctt caccggcgcc    1020
gtgatcctga tgatcgccca cggcctgacc agcagcctgc tgttctgcct ggccaacagc    1080
```

| aactacgagc gcacccacag ccgcatcatg atcctgagcc agggcctgca gaccctgctg | 1140 |
| cccctgatgg ccttctggtg gctgctggcc agcctggcca acctggccct gcccccacc | 1200 |
| atcaacctgc tgggcgagct gagcgtgctg gtgaccacct cagctggag caacatcacc | 1260 |
| ctgctgctga ccggcctgaa catgctggtg accgccctgt acagcctgta catgttcacc | 1320 |
| accacccagt ggggcagcct gacccaccac atcaacaaca tgaagcccag cttcacccgc | 1380 |
| gagaacaccc tgatgttcat gcacctgagc cccatcctgc tgctgagcct gaaccccgac | 1440 |
| atcatcaccg gcttcagcag ctaagagcac tgggacgccc accgcccctt tccctccgct | 1500 |
| gccaggcgag catgttgtgg taattctgga acacaagaag agaaattgct gggtttagaa | 1560 |
| caagattata acgaattcg gtgctcagtg atcacttgac agtttttttt tttttaaat | 1620 |
| attacccaaa atgctcccca aataagaaat gcatcagctc agtcagtgaa tacaaaaaag | 1680 |
| gaattatttt tcccttgag ggtcttttat acatctctcc tccaaccca ccctctattc | 1740 |
| tgtttcttcc tcctcacatg ggggtacaca tacacagctt cctctttgg ttccatcctt | 1800 |
| accaccacac cacacgcaca ctccacatgc ccagcagagt ggcacttggt ggccagaaag | 1860 |
| tgtgagcctc atgatctgct gtctgtagtt ctgtgagctc aggtccctca aaggcctcgg | 1920 |
| agcaccccct tccttgtgac tgagccaggg cctgcatttt tggttttccc caccccacac | 1980 |
| attctcaacc atagtccttc taacaatacc aatagctagg accggctgc tgtgcactgg | 2040 |
| gactggggat tccacatgtt tgccttggga gtctcaagct ggactgccag ccctgtcct | 2100 |
| cccttcaccc ccattgcgta tgagcatttc agaactccaa ggagtcacag gcatctttat | 2160 |
| agttcacgtt aacatataga cactgttgga agcagttcct tctaaaaggg tagccctgga | 2220 |
| cttaatacca gccggatacc tctggccccc accccattac tgtacctctg gagtcactac | 2280 |
| tgtgggtcgc cactcctctg ctacacagca cggcttttc aaggctgtat tgagaaggga | 2340 |
| agttaggaag aagggtgtgc tgggctaacc agcccacaga gctcacattc ctgtcccttg | 2400 |
| ggtgaaaaat acatgtccat cctgatatct cctgaattca gaaattagcc tccacatgtg | 2460 |
| caatggcttt aagagccaga agcagggttc tgggaatttt gcaagttacc tgtggccagg | 2520 |
| tgtggtctcg gttaccaaat acggttacct gcagctttt agtcctttgt gctcccacgg | 2580 |
| gtctacagag tcccatctgc ccaaaggtct tgaagcttga caggatgttt tcgattactc | 2640 |
| agtctcccag ggcactactg gtccgtagga ttcgattggt cggggtagga gagttaaaca | 2700 |
| acatttaaac agagttctct caaaaatgtc taaagggatt gtaggtagat aacatccaat | 2760 |
| cactgtttgc acttatctga aatcttccct cttggctgcc cccaggtatt tactgtggag | 2820 |
| aacattgcat aggaatgtct ggaaaaagct tctacaactt gttacagcct tcacatttgt | 2880 |
| agaagcttt | 2889 |

<210> SEQ ID NO 20
<211> LENGTH: 2089
<212> TYPE: DNA
<213> ORGANISM: Artificial Sequence
<220> FEATURE:
<223> OTHER INFORMATION: COX10-opt_ND4*-3'UTR*

<400> SEQUENCE: 20

| atggccgcat ctccgcacac tctctcctca cgcctcctga caggttgcgt aggaggctct | 60 |
| gtctggtatc ttgaaagaag aactatgctg aagctgatcg tgcccaccat catgctgctg | 120 |
| cccctgaccg gctgagcaa gaagcacatg atctggatca caccaccac ccacagcctg | 180 |
| atcatcagca tcatccccct gctgttcttc aaccagatca caacaacct gttcagctgc | 240 |

```
agccccacct tcagcagcga ccccctgacc accccctgc tgatgctgac cacctggctg      300
ctgcccctga ccatcatggc cagccagcgc cacctgagca gcgagcccct gagccgcaag      360
aagctgtacc tgagcatgct gatcagcctg cagatcagcc tgatcatgac cttcaccgcc      420
accgagctga tcatgttcta catcttcttc gagaccaccc tgatcccac cctggccatc       480 atcacccgct ggggcaacca gcccgagcgc ctgaacgccg gcacctactt cctgttctac      540
accctggtgg gcagcctgcc cctgctgatc gccctgatct acacccacaa caccctgggc      600
agcctgaaca tcctgctgct gaccctgacc gcccaggagc tgagcaacag ctgggccaac      660
aacctgatgt ggctggccta caccatggcc ttcatggtga agatgcccct gtacggcctg      720
cacctgtggc tgcccaaggc ccacgtggag gccccatcg ccggcagcat ggtgctggcc       780
gccgtgctgc tgaagctggg cggctacggc atgatgcgcc tgaccctgat cctgaacccc      840
ctgaccaagc acatggccta ccccttcctg gtgctgagcc tgtggggcat gatcatgacc      900
agcagcatct gcctgcgcca gaccgacctg aagagcctga tcgcctacag cagcatcagc      960
cacatggccc tggtggtgac cgccatcctg atccagaccc cctggagctt caccggcgcc     1020
gtgatcctga tgatcgccca cggcctgacc agcagcctgc tgttctgcct ggccaacagc     1080
aactacgagc gcacccacag ccgcatcatg atcctgagcc agggcctgca gaccctgctg     1140 ccctgatgg ccttctggtg gctgctggcc agcctggcca acctggccct gccccccacc      1200
atcaacctgc tgggcgagct gagcgtgctg gtgaccacct cagctggag caacatcacc      1260 ctgctgctga ccggcctgaa catgctggtg accgccctgt acagcctgta catgttcacc     1320
accacccagt ggggcagcct gacccaccac atcaacaaca tgaagcccag cttcacccgc     1380
gagaacaccc tgatgttcat gcacctgagc cccatcctgc tgctgagcct gaaccccgac     1440
atcatcaccg gcttcagcag ctaagagcac tgggacgccc accgcccctt ccctccgct      1500 gccaggcgag catgttgtgg taattctgga acacaagaag agaaattgct gggtttagaa     1560
caagattata acgaattcg gtgctcagtg atcacttgac agttttttt tttttttaaat      1620 attacccaaa atgctcccca aataagaaat gcatcagctc agtcagtgaa tacaaaaaag     1680
gaattatttt tccctttgag ggtctttttat acatctctcc tccaacccca ccctctattc     1740
tgtttcttcc tcctcacatg ggggtacaca tacacagctt cctcttttgg ttccatcctt     1800
accaccacac cacacgcaca ctccacatgc ccagcagagt ggcacttggt ggccagaaag     1860
tgtgagcctc atgatctgct gtctgtagtt ctgtgagctc aggtccctca aaggcctcgg     1920
agcaccccct tccttgtgac tgagccaggg cctgcatttt tggttttccc caccccacac     1980
attctcaacc atagtccttc taacaatacc aatagctagg accggctgc tgtgcactgg      2040 gactggggat ccacatgtt tgccttggga gtctcaagct ggactgcca                  2089
```

<210> SEQ ID NO 21
<211> LENGTH: 2034
<212> TYPE: DNA
<213> ORGANISM: Artificial Sequence
<220> FEATURE:
<223> OTHER INFORMATION: COX10-ND6-3'UTR

<400> SEQUENCE: 21

```
atggccgcat ctccgcacac tctctcctca cgcctcctga caggttgcgt aggaggctct       60
gtctggtatc ttgaaagaag aactatgatg tatgctttgt ttctgttgag tgtgggttta      120
gtaatggggt ttgtggggtt ttcttctaag ccttctcctta tttatggggg tttagtattg     180
```

| | |
|---|---|
| attgttagcg gtgtggtcgg gtgtgttatt attctgaatt ttgggggagg ttatatgggt | 240 |
| ttaatggttt ttttaattta tttaggggga atgatggttg tctttggata tactacagcg | 300 |
| atggctattg aggagtatcc tgaggcatgg gggtcagggg ttgaggtctt ggtgagtgtt | 360 |
| ttagtggggt tagcgatgga ggtaggattg gtgctgtggg tgaaagagta tgatggggtg | 420 |
| gtggttgtgg taaactttaa tagtgtagga agctggatga tttatgaagg agagggtca | 480 |
| gggttgattc gggaggatcc tattggtgcg ggggctttgt atgattatgg gcgttggtta | 540 |
| gtagtagtta ctggttggac attgtttgtt ggtgtatata ttgtaattga gattgctcgg | 600 |
| gggaattagg agcactggga cgcccaccgc cccttccct ccgctgccag gcgagcatgt | 660 |
| tgtggtaatt ctgaacacaa agaagagaaa ttgctgggtt tagaacaaga ttataaacga | 720 |
| attcggtgct cagtgatcac ttgacagttt tttttttttt taaatattac ccaaaatgct | 780 |
| ccccaaataa gaaatgcatc agctcagtca gtgaatacaa aaaggaatt attttttccct | 840 |
| ttgagggtct tttatacatc tctcctccaa ccccaccctc tattctgttt cttcctcctc | 900 |
| acatggggt acacatacac agcttcctct tttggttcca tccttaccac cacaccacac | 960 |
| gcacactcca catgcccagc agagtggcac ttggtggcca gaaagtgtga gcctcatgat | 1020 |
| ctgctgtctg tagttctgtg agctcaggtc cctcaaaggc ctcggagcac ccccttcctt | 1080 |
| gtgactgagc cagggcctgc attttttggtt ttccccaccc cacacattct caaccatagt | 1140 |
| ccttctaaca ataccaatag ctaggacccg gctgctgtgc actgggactg gggattccac | 1200 |
| atgtttgcct tgggagtctc aagctggact gccagcccct gtcctcccctt caccccatt | 1260 |
| gcgtatgagc atttcagaac tccaaggagt cacaggcatc tttatagttc acgttaacat | 1320 |
| atagacactg ttggaagcag ttccttctaa aagggtagcc ctggacttaa taccagccgg | 1380 |
| atacctctgg cccccacccc attactgtac ctctggagtc actactgtgg gtcgccactc | 1440 |
| ctctgctaca cagcacggct ttttcaaggc tgtattgaga agggaagtta ggaagaaggg | 1500 |
| tgtgctgggc taaccagccc acagagctca cattcctgtc ccttgggtga aaaatacatg | 1560 |
| tccatcctga tatctcctga attcagaaat tagcctccac atgtgcaatg ctttaagag | 1620 |
| ccagaagcag ggttctggga attttgcaag ttacctgtgg ccaggtgtgg tctcggttac | 1680 |
| caaatacggt tacctgcagc ttttagtcc tttgtgctcc cacgggtcta cagagtccca | 1740 |
| tctgcccaaa ggtcttgaag cttgacagga tgttttcgat tactcagtct cccagggcac | 1800 |
| tactggtccg taggattcga ttggtcgggg taggagagtt aaacaacatt taaacagagt | 1860 |
| tctctcaaaa atgtctaaag ggattgtagg tagataacat ccaatcactg tttgcactta | 1920 |
| tctgaaatct tccctcttgg ctgccccag gtatttactg tggagaacat tgcataggaa | 1980 |
| tgtctggaaa aagcttctac aacttgttac agccttcaca tttgtagaag cttt | 2034 |

<210> SEQ ID NO 22
<211> LENGTH: 1234
<212> TYPE: DNA
<213> ORGANISM: Artificial Sequence
<220> FEATURE:
<223> OTHER INFORMATION: COX10-ND6-3'UTR*

<400> SEQUENCE: 22

| | |
|---|---|
| atggccgcat ctccgcacac tctctcctca cgcctcctga caggttgcgt aggaggctct | 60 |
| gtctggtatc ttgaaagaag aactatgatg tatgctttgt ttctgttgag tgtgggttta | 120 |
| gtaatggggt ttgtggggtt ttcttctaag ccttctccta tttatggggg tttagtattg | 180 |
| attgttagcg gtgtggtcgg gtgtgttatt attctgaatt ttgggggagg ttatatgggt | 240 |

```
ttaatggttt ttttaattta tttaggggga atgatggttg tctttggata tactacagcg    300
atggctattg aggagtatcc tgaggcatgg gggtcagggg ttgaggtctt ggtgagtgtt    360
ttagtggggt tagcgatgga ggtaggattg gtgctgtggg tgaaagagta tgatggggtg    420
gtggttgtgg taaactttaa tagtgtagga agctggatga tttatgaagg agagggtca    480 gggttgattc gggaggatcc tattggtgcg ggggctttgt atgattatgg gcgttggtta    540
gtagtagtta ctggttggac attgtttgtt ggtgtatata ttgtaattga gattgctcgg    600
gggaattagg agcactggga cgcccaccgc cccttccct ccgctgccag gcgagcatgt    660
tgtggtaatt ctggaacaca agaagagaaa ttgctgggtt tagaacaaga ttataaacga    720
attcggtgct cagtgatcac ttgacagttt tttttttttt taaatattac ccaaaatgct    780
ccccaaataa gaaatgcatc agctcagtca gtgaatacaa aaaggaatt attttttccct    840 ttgagggtct tttatacatc tctcctccaa ccccacctc tattctgttt cttcctcctc    900
acatgggggt acatacac agcttcctct tttggttcca tccttaccac cacaccacac    960
gcacactcca catgcccagc agagtggcac ttggtggcca gaaagtgtga gcctcatgat   1020
ctgctgtctg tagttctgtg agctcaggtc cctcaaaggc ctcggagcac ccccttcctt   1080
gtgactgagc cagggcctgc attttttggtt ttccccaccc cacacattct caaccatagt   1140
ccttctaaca ataccaatag ctaggacccg gctgctgtgc actgggactg gggattccac   1200
atgtttgcct tgggagtctc aagctggact gcca                                1234

<210> SEQ ID NO 23
<211> LENGTH: 2034
<212> TYPE: DNA
<213> ORGANISM: Artificial Sequence
<220> FEATURE:
<223> OTHER INFORMATION: COX10-opt_ND6-3'UTR

<400> SEQUENCE: 23
atggccgcat ctccgcacac tctctcctca cgcctcctga caggttgcgt aggaggctct     60
gtctggtatc ttgaaagaag aactatgatg tacgccctgt tcctgctgag cgtgggcctg    120
gtgatgggct tcgtgggctt cagcagcaag cccagcccca tctacggcgg cctggtgctg    180
atcgtgagcg gcgtggtggg ctgcgtgatc atcctgaact tcggcggcgg ctacatgggc    240
ctgatggtgt tcctgatcta cctgggcggc atgatggtgg tgttcggcta caccaccgcc    300
atggccatcg aggagtaccc cgaggcctgg ggcagcggcg tggaggtgct ggtgagcgtg    360 ctggtggggcc tggccatgga ggtgggcctg gtgctgtggg tgaaggagta cgacggcgtg    420
gtggtggtgg tgaacttcaa cagcgtgggc agctggatga tctacgaggg cgagggcagc    480
ggcctgatcc gcgaggaccc catcggcgcc ggcgccctgt acgactacgg ccgctggctg    540
gtggtggtga ccggctggac cctgttcgtg ggcgtgtaca tcgtgatcga atcgcccgc    600 ggcaactaag agcactggga cgcccaccgc cccttccct ccgctgccag gcgagcatgt    660
tgtggtaatt ctggaacaca agaagagaaa ttgctgggtt tagaacaaga ttataaacga    720
attcggtgct cagtgatcac ttgacagttt tttttttttt taaatattac ccaaaatgct    780
ccccaaataa gaaatgcatc agctcagtca gtgaatacaa aaaggaatt attttttccct    840 ttgagggtct tttatacatc tctcctccaa ccccacctc tattctgttt cttcctcctc    900
acatgggggt acatacac agcttcctct tttggttcca tccttaccac cacaccacac    960
gcacactcca catgcccagc agagtggcac ttggtggcca gaaagtgtga gcctcatgat   1020
```

```
ctgctgtctg tagttctgtg agctcaggtc cctcaaaggc ctcggagcac ccccttcctt    1080
gtgactgagc cagggcctgc attttttggtt ttccccaccc cacacattct caaccatagt    1140
ccttctaaca ataccaatag ctaggacccg gctgctgtgc actgggactg gggattccac    1200
atgtttgcct tgggagtctc aagctggact gccagcccct gtcctcsctt caccccatt     1260 gcgtatgagc atttcagaac tccaaggagt cacaggcatc tttatagttc acgttaacat    1320
atagacactg ttggaagcag ttccttctaa aagggtagcc ctggacttaa taccagccgg    1380
atacctctgg cccccacccc attactgtac ctctggagtc actactgtgg gtcgccactc    1440
ctctgctaca cagcacggct ttttcaaggc tgtattgaga agggaagtta ggaagaaggg    1500
tgtgctgggc taaccagccc acagagctca cattcctgtc ccttgggtga aaaatacatg    1560
tccatcctga tatctcctga attcagaaat tagcctccac atgtgcaatg ctttaagag    1620 ccagaagcag ggttctggga attttgcaag ttacctgtgg ccaggtgtgg tctcggttac    1680
caaatacggt tacctgcagc ttttagtcc tttgtgctcc cacgggtcta cagagtccca    1740
tctgcccaaa ggtcttgaag cttgacagga tgttttcgat tactcagtct cccagggcac    1800
tactggtccg taggattcga ttggtcgggg taggagagtt aaacaacatt taaacagagt    1860
tctctcaaaa atgtctaaag ggattgtagg tagataacat ccaatcactg tttgcactta    1920
tctgaaatct tccctcttgg ctgccccag gtatttactg tggagaacat tgcataggaa     1980
tgtctggaaa aagcttctac aacttgttac agccttcaca tttgtagaag cttt           2034
```

<210> SEQ ID NO 24
<211> LENGTH: 1234
<212> TYPE: DNA
<213> ORGANISM: Artificial Sequence
<220> FEATURE:
<223> OTHER INFORMATION: COX10-opt_ND6-3'UTR*

<400> SEQUENCE: 24

```
atggccgcat ctccgcacac tctctcctca cgcctcctga caggttgcgt aggaggctct      60
gtctggtatc ttgaaagaag aactatgatg tacgccctgt tcctgctgag cgtgggcctg     120
gtgatgggct tcgtgggctt cagcagcaag cccagcccca tctacggcgg cctggtgctg    180
atcgtgagcg gcgtggtggg ctgcgtgatc atcctgaact tcggcggcgg ctacatgggc    240
ctgatggtgt tcctgatcta cctgggcggc atgatggtgg tgttcggcta caccaccgcc    300
atggccatcg aggagtaccc cgaggcctgg ggcagcggcg tggaggtgct ggtgagcgtg    360 ctggtggggcc tggccatgga ggtgggcctg gtgctgtggg tgaaggagta cgacggcgtg    420
gtggtggtgg tgaacttcaa cagcgtgggc agctggatga tctacgaggg cgagggcagc    480
ggcctgatcc gcgaggaccc catcggcgcc ggcgccctgt acgactacgg ccgctggctg    540
gtggtggtga ccggctggac cctgttcgtg ggcgtgtaca tcgtgatcga gatcgcccgc    600
ggcaactaag agcactggga cgcccaccgc cccttccct ccgctgccag gcgagcatgt     660
tgtggtaatt ctgaacacag agaagagaaa ttgctgggtt tagaacaaga ttataaacga    720
attcggtgct cagtgatcac ttgacagttt tttttttttt taaatattac ccaaaatgct    780
ccccaaataa gaaatgcatc agctcagtca gtgaatacaa aaaaggaatt atttttcct    840 ttgagggtct tttatacatc tctcctccaa ccccacccte tattctgttt cttcctcctc    900
acatgggggt acacatacac agcttcctct tttggttcca tccttaccac cacaccacac    960
gcacactcca catgcccagc agagtggcac ttggtggcca gaaagtgtga gcctcatgat    1020
ctgctgtctg tagttctgtg agctcaggtc cctcaaaggc ctcggagcac ccccttcctt    1080
```

```
gtgactgagc cagggcctgc attttttggtt ttccccaccc cacacattct caaccatagt    1140
ccttctaaca ataccaatag ctaggacccg gctgctgtgc actgggactg gggattccac    1200
atgtttgcct tgggagtctc aagctggact gcca                                1234
```

<210> SEQ ID NO 25
<211> LENGTH: 2460
<212> TYPE: DNA
<213> ORGANISM: Artificial Sequence
<220> FEATURE:
<223> OTHER INFORMATION: COX10-ND1-3'UTR

<400> SEQUENCE: 25

```
atggccgcat ctccgcacac tctctcctca cgcctcctga caggttgcgt aggaggctct      60
gtctggtatc ttgaaagaag aactatggcc aacctcctac tcctcattgt acccattcta     120
atcgcaatgg cattcctaat gcttaccgaa cgaaaaattc taggctatat gcaactacgc     180
aaaggcccca acgttgtagg cccctacggg ctactacaac ccttcgctga cgccataaaa     240
ctcttcacca agagcccct aaaacccgcc acatctacca tcaccctcta catcaccgcc      300
ccgaccttag ctctcaccat cgctcttcta ctatggaccc cctcccat gcccaacccc       360 ctggtcaacc tcaacctagg cctcctattt attctagcca cctctagcct agccgtttac     420
tcaatcctct ggtcagggtg ggcatcaaac tcaaactacg ccctgatcgg cgcactgcga     480
gcagtagccc aaacaatctc atatgaagtc accctagcca tcattctact atcaacatta     540
ctaatgagtg gctcctttaa cctctccacc cttatcacaa cacaagaaca cctctggtta     600
ctcctgccat catggccctt ggccatgatg tggtttatct ccacactagc agagaccaac     660
cgaaccccct tcgaccttgc cgaaggggag tccgaactag tctcaggctt caacatcgaa     720
tacgccgcag gccccttcgc cctattcttc atggccgaat acacaaacat tattatgatg     780
aacaccctca ccactacaat cttcctagga acaacatatg acgcactctc ccctgaactc     840
tacacaacat attttgtcac caagacccta cttctaacct ccctgttctt atggattcga     900
acagcatacc cccgattccg ctacgaccaa ctcatgcacc tcctatggaa aaacttccta     960
ccactcaccc tagcattact tatgtggtat gtctccatgc ccattacaat ctccagcatt    1020
ccccctcaaa cctaagagca ctgggacgcc caccgcccct tccctccgc tgccaggcga     1080 gcatgttgtg gtaattctgg aacacaagaa gagaaattgc tgggtttaga acaagattat    1140
aaacgaattc ggtgctcagt gatcacttga cagttttttt tttttttaaa tattacccaa    1200
aatgctcccc aaataagaaa tgcatcagct cagtcagtga atacaaaaaa ggaattattt    1260 ttcccttga gggtctttta tacatctctc ctccaacccc acctctatt ctgtttcttc      1320 ctcctcacat ggggtacac atacacagct tcctcttttg gttccatcct taccaccaca    1380
ccacacgcac actccacatg cccagcagag tggcacttgg tggccagaaa gtgtgagcct   1440
catgatctgc tgtctgtagt tctgtgagct caggtccctc aaaggcctcg gagcacccc    1500 ttccttgtga ctgagccagg gcctgcattt ttggttttcc ccaccccaca cattctcaac    1560
catagtcctt ctaacaatac caatagctag gacccggctg ctgtgcactg ggactgggga    1620
ttccacatgt ttgccttggg agtctcaagc tggactgcca gccctgtcc tcccttcacc    1680 cccattgcgt atgagcattt cagaactcca aggagtcaca ggcatcttta tagttcacgt    1740
taacatatag acactgttgg aagcagttcc ttctaaaagg gtagccctgg acttaatacc    1800
agccggatac ctctggcccc cacccccatta ctgtacctct ggagtcacta ctgtgggtcg    1860
```

```
ccactcctct gctacacagc acggctttt caaggctgta ttgagaaggg aagttaggaa   1920
gaagggtgtg ctgggctaac cagcccacag agctcacatt cctgtccctt gggtgaaaaa   1980
tacatgtcca tcctgatatc tcctgaattc agaaattagc ctccacatgt gcaatggctt   2040
taagagccag aagcagggtt ctgggaattt tgcaagttac ctgtggccag gtgtggtctc   2100
ggttaccaaa tacggttacc tgcagctttt tagtcctttg tgctcccacg ggtctacaga   2160
gtcccatctg cccaaaggtc ttgaagcttg acaggatgtt ttcgattact cagtctccca   2220
gggcactact ggtccgtagg attcgattgg tcggggtagg agagttaaac aacatttaaa   2280
cagagttctc tcaaaaatgt ctaaagggat tgtaggtaga taacatccaa tcactgtttg   2340
cacttatctg aaatcttccc tcttggctgc ccccaggtat ttactgtgga gaacattgca   2400
taggaatgtc tggaaaaagc ttctacaact tgttacagcc ttcacatttg tagaagcttt   2460
```

<210> SEQ ID NO 26
<211> LENGTH: 1660
<212> TYPE: DNA
<213> ORGANISM: Artificial Sequence
<220> FEATURE:
<223> OTHER INFORMATION: COX10-ND1-3'UTR*

<400> SEQUENCE: 26

```
atggccgcat ctccgcacac tctctcctca cgcctcctga caggttgcgt aggaggctct     60
gtctggtatc ttgaaagaag aactatggcc aacctcctac tcctcattgt acccattcta    120
atcgcaatgg cattcctaat gcttaccgaa cgaaaaattc taggctatat gcaactacgc    180
aaaggcccca acgttgtagg cccctacggg ctactacaac ccttcgctga cgccataaaa    240
ctcttcacca aagagcccct aaaacccgcc acatctacca tcaccctcta catcaccgcc    300
ccgaccttag ctctcaccat cgctcttcta ctatggaccc cctccccat gcccaacccc    360 ctggtcaacc tcaacctagg cctcctattt attctagcca cctctagcct agccgtttac    420
tcaatcctct ggtcagggtg gcatcaaac tcaaactacg ccctgatcgg cgcactgcga    480
gcagtagccc aaacaatctc atatgaagtc accctagcca tcattctact atcaacatta    540
ctaatgagtg gctcctttaa cctctccacc cttatcacaa cacaagaaca cctctggtta    600
ctcctgccat catggccctt ggccatgatg tggtttatct ccacactagc agagaccaac    660 cgaacccccct tcgaccttgc cgaaggggag tccgaactag tctcaggctt caacatcgaa    720
tacgccgcag gccccttcgc cctattcttc atggccgaat acacaaacat tattatgatg    780 aacacccctca ccactacaat cttcctagga acaacatatg acgcactctc cctgaactc    840 tacacaacat attttgtcac caagacccta cttctaacct ccctgttctt atggattcga    900
acagcatacc cccgattccg ctacgaccaa ctcatgcacc tcctatggaa aaacttccta    960
ccactcaccc tagcattact tatgtggtat gtctccatgc ccattacaat ctccagcatt   1020 cccctcaaa cctaagagca ctgggacgcc accgcccct ttccctccgc tgccaggcga   1080
gcatgttgtg gtaattctgg aacacaagaa gagaaattgc tgggttaga caagattat   1140 aaacgaattc ggtgctcagt gatcacttga cagtttttt tttttttaaa tattacccaa   1200
aatgctcccc aaataagaaa tgcatcagct cagtcagtga atacaaaaaa ggaattattt   1260
ttccctttga gggtctttta tacatctctc ctccaacccc accctctatt ctgtttcttc   1320
ctcctcacat gggggtacac atacacagct tcctcttttg gttccatcct taccaccaca   1380
ccacacgcac actccacatg cccagcagag tggcacttgg tggccagaaa gtgtgagcct   1440
catgatctgc tgtctgtagt tctgtgagct caggtccctc aaaggcctcg gagcaccccc   1500
```

<210> SEQ ID NO 27
<211> LENGTH: 2460
<212> TYPE: DNA
<213> ORGANISM: Artificial Sequence
<220> FEATURE:
<223> OTHER INFORMATION: COX10-opt_ND1-3'UTR

<400> SEQUENCE: 27

```
atggccgcat ctccgcacac tctctcctca cgcctcctga caggttgcgt aggaggctct      60
gtctggtatc ttgaaagaag aactatggcc aacctgctgc tgctgatcgt gcccatcctg     120
atcgccatgg ccttcctgat gctgaccgag cgcaagatcc tgggctacat gcagctgcgc     180
aagggcccca cgtggtgggc ccctacggc tgctgcagc cttcgccga cgccatcaag     240
ctgttcacca aggagcccct gaagcccgcc accagcacca tcaccctgta catcaccgcc     300
cccaccctgg ccctgaccat cgccctgctg ctgtggaccc cctgcccat gcccaacccc     360
ctggtgaacc tgaacctggg cctgctgttc atcctggcca ccagcagcct ggccgtgtac     420
agcatcctgt ggagcggctg ggccagcaac agcaactacg ccctgatcgg cgccctgcgc     480
gccgtggccc agaccatcag ctacgaggtg accctggcca tcatcctgct gagcaccctg     540
ctgatgagcg gcagcttcaa cctgagcacc ctgatcacca cccaggagca cctgtggctg     600
ctgctgccca gctggcccct ggccatgatg tggttcatca gcaccctggc cgagaccaac     660
cgcacccccct tcgacctggc cgagggcgag agcgagctgg tgagcggctt caacatcgag     720
tacgccgccg gccccttcgc cctgttcttc atggccgagt acaccaacat catcatgatg     780
aacaccctga ccaccaccat cttcctgggc accacctacg acgccctgag ccccgagctg     840
tacaccacct acttcgtgac caagaccctg ctgctgacca gcctgttcct gtggatccgc     900
accgcctacc ccgcttccg ctacgaccag ctgatgcacc tgctgtggaa gaacttcctg     960
cccctgaccc tggccctgct gatgtggtac gtgagcatgc ccatcaccat cagcagcatc    1020
cccccccaga cctaagagca ctgggacgcc caccgcccct tccctccgc tgccaggcga    1080
gcatgttgtg gtaattctgg aacacaagaa gagaaattgc tgggtttaga caagattat    1140
aaacgaattc ggtgctcagt gatcacttga cagttttttt tttttttaaa tattacccaa    1200
aatgctcccc aaataagaaa tgcatcagct cagtcagtga atacaaaaaa ggaattattt    1260
ttccctttga gggtctttta tacatctctc ctccaacccc accctctatt ctgtttcttc    1320
ctcctcacat gggggtacac atacacagct tcctcttttg gttccatcct taccaccaca    1380
ccacacgcac actccacatg cccagcagag tggcacttgg tggccagaaa gtgtgagcct    1440
catgatctgc tgtctgtagt tctgtgagct caggtccctc aaaggcctcg agcaccccc    1500
ttccttgtga ctgagccagg gcctgcattt ttggttttcc ccaccccaca cattctcaac    1560
catagtcctt ctaacaatac caatagctag gacccggctg ctgtgcactg ggactgggga    1620
ttccacatgt ttgccttggg agtctcaagc tggactgcca ccccgtcc tcccttcacc    1680
cccattgcgt atgagcattt cagaactcca aggagtcaca ggcatcttta tagttcacgt    1740
taacatatag acactgttgg aagcagttcc ttctaaaagg gtagccctgg acttaatacc    1800
agccggatac ctctggcccc caccccatta ctgtacctct ggagtcacta ctgtgggtcg    1860
```

| ccactcctct gctacacagc acggcttttt caaggctgta ttgagaaggg aagttaggaa | 1920 |
| gaagggtgtg ctgggctaac cagcccacag agctcacatt cctgtcccct gggtgaaaaa | 1980 |
| tacatgtcca tcctgatatc tcctgaattc agaaattagc ctccacatgt gcaatggctt | 2040 |
| taagagccag aagcagggtt ctgggaattt tgcaagttac ctgtggccag gtgtggtctc | 2100 |
| ggttaccaaa tacggttacc tgcagctttt tagtcctttg tgctcccacg ggtctacaga | 2160 |
| gtcccatctg cccaaaggtc ttgaagcttg acaggatgtt ttcgattact cagtctccca | 2220 |
| gggcactact ggtccgtagg attcgattgg tcggggtagg agagttaaac aacatttaaa | 2280 |
| cagagttctc tcaaaaatgt ctaaagggat tgtaggtaga taacatccaa tcactgtttg | 2340 |
| cacttatctg aaatcttccc tcttggctgc ccccaggtat ttactgtgga gaacattgca | 2400 |
| taggaatgtc tggaaaaagc ttctacaact tgttacagcc ttcacatttg tagaagcttt | 2460 |

<210> SEQ ID NO 28
<211> LENGTH: 1660
<212> TYPE: DNA
<213> ORGANISM: Artificial Sequence
<220> FEATURE:
<223> OTHER INFORMATION: COX10-opt_ND1-3'UTR*

<400> SEQUENCE: 28

| atggccgcat ctccgcacac tctctcctca cgcctcctga caggttgcgt aggaggctct | 60 |
| gtctggtatc ttgaaagaag aactatggcc aacctgctgc tgctgatcgt gcccatcctg | 120 |
| atcgccatgg ccttcctgat gctgaccgag cgcaagatcc tgggctacat gcagctgcgc | 180 |
| aagggcccca acgtggtggg ccccacggc ctgctgcagc ccttcgccga cgccatcaag | 240 |
| ctgttcacca aggagcccct gaagcccgcc accagcacca tcaccctgta catcaccgcc | 300 |
| cccaccctgg ccctgaccat cgccctgctg ctgtggaccc cctgcccat gcccaacccc | 360 |
| ctggtgaacc tgaacctggg cctgctgttc atcctggcca ccagcagcct ggccgtgtac | 420 |
| agcatcctgt ggagcggctg ggccagcaac agcaactacg ccctgatcgg cgccctgcgc | 480 |
| gccgtggccc agaccatcag ctacgaggtg accctggcca tcatcctgct gagcaccctg | 540 |
| ctgatgagcg cagcttcaa cctgagcacc ctgatcacca cccaggagca cctgtggctg | 600 |
| ctgctgccca gctggcccct ggccatgatg tggttcatca gcaccctggc cgagaccaac | 660 |
| cgcacccccct cgacctggc cgagggcgag agcgagctgg tgagcggctt caacatcgag | 720 |
| tacgccgccg gcccccttcgc cctgttcttc atggccgagt acaccaacat catcatgatg | 780 |
| aacaccctga ccaccaccat cttcctgggc accacctacg acgccctgag ccccgagctg | 840 |
| tacaccacct acttcgtgac caagaccctg ctgctgacca gcctgttcct gtggatccgc | 900 |
| accgcctacc ccgcttccg ctacgaccag ctgatgcacc tgctgtggaa gaacttcctg | 960 |
| cccctgaccc tggccctgct gatgtggtac gtgagcatgc ccatcaccat cagcagcatc | 1020 |
| ccccccagag cctaagagca ctgggacgcc accgcccct ttccctccgc tgccaggcga | 1080 |
| gcatgttgtg gtaattctgg aacacaagaa gagaaattgc tgggtttaga acaagattat | 1140 |
| aaacgaattc ggtgctcagt gatcacttga cagttttttt tttttttaaa tattacccaa | 1200 |
| aatgctcccc aaataagaaa tgcatcagct cagtcagtga atacaaaaaa ggaattattt | 1260 |
| ttcccttga gggtctttta tacatctctc ctccaacccc accctctatt ctgtttcttc | 1320 |
| ctcctcacat gggggtacac atacacagct tcctcttttg gttccatcct taccaccaca | 1380 |
| ccacacgcac actccacatg cccagcagag tggcacttgg tggccagaaa gtgtgagcct | 1440 |
| catgatctgc tgtctgtagt tctgtgagct caggtccctc aaaggcctcg agcacccccc | 1500 |

| | |
|---|---:|
| ttccttgtga ctgagccagg gcctgcattt ttggttttcc ccaccccaca cattctcaac | 1560 |
| catagtcctt ctaacaatac caatagctag gacccggctg ctgtgcactg ggactgggga | 1620 |
| ttccacatgt ttgccttggg agtctcaagc tggactgcca | 1660 |

<210> SEQ ID NO 29
<211> LENGTH: 2889
<212> TYPE: DNA
<213> ORGANISM: Artificial Sequence
<220> FEATURE:
<223> OTHER INFORMATION: opt_COX10-ND4-3'UTR

<400> SEQUENCE: 29

| | |
|---|---:|
| atggccgcct ctccacacac actgagtagc agactgctga ccggctgtgt tggcggctct | 60 |
| gtgtggtatc tggaacggcg gacaatgcta aaactaatcg tcccaacaat tatgttacta | 120 |
| ccactgacat ggcttttccaa aaaacacatg atttggatca cacaaccac ccacagccta | 180 |
| attattagca tcatccctct actatttttt aaccaaatca caacaaccct atttagctgt | 240 |
| tccccaacct tttcctccga ccccctaaca accccctcc taatgctaac tacctggctc | 300 |
| ctacccctca caatcatggc aagccaacgc cacttatcca gtgaaccact atcacgaaaa | 360 |
| aaactctacc tctctatgct aatctcccta caaatctcct taattatgac attcacagcc | 420 |
| acagaactaa tcatgtttta tatcttcttc gaaaccacac ttatccccac cttggctatc | 480 |
| atcacccgat ggggcaacca gccagaacgc ctgaacgcag gcacatactt cctattctac | 540 |
| accctagtag gctcccttcc cctactcatc gcactaattt acactcacaa cccctaggc | 600 |
| tcactaaaca ttctactact cactctcact gcccaagaac tatcaaactc ctgggccaac | 660 |
| aacttaatgt ggctagctta cacaatggct tttatggtaa agatgcctct ttacggactc | 720 |
| cacttatggc tccctaaagc ccatgtcgaa gcccccatcg ctgggtcaat ggtacttgcc | 780 |
| gcagtactct taaaactagg cggctatggt atgatgcgcc tcacactcat tctcaacccc | 840 |
| ctgacaaaac acatggccta ccccttcctt gtactatccc tatggggcat gattatgaca | 900 |
| agctccatct gcctacgaca aacagaccta aaatcgctca ttgcatactc ttcaatcagc | 960 |
| cacatggccc tcgtagtaac agccattctc atccaaaccc cctggagctt caccggcgca | 1020 |
| gtcattctca tgatcgccca cgggcttaca tcctcattac tattctgcct agcaaactca | 1080 |
| aactacgaac gcactcacag tcgcatcatg atcctctctc aaggacttca aactctactc | 1140 |
| ccactaatgg cttttggtg gcttctagca agcctcgcta acctcgcctt accccccact | 1200 |
| attaacctac tgggagaact ctctgtgcta gtaaccacgt tctcctggtc aaatatcact | 1260 |
| ctcctactta caggactcaa catgctagtc acagccctat actccctcta catgtttacc | 1320 |
| acaacacaat ggggctcact cacccaccac attaacaaca tgaaaccctc attcacacga | 1380 |
| gaaaacaccc tcatgttcat gcacctatcc cccattctcc tcctatccct caaccccgac | 1440 |
| atcattaccg ggttttcctc ttaagagcac tgggacgccc accgccctt tcctccgct | 1500 |
| gccaggcgag catgttgtgg taattctgga acacaagaag agaaattgct gggtttagaa | 1560 |
| caagattata aacgaattcg gtgctcagtg atcacttgac agttttttt ttttttaaat | 1620 |
| attacccaaa atgctcccca aataagaaat gcatcagctc agtcagtgaa tacaaaaaag | 1680 |
| gaattatttt tcccttttgag ggtcttttat acatctctcc tccaacccca ccctctattc | 1740 |
| tgtttcttcc tcctcacatg ggggtacaca tacacagctt cctcttttgg ttccatcctt | 1800 |
| accaccacac cacacgcaca ctccacatgc ccagcagagt ggcacttggt ggccagaaag | 1860 |

```
tgtgagcctc atgatctgct gtctgtagtt ctgtgagctc aggtccctca aaggcctcgg    1920
agcaccccct tccttgtgac tgagccaggg cctgcatttt tggttttccc caccccacac    1980
attctcaacc atagtccttc taacaatacc aatagctagg acccggctgc tgtgcactgg    2040
gactggggat tccacatgtt tgccttggga gtctcaagct ggactgccag ccctgtcct    2100 cccttcaccc ccattgcgta tgagcatttc agaactccaa ggagtcacag gcatctttat    2160
agttcacgtt aacatataga cactgttgga agcagttcct tctaaaaggg tagccctgga    2220
cttaatacca gccggatacc tctggccccc accccattac tgtacctctg gagtcactac    2280
tgtgggtcgc cactcctctg ctacacagca cggcttttc aaggctgtat tgagaaggga    2340
agttaggaag aagggtgtgc tgggctaacc agcccacaga gctcacattc ctgtcccttg    2400
ggtgaaaaat acatgtccat cctgatatct cctgaattca gaaattagcc tccacatgtg    2460
caatggcttt aagagccaga agcagggttc tgggaatttt gcaagttacc tgtggccagg    2520
tgtggtctcg gttaccaaat acggttacct gcagcttttt agtcctttgt gctcccacgg    2580
gtctacagag tcccatctgc ccaaaggtct tgaagcttga caggatgttt tcgattactc    2640
agtctcccag ggcactactg gtccgtagga ttcgattggt cggggtagga gagttaaaca    2700
acatttaaac agagttctct caaaaatgtc taaagggatt gtaggtagat aacatccaat    2760
cactgtttgc acttatctga aatcttccct cttggctgcc cccaggtatt tactgtggag    2820
aacattgcat aggaatgtct ggaaaaagct tctacaactt gttacagcct tcacatttgt    2880
agaagcttt                                                            2889

<210> SEQ ID NO 30
<211> LENGTH: 2089
<212> TYPE: DNA
<213> ORGANISM: Artificial Sequence
<220> FEATURE:
<223> OTHER INFORMATION: opt_COX10-ND4-3'UTR*

<400> SEQUENCE: 30
atggccgcct ctccacacac actgagtagc agactgctga ccggctgtgt tggcggctct      60
gtgtggtatc tggaacggcg gacaatgcta aaactaatcg tcccaacaat tatgttacta    120
ccactgacat ggcttccaa aaaacacatg atttggatca acacaaccac ccacagccta    180
attattagca tcatccctct actatttttt aaccaaatca caacaacct atttagctgt    240 tccccaacct tttcctccga ccccctaaca acccccctcc taatgctaac tacctggctc    300 ctaccccctca caatcatggc aagccaacgc cacttatcca gtgaaccact atcacgaaaa    360
aaactctacc tctctatgct aatctcccta caaatctcct taattatgac attcacagcc    420
acagaactaa tcatgtttta tatcttcttc gaaaccacac ttatcccac cttggctatc    480 atcacccgat ggggcaacca gccagaacgc tgaacgcag gcacatactt cctattctac    540
accctagtag gctcccttcc cctactcatc gcactaattt acactcacaa cccctaggc    600 tcactaaaca ttctactact cactctcact gcccaagaac tatcaaactc ctgggccaac    660
aacttaatgt ggctagctta cacaatggct tttatggtaa agatgcctct ttacggactc    720
cacttatggc tccctaaagc ccatgtcgaa gcccccatcg ctgggtcaat ggtacttgcc    780
gcagtactct taaaactagg cggctatggt atgatgcgcc tcacactcat tctcaacccc    840
ctgacaaaac acatggccta cccttcctt gtactatccc tatggggcat gattatgaca    900
agctccatct gcctacgaca aacagaccta aaatcgctca ttgcatactc ttcaatcagc    960
cacatggccc tcgtagtaac agccattctc atccaaaccc cctggagctt caccggcgca    1020
```

```
gtcattctca tgatcgccca cgggcttaca tcctcattac tattctgcct agcaaactca    1080
aactacgaac gcactcacag tcgcatcatg atcctctctc aaggacttca aactctactc    1140
ccactaatgg cttttggtg gcttctagca agcctcgcta acctcgcctt accccccact     1200
attaacctac tgggagaact ctctgtgcta gtaaccacgt tctcctggtc aaatatcact    1260
ctcctactta caggactcaa catgctagtc acagccctat actccctcta catgtttacc    1320
acaacacaat ggggctcact cacccaccac attaacaaca tgaaaccctc attcacacga    1380
gaaaacaccc tcatgttcat gcacctatcc cccattctcc tcctatccct caaccccgac    1440
atcattaccg ggttttcctc ttaagagcac tgggacgccc accgcccctt ccctccgct    1500 gccaggcgag catgttgtgg taattctgga acacaagaag agaaattgct gggtttagaa    1560
caagattata aacgaattcg gtgctcagtg atcacttgac agttttttt ttttttaaat     1620 attacccaaa atgctcccca ataagaaat gcatcagctc agtcagtgaa tacaaaaaag    1680
gaattatttt tcccttgag ggtctttat acatctctcc tccaaccca ccctctattc       1740 tgtttcttcc tcctcacatg ggggtacaca tacacagctt cctcttttgg ttccatcctt    1800
accaccacac cacacgcaca ctccacatgc ccagcagagt ggcacttggt ggccagaaag    1860
tgtgagcctc atgatctgct gtctgtagtt ctgtgagctc aggtccctca aaggcctcgg    1920
agcaccccct tccttgtgac tgagccaggg cctgcatttt tggttttccc cacccccacac    1980 attctcaacc atagtccttc taacaatacc aatagctagg acccggctgc tgtgcactgg    2040
gactggggat tccacatgtt tgccttggga gtctcaagct ggactgcca                2089

<210> SEQ ID NO 31
<211> LENGTH: 2889
<212> TYPE: DNA
<213> ORGANISM: Artificial Sequence
<220> FEATURE:
<223> OTHER INFORMATION: opt_COX10-opt_ND4-3'UTR

<400> SEQUENCE: 31
atggccgcct ctccacacac actgagtagc agactgctga ccggctgtgt tggcggctct      60
gtgtggtatc tggaacggcg gacaatgctg aagctgatcg tgcccaccat catgctgctg     120
cctctgacct ggctgagcaa gaaacacatg atctggatca acaccaccac gcacagcctg     180
atcatcagca tcatccctct gctgttcttc aaccagatca caacaacct gttcagctgc     240 agccccacct tcagcagcga ccctctgaca cacctctgc tgatgctgac cacctggctg      300 ctgccccctca caatcatggc ctctcagaga cacctgagca gcgagcccct gagccggaag    360
aaactgtacc tgagcatgct gatctccctg cagatctctc tgatcatgac cttcaccgcc    420
accgagctga tcatgttcta catcttttc gagacaacgc tgatcccac actggccatc      480 atcaccagat ggggcaacca gcctgagaga ctgaacgccg gcacctactt tctgttctac    540
accctcgtgg gcagcctgcc actgctgatt gccctgatct acacccacaa cccctgggc     600 tccctgaaca tcctgctgct gacactgaca gcccaagagc tgagcaacag ctgggccaac   660
aatctgatgt ggctggccta cacaatggcc ttcatggtca agatgccct gtacggcctg    720 cacctgtggc tgcctaaagc tcatgtggaa gcccctatcg ccggctctat ggtgctggct    780
gcagtgctgc tgaaactcgg cggctacggc atgatgcggc tgaccctgat tctgaatccc    840
ctgaccaagc acatggccta tcatttctgt gtgctgagcc tgtggggcat gattatgacc    900
agcagcatct gcctgcggca gaccgatctg aagtccctga tcgcctacag ctccatcagc   960
```

```
cacatggccc tggtggtcac cgccatcctg attcagaccc cttggagctt tacaggcgcc    1020
gtgatcctga tgattgccca cggcctgaca agcagcctgc tgttttgtct ggccaacagc    1080
aactacgagc ggacccacag cagaatcatg atcctgtctc agggcctgca gaccctcctg    1140
cctcttatgg cttttggtg gctgctggcc tctctggcca atctggcact gcctcctacc     1200
atcaatctgc tgggcgagct gagcgtgctg gtcaccacat tcagctggtc caatatcacc    1260
ctgctgctca ccggcctgaa catgctggtt acagccctgt actccctgta catgttcacc    1320
accacacagt ggggaagcct gacacaccac atcaacaata tgaagcccag cttcacccgc    1380
gagaacaccc tgatgttcat gcatctgagc cccattctgc tgctgtccct gaatcctgat    1440
atcatcaccg gcttctccag ctgagagcac tgggacgccc accgcccctt tccctccgct    1500
gccaggcgag catgttgtgg taattctgga acacaagaag agaaattgct gggtttagaa    1560
caagattata aacgaattcg gtgctcagtg atcacttgac agtttttttt ttttttaaat    1620
attacccaaa atgctcccca aataagaaat gcatcagctc agtcagtgaa tacaaaaaag    1680
gaattatttt tcccttgag ggtcttttat acatctctcc tccaacccca ccctctattc     1740
tgtttcttcc tcctcacatg ggggtacaca tacacagctt cctcttttgg ttccatcctt    1800
accaccacac cacacgcaca ctccacatgc ccagcagagt ggcacttggt ggccagaaag    1860
tgtgagcctc atgatctgct gtctgtagtt ctgtgagctc aggtccctca aaggcctcgg    1920
agcaccccct tccttgtgac tgagccaggg cctgcatttt tggttttccc caccccacac    1980
attctcaacc atagtccttc taacaatacc aatagctagg acccggctgc tgtgcactgg    2040
gactggggat tccacatgtt tgccttggga gtctcaagct ggactgccag ccctgtcct    2100 cccttcaccc ccattgcgta tgagcatttc agaactccaa ggagtcacag gcatctttat    2160
agttcacgtt aacatataga cactgttgga agcagttcct tctaaagggg tagccctgga    2220
cttaatacca gccggatacc tctggccccc accccattac tgtacctctg gagtcactac    2280
tgtgggtcgc cactcctctg ctacacagca cggcttttc aaggctgtat tgagaaggga     2340
agttaggaag aagggtgtgc tgggctaacc agcccacaga gctcacattc ctgtcccttg    2400
ggtgaaaaat acatgtccat cctgatatct cctgaattca gaaattagcc tccacatgtg    2460
caatggcttt aagagccaga agcagggttc tgggaatttt gcaagttacc tgtggccagg    2520
tgtggtctcg gttaccaaat acggttacct gcagcttttt agtcctttgt gctcccacgg    2580
gtctacagag tcccatctgc ccaaaggtct tgaagcttga caggatgttt tcgattactc    2640
agtctcccag ggcactactg gtccgtagga ttcgattggt cggggtagga gagttaaaca    2700
acatttaaac agagttctct caaaaatgtc taaagggatt gtaggtagat aacatccaat    2760
cactgtttgc acttatctga aatcttccct cttggctgcc cccaggtatt tactgtggag    2820
aacattgcat aggaatgtct ggaaaaagct tctacaactt gttacagcct tcacatttgt    2880
agaagcttt                                                            2889
```

<210> SEQ ID NO 32
<211> LENGTH: 2089
<212> TYPE: DNA
<213> ORGANISM: Artificial Sequence
<220> FEATURE:
<223> OTHER INFORMATION: opt_COX10-opt_ND4-3'UTR*

<400> SEQUENCE: 32

```
atggccgcct ctccacacac actgagtagc agactgctga ccggctgtgt tggcggctct      60
gtgtggtatc tggaacggcg gacaatgctg aagctgatcg tgcccaccat catgctgctg     120
```

```
cctctgacct ggctgagcaa gaaacacatg atctggatca acaccaccac gcacagcctg    180
atcatcagca tcatccctct gctgttcttc aaccagatca caacaaccct gttcagctgc    240
agccccacct tcagcagcga ccctctgaca cacctctgc tgatgctgac cacctggctg     300
ctgcccctca caatcatggc ctctcagaga cacctgagca gcgagcccct gagccggaag    360
aaactgtacc tgagcatgct gatctccctg cagatctctc tgatcatgac cttcaccgcc    420
accgagctga tcatgttcta catcttttc gagacaacgc tgatcccac actggccatc      480 atcaccagat ggggcaacca gcctgagaga ctgaacgccg gcacctactt tctgttctac    540
accctcgtgg gcagcctgcc actgctgatt gccctgatct acccacaa caccctgggc      600 tccctgaaca tcctgctgct gacactgaca gcccaagagc tgagcaacag ctgggccaac    660
aatctgatgt ggctggccta cacaatggcc ttcatggtca agatgcccct gtacggcctg    720
cacctgtggc tgcctaaagc tcatgtggaa gcccctatcg ccggctctat ggtgctggct    780
gcagtgctgc tgaaactcgg cggctacgg atgatgcggc tgaccctgat tctgaatccc     840
ctgaccaagc acatggccta tccatttctg gtgctgagcc tgtggggcat gattatgacc    900
agcagcatct gcctgcggca gaccgatctg aagtccctga tcgcctacag ctccatcagc    960
cacatggccc tggtggtcac cgccatcctg attcagaccc cttggagctt tacaggcgcc    1020
gtgatcctga tgattgccca cggcctgaca agcagcctgc tgttttgtct ggccaacagc    1080
aactacgagc ggacccacag cagaatcatg atcctgtctc agggcctgca gaccctcctg    1140
cctcttatgg ctttttggtg gctgctggcc tctctggcca atctggcact gcctcctacc    1200
atcaatctgc tgggcgagct gagcgtgctg gtcaccacat tcagctggtc caatatcacc    1260
ctgctgctca ccggcctgaa catgctggtt acagccctgt actccctgta catgttcacc    1320
accacacagt ggggaagcct gacacaccac atcaacaata tgaagcccag cttcacccgc    1380
gagaacaccc tgatgttcat gcatctgagc cccattctgc tgctgtccct gaatcctgat    1440
atcatcaccg gcttctccag ctgagagcac tgggacgccc accgcccctt tccctccgct    1500
gccaggcgag catgttgtgg taattctgga acacaagaag agaaattgct gggtttagaa    1560
caagattata aacgaattcg gtgctcagtg atcacttgac agtttttttt ttttttaaat    1620
attacccaaa atgctcccca aataagaaat gcatcagctc agtcagtgaa tacaaaaaag    1680
gaattatttt tccctttgag ggtcttttat acatctctcc tccaaccca ccctctattc      1740 tgtttcttcc tcctcacatg ggggtacaca tacacagctt cctctttttgg ttccatcctt    1800 accaccacac cacacgcaca ctccacatgc ccagcagagt ggcacttggt ggccagaaag    1860
tgtgagcctc atgatctgct gtctgtagtt ctgtgagctc aggtccctca aaggcctcgg    1920 agcacccct tccttgtgac tgagccaggg cctgcatttt tggtttttccc cacccccacac    1980 attctcaacc atagtccttc taacaatacc aatagctagg acccggctgc tgtgcactgg    2040
gactggggat ccacatgtt tgccttggga gtctcaagct ggactgcca                  2089
```

<210> SEQ ID NO 33
<211> LENGTH: 2889
<212> TYPE: DNA
<213> ORGANISM: Artificial Sequence
<220> FEATURE:
<223> OTHER INFORMATION: opt_COX10-opt_ND4*-3'UTR

<400> SEQUENCE: 33

```
atggccgcct ctccacacac actgagtagc agactgctga ccggctgtgt tggcggctct    60
```

-continued

```
gtgtggtatc tggaacggcg acaatgctg aagctgatcg tgcccaccat catgctgctg      120
cccctgacct ggctgagcaa gaagcacatg atctggatca acaccaccac ccacagcctg      180
atcatcagca tcatcccct gctgttcttc aaccagatca caacaacct gttcagctgc       240 agccccacct tcagcagcga ccccctgacc accccctgc tgatgctgac cacctggctg      300
ctgcccctga ccatcatggc cagccagcgc cacctgagca gcgagcccct gagccgcaag     360
aagctgtacc tgagcatgct gatcagcctg cagatcagcc tgatcatgac cttcaccgcc    420
accgagctga tcatgttcta catcttcttc gagaccaccc tgatcccac cctggccatc     480 atcacccgct ggggcaacca gcccgagcgc ctgaacgccg gcacctactt cctgttctac    540
accctggtgg gcagcctgcc cctgctgatc gccctgatct acacccacaa caccctgggc    600
agcctgaaca tcctgctgct gaccctgacc gcccaggagc tgagcaacag ctgggccaac    660
aacctgatgt ggctggccta ccatggccc ttcatggtga agatgcccct gtacggcctg     720
cacctgtggc tgcccaaggc ccacgtggag gccccatcg ccggcagcat ggtgctggcc     780
gccgtgctgc tgaagctggg cggctacgga catgatgcgcc tgaccctgat cctgaacccc   840
ctgaccaagc acatggccta ccccttcctg gtgctgagcc tgtggggcat gatcatgacc    900
agcagcatct gcctgcgcca gaccgacctg aagagcctga tcgcctacag cagcatcagc    960
cacatggccc tggtggtgac cgccatcctg atccagaccc cctggagctt caccggcgcc   1020
gtgatcctga tgatcgccca cggcctgacc agcagcctgc tgttctgcct ggccaacagc   1080
aactacgagc gcacccacag ccgcatcatg atcctgagcc agggcctgca gaccctgctg   1140
cccctgatgg ccttctggtg gctgctggcc agcctggcca acctggccct gccccccacc   1200
atcaacctgc tgggcgagct gagcgtgctg gtgaccacct tcagctggag caacatcacc   1260
ctgctgctga ccggcctgaa catgctggtg accgccctgt acagcctgta catgttcacc   1320
accacccagt ggggcagcct gacccaccac atcaacaaca tgaagcccag cttcacccgc   1380
gagaacaccc tgatgttcat gcacctgagc cccatcctgc tgctgagcct gaaccccgac   1440
atcatcaccg gcttcagcag ctaagagcac tgggacgccc accgcccctt ccctccgct    1500 gccaggcgag catgttgtgg taattctgga acacaagaag agaaattgct gggtttagaa    1560
caagattata acgaattcg gtgctcagtg atcacttgac agtttttttt tttttaaat      1620 attacccaaa atgctcccca ataagaaat gcatcagctc agtcagtgaa tacaaaaaag    1680
gaattatttt tcccttgag ggtcttttat acatctctcc tccaacccca ccctctattc    1740
tgtttcttcc tcctcacatg ggggtacaca tacacagctt cctctttgg ttccatcctt    1800 accaccacac cacacgcaca ctccacatgc ccagcagagt ggcacttggt ggccagaaag    1860
tgtgagcctc atgatctgct gtctgtagtt ctgtgagctc aggtccctca aaggcctcgg    1920 agcacccct tccttgtgac tgagccaggg cctgcatttt tggttttccc caccccacac    1980
attctcaacc atagtccttc taacaatacc aatagctagg accggctgc tgtgcactgg    2040 gactggggat tccacatgtt tgccttggga gtctcaagct ggactgccag cccctgtcct    2100
cccttcaccc ccattgcgta tgagcatttc agaactccaa ggagtcacag gcatctttat    2160
agttcacgtt aacatataga cactgttgga agcagttcct tctaaaaggg tagccctgga    2220
cttaatacca gccggatacc tctggccccc accccattac tgtacctctg gagtcactac    2280
tgtgggtcgc cactcctctg ctacacagca cggcttttc aaggctgtat tgagaaggga    2340
agttaggaag aagggtgtgc tgggctaacc agcccacaga gctcacattc ctgtcccttg    2400
ggtgaaaaat acatgtccat cctgatatct cctgaattca gaaattagcc tccacatgtg    2460
```

| | |
|---|---|
| caatggcttt aagagccaga agcagggttc tgggaatttt gcaagttacc tgtggccagg | 2520 |
| tgtggtctcg gttaccaaat acggttacct gcagctttt agtcctttgt gctcccacgg | 2580 |
| gtctacagag tcccatctgc ccaaaggtct tgaagcttga caggatgttt tcgattactc | 2640 |
| agtctcccag ggcactactg gtccgtagga ttcgattggt cggggtagga gagttaaaca | 2700 |
| acatttaaac agagttctct caaaaatgtc taaagggatt gtaggtagat aacatccaat | 2760 |
| cactgtttgc acttatctga aatcttccct cttggctgcc cccaggtatt tactgtggag | 2820 |
| aacattgcat aggaatgtct ggaaaaagct tctacaactt gttacagcct tcacatttgt | 2880 |
| agaagctttt | 2889 |

<210> SEQ ID NO 34
<211> LENGTH: 2089
<212> TYPE: DNA
<213> ORGANISM: Artificial Sequence
<220> FEATURE:
<223> OTHER INFORMATION: opt_COX10-opt_ND4*-3'UTR*

<400> SEQUENCE: 34

| | |
|---|---|
| atggccgcct ctccacacac actgagtagc agactgctga ccggctgtgt tggcggctct | 60 |
| gtgtggtatc tggaacggcg gacaatgctg aagctgatcg tgcccaccat catgctgctg | 120 |
| cccctgacct ggctgagcaa gaagcacatg atctggatca acaccaccac ccacagcctg | 180 |
| atcatcagca tcatccccct gctgttcttc aaccagatca caacaaccct gttcagctgc | 240 |
| agccccacct tcagcagcga ccccctgacc acccccctgc tgatgctgac cacctggctg | 300 |
| ctgcccctga ccatcatggc cagccagcgc cacctgagca gcgagcccct gagccgcaag | 360 |
| aagctgtacc tgagcatgct gatcagcctg cagatcagcc tgatcatgac cttcaccgcc | 420 |
| accgagctga tcatgttcta catcttcttc gagaccaccc tgatccccac cctggccatc | 480 |
| atcacccgct ggggcaacca gcccgagcgc ctgaacgccg gcacctactt cctgttctac | 540 |
| accctggtgg gcagcctgcc cctgctgatc gccctgatct acacccacaa cacccctgggc | 600 |
| agcctgaaca tcctgctgct gaccctgacc gcccaggagc tgagcaacag ctgggccaac | 660 |
| aacctgatgt ggctggccta caccatggcc ttcatggtga gatgcccct gtacggcctg | 720 |
| cacctgtggc tgcccaaggc ccacgtggag gcccccatcg ccggcagcat ggtgctggcc | 780 |
| gccgtgctgc tgaagctggg cggctacggc atgatgcgcc tgaccctgat cctgaacccc | 840 |
| ctgaccaagc acatggccta ccccttcctg gtgctgagcc tgtggggcat gatcatgacc | 900 |
| agcagcatct gcctgcgcca gaccgacctg aagagcctga tcgcctacag cagcatcagc | 960 |
| cacatggccc tggtggtgac cgccatcctg atccagaccc cctggagctt caccggcgcc | 1020 |
| gtgatcctga tgatcgccca cggcctgacc agcagcctgc tgttctgcct ggccaacagc | 1080 |
| aactacgagc gcacccacag ccgcatcatg atcctgagcc agggcctgca gaccctgctg | 1140 |
| ccctgatgg ccttctggtg gctgctggcc agcctggcca acctggccct gccccccacc | 1200 |
| atcaacctgc tgggcgagct gagcgtgctg gtgaccacct tcagctggag caacatcacc | 1260 |
| ctgctgctga ccggcctgaa catgctggtg accgccctgt acagcctgta catgttcacc | 1320 |
| accacccagt ggggcagcct gacccaccac atcaacaaca tgaagcccag cttcacccgc | 1380 |
| gagaacaccc tgatgttcat gcacctgagc cccatcctgc tgctgagcct gaaccccgac | 1440 |
| atcatcaccg gcttcagcag ctaagagcac tgggacgccc accgcccctt ccctccgct | 1500 |
| gccaggcgag catgttgtgg taattctgga acacaagaag agaaattgct gggtttagaa | 1560 |

-continued

| | |
|---|---|
| caagattata aacgaattcg gtgctcagtg atcacttgac agttttttt tttttttaaat | 1620 |
| attacccaaa atgctcccca aataagaaat gcatcagctc agtcagtgaa tacaaaaaag | 1680 |
| gaattatttt tcccttgag ggtcttttat acatctctcc tccaacccca ccctctattc | 1740 |
| tgtttcttcc tcctcacatg ggggtacaca tacacagctt cctcttttgg ttccatcctt | 1800 |
| accaccacac cacacgcaca ctccacatgc ccagcagagt ggcacttggt ggccagaaag | 1860 |
| tgtgagcctc atgatctgct gtctgtagtt ctgtgagctc aggtccctca aaggcctcgg | 1920 |
| agcaccccct tccttgtgac tgagccaggg cctgcatttt tggttttccc caccccacac | 1980 |
| attctcaacc atagtccttc taacaatacc aatagctagg accggctgc tgtgcactgg | 2040 |
| gactggggat tccacatgtt tgccttggga gtctcaagct ggactgcca | 2089 |

<210> SEQ ID NO 35
<211> LENGTH: 2034
<212> TYPE: DNA
<213> ORGANISM: Artificial Sequence
<220> FEATURE:
<223> OTHER INFORMATION: opt_COX10-ND6-3'UTR

<400> SEQUENCE: 35

| | |
|---|---|
| atggccgcct ctccacacac actgagtagc agactgctga ccggctgtgt tggcggctct | 60 |
| gtgtggtatc tggaacggcg gacaatgatg tatgctttgt ttctgttgag tgtgggttta | 120 |
| gtaatggggt ttgtggggtt ttcttctaag ccttctccta tttatggggg tttagtattg | 180 |
| attgttagcg gtgtggtcgg gtgtgttatt attctgaatt tgggggagg ttatatgggt | 240 |
| ttaatggttt ttttaattta tttaggggga atgatggttg tctttggata tactacagcg | 300 |
| atggctattg aggagtatcc tgaggcatgg gggtcagggg ttgaggtctt ggtgagtgtt | 360 |
| ttagtggggt tagcgatgga ggtaggattg gtgctgtggg tgaaagagta tgatggggtg | 420 |
| gtggttgtgg taaactttaa tagtgtagga agctggatga tttatgaagg agaggggtca | 480 |
| gggttgattc gggaggatcc tattggtgcg ggggctttgt atgattatgg gcgttggtta | 540 |
| gtagtagtta ctggttggac attgtttgtt ggtgtatata ttgtaattga gattgctcgg | 600 |
| gggaattagg agcactggga cgcccaccgc cccttccct ccgctgccag gcgagcatgt | 660 |
| tgtggtaatt ctggaacaca agaagagaaa ttgctgggtt tagaacaaga ttataaacga | 720 |
| attcggtgct cagtgatcac ttgacagttt tttttttt taaatattac caaaatgct | 780 |
| ccccaaataa gaaatgcatc agctcagtca gtgaatacaa aaaggaatt attttccct | 840 |
| ttgagggtct tttatacatc tctcctccaa ccccaccctc tattctgttt cttcctcctc | 900 |
| acatggggt acacatacac agcttcctct tttggttcca tccttaccac cacaccacac | 960 |
| gcacactcca catgcccagc agagtggcac ttggtggcca gaaagtgtga gcctcatgat | 1020 |
| ctgctgtctg tagttctgtg agctcaggtc cctcaaaggc tcggagcac cccttcctt | 1080 |
| gtgactgagc cagggcctgc attttggtt tccccaccc cacacattct caaccatagt | 1140 |
| ccttctaaca ataccaatag ctaggacccg gctgctgtgc actgggactg gggattccac | 1200 |
| atgtttgcct ggagtctc aagctggact gccagcccct gtcctccctt caccccatt | 1260 |
| gcgtatgagc atttcagaac tccaaggagt cacaggcatc tttatagttc acgttaacat | 1320 |
| atagacactg ttggaagcag ttccttctaa aagggtagcc ctggacttaa taccagccgg | 1380 |
| atacctctgg ccccacccc attactgtac ctctggagtc actactgtgg gtcgccactc | 1440 |
| ctctgctaca cagcacggct ttttcaaggc tgtattgaga agggaagtta ggaagaaggg | 1500 |
| tgtgctgggc taaccagccc acagagctca cattcctgtc ccttgggtga aaaatacatg | 1560 |

```
tccatcctga tatctcctga attcagaaat tagcctccac atgtgcaatg gctttaagag    1620
ccagaagcag ggttctggga attttgcaag ttacctgtgg ccaggtgtgg tctcggttac    1680
caaatacggt tacctgcagc ttttagtcc tttgtgctcc cacgggtcta cagagtccca     1740
tctgcccaaa ggtcttgaag cttgacagga tgttttcgat tactcagtct cccagggcac   1800
tactggtccg taggattcga ttggtcgggg taggagagtt aaacaacatt taaacagagt   1860
tctctcaaaa atgtctaaag ggattgtagg tagataacat ccaatcactg tttgcactta   1920
tctgaaatct tccctcttgg ctgccccag gtatttactg tggagaacat tgcataggaa    1980
tgtctggaaa aagcttctac aacttgttac agccttcaca tttgtagaag cttt         2034
```

<210> SEQ ID NO 36
<211> LENGTH: 1234
<212> TYPE: DNA
<213> ORGANISM: Artificial Sequence
<220> FEATURE:
<223> OTHER INFORMATION: opt_COX10-ND6-3'UTR*

<400> SEQUENCE: 36

```
atggccgcct ctccacacac actgagtagc agactgctga ccggctgtgt tggcggctct     60
gtgtggtatc tggaacggcg gacaatgatg tatgctttgt ttctgttgag tgtgggttta   120
gtaatggggt ttgtggggtt ttcttctaag ccttctccta tttatggggg tttagtattg   180
attgttagcg gtgtggtcgg gtgtgttatt attctgaatt ttggggagg ttatatgggt    240 ttaatggttt ttttaattta tttagggga atgatggttg tctttggata tactacagcg    300
atggctattg aggagtatcc tgaggcatgg gggtcagggg ttgaggtctt ggtgagtgtt   360
ttagtggggt tagcgatgga ggtaggattg gtgctgtggg tgaaagagta tgatggggtg   420
gtggttgtgg taaactttaa tagtgtagga agctggatga tttatgaagg agagggtca    480 gggttgattc gggaggatcc tattggtgcg ggggctttgt atgattatgg gcgttggtta   540
gtagtagtta ctggttggac attgtttgtt ggtgtatata ttgtaattga gattgctcgg   600
gggaattagg agcactggga cgcccaccgc cctttccct ccgctgccag gcgagcatgt    660
tgtggtaatt ctgaacacag aagagaaa ttgctgggtt tagaacaaga ttataaacga     720
attcggtgct cagtgatcac ttgacagttt tttttttttt taaatattac ccaaaatgct   780
ccccaaataa gaaatgcatc agctcagtca gtgaatacaa aaaaggaatt atttttcct    840 ttgagggtct tttatacatc tctcctccaa ccccaccctc tattctgttt cttcctcctc   900 acatggggt acacatacac agcttcctct tttggttcca tccttaccac cacaccacac    960
gcacactcca catgcccagc agagtggcac ttggtggcca gaaagtgtga gcctcatgat   1020
ctgctgtctg tagttctgtg agctcaggtc cctcaaaggc ctcggagcac ccccttcctt   1080
gtgactgagc cagggcctgc attttttggtt ttccccaccc cacacattct caaccatagt   1140
ccttctaaca ataccaatag ctaggacccg gctgctgtgc actgggactg gggattccac   1200
atgtttgcct tgggagtctc aagctggact gcca                               1234
```

<210> SEQ ID NO 37
<211> LENGTH: 2034
<212> TYPE: DNA
<213> ORGANISM: Artificial Sequence
<220> FEATURE:
<223> OTHER INFORMATION: opt_COX10-opt_ND6-3'UTR

<400> SEQUENCE: 37

```
atggccgcct ctccacacac actgagtagc agactgctga ccggctgtgt tggcggctct    60
gtgtggtatc tggaacggcg gacaatgatg tacgccctgt tcctgctgag cgtgggcctg   120
gtgatgggct tcgtgggctt cagcagcaag cccagcccca tctacggcgg cctggtgctg   180
atcgtgagcg gcgtggtggg ctgcgtgatc atcctgaact tcggcggcgg ctacatgggc   240
ctgatggtgt tcctgatcta cctgggcggc atgatggtgg tgttcggcta caccaccgcc   300
atggccatcg aggagtaccc cgaggcctgg ggcagcggcg tggaggtgct ggtgagcgtg   360
ctggtgggcc tggccatgga ggtgggcctg gtgctgtggg tgaaggagta cgacggcgtg   420
gtggtggtgg tgaacttcaa cagcgtgggc agctggatga tctacgaggg cgagggcagc   480
ggcctgatcc gcgaggaccc catcggcgcc ggcgccctgt acgactacgg ccgctggctg   540
gtggtggtga ccggctggac cctgttcgtg ggcgtgtaca tcgtgatcga gatcgcccgc   600
ggcaactaag agcactggga cgcccaccgc cccttcccct ccgctgccag gcgagcatgt   660
tgtggtaatt ctggaacaca agaagagaaa ttgctgggtt tagaacaaga ttataaacga   720
attcggtgct cagtgatcac ttgacagttt ttttttttt taaatattac ccaaaatgct   780
ccccaaataa gaaatgcatc agctcagtca gtgaatacaa aaaggaatt attttttccct   840
ttgagggtct tttatacatc tctcctccaa ccccacctc tattctgttt cttcctcctc   900
acatggggt acacatacac agcttcctct tttggttcca tccttaccac cacaccacac   960
gcacactcca catgcccagc agagtggcac ttggtggcca gaaagtgtga gcctcatgat  1020
ctgctgtctg tagttctgtg agctcaggtc cctcaaaggc ctcggagcac cccttccctt  1080
gtgactgagc cagggcctgc atttttggtt ttccccaccc cacacattct caaccatagt  1140
ccttctaaca ataccaatag ctaggacccg gctgctgtgc actgggactg gggattccac  1200
atgtttgcct tgggagtctc aagctggact gccagcccct gtcctccctt cacccccatt  1260
gcgtatgagc atttcagaac tccaaggagt cacaggcatc tttatagttc acgttaacat  1320
atagacactg ttggaagcag ttccttctaa aagggtagcc ctggacttaa taccagccgg  1380
atacctctgg ccccaccc attactgtac ctctggagtc actactgtgg gtcgccactc  1440
ctctgctaca cagcacggct ttttcaaggc tgtattgaga agggaagtta ggaagaaggg  1500
tgtgctgggc taaccagccc acagagctca cattcctgtc ccttgggtga aaaatacatg  1560
tccatcctga tatctcctga attcagaaat tagcctccac atgtgcaatg gctttaagag  1620
ccagaagcag ggttctggga attttgcaag ttacctgtgg ccaggtgtgg tctcggttac  1680
caaatacggt tacctgcagc ttttttagtcc tttgtgctcc cacgggtcta cagagtccca  1740
tctgcccaaa ggtcttgaag cttgacagga tgttttcgat tactcagtct cccagggcac  1800
tactggtccg taggattcga ttggtcgggg taggagagtt aaacaacatt taaacagagt  1860
tctctcaaaa atgtctaaag ggattgtagg tagataacat ccaatcactg tttgcactta  1920
tctgaaatct tccctcttgg ctgccccag gtatttactg tggagaacat tgcataggaa  1980
tgtctggaaa aagcttctac aacttgttac agccttcaca tttgtagaag cttt         2034
```

<210> SEQ ID NO 38
<211> LENGTH: 1234
<212> TYPE: DNA
<213> ORGANISM: Artificial Sequence
<220> FEATURE:
<223> OTHER INFORMATION: opt_COX10-opt_ND6-3'UTR*

<400> SEQUENCE: 38

```
atggccgcct ctccacacac actgagtagc agactgctga ccggctgtgt tggcggctct    60
```

-continued

```
gtgtggtatc tggaacggcg acaatgatg tacgccctgt tcctgctgag cgtgggcctg      120
gtgatgggct tcgtgggctt cagcagcaag cccagcccca tctacggcgg cctggtgctg      180
atcgtgagcg gcgtggtggg ctgcgtgatc atcctgaact tcggcggcgg ctacatgggc      240
ctgatggtgt tcctgatcta cctgggcggc atgatggtgg tgttcggcta caccaccgcc      300
atggccatcg aggagtaccc cgaggcctgg ggcagcggcg tggaggtgct ggtgagcgtg      360
ctggtgggcc tggccatgga ggtgggcctg gtgctgtggg tgaaggagta cgacggcgtg      420
gtggtggtgg tgaacttcaa cagcgtgggc agctggatga tctacgaggg cgagggcagc      480
ggcctgatcc gcaggaccc catcggcgcc ggcgccctgt acgactacgg ccgctggctg      540
gtggtggtga ccggctggac cctgttcgtg ggcgtgtaca tcgtgatcga gatcgcccgc      600
ggcaactaag agcactggga cgcccaccgc cccctttccct ccgctgccag gcgagcatgt      660
tgtggtaatt ctggaacaca agaagagaaa ttgctgggtt tagaacaaga ttataaacga      720
attcggtgct cagtgatcac ttgacagttt tttttttttt taaatattac ccaaaatgct      780
ccccaaataa gaaatgcatc agctcagtca gtgaatacaa aaaggaatt attttttccct      840 ttgagggtct tttatacatc tctcctccaa ccccacccctc tattctgttt cttcctcctc      900
acatgggggt acacatacac agcttcctct tttggttcca tccttaccac cacaccacac      960
gcacactcca catgcccagc agagtggcac ttggtggcca gaaagtgtga gcctcatgat     1020
ctgctgtctg tagttctgtg agctcaggtc cctcaaaggc ctcggagcac cccttccttc     1080
gtgactgagc cagggcctgc attttttggtt ttccccaccc cacacattct caaccatagt     1140
ccttctaaca ataccaatag ctaggacccg gctgctgtgc actgggactg gggattccac     1200
atgtttgcct tgggagtctc aagctggact gcca                                 1234
```

<210> SEQ ID NO 39
<211> LENGTH: 2460
<212> TYPE: DNA
<213> ORGANISM: Artificial Sequence
<220> FEATURE:
<223> OTHER INFORMATION: opt_COX10-ND1-3'UTR

<400> SEQUENCE: 39

```
atggccgcct ctccacacac actgagtagc agactgctga ccggctgtgt tggcggctct       60
gtgtggtatc tggaacggcg acaatggcc aacctcctac tcctcattgt acccattcta      120
atcgcaatgg cattcctaat gcttaccgaa cgaaaaattc taggctatat gcaactacgc      180
aaaggcccca acgttgtagg cccctacggg ctactacaac ccttcgctga cgccataaaa      240
ctcttcacca aagagcccct aaaacccgcc acatctacca tcaccctcta catcaccgcc      300
ccgaccttag ctctcaccat cgctcttcta ctatggaccc cctcccccat gcccaacccc      360
ctggtcaacc tcaacctagg cctcctattt attctagcca cctctagcct agccgtttac      420
tcaatcctct ggtcagggtg ggcatcaaac tcaaactacg ccctgatcgg cgcactgcga      480
gcagtagccc aaacaatctc atatgaagtc accctagcca tcattctact atcaacatta      540
ctaatgagtg gctcctttaa cctctccacc cttatcacaa cacaagaaca cctctggtta      600
ctcctgccat catggccctt ggccatgatg tggtttatct ccacactagc agagaccaac      660 cgaacccccct tcgaccttgc cgaaggggag tccgaactag tctcaggctt caacatcgaa      720
tacgccgcag gccccttcgc cctattcttc atggccgaat acacaaacat tattatgatg      780 aacacccctca ccactacaat cttcctagga acaacatatg acgcactctc ccctgaactc      840
```

| | |
|---|---|
| tacacaacat attttgtcac caagacccta cttctaacct ccctgttctt atggattcga | 900 |
| acagcatacc cccgattccg ctacgaccaa ctcatgcacc tcctatggaa aaacttccta | 960 |
| ccactcaccc tagcattact tatgtggtat gtctccatgc ccattacaat ctccagcatt | 1020 |
| cccctcaaa cctaagagca ctgggacgcc caccgcccct ttccctccgc tgccaggcga | 1080 |
| gcatgttgtg gtaattctgg aacacaagaa gagaaattgc tgggtttaga acaagattat | 1140 |
| aaacgaattc ggtgctcagt gatcacttga cagttttttt ttttttttaaa tattacccaa | 1200 |
| aatgctcccc aaataagaaa tgcatcagct cagtcagtga atacaaaaaa ggaattattt | 1260 |
| ttcccttttga gggtcttta tacatctctc ctccaacccc accctctatt ctgtttcttc | 1320 |
| ctcctcacat gggggtacac atacacagct tcctcttttg gttccatcct taccaccaca | 1380 |
| ccacacgcac actccacatg cccagcagag tggcacttgg tggccagaaa gtgtgagcct | 1440 |
| catgatctgc tgtctgtagt tctgtgagct caggtccctc aaaggcctcg gagcaccccc | 1500 |
| ttccttgtga ctgagccagg gcctgcattt ttggttttcc ccaccccaca cattctcaac | 1560 |
| catagtcctt ctaacaatac caatagctag gacccggctg ctgtgcactg ggactgggga | 1620 |
| ttccacatgt ttgccttggg agtctcaagc tggactgcca gccctgtcc tccttcacc | 1680 |
| cccattgcgt atgagcattt cagaactcca aggagtcaca ggcatcttta tagttcacgt | 1740 |
| taacatatag acactgttgg aagcagttcc ttctaaaagg gtagccctgg acttaatacc | 1800 |
| agccggatac ctctggcccc caccccatta ctgtacctct ggagtcacta ctgtgggtcg | 1860 |
| ccactcctct gctacacagc acggcttttt caaggctgta ttgagaaggg aagttaggaa | 1920 |
| gaagggtgtg ctgggctaac cagcccacag agctcacatt cctgtccctt gggtgaaaaa | 1980 |
| tacatgtcca tcctgatatc tcctgaattc agaaattagc ctccacatgt gcaatggctt | 2040 |
| taagagccag aagcagggtt ctgggaattt tgcaagttac ctgtggccag gtgtggtctc | 2100 |
| ggttaccaaa tacggttacc tgcagctttt tagtcctttg tgctcccacg ggtctacaga | 2160 |
| gtcccatctg cccaaaggtc ttgaagcttg acaggatgtt ttcgattact cagtctccca | 2220 |
| gggcactact ggtccgtagg attcgattgg tcggggtagg agagttaaac aacatttaaa | 2280 |
| cagagttctc tcaaaaatgt ctaaagggat tgtaggtaga taacatccaa tcactgtttg | 2340 |
| cacttatctg aaatcttccc tcttggctgc ccccaggtat ttactgtgga gaacattgca | 2400 |
| taggaatgtc tggaaaaagc ttctacaact tgttacagcc ttcacatttg tagaagcttt | 2460 |

<210> SEQ ID NO 40
<211> LENGTH: 1660
<212> TYPE: DNA
<213> ORGANISM: Artificial Sequence
<220> FEATURE:
<223> OTHER INFORMATION: opt_COX10-ND1-3'UTR*

<400> SEQUENCE: 40

| | |
|---|---|
| atggccgcct ctccacacac actgagtagc agactgctga ccggctgtgt tggcggctct | 60 |
| gtgtggtatc tggaacggcg acaatggcc aacctcctac tcctcattgt acccattcta | 120 |
| atcgcaatgg cattcctaat gcttaccgaa cgaaaaattc taggctatat gcaactacgc | 180 |
| aaaggcccca acgttgtagg cccctacggg ctactacaac cttcgctga cgccataaaa | 240 |
| ctcttcacca aagagcccct aaaacccgcc acatctacca tcaccctcta catcaccgcc | 300 |
| ccgaccttag ctctcaccat cgctcttcta ctatggaccc cctcccat gcccaacccc | 360 |
| ctggtcaacc tcaacctagg cctcctattt attctagcca cctctagcct agccgtttac | 420 |
| tcaatcctct ggtcagggtg ggcatcaaac tcaaactacg ccctgatcgg cgcactgcga | 480 |

```
gcagtagccc aaacaatctc atatgaagtc accctagcca tcattctact atcaacatta    540
ctaatgagtg gctcctttaa cctctccacc cttatcacaa cacaagaaca cctctggtta    600
ctcctgccat catggccctt ggccatgatg tggtttatct ccacactagc agagaccaac    660 cgaacccct tcgaccttgc cgaaggggag tccgaactag tctcaggctt caacatcgaa    720
tacgccgcag gccccttcgc cctattcttc atggccgaat acacaaacat tattatgatg    780
aacaccctca ccactacaat cttcctagga acaacatatg acgcactctc ccctgaactc    840
tacacaacat attttgtcac caagacccta cttctaacct ccctgttctt atggattcga    900
acagcatacc cccgattccg ctacgaccaa ctcatgcacc tcctatggaa aaacttccta    960
ccactcaccc tagcattact tatgtggtat gtctccatgc ccattacaat ctccagcatt   1020 cccctcaaa cctaagagca ctgggacgcc caccgcccct ttccctccgc tgccaggcga   1080
gcatgttgtg gtaattctgg aacacaagaa gagaaattgc tgggtttaga acaagattat   1140
aaacgaattc ggtgctcagt gatcacttga cagttttttt tttttttaaa tattacccaa   1200
aatgctcccc aaataagaaa tgcatcagct cagtcagtga atacaaaaaa ggaattattt   1260 ttcccttga gggtctttta tacatctctc ctccaacccc accctctatt ctgtttcttc   1320
ctcctcacat gggggtacac atacacagct tcctcttttg gttccatcct taccaccaca   1380
ccacacgcac actccacatg cccagcgagg tggcacttgg tggccagaaa gtgtgagcct   1440
catgatctgc tgtctgtagt tctgtgagct caggtccctc aaaggcctcg gagcaccccc   1500
ttccttgtga ctgagccagg gcctgcattt ttggttttcc ccaccccaca cattctcaac   1560
catagtcctt ctaacaatac caatagctag gacccggctg ctgtgcactg ggactgggga   1620
ttccacatgt ttgccttggg agtctcaagc tggactgcca                          1660

<210> SEQ ID NO 41
<211> LENGTH: 2460
<212> TYPE: DNA
<213> ORGANISM: Artificial Sequence
<220> FEATURE:
<223> OTHER INFORMATION: opt_COX10-opt_ND1-3'UTR

<400> SEQUENCE: 41
atggccgcct ctccacacac actgagtagc agactgctga ccggctgtgt tggcggctct     60
gtgtggtatc tggaacggcg gacaatggcc aacctgctgc tgctgatcgt gcccatcctg    120
atcgccatgg ccttcctgat gctgaccgag cgcaagatcc tgggctacat gcagctgcgc    180
aagggcccca acgtggtggg ccccctacggc ctgctgcagc ccttcgccga cgccatcaag    240
ctgttcacca aggagcccct gaagcccgcc accagcacca tcaccctgta catcaccgcc    300
cccaccctgg ccctgaccat cgccctgctg ctgtggaccc cctgcccat gcccaacccc    360 ctggtgaacc tgaacctggg cctgctgttc atcctggcca ccagcagcct ggccgtgtac    420
agcatcctgt ggagcggctg gccagcaac agcaactacg ccctgatcgg cgccctgcgc    480
gccgtggccc agaccatcag ctacgaggtg accctggcca tcatcctgct gagcaccctg    540
ctgatgagcg gcagcttcaa cctgagcacc ctgatcacca ccccaggagca cctgtggctg    600 ctgctgccca gctggcccct ggccatgatg tggttcatca gcaccctggc cgagaccaac    660
cgcaccccct tcgacctggc cgagggcgag agcgagctgg tgagcggctt caacatcgag    720
tacgccgccg gccccttcgc cctgttcttc atggccgagt acaccaacat catcatgatg    780
aacaccctga ccaccaccat cttcctgggc accacctacg acgccctgag ccccgagctg    840
```

-continued

```
tacaccacct acttcgtgac caagaccctg ctgctgacca gcctgttcct gtggatccgc      900
accgcctacc cccgcttccg ctacgaccag ctgatgcacc tgctgtggaa gaacttcctg      960
cccctgaccc tggccctgct gatgtggtac gtgagcatgc ccatcaccat cagcagcatc     1020 ccccccccaga cctaagagca ctgggacgcc accgcccct ttccctccgc tgccaggcga     1080
gcatgttgtg gtaattctgg aacacaagaa gagaaattgc tgggtttaga acaagattat     1140
aaacgaattc ggtgctcagt gatcacttga cagttttttt tttttttaaa tattacccaa     1200
aatgctcccc aaataagaaa tgcatcagct cagtcagtga atacaaaaaa ggaattattt     1260
ttccctttga gggtctttta tacatctctc ctccaaccc accctctatt ctgtttcttc     1320
ctcctcacat gggggtacac atacacagct tcctcttttg gttccatcct taccaccaca     1380
ccacacgcac actccacatg cccagcagag tggcacttgg tggccagaaa gtgtgagcct     1440
catgatctgc tgtctgtagt tctgtgagct caggtccctc aaaggcctcg gagcaccccc     1500
ttccttgtga ctgagccagg gcctgcattt ttggttttcc ccaccccaca cattctcaac     1560
catagtcctt ctaacaatac caatagctag daccccggctg ctgtgcactg ggactgggga     1620
ttccacatgt ttgccttggg agtctcaagc tggactgcca gccctgtcc tcccttcacc     1680 cccattgcgt atgagcattt cagaactcca aggagtcaca ggcatcttta tagttcacgt     1740
taacatatag acactgttgg aagcagttcc ttctaaaagg gtagccctgg acttaatacc     1800
agccggatac ctctggcccc caccccatta ctgtacctct ggagtcacta ctgtgggtcg     1860
ccactcctct gctacacagc acggcttttt caaggctgta ttgagaaggg aagttaggaa     1920
gaagggtgtg ctgggctaac cagcccacag agctcacatt cctgtccctt gggtgaaaaa     1980
tacatgtcca tcctgatatc tcctgaattc agaaattagc ctccacatgt gcaatggctt     2040
taagagccag aagcagggtt ctgggaattt tgcaagttac ctgtggccag gtgtggtctc     2100
ggttaccaaa tacggttacc tgcagctttt tagtcctttg tgctcccacg ggtctacaga     2160
gtcccatctg cccaaaggtc ttgaagcttg acaggatgtt ttcgattact cagtctccca     2220
gggcactact ggtccgtagg attcgattgg tcggggtagg agagttaaac aacatttaaa     2280
cagagttctc tcaaaaatgt ctaaagggat tgtaggtaga taacatccaa tcactgtttg     2340
cacttatctg aaatcttccc tcttggctgc ccccaggtat ttactgtgga gaacattgca     2400
taggaatgtc tggaaaaagc ttctacaact tgttacagcc ttcacatttg tagaagcttt     2460
```

<210> SEQ ID NO 42
<211> LENGTH: 1660
<212> TYPE: DNA
<213> ORGANISM: Artificial Sequence
<220> FEATURE:
<223> OTHER INFORMATION: opt_COX10-opt_ND1-3'UTR*

<400> SEQUENCE: 42

```
atggccgcct ctccacacac actgagtagc agactgctga ccggctgtgt tggcggctct       60
gtgtggtatc tggaacggcg acaatggcc aacctgctgc tgctgatcgt gcccatcctg      120
atcgccatgg ccttcctgat gctgaccgag cgcaagatcc tgggctacat gcagctgcgc      180
aagggcccca acgtggtggg ccccctacggc ctgctgcagc ccttcgccga cgccatcaag      240
ctgttcacca aggagcccct gaagcccgcc accagcacca tcaccctgta catcaccgcc      300
cccaccctgg ccctgaccat cgccctgctg ctgtggaccc cctgccat gcccaaccc      360 ctggtgaacc tgaacctggg cctgctgttc atcctggcca ccagcagcct ggccgtgtac      420
agcatcctgt ggagcggctg ggccagcaac agcaactacg ccctgatcgg cgccctgcgc      480
```

```
gccgtggccc agaccatcag ctacgaggtg accctggcca tcatcctgct gagcaccctg    540
ctgatgagcg gcagcttcaa cctgagcacc ctgatcacca cccaggagca cctgtggctg    600
ctgctgccca gctggcccct ggccatgatg tggttcatca gcaccctggc cgagaccaac    660 cgcacccct tcgacctggc cgagggcgag agcgagctgg tgagcggctt caacatcgag    720
tacgccgccg gccccttcgc cctgttcttc atggccgagt acaccaacat catcatgatg    780
aacaccctga ccaccaccat cttcctgggc accacctacg acgccctgag ccccgagctg    840
tacaccacct acttcgtgac caagaccctg ctgctgacca gcctgttcct gtggatccgc    900
accgcctacc cccgcttccg ctacgaccag ctgatgcacc tgctgtggaa gaacttcctg    960
cccctgaccc tggccctgct gatgtggtac gtgagcatgc ccatcaccat cagcagcatc   1020
cccccccaga cctaagagca ctgggacgcc accgcccct ttccctccgc tgccaggcga   1080
gcatgttgtg gtaattctgg aacacaagaa gagaaattgc tgggtttaga caagattat   1140 aaacgaattc ggtgctcagt gatcacttga cagttttttt ttttttaaa tattacccaa   1200 aatgctcccc aaataagaaa tgcatcagct cagtcagtga atacaaaaaa ggaattattt   1260 ttcccttga gggtctttta tacatctctc ctccaacccc accctctatt ctgtttcttc   1320
ctcctcacat gggggtacac atacacagct tcctcttttg gttccatcct taccaccaca   1380 ccacgcac actccacatg cccagcagag tggcacttgg tggccagaaa gtgtgagcct   1440
catgatctgc tgtctgtagt tctgtgagct caggtccctc aaaggcctcg gagcacccc   1500 ttccttgtga ctgagccagg gcctgcattt ttggttttcc ccaccccaca cattctcaac   1560
catagtcctt ctaacaatac caatagctag gacccggctg ctgtgcactg ggactgggga   1620
ttccacatgt ttgccttggg agtctcaagc tggactgcca                        1660

<210> SEQ ID NO 43
<211> LENGTH: 2889
<212> TYPE: DNA
<213> ORGANISM: Artificial Sequence
<220> FEATURE:
<223> OTHER INFORMATION: opt_COX10*-ND4-3'UTR

<400> SEQUENCE: 43
atggccgcca gccccacac cctgagcagc cgcctgctga ccggctgcgt gggcggcagc     60
gtgtggtacc tggagcgccg caccatgcta aaactaatcg tcccaacaat tatgttacta    120
ccactgacat ggcttcccaa aaaacacatt atttggatca acacaaccac ccacagccta    180
attattagca tcatccctct actattttt aaccaaatca caacaacct atttagctgt    240 tccccaacct tttcctccga ccccctaaca accccctcc taatgctaac tacctggctc    300
ctacccctca caatcatggc aagccaacgc acttatccca gtgaaccact atcacgaaaa    360
aaactctacc tctctatgct aatctcccta caaatctcct taattatgac attcacagcc    420
acagaactaa tcatgtttta tatcttcttc gaaaccacac ttatcccac cttggctatc    480 atcacccgat ggggcaacca gccagaacgc ctgaacgcag gcacatactt cctattctac    540
accctagtag gctcccttcc cctactcatc gcactaattt acactcacaa cccctaggc    600 tcactaaaca ttctactact cactctcact gcccaagaac tatcaaactc ctgggccaac    660
aacttaatgt ggctagctta cacaatggct tttatggtaa agatgcctct ttacggactc    720
cacttatggc tccctaaagc ccatgtcgaa gcccccatcg ctgggtcaat ggtacttgcc    780
gcagtactct taaaactagg cggctatggt atgatgcgcc tcacactcat tctcaacccc    840
```

```
ctgacaaaac acatggccta ccccttcctt gtactatccc tatggggcat gattatgaca    900
agctccatct gcctacgaca aacagaccta aaatcgctca ttgcatactc ttcaatcagc    960
cacatggccc tcgtagtaac agccattctc atccaaaccc cctggagctt caccggcgca   1020
gtcattctca tgatcgccca cgggcttaca tcctcattac tattctgcct agcaaactca   1080
aactacgaac gcactcacag tcgcatcatg atcctctctc aaggacttca aactctactc   1140
ccactaatgg cttttggtg gcttctagca agcctcgcta acctcgcctt accccccact    1200
attaacctac tgggagaact ctctgtgcta gtaaccacgt tctcctggtc aaatatcact   1260
ctcctactta caggactcaa catgctagtc acagccctat actccctcta catgtttacc   1320
acaacacaat ggggctcact cacccaccac attaacaaca tgaaaccctc attcacacga   1380
gaaaacaccc tcatgttcat gcacctatcc cccattctcc tcctatccct caaccccgac   1440
atcattaccg ggttttcctc ttaagagcac tgggacgccc accgccccctt tcctccgct   1500
gccaggcgag catgttgtgg taattctgga acacaagaag agaaattgct gggtttagaa   1560
caagattata aacgaattcg gtgctcagtg atcacttgac agttttttttt tttttttaaat 1620
attacccaaa atgctcccca aataagaaat gcatcagctc agtcagtgaa tacaaaaaag   1680
gaattatttt tcccttttgag ggtcttttat acatctctcc tccaaccccca ccctctattc 1740
tgtttcttcc tcctcacatg ggggtacaca tacacagctt cctcttttgg ttccatcctt   1800
accaccacac cacacgcaca ctccacatgc ccagcagagt ggcacttggt ggccagaaag   1860
tgtgagcctc atgatctgct gtctgtagtt ctgtgagctc aggtccctca aaggcctcgg   1920
agcaccccct tccttgtgac tgagccaggg cctgcatttt tggttttccc caccccacac   1980
attctcaacc atagtccttc taacaatacc aatagctagg accggctgc tgtgcactgg    2040
gactggggat tccacatgtt tgccttggga gtctcaagct ggactgccag ccctgtcct    2100
cccttcaccc ccattgcgta tgagcatttc agaactccaa ggagtcacag gcatctttat   2160
agttcacgtt aacatataga cactgttgga agcagttcct tctaaagggg tagccctgga   2220
cttaatacca gccggatacc tctggccccc accccattac tgtacctctg gagtcactac   2280
tgtgggtcgc cactcctctg ctacacagca cggcttttc aaggctgtat tgagaaggga   2340
agttaggaag aagggtgtgc tgggctaacc agcccacaga gctcacattc ctgtcccttg   2400
ggtgaaaaat acatgtccat cctgatatct cctgaattca gaaattagcc tccacatgtg   2460
caatggcttt aagagccaga agcagggttc tgggaatttt gcaagttacc tgtggccagg   2520
tgtggtctcg gttaccaaat acggttacct gcagcttttt agtcctttgt gctcccacgg   2580
gtctacagag tcccatctgc ccaaaggtct tgaagcttga caggatgttt tcgattactc   2640
agtctcccag ggcactactg gtccgtagga ttcgattggt cggggtagga gagttaaaca   2700
acatttaaac agagttctct caaaaatgtc taaagggatt gtaggtagat aacatccaat   2760
cactgtttgc acttatctga aatcttccct cttggctgcc cccaggtatt tactgtggag   2820
aacattgcat aggaatgtct ggaaaaagct tctacaactt gttacagcct tcacatttgt   2880
agaagcttt                                                           2889
```

<210> SEQ ID NO 44
<211> LENGTH: 2089
<212> TYPE: DNA
<213> ORGANISM: Artificial Sequence
<220> FEATURE:
<223> OTHER INFORMATION: opt_COX10*-ND4-3'UTR*

<400> SEQUENCE: 44

```
atggccgcca gcccccacac cctgagcagc cgcctgctga ccggctgcgt gggcggcagc      60
gtgtggtacc tggagcgccg caccatgcta aaactaatcg tcccaacaat tatgttacta     120
ccactgacat ggcttttccaa aaaacacatg atttggatca acacaaccac ccacagccta    180
attattagca tcatccctct actatttttt aaccaaatca caacaaccct atttagctgt     240
tccccaacct tttcctccga cccccctaaca acccccctcc taatgctaac tacctggctc    300
ctaccccctca caatcatggc aagccaacgc cacttatcca gtgaaccact atcacgaaaa    360
aaactctacc tctctatgct aatctcccta caaatctcct taattatgac attcacagcc    420
acagaactaa tcatgtttta tatcttcttc gaaaccacac ttatccccac cttggctatc    480
atcacccgat ggggcaacca gccagaacgc ctgaacgcag gcacatactt cctattctac    540
accctagtag ctcccttcc cctactcatc gcactaattt acactcacaa cccctaggc      600
tcactaaaca ttctactact cactctcact gcccaagaac tatcaaactc ctgggccaac    660
aacttaatgt ggctagctta cacaatggct tttatggtaa agatgcctct ttacggactc    720
cacttatggc tccctaaagc ccatgtcgaa gcccccatcg ctgggtcaat ggtacttgcc    780
gcagtactct taaaactagg cggctatggt atgatgcgcc tcacactcat tctcaaccccc   840
ctgacaaaac acatggccta ccccttcctt gtactatccc tatggggcat gattatgaca    900
agctccatct gcctacgaca aacagaccta aaatcgctca ttgcatactc ttcaatcagc    960
cacatggccc tcgtagtaac agccattctc atccaaaccc cctggagctt caccggcgca   1020
gtcattctca tgatcgccca cgggcttaca tcctcattac tattctgcct agcaaactca   1080
aactacgaac gcactcacag tcgcatcatg atcctctctc aaggacttca aactctactc   1140
ccactaatgg cttttttggtg gcttctagca agcctcgcta acctcgcctt accccccact   1200
attaacctac tgggagaact ctctgtgcta gtaaccacgt tctcctggtc aaatatcact   1260
ctcctactta caggactcaa catgctagtc acagccctat actccctcta catgtttacc   1320
acaacacaat ggggctcact caccccaccac attaacaaca tgaaaccctc attcacacga   1380
gaaaacaccc tcatgttcat gcacctatcc cccattctcc tcctatccct caaccccgac   1440
atcattaccg ggttttcctc ttaagagcac tgggacgccc accgccccctt tccctccgct   1500
gccaggcgag catgttgtgg taattctgga acacaagaag agaaattgct gggtttagaa   1560
caagattata aacgaattcg gtgctcagtg atcacttgac agttttttttt ttttttaaat   1620
attacccaaa atgctcccca aataagaaat gcatcagctc agtcagtgaa tacaaaaaag   1680
gaattattt tcccttgtgag ggtctttttat acatctctcc tccaacccca ccctctattc   1740
tgtttcttcc tcctcacatg ggggtacaca tacacagctt cctcttttgg ttccatcctt   1800
accaccacac cacacgcaca ctccacatgc ccagcagagt ggcacttggt ggccagaaag   1860
tgtgagcctc atgatctgct gtctgtagtt ctgtgagctc aggtccctca aaggcctcgg   1920
agcaccccct tccttgtgac tgagccaggg cctgcatttt tggttttccc cacccccacac  1980
attctcaacc atagtccttc taacaatacc aatagctagg acccggctgc tgtgcactgg   2040
gactggggat tccacatgtt tgccttggga gtctcaagct ggactgcca                2089
```

<210> SEQ ID NO 45
<211> LENGTH: 2889
<212> TYPE: DNA
<213> ORGANISM: Artificial Sequence
<220> FEATURE:
<223> OTHER INFORMATION: opt_COX10*-opt_ND4-3'UTR

<400> SEQUENCE: 45

```
atggccgcca gccccacac cctgagcagc cgcctgctga ccggctgcgt gggcggcagc      60
gtgtggtacc tggagcgccg caccatgctg aagctgatcg tgcccaccat catgctgctg     120
cctctgacct ggctgagcaa gaaacacatg atctggatca acaccaccac gcacagcctg     180
atcatcagca tcatccctct gctgttcttc aaccagatca caacaaccct gttcagctgc     240
agccccacct tcagcagcga ccctctgaca acacctctgc tgatgctgac cacctggctg     300
ctgcccctca caatcatggc ctctcagaga cacctgagca gcgagcccct gagccggaag     360
aaactgtacc tgagcatgct gatctccctg cagatctctc tgatcatgac cttcaccgcc     420
accgagctga tcatgttcta catctttttc gagacaacgc tgatccccac actggccatc     480
atcaccagat ggggcaacca gcctgagaga ctgaacgccg gcacctactt tctgttctac     540
accctcgtgg gcagcctgcc actgctgatt gccctgatct acacccacaa caccctgggc     600
tccctgaaca tcctgctgct gacactgaca gcccaagagc tgagcaacag ctgggccaac     660
aatctgatgt ggctggccta cacaatggcc ttcatggtca gatgcccct gtacggcctg      720
cacctgtggc tgcctaaagc tcatgtggaa gcccctatcg ccggctctat ggtgctggct     780
gcagtgctgc tgaaactcgg cggctacggc atgatgcggc tgaccctgat tctgaatccc     840
ctgaccaagc acatggccta tccatttctg gtgctgagcc tgtggggcat gattatgacc     900
agcagcatct gcctgcggca gaccgatctg aagtccctga tcgcctacag ctccatcagc     960
cacatggccc tggtggtcac cgccatcctg attcagaccc cttggagctt acaggcgcc     1020
gtgatcctga tgattgccca cggcctgaca agcagcctgc tgttttgtct ggccaacagc     1080
aactacgagc ggacccacag cagaatcatg atcctgtctc agggcctgca gaccctcctg     1140
cctcttatgg cttttggtg gctgctggcc tctctggcca atctggcact gcctcctacc     1200
atcaatctgc tgggcgagct gagcgtgctg gtcaccacat tcagctggtc caatatcacc     1260
ctgctgctca ccgcctgaa catgctggtt acagccctgt actccctgta catgttcacc     1320
accacacagt ggggaagcct gacacaccac atcaacaata tgaagcccag cttcacccgc     1380
gagaacaccc tgatgttcat gcatctgagc cccattctgc tgctgtccct gaatcctgat     1440
atcatcaccg gcttctccag ctgagagcac tgggacgccc accgcccctt tccctccgct     1500
gccaggcgag catgttgtgg taattctgga acacaagaag agaaattgct gggtttagaa     1560
caagattata aacgaattcg gtgctcagtg atcacttgac agttttttt tttttaaat      1620
attacccaaa atgctcccca aataagaaat gcatcagctc agtcagtgaa tacaaaaaag     1680
gaattatttt tcccttgag ggtctttat acatctctcc tccaacccca ccctctattc       1740
tgtttcttcc tcctcacatg ggggtacaca tacacagctt cctctttgg ttccatcctt      1800
accaccacac cacacgcaca ctccacatgc ccagcagagt ggcacttggt ggccagaaag     1860
tgtgagcctc atgatctgct gtctgtagtt ctgtgagctc aggtccctca aaggcctcgg     1920
agcacccct tccttgtgac tgagccaggg cctgcatttt tggttttccc cacccacac      1980
attctcaacc atagtccttc taacaatacc aatagctagg accggctgc tgtgcactgg      2040
gactggggat tccacatgtt tgccttggga gtctcaagct ggactgccag ccctgtcct     2100
cccttcaccc ccattgcgta tgagcatttc agaactccaa ggagtcacag gcatctttat     2160
agttcacgtt aacatataga cactgttgga agcagttcct tctaaaaggg tagccctgga    2220
cttaatacca gccggatacc tctggccccc accccattac tgtacctctg gagtcactac    2280
tgtgggtcgc cactcctctg ctacacagca cggcttttt aaggctgtat tgagaaggga     2340
```

```
agttaggaag aagggtgtgc tgggctaacc agcccacaga gctcacattc ctgtcccttg   2400
ggtgaaaaat acatgtccat cctgatatct cctgaattca gaaattagcc tccacatgtg   2460
caatggcttt aagagccaga agcagggttc tgggaatttt gcaagttacc tgtggccagg   2520
tgtggtctcg gttaccaaat acggttacct gcagcttttt agtcctttgt gctcccacgg   2580
gtctacagag tcccatctgc ccaaaggtct tgaagcttga caggatgttt tcgattactc   2640
agtctcccag ggcactactg gtccgtagga ttcgattggt cggggtagga gagttaaaca   2700
acatttaaac agagttctct caaaaatgtc taaagggatt gtaggtagat aacatccaat   2760
cactgtttgc acttatctga aatcttccct cttggctgcc cccaggtatt tactgtggag   2820
aacattgcat aggaatgtct ggaaaaagct tctacaactt gttacagcct tcacatttgt   2880
agaagcttt                                                           2889

<210> SEQ ID NO 46
<211> LENGTH: 2089
<212> TYPE: DNA
<213> ORGANISM: Artificial Sequence
<220> FEATURE:
<223> OTHER INFORMATION: opt_COX10*-opt_ND4-3'UTR*

<400> SEQUENCE: 46
atggccgcca gccccacac cctgagcagc cgcctgctga ccggctgcgt gggcggcagc     60
gtgtggtacc tggagcgccg caccatgctg aagctgatcg tgcccaccat catgctgctg    120
cctctgacct ggctgagcaa gaaacacatg atctggatca acaccaccac gcacagcctg    180
atcatcagca tcatccctct gctgttcttc aaccagatca caacaaccct gttcagctgc    240
agccccacct tcagcagcga ccctctgaca acacctctgc tgatgctgac cacctggctg    300
ctgcccctca caatcatggc ctctcagaga cacctgagca gcgagcccct gagccggaag    360
aaactgtacc tgagcatgct gatctccctg cagatctctc tgatcatgac cttcaccgcc    420
accgagctga tcatgttcta catctttttc gagacaacgc tgatccccac actggccatc    480
atcaccagat ggggcaacca gcctgagaga ctgaacgccg gcacctactt tctgttctac    540
accctcgtgg gcagcctgcc actgctgatt gccctgatca cacccacaa cacccctgggc   600 tccctgaaca tcctgctgct gacactgaca gcccaagagc tgagcaacag ctgggccaac    660
aatctgatgt ggctggccta cacaatggcc ttcatggtca agatgcccct gtacggcctg    720
cacctgtggc tgcctaaagc tcatgtggaa gccccatcg ccggctctat ggtgctggct    780
gcagtgctgc tgaaactcgg cggctacggc atgatgcggc tgaccctgat tctgaatccc    840
ctgaccaagc acatggccta tccatttctg gtgctgagcc tgtggggcat gattatgacc    900
agcagcatct gcctgcggca gaccgatctg aagtccctga tcgcctacag ctccatcagc    960
cacatggccc tggtggtcac cgccatcctg attcagaccc cttggagctt tacaggcgcc   1020
gtgatcctga tgattgccca cggcctgaca agcagcctgc tgttttgtct ggccaacagc   1080
aactacgagc ggacccacag cagaatcatg atcctgtctc agggcctgca gaccctcctg   1140
cctcttatgg cttttttggtg gctgctggcc tctctggcca atctggcact gcctcctacc   1200
atcaatctgc tgggcgagct gagcgtgctg gtcaccacat tcagctggtc caatatcacc   1260
ctgctgctca ccggcctgaa catgctggtt acagccctgt actccctgta catgttcacc   1320
accacacagt ggggaagcct gacacaccac atcaacaata tgaagcccag cttcacccgc   1380
gagaacaccc tgatgttcat gcatctgagc cccattctgc tgctgtccct gaatcctgat   1440
```

| | | | | |
|---|---|---|---|---|
| atcatcaccg | gcttctccag | ctgagagcac | tgggacgccc | accgccccttc ccctccgct | 1500 |
| gccaggcgag | catgttgtgg | taattctgga | acacaagaag | agaaattgct gggtttagaa | 1560 |
| caagattata | aacgaattcg | gtgctcagtg | atcacttgac | agtttttttt ttttttaaat | 1620 |
| attacccaaa | atgctcccca | aataagaaat | gcatcagctc | agtcagtgaa tacaaaaaag | 1680 |
| gaattatttt | tcccttgag | ggtcttttat | acatctctcc | tccaacccca ccctctattc | 1740 |
| tgtttcttcc | tcctcacatg | ggggtacaca | tacacagctt | cctctttgg ttccatcctt | 1800 |
| accaccacac | cacacgcaca | ctccacatgc | ccagcagagt | ggcacttggt ggccagaaag | 1860 |
| tgtgagcctc | atgatctgct | gtctgtagtt | ctgtgagctc | aggtccctca aaggcctcgg | 1920 |
| agcacccct | tccttgtgac | tgagccaggg | cctgcatttt | tggttttccc caccccacac | 1980 |
| attctcaacc | atagtccttc | taacaatacc | aatagctagg | accggctgc tgtgcactgg | 2040 |
| gactggggat | tccacatgtt | tgccttggga | gtctcaagct | ggactgcca | 2089 |

<210> SEQ ID NO 47
<211> LENGTH: 2889
<212> TYPE: DNA
<213> ORGANISM: Artificial Sequence
<220> FEATURE:
<223> OTHER INFORMATION: opt_COX10*-opt_ND4*-3'UTR

<400> SEQUENCE: 47

| | | | | |
|---|---|---|---|---|
| atggccgcca | gccccacac | cctgagcagc | cgcctgctga | ccggctgcgt gggcggcagc | 60 |
| gtgtggtacc | tggagcgccg | caccatgctg | aagctgatcg | tgcccaccat catgctgctg | 120 |
| cccctgacct | ggctgagcaa | gaagcacatg | atctggatca | caccaccac ccacagcctg | 180 |
| atcatcagca | tcatcccct | gctgttcttc | aaccagatca | caacaacct gttcagctgc | 240 |
| agccccacct | tcagcagcga | ccccctgacc | accccctgc | tgatgctgac cacctggctg | 300 |
| ctgcccctga | ccatcatggc | cagccagcgc | cacctgagca | gcgagcccct gagccgcaag | 360 |
| aagctgtacc | tgagcatgct | gatcagcctg | cagatcagcc | tgatcatgac cttcaccgcc | 420 |
| accgagctga | tcatgttcta | catcttcttc | gagaccaccc | tgatccccac cctggccatc | 480 |
| atcacccgct | ggggcaacca | gcccgagcgc | ctgaacgccg | gcacctactt cctgttctac | 540 |
| accctggtgg | gcagcctgcc | cctgctgatc | gccctgatct | acacccacaa cacctgggc | 600 |
| agcctgaaca | tcctgctgct | gaccctgacc | gcccaggagc | tgagcaacag ctgggccaac | 660 |
| aacctgatgt | ggctggccta | caccatggcc | ttcatggtga | agatgccct gtacggcctg | 720 |
| cacctgtggc | tgcccaaggc | ccacgtggag | gcccccatcg | ccggcagcat ggtgctggcc | 780 |
| gccgtgctgc | tgaagctggg | cggctacggc | atgatgcgcc | tgaccctgat cctgaacccc | 840 |
| ctgaccaagc | acatggccta | ccccttcctg | gtgctgagcc | tgtggggcat gatcatgacc | 900 |
| agcagcatct | gcctgcgcca | gaccgacctg | aagagcctga | tcgcctacag cagcatcagc | 960 |
| cacatggccc | tggtggtgac | cgccatcctg | atccagaccc | cctggagctt caccggcgcc | 1020 |
| gtgatcctga | tgatcgccca | cggcctgacc | agcagcctgc | tgttctgcct ggccaacagc | 1080 |
| aactacgagc | gcacccacag | ccgcatcatg | atcctgagcc | agggcctgca gaccctgctg | 1140 |
| cccctgatgg | ccttctggtg | gctgctggcc | agcctggcca | acctggccct gccccccacc | 1200 |
| atcaacctgc | tgggcgagct | gagcgtgctg | gtgaccacct | cagctggag caacatcacc | 1260 |
| ctgctgctga | ccggcctgaa | catgctggtg | accgccctgt | acagcctgta catgttcacc | 1320 |
| accacccagt | ggggcagcct | gacccaccac | atcaacaaca | tgaagcccag cttcacccgc | 1380 |
| gagaacaccc | tgatgttcat | gcacctgagc | cccatcctgc | tgctgagcct gaaccccgac | 1440 |

```
atcatcaccg gcttcagcag ctaagagcac tgggacgccc accgcccctt tccctccgct    1500
gccaggcgag catgttgtgg taattctgga acacaagaag agaaattgct gggtttagaa    1560
caagattata aacgaattcg gtgctcagtg atcacttgac agttttttt ttttttaaat    1620 attacccaaa atgctcccca aataagaaat gcatcagctc agtcagtgaa tacaaaaaag    1680
gaattatttt tcccttgag ggtcttttat acatctctcc tccaacccca ccctctattc    1740
tgtttcttcc tcctcacatg ggggtacaca tacacagctt cctcttttgg ttccatcctt    1800
accaccacac cacacgcaca ctccacatgc ccagcagagt ggcacttggt ggccagaaag    1860
tgtgagcctc atgatctgct gtctgtagtt ctgtgagctc aggtccctca aaggcctcgg    1920 agcacccct tccttgtgac tgagccaggg cctgcatttt tggttttccc caccccacac     1980
attctcaacc atagtccttc taacaatacc aatagctagg accggctgc tgtgcactgg     2040 gactggggat tccacatgtt tgccttggga gtctcaagct ggactgccag ccctgtcct    2100 cccttcaccc ccattgcgta tgagcatttc agaactccaa ggagtcacag gcatctttat    2160
agttcacgtt aacatataga cactgttgga agcagttcct tctaaaaggg tagccctgga    2220
cttaatacca gccggatacc tctggccccc accccattac tgtacctctg gagtcactac    2280
tgtgggtcgc cactcctctg ctacacagca cggcttttc aaggctgtat tgagaaggga    2340
agttaggaag aagggtgtgc tgggctaacc agcccacaga gctcacattc ctgtcccttg    2400
ggtgaaaaat acatgtccat cctgatatct cctgaattca gaaattagcc tccacatgtg    2460
caatggcttt aagagccaga agcagggttc tgggaatttt gcaagttacc tgtggccagg    2520
tgtggtctcg gttaccaaat acggttacct gcagcttttt agtcctttgt gctcccacgg    2580
gtctacagag tcccatctgc ccaaaggtct tgaagcttga caggatgttt tcgattactc    2640
agtctcccag ggcactactg gtccgtagga ttcgattggt cggggtagga gagttaaaca    2700
acatttaaac agagttctct caaaaatgtc taagggatt gtaggtagat aacatccaat    2760
cactgtttgc acttatctga aatcttccct cttggctgcc cccaggtatt tactgtggag    2820
aacattgcat aggaatgtct ggaaaaagct tctacaactt gttacagcct tcacatttgt    2880
agaagcttt                                                           2889
```

<210> SEQ ID NO 48
<211> LENGTH: 2089
<212> TYPE: DNA
<213> ORGANISM: Artificial Sequence
<220> FEATURE:
<223> OTHER INFORMATION: opt_COX10*-opt_ND4*-3'UTR*

<400> SEQUENCE: 48

```
atggccgcca gccccacac cctgagcagc cgcctgctga ccggctgcgt gggcggcagc      60
gtgtggtacc tggagcgccg caccatgctg aagctgatcg tgcccaccat catgctgctg    120
cccctgacct ggctgagcaa gaagcacatg atctggatca acaccaccac ccacagcctg    180
atcatcagca tcatcccct gctgttcttc aaccagatca caacaaccct gttcagctgc    240
agccccacct tcagcagcga ccccctgacc acccccctgc tgatgctgac cacctggctg    300
ctgcccctga ccatcatggc cagccagcgc cacctgagca gcgagcccct gagccgcaag    360
aagctgtacc tgagcatgct gatcagcctg cagatcagcc tgatcatgac cttcaccgcc    420
accgagctga tcatgttcta catcttcttc gagaccaccc tgatccccac cctggccatc    480
atcacccgct ggggcaacca gccgagcgc ctgaacgccg gcacctactt cctgttctac    540
```

```
acctggtgg gcagcctgcc cctgctgatc gccctgatct acacccacaa caccctgggc     600
agcctgaaca tcctgctgct gaccctgacc gcccaggagc tgagcaacag ctgggccaac     660
aacctgatgt ggctggccta caccatggcc ttcatggtga agatgcccct gtacggcctg     720
cacctgtggc tgcccaaggc ccacgtggag gcccccatcg ccggcagcat ggtgctggcc     780
gccgtgctgc tgaagctggg cggctacggc atgatgcgcc tgaccctgat cctgaacccc     840
ctgaccaagc acatggccta ccccttcctg gtgctgagcc tgtggggcat gatcatgacc     900
agcagcatct gcctgcgcca gaccgacctg aagagcctga tcgcctacag cagcatcagc     960
cacatggccc tggtggtgac cgccatcctg atccagaccc cctggagctt caccggcgcc    1020
gtgatcctga tgatcgccca cggcctgacc agcagcctgc tgttctgcct ggccaacagc    1080
aactacgagc gcacccacag ccgcatcatg atcctgagcc agggcctgca gaccctgctg    1140
cccctgatgg ccttctggtg gctgctggcc agcctggcca acctggccct gccccccacc    1200
atcaacctgc tgggcgagct gagcgtgctg gtgaccacct tcagctggag caacatcacc    1260
ctgctgctga ccggcctgaa catgctgtg accgccctgt acagcctgta catgttcacc    1320
accacccagt ggggcagcct gacccaccac atcaacaaca tgaagcccag cttcacccgc    1380
gagaacaccc tgatgttcat gcacctgagc cccatcctgc tgctgagcct gaaccccgac    1440
atcatcaccg gcttcagcag ctaagagcac tgggacgccc accgcccctt ccctccgct    1500 gccaggcgag catgttgtgg taattctgga acacaagaag agaaattgct gggtttagaa    1560
caagattata acgaattcg gtgctcagtg atcacttgac agtttttttt ttttttaaat    1620
attacccaaa atgctcccca ataagaaat gcatcagctc agtcagtgaa acaaaaaag    1680 gaattatttt tcccttgag ggtcttttat acatctctcc tccaaccca ccctctattc    1740 tgtttcttcc tcctcacatg ggggtacaca tacacagctt cctctttgg ttccatcctt    1800 accaccacac cacacgcaca ctccacatgc ccagcagagt ggcacttggt ggccagaaag    1860
tgtgagcctc atgatctgct gtctgtagtt ctgtgagctc aggtccctca aaggcctcgg    1920
agcaccccct tccttgtgac tgagccaggg cctgcatttt tggttttccc caccccacac    1980
attctcaacc atagtccttc taacaatacc aatagctagg accggctgc tgtgcactgg    2040 gactggggat tccacatgtt tgccttggga gtctcaagct ggactgcca               2089
```

<210> SEQ ID NO 49
<211> LENGTH: 2034
<212> TYPE: DNA
<213> ORGANISM: Artificial Sequence
<220> FEATURE:
<223> OTHER INFORMATION: opt_COX10*-ND6-3'UTR

<400> SEQUENCE: 49

```
atggccgcca gccccacac cctgagcagc cgcctgctga ccggctgcgt gggcggcagc      60
gtgtggtacc tggagcgccg caccatgatg tatgctttgt ttctgttgag tgtgggttta     120
gtaatggggt ttgtggggtt ttcttctaag ccttctccta tttatggggg tttagtattg     180
attgttagcg gtgtggtcgg gtgtgttatt attctgaatt ttgggggagg ttatatgggt     240
ttaatggttt ttttaattta tttagggga atgatggttg tctttggata tactacagcg     300
atggctattg aggagtatcc tgaggcatgg gggtcagggg ttgaggtctt ggtgagtgtt     360
ttagtggggt tagcgatgga ggtaggattg gtgctgtggg tgaaagagta tgatggggtg     420 gtggttgtg taaactttaa tagtgtagga agctggatga tttatgaagg agaggggtca     480
gggttgattc gggaggatcc tattggtgcg ggggctttgt atgattatgg gcgttggtta     540
```

```
gtagtagtta ctggttggac attgtttgtt ggtgtatata ttgtaattga gattgctcgg      600
gggaattagg agcactggga cgcccaccgc cccttcccct ccgctgccag gcgagcatgt      660
tgtggtaatt ctggaacaca agaagagaaa ttgctgggtt tagaacaaga ttataaacga      720
attcggtgct cagtgatcac ttgacagttt tttttttttt taaatattac ccaaaatgct      780
ccccaaataa gaaatgcatc agctcagtca gtgaatacaa aaaggaatt attttttccct     840 ttgagggtct tttatacatc tctcctccaa ccccaccctc tattctgttt cttcctcctc      900 acatggggt acacatacac agcttcctct tttggttcca tccttaccac cacaccacac      960
gcacactcca catgcccagc agagtggcac ttggtggcca gaaagtgtga gcctcatgat     1020
ctgctgtctg tagttctgtg agctcaggtc cctcaaaggc ctcggagcac ccccttcctt     1080
gtgactgagc cagggcctgc attttttggtt ttccccaccc cacacattct caaccatagt    1140
ccttctaaca ataccaatag ctaggacccg gctgctgtgc actgggactg gggattccac     1200
atgtttgcct tgggagtctc aagctggact gccagcccct gtcctccctt caccccccatt   1260 gcgtatgagc atttcagaac tccaaggagt cacaggcatc tttatagttc acgttaacat    1320
atagacactg ttggaagcag ttccttctaa aagggtagcc ctggacttaa taccagccgg    1380
atacctctgg ccccccacccc attactgtac ctctggagtc actactgtgg gtcgccactc   1440
ctctgctaca cagcacggct ttttcaaggc tgtattgaga agggaagtta ggaagaaggg   1500
tgtgctgggc taaccagccc acagagctca cattcctgtc ccttgggtga aaaatacatg   1560
tccatcctga tatctcctga attcagaaat tagcctccac atgtgcaatg ctttaagag    1620 ccagaagcag ggttctggga attttgcaag ttacctgtgg ccaggtgtgg tctcggttac    1680
caaatacggt tacctgcagc tttttagtcc tttgtgctcc cacgggtcta cagagtccca   1740
tctgcccaaa ggtcttgaag cttgacagga tgttttcgat tactcagtct cccagggcac   1800
tactggtccg taggattcga ttggtcgggg taggagagtt aaacaacatt taaacagagt   1860
tctctcaaaa atgtctaaag ggattgtagg tagataacat ccaatcactg tttgcactta   1920
tctgaaatct tccctcttgg ctgccccag gtatttactg tggagaacat tgcataggaa    1980
tgtctggaaa aagcttctac aacttgttac agccttcaca tttgtagaag cttt          2034
```

<210> SEQ ID NO 50
<211> LENGTH: 1234
<212> TYPE: DNA
<213> ORGANISM: Artificial Sequence
<220> FEATURE:
<223> OTHER INFORMATION: opt_COX10*-ND6-3'UTR*

<400> SEQUENCE: 50

```
atggccgcca gccccacac cctgagcagc cgcctgctga ccggctgcgt gggcggcagc        60
gtgtggtacc tggagcgccg caccatgatg tatgctttgt ttctgttgag tgtgggttta    120
gtaatggggt ttgtggggtt ttcttctaag ccttctccta tttatggggg tttagtattg     180
attgttagcg gtgtggtcgg gtgtgttatt attctgaatt ttgggggagg ttatatgggt    240
ttaatggttt ttttaattta tttaggggga atgatggttg tctttggata tactacagcg    300
atggctattg aggagtatcc tgaggcatgg ggtcagggg ttgaggtctt ggtgagtgtt     360
ttagtggggt tagcgatgga ggtaggattg gtgctgtggg tgaaagagta tgatgggtg    420 gtggttgtgg taaactttaa tagtgtagga agctggatga tttatgaagg agaggggtca   480
gggttgattc gggaggatcc tattggtgcg ggggctttgt atgattatgg gcgttggtta   540
```

```
gtagtagtta ctggttggac attgtttgtt ggtgtatata ttgtaattga gattgctcgg      600
gggaattagg agcactggga cgcccaccgc ccctttccct ccgctgccag gcgagcatgt      660
tgtggtaatt ctggaacaca agaagagaaa ttgctgggtt tagaacaaga ttataaacga      720
attcggtgct cagtgatcac ttgacagttt ttttttttt  taaatattac ccaaaatgct      780
ccccaaataa gaaatgcatc agctcagtca gtgaatacaa aaaggaatt  attttttccct    840
ttgagggtct tttatacatc tctcctccaa ccccaccctc tattctgttt cttcctcctc     900
acatggggt  acacatacac agcttcctct tttggttcca tccttaccac cacaccacac     960
gcacactcca catgcccagc agagtggcac ttggtggcca gaaagtgtga gcctcatgat    1020
ctgctgtctg tagttctgtg agctcaggtc cctcaaaggc ctcggagcac cccttcctt    1080
gtgactgagc cagggcctgc attttttggtt ttccccaccc cacacattct caaccatagt   1140
ccttctaaca ataccaatag ctaggacccg gctgctgtgc actgggactg gggattccac   1200
atgtttgcct tgggagtctc aagctggact gcca                                 1234
```

<210> SEQ ID NO 51
<211> LENGTH: 2034
<212> TYPE: DNA
<213> ORGANISM: Artificial Sequence
<220> FEATURE:
<223> OTHER INFORMATION: opt_COX10*-opt_ND6-3'UTR

<400> SEQUENCE: 51

```
atggccgcca gccccacac  cctgagcagc cgcctgctga ccggctgcgt gggcggcagc       60
gtgtggtacc tggagcgccg caccatgatg tacgccctgt tcctgctgag cgtgggcctg      120
gtgatgggct tcgtgggctt cagcagcaag cccagcccca tctacggcgg cctggtgctg      180
atcgtgagcg cgtggtggg  ctgcgtgatc atcctgaact tcggcggcgg ctacatgggc      240
ctgatggtgt tcctgatcta cctgggcggc atgatggtgg tgttcggcta caccaccgcc      300
atggccatcg aggagtaccc cgaggcctgg ggcagcggcg tggaggtgct ggtgagcgtg      360
ctggtggggcc tggccatgga ggtgggcctg gtgctgtggg tgaaggagta cgacggcgtg      420
gtggtggtgg tgaacttcaa cagcgtgggc agctggatga tctacgaggg cgagggcagc      480
ggcctgatcc gcgaggaccc catcggcgcc ggcgccctgt acgactacgg ccgctggctg      540
gtggtggtga ccggctggac cctgttcgtg ggcgtgtaca tcgtgatcga gatcgcccgc      600
ggcaactaag agcactggga cgcccaccgc ccctttccct ccgctgccag gcgagcatgt      660
tgtggtaatt ctggaacaca agaagagaaa ttgctgggtt tagaacaaga ttataaacga      720
attcggtgct cagtgatcac ttgacagttt ttttttttt  taaatattac ccaaaatgct      780
ccccaaataa gaaatgcatc agctcagtca gtgaatacaa aaaggaatt  attttttccct    840
ttgagggtct tttatacatc tctcctccaa ccccaccctc tattctgttt cttcctcctc     900
acatggggt  acacatacac agcttcctct tttggttcca tccttaccac cacaccacac     960
gcacactcca catgcccagc agagtggcac ttggtggcca gaaagtgtga gcctcatgat    1020
ctgctgtctg tagttctgtg agctcaggtc cctcaaaggc ctcggagcac cccttcctt    1080
gtgactgagc cagggcctgc attttttggtt ttccccaccc cacacattct caaccatagt   1140
ccttctaaca ataccaatag ctaggacccg gctgctgtgc actgggactg gggattccac   1200
atgtttgcct tgggagtctc aagctggact gccagcccct gtcctccctt caccccatt    1260
gcgtatgagc atttcagaac tccaaggagt cacaggcatc tttatagttc acgttaacat    1320
atagacactg ttgaagcag  ttccttctaa aagggtagcc ctggacttaa taccagccgg    1380
```

| | |
|---|---|
| atacctctgg ccccccacccc attactgtac ctctggagtc actactgtgg gtcgccactc | 1440 |
| ctctgctaca cagcacggct tttcaaggc tgtattgaga agggaagtta ggaagaaggg | 1500 |
| tgtgctgggc taaccagccc acagagctca cattcctgtc ccttgggtga aaaatacatg | 1560 |
| tccatcctga tatctcctga attcagaaat tagcctccac atgtgcaatg gctttaagag | 1620 |
| ccagaagcag ggttctggga attttgcaag ttacctgtgg ccaggtgtgg tctcggttac | 1680 |
| caaatacggt tacctgcagc ttttagtcc tttgtgctcc cacgggtcta cagagtccca | 1740 |
| tctgcccaaa ggtcttgaag cttgacagga tgtttcgat tactcagtct cccagggcac | 1800 |
| tactggtccg taggattcga ttggtcgggg taggagagtt aaacaacatt taaacagagt | 1860 |
| tctctcaaaa atgtctaaag ggattgtagg tagataacat ccaatcactg tttgcactta | 1920 |
| tctgaaatct tccctcttgg ctgcccccag gtatttactg tggagaacat tgcataggaa | 1980 |
| tgtctggaaa aagcttctac aacttgttac agccttcaca tttgtagaag cttt | 2034 |

<210> SEQ ID NO 52
<211> LENGTH: 1234
<212> TYPE: DNA
<213> ORGANISM: Artificial Sequence
<220> FEATURE:
<223> OTHER INFORMATION: opt_COX10*-opt_ND6-3'UTR*

<400> SEQUENCE: 52

| | |
|---|---|
| atggccgcca gcccccacac cctgagcagc cgcctgctga ccggctgcgt gggcggcagc | 60 |
| gtgtggtacc tggagcgccg caccatgatg tacgccctgt tcctgctgag cgtgggcctg | 120 |
| gtgatgggct tcgtgggctt cagcagcaag cccagcccca tctacggcgg cctggtgctg | 180 |
| atcgtgagcg cgctggtggg ctgcgtgatc atcctgaact tcggcggcgg ctacatgggc | 240 |
| ctgatggtgt tcctgatcta cctgggcggc atgatggtgg tgttcggcta caccaccgcc | 300 |
| atggccatcg aggagtaccc cgaggcctgg ggcagcggcg tggaggtgct ggtgagcgtg | 360 |
| ctggtgggcc tggccatgga ggtgggcctg gtgctgtggg tgaaggagta cgacggcgtg | 420 |
| gtggtggtgg tgaacttcaa cagcgtgggc agctggatga tctacgaggg cgagggcagc | 480 |
| ggcctgatcc gcgaggaccc catcggcgcc ggcgccctgt acgactacgg ccgctggctg | 540 |
| gtggtggtga ccggctggac cctgttcgtg ggcgtgtaca tcgtgatcga gatcgcccgc | 600 |
| ggcaactaag agcactggga cgcccaccgc cccttccct ccgctgccag gcgagcatgt | 660 |
| tgtggtaatt ctggaacaca agaagagaaa ttgctgggtt tagaacaaga ttataaacga | 720 |
| attcggtgct cagtgatcac ttgacagttt ttttttttt taaatattac ccaaaatgct | 780 |
| ccccaaataa gaaatgcatc agctcagtca gtgaatacaa aaaggaatt atttttccct | 840 |
| ttgagggtct tttatacatc tctcctccaa ccccacctc tattctgttt cttcctcctc | 900 |
| acatggggt acacatacac agcttcctct tttggttcca tccttaccac cacaccacac | 960 |
| gcacactcca catgcccagc agagtggcac ttggtggcca gaaagtgtga gcctcatgat | 1020 |
| ctgctgtctg tagttctgtg agctcaggtc cctcaaaggc ctcggagcac cccttcctt | 1080 |
| gtgactgagc cagggcctgc atttttggtt ttccccaccc cacacattct caaccatagt | 1140 |
| ccttctaaca ataccaatag ctaggacccg gctgctgtgc actgggactg gggattccac | 1200 |
| atgtttgcct tgggagtctc aagctggact gcca | 1234 |

<210> SEQ ID NO 53
<211> LENGTH: 2460
<212> TYPE: DNA

<213> ORGANISM: Artificial Sequence
<220> FEATURE:
<223> OTHER INFORMATION: opt_COX10*-ND1-3'UTR

<400> SEQUENCE: 53

```
atggccgcca gccccacac cctgagcagc cgcctgctga ccggctgcgt gggcggcagc      60
gtgtggtacc tggagcgccg caccatggcc aacctcctac tcctcattgt acccattcta     120
atcgcaatgg cattcctaat gcttaccgaa cgaaaaattc taggctatat gcaactacgc     180
aaaggcccca acgttgtagg cccctacggg ctactacaac ccttcgctga cgccataaaa     240
ctcttcacca aagagcccct aaacccgcc acatctacca tcaccctcta catcaccgcc      300
ccgaccttag ctctcaccat cgctcttcta ctatggaccc cctccccat gcccaacccc     360
ctggtcaacc tcaacctagg cctcctattt attctagcca cctctagcct agccgtttac     420
tcaatcctct ggtcaggggtg ggcatcaaac tcaaactacg ccctgatcgg cgcactgcga    480
gcagtagccc aaacaatctc atatgaagtc accctagcca tcattctact atcaacatta    540
ctaatgagtg gctcctttaa cctctccacc cttatcacaa caagaaaca cctctggtta     600
ctcctgccat catggccctt ggccatgatg tggtttatct ccacactagc agagaccaac    660
cgaaccccct tcgaccttgc cgaaggggag tccgaactag tctcaggctt caacatcgaa    720
tacgccgcag gccccttcgc cctattcttc atggccgaat acacaaacat tattatgatg    780
aacaccctca ccactacaat cttcctagga acaacatatg acgcactctc ccctgaactc    840
tacacaacat attttgtcac caagacccta cttctaacct ccctgttctt atggattcga    900
acagcatacc cccgattccg ctacgaccaa ctcatgcacc tcctatggaa aaacttccta    960
ccactcaccc tagcattact tatgtggtat gtctccatgc ccattacaat ctccagcatt    1020
cccctcaaa cctaagagca ctgggacgcc caccgcccct ttcctccgc tgccaggcga    1080
gcatgttgtg gtaattctgg aacacaagaa gagaaattgc tgggtttaga caagattat     1140
aaacgaattc ggtgctcagt gatcacttga cagtttttttt tttttttaaa tattacccaa    1200
aatgctcccc aaataagaaa tgcatcagct cagtcagtga atacaaaaaa ggaattattt     1260
ttccctttga gggtctttta tacatctctc ctccaacccc accctctatt ctgtttcttc     1320
ctcctcacat gggggtacac atacacagct tcctcttttg gttccatcct taccaccaca    1380
ccacacgcac actccacatg cccagcagag tggcacttgg tggccagaaa gtgtgagcct    1440
catgatctgc tgtctgtagt tctgtgagct caggtccctc aaaggcctcg gagcaccccc    1500
ttccttgtga ctgagccagg gcctgcattt ttggttttcc ccaccccaca cattctcaac    1560
catagtcctt ctaacaatac caatagctag gacccggctg ctgtgcactg ggactgggga    1620
ttccacatgt ttgccttggg agtctcaagc tggactgcca gccctgtcc tcccttcacc     1680
cccattgcgt atgagcattt cagaactcca aggagtcaca ggcatcttta tagttcacgt    1740
taacatatag acactgttgg aagcagttcc ttctaaaagg gtagccctgg acttaatacc    1800
agccggatac ctctggcccc cacccatta ctgtacctct ggagtcacta ctgtgggtcg    1860
ccactcctct gctacacagc acggcttttt caaggctgta ttgagaaggg aagttaggaa    1920
gaagggtgtg ctgggctaac cagcccacag agctcacatt cctgtcccct gggtgaaaaa    1980
tacatgtcca tcctgatatc tcctgaattc agaaattagc ctccacatgt gcaatggctt    2040
taagagccag aagcagggtt ctgggaattt tgcaagttac ctgtggccag gtgtggtctc    2100
ggttaccaaa tacggttacc tgcagctttt tagtcctttg tgctcccacg ggtctacaga    2160
gtcccatctg cccaaaggtc ttgaagcttg acaggatgtt ttcgattact cagtctccca    2220
```

```
gggcactact ggtccgtagg attcgattgg tcggggtagg agagttaaac aacatttaaa    2280
cagagttctc tcaaaaatgt ctaaagggat tgtaggtaga taacatccaa tcactgtttg    2340
cacttatctg aaatcttccc tcttggctgc ccccaggtat ttactgtgga gaacattgca    2400
taggaatgtc tggaaaaagc ttctacaact tgttacagcc ttcacatttg tagaagcttt    2460
```

<210> SEQ ID NO 54
<211> LENGTH: 1660
<212> TYPE: DNA
<213> ORGANISM: Artificial Sequence
<220> FEATURE:
<223> OTHER INFORMATION: opt_COX10*-ND1-3'UTR*

<400> SEQUENCE: 54

```
atggccgcca gccccacac cctgagcagc cgcctgctga ccggctgcgt gggcggcagc      60
gtgtggtacc tggagcgccg caccatggcc aacctcctac tcctcattgt acccattcta     120
atcgcaatgg cattcctaat gcttaccgaa cgaaaaattc taggctatat gcaactacgc     180
aaaggcccca acgttgtagg cccctacggg ctactacaac ccttcgctga cgccataaaa     240
ctcttcacca aagagcccct aaaaccgcc acatctacca tcaccctcta catcaccgcc      300
ccgaccttag ctctcaccat cgctcttcta ctatggaccc cctccccat gcccaacccc     360 ctggtcaacc tcaacctagg cctcctattt attctagcca cctctagcct agccgtttac     420
tcaatcctct ggtcagggtg gcatcaaac tcaaactacg cctgatcgg cgcactgcga      480 gcagtagccc aaacaatctc atatgaagtc accctagcca tcattctact atcaacatta     540
ctaatgagtg gctcctttaa cctctccacc cttatcacaa cacaagaaca cctctggtta     600
ctcctgccat catggccctt ggccatgatg tggtttatct ccacactagc agagaccaac     660
cgaaccccct tcgaccttgc cgaaggggag tccgaactag tctcaggctt caacatcgaa     720
tacgccgcag gccccttcgc cctattcttc atggccgaat acacaaacat tattatgatg     780
aacacctcca ccactacaat cttcctagga acaacatatg acgcactctc ccctgaactc     840
tacacaacat attttgtcac caagaccta cttctaacct ccctgttctt atggattcga     900
acagcatacc cccgattccg ctacgaccaa tcatgcacc tcctatggaa aaacttccta     960
ccactcaccc tagcattact tatgtggtat gtctccatgc ccattacaat ctccagcatt    1020 cccctcaaa cctaagagca ctgggacgcc caccgcccct tccctccgc tgccaggcga      1080 gcatgttgtg gtaattctgg aacacaagaa gagaaattgc tgggtttaga acaagattat    1140
aaacgaattc ggtgctcagt gatcacttga cagttttttt ttttttaaa tattacccaa     1200 aatgctcccc aaataagaaa tgcatcagct cagtcagtga atacaaaaaa ggaattattt    1260 ttcccttga gggtctttta tacatctctc ctccaacccc accctctatt ctgtttcttc     1320
ctcctcacat gggggtacac atacacagct tcctcttttg gttccatcct taccaccaca    1380
ccacacgcac actccacatg cccagcagag tggcacttgg tggccagaaa gtgtgagcct    1440
catgatctgc tgtctgtagt tctgtgagct caggtccctc aaaggcctcg gagcaccccc    1500
ttccttgtga ctgagccagg gcctgcattt ttggttttcc ccaccccaca cattctcaac    1560
catagtcctt ctaacaatac caatagctag gacccggctg ctgtgcactg ggactgggga    1620
ttccacatgt ttgccttggg agtctcaagc tggactgcca                          1660
```

<210> SEQ ID NO 55
<211> LENGTH: 2460
<212> TYPE: DNA

<213> ORGANISM: Artificial Sequence
<220> FEATURE:
<223> OTHER INFORMATION: opt_COX10*-opt_ND1-3'UTR

<400> SEQUENCE: 55

```
atggccgcca gccccacac cctgagcagc cgcctgctga ccggctgcgt gggcggcagc      60
gtgtggtacc tggagcgccg caccatggcc aacctgctgc tgctgatcgt gcccatcctg     120
atcgccatgg ccttcctgat gctgaccgag cgcaagatcc tgggctacat gcagctgcgc     180
aagggcccca acgtggtggg ccctacggc ctgctgcagc ccttcgccga cgccatcaag     240
ctgttcacca aggagcccct gaagcccgcc accagcacca tcaccctgta catcaccgcc     300
cccaccctgg ccctgaccat cgccctgctg ctgtggaccc cctgcccat gcccaacccc     360
ctggtgaacc tgaacctggg cctgctgttc atcctggcca ccagcagcct ggccgtgtac     420
agcatcctgt ggagcggctg ggccagcaac agcaactacg ccctgatcgg cgccctgcgc     480
gccgtggccc agaccatcag ctacgaggtg accctggcca tcatcctgct gagcaccctg     540
ctgatgagcg gcagcttcaa cctgagcacc ctgatcacca cccaggagca cctgtggctg     600
ctgctgccca gctggcccct ggccatgatg tggttcatca gcaccctggc cgagaccaac     660
cgcacccct tcgacctggc cgagggcgag agcgagctgg tgagcggctt caacatcgag     720
tacgccgccg gccccttcgc cctgttcttc atggccgagt acaccaacat catcatgatg     780
aacaccctga ccaccaccat cttcctgggc accacctacg acgccctgag ccccgagctg     840
tacaccacct acttcgtgac caagaccctg ctgctgacca gcctgttcct gtggatccgc     900
accgcctacc cccgcttccg ctacgaccag ctgatgcacc tgctgtggaa gaacttcctg     960
cccctgaccc tggccctgct gatgtggtac gtgagcatgc ccatcaccat cagcagcatc    1020
cccccccaga cctaagagca ctgggacgcc caccgcccct ttccctccgc tgccaggcga    1080
gcatgttgtg gtaattctgg aacacaagaa gagaaattgc tgggtttaga acaagattat    1140
aaacgaattc ggtgctcagt gatcacttga cagtttttt tttttttaaa tattacccaa    1200
aatgctcccc aaataagaaa tgcatcagct cagtcagtga atacaaaaaa ggaattattt    1260
ttccctttga gggtctttta tacatctctc ctccaacccc accctctatt ctgtttcttc    1320
ctcctcacat gggggtacac atacacagct tcctcttttg gttccatcct taccaccaca    1380
ccacacgcac actccacatg cccagcagag tggcacttgg tggccagaaa gtgtgagcct    1440
catgatctgc tgtctgtagt tctgtgagct caggtccctc aaaggcctcg gagcaccccc    1500
ttccttgtga ctgagccagg gcctgcattt ttggttttcc ccaccccaca cattctcaac    1560
catagtcctt ctaacaatac caatagctag gaccggctg ctgtgcactg ggactgggga    1620
ttccacatgt ttgccttggg agtctcaagc tggactgcca gccctgtcc tcccttcacc    1680
cccattgcgt atgagcattt cagaactcca aggagtcaca ggcatcttta tagttcacgt    1740
taacatatag acactgttgg aagcagttcc ttctaaaagg gtagccctgg acttaatacc    1800
agccggatac ctctggcccc caccccatta ctgtacctct ggagtcacta ctgtgggtcg    1860
ccactcctct gctacacagc acggcttttt caaggctgta ttgagaaggg aagttaggaa    1920
gaagggtgtg ctgggctaac cagcccacag agctcacatt cctgtccctt gggtgaaaaa    1980
tacatgtcca tcctgatatc tcctgaattc agaaattagc ctccacatgt gcaatggctt    2040
taagagccag aagcagggtt ctgggaattt tgcaagttac ctgtggccag gtgtggtctc    2100
ggttaccaaa tacggttacc tgcagctttt tagtcctttg tgctcccacg ggtctacaga    2160
gtcccatctg cccaaaggtc ttgaagcttg acaggatgtt ttcgattact cagtctccca    2220
```

```
gggcactact ggtccgtagg attcgattgg tcggggtagg agagttaaac aacatttaaa    2280
cagagttctc tcaaaaatgt ctaaagggat tgtaggtaga taacatccaa tcactgtttg    2340
cacttatctg aaatcttccc tcttggctgc ccccaggtat ttactgtgga gaacattgca    2400
taggaatgtc tggaaaaagc ttctacaact tgttacagcc ttcacatttg tagaagcttt    2460
```

<210> SEQ ID NO 56
<211> LENGTH: 1660
<212> TYPE: DNA
<213> ORGANISM: Artificial Sequence
<220> FEATURE:
<223> OTHER INFORMATION: opt_COX10*-opt_ND1-3'UTR*

<400> SEQUENCE: 56

```
atggccgcca gccccacac cctgagcagc cgcctgctga ccggctgcgt gggcggcagc      60
gtgtggtacc tggagcgccg caccatggcc aacctgctgc tgctgatcgt gcccatcctg     120
atcgccatgg ccttcctgat gctgaccgag cgcaagatcc tggctacat gcagctgcgc     180 aagggcccca acgtggtggg ccctacggc ctgctgcagc ccttcgccga cgccatcaag     240 ctgttccacca aggagcccct gaagcccgcc accagcacca tcaccctgta catcaccgcc    300
cccaccctgg ccctgaccat cgccctgctg ctgtggaccc cctgcccat gcccaacccc    360 ctggtgaacc tgaacctggg cctgctgttc atcctggcca ccagcagcct ggccgtgtac    420
agcatcctgt ggagcggctg ggccagcaac agcaactacg ccctgatcgg cgccctgcgc    480
gccgtggccc agaccatcag ctacgaggtg accctggcca tcatcctgct gagcaccctg    540
ctgatgagcg gcagcttcaa cctgagcacc ctgatcacca cccaggagca cctgtggctg    600
ctgctgccca gctggcccct ggccatgatg tggttcatca gcaccctggc cgagaccaac    660 cgcacccct tcgacctggc cgagggcgag agcgagctgg tgagcggctt caacatcgag    720
tacgccgccg cccccttcgc cctgttcttc atggccgagt acaccaacat catcatgatg    780
aacaccctga ccaccaccat cttcctgggc accacctacg acgccctgag ccccgagctg    840
tacaccacct acttcgtgac caagacccctg ctgctgacca gcctgttcct gtggatccgc    900
accgcctacc cccgcttccg ctacgaccag ctgatgcacc tgctgtggaa gaacttcctg    960
cccctgaccc tggccctgct gatgtggtac gtgagcatgc ccatcaccat cagcagcatc   1020 ccccccaga cctaagagca ctgggacgcc caccgcccct tccctccgc tgccaggcga   1080 gcatgttgtg gtaattctgg aacacaagaa gagaaattgc tgggtttaga acaagattat   1140
aaacgaattc ggtgctcagt gatcacttga cagttttttt ttttttaaa tattacccaa   1200 aatgctcccc aaataagaaa tgcatcagct cagtcagtga atacaaaaaa ggaattattt   1260 ttcctttga gggtctttta tacatctctc ctccaacccc accctctatt ctgtttcttc   1320
ctcctcacat gggggtacac atacacagct tcctcttttg gttccatcct taccaccaca   1380
ccacacgcac actccacatg cccagcagag tggcacttgg tggccagaaa gtgtgagcct   1440
catgatctgc tgtctgtagt tctgtgagct caggtccctc aaaggcctcg gagcaccccc   1500
ttccttgtga ctgagccagg gcctgcattt ttggttttcc ccaccccaca cattctcaac   1560
catagtcctt ctaacaatac caatagctag gaccggctg ctgtgcactg ggactgggga   1620
ttccacatgt ttgccttggg agtctcaagc tggactgcca                         1660
```

<210> SEQ ID NO 57
<211> LENGTH: 2892
<212> TYPE: DNA

<213> ORGANISM: Artificial Sequence
<220> FEATURE:
<223> OTHER INFORMATION: COX8-ND4-3'UTR

<400> SEQUENCE: 57

```
atgtccgtcc tgacgcgcct gctgctgcgg ggcttgacac ggctcggctc ggcggctcca      60
gtgcggcgcg ccagaatcca ttcgttgatg ctaaaactaa tcgtcccaac aattatgtta     120
ctaccactga catggctttc caaaaaacac atgatttgga tcaacacaac cacccacagc     180
ctaattatta gcatcatccc tctactattt tttaaccaaa tcaacaacaa cctatttagc     240
tgttccccaa ccttttcctc cgaccccta acaaccccc tcctaatgct aactacctgg      300
ctcctacccc tcacaatcat ggcaagccaa cgccacttat ccagtgaacc actatcacga     360
aaaaaactct acctctctat gctaatctcc ctacaaatct ccttaattat gacattcaca     420
gccacagaac taatcatgtt ttatatcttc ttcgaaacca cacttatccc caccttggct     480
atcatcaccc gatggggcaa ccagccagaa cgcctgaacg caggcacata cttcctattc     540
tacaccctag taggctccct tccctactc atcgcactaa tttacactca caacaccta      600
ggctcactaa acattctact actcactctc actgcccaag aactatcaaa ctcctgggcc     660
aacaacttaa tgtggctagc ttacacaatg cttttatgg taaagatgcc tctttacgga     720
ctccacttat ggctccctaa agcccatgtc gaagccccca tcgctgggtc aatggtactt     780
gccgcagtac tcttaaaact aggcggctat ggtatgatgc cctcacact cattctcaac     840
cccctgacaa acacatggc ctaccccttc cttgtactat ccctatgggg catgattatg     900
acaagctcca tctgcctacg acaaacagac ctaaaatcgc tcattgcata ctcttcaatc     960
agccacatgg ccctcgtagt aacagccatt ctcatccaaa cccctggag cttcaccggc    1020
gcagtcattc tcatgatcgc ccacgggctt acatcctcat tactattctg cctagcaaac    1080
tcaaactacg aacgcactca cagtcgcatc atgatcctct ctcaaggact tcaaactcta    1140
ctcccactaa tggcttttg gtggcttcta gcaagcctcg ctaacctcgc cttacccccc    1200
actattaacc tactgggaga actctctgtg ctagtaacca cgttctcctg gtcaaatatc    1260
actctcctac ttacaggact caacatgcta gtcacagccc tatactccct ctacatgttt    1320
accacaacac aatggggctc actcacccac cacattaaca acatgaaacc ctcattcaca    1380
cgagaaaaca ccctcatgtt catgcaccta tcccccattc tcctcctatc cctcaacccc    1440
gacatcatta ccgggttttc ctcttaagag cactgggacg cccaccgccc ctttccctcc    1500
gctgccaggc gagcatgttg tggtaattct ggaacacaag aagagaaatt gctgggttta    1560
gaacaagatt ataaacgaat tcggtgctca gtgatcactt gacagttttt tttttttta    1620
aatattaccc aaaatgctcc ccaaataaga aatgcatcag ctcagtcagt gaatacaaaa    1680
aaggaattat ttttcccttt gagggtcttt tatacatctc tcctccaacc ccaccctcta    1740
ttctgtttct tcctcctcac atgggggtac acatacacag cttcctcttt tggttccatc    1800
cttaccacca caccacacgc acactccaca tgcccagcag agtggcactt ggtggccaga    1860
aagtgtgagc ctcatgatct gctgtctgta gttctgtgag ctcaggtccc tcaaaggcct    1920
cggagcaccc ccttccttgt gactgagcca gggcctgcat ttttggtttt ccccacccca    1980
cacattctca accatagtcc ttctaacaat accaatagct aggacccggc tgctgtgcac    2040
tgggactggg gattccacat gtttgccttg ggagtctcaa gctggactgc cagcccctgt    2100
cctcccttca cccccattgc gtatgagcat ttcagaactc caaggagtca caggcatctt    2160
tatagttcac gttaacatat agacactgtt ggaagcagtt ccttctaaaa gggtagccct    2220
```

| | |
|---|---|
| ggacttaata ccagccggat acctctggcc cccaccccat tactgtacct ctggagtcac | 2280 |
| tactgtgggt cgccactcct ctgctacaca gcacggcttt ttcaaggctg tattgagaag | 2340 |
| ggaagttagg aagaagggtg tgctgggcta accagcccac agagctcaca ttcctgtccc | 2400 |
| ttgggtgaaa aatacatgtc catcctgata tctcctgaat tcagaaatta gcctccacat | 2460 |
| gtgcaatggc tttaagagcc agaagcaggg ttctgggaat tttgcaagtt acctgtggcc | 2520 |
| aggtgtggtc tcggttacca aatacggtta cctgcagctt tttagtcctt tgtgctccca | 2580 |
| cgggtctaca gagtcccatc tgcccaaagg tcttgaagct tgacaggatg ttttcgatta | 2640 |
| ctcagtctcc cagggcacta ctggtccgta ggattcgatt ggtcggggta ggagagttaa | 2700 |
| acaacattta aacagagttc tctcaaaaat gtctaaaggg attgtaggta gataacatcc | 2760 |
| aatcactgtt tgcacttatc tgaaatcttc cctcttggct gcccccaggt atttactgtg | 2820 |
| gagaacattg cataggaatg tctggaaaaa gcttctacaa cttgttacag ccttcacatt | 2880 |
| tgtagaagct tt | 2892 |

<210> SEQ ID NO 58
<211> LENGTH: 2092
<212> TYPE: DNA
<213> ORGANISM: Artificial Sequence
<220> FEATURE:
<223> OTHER INFORMATION: COX8-ND4-3'UTR*

<400> SEQUENCE: 58

| | |
|---|---|
| atgtccgtcc tgacgcgcct gctgctgcgg ggcttgacac ggctcggctc ggcggctcca | 60 |
| gtgcggcgcg ccagaatcca ttcgttgatg ctaaaactaa tcgtcccaac aattatgtta | 120 |
| ctaccactga catggctttc caaaaaacac atgatttgga tcaacacaac cacccacagc | 180 |
| ctaattatta gcatcatccc tctactattt tttaaccaaa tcaacaacaa cctatttagc | 240 |
| tgttccccaa cctttcctc cgacccccta acaaccccc tcctaatgct aactacctgg | 300 |
| ctcctacccc tcacaatcat ggcaagccaa cgccacttat ccagtgaacc actatcacga | 360 |
| aaaaaactct acctctctat gctaatctcc ctacaaatct ccttaattat gacattcaca | 420 |
| gccacagaac taatcatgtt ttatatcttc ttcgaaacca cacttatccc cacccttggct | 480 |
| atcatcaccc gatggggcaa ccagccagaa cgcctgaacg caggcacata cttcctattc | 540 |
| tacaccctag taggctccct tcccctactc atcgcactaa tttacactca caacacccta | 600 |
| ggctcactaa acattctact actcactctc actgcccaag aactatcaaa ctcctgggcc | 660 |
| aacaacttaa tgtggctagc ttacacaatg gcttttatgg taaagatgcc tctttacgga | 720 |
| ctccacttat ggctccctaa agcccatgtc gaagccccca tcgctgggtc aatggtactt | 780 |
| gccgcagtac tcttaaaact aggcggctat ggtatgatgc cctcacact cattctcaac | 840 |
| cccctgacaa aacacatggc ctaccccttc cttgtactat ccctatgggg catgattatg | 900 |
| acaagctcca tctgcctacg acaaacagac ctaaaatcgc tcattgcata ctcttcaatc | 960 |
| agccacatgg ccctcgtagt aacagccatt ctcatccaaa cccctggag cttcaccggc | 1020 |
| gcagtcattc tcatgatcgc ccacgggctt acatcctcat tactattctg cctagcaaac | 1080 |
| tcaaactacg aacgcactca cagtcgcatc atgatcctct ctcaaggact tcaaactcta | 1140 |
| ctcccactaa tggcttttg gtggcttcta gcaagcctcg ctaacctcgc cttaccccc | 1200 |
| actattaacc tactgggaga actctctgtg ctagtaacca cgttctcctg gtcaaatatc | 1260 |
| actctcctac ttacaggact caacatgcta gtcacagccc tatactccct ctacatgttt | 1320 |

| | |
|---|---|
| accacaacac aatggggctc actcacccac acattaaca acatgaaacc ctcattcaca | 1380 |
| cgagaaaaca ccctcatgtt catgcaccta tcccccattc tcctcctatc cctcaacccc | 1440 |
| gacatcatta ccgggttttc ctcttaagag cactgggacg cccaccgccc ctttccctcc | 1500 |
| gctgccaggc gagcatgttg tggtaattct ggaacacaag aagagaaatt gctgggttta | 1560 |
| gaacaagatt ataaacgaat tcggtgctca gtgatcactt gacagttttt ttttttttta | 1620 |
| aatattaccc aaaatgctcc ccaaataaga aatgcatcag ctcagtcagt gaatacaaaa | 1680 |
| aaggaattat ttttcccttt gagggtcttt tatacatctc tcctccaacc ccaccctcta | 1740 |
| ttctgtttct tcctcctcac atgggggtac acatacacag cttcctcttt tggttccatc | 1800 |
| cttaccacca caccacacgc acactccaca tgcccagcag agtggcactt ggtggccaga | 1860 |
| aagtgtgagc ctcatgatct gctgtctgta gttctgtgag ctcaggtccc tcaaaggcct | 1920 |
| cggagcaccc ccttccttgt gactgagcca gggcctgcat ttttggtttt ccccacccca | 1980 |
| cacattctca accatagtcc ttctaacaat accaatagct aggacccggc tgctgtgcac | 2040 |
| tgggactggg gattccacat gtttgccttg ggagtctcaa gctggactgc ca | 2092 |

<210> SEQ ID NO 59
<211> LENGTH: 2892
<212> TYPE: DNA
<213> ORGANISM: Artificial Sequence
<220> FEATURE:
<223> OTHER INFORMATION: COX8-opt_ND4-3'UTR

<400> SEQUENCE: 59

| | |
|---|---|
| atgtccgtcc tgacgcgcct gctgctgcgg ggcttgacac ggctcggctc ggcggctcca | 60 |
| gtgcggcgcg ccagaatcca ttcgttgatg ctgaagctga tcgtgcccac catcatgctg | 120 |
| ctgcctctga cctggctgag caagaaacac atgatctgga tcaacaccac cacgcacagc | 180 |
| ctgatcatca gcatcatccc tctgctgttc ttcaaccaga tcaacaacaa cctgttcagc | 240 |
| tgcagcccca ccttcagcag cgaccctctg acaacacctc tgctgatgct gaccacctgg | 300 |
| ctgctgcccc tcacaatcat ggcctctcag agacacctga gcagcgagcc cctgagccgg | 360 |
| aagaaactgt acctgagcat gctgatctcc ctgcagatct ctctgatcat gaccttcacc | 420 |
| gccaccgagc tgatcatgtt ctacatcttt ttcgagacaa cgctgatccc cacactggcc | 480 |
| atcatcacca gatggggcaa ccagcctgag agactgaacg ccggcaccta ctttctgttc | 540 |
| tacaccctcg tgggcagcct gccactgctg attgccctga tctacaccca caacaccctg | 600 |
| ggctccctga acatcctgct gctgacactg acagcccaag agctgagcaa cagctgggcc | 660 |
| aacaatctga tgtggctggc ctacacaatg gccttcatgg tcaagatgcc cctgtacggc | 720 |
| ctgcacctgt ggctgcctaa agctcatgtg aagcccctat cgccggctc tatggtgctg | 780 |
| gctgcagtgc tgctgaaact cggcggctac ggcatgatgc ggctgaccct gattctgaat | 840 |
| cccctgacca agcacatggc ctatccattt ctggtgctga cctgtgggg catgattatg | 900 |
| accagcagca tctgcctgcg gcagaccgat ctgagtccc tgatcgccta cagctccatc | 960 |
| agccacatgg ccctggtggt caccgccatc ctgattcaga ccccttggag ctttacaggc | 1020 |
| gccgtgatcc tgatgattgc ccacggcctg acaagcagcc tgctgttttg tctggccaac | 1080 |
| agcaactacg agcggaccca cagcagaatc atgatcctgt ctcagggcct gcagaccctc | 1140 |
| ctgcctctta tggcttttg gtggctgctg gcctctctgg ccaatctggc actgcctcct | 1200 |
| accatcaatc tgctgggcga gctgagcgtg ctggtcacca cattcagctg gtccaatatc | 1260 |
| accctgctgc tcaccggcct gaacatgctg gttacagccc tgtactccct gtacatgttc | 1320 |

```
accaccacac agtggggaag cctgacacac cacatcaaca atatgaagcc cagcttcacc    1380
cgcgagaaca ccctgatgtt catgcatctg agccccattc tgctgctgtc cctgaatcct    1440
gatatcatca ccggcttctc cagctgagag cactgggacg cccaccgccc ctttccctcc    1500
gctgccaggc gagcatgttg tggtaattct ggaacacaag aagagaaatt gctgggttta    1560
gaacaagatt ataaacgaat tcggtgctca gtgatcactt gacagttttt ttttttttta    1620
aatattaccc aaaatgctcc ccaaataaga aatgcatcag ctcagtcagt gaatacaaaa    1680
aaggaattat ttttcccttt gagggtcttt tatacatctc tcctccaacc ccaccctcta    1740
ttctgtttct tcctcctcac atggggtac acatacacag cttcctcttt tggttccatc     1800
cttaccacca caccacacgc acactccaca tgcccagcag agtggcactt ggtggccaga    1860
aagtgtgagc ctcatgatct gctgtctgta gttctgtgag ctcaggtccc tcaaaggcct    1920
cggagcaccc ccttccttgt gactgagcca gggcctgcat ttttggtttt ccccacccca    1980
cacattctca accatagtcc ttctaacaat accaatagct aggacccggc tgctgtgcac    2040
tgggactggg gattccacat gtttgccttg ggagtctcaa gctggactgc cagcccctgt    2100
cctcccttca cccccattgc gtatgagcat ttcagaactc caaggagtca caggcatctt    2160
tatagttcac gttaacatat agacactgtt ggaagcagtt ccttctaaaa gggtagccct    2220
ggacttaata ccagccggat acctctggcc cccaccccat tactgtacct ctggagtcac    2280
tactgtgggt cgccactcct ctgctacaca gcacggcttt ttcaaggctg tattgagaag    2340
ggaagttagg aagaagggtg tgctgggcta accagcccac agagctcaca ttcctgtccc    2400
ttgggtgaaa aatacatgtc catcctgata tctcctgaat tcagaaatta gcctccacat    2460
gtgcaatggc tttaagagcc agaagcaggg ttctgggaat tttgcaagtt acctgtggcc    2520
aggtgtggtc tcggttacca aatacggtta cctgcagctt tttagtcctt tgtgctccca    2580
cgggtctaca gagtcccatc tgcccaaagg tcttgaagct tgacaggatg ttttcgatta    2640
ctcagtctcc cagggcacta ctggtccgta ggattcgatt ggtcggggta ggagagttaa    2700
acaacattta aacagagttc tctcaaaaat gtctaaaggg attgtaggta gataacatcc    2760
aatcactgtt tgcacttatc tgaaatcttc cctcttggct gccccaggt atttactgtg      2820 gagaacattg cataggaatg tctggaaaaa gcttctacaa cttgttacag ccttcacatt    2880
tgtagaagct tt                                                          2892
```

<210> SEQ ID NO 60
<211> LENGTH: 2092
<212> TYPE: DNA
<213> ORGANISM: Artificial Sequence
<220> FEATURE:
<223> OTHER INFORMATION: COX8-opt_ND4-3'UTR*

<400> SEQUENCE: 60

```
atgtccgtcc tgacgcgcct gctgctgcgg ggcttgacac ggctcggctc ggcggctcca      60
gtgcggcgcg ccagaatcca ttcgttgatg ctgaagctga tcgtgcccac catcatgctg    120
ctgcctctga cctggctgag caagaaacac atgatctgga tcaacaccac cacgcacagc    180
ctgatcatca gcatcatccc tctgctgttc ttcaaccaga tcaacaacaa cctgttcagc    240
tgcagcccca ccttcagcag cgaccctctg acaacacctc tgctgatgct gaccacctgg    300
ctgctgcccc tcacaatcat ggcctctcag agacacctga gcagcgagcc cctgagccgg    360
aagaaactgt acctgagcat gctgatctcc ctgcagatct ctctgatcat gaccttcacc    420
```

```
gccaccgagc tgatcatgtt ctacatcttt tcgagacaa cgctgatccc cacactggcc    480
atcatcacca gatggggcaa ccagcctgag agactgaacg ccggcaccta ctttctgttc    540
tacaccctcg tgggcagcct gccactgctg attgccctga tctacaccca caacaccctg    600
ggctccctga acatcctgct gctgacactg acagccaag agctgagcaa cagctgggcc     660
aacaatctga tgtggctggc ctacacaatg gccttcatgg tcaagatgcc cctgtacggc    720
ctgcacctgt ggctgcctaa agctcatgtg aagcccta tcgccggctc tatggtgctg      780
gctgcagtgc tgctgaaaact cggcggctac ggcatgatgc ggctgaccct gattctgaat   840
cccctgacca agcacatggc ctatccattt ctggtgctga cctgtgggg catgattatg     900 accagcagca tctgcctgcg gcagaccgat ctgaagtccc tgatcgccta cagctccatc    960
agccacatgg ccctggtggt caccgccatc ctgattcaga ccccttggag ctttacaggc   1020
gccgtgatcc tgatgattgc ccacggcctg acaagcagcc tgctgttttg tctggccaac   1080
agcaactacg agcggaccca cagcagaatc atgatcctgt ctcagggcct gcagaccctc   1140
ctgcctctta tggctttttg gtggctgctg gcctctctgg ccaatctggc actgcctcct   1200
accatcaatc tgctgggcga ctgagcgtg ctggtcacca cattcagctg gtccaatatc    1260
accctgctgc tcaccggcct gaacatgctg gttacagccc tgtactccct gtacatgttc   1320
accaccacac agtggggaag cctgacacac acatcaaca atatgaagcc cagcttcacc   1380
cgcgagaaca ccctgatgtt catgcatctg agccccattc tgctgctgtc cctgaatcct   1440
gatatcatca ccggcttctc cagctgagag cactgggacg cccaccgccc ctttccctcc   1500
gctgccaggc gagcatgttg tggtaattct ggaacacaag aagagaaatt gctgggttta   1560
gaacaagatt ataaacgaat tcggtgctca gtgatcactt gacagttttt tttttttta     1620 aatattaccc aaaatgctcc ccaaataaga aatgcatcag ctcagtcagt gaatacaaaa   1680
aaggaattat ttttcccttt gagggtcttt tatacatctc tcctccaacc ccaccctcta   1740 ttctgttct tcctcctcac atgggggtac acatacacag cttcctcttt tggttccatc    1800
cttaccacca caccacacgc acactccaca tgcccagcag agtggcactt ggtggccaga   1860
aagtgtgagc ctcatgatct gctgtctgta gttctgtgag ctcaggtccc tcaaaggcct   1920
cggagcaccc ccttccttgt gactgagcca gggcctgcat ttttggtttt ccccacccca   1980
cacattctca accatagtcc ttctaacaat accaatagct aggacccggc tgctgtgcac   2040
tgggactggg gattccacat gttttgccttg ggagtctcaa gctggactgc ca          2092

<210> SEQ ID NO 61
<211> LENGTH: 2892
<212> TYPE: DNA
<213> ORGANISM: Artificial Sequence
<220> FEATURE:
<223> OTHER INFORMATION: COX8-opt_ND4*-3'UTR

<400> SEQUENCE: 61
atgtccgtcc tgacgcgcct gctgctgcgg ggcttgacac ggctcggctc ggcggctcca     60
gtgcggcgcg ccagaatcca ttcgttgatg ctgaagctga tcgtgcccac catcatgctg    120
ctgcccctga cctggctgag caagaagcac atgatctgga tcaacaccac cacccacagc    180
ctgatcatca gcatcatccc cctgctgttc ttcaaccaga tcaacaacaa cctgttcagc    240
tgcagcccca ccttcagcag cgaccccctg accaccccc tgctgatgct gaccacctgg    300
ctgctgcccc tgaccatcat ggccagccag cgccacctga gcagcgagcc cctgagccgc    360
aagaagctgt acctgagcat gctgatcagc ctgcagatca gcctgatcat gaccttcacc    420
```

```
gccaccgagc tgatcatgtt ctacatcttc ttcgagacca ccctgatccc caccctggcc    480
atcatcaccc gctggggcaa ccagcccgag cgcctgaacg ccggcaccta cttcctgttc    540
tacaccctgg tgggcagcct gcccctgctg atcgccctga tctacaccca caacaccctg    600
ggcagcctga acatcctgct gctgaccctg accgcccagg agctgagcaa cagctgggcc    660
aacaacctga tgtggctggc ctacaccatg gccttcatgg tgaagatgcc cctgtacggc    720
ctgcacctgt ggctgcccaa ggcccacgtg gaggccccca tcgccggcag catggtgctg    780
gccgccgtgc tgctgaagct gggcggctac ggcatgatgc gcctgaccct gatcctgaac    840
cccctgacca gcacatggc ctaccccttc tggtgctga gctgtgggg catgatcatg    900 accagcagca tctgcctgcg ccagaccgac ctgaagagcc tgatcgccta cagcagcatc    960
agccacatgg ccctggtggt gaccgccatc ctgatccaga ccccctggag cttcaccggc   1020
gccgtgatcc tgatgatcgc ccacggcctg accagcagcc tgctgttctg cctggccaac   1080
agcaactacg agcgcaccca cagccgcatc atgatcctga ccagggcct gcagaccctg   1140 ctgcccctga tggccttctg gtggctgctg gccagcctgg ccaacctggc cctgcccccc   1200
accatcaacc tgctgggcga gctgagcgtg ctggtgacca ccttcagctg gagcaacatc   1260
accctgctgc tgaccggcct gaacatgctg gtgaccgccc tgtacagcct gtacatgttc   1320
accaccaccc agtggggcag cctgacccac cacatcaaca acatgaagcc cagcttcacc   1380
cgcgagaaca ccctgatgtt catgcacctg agccccatcc tgctgctgag cctgaacccc   1440
gacatcatca ccggcttcag cagctaagag cactgggacg cccaccgccc ctttccctcc   1500
gctgccaggc gagcatgttg tggtaattct ggaacacaag aagagaaatt gctgggttta   1560
gaacaagatt ataaacgaat tcggtgctca gtgatcactt gacagttttt tttttttta   1620 aatattaccc aaaatgctcc ccaaataaga aatgcatcag ctcagtcagt gaatacaaaa   1680
aaggaattat ttttcccttt gagggtcttt tatacatctc tcctccaacc ccaccctcta   1740
ttctgtttct tcctcctcac atgggggtac acatacacag cttcctcttt tggttccatc   1800
cttaccacca caccacacgc acactccaca tgcccagcag agtggcactt ggtggccaga   1860
aagtgtgagc ctcatgatct gctgtctgta gttctgtgag ctcaggtccc tcaaaggcct   1920
cggagcaccc ccttccttgt gactgagcca gggcctgcat ttttggtttt ccccaccca    1980 cacattctca accatagtcc ttctaacaat accaatagct aggacccggc tgctgtgcac   2040
tgggactggg gattccacat gtttgccttg ggagtctcaa gctggactgc cagcccctgt   2100
cctcccttca cccccattgc gtatgagcat ttcagaactc caaggagtca caggcatctt   2160
tatagttcac gttaacatat agacactgtt ggaagcagtt ccttctaaaa gggtagccct   2220
ggacttaata ccagccggat acctctggcc cccacccat tactgtacct ctggagtcac   2280
tactgtgggt cgccactcct ctgctacaca gcacggcttt ttcaaggctg tattgagaag   2340
ggaagttagg aagaagggtg tgctgggcta accagcccac agagctcaca ttcctgtccc   2400
ttgggtgaaa aatacatgtc catcctgata tctcctgaat tcagaaatta gcctccacat   2460
gtgcaatggc tttaagagcc agaagcaggg ttctgggaat tttgcaagtt acctgtggcc   2520
aggtgtggtc tcggttacca aatacggtta cctgcagctt tttagtcctt tgtgctccca   2580
cgggtctaca gagtcccatc tgcccaaagg tcttgaagct tgacaggatg ttttcgatta   2640
ctcagtctcc cagggcacta ctggtccgta ggattcgatt ggtcggggta ggagagttaa   2700
acaacattta aacagagttc tctcaaaaat gtctaaaggg attgtaggta gataacatcc   2760
```

| aatcactgtt tgcacttatc tgaaatcttc cctcttggct gccccaggt atttactgtg | 2820 |
| gagaacattg cataggaatg tctggaaaaa gcttctacaa cttgttacag ccttcacatt | 2880 |
| tgtagaagct tt | 2892 |

<210> SEQ ID NO 62
<211> LENGTH: 2092
<212> TYPE: DNA
<213> ORGANISM: Artificial Sequence
<220> FEATURE:
<223> OTHER INFORMATION: COX8-opt_ND4*-3'UTR*

<400> SEQUENCE: 62

| atgtccgtcc tgacgcgcct gctgctgcgg ggcttgacac ggctcggctc ggcggctcca | 60 |
| gtgcggcgcg ccagaatcca ttcgttgatg ctgaagctga tcgtgcccac catcatgctg | 120 |
| ctgcccctga cctggctgag caagaagcac atgatctgga tcaacaccac cacccacagc | 180 |
| ctgatcatca gcatcatccc cctgctgttc ttcaaccaga tcaacaacaa cctgttcagc | 240 |
| tgcagcccca ccttcagcag cgaccccctg accacccccc tgctgatgct gaccacctgg | 300 |
| ctgctgcccc tgaccatcat ggccagccag cgccacctga gcagcgagcc cctgagccgc | 360 |
| aagaagctgt acctgagcat gctgatcagc ctgcagatca gcctgatcat gaccttcacc | 420 |
| gccaccgagc tgatcatgtt ctacatcttc ttcgagacca ccctgatccc caccctggcc | 480 |
| atcatcaccc gctggggcaa ccagcccgag cgcctgaacg ccggcaccta cttcctgttc | 540 |
| tacaccctgg tgggcagcct gcccctgctg atcgccctga tctacaccca caacaccctg | 600 |
| ggcagcctga catcctgct gctgaccctg accgccagg agctgagcaa cagctgggcc | 660 |
| aacaacctga tgtggctggc ctacaccatg gccttcatgg tgaagatgcc cctgtacggc | 720 |
| ctgcacctgt ggctgcccaa ggcccacgtg gaggccccca tcgccggcag catggtgctg | 780 |
| gccgccgtgc tgctgaagct gggcggctac ggcatgatgc gcctgacct gatcctgaac | 840 |
| cccctgacca gcacatggc ctaccccttc ctggtgctga gcctgtgggg catgatcatg | 900 |
| accagcagca tctgcctgcg ccagaccgac ctgaagagcc tgatcgccta cagcagcatc | 960 |
| agccacatgg ccctggtggt gaccgccatc ctgatccaga cccctggag cttcaccggc | 1020 |
| gccgtgatcc tgatgatcgc ccacggcctg accagcagcc tgctgttctg cctggccaac | 1080 |
| agcaactacg agcgcaccca cagccgcatc atgatcctga ccagggcct gcagaccctg | 1140 |
| ctgcccctga tggccttctg gtggctgctg gccagcctgg ccaacctggc cctgcccccc | 1200 |
| accatcaacc tgctgggcga gctgagcgtg ctggtgacca ccttcagctg gagcaacatc | 1260 |
| accctgctgc tgaccggcct gaacatgctg gtgaccgccc tgtacagcct gtacatgttc | 1320 |
| accaccaccc agtggggcag cctgacccac cacatcaaca acatgaagcc cagcttcacc | 1380 |
| cgcgagaaca ccctgatgtt catgcacctg agccccatcc tgctgctgag cctgaacccc | 1440 |
| gacatcatca ccggcttcag cagctaagag cactgggacg cccaccgccc ctttccctcc | 1500 |
| gctgccaggc gagcatgttg tggtaattct ggaacacaag aagagaaatt gctgggttta | 1560 |
| gaacaagatt ataaacgaat tcggtgctca gtgatcactt gacagttttt ttttttttta | 1620 |
| aatattaccc aaaatgctcc ccaaataaga aatgcatcag ctcagtcagt gaatacaaaa | 1680 |
| aaggaattat ttttcccttt gagggtcttt tatacatctc tcctccaacc ccaccctcta | 1740 |
| ttctgtttct tcctcctcac atgggggtac acatacacag cttcctcttt tggttccatc | 1800 |
| cttaccacca caccacacgc acactccaca tgcccagcag agtggcactt ggtggccaga | 1860 |
| aagtgtgagc tcatgatct gctgtctgta gttctgtgag ctcaggtccc tcaaaggcct | 1920 |

| cggagcaccc cctccttgt gactgagcca gggcctgcat ttttggtttt ccccaccca | 1980 |
| cacattctca accatagtcc ttctaacaat accaatagct aggacccggc tgctgtgcac | 2040 |
| tgggactggg gattccacat gtttgccttg ggagtctcaa gctggactgc ca | 2092 |

<210> SEQ ID NO 63
<211> LENGTH: 2037
<212> TYPE: DNA
<213> ORGANISM: Artificial Sequence
<220> FEATURE:
<223> OTHER INFORMATION: COX8-ND6-3'UTR

<400> SEQUENCE: 63

| atgtccgtcc tgacgcgcct gctgctgcgg ggcttgacac ggctcggctc ggcggctcca | 60 |
| gtgcggcgcg ccagaatcca ttcgttgatg atgtatgctt tgtttctgtt gagtgtgggt | 120 |
| ttagtaatgg ggtttgtggg gttttcttct aagccttctc ctatttatgg gggtttagta | 180 |
| ttgattgtta gcggtgtggt cgggtgtgtt attattctga attttggggg aggttatatg | 240 |
| ggtttaatgg ttttttttaat ttatttaggg ggaatgatgg ttgtctttgg atatactaca | 300 |
| gcgatggcta ttgaggagta tcctgaggca tggggtcag gggttgaggt cttggtgagt | 360 |
| gttttagtgg ggttagcgat ggaggtagga ttggtgctgt gggtgaaaga gtatgatggg | 420 |
| gtggtggttg tggtaaactt taatagtgta ggaagctgga tgatttatga aggagagggg | 480 |
| tcagggttga ttcgggagga tcctattggt gcggggctt tgtatgatta tgggcgttgg | 540 |
| ttagtagtag ttactggttg gacattgttt gttggtgtat atattgtaat tgagattgct | 600 |
| cgggggaatt aggagcactg ggacgcccac cgccccttc cctccgctgc caggcgagca | 660 |
| tgttgtggta attctggaac acaagaagag aaattgctgg gtttagaaca agattataaa | 720 |
| cgaattcggt gctcagtgat cacttgacag ttttttttttt ttttaaatat acccaaaat | 780 |
| gctccccaaa taagaaatgc atcagctcag tcagtgaata caaaaaagga attattttc | 840 |
| cctttgaggg tcttttatac atctctcctc caacccacc ctctattctg tttcttcctc | 900 |
| ctcacatggg ggtacacata cacagcttcc tcttttggtt ccatccttac caccacacca | 960 |
| cacgcacact ccacatgccc agcagagtgg cacttggtgg ccagaaagtg tgagcctcat | 1020 |
| gatctgctgt ctgtagttct gtgagctcag gtccctcaaa ggcctcggag cacccccttc | 1080 |
| cttgtgactg agccagggcc tgcatttttg gttttcccca ccccacacat tctcaaccat | 1140 |
| agtccttcta acaataccaa tagctaggac ccggctgctg tgcactggga ctggggattc | 1200 |
| cacatgtttg ccttgggagt ctcaagctgg actgccagcc cctgtcctcc cttcacccc | 1260 |
| attgcgtatg agcatttcag aactccaagg agtcacaggc atctttatag ttcacgttaa | 1320 |
| catatagaca ctgttggaag cagttccttc taaaagggta gccctggact taataccagc | 1380 |
| cggataccctc tggcccccac cccattactg tacctctgga gtcactactg tgggtcgcca | 1440 |
| ctcctctgct acacagcacg gcttttcaa ggctgtattg agaagggaag ttaggaagaa | 1500 |
| gggtgtgctg ggctaaccag cccacagagc tcacattcct gtcccttggg tgaaaaatac | 1560 |
| atgtccatcc tgatatctcc tgaattcaga aattagcctc cacatgtgca atggctttaa | 1620 |
| gagccagaag cagggttctg ggaattttgc aagttacctg tggccaggtg tggtctcggt | 1680 |
| taccaaatac ggttacctgc agctttttag tcctttgtgc tcccacgggt ctacagagtc | 1740 |
| ccatctgccc aaaggtcttg aagcttgaca ggatgtttc gattactcag tctcccaggg | 1800 |
| cactactggt ccgtaggatt cgattggtcg gggtaggaga gttaaacaac atttaaacag | 1860 |

| | |
|---|---|
| agttctctca aaaatgtcta aagggattgt aggtagataa catccaatca ctgtttgcac | 1920 |
| ttatctgaaa tcttccctct tggctgcccc caggtattta ctgtggagaa cattgcatag | 1980 |
| gaatgtctgg aaaaagcttc tacaacttgt tacagccttc acatttgtag aagcttt | 2037 |

<210> SEQ ID NO 64
<211> LENGTH: 1237
<212> TYPE: DNA
<213> ORGANISM: Artificial Sequence
<220> FEATURE:
<223> OTHER INFORMATION: COX8-ND6-3'UTR*

<400> SEQUENCE: 64

| | |
|---|---|
| atgtccgtcc tgacgcgcct gctgctgcgg ggcttgacac ggctcggctc ggcggctcca | 60 |
| gtgcggcgcg ccagaatcca ttcgttgatg atgtatgctt tgtttctgtt gagtgtgggt | 120 |
| ttagtaatgg ggtttgtggg gttttcttct aagccttctc ctatttatgg gggtttagta | 180 |
| ttgattgtta gcggtgtggt cgggtgtgtt attattctga attttggggg aggttatatg | 240 |
| ggtttaatgg ttttttttaat ttatttaggg ggaatgatgg ttgtctttgg atatactaca | 300 |
| gcgatggcta ttgaggagta tcctgaggca tggggtcag gggttgaggt cttggtgagt | 360 |
| gttttagtgg ggttagcgat ggaggtagga ttggtgctgt gggtgaaaga gtatgatggg | 420 |
| gtggtggttg tggtaaactt taatagtgta ggaagctgga tgatttatga aggagagggg | 480 |
| tcagggttga ttcgggagga tcctattggt gcggggggtt tgtatgatta tgggcgttgg | 540 |
| ttagtagtag ttactggttg gacattgttt gttggtgtat atattgtaat tgagattgct | 600 |
| cggggggaatt aggagcactg ggacgcccac cgccccttc cctccgctgc caggcgagca | 660 |
| tgttgtggta attctggaac acaagaagag aaattgctgg gtttagaaca agattataaa | 720 |
| cgaattcggt gctcagtgat cacttgacag ttttttttt ttttaaatat tacccaaaat | 780 |
| gctccccaaa taagaaatgc atcagctcag tcagtgaata caaaaaagga attattttc | 840 |
| cctttgaggg tcttttatac atctctcctc caacccacc ctctattctg tttcttcctc | 900 |
| ctcacatggg ggtacacata cacagcttcc tcttttggtt ccatccttac caccacacca | 960 |
| cacgcacact ccacatgccc agcagagtgg cacttggtgg ccagaaagtg tgagcctcat | 1020 |
| gatctgctgt ctgtagttct gtgagctcag gtccctcaaa ggcctcggag cacccccttc | 1080 |
| cttgtgactg agccagggcc tgcatttttg gttttcccca ccccacacat tctcaaccat | 1140 |
| agtccttcta acaataccaa tagctaggac ccggctgctg tgcactggga ctggggattc | 1200 |
| cacatgtttg ccttgggagt ctcaagctgg actgcca | 1237 |

<210> SEQ ID NO 65
<211> LENGTH: 2037
<212> TYPE: DNA
<213> ORGANISM: Artificial Sequence
<220> FEATURE:
<223> OTHER INFORMATION: COX8-opt_ND6-3'UTR

<400> SEQUENCE: 65

| | |
|---|---|
| atgtccgtcc tgacgcgcct gctgctgcgg ggcttgacac ggctcggctc ggcggctcca | 60 |
| gtgcggcgcg ccagaatcca ttcgttgatg atgtacgccc tgttcctgct gagcgtgggc | 120 |
| ctggtgatgg gcttcgtggg cttcagcagc aagcccagcc ccatctacgg cggcctggtg | 180 |
| ctgatcgtga gcggcgtggt gggctgcgtg atcatcctga acttcggcgg cggctacatg | 240 |
| ggcctgatgg tgttcctgat ctacctgggc ggcatgatgg tggtgttcgg ctacaccacc | 300 |
| gccatggcca tcgaggagta ccccgaggcc tggggcagcg gcgtggaggt gctggtgagc | 360 |

```
gtgctggtgg gcctggccat ggaggtgggc ctggtgctgt gggtgaagga gtacgacggc    420
gtggtggtgg tggtgaactt caacagcgtg ggcagctgga tgatctacga gggcgagggc    480
agcggcctga tccgcgagga ccccatcggc gccggcgccc tgtacgacta cggccgctgg    540
ctggtggtgg tgaccggctg gaccctgttc gtgggcgtgt acatcgtgat cgagatcgcc    600
cgcggcaact aagagcactg ggacgcccac cgccccttc cctccgctgc caggcgagca    660
tgttgtggta attctggaac acaagaagag aaattgctgg gtttagaaca agattataaa    720
cgaattcggt gctcagtgat cacttgacag ttttttttt ttttaaatat tacccaaaat    780
gctccccaaa taagaaatgc atcagctcag tcagtgaata caaaaaagga attatttttc    840
cctttgaggg tcttttatac atctctcctc caaccccacc ctctattctg tttcttcctc    900
ctcacatggg ggtacacata cacagcttcc tcttttggtt ccatccttac caccacacca    960
cacgcacact ccacatgccc agcagagtgg cacttggtgg ccagaaagtg tgagcctcat   1020
gatctgctgt ctgtagttct gtgagctcag gtccctcaaa ggcctcggag cacccccttc   1080
cttgtgactg agccagggcc tgcattttg gttttcccca ccccacacat tctcaaccat   1140
agtccttcta acaataccaa tagctaggac ccggctgctg tgcactggga ctggggattc   1200
cacatgtttg ccttgggagt ctcaagctgg actgccagcc cctgtcctcc cttcaccccc   1260
attgcgtatg agcatttcag aactccaagg agtcacaggc atctttatag ttcacgttaa   1320
catatagaca ctgttggaag cagttccttc taaaagggta gccctggact aataccagc   1380 cggatacctc tggcccccac cccattactg tacctctgga gtcactactg tgggtcgcca   1440
ctcctctgct acacagcacg gcttttcaa ggctgtattg agaagggaag ttaggaagaa   1500
gggtgtgctg ggctaaccag cccacagagc tcacattcct gtcccttggg tgaaaaatac   1560
atgtccatcc tgatatctcc tgaattcaga aattagcctc cacatgtgca atggctttaa   1620
gagccagaag cagggttctg ggaattttgc aagttacctg tggccaggtg tggtctcggt   1680
taccaaatac ggttacctgc agcttttag tcctttgtgc tcccacgggt ctacagagtc   1740
ccatctgccc aaaggtcttg aagcttgaca ggatgttttc gattactcag tctcccaggg   1800
cactactggt ccgtaggatt cgattggtcg gggtaggaga gttaaacaac atttaaacag   1860
agttctctca aaaatgtcta aagggattgt aggtagataa catccaatca ctgtttgcac   1920
ttatctgaaa tcttccctct tggctgcccc caggtattta ctgtggagaa cattgcatag   1980
gaatgtctgg aaaaagcttc tacaacttgt tacagccttc acatttgtag aagcttt       2037
```

<210> SEQ ID NO 66  
<211> LENGTH: 1237  
<212> TYPE: DNA  
<213> ORGANISM: Artificial Sequence  
<220> FEATURE:  
<223> OTHER INFORMATION: COX8-opt_ND6-3'UTR*

<400> SEQUENCE: 66

```
atgtccgtcc tgacgcgcct gctgctgcgg ggcttgacac ggctcggctc ggcggctcca     60
gtgcggcgcg ccagaatcca ttcgttgatg atgtacgccc tgttcctgct gagcgtgggc    120
ctggtgatgg gcttcgtggg cttcagcagc aagcccagcc ccatctacgg cggcctggtg    180
ctgatcgtga gcggcgtggt gggctgcgtg atcatcctga acttcggcgg cggctacatg    240
ggcctgatgg tgttcctgat ctacctgggc ggcatgatgg tggtgttcgg ctacaccacc    300
gccatggcca tcgaggagta ccccgaggcc tggggcagcg gcgtggaggt gctggtgagc    360
```

```
gtgctggtgg gcctggccat ggaggtgggc ctggtgctgt gggtgaagga gtacgacggc    420
gtggtggtgg tggtgaactt caacagcgtg ggcagctgga tgatctacga gggcgagggc    480
agcggcctga tccgcgagga ccccatcggc gccggcgccc tgtacgacta cggccgctgg    540
ctggtggtgg tgaccggctg gaccctgttc gtgggcgtgt acatcgtgat cgagatcgcc    600
cgcggcaact aagagcactg gacgcccac cgccccttc cctccgctgc caggcgagca     660
tgttgtggta attctggaac acaagaagag aaattgctgg gtttagaaca agattataaa    720
cgaattcggt gctcagtgat cacttgacag tttttttttt ttttaaatat tacccaaaat    780
gctccccaaa taagaaatgc atcagctcag tcagtgaata caaaaaagga attattttc     840
cctttgaggg tcttttatac atctctcctc caaccccacc ctctattctg tttcttcctc    900
ctcacatggg ggtacacata cacagcttcc tcttttggtt ccatccttac caccacacca    960
cacgcacact ccacatgccc agcagagtgg cacttggtgg ccagaaagtg tgagcctcat   1020
gatctgctgt ctgtagttct gtgagctcag gtccctcaaa ggcctcggag cacccccttc   1080
cttgtgactg agccagggcc tgcattttg gttttcccca ccccacacat tctcaaccat    1140
agtccttcta acaataccaa tagctaggac ccggctgctg tgcactggga ctggggattc   1200
cacatgtttg ccttgggagt ctcaagctgg actgcca                            1237
```

<210> SEQ ID NO 67
<211> LENGTH: 2463
<212> TYPE: DNA
<213> ORGANISM: Artificial Sequence
<220> FEATURE:
<223> OTHER INFORMATION: COX8-ND1-3'UTR

<400> SEQUENCE: 67

```
atgtccgtcc tgacgcgcct gctgctgcgg ggcttgacac ggctcggctc ggcggctcca     60
gtgcggcgcg ccagaatcca ttcgttgatg gccaacctcc tactcctcat tgtacccatt    120
ctaatcgcaa tggcattcct aatgcttacc gaacgaaaaa ttctaggcta tatgcaacta    180
cgcaaaggcc ccaacgttgt aggcccctac gggctactac aacccttcgc tgacgccata    240
aaactcttca ccaaagagcc cctaaaaccc gccacatcta ccatcaccct ctacatcacc    300
gccccgacct tagctctcac catcgctctt ctactatgga ccccctccc catgcccaac    360
cccctggtca acctcaacct aggcctccta tttattctag ccacctctag cctagccgtt    420
tactcaatcc tctggtcagg gtgggcatca aactcaaact acgccctgat cggcgcactg    480
cgagcagtag cccaaacaat ctcatatgaa gtcaccctag ccatcattct actatcaaca    540
ttactaatga gtggctcctt taacctctcc acccttatca acacaaga acacctctgg     600
ttactcctgc catcatggcc cttggccatg atgtggttta ctccacact agcagagacc    660
aaccgaaccc ccttcgacct tgccgaaggg gagtccgaac tagtctcagg cttcaacatc   720
gaatacgccg caggcccctt cgccctattc ttcatggccg aatacacaaa cattattatg    780
atgaacaccc tcaccactac aatcttccta ggaacaacat atgacgcact ctcccctgaa    840
ctctacacaa catattttgt caccaagacc ctacttctaa cctcctgtt cttatggatt    900
cgaacagcat accccgatt ccgctacgac caactcatgc acctcctatg gaaaaacttc    960
ctaccactca ccctagcatt acttatgtgg tatgtctcca tgcccattac aatctccagc   1020
attcccctc aaacctaaga gcactggac gccaccgcc ctttccctc cgctgccagg       1080
cgagcatgtt gtggtaattc tggaacacaa gaagagaaat tgctgggttt agaacaagat   1140
tataaacgaa ttcggtgctc agtgatcact tgacagtttt ttttttttt aaatattacc    1200
```

| | |
|---|---|
| caaaatgctc cccaaataag aaatgcatca gctcagtcag tgaatacaaa aaaggaatta | 1260 |
| ttttccctt tgagggtctt ttatacatct ctcctccaac cccaccctct attctgtttc | 1320 |
| ttcctcctca catggggta cacatacaca gcttcctctt ttggttccat ccttaccacc | 1380 |
| acaccacacg cacactccac atgcccagca gagtggcact tggtggccag aaagtgtgag | 1440 |
| cctcatgatc tgctgtctgt agttctgtga gctcaggtcc ctcaaaggcc tcggagcacc | 1500 |
| cccttccttg tgactgagcc agggcctgca ttttggttt tccccacccc acacattctc | 1560 |
| aaccatagtc cttctaacaa taccaatagc taggacccgg ctgctgtgca ctgggactgg | 1620 |
| ggattccaca tgtttgcctt gggagtctca agctggactg ccagcccctg tcctcccttc | 1680 |
| accccattg cgtatgagca tttcagaact ccaaggagtc acaggcatct ttatagttca | 1740 |
| cgttaacata tagacactgt tggaagcagt tccttctaaa agggtagccc tggacttaat | 1800 |
| accagccgga tacctctggc ccccacccca ttactgtacc tctggagtca ctactgtggg | 1860 |
| tcgccactcc tctgctacac agcacggctt tttcaaggct gtattgagaa gggaagttag | 1920 |
| gaagaagggt gtgctgggct aaccagccca cagagctcac attcctgtcc cttgggtgaa | 1980 |
| aaatacatgt ccatcctgat atctcctgaa ttcagaaatt agcctccaca tgtgcaatgg | 2040 |
| ctttaagagc cagaagcagg gttctgggaa ttttgcaagt tacctgtggc caggtgtggt | 2100 |
| ctcggttacc aaatacggtt acctgcagct ttttagtcct ttgtgctccc acgggtctac | 2160 |
| agagtcccat ctgcccaaag gtcttgaagc ttgacaggat gttttcgatt actcagtctc | 2220 |
| ccagggcact actggtccgt aggattcgat tggtcgggt aggagagtta aacaacattt | 2280 |
| aaacagagtt ctctcaaaaa tgtctaaagg gattgtaggt agataacatc caatcactgt | 2340 |
| ttgcacttat ctgaaatctt ccctcttggc tgccccagg tatttactgt ggagaacatt | 2400 |
| gcataggaat gtctggaaaa agcttctaca acttgttaca gccttcacat ttgtagaagc | 2460 |
| ttt | 2463 |

<210> SEQ ID NO 68
<211> LENGTH: 1663
<212> TYPE: DNA
<213> ORGANISM: Artificial Sequence
<220> FEATURE:
<223> OTHER INFORMATION: COX8-ND1-3'UTR*

<400> SEQUENCE: 68

| | |
|---|---|
| atgtccgtcc tgacgcgcct gctgctgcgg ggcttgacac ggctcggctc ggcggctcca | 60 |
| gtgcggcgcg ccagaatcca ttcgttgatg gccaacctcc tactcctcat tgtacccatt | 120 |
| ctaatcgcaa tggcattcct aatgcttacc gaacgaaaaa ttctaggcta tatgcaacta | 180 |
| cgcaaaggcc ccaacgttgt aggcccctac gggctactac aacccttcgc tgacgccata | 240 |
| aaactcttca ccaaagagcc cctaaaaccc gccacatcta ccatcaccct ctacatcacc | 300 |
| gccccgacct tagctctcac catcgctctt ctactatgga ccccctccc catgcccaac | 360 |
| cccctggtca acctcaacct aggcctccta tttattctag ccacctctag cctagccgtt | 420 |
| tactcaatcc tctggtcagg gtgggcatca aactcaaact acgccctgat cggcgcactg | 480 |
| cgagcagtag cccaaacaat ctcatatgaa gtcaccctag ccatcattct actatcaaca | 540 |
| ttactaatga gtggctcctt taacctctcc acccttatca aacacaaga cacctctgg | 600 |
| ttactcctgc catcatggcc cttggccatg atgtggttta tctccacact agcagagacc | 660 |
| aaccgaaccc ccttcgacct tgccgaaggg gagtccgaac tagtctcagg cttcaacatc | 720 |

```
gaatacgccg caggccccett cgccctattc ttcatggccg aatacacaaa cattattatg    780
atgaacaccc tcaccactac aatcttccta ggaacaacat atgacgcact ctcccctgaa    840
ctctacacaa catatttgt caccaagacc ctacttctaa cctccctgtt cttatggatt     900
cgaacagcat accccgatt ccgctacgac caactcatgc acctcctatg gaaaaacttc     960
ctaccactca ccctagcatt acttatgtgg tatgtctcca tgcccattac aatctccagc   1020
attcccctc aaacctaaga gcactgggac gccaccgcc cctttccctc cgctgccagg     1080
cgagcatgtt gtggtaattc tggaacacaa gaagagaaat tgctgggttt agaacaagat   1140
tataaacgaa ttcggtgctc agtgatcact tgacagtttt ttttttttt aaatattacc    1200
caaaatgctc cccaaataag aaatgcatca gctcagtcag tgaatacaaa aaaggaatta   1260
ttttcccctt tgagggtctt ttatacatct ctcctccaac cccaccctct attctgtttc   1320
ttcctcctca catgggggta cacatacaca gcttcctctt ttggttccat ccttaccacc   1380
acaccacacg cacactccac atgcccagca gagtggcact tggtggccag aaagtgtgag   1440
cctcatgatc tgctgtctgt agttctgtga gctcaggtcc ctcaaaggcc tcggagcacc   1500
cccttccttg tgactgagcc agggcctgca ttttggtttt tccccacccc acacattctc   1560
aaccatagtc cttctaacaa taccaatagc taggacccgg ctgctgtgca ctgggactgg   1620
ggattccaca tgtttgcctt gggagtctca agctggactg cca                    1663
```

<210> SEQ ID NO 69  
<211> LENGTH: 2463  
<212> TYPE: DNA  
<213> ORGANISM: Artificial Sequence  
<220> FEATURE:  
<223> OTHER INFORMATION: COX8-opt_ND1-3'UTR

<400> SEQUENCE: 69

```
atgtccgtcc tgacgcgcct gctgctgcgg ggcttgacac ggctcggctc ggcggctcca    60
gtgcggcgcg ccagaatcca ttcgttgatg gccaacctgc tgctgctgat cgtgcccatc   120
ctgatcgcca tggccttcct gatgctgacc gagcgcaaga tcctgggcta catgcagctg   180
cgcaagggcc ccaacgtggt gggccctac ggctgctgc agcccttcgc cgacgccatc    240
aagctgttca ccaaggagcc cctgaagccc gccaccagca ccatcaccct gtacatcacc    300
gccccacc tggccctgac catcgccctg ctgctgtgga cccccctgcc catgcccaac    360
cccctggtga acctgaacct gggcctgctg ttcatcctgg ccaccagcag cctggccgtg   420
tacagcatcc tgtggagcgg ctgggccagc aacagcaact acgccctgat cggcgccctg   480
cgcgccgtgg cccagaccat cagctacgag gtgaccctgg ccatcatcct gctgagcacc   540
ctgctgatga cggcagctt caacctgagc accctgatca ccacccagga gcacctgtgg   600
ctgctgctgc ccagctggcc cctggccatg atgtggttca tcagcacccct ggccgagacc   660
aaccgcaccc ccttcgacct ggccgagggc gagagcgagc tggtgagcgg cttcaacatc   720
gagtacgccg ccggcccctt cgccctgttc ttcatggccg agtacaccaa catcatcatg    780
atgaacaccc tgaccaccac catcttcctg gcaccacct acgacgccct gagccccgag    840
ctgtacacca cctacttcgt gaccaagacc ctgctgctga ccagcctgtt cctgtggatc    900
cgcaccgcct accccgctt ccgctacgac cagctgatgc acctgctgtg gaagaacttc    960
ctgcccctga ccctggccct gctgatgtgg tacgtgagca tgcccatcac catcagcagc   1020
atccccccc agacctaaga gcactgggac gccaccgcc cctttccctc cgctgccagg    1080
cgagcatgtt gtggtaattc tggaacacaa gaagagaaat tgctgggttt agaacaagat   1140
```

```
tataaacgaa ttcggtgctc agtgatcact tgacagtttt tttttttttt aaatattacc   1200
caaaatgctc cccaaataag aaatgcatca gctcagtcag tgaatacaaa aaaggaatta   1260
tttttccctt tgagggtctt ttatacatct ctcctccaac cccaccctct attctgtttc   1320
ttcctcctca catgggggta cacatacaca gcttcctctt ttggttccat ccttaccacc   1380
acaccacacg cacactccac atgcccagca gagtggcact tggtggccag aaagtgtgag   1440
cctcatgatc tgctgtctgt agttctgtga gctcaggtcc ctcaaaggcc tcggagcacc   1500
cccttccttg tgactgagcc agggcctgca ttttggtttt tccccacccc acacattctc   1560
aaccatagtc cttctaacaa taccaatagc taggacccgg ctgctgtgca ctgggactgg   1620
ggattccaca tgtttgcctt gggagtctca agctggactg ccagcccctg tcctcccttc   1680 accccattg cgtatgagca tttcagaact ccaaggagtc acaggcatct ttatagttca   1740
cgttaacata tagacactgt tggaagcagt tccttctaaa agggtagccc tggacttaat   1800
accagccgga tacctctggc ccccacccca ttactgtacc tctggagtca ctactgtggg   1860
tcgccactcc tctgctacac agcacggctt tttcaaggct gtattgagaa gggaagttag   1920
gaagaagggt gtgctgggct aaccagccca cagagctcac attcctgtcc cttgggtgaa   1980
aaatacatgt ccatcctgat atctcctgaa ttcagaaatt agcctccaca tgtgcaatgg   2040
ctttaagagc cagaagcagg gttctgggaa ttttgcaagt tacctgtggc caggtgtggt   2100
ctcggttacc aaatacggtt acctgcagct ttttagtcct ttgtgctccc acgggtctac   2160
agagtcccat ctgcccaaag gtcttgaagc ttgacaggat gttttcgatt actcagtctc   2220
ccagggcact actggtccgt aggattcgat tggtcggggt aggagagtta acaacatt    2280 aaacagagtt ctctcaaaaa tgtctaaagg gattgtaggt agataacatc caatcactgt   2340
ttgcacttat ctgaaatctt ccctcttggc tgccccagg  tatttactgt ggagaacatt   2400
gcataggaat gtctggaaaa agcttctaca acttgttaca gccttcacat ttgtagaagc   2460
ttt                                                                 2463

<210> SEQ ID NO 70
<211> LENGTH: 1663
<212> TYPE: DNA
<213> ORGANISM: Artificial Sequence
<220> FEATURE:
<223> OTHER INFORMATION: COX8-opt_ND1-3'UTR*

<400> SEQUENCE: 70
atgtccgtcc tgacgcgcct gctgctgcgg ggcttgacac ggctcggctc ggcggctcca     60
gtgcggcgcg ccagaatcca ttcgttgatg gccaacctgc tgctgctgat cgtgcccatc    120
ctgatcgcca tggccttcct gatgctgacc gagcgcaaga tcctgggcta catgcagctg    180
cgcaagggcc ccaacgtggt gggcccctac ggcctgctgc agcccttcgc cgacgccatc    240
aagctgttca ccaaggagcc cctgaagccc gccaccagca ccatcaccct gtacatcacc    300
gcccccaccc tggccctgac catcgccctg ctgctgtgga ccccctgcc catgcccaac    360 cccctggtga acctgaacct gggcctgctg ttcatcctgg ccaccagcag cctggccgtg    420
tacagcatcc tgtggagcgg ctgggccagc aacagcaact acgccctgat cggcgccctg    480
cgcgccgtgg cccagaccat cagctacgag gtgaccctgg ccatcatcct gctgagcacc    540
ctgctgatga cgcgcagctt caacctgagc accctgatca ccacccagga gcacctgtgg    600
ctgctgctgc ccagctggcc cctggccatg atgtggttca tcagcaccct ggccgagacc    660
```

| | |
|---|---|
| aaccgcaccc ccttcgacct ggccgagggc gagagcgagc tggtgagcgg cttcaacatc | 720 |
| gagtacgccg ccggccccTT cgccctgttc ttcatggccg agtacaccaa catcatcatg | 780 |
| atgaacaccc tgaccaccac catcttcctg ggcaccacct acgacgccct gagccccgag | 840 |
| ctgtacacca cctacttcgt gaccaagacc ctgctgctga ccagcctgtt cctgtggatc | 900 |
| cgcaccgcct accccgcTT ccgctacgac cagctgatgc acctgctgtg gaagaacttc | 960 |
| ctgcccctga ccctggccct gctgatgtgg tacgtgagca tgcccatcac catcagcagc | 1020 |
| atccccccccc agacctaaga gcactgggac gcccaccgcc cctttccctc cgctgccagg | 1080 |
| cgagcatgtt gtggtaattc tggaacacaa gaagagaaat tgctgggttt agaacaagat | 1140 |
| tataaacgaa ttcggtgctc agtgatcact tgacagtttt ttttttttt aaatattacc | 1200 |
| caaaatgctc cccaaataag aaatgcatca gctcagtcag tgaatacaaa aaaggaatta | 1260 |
| ttttTCCCTT tgagggtctt ttatacatct ctcctccaac cccacccTCT attctgtttc | 1320 |
| ttcctcctca catgggggta cacatacaca gcttcctctt ttggttccat ccttaccacc | 1380 |
| acaccacacg cacactccac atgcccagca gagtggcact tggtggccag aaagtgtgag | 1440 |
| cctcatgatc tgctgtctgt agttctgtga gctcaggtcc ctcaaaggcc tcggagcacc | 1500 |
| cccttccTTg tgactgagcc agggcctgca ttTTTggTTT tccccacccc acacattctc | 1560 |
| aaccatagtc cttctaacaa taccaatagc taggacccgg ctgctgtgca ctgggactgg | 1620 |
| ggattccaca tgtttgcctt gggagtctca agctggactg cca | 1663 |

<210> SEQ ID NO 71
<211> LENGTH: 3071
<212> TYPE: DNA
<213> ORGANISM: Artificial Sequence
<220> FEATURE:
<223> OTHER INFORMATION: OPA1-ND4-3'UTR

<400> SEQUENCE: 71

| | |
|---|---|
| gtgctgcccg cctagaaagg gtgaagtggt tgtttccgtg acggactgag tacgggtgcc | 60 |
| tgtcaggctc ttgcggaagt ccatgcgcca ttgggagggc ctcggccgcg gctctgtgcc | 120 |
| cttgctgctg agggccactt cctgggtcat tcctggaccg ggagccgggc tggggctcac | 180 |
| acggggctc ccgcgtggcc gtctcggcgc ctgcgtgacc tccccgccgg cgggatgtgg | 240 |
| cgactacgtc gggccgctgt ggcctgatgc taaaactaat cgtcccaaca attatgttac | 300 |
| taccactgac atggctttcc aaaaaacaca tgatttggat caacacaacc acccacagcc | 360 |
| taattattag catcatccct ctactatttt ttaaccaaat caacaacaac ctatttagct | 420 |
| gttccccaac cttttcctcc gaccccctaa caaccccccT cctaatgcta actacctggc | 480 |
| tcctaccccT cacaatcatg gcaagccaac gccacttatc cagtgaacca ctatcacgaa | 540 |
| aaaaactcta cctctctatg ctaatctccc tacaaatctc cttaattatg acattcacag | 600 |
| ccacagaact aatcatgttt tatatcttct tcgaaccac acttatcccc accttggcta | 660 |
| tcatcacccg atggggcaac cagccagaac gcctgaacgc aggcacatac ttcctattct | 720 |
| acaccctagt aggctcccTT cccctactca tcgcactaat ttacactcac aacaccctag | 780 |
| gctcactaaa cattctacta ctcactctca ctgcccaaga actatcaaac tcctgggcca | 840 |
| acaacttaat gtggctagct tacacaatgg cttttatggt aaagatgcct ctttacggac | 900 |
| tccacttatg gctccctaaa gcccatgtcg aagcccccat cgctgggtca atggtacttg | 960 |
| ccgcagtact cttaaaacta ggcggctatg gtatgatgcg cctcacactc attctcaacc | 1020 |
| ccctgacaaa acacatggcc taccccttcc ttgtactatc cctatggggc atgattatga | 1080 |

```
caagctccat ctgcctacga caaacagacc taaaatcgct cattgcatac tcttcaatca    1140
gccacatggc cctcgtagta acagccattc tcatccaaac cccctggagc ttcaccggcg    1200
cagtcattct catgatcgcc cacgggctta catcctcatt actattctgc ctagcaaact    1260
caaactacga acgcactcac agtcgcatca tgatcctctc tcaaggactt caaactctac    1320
tcccactaat ggcttttggt ggcttctag caagcctcgc taacctcgcc ttacccccca    1380
ctattaacct actgggagaa ctctctgtgc tagtaaccac gttctcctgg tcaaatatca    1440
ctctcctact tacaggactc aacatgctag tcacagccct atactccctc tacatgttta    1500
ccacaacaca atggggctca ctcacccacc acattaacaa catgaaaccc tcattcacac    1560
gagaaaacac cctcatgttc atgcacctat cccccattct cctcctatcc ctcaaccccg    1620
acatcattac cgggttttcc tcttaagagc actgggacgc ccaccgcccc tttccctccg    1680
ctgccaggcg agcatgttgt ggtaattctg aacacaaga agagaaattg ctgggtttag    1740
aacaagatta taaacgaatt cggtgctcag tgatcacttg acagtttttt ttttttttaa    1800
atattaccca aaatgctccc caaataagaa atgcatcagc tcagtcagtg aatacaaaaa    1860
aggaattatt tttcccttg agggtctttt atacatctct cctccaaccc caccctctat    1920
tctgtttctt cctcctcaca tgggggtaca catacacagc ttcctctttt ggttccatcc    1980
ttaccaccac accacacgca cactccacat gcccagcaga gtggcacttg gtggccagaa    2040
agtgtgagcc tcatgatctg ctgtctgtag ttctgtgagc tcaggtccct caaaggcctc    2100
ggagcacccc cttccttgtg actgagccag ggcctgcatt tttggttttc cccacccac    2160 acattctcaa ccatagtcct tctaacaata ccaatagcta ggacccggct gctgtgcact    2220
gggactgggg attccacatg tttgccttgg gagtctcaag ctggactgcc agccctgtc    2280 ctcccttcac ccccattgcg tatgagcatt tcagaactcc aaggagtcac aggcatcttt    2340
atagttcacg ttaacatata gacactgttg gaagcagttc cttctaaaag ggtagccctg    2400
gacttaatac cagccggata cctctggccc ccaccccatt actgtacctc tggagtcact    2460
actgtgggtc gccactcctc tgctacacag cacggctttt tcaaggctgt attgagaagg    2520
gaagttagga agaagggtgt gctgggctaa ccagcccaca gagctcacat tcctgtccct    2580
tgggtgaaaa atacatgtcc atcctgatat ctcctgaatt cagaaattag cctccacatg    2640
tgcaatggct ttaagagcca gaagcagggt tctgggaatt ttgcaagtta cctgtggcca    2700
ggtgtggtct cggttaccaa atacggttac ctgcagcttt ttagtccttt gtgctcccac    2760
gggtctacag agtcccatct gcccaaaggt cttgaagctt gacaggatgt tttcgattac    2820
tcagtctccc agggcactac tggtccgtag gattcgattg gtcggggtag gagagttaaa    2880
caacatttaa acagagttct ctcaaaaatg tctaaaggga ttgtaggtag ataacatcca    2940
atcactgttt gcacttatct gaaatcttcc ctcttggctg cccccaggta tttactgtgg    3000
agaacattgc ataggaatgt ctggaaaaag cttctacaac ttgttacagc cttcacattt    3060
gtagaagctt t                                                        3071
```

<210> SEQ ID NO 72
<211> LENGTH: 2271
<212> TYPE: DNA
<213> ORGANISM: Artificial Sequence
<220> FEATURE:
<223> OTHER INFORMATION: OPA1-ND4-3'UTR*

<400> SEQUENCE: 72

```
gtgctgcccg cctagaaagg gtgaagtggt tgtttccgtg acggactgag tacgggtgcc      60
tgtcaggctc ttgcggaagt ccatgcgcca ttgggagggc ctcggccgcg gctctgtgcc     120
cttgctgctg agggccactt cctgggtcat tcctggaccg ggagccgggc tggggctcac     180
acggggcctc ccgcgtggcc gtctcggcgc ctgcgtgacc tccccgccgg cgggatgtgg     240
cgactacgtc gggccgctgt ggcctgatgc taaaactaat cgtcccaaca attatgttac     300
taccactgac atggctttcc aaaaaacaca tgatttggat caacacaacc acccacagcc     360
taattattag catcatccct ctactatttt ttaaccaaat caacaacaac ctatttagct     420
gttccccaac cttttcctcc gaccccctaa caacccccct cctaatgcta actacctggc     480
tcctacccct cacaatcatg gcaagccaac gccacttatc cagtgaacca ctatcacgaa     540
aaaaactcta cctctctatg ctaatctccc tacaaatctc cttaattatg acattcacag     600
ccacagaact aatcatgttt tatatcttct tcgaaaccac acttatcccc accttggcta     660
tcatcacccg atggggcaac cagccagaac gcctgaacgc aggcacatac ttcctattct     720
acaccctagt aggctccctt cccctactca tcgcactaat ttacactcac aacaccctag     780
gctcactaaa cattctacta ctcactctca ctgcccaaga actatcaaac tcctgggcca     840
acaacttaat gtggctagct tacacaatgg cttttatggt aaagatgcct ctttacggac     900
tccacttatg gctccctaaa gcccatgtcg aagcccccat cgctgggtca atggtacttg     960
ccgcagtact cttaaaacta ggcggctatg gtatgatgcg cctcacactc attctcaacc    1020
ccctgacaaa acacatggcc taccccttcc ttgtactatc cctatggggc atgattatga    1080
caagctccat ctgcctacga caaacagacc taaaatcgct cattgcatac tcttcaatca    1140
gccacatggc cctcgtagta acagccattc tcatccaaac ccctggagc ttcaccggcg    1200
cagtcattct catgatcgcc cacgggctta catcctcatt actattctgc ctagcaaact    1260
caaactacga acgcactcac agtcgcatca tgatcctctc tcaaggactt caaactctac    1320
tcccactaat ggcttttttgg tggcttctag caagcctcgc taacctcgcc ttaccccca    1380
ctattaacct actgggagaa ctctctgtgc tagtaaccac gttctcctgg tcaaatatca    1440
ctctcctact tacaggactc aacatgctag tcacagccct atactccctc tacatgttta    1500
ccacaacaca atgggctca ctcacccacc acattaacaa catgaaaccc tcattcacac    1560
gagaaaacac cctcatgttc atgcacctat ccccattct cctcctatcc ctcaaccccg    1620
acatcattac cgggttttcc tcttaagagc actgggacgc ccaccgcccc tttccctccg    1680
ctgccaggcg agcatgttgt ggtaattctg gaacacaaga agagaaattg ctgggtttag    1740
aacaagatta taaacgaatt cggtgctcag tgatcacttg acagtttttt ttttttttaa    1800
atattaccca aaatgctccc caaataagaa atgcatcagc tcagtcagtg aatacaaaaa    1860
aggaattatt tttcccttg agggtctttt atacatctct cctccaaccc caccctctat    1920
tctgtttctt cctcctcaca tgggggtaca catacacagc ttcctctttt ggttccatcc    1980
ttaccaccac accacacgca cactccacat gcccagcaga gtggcacttg gtggccagaa    2040
agtgtgagcc tcatgatctg ctgtctgtag ttctgtgagc tcaggtccct caaaggcctc    2100
ggagcacccc cttccttgtg actgagccag ggcctgcatt tttggttttc cccaccccac    2160
acattctcaa ccatagtcct tctaacaata ccaatagcta ggacccggct gctgtgcact    2220
gggactgggg attccacatg tttgccttgg gagtctcaag ctggactgcc a             2271
```

<210> SEQ ID NO 73
<211> LENGTH: 3071

<212> TYPE: DNA
<213> ORGANISM: Artificial Sequence
<220> FEATURE:
<223> OTHER INFORMATION: OPA1-opt_ND4-3'UTR

<400> SEQUENCE: 73

| | | | | | |
|---|---|---|---|---|---|
| gtgctgcccg | cctagaaagg | gtgaagtggt | tgtttccgtg | acggactgag | tacgggtgcc | 60 |
| tgtcaggctc | ttgcggaagt | ccatgcgcca | ttgggagggc | ctcggccgcg | gctctgtgcc | 120 |
| cttgctgctg | agggccactt | cctgggtcat | tcctggaccg | ggagccgggc | tggggctcac | 180 |
| acggggggctc | ccgcgtggcc | gtctcggcgc | ctgcgtgacc | tccccgccgg | cgggatgtgg | 240 |
| cgactacgtc | gggccgctgt | ggcctgatgc | tgaagctgat | cgtgcccacc | atcatgctgc | 300 |
| tgcctctgac | ctggctgagc | aagaaacaca | tgatctggat | caacaccacc | acgcacagcc | 360 |
| tgatcatcag | catcatccct | ctgctgttct | tcaaccagat | caacaacaac | ctgttcagct | 420 |
| gcagccccac | cttcagcagc | gaccctctga | caacacctct | gctgatgctg | accacctggc | 480 |
| tgctgccccct | cacaatcatg | gcctctcaga | gacacctgag | cagcgagccc | ctgagccgga | 540 |
| agaaactgta | cctgagcatg | ctgatctccc | tgcagatctc | tctgatcatg | accttcaccg | 600 |
| ccaccgagct | gatcatgttc | tacatctttt | tcgagacaac | gctgatcccc | acactggcca | 660 |
| tcatcaccag | atggggcaac | cagcctgaga | gactgaacgc | cggcacctac | tttctgttct | 720 |
| acacccctcgt | gggcagcctg | ccactgctga | ttgccctgat | ctacacccac | aacaccctgg | 780 |
| gctcccctgaa | catcctgctg | ctgacactga | gcccaagag | ctgagcaac | agctgggcca | 840 |
| acaatctgat | gtggctggcc | tacacaatgg | ccttcatggt | caagatgccc | ctgtacggcc | 900 |
| tgcacctgtg | gctgcctaaa | gctcatgtgg | aagcccctat | cgccggctct | atggtgctgg | 960 |
| ctgcagtgct | gctgaaactc | ggcggctacg | gcatgatgcg | gctgacccctg | attctgaatc | 1020 |
| ccctgaccaa | gcacatggcc | tatccatttc | tggtgctgag | cctgtggggc | atgattatga | 1080 |
| ccagcagcat | ctgcctgcgg | cagaccgatc | tgaagtccct | gatcgcctac | agctccatca | 1140 |
| gccacatggc | cctggtggtc | accgccatcc | tgattcagac | cccttggagc | tttacaggcg | 1200 |
| ccgtgatcct | gatgattgcc | cacggcctga | caagcagcct | gctgttttgt | ctggccaaca | 1260 |
| gcaactacga | gcggacccac | agcagaatca | tgatcctgtc | tcagggcctg | cagaccctcc | 1320 |
| tgcctcttat | ggcttttttgg | tggctgctgg | cctctctggc | caatctggca | ctgcctccta | 1380 |
| ccatcaatct | gctgggcgag | ctgagcgtgc | tggtcaccac | attcagctgg | tccaatatca | 1440 |
| ccctgctgct | caccggcctg | aacatgctgg | ttacagccct | gtactccctg | tacatgttca | 1500 |
| ccaccacaca | gtggggaagc | ctgacacacc | acatcaacaa | tatgaagccc | agcttcaccc | 1560 |
| gcgagaacac | cctgatgttc | atgcatctga | gccccattct | gctgctgtcc | ctgaatcctg | 1620 |
| atatcatcac | cggcttctcc | agctgagagc | actgggacgc | ccaccgcccc | tttccctccg | 1680 |
| ctgccaggcg | agcatgttgt | ggtaattctg | gaacacaaga | agagaaattg | ctgggtttag | 1740 |
| aacaagatta | taaacgaatt | cggtgctcag | tgatcacttg | acagtttttt | ttttttttaa | 1800 |
| atattaccca | aaatgctccc | caaataagaa | atgcatcagc | tcagtcagtg | aatacaaaaa | 1860 |
| aggaattatt | tttcccttttg | agggtctttt | atacatctct | cctccaaccc | caccctctat | 1920 |
| tctgtttctt | cctcctcaca | tgggggtaca | catacacagc | ttcctcttttt | ggttccatcc | 1980 |
| ttaccaccac | accacacgca | cactccacat | gcccagcaga | gtggcacttg | gtggccagaa | 2040 |
| agtgtgagcc | tcatgatctg | ctgtctgtag | ttctgtgagc | tcaggtccct | caaaggcctc | 2100 |
| ggagcacccc | cttccttgtg | actgagccag | ggcctgcatt | tttggttttc | cccacccccac | 2160 |

| | |
|---|---|
| acattctcaa ccatagtcct tctaacaata ccaatagcta ggacccggct gctgtgcact | 2220 |
| gggactgggg attccacatg tttgccttgg gagtctcaag ctggactgcc agccctgtc | 2280 |
| ctcccttcac ccccattgcg tatgagcatt tcagaactcc aaggagtcac aggcatcttt | 2340 |
| atagttcacg ttaacatata gacactgttg gaagcagttc cttctaaaag ggtagccctg | 2400 |
| gacttaatac cagccggata cctctggccc ccaccccatt actgtacctc tggagtcact | 2460 |
| actgtgggtc gccactcctc tgctacacag cacggctttt tcaaggctgt attgagaagg | 2520 |
| gaagttagga agaagggtgt gctgggctaa ccagcccaca gagctcacat tcctgtccct | 2580 |
| tgggtgaaaa atacatgtcc atcctgatat ctcctgaatt cagaaattag cctccacatg | 2640 |
| tgcaatggct ttaagagcca gaagcagggt tctgggaatt ttgcaagtta cctgtggcca | 2700 |
| ggtgtggtct cggttaccaa atacggttac ctgcagcttt ttagtccttt gtgctcccac | 2760 |
| gggtctacag agtcccatct gcccaaaggt cttgaagctt gacaggatgt tttcgattac | 2820 |
| tcagtctccc agggcactac tggtcctag gattcgattg gtcggggtag gagagttaaa | 2880 |
| caacatttaa acagagttct ctcaaaaatg tctaaaggga ttgtaggtag ataacatcca | 2940 |
| atcactgttt gcacttatct gaaatcttcc ctcttggctg cccccaggta tttactgtgg | 3000 |
| agaacattgc ataggaatgt ctggaaaaag cttctacaac ttgttacagc cttcacattt | 3060 |
| gtagaagctt t | 3071 |

<210> SEQ ID NO 74
<211> LENGTH: 2271
<212> TYPE: DNA
<213> ORGANISM: Artificial Sequence
<220> FEATURE:
<223> OTHER INFORMATION: OPA1-opt_ND4-3'UTR*

<400> SEQUENCE: 74

| | |
|---|---|
| gtgctgcccg cctagaaagg gtgaagtggt tgtttccgtg acggactgag tacgggtgcc | 60 |
| tgtcaggctc ttgcggaagt ccatgcgcca ttgggagggc ctcggccgcg gctctgtgcc | 120 |
| cttgctgctg agggccactt cctgggtcat tcctggaccg ggagccgggc tggggctcac | 180 |
| acggggctc ccgcgtggcc gtctcggcgc ctgcgtgacc tccccgccgg cgggatgtgg | 240 |
| cgactacgtc gggccgctgt ggcctgatgc tgaagctgat cgtgcccacc atcatgctgc | 300 |
| tgcctctgac ctggctgagc aagaaacaca tgatctggat caacaccacc acgcacagcc | 360 |
| tgatcatcag catcatccct ctgctgttct tcaaccagat caacaacaac ctgttcagct | 420 |
| gcagccccac cttcagcagc gaccctctga acacacctct gctgatgctg accacctggc | 480 |
| tgctgccct cacaatcatg gcctctcaga gacacctgag cagcgagccc ctgagccgga | 540 |
| agaaactgta cctgagcatg ctgatctccc tgcagatctc tctgatcatg accttcaccg | 600 |
| ccaccgagct gatcatgttc tacatctttt tcgagacaac gctgatcccc acactggcca | 660 |
| tcatcaccag atggggcaac cagcctgaga gactgaacgc cggcacctac tttctgttct | 720 |
| acaccctcgt gggcagcctg ccactgctga ttgccctgat ctacacccac aacacccctgg | 780 |
| gctccctgaa catcctgctg ctgacactga gcccaagac gctgagcaac agctgggcca | 840 |
| acaatctgat gtggctggcc tacacaatgg ccttcatggt caagatgccc ctgtacggcc | 900 |
| tgcacctgtg gctgcctaaa gctcatgtgg aagcccctat cgccggctct atggtgctgg | 960 |
| ctgcagtgct gctgaaactc ggcggctacg catgatgcg gctgaccctg attctgaatc | 1020 |
| ccctgaccaa gcacatggcc tatccatttc tggtgctgag cctgtggggc atgattatga | 1080 |
| ccagcagcat ctgcctgcgg cagaccgatc tgaagtccct gatcgcctac agctccatca | 1140 |

```
gccacatggc cctggtggtc accgccatcc tgattcagac cccttggagc tttacaggcg    1200
ccgtgatcct gatgattgcc cacggcctga caagcagcct gctgttttgt ctggccaaca    1260
gcaactacga gcggacccac agcagaatca tgatcctgtc tcagggcctg cagaccctcc    1320
tgcctcttat ggcttttttgg tggctgctgg cctctctggc caatctggca ctgcctccta    1380
ccatcaatct gctgggcgag ctgagcgtgc tggtcaccac attcagctgg tccaatatca    1440
ccctgctgct caccggcctg aacatgtggg ttacagccct gtactccctg tacatgttca    1500
ccaccacaca gtggggaagc ctgacacacc acatcaacaa tatgaagccc agcttcaccc    1560
gcgagaacac cctgatgttc atgcatctga gccccattct gctgctgtcc ctgaatcctg    1620
atatcatcac cggcttctcc agctgagagc actgggacgc ccaccgcccc tttccctccg    1680
ctgccaggcg agcatgttgt ggtaattctg aacacaagag agagaaattg ctgggtttag    1740
aacaagatta taaacgaatt cggtgctcag tgatcacttg acagtttttt tttttttaa     1800 atattaccca aaatgctccc caaataagaa atgcatcagc tcagtcagtg aatacaaaaa    1860
aggaattatt tttcccttttg agggtctttt atacatctct cctccaaccc caccctctat    1920
tctgtttctt cctcctcaca tgggggtaca catacacagc ttcctcttttt ggttccatcc    1980 ttaccaccac accacacgca cactccacat gcccagcaga gtggcacttg gtggccagaa    2040
agtgtgagcc tcatgatctg ctgtctgtag ttctgtgagc tcaggtccct caaaggcctc    2100
ggagcacccc cttccttgtg actgagccag ggcctgcatt tttggttttc cccacccac    2160 acattctcaa cctagtcct tctaacaata ccaatagcta ggacccggct gctgtgcact    2220
gggactgggg attccacatg tttgccttgg gagtctcaag ctggactgcc a              2271

<210> SEQ ID NO 75
<211> LENGTH: 3071
<212> TYPE: DNA
<213> ORGANISM: Artificial Sequence
<220> FEATURE:
<223> OTHER INFORMATION: OPA1-opt_ND4*-3'UTR

<400> SEQUENCE: 75
gtgctgcccg cctagaaagg gtgaagtggt tgtttccgtg acggactgag tacgggtgcc      60
tgtcaggctc ttgcggaagt ccatgcgcca ttgggagggc ctcggccgcg gctctgtgcc     120
cttgctgctg agggccactt cctgggtcat tcctggaccg ggagccgggc tggggctcac     180 acggggggctc ccgcgtggcc gtctcggcgc ctgcgtgacc tccccgccgg cgggatgtgg     240
cgactacgtc gggccgctgt ggcctgatgc tgaagctgat cgtgcccacc atcatgctgc     300 tgccccctgac ctggctgagc aagaagcaca tgatctggat caacaccacc acccacagcc    360
tgatcatcag catcatcccc ctgctgttct tcaaccagat caacaacaac ctgttcagct    420
gcagccccac cttcagcagc gacccctgga ccacccccct gctgatgctg accacctggc    480 tgctgccccct gaccatcatg gccagccagc gccacctgag cagcgagccc ctgagccgca    540
agaagctgta cctgagcatg ctgatcagcc tgcagatcag cctgatcatg accttcaccg    600
ccaccgagct gatcatgttc tacatcttct tcgagaccac cctgatcccc acctggccaa     660
tcatcacccg ctggggcaac cagcccgagc gcctgaacgc cggcacctac ttcctgttct    720
acaccctggt gggcagcctg ccctgctga tcgccctgat ctacacccac aacaccctgg    780
gcagcctgaa catcctgctg ctgacccctga ccgcccagga gctgagcaac agctgggcca    840
acaacctgat gtggctggcc tacaccatgg ccttcatggt gaagatgccc ctgtacggcc    900
```

```
tgcacctgtg gctgcccaag gcccacgtgg aggcccccat cgccggcagc atggtgctgg      960
ccgccgtgct gctgaagctg ggcggctacg gcatgatgcg cctgaccctg atcctgaacc     1020
ccctgaccaa gcacatggcc tacccctttcc tggtgctgag cctgtggggc atgatcatga    1080
ccagcagcat ctgcctgcgc cagaccgacc tgaagagcct gatcgcctac agcagcatca    1140
gccacatggc cctggtggtg accgccatcc tgatccagac ccctggagc ttcaccggcg      1200
ccgtgatcct gatgatcgcc cacggcctga ccagcagcct gctgttctgc ctggccaaca    1260
gcaactacga gcgcacccac agccgcatca tgatcctgag ccagggcctg cagaccctgc    1320
tgcccctgat ggccttctgg tggctgctgg ccagcctggc caacctggcc ctgcccccca    1380
ccatcaacct gctgggcgag ctgagcgtgc tggtgaccac cttcagctgg agcaacatca    1440
ccctgctgct gaccggcctg aacatgctgg tgaccgccct gtacagcctg tacatgttca    1500
ccaccaccca gtggggcagc ctgacccacc acatcaacaa catgaagccc agcttcaccc    1560
gcgagaacac cctgatgttc atgcacctga gccccatcct gctgctgagc ctgaaccccg    1620
acatcatcac cggcttcagc agctaagagc actgggacgc ccaccgcccc tttccctccg    1680
ctgccaggcg agcatgttgt ggtaattctg gaacacaaga agagaaattg ctgggtttag    1740
aacaagatta taaacgaatt cggtgctcag tgatcacttg acagtttttt tttttttaa     1800
atattaccca aaatgctccc caaataagaa atgcatcagc tcagtcagtg aatacaaaaa    1860
aggaattatt tttccctttg agggtctttt atacatctct cctccaaccc caccctctat    1920
tctgtttctt cctcctcaca tgggggtaca catacacagc ttcctctttt ggttccatcc    1980
ttaccaccac accacacgca cactccacat gcccagcaga gtggcacttg gtggccagaa    2040
agtgtgagcc tcatgatctg ctgtctgtag ttctgtgagc tcaggtccct caaaggcctc    2100
ggagcacccc cttccttgtg actgagccag ggcctgcatt tttggttttc cccacccac     2160
acattctcaa ccatagtcct tctaacaata ccaatagcta ggacccggct gctgtgcact    2220
gggactgggg attccacatg tttgccttgg gagtctcaag ctggactgcc agcccctgtc    2280
ctcccttcac ccccattgcg tatgagcatt tcagaactcc aaggagtcac aggcatcttt    2340
atagttcacg ttaacatata gacactgttg gaagcagttc cttctaaaag ggtagccctg    2400
gacttaatac cagccggata cctctggccc ccaccccatt actgtacctc tggagtcact    2460
actgtgggtc gccactcctc tgctacacag cacggctttt tcaaggctgt attgagaagg    2520
gaagttagga agaagggtgt gctgggctaa ccagcccaca gagctcacat tcctgtccct    2580
tgggtgaaaa atacatgtcc atcctgatat ctcctgaatt cagaaattag cctccacatg    2640
tgcaatggct ttaagagcca gaagcagggt tctgggaatt ttgcaagtta cctgtggcca    2700
ggtgtggtct cggttaccaa atacggttac ctgcagcttt ttagtccttt gtgctcccac    2760
gggtctacag agtcccatct gcccaaaggt cttgaagctt gacaggatgt tttcgattac    2820
tcagtctccc agggcactac tggtccgtag gattcgattg gtcggggtag gagagttaaa    2880
caacatttaa acagagttct ctcaaaaatg tctaaaggga ttgtaggtag ataacatcca    2940
atcactgttt gcacttatct gaaatcttcc ctcttggctg ccccccaggta tttactgtgg  3000
agaacattgc ataggaatgt ctggaaaaag cttctacaac ttgttacagc cttcacattt    3060
gtagaagctt t                                                          3071
```

<210> SEQ ID NO 76
<211> LENGTH: 2271
<212> TYPE: DNA
<213> ORGANISM: Artificial Sequence
<220> FEATURE:
<223> OTHER INFORMATION: OPA1-opt_ND4*-3'UTR*

<400> SEQUENCE: 76

```
gtgctgcccg cctagaaagg gtgaagtggt tgtttccgtg acggactgag tacgggtgcc    60
tgtcaggctc ttgcggaagt ccatgcgcca ttgggagggc ctcggccgcg gctctgtgcc   120
cttgctgctg agggccactt cctgggtcat tcctggaccg ggagccgggc tggggctcac   180
acggggctc ccgcgtggcc gtctcggcgc ctgcgtgacc tccccgccgg cgggatgtgg    240
cgactacgtc gggccgctgt ggcctgatgc tgaagctgat cgtgcccacc atcatgctgc   300
tgcccctgac ctggctgagc aagaagcaca tgatctggat caacaccacc cccacagcc   360
tgatcatcag catcatcccc ctgctgttct caaccagat caacaacaac ctgttcagct    420
gcagccccac cttcagcagc gaccccctga ccaccccct gctgatgctg accacctggc    480
tgctgcccct gaccatcatg ccagccagc gccacctgag cagcgagccc ctgagccgca    540
agaagctgta cctgagcatg ctgatcagcc tgcagatcag cctgatcatg accttcaccg    600
ccaccgagct gatcatgttc tacatcttct tcgagaccac cctgatcccc accctggcca   660
tcatcacccg ctgggggcaac cagcccgagc gcctgaacgc cggcacctac ttcctgttct   720
acaccctggt gggcagcctg cccctgctga tcgccctgat ctacacccac aacaccctgg   780
gcagcctgaa catcctgctg ctgacccctga ccgcccagga gctgagcaac agctgggcca   840
acaacctgat gtggctggcc tacaccatgg ccttcatggt gaagatgccc ctgtacggcc    900
tgcacctgtg gctgcccaag gcccacgtgg aggcccccat cgccggcagc atggtgctgg    960
ccgccgtgct gctgaagctg gcggctacg gcatgatgcg cctgaccctg atcctgaacc   1020
ccctgaccaa gcacatggcc tacccctccc tggtgctgag cctgtggggc atgatcatga   1080
ccagcagcat ctgcctgcgc cagaccgacc tgaagagcct gatcgcctac agcagcatca   1140
gccacatggc cctggtggtg accgccatcc tgatccagac ccctggagc ttcaccggcg    1200
ccgtgatcct gatgatcgcc cacggcctga ccagcagcct gctgttctgc ctggccaaca   1260
gcaactacga gcgcacccac agccgcatca tgatcctgag ccagggcctg cagaccctgc   1320
tgccctgat ggccttctgg tggctgctgg ccagcctggc caacctggcc ctgcccccca   1380
ccatcaacct gctgggcgag ctgagcgtgc tggtgaccac cttcagctgg agcaacatca   1440
ccctgctgct gaccggcctg aacatgctgg tgaccgccct gtacagctg tacatgttca    1500
ccaccaccca gtggggcagc ctgacccacc acatcaacaa catgaagccc agcttcaccc   1560
gcgagaacac cctgatgttc atgcacctga gcccccatcct gctgctgagc ctgaaccccg   1620
acatcatcac cggcttcagc agctaagagc actgggacgc ccaccgcccc ttccctccg    1680
ctgccaggcg agcatgttgt ggtaattctg aacacaaga agagaaattg ctgggtttag   1740
aacaagatta taaacgaatt cggtgctcag tgatcacttg acagtttttt tttttttaa   1800
atattaccca aaatgctccc caaataagaa atgcatcagc tcagtcagtg aatacaaaaa   1860
aggaattatt tttcccttttg agggtctttt atacatctct cctccaaccc caccctctat   1920
tctgtttctt cctcctcaca tgggggtaca catacacagc ttcctctttt ggttccatcc   1980
ttaccaccac accacacgca cactccacat gccagcaga gtggcacttg gtggccagaa    2040
agtgtgagcc tcatgatctg ctgtctgtag ttctgtgagc tcaggtccct caaaggcctc   2100
ggagcacccc cttccttgtg actgagccag ggcctgcatt tttggttttc ccacccac     2160
acattctcaa ccatagtcct tctaacaata ccaatagcta ggaccggct gctgtgcact    2220
```

```
gggactgggg attccacatg tttgccttgg gagtctcaag ctggactgcc a         2271
```

<210> SEQ ID NO 77
<211> LENGTH: 2216
<212> TYPE: DNA
<213> ORGANISM: Artificial Sequence
<220> FEATURE:
<223> OTHER INFORMATION: OPA1-ND6-3'UTR

<400> SEQUENCE: 77

```
gtgctgcccg cctagaaagg gtgaagtggt tgtttccgtg acggactgag tacgggtgcc    60
tgtcaggctc ttgcggaagt ccatgcgcca ttgggagggc ctcggccgcg gctctgtgcc   120
cttgctgctg agggccactt cctgggtcat tcctggaccg ggagccgggc tggggctcac   180
acggggcctc ccgcgtggcc gtctcggcgc ctgcgtgacc tccccgccgg cgggatgtgg   240
cgactacgtc gggccgctgt ggcctgatga tgtatgcttt gtttctgttg agtgtgggtt   300
tagtaatggg gtttgtgggg ttttcttcta agccttctcc tatttatggg ggtttagtat   360
tgattgttag cggtgtggtc gggtgtgtta ttattctgaa ttttggggga ggttatatgg   420
gtttaatggt ttttttaatt tatttagggg gaatgatggt tgtctttgga tatactacag   480
cgatggctat tgaggagtat cctgaggcat gggggtcagg ggttgaggtc ttggtgagtg   540
ttttagtggg gttagcgatg gaggtaggat tggtgctgtg ggtgaaagag tatgatgggg   600
tggtggttgt ggtaaacttt aatagtgtag gaagctggat gatttatgaa ggagaggggg   660
cagggttgat tcgggaggat cctattggtg cgggggcttt gtatgattat gggcgttggt   720
tagtagtagt tactggttgg acattgtttg ttggtgtata tattgtaatt gagattgctc   780
gggggaatta ggagcactgg gacgcccacc gcccctttcc ctccgctgcc aggcgagcat   840
gttgtggtaa ttctggaaca caagaagaga aattgctggg tttagaacaa gattataaac   900
gaattcggtg ctcagtgatc acttgacagt tttttttttt tttaaatatt acccaaaatg   960
ctccccaaat aagaaatgca tcagctcagt cagtgaatac aaaaaaggaa ttattttttcc  1020
ctttgagggt cttttataca tctctcctcc aaccccaccc tctattctgt ttcttcctcc  1080
tcacatgggg gtacacatac acagcttcct cttttggttc catccttacc accacaccac  1140
acgcacactc cacatgccca gcagagtggc acttggtggc cagaaagtgt gagcctcatg  1200
atctgctgtc tgtagttctg tgagctcagg tccctcaaag gcctcggagc accccccttcc  1260
ttgtgactga gccagggcct gcatttttgg ttttccccac cccacacatt ctcaaccata  1320
gtccttctaa caataccaat agctaggacc cggctgctgt gcactgggac tggggattcc  1380
acatgtttgc cttgggagtc tcaagctgga ctgccagccc ctgtcctccc ttcaccccca  1440
ttgcgtatga gcatttcaga actccaagga gtcacaggca tctttatagt tcacgttaac  1500
atatagacac tgttggaagc agttccttct aaaagggtag ccctggactt aataccagcc  1560
ggatacctct ggcccccacc ccattactgt acctctggag tcactactgt gggtcgccac  1620
tcctctgcta cacagcacgg cttttttcaag gctgtattga gaagggaagt taggaagaag  1680
ggtgtgctgg gctaaccagc ccacagagct cacattcctg tcccttgggt gaaaaataca  1740
tgtccatcct gatatctcct gaattcagaa attagcctcc acatgtgcaa tggctttaag  1800
agccagaagc agggttctgg gaattttgca agttacctgt ggccaggtgt ggtctcggtt  1860
accaaatacg gttacctgca gctttttagt cctttgtgct cccacgggtc tacagagtcc  1920
catctgccca aaggtcttga agcttgacag gatgttttcg attactcagt ctcccagggc  1980
actactggtc cgtaggattc gattggtcgg ggtaggagag ttaaacaaca tttaaacaga  2040
```

```
gttctctcaa aaatgtctaa agggattgta ggtagataac atccaatcac tgtttgcact    2100
tatctgaaat cttccctctt ggctgccccc aggtatttac tgtggagaac attgcatagg    2160
aatgtctgga aaaagcttct acaacttgtt acagccttca catttgtaga agcttt         2216
```

<210> SEQ ID NO 78
<211> LENGTH: 1416
<212> TYPE: DNA
<213> ORGANISM: Artificial Sequence
<220> FEATURE:
<223> OTHER INFORMATION: OPA1-ND6-3'UTR*

<400> SEQUENCE: 78

```
gtgctgcccg cctagaaagg gtgaagtggt tgtttccgtg acggactgag tacgggtgcc      60
tgtcaggctc ttgcggaagt ccatgcgcca ttgggagggc ctcggccgcg gctctgtgcc    120
cttgctgctg agggccactt cctgggtcat tcctggaccg ggagccgggc tggggctcac    180 acggggctc ccgcgtggcc gtctcggcgc ctgcgtgacc tccccgccgg cgggatgtgg     240
cgactacgtc gggccgctgt ggcctgatga tgtatgcttt gtttctgttg agtgtgggtt    300
tagtaatggg gtttgtgggg ttttcttcta agccttctcc tatttatggg ggtttagtat    360
tgattgttag cggtgtggtc gggtgtgtta ttattctgaa ttttggggga ggttatatgg    420
gtttaatggg ttttttaatt tatttagggg gaatgatggt tgtctttgga tatactacag    480
cgatggctat tgaggagtat cctgaggcat gggggtcagg ggttgaggtc ttggtgagtg    540
ttttagtggg gttagcgatg gaggtaggat tggtgctgtg ggtgaaagag tatgatgggg    600
tggtggttgt ggtaaacttt aatagtgtag gaagctggat gatttatgaa ggagaggggt    660
cagggttgat tcgggaggat cctattggtg cggggctttt gtatgattat gggcgttggt    720
tagtagtagt tactggttgg acattgtttg ttggtgtata tattgtaatt gagattgctc    780
gggggaatta ggagcactgg gacgcccacc gccccttttcc ctccgctgcc aggcgagcat   840
gttgtggtaa ttctggaaca caagaagaga aattgctggg tttagaacaa gattataaac    900
gaattcggtg ctcagtgatc acttgacagt tttttttttt tttaaatatt acccaaaatg    960
ctccccaaat aagaaatgca tcagctcagt cagtgaatac aaaaaaggaa ttattttttcc   1020 cttttgagggt cttttataca tctctcctcc aaccccaccc tctattctgt ttcttcctcc   1080
tcacatgggg gtacacatac acagcttcct cttttggttc catccttacc accacaccac    1140
acgcacactc cacatgccca gcagagtggc acttggtggc cagaaagtgt gagcctcatg    1200
atctgctgtc tgtagttctg tgagctcagg tccctcaaag gctcggagc acccccttcc     1260 ttgtgactga gccagggcct gcattttttgg ttttccccac cccacacatt ctcaaccata   1320
gtccttctaa aataccaat agctaggacc cggctgctgt gcactgggac tggggattcc    1380
acatgtttgc cttgggagtc tcaagctgga ctgcca                               1416
```

<210> SEQ ID NO 79
<211> LENGTH: 2216
<212> TYPE: DNA
<213> ORGANISM: Artificial Sequence
<220> FEATURE:
<223> OTHER INFORMATION: OPA1-opt_ND6-3'UTR

<400> SEQUENCE: 79

```
gtgctgcccg cctagaaagg gtgaagtggt tgtttccgtg acggactgag tacgggtgcc      60
tgtcaggctc ttgcggaagt ccatgcgcca ttgggagggc ctcggccgcg gctctgtgcc    120
```

```
cttgctgctg agggccactt cctgggtcat tcctggaccg ggagccgggc tggggctcac    180 acggggctc ccgcgtggcc gtctcggcgc ctgcgtgacc tccccgccgg cgggatgtgg    240
cgactacgtc gggccgctgt ggcctgatga tgtacgccct gttcctgctg agcgtgggcc    300
tggtgatggg cttcgtgggc ttcagcagca agcccagccc catctacggc ggcctggtgc    360
tgatcgtgag cggcgtggtg ggctgcgtga tcatcctgaa cttcggcggc ggctacatgg    420
gcctgatggt gttcctgatc tacctgggcg gcatgatggt ggtgttcggc tacaccaccg    480
ccatggccat cgaggagtac cccgaggcct ggggcagcgg cgtggaggtg ctggtgagcg    540
tgctggtggg cctggccatg gaggtgggcc tggtgctgtg ggtgaaggag tacgacggcg    600
tggtggtggt ggtgaacttc aacagcgtgg gcagctggat gatctacgag ggcgagggca    660
gcggcctgat ccgcgaggac cccatcggcc cggcgccct gtacgactac ggccgctggc    720
tggtggtggt gaccggctgg accctgttcg tgggcgtgta catcgtgatc gagatcgccc    780
gcggcaacta gagcactgg gacgccacc gcccctttcc ctccgctgcc aggcgagcat    840
gttgtggtaa ttctggaaca caagaagaga aattgctggg tttagaacaa gattataaac    900
gaattcggtg ctcagtgatc acttgacagt tttttttttt tttaaatatt acccaaaatg    960
ctccccaaat aagaaatgca tcagctcagt cagtgaatac aaaaaaggaa ttattttcc   1020 ctttgagggt cttttataca tctctcctcc aaccccaccc tctattctgt ttcttcctcc   1080
tcacatgggg gtacacatac acagcttcct cttttggttc catccttacc accacaccac   1140
acgcacactc cacatgccca gcagagtggc acttggtggc cagaaagtgt gagcctcatg   1200
atctgctgtc tgtagttctg tgagctcagg tccctcaaag gcctcggagc accccttcc   1260 ttgtgactga gccagggcct gcatttttgg ttttccccac cccacacatt ctcaaccata   1320
gtccttctaa caataccaat agctaggacc cggctgctgt gcactgggac tggggattcc   1380
acatgtttgc cttgggagtc tcaagctgga ctgccagccc ctgtcctccc ttcaccccca   1440
ttgcgtatga gcatttcaga actccaagga gtcacaggca tctttatagt tcacgttaac   1500
atatagacac tgttggaagc agttccttct aaaagggtag ccctggactt aataccagcc   1560
ggatacctct ggcccccacc ccattactgt acctctggag tcactactgt gggtcgccac   1620
tcctctgcta cacagcacgg ctttttcaag gctgtattga aagggaagt taggaagaag   1680 ggtgtgctgg gctaaccagc ccacagagct cacattcctg tcccttgggt gaaaaataca   1740
tgtccatcct gatatctcct gaattcagaa attagcctcc acatgtgcaa tggctttaag   1800
agccagaagc agggttctgg gaattttgca agttacctgt ggccaggtgt ggtctcggtt   1860
accaaatacg gttacctgca gcttttttagt cctttgtgct cccacgggtc tacagagtcc   1920
catctgccca aaggtcttga agcttgacag gatgttttcg attactcagt ctcccagggc   1980
actactggtc cgtaggattc gattggtcgg ggtaggagag ttaaacaaca tttaaacaga   2040
gttctctcaa aaatgtctaa agggattgta ggtagataac atccaatcac tgtttgcact   2100
tatctgaaat cttccctctt ggctgccccc aggtatttac tgtggagaac attgcatagg   2160
aatgtctgga aaaagcttct acaacttgtt acagccttca catttgtaga agcttt       2216
```

<210> SEQ ID NO 80
<211> LENGTH: 1416
<212> TYPE: DNA
<213> ORGANISM: Artificial Sequence
<220> FEATURE:
<223> OTHER INFORMATION: OPA1-opt_ND6-3'UTR*

<400> SEQUENCE: 80

```
gtgctgcccg cctagaaagg gtgaagtggt tgtttccgtg acggactgag tacgggtgcc      60
tgtcaggctc ttgcggaagt ccatgcgcca ttgggagggc ctcggccgcg gctctgtgcc     120
cttgctgctg agggccactt cctgggtcat tcctggaccg ggagccgggc tggggctcac     180
acggggctc ccgcgtggcc gtctcggcgc ctgcgtgacc tccccgccgg cgggatgtgg      240
cgactacgtc gggccgctgt ggcctgatga tgtacgccct gttcctgctg agcgtgggcc     300
tggtgatggg cttcgtgggc ttcagcagca agcccagccc catctacggc ggcctggtgc     360
tgatcgtgag cggcgtggtg ggctgcgtga tcatcctgaa cttcggcggc ggctacatgg     420
gcctgatggt gttcctgatc tacctgggcg gcatgatggt ggtgttcggc tacaccaccg     480
ccatggccat cgaggagtac cccgaggcct ggggcagcgg cgtggaggtg ctggtgagcg     540
tgctggtggg cctggccatg gaggtgggcc tggtgctgtg ggtgaaggag tacgacggcg     600
tggtggtggt ggtgaacttc aacagcgtgg gcagctggat gatctacgag ggcgagggca     660
gcggcctgat ccgcgaggac cccatcgcg ccggcgccct gtacgactac ggccgctggc      720
tggtggtggt gaccggctgg accctgttcg tgggcgtgta catcgtgatc gagatcgccc     780
gcggcaacta agagcactgg gacgcccacc gccccttcc ctccgctgcc aggcgagcat      840
gttgtggtaa ttctggaaca caagaagaga aattgctggg tttagaacaa gattataaac     900
gaattcggtg ctcagtgatc acttgacagt ttttttttt tttaaatatt acccaaaatg      960
ctccccaaat aagaaatgca tcagctcagt cagtgaatac aaaaaaggaa ttatttttcc    1020
cttttgagggt ctttttataca tctctcctcc aacccaccc tctattctgt ttcttcctcc   1080
tcacatgggg gtacacatac acagcttcct cttttggttc catccttacc accacaccac   1140
acgcacactc cacatgccca gcagagtggc acttggtggc cagaaagtgt gagcctcatg   1200
atctgctgtc tgtagttctg tgagctcagg tccctcaaag gcctcggagc accccttcc    1260
ttgtgactga gccagggcct gcattttgg ttttccccac cccacacatt ctcaaccata    1320
gtccttctaa caataccaat agctaggacc cggctgctgt gcactgggac tgggattcc    1380
acatgtttgc cttgggagtc tcaagctgga ctgcca                             1416
```

<210> SEQ ID NO 81  
<211> LENGTH: 2642  
<212> TYPE: DNA  
<213> ORGANISM: Artificial Sequence  
<220> FEATURE:  
<223> OTHER INFORMATION: OPA1-ND1-3'UTR

<400> SEQUENCE: 81

```
gtgctgcccg cctagaaagg gtgaagtggt tgtttccgtg acggactgag tacgggtgcc      60
tgtcaggctc ttgcggaagt ccatgcgcca ttgggagggc ctcggccgcg gctctgtgcc     120
cttgctgctg agggccactt cctgggtcat tcctggaccg ggagccgggc tggggctcac     180
acggggctc ccgcgtggcc gtctcggcgc ctgcgtgacc tccccgccgg cgggatgtgg      240
cgactacgtc gggccgctgt ggcctgatgg ccaacctcct actcctcatt gtacccattc     300
taatcgcaat ggcattccta atgcttaccg aacgaaaaat tctaggctat atgcaactac     360
gcaaaggccc caacgttgta ggcccctacg ggctactaca accttcgct gacgccataa      420
aactcttcac caaagagccc ctaaaacccg ccacatctac catcaccctc tacatcaccg     480
ccccgacctt agctctcacc atcgctcttc tactatggac ccccctcccc atgcccaacc     540
ccctggtcaa cctcaaccta ggcctcctat ttattctagc cacctctagc ctagccgttt     600
```

```
actcaatcct ctggtcaggg tgggcatcaa actcaaacta cgccctgatc ggcgcactgc    660
gagcagtagc ccaaacaatc tcatatgaag tcaccctagc catcattcta ctatcaacat    720
tactaatgag tggctccttt aacctctcca cccttatcac aacacaagaa cacctctggt    780
tactcctgcc atcatggccc ttggccatga tgtggtttat ctccacacta gcagagacca    840
accgaacccc cttcgacctt gccgaagggg agtccgaact agtctcaggc ttcaacatcg    900
aatacgccgc aggccccttc gccctattct tcatggccga atacacaaac attattatga    960
tgaacaccct caccactaca atcttcctag gaacaacata tgacgcactc tcccctgaac   1020
tctacacaac atattttgtc accaagaccc tacttctaac ctccctgttc ttatggattc   1080
gaacagcata ccccgattc cgctacgacc aactcatgca cctcctatgg aaaaacttcc   1140
taccactcac cctagcatta cttatgtggt atgtctccat gcccattaca atctccagca   1200
ttccccctca aacctaagag cactgggacg cccaccgccc ctttcctcc gctgccaggc    1260 gagcatgttg tggtaattct ggaacacaag aagagaaatt gctgggttta gaacaagatt   1320
ataaacgaat tcggtgctca gtgatcactt gacagttttt tttttttta aatattaccc    1380 aaaatgctcc ccaaataaga aatgcatcag ctcagtcagt gaatacaaaa aaggaattat   1440
ttttcccttt gagggtcttt tatacatctc cctccaacc ccaccctcta ttctgtttct    1500
tcctcctcac atgggggtac acatacacag cttcctcttt tggttccatc cttaccacca   1560
caccacacgc acactccaca tgcccagcag agtggcactt ggtggccaga aagtgtgagc   1620
ctcatgatct gctgtctgta gttctgtgag ctcaggtccc tcaaaggcct cggagcaccc   1680
ccttccttgt gactgagcca gggcctgcat ttttggtttt ccccaccca cacattctca    1740 accatagtcc ttctaacaat accaatagct aggacccggc tgctgtgcac tgggactggg   1800
gattccacat gtttgccttg ggagtctcaa gctggactgc cagcccctgt cctcccttca   1860
cccccattgc gtatgagcat ttcagaactc caaggagtca caggcatctt tatagttcac   1920
gttaacatat agacactgtt ggaagcagtt ccttctaaaa gggtagccct ggacttaata   1980
ccagccggat acctctggcc cccacccccat tactgtacct ctggagtcac tactgtgggt   2040
cgccactcct ctgctacaca gcacggcttt ttcaaggctg tattgagaag ggaagttagg   2100
aagaagggtg tgctgggcta accagcccac agagctcaca ttcctgtccc ttgggtgaaa   2160
aatacatgtc catcctgata tctcctgaat tcagaaatta gcctccacat gtgcaatggc   2220
tttaagagcc agaagcaggg ttctgggaat tttgcaagtt acctgtggcc aggtgtggtc   2280
tcggttacca aatacggtta cctgcagctt tttagtcctt tgtgctccca cgggtctaca   2340
gagtcccatc tgcccaaagg tcttgaagct tgacaggatg ttttcgatta ctcagtctcc   2400
cagggcacta ctggtccgta ggattcgatt ggtcggggta ggagagttaa acaacattta   2460
aacagagttc tctcaaaaat gtctaaaggg attgtaggta gataacatcc aatcactgtt   2520
tgcacttatc tgaaatcttc cctcttggct gccccaggt atttactgtg gagaacattg    2580
cataggaatg tctggaaaaa gcttctacaa cttgttacag ccttcacatt tgtagaagct   2640
tt                                                                  2642

<210> SEQ ID NO 82
<211> LENGTH: 1842
<212> TYPE: DNA
<213> ORGANISM: Artificial Sequence
<220> FEATURE:
<223> OTHER INFORMATION: OPA1-ND1-3'UTR*

<400> SEQUENCE: 82
```

```
gtgctgcccg cctagaaagg gtgaagtggt tgtttccgtg acggactgag tacgggtgcc      60
tgtcaggctc ttgcggaagt ccatgcgcca ttgggagggc ctcggccgcg gctctgtgcc     120
cttgctgctg agggccactt cctgggtcat tcctggaccg ggagccgggc tggggctcac     180 acggggctc ccgcgtggcc gtctcggcgc ctgcgtgacc tccccgccgg cgggatgtgg      240
cgactacgtc gggccgctgt ggcctgatgg ccaacctcct actcctcatt gtacccattc     300
taatcgcaat ggcattccta atgcttaccg aacgaaaaat tctaggctat atgcaactac     360
gcaaaggccc caacgttgta ggcccctacg gctactaca acccttcgct gacgccataa      420
aactcttcac caaagagccc ctaaaacccg ccacatctac catcaccctc tacatcaccg     480
ccccgacctt agctctcacc atcgctcttc tactatggac ccccctcccc atgcccaacc    540
ccctggtcaa cctcaaccta ggcctcctat ttattctagc cacctctagc ctagccgttt     600
actcaatcct ctggtcaggg tgggcatcaa actcaaacta cgccctgatc ggcgcactgc    660
gagcagtagc ccaaacaatc tcatatgaag tcaccctagc catcattcta ctatcaacat    720
tactaatgag tggctccttt aacctctcca cccttatcac aacacaagaa cacctctggt    780
tactcctgcc atcatggccc ttggccatga tgtggtttat ctccacacta gcagagacca   840
accgaacccc cttcgacctt gccgaagggg agtccgaact agtctcaggc ttcaacatcg    900
aatacgccgc aggccccttc gccctattct tcatggccga atacaaaac attattatga     960 tgaacaccct caccactaca atcttcctag gaacaacata tgacgcactc tcccctgaac    1020
tctacacaac atattttgtc accaagaccc tacttctaac ctcccgttc ttatggattc     1080 gaacagcata ccccgattc cgctacgacc aactcatgca cctcctatgg aaaaacttcc    1140
taccactcac cctagcatta cttatgtggt atgtctccat gcccattaca atctccagca    1200
ttccccctca aacctaagag cactgggacg cccaccgccc ctttccctcc gctgccaggc    1260
gagcatgttg tggtaattct ggaacacaag aagagaaatt gctgggttta gaacaagatt    1320
ataaacgaat tcggtgctca gtgatcactt gacagttttt tttttttta aatattaccc    1380 aaaatgctcc ccaaataaga aatgcatcag ctcagtcagt gaatacaaaa aaggaattat    1440
ttttcccttt gagggtcttt tatacatctc tcctccaacc ccaccctcta ttctgtttct    1500
tcctcctcac atgggggtac acatacacag cttcctcttt tggttccatc cttaccacca    1560
caccacacgc acactccaca tgcccagcag agtggcactt ggtggccaga aagtgtgagc    1620
ctcatgatct gctgtctgta gttctgtgag ctcaggtccc tcaaaggcct cggagcaccc   1680
ccttccttgt gactgagcca gggctgcat ttttggtttt ccccacccca cacattctca    1740
accatagtcc ttctaacaat accaatagct aggacccggc tgctgtgcac tgggactggg    1800
gattccacat gtttgccttg ggagtctcaa gctggactgc ca                       1842
```

<210> SEQ ID NO 83
<211> LENGTH: 2642
<212> TYPE: DNA
<213> ORGANISM: Artificial Sequence
<220> FEATURE:
<223> OTHER INFORMATION: OPA1-opt_ND1-3'UTR

<400> SEQUENCE: 83

```
gtgctgcccg cctagaaagg gtgaagtggt tgtttccgtg acggactgag tacgggtgcc      60
tgtcaggctc ttgcggaagt ccatgcgcca ttgggagggc ctcggccgcg gctctgtgcc     120
cttgctgctg agggccactt cctgggtcat tcctggaccg ggagccgggc tggggctcac     180
```

```
acgggggctc cgcgtggcc gtctcggcgc ctgcgtgacc tccccgccgg cgggatgtgg    240
cgactacgtc gggccgctgt ggcctgatgg ccaacctgct gctgctgatc gtgcccatcc    300
tgatcgccat ggccttcctg atgctgaccg agcgcaagat cctgggctac atgcagctgc    360
gcaagggccc caacgtggtg ggcccctacg gcctgctgca gcccttcgcc gacgccatca    420
agctgttcac caaggagccc ctgaagcccg ccaccagcac catcaccctg tacatcaccg    480
cccccaccct ggccctgacc atcgccctgc tgctgtggac cccctgccc atgcccaacc    540
ccctggtgaa cctgaacctg gcctgctgt tcatcctggc caccagcagc ctggccgtgt    600
acagcatcct gtggagcggc tgggccagca cagcaacta cgccctgatc ggcgccctgc    660
gcgccgtggc ccagaccatc agctacgagg tgaccctggc catcatcctg ctgagcaccc    720
tgctgatgag cggcagcttc aacctgagca ccctgatcac cacccaggag cacctgtggc    780
tgctgctgcc cagctggccc ctggccatga tgtggttcat cagcaccctg gccgagacca    840
accgcacccc cttcgacctg gccgagggcg agagcgagct ggtgagcggc ttcaacatcg    900
agtacgccgc cggccccttc gccctgttct tcatggccga gtacaccaac atcatcatga    960
tgaacaccct gaccaccacc atcttcctgg gcaccaccta cgacgccctg agccccgagc    1020
tgtacaccac ctacttcgtg accaagaccc tgctgctgac cagcctgttc ctgtggatcc    1080
gcaccgccta ccccgcttc cgctacgacc agctgatgca cctgctgtgg aagaacttcc    1140
tgcccctgac cctggccctg ctgatgtggt acgtgagcat gcccatcacc atcagcagca    1200
tccccccca gacctaagag cactgggacg cccaccgccc ctttccctcc gctgccaggc    1260
gagcatgttg tggtaattct ggaacacaag aagagaaatt gctgggttta gaacaagatt    1320
ataaacgaat tcggtgctca gtgatcactt gacagttttt ttttttttta aatattaccc    1380
aaaatgctcc ccaaataaga aatgcatcag ctcagtcagt gaatacaaaa aaggaattat    1440
ttttcccttt gagggtcttt tatacatctc tcctccaacc ccaccctcta ttctgtttct    1500
tcctcctcac atgggggtac acatacacag cttcctcttt tggttccatc cttaccacca    1560
caccacacgc acactccaca tgcccagcag agtggcactt ggtggccaga agtgtgagc    1620
ctcatgatct gctgtctgta gttctgtgag ctcaggtccc tcaaaggcct cggagcaccc    1680
ccttccttgt gactgagcca gggcctgcat ttttggtttt ccccaccccca cacattctca    1740
accatagtcc ttctaacaat accaatagct aggacccggc tgctgtgcac tgggactggg    1800
gattccacat gtttgccttg ggagtctcaa gctggactgc cagcccctgt cctcccttca    1860
ccccattgc gtatgagcat ttcagaactc caaggagtca caggcatctt tatagttcac    1920
gttaacatat agacactgtt ggaagcagtt ccttctaaaa gggtagccct ggacttaata    1980
ccagccggat acctctggcc cccacccat tactgtacct ctggagtcac tactgtgggt    2040
cgccactcct ctgctacaca gcacggcttt ttcaaggctg tattgagaag ggaagttagg    2100
aagaagggtg tgctgggcta accagcccac agagctcaca ttcctgtccc ttgggtgaaa    2160
aatacatgtc catcctgata tctcctgaat tcagaaatta gcctccacat gtgcaatggc    2220
tttaagagcc agaagcaggg ttctgggaat tttgcaagtt acctgtggcc aggtgtggtc    2280
tcggttacca aatacggtta cctgcagctt tttagtcctt tgtgctccca cgggtctaca    2340
gagtcccatc tgcccaaagg tcttgaagct tgacaggatg ttttcgatta ctcagtctcc    2400
cagggcacta ctggtccgta ggattcgatt ggtcggggta ggagagttaa acaacattta    2460
aacagagttc tctcaaaaat gtctaaaggg attgtaggta gataacatcc aatcactgtt    2520
tgcacttatc tgaaatcttc cctcttggct gcccccaggt atttactgtg gagaacattg    2580
```

| cataggaatg tctggaaaaa gcttctacaa cttgttacag ccttcacatt tgtagaagct | 2640 |
| tt | 2642 |

<210> SEQ ID NO 84
<211> LENGTH: 1842
<212> TYPE: DNA
<213> ORGANISM: Artificial Sequence
<220> FEATURE:
<223> OTHER INFORMATION: OPA1-opt_ND1-3'UTR*

<400> SEQUENCE: 84

| gtgctgcccg cctagaaagg gtgaagtggt tgtttccgtg acggactgag tacgggtgcc | 60 |
| tgtcaggctc ttgcggaagt ccatgcgcca ttgggagggc ctcggccgcg gctctgtgcc | 120 |
| cttgctgctg agggccactt cctgggtcat tcctggaccg ggagccgggc tggggctcac | 180 |
| acggggcctc ccgcgtggcc gtctcggcgc ctgcgtgacc tccccgccgg cgggatgtgg | 240 |
| cgactacgtc gggccgctgt ggcctgatgg ccaacctgct gctgctgatc gtgcccatcc | 300 |
| tgatcgccat ggccttcctg atgctgaccg agcgcaagat cctgggctac atgcagctgc | 360 |
| gcaagggccc caacgtggtg ggcccctacg gcctgctgca gcccttcgcc gacgccatca | 420 |
| agctgttcac caaggagccc ctgaagcccg ccaccagcac catcaccctg tacatcaccg | 480 |
| cccccaccct ggccctgacc atcgccctgc tgctgtggac cccctgccc atgcccaacc | 540 |
| ccctggtgaa cctgaacctg ggcctgctgt tcatcctggc caccagcagc ctggccgtgt | 600 |
| acagcatcct gtggagcggc tgggccagca acagcaacta cgccctgatc ggcgccctgc | 660 |
| gcgccgtggc ccagaccatc agctacgagg tgaccctggc catcatcctg ctgagcaccc | 720 |
| tgctgatgag cggcagcttc aacctgagca ccctgatcac cacccaggag cacctgtggc | 780 |
| tgctgctgcc cagctggccc ctggccatga tgtggttcat cagcaccctg gccgagacca | 840 |
| accgcacccc cttcgacctg gccgagggcg agagcgagct ggtgagcggc ttcaacatcg | 900 |
| agtacgccgc cggcccctttc gccctgttct tcatggccga gtacaccaac atcatcatga | 960 |
| tgaacaccct gaccaccacc atcttcctgg gcaccaccta cgacgccctg agccccgagc | 1020 |
| tgtacaccac ctacttcgtg accaagaccc tgctgctgac cagcctgttc ctgtggatcc | 1080 |
| gcaccgccta ccccgcttc cgctacgacc agctgatgca cctgctgtgg aagaacttcc | 1140 |
| tgcccctgac cctggccctg ctgatgtggt acgtgagcat gcccatcacc atcagcagca | 1200 |
| tcccccccca gacctaagag cactgggacg cccaccgccc ctttccctcc gctgccaggc | 1260 |
| gagcatgttg tggtaattct ggaacacaag aagagaaatt gctgggttta gaacaagatt | 1320 |
| ataaacgaat tcggtgctca gtgatcactt gacagttttt tttttttta aatattaccc | 1380 |
| aaaatgctcc ccaaataaga aatgcatcag ctcagtcagt gaatacaaaa aaggaattat | 1440 |
| ttttcccttt gagggtcttt tatacatctc tcctccaacc ccaccctcta ttctgtttct | 1500 |
| tcctcctcac atgggggtac acatacacag cttcctcttt tggttccatc cttaccacca | 1560 |
| caccacacgc acactccaca tgcccagcag agtggcactt ggtggccaga aagtgtgagc | 1620 |
| ctcatgatct gctgtctgta gttctgtgag ctcaggtccc tcaaaggcct cggagcaccc | 1680 |
| ccttccttgt gactgagcca gggcctgcat ttttggtttt ccccaccca cacattctca | 1740 |
| accatagtcc ttctaacaat accaatagct aggacccggc tgctgtgcac tgggactggg | 1800 |
| gattccacat gtttgccttg ggagtctcaa gctggactgc ca | 1842 |

<210> SEQ ID NO 85

```
<211> LENGTH: 18
<212> TYPE: DNA
<213> ORGANISM: Artificial Sequence
<220> FEATURE:
<223> OTHER INFORMATION: beta-actin-S primer

<400> SEQUENCE: 85
cgagatcgtg cgggacat                                              18

<210> SEQ ID NO 86
<211> LENGTH: 19
<212> TYPE: DNA
<213> ORGANISM: Artificial Sequence
<220> FEATURE:
<223> OTHER INFORMATION: beta-actin-A primer

<400> SEQUENCE: 86
caggaaggag ggctggaac                                             19

<210> SEQ ID NO 87
<211> LENGTH: 19
<212> TYPE: DNA
<213> ORGANISM: Artificial Sequence
<220> FEATURE:
<223> OTHER INFORMATION: ND4-S primer

<400> SEQUENCE: 87
ctgcctacga caaacagac                                             19

<210> SEQ ID NO 88
<211> LENGTH: 19
<212> TYPE: DNA
<213> ORGANISM: Artificial Sequence
<220> FEATURE:
<223> OTHER INFORMATION: ND4-A primer

<400> SEQUENCE: 88
agtgcgttcg tagtttgag                                             19

<210> SEQ ID NO 89
<211> LENGTH: 21
<212> TYPE: DNA
<213> ORGANISM: Artificial Sequence
<220> FEATURE:
<223> OTHER INFORMATION: ND6-F primer

<400> SEQUENCE: 89
atgatgtatg ctttgtttct g                                          21

<210> SEQ ID NO 90
<211> LENGTH: 21
<212> TYPE: DNA
<213> ORGANISM: Artificial Sequence
<220> FEATURE:
<223> OTHER INFORMATION: ND6-R primer

<400> SEQUENCE: 90
ctaattcccc cgagcaatct c                                          21

<210> SEQ ID NO 91
<211> LENGTH: 18
<212> TYPE: DNA
<213> ORGANISM: Artificial Sequence
<220> FEATURE:
<223> OTHER INFORMATION: ND6-S primer

<400> SEQUENCE: 91
```
agtgtgggtt tagtaatg                                                           18

<210> SEQ ID NO 92
<211> LENGTH: 18
<212> TYPE: DNA
<213> ORGANISM: Artificial Sequence
<220> FEATURE:
<223> OTHER INFORMATION: ND6-A  primer

<400> SEQUENCE: 92
tgcctcagga tactcctc                                                           18

<210> SEQ ID NO 93
<211> LENGTH: 20
<212> TYPE: DNA
<213> ORGANISM: Artificial Sequence
<220> FEATURE:
<223> OTHER INFORMATION: beta-actin-F primer

<400> SEQUENCE: 93
ctccatcctg gcctcgctgt                                                         20

<210> SEQ ID NO 94
<211> LENGTH: 20
<212> TYPE: DNA
<213> ORGANISM: Artificial Sequence
<220> FEATURE:
<223> OTHER INFORMATION: beta-actin-R primer

<400> SEQUENCE: 94
gctgtcacct tcaccgttcc                                                         20

<210> SEQ ID NO 95
<211> LENGTH: 23
<212> TYPE: DNA
<213> ORGANISM: Artificial Sequence
<220> FEATURE:
<223> OTHER INFORMATION: ND6-F primer

<400> SEQUENCE: 95
gggttttctt ctaagccttc tcc                                                     23

<210> SEQ ID NO 96
<211> LENGTH: 23
<212> TYPE: DNA
<213> ORGANISM: Artificial Sequence
<220> FEATURE:
<223> OTHER INFORMATION: ND6-R primer

<400> SEQUENCE: 96
ccatcatact ctttcaccca cag                                                     23

<210> SEQ ID NO 97
<211> LENGTH: 20
<212> TYPE: DNA
<213> ORGANISM: Artificial Sequence
<220> FEATURE:
<223> OTHER INFORMATION: opt_ND6-F primer

<400> SEQUENCE: 97
cgcctgctga ccggctgcgt                                                         20

<210> SEQ ID NO 98
<211> LENGTH: 20
<212> TYPE: DNA

```
<213> ORGANISM: Artificial Sequence
<220> FEATURE:
<223> OTHER INFORMATION: opt_ND6-R

<400> SEQUENCE: 98
ccaggcctcg gggtactcct                                                    20

<210> SEQ ID NO 99
<211> LENGTH: 21
<212> TYPE: DNA
<213> ORGANISM: Artificial Sequence
<220> FEATURE:
<223> OTHER INFORMATION: ND1-F primer

<400> SEQUENCE: 99
atggccgcat ctccgcacac t                                                  21

<210> SEQ ID NO 100
<211> LENGTH: 21
<212> TYPE: DNA
<213> ORGANISM: Artificial Sequence
<220> FEATURE:
<223> OTHER INFORMATION: ND1-R primer

<400> SEQUENCE: 100
ttaggtttga gggggaatgc t                                                  21

<210> SEQ ID NO 101
<211> LENGTH: 21
<212> TYPE: DNA
<213> ORGANISM: Artificial Sequence
<220> FEATURE:
<223> OTHER INFORMATION: ND1-F primer

<400> SEQUENCE: 101
aacctcaacc taggcctcct a                                                  21

<210> SEQ ID NO 102
<211> LENGTH: 21
<212> TYPE: DNA
<213> ORGANISM: Artificial Sequence
<220> FEATURE:
<223> OTHER INFORMATION: ND1-R primer

<400> SEQUENCE: 102
tggcaggagt aaccagaggt g                                                  21

<210> SEQ ID NO 103
<211> LENGTH: 23
<212> TYPE: DNA
<213> ORGANISM: Artificial Sequence
<220> FEATURE:
<223> OTHER INFORMATION: ND1-F primer

<400> SEQUENCE: 103
aggaggctct gtctggtatc ttg                                                23

<210> SEQ ID NO 104
<211> LENGTH: 21
<212> TYPE: DNA
<213> ORGANISM: Artificial Sequence
<220> FEATURE:
<223> OTHER INFORMATION: ND1-R primer

<400> SEQUENCE: 104
ttttaggggc tctttggtga a                                                  21
```

<210> SEQ ID NO 105
<211> LENGTH: 22
<212> TYPE: DNA
<213> ORGANISM: Artificial Sequence
<220> FEATURE:
<223> OTHER INFORMATION: opt-ND1-F primer

<400> SEQUENCE: 105
gccgcctgct gaccggctgc gt                                    22

<210> SEQ ID NO 106
<211> LENGTH: 24
<212> TYPE: DNA
<213> ORGANISM: Artificial Sequence
<220> FEATURE:
<223> OTHER INFORMATION: opt-ND1-R primer

<400> SEQUENCE: 106
tgatgtacag ggtgatggtg ctgg                                  24

<210> SEQ ID NO 107
<211> LENGTH: 19
<212> TYPE: DNA
<213> ORGANISM: Artificial Sequence
<220> FEATURE:
<223> OTHER INFORMATION: ND4-S primer

<400> SEQUENCE: 107
gccaacagca actacgagc                                        19

<210> SEQ ID NO 108
<211> LENGTH: 20
<212> TYPE: DNA
<213> ORGANISM: Artificial Sequence
<220> FEATURE:
<223> OTHER INFORMATION: ND4-A  primer

<400> SEQUENCE: 108
tgatgttgct ccagctgaag                                       20

<210> SEQ ID NO 109
<211> LENGTH: 20
<212> TYPE: DNA
<213> ORGANISM: Artificial Sequence
<220> FEATURE:
<223> OTHER INFORMATION: opt-ND4-S primer

<400> SEQUENCE: 109
gcctgaccct gatcctgaac                                       20

<210> SEQ ID NO 110
<211> LENGTH: 20
<212> TYPE: DNA
<213> ORGANISM: Artificial Sequence
<220> FEATURE:
<223> OTHER INFORMATION: opt-ND4-A primer

<400> SEQUENCE: 110
gtgcgctcgt agttgctgtt                                       20

<210> SEQ ID NO 111
<211> LENGTH: 376
<212> TYPE: DNA
<213> ORGANISM: Homo sapiens

```
<400> SEQUENCE: 111
gggcagtgcc tccccgcccc gccgctggcg tcaagttcag ctccacgtgt gccatcagtg      60
gatccgatcc gtccagccat ggcttcctat tccaagatgg tgtgaccaga catgcttcct     120
gctccccgct tagcccacgg agtgactgtg gttgtggtgg gggggttctt aaaataactt     180
tttagccccc gtcttcctat tttgagtttg gttcagatct taagcagctc catgcaactg     240
tatttatttt tgatgacaag actcccatct aaagttttc tcctgcctga tcatttcatt      300
ggtggctgaa ggattctaga gaaccttttg ttcttgcaag gaaaacaaga atccaaaacc     360
agtgactgtt ctgtga                                                      376

<210> SEQ ID NO 112
<211> LENGTH: 146
<212> TYPE: DNA
<213> ORGANISM: Homo sapiens

<400> SEQUENCE: 112
ggggtctttg tcctctgtac tgtctctctc cttgccccta acccaaaaag cttcattttt      60
ctgtgtaggc tgcacaagag ccttgattga agatatattc tttctgaaca gtatttaagg     120
tttccaataa aatgtacacc cctcag                                           146

<210> SEQ ID NO 113
<211> LENGTH: 1956
<212> TYPE: DNA
<213> ORGANISM: Homo sapiens

<400> SEQUENCE: 113
tgttgggtcc aagaaggaat ttctttccat ccctgtgagg caatgggtgg gaatgatagg      60
acaggcaaag agaagcttcc tcaggctagc aaaaatatca tttgatgtat tgattaaaaa     120
agcacttgct tgatgtatct ttggcgtgtg tgctactctc atctgtgtgt atgtgtgttg     180
tgtgtgtgtg tgtgtgcatg cacatatgtg ttcactctgc tactttgtaa gttttaggct     240 aggttgctt accagctgtt tacttctttt ttgttgttgt tttgagacaa ggtttcgctc      300
tgccaccctg gctggagtgc agtggcgtga tcttggctca cggcaacctc tgcctcctgg     360
ggctcaagca attatcccac ctcagcctcc tgagcagctg ggactacagg tgcatgccac     420
aacacctggc tgatatttgt attttttgta gagacaggat tttgccaagt tgcccaggct     480
ggtcttgaac tcctaggctt aagcaatcca cccaccttgg cctcctgaag tgccaggatc     540
acagacgtga gccactacac ccagcccagc tgtttacttc tttaaccata cttttgattt     600
tattttttga ccaaaatgaa ctaacccagg taatcttcca gggaccgcaa ttccagaacc     660
tcatagtatt tcttccattt ccagcagctg attagaagtc caggatcatg tgaagtcagg     720
cagggtcaca gttcctgatg gcacattatg gacagagaat tccattttgt tttctaaccc     780
atgatgaaaa cccacgtgag tcagtgtgtg aacaggggatc attaattttt tccccctagg     840
tggaaggaaa aaggcactta cttttgcaggt tacagaaatt actgggagag gatatcgtca     900
taaaaagagc caggccaaat tggaatattt ttgtgatctg catcatgatg ctgaaaatag     960
caattatttg ggaattgggt ttgaaaactg aattgttgcc agagaattaa accaggtgaa    1020
aggtcctttt gaattcagat tgtcttctga acatccaggc tgatcatctg agagcagtca    1080
aatctacttc cccaaaaaga gaccagggta ggtttatttg cttttatttt taatgtttgc    1140
ctgtgtttcc aagtgtgaac aaaacagtgt gtgatctatt cttggattca ttttgatcag    1200
tatttattca aacccagtct ctctccagga cataaaactg aaatcagata tgttctttt    1260
```

```
aagcccaaac cctctccttt ctagatccaa cccttcaccc ctaattttat gatggctata    1320
gccatggact tccccaagaa aagatcaccc agaaataaga ccacctgtga cagttaccag    1380
cttttattca taaccttagc ttcccaacta ttgagcattt tctaaggtcc ctgctgtctt    1440
ttggtctctg gtttgatttg tggcaaacag atgaagtaac agactgctat gaaggaccac    1500
aaaaacggca gcctctggaa aaaccattag aaagtcagtg gcagatccag taaataatat    1560
cgccagcctc agcataatct gctgctgact cgattcagtg gactctaaag tgcccagcct    1620
cctgacctga gctctcctgc catctgtgag actaccagag gtcttatctg ctgtccacat    1680
ggcaactggg catgagtacc tggccacctt gcttccctct ttgcctggtc caagtgagtg    1740
tctgctgcct ctgtcctgcc ttgttttcct ggctctaaac caactccacc cactcttaat    1800
ggaaactcag tctggctttg tgtgtttctg ggaagcacat gacttctggg aatgggcaag    1860
gaagaggagt gaaacaaaaa ctgtcagcta tgtgtgcctg gtctgggatc cttctctggg    1920
tgacagtggc atcatgaatc ttagaatcag ctcccc                              1956

<210> SEQ ID NO 114
<211> LENGTH: 411
<212> TYPE: DNA
<213> ORGANISM: Homo sapiens

<400> SEQUENCE: 114
gaatcatgca agcttcctcc ctcagccatt gatggaaagt tcagcaagat cagcaacaaa      60
accaagaaaa atgatccttg cgtgctgaat atctgaaaag agaattttt cctacaaaat     120 ctcttgggtc aagaaagttc tagaatttga attgataaac atggtgggtt ggctgagggt    180
aagagtatat gaggaacctt ttaaacgaca acaatactgc tagctttcag gatgattttt    240
aaaaaataga ttcaaatgtg ttatcctctc tctgaaacgc ttcctataac tcgagtttat    300
aggggaagaa aaagctattg tttacaatta tatcaccatt aaggcaactg ctacaccctg    360 cttttgtattc tgggctaaga ttcattaaaa actagctgct cttaacttac a            411

<210> SEQ ID NO 115
<211> LENGTH: 1465
<212> TYPE: DNA
<213> ORGANISM: Homo sapiens

<400> SEQUENCE: 115
gagcactggg acgcccaccg cccctttccc tccgctgcca ggcgagcatg ttgtggtaat      60
tctggaacac aagaagagaa attgctgggt ttagaacaag attataaacg aattcggtgc    120
tcagtgatca cttgacagtt tttttttttt ttaaatatta cccaaaatgc tccccaaata    180
agaaatgcat cagctcagtc agtgaataca aaaaaggaat tattttttccc tttgagggtc    240 tttatacatc tctcctccaa ccccacccctc tattctgttt cttcctcctc acatgggggt    300
acacatacac agcttcctct tttggttcca tccttaccac cacaccacac gcacactcca    360
catgcccagc agagtggcac ttggtggcca gaaagtgtga gcctcatgat ctgctgtctg    420
tagttctgtg agctcaggtc cctcaaaggc ctcggagcac ccccttcctg gtgactgagc    480
cagggcctgc attttggtt ttccccaccc cacacattct caaccatagt ccttctaaca    540
ataccaatag ctaggacccg gctgctgtgc actgggactg gggattccac atgtttgcct    600
tgggagtctc aagctggact gccagcccct gtcctccctt caccccatt gcgtatgagc    660 atttcagaac tccaaggagt cacaggcatc tttatagttc acgttaacat atagacactg    720
```

```
ttggaagcag ttccttctaa aagggtagcc ctggacttaa taccagccgg atacctctgg    780
cccccacccc attactgtac ctctggagtc actactgtgg gtcgccactc ctctgctaca    840
cagcacggct ttttcaaggc tgtattgaga agggaagtta ggaagaaggg tgtgctgggc    900
taaccagccc acagagctca cattcctgtc ccttgggtga aaaatacatg tccatcctga    960
tatctcctga attcagaaat tagcctccac atgtgcaatg gctttaagag ccagaagcag   1020
ggttctggga attttgcaag ttatcctgtg gccaggtgtg gtctcggtta ccaaatacgg   1080
ttacctgcag cttttagtc ctttgtgctc ccacgggtct gcagagtccc atctgcccaa    1140
aggtcttgaa gcttgacagg atgttttcat tactcagtct cccagggcac tgctggtccg   1200
tagggattca ttggtcgggg tgggagagtt aaacaacatt taaacagagt tctctcaaaa   1260
atgtctaaag ggattgtagg tagataacat ccaatcactg tttgcactta tctgaaatct   1320
tccctcttgg ctgcccccag gtatttactg tggagaacat tgcataggaa tgtctggaaa   1380
aagcctctac aacttgttac agccttcaca tttgtacaat tcattgattc tcttttcctt   1440
ccacaataaa atggtataca agaac                                          1465

<210> SEQ ID NO 116
<211> LENGTH: 288
<212> TYPE: DNA
<213> ORGANISM: Homo sapiens

<400> SEQUENCE: 116
gagacttgga ctcaagtcat aggcttcttt cagtctttat gtcacctcag gagacttatt     60
tgagaggaag ccttctgtac ttgaagttga tttgaaatat gtaagaattg atgatgtatt    120
tgcaaacatt aatgtgaaat aaattgaatt taatgttgaa tactttcagg cattcactta    180
ataaagacac tgttaagcac tgttatgctc agtcatacac gcgaaaggta caatgtcttt    240
tagctaattc taattaaaaa ttacagactg gtgtacaaga tacttgtg                 288

<210> SEQ ID NO 117
<211> LENGTH: 83
<212> TYPE: DNA
<213> ORGANISM: Homo sapiens

<400> SEQUENCE: 117
cccaccaccc tggcctgctg tcctgcgtct atccatgtgg aatgctggac aataaagcga     60
gtgctgccca ccctccagct gcc                                             83

<210> SEQ ID NO 118
<211> LENGTH: 66
<212> TYPE: DNA
<213> ORGANISM: Homo sapiens

<400> SEQUENCE: 118
tttatattga actgtaaata tgtcactaga gaaataaaat atggacttcc aatctacgta     60
aactta                                                                66

<210> SEQ ID NO 119
<211> LENGTH: 214
<212> TYPE: DNA
<213> ORGANISM: Homo sapiens

<400> SEQUENCE: 119
accacgatcg ttatgctgag tatgttaagc tctttatgac tgttttttgta gtggtataga     60 gtactgcaga atacagtaag ctgctctatt gtagcatttc ttgatgttgc ttagtcactt    120
```

```
atttcataaa caacttaatg ttctgaataa tttcttacta aacattttgt tattgggcaa    180
gtgattgaaa atagtaaatg ctttgtgtga ttga                                214

<210> SEQ ID NO 120
<211> LENGTH: 286
<212> TYPE: DNA
<213> ORGANISM: Homo sapiens

<400> SEQUENCE: 120
tcttggaata taaagaattt cttcaggttg aattacctag aagtttgtca ctgacttgtg     60
ttcctgaact atgacacatg aatatgtggg ctaagaaata gttcctcttg ataaataaac    120
aattaacaaa tactttggac agtaagtctt tctcagttct taatgataat gcagggcact    180
tactagcata agaattggtt tgggatttaa ctgtttatga agctaacttg atttccgtgt    240
tttgttaaaa tttcattgtt ctagcacatc tttaactgtg atagtt                   286

<210> SEQ ID NO 121
<211> LENGTH: 721
<212> TYPE: DNA
<213> ORGANISM: Homo sapiens

<400> SEQUENCE: 121
gagacgtgca cttggtcgtg cgcccaggga ggaagccgca ccaccagcca gcgcaggccc     60
tggtggagag gcctccctgg ctgcctctgg gaggggtgct gccttgtaga tggagcaagt    120
gagcactgag ggtctggtgc caatcctgta ggcacaaaac cagaagtttc tacattctct    180
atttttgtta atcatcttct cttttttccag aatttggaag ctagaatggt gggaatgtca   240
gtagtgccag aaagagagaa ccaagcttgt ctttaaagtt actgatcaca ggacgttgct    300
ttttcactgt ttcctattaa tcttcagctg aacacaagca aaccttctca ggaggtgtct    360
cctaccctct tattgttcct cttacgctct gctcaatgaa accttcctct tgagggtcat    420
tttcctttct gtattaatta taccagtgtt aagtgacata gataagaact ttgcacactt    480
caaatcagag cagtgattct ctcttctctc ccctttttcct tcagagtgaa tcatccagac   540
tcctcatgga taggtcgggt gttaaagttg ttttgattat gtacctttg atagatccac     600 ataaaaagaa atgtgaagtt ttcttttact atcttttcat ttatcaagca gagacctttg    660
ttgggaggcg gtttgggaga acacatttct aatttgaatg aaatgaaatc tattttcagt    720
g                                                                    721

<210> SEQ ID NO 122
<211> LENGTH: 163
<212> TYPE: DNA
<213> ORGANISM: Homo sapiens

<400> SEQUENCE: 122
cagaagaagt gacggctggg ggcacagtgg gctgggcgcc cctgcagaac atgaaccttc     60
cgctcctggc tgccacaggg tcctccgatg ctggcctttg cgcctctaga ggcagccact    120
catggattca agtcctggct ccgcctcttc catcaggacc act                      163

<210> SEQ ID NO 123
<211> LENGTH: 60
<212> TYPE: DNA
<213> ORGANISM: Homo sapiens

<400> SEQUENCE: 123
```

-continued agaggacaca ctctgcaccc ccccacccca cgaccttggc ccgagcccct ccgtgaggaa    60

<210> SEQ ID NO 124
<211> LENGTH: 65
<212> TYPE: DNA
<213> ORGANISM: Rattus norvegicus

<400> SEQUENCE: 124
agcccttccg ccaggctgtg tgtcaggccc gtggtgggtg ttttgtagta gtgtagagca    60
ttgca                                                                65

<210> SEQ ID NO 125
<211> LENGTH: 231
<212> TYPE: DNA
<213> ORGANISM: Homo sapiens

<400> SEQUENCE: 125
cttatgttct gtgcgcattc tggcaggaat tctgtctctt cagagactca tcctcaaaac    60
aagacttgac actgtgtcct tgccccagtc ctaggaactg tggcacacag agatgttcat   120
tttaaaaacg gatttcatga aacactcttg tacttatgtt tataagagag cactgggtag   180
ccaagtgatc ttcccattca cagagttagt aaacctctgt actacatgct g            231

<210> SEQ ID NO 126
<211> LENGTH: 28
<212> TYPE: PRT
<213> ORGANISM: Homo sapiens

<400> SEQUENCE: 126

Met Ala Ala Ser Pro His Thr Leu Ser Ser Arg Leu Leu Thr Gly Cys
1               5                   10                  15

Val Gly Gly Ser Val Trp Tyr Leu Glu Arg Arg Thr
            20                  25

<210> SEQ ID NO 127
<211> LENGTH: 29
<212> TYPE: PRT
<213> ORGANISM: Homo sapiens

<400> SEQUENCE: 127

Met Ser Val Leu Thr Arg Leu Leu Leu Arg Gly Leu Thr Arg Leu Gly
1               5                   10                  15

Ser Ala Ala Pro Val Arg Arg Ala Arg Ile His Ser Leu
            20                  25

<210> SEQ ID NO 128
<211> LENGTH: 10
<212> TYPE: PRT
<213> ORGANISM: Homo sapiens

<400> SEQUENCE: 128

Met Trp Arg Leu Arg Arg Ala Ala Val Ala
1               5                   10

<210> SEQ ID NO 129
<211> LENGTH: 28
<212> TYPE: PRT
<213> ORGANISM: Homo sapiens

<400> SEQUENCE: 129

Met Ala Ala Ser Pro His Thr Leu Ser Ser Arg Leu Leu Thr Gly Cys
1               5                   10                  15

```
Val Gly Gly Ser Val Trp Tyr Leu Glu Arg Arg Thr
            20                  25

<210> SEQ ID NO 130
<211> LENGTH: 122
<212> TYPE: PRT
<213> ORGANISM: Saccharomyces cerevisiae

<400> SEQUENCE: 130

Met Ala Phe Lys Ser Phe Ile Tyr Ser Lys Gly Tyr His Arg Ser Ala
1               5                   10                  15

Ala Gln Lys Lys Thr Ala Thr Ser Phe Phe Asp Ser Ser Tyr Gln Tyr
            20                  25                  30

Leu Arg Gln Asn Gln Gly Leu Val Asn Ser Asp Pro Val Leu His Ala
        35                  40                  45

Ser His Leu His Pro His Pro Val Val Ala Asn Val Asn Tyr Asn
    50                  55                  60

Asn Val Asp Asp Ile Leu His Pro His Asp Leu Asp Ser Ser Ile Asn
65                  70                  75                  80

Asn Thr Asn Asn Pro Leu Thr His Glu Glu Leu Leu Tyr Asn Gln Asn
                85                  90                  95

Val Ser Leu Arg Ser Leu Lys Gln Gln Gln Ser Thr Asn Tyr Val Asn
            100                 105                 110

Asn Asn Asn Asn Asn Gln His Arg Tyr Tyr
            115                 120

<210> SEQ ID NO 131
<211> LENGTH: 174
<212> TYPE: PRT
<213> ORGANISM: Larimichthys crocea

<400> SEQUENCE: 131

Met Arg Lys Arg Ser Leu Arg Cys His Leu Trp Ser Ala Asn Ala Ser
1               5                   10                  15

Leu Ser Pro Arg Lys Asp Glu Val Thr Ser Arg Lys Glu Ser Glu Asn
            20                  25                  30

Leu Val Lys Gly Lys Asn Lys Ser His Leu His Leu Leu
        35                  40                  45

Phe Thr Ala Ser Lys Ile Gly Thr Asp Ser Val Phe Asp Val Gln Lys
    50                  55                  60

Ser Lys Glu Cys Cys Lys Glu Leu Gly Leu Leu Phe Thr Ser Leu Ile
65                  70                  75                  80

His Ser Ile Gly Ser Phe Pro Phe Asp Glu Glu Pro Lys Ala Ala Ala
                85                  90                  95

Val Phe Leu Pro Gly Ser Leu Pro Gln Leu Thr Val Leu Val Leu Ala
            100                 105                 110

Pro Gly Ser Gly Ser Cys Pro Thr Gly Lys Ser Thr Pro His Leu Ala
            115                 120                 125

Ala Ser Gly Arg Asn Ala Glu Leu Leu Arg Pro Gln Asn Ser Met Ile
    130                 135                 140

Val Arg Gln Phe Thr Cys Arg Gly Thr Ile Ser Ser His Leu Cys Ala
145                 150                 155                 160

His Leu Arg Lys Pro His Asp Ser Arg Asn Met Ala Arg Pro
                165                 170

<210> SEQ ID NO 132
```

<211> LENGTH: 56
<212> TYPE: PRT
<213> ORGANISM: Trypanosoma brucei

<400> SEQUENCE: 132

Met Leu Arg Arg Thr Ser Phe Asn Phe Thr Gly Arg Ala Met Ile Ser
1               5                   10                  15

Arg Gly Ser Pro Glu Trp Ser His Arg Leu Asp Leu Lys Lys Gly Lys
            20                  25                  30

Lys Thr Thr Met Met His Lys Leu Gly Thr Ser Lys Pro Asn Asn Ala
        35                  40                  45

Leu Gln Tyr Ala Gln Met Thr Leu
    50                  55

<210> SEQ ID NO 133
<211> LENGTH: 46
<212> TYPE: PRT
<213> ORGANISM: Neurospora crassa

<400> SEQUENCE: 133

Met Ile Ser Arg Ser Ala Leu Ser Arg Gly Ser Gln Leu Ala Leu Arg
1               5                   10                  15

Arg Pro Ala Ala Ala Lys Thr Ala Gln Arg Gly Phe Ala Ala Ala Ala
            20                  25                  30

Ala Ser Pro Ala Ala Ser Tyr Glu Pro Thr Thr Ile Ala Gly
        35                  40                  45

<210> SEQ ID NO 134
<211> LENGTH: 128
<212> TYPE: PRT
<213> ORGANISM: Homo sapiens

<400> SEQUENCE: 134

Met Pro Glu Leu Ile Leu Tyr Val Ala Ile Thr Leu Ser Val Ala Glu
1               5                   10                  15

Arg Leu Val Gly Pro Gly His Ala Cys Ala Glu Pro Ser Phe Arg Ser
            20                  25                  30

Ser Arg Cys Ser Ala Pro Leu Cys Leu Leu Cys Ser Gly Ser Ser Ser
        35                  40                  45

Pro Ala Thr Ala Pro His Pro Leu Lys Met Phe Ala Cys Ser Lys Phe
    50                  55                  60

Val Ser Thr Pro Ser Leu Val Lys Ser Thr Ser Gln Leu Leu Ser Arg
65                  70                  75                  80

Pro Leu Ser Ala Val Val Leu Lys Arg Pro Glu Ile Leu Thr Asp Glu
                85                  90                  95

Ser Leu Ser Ser Leu Ala Val Ser Cys Pro Leu Thr Ser Leu Val Ser
            100                 105                 110

Ser Arg Ser Phe Gln Thr Ser Ala Ile Ser Arg Asp Ile Asp Thr Ala
        115                 120                 125

<210> SEQ ID NO 135
<211> LENGTH: 115
<212> TYPE: PRT
<213> ORGANISM: Homo sapiens

<400> SEQUENCE: 135

Met Tyr Arg Leu Met Ser Ala Val Thr Ala Arg Ala Ala Ala Pro Gly
1               5                   10                  15

Gly Leu Ala Ser Ser Cys Gly Arg Arg Gly Val His Gln Arg Ala Gly

```
            20                  25                  30
Leu Pro Pro Leu Gly His Gly Trp Val Gly Gly Leu Gly Leu Gly Leu
            35                  40                  45

Gly Leu Ala Leu Gly Val Lys Leu Ala Gly Gly Leu Arg Gly Ala Ala
        50                  55                  60

Pro Ala Gln Ser Pro Ala Ala Pro Asp Pro Glu Ala Ser Pro Leu Ala
65                  70                  75                  80

Glu Pro Pro Gln Glu Gln Ser Leu Ala Pro Trp Ser Pro Gln Thr Pro
                85                  90                  95

Ala Pro Pro Cys Ser Arg Cys Phe Ala Arg Ala Ile Glu Ser Ser Arg
            100                 105                 110

Asp Leu Leu
        115

<210> SEQ ID NO 136
<211> LENGTH: 140
<212> TYPE: PRT
<213> ORGANISM: Schizosaccharomyces pombe

<400> SEQUENCE: 136

Met Thr Val Leu Ala Pro Leu Arg Arg Leu His Thr Arg Ala Ala Phe
1               5                   10                  15

Ser Ser Tyr Gly Arg Glu Ile Ala Leu Gln Lys Arg Phe Leu Asn Leu
            20                  25                  30

Asn Ser Cys Ser Ala Val Arg Arg Tyr Gly Thr Gly Phe Ser Asn Asn
        35                  40                  45

Leu Arg Ile Lys Lys Leu Lys Asn Ala Phe Gly Val Val Arg Ala Asn
    50                  55                  60

Ser Thr Lys Ser Thr Ser Thr Val Thr Thr Ala Ser Pro Ile Lys Tyr
65                  70                  75                  80

Asp Ser Ser Phe Val Gly Lys Thr Gly Gly Glu Ile Phe His Asp Met
                85                  90                  95

Met Leu Lys His Asn Val Lys His Val Phe Gly Tyr Pro Gly Gly Ala
            100                 105                 110

Ile Leu Pro Val Phe Asp Ala Ile Tyr Arg Ser Pro His Phe Glu Phe
        115                 120                 125

Ile Leu Pro Arg His Glu Gln Ala Ala Gly His Ala
    130                 135                 140

<210> SEQ ID NO 137
<211> LENGTH: 125
<212> TYPE: PRT
<213> ORGANISM: Glycine max

<400> SEQUENCE: 137

Met Ile Leu Cys Pro Leu Glu Ala Phe Ile Val Gln His Ile Leu Thr
1               5                   10                  15

Ile Ser Val Met Gly Leu Leu Ser Cys Phe Arg Ser Thr Val Leu Arg
            20                  25                  30

Lys Cys Ser Lys Gly Ser Ser Gly Met Ser Arg Phe Leu Tyr Thr Asn
        35                  40                  45

Asn Phe Gln Arg Asn Leu Ile Ser Gly Gly Asn Glu Ser Tyr Tyr
    50                  55                  60

Gly Tyr Phe Asn Arg Arg Ser Tyr Thr Ser Leu Tyr Met Gly Thr Gly
65                  70                  75                  80

Thr Val Gly Gly Ile Thr Ser Ala Arg Ile Arg Val Pro Asn Val Gly
```

```
                    85                  90                  95

Cys Glu Gly Phe Met Cys Ser Ser His Leu Ser Ile Thr Gln Arg Asn
                100                 105                 110

Ser Arg Leu Ile His Ser Thr Ser Lys Ile Val Pro Asn
        115                 120                 125

<210> SEQ ID NO 138
<211> LENGTH: 107
<212> TYPE: PRT
<213> ORGANISM: Chlamydomonas reinhardtii

<400> SEQUENCE: 138

Met Ala Leu Gln Gln Ala Ala Pro Arg Val Phe Gly Leu Leu Gly Arg
1               5                   10                  15

Ala Pro Val Ala Leu Gly Gln Ser Gly Ile Leu Thr Gly Ser Ser Gly
            20                  25                  30

Phe Lys Asn Gln Gly Phe Asn Gly Ser Leu Gln Ser Val Glu Asn His
        35                  40                  45

Val Tyr Ala Gln Ala Phe Ser Thr Ser Ser Gln Glu Gln Ala Ala
    50                  55                  60

Pro Ser Ile Gln Gly Ala Ser Gly Met Lys Leu Pro Gly Met Ala Gly
65                  70                  75                  80

Ser Met Leu Leu Gly Lys Ser Arg Ser Gly Leu Arg Thr Gly Ser Met
                85                  90                  95

Val Pro Phe Ala Ala Gln Gln Ala Met Asn Met
            100                 105

<210> SEQ ID NO 139
<211> LENGTH: 87
<212> TYPE: PRT
<213> ORGANISM: Homo sapiens

<400> SEQUENCE: 139

Met Trp Arg Leu Arg Arg Ala Ala Val Ala Cys Glu Val Cys Gln Ser
1               5                   10                  15

Leu Val Lys His Ser Ser Gly Ile Lys Gly Ser Leu Pro Leu Gln Lys
            20                  25                  30

Leu His Leu Val Ser Arg Ser Ile Tyr His Ser His Pro Thr Leu
        35                  40                  45

Lys Leu Gln Arg Pro Gln Leu Arg Thr Ser Phe Gln Gln Phe Ser Ser
        50                  55                  60

Leu Thr Asn Leu Pro Leu Arg Lys Leu Lys Phe Ser Pro Ile Lys Tyr
65                  70                  75                  80

Gly Tyr Gln Pro Arg Arg Asn
                85

<210> SEQ ID NO 140
<211> LENGTH: 56
<212> TYPE: PRT
<213> ORGANISM: Homo sapiens

<400> SEQUENCE: 140

Met Ala Val Leu Trp Arg Leu Ser Ala Val Cys Gly Ala Leu Gly Gly
1               5                   10                  15

Arg Ala Leu Leu Leu Arg Thr Pro Val Val Arg Pro Ala His Ile Ser
            20                  25                  30

Ala Phe Leu Gln Asp Arg Pro Ile Pro Glu Trp Cys Gly Val Gln His
        35                  40                  45
```

```
Ile His Leu Ser Pro Ser His His
    50              55

<210> SEQ ID NO 141
<211> LENGTH: 162
<212> TYPE: PRT
<213> ORGANISM: Homo sapiens

<400> SEQUENCE: 141

Met Ala Ala Ile Leu Gly Asp Thr Ile Met Val Ala Lys Gly Leu Val
1               5                   10                  15

Lys Leu Thr Gln Ala Ala Val Glu Thr His Leu Gln His Leu Gly Ile
            20                  25                  30

Gly Gly Glu Leu Ile Met Ala Ala Arg Ala Leu Gln Ser Thr Ala Val
        35                  40                  45

Glu Gln Ile Gly Met Phe Leu Gly Lys Val Gln Gly Gln Asp Lys His
    50                  55                  60

Glu Glu Tyr Phe Ala Glu Asn Phe Gly Pro Glu Gly Glu Phe His
65                  70                  75                  80

Phe Ser Val Pro His Ala Ala Gly Ala Ser Thr Asp Phe Ser Ser Ala
                85                  90                  95

Ser Ala Pro Asp Gln Ser Ala Pro Ser Leu Gly His Ala His Ser
            100                 105                 110

Glu Gly Pro Ala Pro Ala Tyr Val Ala Ser Gly Pro Phe Arg Glu Ala
        115                 120                 125

Gly Phe Pro Gly Gln Ala Ser Ser Pro Leu Gly Arg Ala Asn Gly Arg
    130                 135                 140

Leu Phe Ala Asn Pro Arg Asp Ser Phe Ser Ala Met Gly Phe Gln Arg
145                 150                 155                 160

Arg Phe

<210> SEQ ID NO 142
<211> LENGTH: 117
<212> TYPE: PRT
<213> ORGANISM: Oryza sativa

<400> SEQUENCE: 142

Met Ala Leu Leu Leu Arg His Ser Pro Lys Leu Arg Arg Ala His Ala
1               5                   10                  15

Ile Leu Gly Cys Glu Arg Gly Thr Val Val Arg His Phe Ser Ser Ser
            20                  25                  30

Thr Cys Ser Ser Leu Val Lys Glu Asp Thr Val Ser Ser Asn Leu
        35                  40                  45

His Pro Glu Tyr Ala Lys Lys Ile Gly Gly Ser Asp Phe Ser His Asp
    50                  55                  60

Arg Gln Ser Gly Lys Glu Leu Gln Asn Phe Lys Val Ser Pro Gln Glu
65                  70                  75                  80

Ala Ser Arg Ala Ser Asn Phe Met Arg Ala Ser Lys Tyr Gly Met Pro
                85                  90                  95

Ile Thr Ala Asn Gly Val His Ser Leu Phe Ser Cys Gly Gln Val Val
            100                 105                 110

Pro Ser Arg Cys Phe
        115

<210> SEQ ID NO 143
<211> LENGTH: 66
```

<212> TYPE: PRT
<213> ORGANISM: Neurospora crassa

<400> SEQUENCE: 143

Met Ala Ser Thr Arg Val Leu Ala Ser Arg Leu Ala Ser Gln Met Ala
1               5                   10                  15

Ala Ser Ala Lys Val Ala Arg Pro Ala Val Arg Val Ala Gln Val Ser
            20                  25                  30

Lys Arg Thr Ile Gln Thr Gly Ser Pro Leu Gln Thr Leu Lys Arg Thr
        35                  40                  45

Gln Met Thr Ser Ile Val Asn Ala Thr Thr Arg Gln Ala Phe Gln Lys
    50                  55                  60

Arg Ala
65

<210> SEQ ID NO 144
<211> LENGTH: 44
<212> TYPE: PRT
<213> ORGANISM: Homo sapiens

<400> SEQUENCE: 144

Met Leu Ala Ala Arg Leu Val Cys Leu Arg Thr Leu Pro Ser Arg Val
1               5                   10                  15

Phe His Pro Ala Phe Thr Lys Ala Ser Pro Val Val Lys Asn Ser Ile
            20                  25                  30

Thr Lys Asn Gln Trp Leu Leu Thr Pro Ser Arg Glu
        35                  40

<210> SEQ ID NO 145
<211> LENGTH: 68
<212> TYPE: PRT
<213> ORGANISM: Homo sapiens

<400> SEQUENCE: 145

Met Ala Ser Arg Val Leu Ser Ala Tyr Val Ser Arg Leu Pro Ala Ala
1               5                   10                  15

Phe Ala Pro Leu Pro Arg Val Arg Met Leu Ala Val Ala Arg Pro Leu
            20                  25                  30

Ser Thr Ala Leu Cys Ser Ala Gly Thr Gln Thr Arg Leu Gly Thr Leu
        35                  40                  45

Gln Pro Ala Leu Val Leu Ala Gln Val Pro Gly Arg Val Thr Gln Leu
    50                  55                  60

Cys Arg Gln Tyr
65

<210> SEQ ID NO 146
<211> LENGTH: 67
<212> TYPE: PRT
<213> ORGANISM: Homo sapiens

<400> SEQUENCE: 146

Met Phe Ala Cys Ala Lys Leu Ala Cys Thr Pro Ser Leu Ile Arg Ala
1               5                   10                  15

Gly Ser Arg Val Ala Tyr Arg Pro Ile Ser Ala Ser Val Leu Ser Arg
            20                  25                  30

Pro Glu Ala Ser Arg Thr Gly Glu Gly Ser Thr Val Phe Asn Gly Ala
        35                  40                  45

Gln Asn Gly Val Ser Gln Leu Ile Gln Arg Glu Phe Gln Thr Ser Ala
    50                  55                  60

Ile Ser Arg
65

<210> SEQ ID NO 147
<211> LENGTH: 273
<212> TYPE: PRT
<213> ORGANISM: Artificial Sequence
<220> FEATURE:
<223> OTHER INFORMATION: crATP6_hsADCK3

<400> SEQUENCE: 147

Met Ala Leu Gln Gln Ala Ala Pro Arg Val Phe Gly Leu Leu Gly Arg
1               5                   10                  15

Ala Pro Val Ala Leu Gly Gln Ser Gly Ile Leu Thr Gly Ser Ser Gly
            20                  25                  30

Phe Lys Asn Gln Gly Phe Asn Gly Ser Leu Gln Ser Val Glu Asn His
        35                  40                  45

Val Tyr Ala Gln Ala Phe Ser Thr Ser Ser Gln Glu Glu Gln Ala Ala
    50                  55                  60

Pro Ser Ile Gln Gly Ala Ser Gly Met Lys Leu Pro Gly Met Ala Gly
65                  70                  75                  80

Ser Met Leu Leu Gly Lys Ser Arg Ser Gly Leu Arg Thr Gly Ser Met
                85                  90                  95

Val Pro Phe Ala Ala Gln Gln Ala Met Asn Met Gly Gly Met Ala Ala
            100                 105                 110

Ile Leu Gly Asp Thr Ile Met Val Ala Lys Gly Leu Val Lys Leu Thr
        115                 120                 125

Gln Ala Ala Val Glu Thr His Leu Gln His Leu Gly Ile Gly Gly Glu
    130                 135                 140

Leu Ile Met Ala Ala Arg Ala Leu Gln Ser Thr Ala Val Glu Gln Ile
145                 150                 155                 160

Gly Met Phe Leu Gly Lys Val Gln Gly Gln Asp Lys His Glu Glu Tyr
                165                 170                 175

Phe Ala Glu Asn Phe Gly Gly Pro Glu Gly Glu Phe His Phe Ser Val
            180                 185                 190

Pro His Ala Ala Gly Ala Ser Thr Asp Phe Ser Ser Ala Ser Ala Pro
        195                 200                 205

Asp Gln Ser Ala Pro Pro Ser Leu Gly His Ala His Ser Glu Gly Pro
    210                 215                 220

Ala Pro Ala Tyr Val Ala Ser Gly Pro Phe Arg Glu Ala Gly Phe Pro
225                 230                 235                 240

Gly Gln Ala Ser Ser Pro Leu Gly Arg Ala Asn Gly Arg Leu Phe Ala
                245                 250                 255

Asn Pro Arg Asp Ser Phe Ser Ala Met Gly Phe Gln Arg Phe Gly
            260                 265                 270

Gly

<210> SEQ ID NO 148
<211> LENGTH: 132
<212> TYPE: PRT
<213> ORGANISM: Artificial Sequence
<220> FEATURE:
<223> OTHER INFORMATION: ncATP9_ncATP9

<400> SEQUENCE: 148

Met Ala Ser Thr Arg Val Leu Ala Ser Arg Leu Ala Ser Gln Met Ala
1               5                   10                  15

```
Ala Ser Ala Lys Val Ala Arg Pro Ala Val Arg Val Ala Gln Val Ser
            20                  25                  30

Lys Arg Thr Ile Gln Thr Gly Ser Pro Leu Gln Thr Leu Lys Arg Thr
        35                  40                  45

Gln Met Thr Ser Ile Val Asn Ala Thr Thr Arg Gln Ala Phe Gln Lys
 50                  55                  60

Arg Ala Met Ala Ser Thr Arg Val Leu Ala Ser Arg Leu Ala Ser Gln
 65                  70                  75                  80

Met Ala Ala Ser Ala Lys Val Ala Arg Pro Ala Val Arg Val Ala Gln
                85                  90                  95

Val Ser Lys Arg Thr Ile Gln Thr Gly Ser Pro Leu Gln Thr Leu Lys
            100                 105                 110

Arg Thr Gln Met Thr Ser Ile Val Asn Ala Thr Thr Arg Gln Ala Phe
        115                 120                 125

Gln Lys Arg Ala
        130

<210> SEQ ID NO 149
<211> LENGTH: 119
<212> TYPE: PRT
<213> ORGANISM: Zea mays

<400> SEQUENCE: 149

Met Ala Leu Leu Arg Ala Ala Val Ser Glu Leu Arg Arg Gly Arg
 1               5                  10                  15

Gly Ala Leu Thr Pro Leu Pro Ala Leu Ser Ser Leu Ser Ser Leu
            20                  25                  30

Ser Pro Arg Ser Pro Ala Ser Thr Arg Pro Glu Pro Asn Asn Pro His
        35                  40                  45

Ala Asp Arg Arg His Val Ile Ala Leu Arg Arg Cys Pro Pro Leu Pro
 50                  55                  60

Ala Ser Ala Val Leu Ala Pro Glu Leu Leu His Ala Arg Gly Leu Leu
 65                  70                  75                  80

Pro Arg His Trp Ser His Ala Ser Pro Leu Ser Thr Ser Ser Ser
                85                  90                  95

Ser Arg Pro Ala Asp Lys Ala Gln Leu Thr Trp Val Asp Lys Trp Ile
            100                 105                 110

Pro Glu Ala Ala Arg Pro Tyr
        115

<210> SEQ ID NO 150
<211> LENGTH: 391
<212> TYPE: PRT
<213> ORGANISM: Artificial Sequence
<220> FEATURE:
<223> OTHER INFORMATION: ncATP9_zmLOC100282174_spilv1_ncATP9

<400> SEQUENCE: 150

Met Ala Ser Thr Arg Val Leu Ala Ser Arg Leu Ala Ser Gln Met Ala
 1               5                  10                  15

Ala Ser Ala Lys Val Ala Arg Pro Ala Val Arg Val Ala Gln Val Ser
            20                  25                  30

Lys Arg Thr Ile Gln Thr Gly Ser Pro Leu Gln Thr Leu Lys Arg Thr
        35                  40                  45

Gln Met Thr Ser Ile Val Asn Ala Thr Thr Arg Gln Ala Phe Gln Lys
 50                  55                  60
```

Arg Ala Met Ala Leu Leu Arg Ala Val Ser Glu Leu Arg Arg Arg
65                  70                  75                  80

Gly Arg Gly Ala Leu Thr Pro Leu Pro Ala Leu Ser Ser Leu Leu Ser
            85                  90                  95

Ser Leu Ser Pro Arg Ser Pro Ala Ser Thr Arg Pro Glu Pro Asn Asn
            100                 105                 110

Pro His Ala Asp Arg Arg His Val Ile Ala Leu Arg Arg Cys Pro Pro
            115                 120                 125

Leu Pro Ala Ser Ala Val Leu Ala Pro Glu Leu Leu His Ala Arg Gly
130                 135                 140

Leu Leu Pro Arg His Trp Ser His Ala Ser Pro Leu Ser Thr Ser Ser
145                 150                 155                 160

Ser Ser Ser Arg Pro Ala Asp Lys Ala Gln Leu Thr Trp Val Asp Lys
            165                 170                 175

Trp Ile Pro Glu Ala Ala Arg Pro Tyr Met Thr Val Leu Ala Pro Leu
            180                 185                 190

Arg Arg Leu His Thr Arg Ala Ala Phe Ser Ser Tyr Gly Arg Glu Ile
            195                 200                 205

Ala Leu Gln Lys Arg Phe Leu Asn Leu Asn Ser Cys Ser Ala Val Arg
210                 215                 220

Arg Tyr Gly Thr Gly Phe Ser Asn Asn Leu Arg Ile Lys Lys Leu Lys
225                 230                 235                 240

Asn Ala Phe Gly Val Val Arg Ala Asn Ser Thr Lys Ser Thr Ser Thr
            245                 250                 255

Val Thr Thr Ala Ser Pro Ile Lys Tyr Asp Ser Ser Phe Val Gly Lys
            260                 265                 270

Thr Gly Gly Glu Ile Phe His Asp Met Met Leu Lys His Asn Val Lys
275                 280                 285

His Val Phe Gly Tyr Pro Gly Gly Ala Ile Leu Pro Val Phe Asp Ala
            290                 295                 300

Ile Tyr Arg Ser Pro His Phe Glu Phe Ile Leu Pro Arg His Glu Gln
305                 310                 315                 320

Ala Ala Gly His Ala Met Ala Ser Thr Arg Val Leu Ala Ser Arg Leu
            325                 330                 335

Ala Ser Gln Met Ala Ala Ser Ala Lys Val Ala Arg Pro Ala Val Arg
            340                 345                 350

Val Ala Gln Val Ser Lys Arg Thr Ile Gln Thr Gly Ser Pro Leu Gln
            355                 360                 365

Thr Leu Lys Arg Thr Gln Met Thr Ser Ile Val Asn Ala Thr Thr Arg
            370                 375                 380

Gln Ala Phe Gln Lys Arg Ala
385                 390

<210> SEQ ID NO 151
<211> LENGTH: 455
<212> TYPE: PRT
<213> ORGANISM: Artificial Sequence
<220> FEATURE:
<223> OTHER INFORMATION: zmLOC100282174_hsADCK3_crATP6 _hsATP5G3

<400> SEQUENCE: 151

Met Ala Leu Leu Arg Ala Ala Val Ser Glu Leu Arg Arg Arg Gly Arg
1               5                   10                  15

Gly Ala Leu Thr Pro Leu Pro Ala Leu Ser Ser Leu Leu Ser Ser Leu
            20                  25                  30

```
Ser Pro Arg Ser Pro Ala Ser Thr Arg Pro Glu Pro Asn Asn Pro His
         35                  40                  45

Ala Asp Arg Arg His Val Ile Ala Leu Arg Arg Cys Pro Pro Leu Pro
 50                  55                  60

Ala Ser Ala Val Leu Ala Pro Glu Leu Leu His Ala Arg Gly Leu Leu
 65              70                  75                       80

Pro Arg His Trp Ser His Ala Ser Pro Leu Ser Thr Ser Ser Ser Ser
                 85                  90                  95

Ser Arg Pro Ala Asp Lys Ala Gln Leu Thr Trp Val Asp Lys Trp Ile
             100                 105                 110

Pro Glu Ala Ala Arg Pro Tyr Met Ala Ala Ile Leu Gly Asp Thr Ile
             115                 120                 125

Met Val Ala Lys Gly Leu Val Lys Leu Thr Gln Ala Ala Val Glu Thr
 130                 135                 140

His Leu Gln His Leu Gly Ile Gly Gly Glu Leu Ile Met Ala Ala Arg
 145                 150                 155                 160

Ala Leu Gln Ser Thr Ala Val Glu Gln Ile Gly Met Phe Leu Gly Lys
                 165                 170                 175

Val Gln Gly Gln Asp Lys His Glu Glu Tyr Phe Ala Glu Asn Phe Gly
             180                 185                 190

Gly Pro Glu Gly Glu Phe His Phe Ser Val Pro His Ala Ala Gly Ala
             195                 200                 205

Ser Thr Asp Phe Ser Ser Ser Ala Ser Ala Pro Asp Gln Ser Ala Pro Pro
 210                 215                 220

Ser Leu Gly His Ala His Ser Glu Gly Pro Ala Pro Ala Tyr Val Ala
 225                 230                 235                 240

Ser Gly Pro Phe Arg Glu Ala Gly Phe Pro Gly Gln Ala Ser Ser Pro
                 245                 250                 255

Leu Gly Arg Ala Asn Gly Arg Leu Phe Ala Asn Pro Arg Asp Ser Phe
                 260                 265                 270

Ser Ala Met Gly Phe Gln Arg Arg Phe Met Ala Leu Gln Gln Ala Ala
                 275                 280                 285

Pro Arg Val Phe Gly Leu Leu Gly Arg Ala Pro Val Ala Leu Gly Gln
 290                 295                 300

Ser Gly Ile Leu Thr Gly Ser Ser Gly Phe Lys Asn Gln Gly Phe Asn
 305                 310                 315                 320

Gly Ser Leu Gln Ser Val Glu Asn His Val Tyr Ala Gln Ala Phe Ser
                 325                 330                 335

Thr Ser Ser Gln Glu Glu Gln Ala Ala Pro Ser Ile Gln Gly Ala Ser
                 340                 345                 350

Gly Met Lys Leu Pro Gly Met Ala Gly Ser Met Leu Leu Gly Lys Ser
                 355                 360                 365

Arg Ser Gly Leu Arg Thr Gly Ser Met Val Pro Phe Ala Ala Gln Gln
 370                 375                 380

Ala Met Asn Met Met Phe Ala Cys Ala Lys Leu Ala Cys Thr Pro Ser
 385                 390                 395                 400

Leu Ile Arg Ala Gly Ser Arg Val Ala Tyr Arg Pro Ile Ser Ala Ser
                 405                 410                 415

Val Leu Ser Arg Pro Glu Ala Ser Arg Thr Gly Glu Gly Ser Thr Val
             420                 425                 430

Phe Asn Gly Ala Gln Asn Gly Val Ser Gln Leu Ile Gln Arg Glu Phe
             435                 440                 445

Gln Thr Ser Ala Ile Ser Arg
```

<210> SEQ ID NO 152
<211> LENGTH: 348
<212> TYPE: PRT
<213> ORGANISM: Artificial Sequence
<220> FEATURE:
<223> OTHER INFORMATION: zmLOC100282174_hsADCK3_hsATP5G3

<400> SEQUENCE: 152

```
Met Ala Leu Leu Arg Ala Ala Val Ser Glu Leu Arg Arg Arg Gly Arg
1               5                  10                  15

Gly Ala Leu Thr Pro Leu Pro Ala Leu Ser Ser Leu Leu Ser Ser Leu
            20                  25                  30

Ser Pro Arg Ser Pro Ala Ser Thr Arg Pro Glu Pro Asn Asn Pro His
        35                  40                  45

Ala Asp Arg Arg His Val Ile Ala Leu Arg Arg Cys Pro Pro Leu Pro
    50                  55                  60

Ala Ser Ala Val Leu Ala Pro Glu Leu Leu His Ala Arg Gly Leu Leu
65                  70                  75                  80

Pro Arg His Trp Ser His Ala Ser Pro Leu Ser Thr Ser Ser Ser Ser
                85                  90                  95

Ser Arg Pro Ala Asp Lys Ala Gln Leu Thr Trp Val Asp Lys Trp Ile
            100                 105                 110

Pro Glu Ala Ala Arg Pro Tyr Met Ala Ala Ile Leu Gly Asp Thr Ile
        115                 120                 125

Met Val Ala Lys Gly Leu Val Lys Leu Thr Gln Ala Ala Val Glu Thr
130                 135                 140

His Leu Gln His Leu Gly Ile Gly Gly Glu Leu Ile Met Ala Ala Arg
145                 150                 155                 160

Ala Leu Gln Ser Thr Ala Val Glu Gln Ile Gly Met Phe Leu Gly Lys
                165                 170                 175

Val Gln Gly Gln Asp Lys His Glu Glu Tyr Phe Ala Glu Asn Phe Gly
            180                 185                 190

Gly Pro Glu Gly Glu Phe His Phe Ser Val Pro His Ala Ala Gly Ala
        195                 200                 205

Ser Thr Asp Phe Ser Ser Ala Ser Ala Pro Asp Gln Ser Ala Pro Pro
    210                 215                 220

Ser Leu Gly His Ala His Ser Glu Gly Pro Ala Pro Ala Tyr Val Ala
225                 230                 235                 240

Ser Gly Pro Phe Arg Glu Ala Gly Phe Pro Gly Gln Ala Ser Ser Pro
                245                 250                 255

Leu Gly Arg Ala Asn Gly Arg Leu Phe Ala Asn Pro Arg Asp Ser Phe
            260                 265                 270

Ser Ala Met Gly Phe Gln Arg Arg Phe Met Phe Ala Cys Ala Lys Leu
        275                 280                 285

Ala Cys Thr Pro Ser Leu Ile Arg Ala Gly Ser Arg Val Ala Tyr Arg
    290                 295                 300

Pro Ile Ser Ala Ser Val Leu Ser Arg Pro Glu Ala Ser Arg Thr Gly
305                 310                 315                 320

Glu Gly Ser Thr Val Phe Asn Gly Ala Gln Asn Gly Val Ser Gln Leu
                325                 330                 335

Ile Gln Arg Glu Phe Gln Thr Ser Ala Ile Ser Arg
            340                 345
```

<210> SEQ ID NO 153
<211> LENGTH: 185
<212> TYPE: PRT
<213> ORGANISM: Artificial Sequence
<220> FEATURE:
<223> OTHER INFORMATION: ncATP9_zmLOC100282174

<400> SEQUENCE: 153

```
Met Ala Ser Thr Arg Val Leu Ala Ser Arg Leu Ala Ser Gln Met Ala
1               5                   10                  15

Ala Ser Ala Lys Val Ala Arg Pro Ala Val Arg Val Ala Gln Val Ser
            20                  25                  30

Lys Arg Thr Ile Gln Thr Gly Ser Pro Leu Gln Thr Leu Lys Arg Thr
        35                  40                  45

Gln Met Thr Ser Ile Val Asn Ala Thr Thr Arg Gln Ala Phe Gln Lys
    50                  55                  60

Arg Ala Met Ala Leu Leu Arg Ala Ala Val Ser Glu Leu Arg Arg Arg
65                  70                  75                  80

Gly Arg Gly Ala Leu Thr Pro Leu Pro Ala Leu Ser Ser Leu Leu Ser
                85                  90                  95

Ser Leu Ser Pro Arg Ser Pro Ala Ser Thr Arg Pro Glu Pro Asn Asn
            100                 105                 110

Pro His Ala Asp Arg Arg His Val Ile Ala Leu Arg Arg Cys Pro Pro
        115                 120                 125

Leu Pro Ala Ser Ala Val Leu Ala Pro Glu Leu Leu His Ala Arg Gly
    130                 135                 140

Leu Leu Pro Arg His Trp Ser His Ala Ser Pro Leu Ser Thr Ser Ser
145                 150                 155                 160

Ser Ser Ser Arg Pro Ala Asp Lys Ala Gln Leu Thr Trp Val Asp Lys
                165                 170                 175

Trp Ile Pro Glu Ala Ala Arg Pro Tyr
            180                 185
```

<210> SEQ ID NO 154
<211> LENGTH: 455
<212> TYPE: PRT
<213> ORGANISM: Artificial Sequence
<220> FEATURE:
<223> OTHER INFORMATION: hsADCK3_zmLOC100282174_crATP6 _hsATP5G3

<400> SEQUENCE: 154

```
Met Ala Ala Ile Leu Gly Asp Thr Ile Met Val Ala Lys Gly Leu Val
1               5                   10                  15

Lys Leu Thr Gln Ala Ala Val Glu Thr His Leu Gln His Leu Gly Ile
            20                  25                  30

Gly Gly Glu Leu Ile Met Ala Ala Arg Ala Leu Gln Ser Thr Ala Val
        35                  40                  45

Glu Gln Ile Gly Met Phe Leu Gly Lys Val Gln Gly Gln Asp Lys His
    50                  55                  60

Glu Glu Tyr Phe Ala Glu Asn Phe Gly Gly Pro Gly Glu Gly Phe His
65                  70                  75                  80

Phe Ser Val Pro His Ala Ala Gly Ala Ser Thr Asp Phe Ser Ser Ala
                85                  90                  95

Ser Ala Pro Asp Gln Ser Ala Pro Pro Ser Leu Gly His Ala His Ser
            100                 105                 110

Glu Gly Pro Ala Pro Ala Tyr Val Ala Ser Gly Pro Phe Arg Glu Ala
        115                 120                 125
```

```
Gly Phe Pro Gly Gln Ala Ser Ser Pro Leu Gly Arg Ala Asn Gly Arg
            130                 135                 140

Leu Phe Ala Asn Pro Arg Asp Ser Phe Ser Ala Met Gly Phe Gln Arg
145                 150                 155                 160

Arg Phe Met Ala Leu Leu Arg Ala Ala Val Ser Glu Leu Arg Arg Arg
                165                 170                 175

Gly Arg Gly Ala Leu Thr Pro Leu Pro Ala Leu Ser Ser Leu Leu Ser
            180                 185                 190

Ser Leu Ser Pro Arg Ser Pro Ala Ser Thr Arg Pro Glu Pro Asn Asn
        195                 200                 205

Pro His Ala Asp Arg Arg His Val Ile Ala Leu Arg Arg Cys Pro Pro
210                 215                 220

Leu Pro Ala Ser Ala Val Leu Ala Pro Glu Leu Leu His Ala Arg Gly
225                 230                 235                 240

Leu Leu Pro Arg His Trp Ser His Ala Ser Pro Leu Ser Thr Ser Ser
                245                 250                 255

Ser Ser Ser Arg Pro Ala Asp Lys Ala Gln Leu Thr Trp Val Asp Lys
            260                 265                 270

Trp Ile Pro Glu Ala Ala Arg Pro Tyr Met Ala Leu Gln Gln Ala Ala
        275                 280                 285

Pro Arg Val Phe Gly Leu Leu Gly Arg Ala Pro Val Ala Leu Gly Gln
290                 295                 300

Ser Gly Ile Leu Thr Gly Ser Ser Gly Phe Lys Asn Gln Gly Phe Asn
305                 310                 315                 320

Gly Ser Leu Gln Ser Val Glu Asn His Val Tyr Ala Gln Ala Phe Ser
                325                 330                 335

Thr Ser Ser Gln Glu Glu Gln Ala Ala Pro Ser Ile Gln Gly Ala Ser
            340                 345                 350

Gly Met Lys Leu Pro Gly Met Ala Gly Ser Met Leu Leu Gly Lys Ser
        355                 360                 365

Arg Ser Gly Leu Arg Thr Gly Ser Met Val Pro Phe Ala Ala Gln Gln
370                 375                 380

Ala Met Asn Met Met Phe Ala Cys Ala Lys Leu Ala Cys Thr Pro Ser
385                 390                 395                 400

Leu Ile Arg Ala Gly Ser Arg Val Ala Tyr Arg Pro Ile Ser Ala Ser
                405                 410                 415

Val Leu Ser Arg Pro Glu Ala Ser Arg Thr Gly Glu Gly Ser Thr Val
            420                 425                 430

Phe Asn Gly Ala Gln Asn Gly Val Ser Gln Leu Ile Gln Arg Glu Phe
        435                 440                 445

Gln Thr Ser Ala Ile Ser Arg
    450                 455

<210> SEQ ID NO 155
<211> LENGTH: 455
<212> TYPE: PRT
<213> ORGANISM: Artificial Sequence
<220> FEATURE:
<223> OTHER INFORMATION: crATP6_hsADCK3_zmLOC100282174_hsATP5G3

<400> SEQUENCE: 155

Met Ala Leu Gln Gln Ala Ala Pro Arg Val Phe Gly Leu Leu Gly Arg
1               5                   10                  15

Ala Pro Val Ala Leu Gly Gln Ser Gly Ile Leu Thr Gly Ser Ser Gly
            20                  25                  30
```

```
Phe Lys Asn Gln Gly Phe Asn Gly Ser Leu Gln Ser Val Glu Asn His
            35                  40                  45
Val Tyr Ala Gln Ala Phe Ser Thr Ser Ser Gln Glu Glu Gln Ala Ala
 50                  55                  60
Pro Ser Ile Gln Gly Ala Ser Gly Met Lys Leu Pro Gly Met Ala Gly
 65                  70                  75                  80
Ser Met Leu Leu Gly Lys Ser Arg Ser Gly Leu Arg Thr Gly Ser Met
                 85                  90                  95
Val Pro Phe Ala Ala Gln Gln Ala Met Asn Met Met Ala Ala Ile Leu
                100                 105                 110
Gly Asp Thr Ile Met Val Ala Lys Gly Leu Val Lys Leu Thr Gln Ala
            115                 120                 125
Ala Val Glu Thr His Leu Gln His Leu Gly Ile Gly Gly Glu Leu Ile
130                 135                 140
Met Ala Ala Arg Ala Leu Gln Ser Thr Ala Val Glu Gln Ile Gly Met
145                 150                 155                 160
Phe Leu Gly Lys Val Gln Gly Gln Asp Lys His Glu Glu Tyr Phe Ala
                165                 170                 175
Glu Asn Phe Gly Gly Pro Glu Gly Glu Phe His Phe Ser Val Pro His
                180                 185                 190
Ala Ala Gly Ala Ser Thr Asp Phe Ser Ser Ala Ser Ala Pro Asp Gln
            195                 200                 205
Ser Ala Pro Pro Ser Leu Gly His Ala His Ser Glu Gly Pro Ala Pro
    210                 215                 220
Ala Tyr Val Ala Ser Gly Pro Phe Arg Glu Ala Gly Phe Pro Gly Gln
225                 230                 235                 240
Ala Ser Ser Pro Leu Gly Arg Ala Asn Gly Arg Leu Phe Ala Asn Pro
                245                 250                 255
Arg Asp Ser Phe Ser Ala Met Gly Phe Gln Arg Arg Phe Met Ala Leu
                260                 265                 270
Leu Arg Ala Ala Val Ser Glu Leu Arg Arg Arg Gly Arg Gly Ala Leu
            275                 280                 285
Thr Pro Leu Pro Ala Leu Ser Ser Leu Leu Ser Ser Leu Ser Pro Arg
    290                 295                 300
Ser Pro Ala Ser Thr Arg Pro Glu Pro Asn Asn Pro His Ala Asp Arg
305                 310                 315                 320
Arg His Val Ile Ala Leu Arg Arg Cys Pro Pro Leu Pro Ala Ser Ala
                325                 330                 335
Val Leu Ala Pro Glu Leu Leu His Ala Arg Gly Leu Leu Pro Arg His
                340                 345                 350
Trp Ser His Ala Ser Pro Leu Ser Thr Ser Ser Ser Ser Arg Pro
            355                 360                 365
Ala Asp Lys Ala Gln Leu Thr Trp Val Asp Lys Trp Ile Pro Glu Ala
    370                 375                 380
Ala Arg Pro Tyr Met Phe Ala Cys Ala Lys Leu Ala Cys Thr Pro Ser
385                 390                 395                 400
Leu Ile Arg Ala Gly Ser Arg Val Ala Tyr Arg Pro Ile Ser Ala Ser
                405                 410                 415
Val Leu Ser Arg Pro Glu Ala Ser Arg Thr Gly Glu Gly Ser Thr Val
            420                 425                 430
Phe Asn Gly Ala Gln Asn Gly Val Ser Gln Leu Ile Gln Arg Glu Phe
    435                 440                 445
Gln Thr Ser Ala Ile Ser Arg
```

<210> SEQ ID NO 156
<211> LENGTH: 285
<212> TYPE: PRT
<213> ORGANISM: Artificial Sequence
<220> FEATURE:
<223> OTHER INFORMATION: hsADCK3_zmLOC100282174

<400> SEQUENCE: 156

```
Met Ala Ala Ile Leu Gly Asp Thr Ile Met Val Ala Lys Gly Leu Val
1               5                   10                  15

Lys Leu Thr Gln Ala Ala Val Glu Thr His Leu Gln His Leu Gly Ile
            20                  25                  30

Gly Gly Glu Leu Ile Met Ala Ala Arg Ala Leu Gln Ser Thr Ala Val
        35                  40                  45

Glu Gln Ile Gly Met Phe Leu Gly Lys Val Gln Gly Gln Asp Lys His
    50                  55                  60

Glu Glu Tyr Phe Ala Glu Asn Phe Gly Gly Pro Glu Gly Glu Phe His
65                  70                  75                  80

Phe Ser Val Pro His Ala Ala Gly Ala Ser Thr Asp Phe Ser Ser Ala
                85                  90                  95

Ser Ala Pro Asp Gln Ser Ala Pro Ser Leu Gly His Ala His Ser
            100                 105                 110

Glu Gly Pro Ala Pro Ala Tyr Val Ala Ser Gly Pro Phe Arg Glu Ala
        115                 120                 125

Gly Phe Pro Gly Gln Ala Ser Ser Pro Leu Gly Arg Ala Asn Gly Arg
    130                 135                 140

Leu Phe Ala Asn Pro Arg Asp Ser Phe Ser Ala Met Gly Phe Gln Arg
145                 150                 155                 160

Arg Phe Gly Gly Met Ala Leu Leu Arg Ala Ala Val Ser Glu Leu Arg
                165                 170                 175

Arg Arg Gly Arg Gly Ala Leu Thr Pro Leu Pro Ala Leu Ser Ser Leu
            180                 185                 190

Leu Ser Ser Leu Ser Pro Arg Ser Pro Ala Ser Thr Arg Pro Glu Pro
        195                 200                 205

Asn Asn Pro His Ala Asp Arg Arg His Val Ile Ala Leu Arg Arg Cys
    210                 215                 220

Pro Pro Leu Pro Ala Ser Ala Val Leu Ala Pro Glu Leu Leu His Ala
225                 230                 235                 240

Arg Gly Leu Leu Pro Arg His Trp Ser His Ala Ser Pro Leu Ser Thr
                245                 250                 255

Ser Ser Ser Ser Ser Arg Pro Ala Asp Lys Ala Gln Leu Thr Trp Val
            260                 265                 270

Asp Lys Trp Ile Pro Glu Ala Ala Arg Pro Tyr Gly Gly
        275                 280                 285
```

<210> SEQ ID NO 157
<211> LENGTH: 394
<212> TYPE: PRT
<213> ORGANISM: Artificial Sequence
<220> FEATURE:
<223> OTHER INFORMATION: hsADCK3_zmLOC100282174_crATP6

<400> SEQUENCE: 157

```
Met Ala Ala Ile Leu Gly Asp Thr Ile Met Val Ala Lys Gly Leu Val
1               5                   10                  15
```

Lys Leu Thr Gln Ala Ala Val Glu Thr His Leu Gln His Leu Gly Ile
            20                  25                  30

Gly Gly Glu Leu Ile Met Ala Ala Arg Ala Leu Gln Ser Thr Ala Val
        35                  40                  45

Glu Gln Ile Gly Met Phe Leu Gly Lys Val Gln Gly Gln Asp Lys His
50                  55                  60

Glu Glu Tyr Phe Ala Glu Asn Phe Gly Gly Pro Gly Glu Phe His
65                  70                  75                  80

Phe Ser Val Pro His Ala Ala Gly Ala Ser Thr Asp Phe Ser Ser Ala
                85                  90                  95

Ser Ala Pro Asp Gln Ser Ala Pro Pro Ser Leu Gly His Ala His Ser
            100                 105                 110

Glu Gly Pro Ala Pro Ala Tyr Val Ala Ser Gly Pro Phe Arg Glu Ala
        115                 120                 125

Gly Phe Pro Gly Gln Ala Ser Ser Pro Leu Gly Arg Ala Asn Gly Arg
    130                 135                 140

Leu Phe Ala Asn Pro Arg Asp Ser Phe Ser Ala Met Gly Phe Gln Arg
145                 150                 155                 160

Arg Phe Gly Gly Met Ala Leu Leu Arg Ala Ala Val Ser Glu Leu Arg
                165                 170                 175

Arg Arg Gly Arg Gly Ala Leu Thr Pro Leu Pro Ala Leu Ser Ser Leu
            180                 185                 190

Leu Ser Ser Leu Ser Pro Arg Ser Pro Ala Ser Thr Arg Pro Glu Pro
        195                 200                 205

Asn Asn Pro His Ala Asp Arg Arg His Val Ile Ala Leu Arg Arg Cys
    210                 215                 220

Pro Pro Leu Pro Ala Ser Ala Val Leu Ala Pro Glu Leu Leu His Ala
225                 230                 235                 240

Arg Gly Leu Leu Pro Arg His Trp Ser His Ala Ser Pro Leu Ser Thr
                245                 250                 255

Ser Ser Ser Ser Ser Arg Pro Ala Asp Lys Ala Gln Leu Thr Trp Val
            260                 265                 270

Asp Lys Trp Ile Pro Glu Ala Ala Arg Pro Tyr Gly Gly Met Ala Leu
        275                 280                 285

Gln Gln Ala Ala Pro Arg Val Phe Gly Leu Leu Gly Arg Ala Pro Val
    290                 295                 300

Ala Leu Gly Gln Ser Gly Ile Leu Thr Gly Ser Ser Gly Phe Lys Asn
305                 310                 315                 320

Gln Gly Phe Asn Gly Ser Leu Gln Ser Val Glu Asn His Val Tyr Ala
                325                 330                 335

Gln Ala Phe Ser Thr Ser Ser Gln Glu Glu Gln Ala Ala Pro Ser Ile
            340                 345                 350

Gln Gly Ala Ser Gly Met Lys Leu Pro Gly Met Ala Gly Ser Met Leu
        355                 360                 365

Leu Gly Lys Ser Arg Ser Gly Leu Arg Thr Gly Ser Met Val Pro Phe
    370                 375                 380

Ala Ala Gln Gln Ala Met Asn Met Gly Gly
385                 390

<210> SEQ ID NO 158
<211> LENGTH: 574
<212> TYPE: PRT
<213> ORGANISM: Artificial Sequence
<220> FEATURE:
<223> OTHER INFORMATION: ncATP9_zmLOC100282174_spilv1_GNFP_ncATP9

<400> SEQUENCE: 158

```
Met Ala Ser Thr Arg Val Leu Ala Ser Arg Leu Ala Ser Gln Met Ala
1               5                   10                  15

Ala Ser Ala Lys Val Ala Arg Pro Ala Val Arg Val Ala Gln Val Ser
            20                  25                  30

Lys Arg Thr Ile Gln Thr Gly Ser Pro Leu Gln Thr Leu Lys Arg Thr
        35                  40                  45

Gln Met Thr Ser Ile Val Asn Ala Thr Thr Arg Gln Ala Phe Gln Lys
    50                  55                  60

Arg Ala Met Ala Leu Leu Arg Ala Ala Val Ser Glu Leu Arg Arg
65                  70                  75                  80

Gly Arg Gly Ala Leu Thr Pro Leu Pro Ala Leu Ser Ser Leu Leu Ser
                85                  90                  95

Ser Leu Ser Pro Arg Ser Pro Ala Ser Thr Arg Pro Glu Pro Asn Asn
            100                 105                 110

Pro His Ala Asp Arg Arg His Val Ile Ala Leu Arg Arg Cys Pro Pro
        115                 120                 125

Leu Pro Ala Ser Ala Val Leu Ala Pro Glu Leu Leu His Ala Arg Gly
    130                 135                 140

Leu Leu Pro Arg His Trp Ser His Ala Ser Pro Leu Ser Thr Ser Ser
145                 150                 155                 160

Ser Ser Ser Arg Pro Ala Asp Lys Ala Gln Leu Thr Trp Val Asp Lys
                165                 170                 175

Trp Ile Pro Glu Ala Ala Arg Pro Tyr Met Thr Val Leu Ala Pro Leu
            180                 185                 190

Arg Arg Leu His Thr Arg Ala Ala Phe Ser Ser Tyr Gly Arg Glu Ile
        195                 200                 205

Ala Leu Gln Lys Arg Phe Leu Asn Leu Asn Ser Cys Ser Ala Val Arg
    210                 215                 220

Arg Tyr Gly Thr Gly Phe Ser Asn Asn Leu Arg Ile Lys Lys Leu Lys
225                 230                 235                 240

Asn Ala Phe Gly Val Val Arg Ala Asn Ser Thr Lys Ser Thr Ser Thr
                245                 250                 255

Val Thr Thr Ala Ser Pro Ile Lys Tyr Asp Ser Ser Phe Val Gly Lys
            260                 265                 270

Thr Gly Gly Glu Ile Phe His Asp Met Met Leu Lys His Asn Val Lys
        275                 280                 285

His Val Phe Gly Tyr Pro Gly Gly Ala Ile Leu Pro Val Phe Asp Ala
    290                 295                 300

Ile Tyr Arg Ser Pro His Phe Glu Phe Ile Leu Pro Arg His Glu Gln
305                 310                 315                 320

Ala Ala Gly His Ala Val Ser Gly Glu Gly Asp Ala Thr Tyr Gly Lys
                325                 330                 335

Leu Thr Leu Lys Phe Ile Cys Thr Thr Gly Lys Leu Pro Val Pro Trp
            340                 345                 350

Pro Thr Leu Val Thr Thr Leu Thr Tyr Gly Val Gln Cys Phe Ser Arg
        355                 360                 365

Tyr Pro Asp His Met Lys Gln His Asp Phe Phe Lys Ser Ala Met Pro
    370                 375                 380

Glu Gly Tyr Val Gln Glu Arg Thr Ile Phe Phe Lys Asp Asp Gly Asn
385                 390                 395                 400

Tyr Lys Thr Arg Ala Glu Val Lys Phe Glu Gly Asp Thr Leu Val Asn
```

```
                      405                 410                 415
Arg Ile Glu Leu Lys Gly Ile Asp Phe Lys Glu Asp Gly Asn Ile Leu
                420                 425                 430

Gly His Lys Leu Glu Tyr Asn Tyr Asn Ser His Asn Val Tyr Ile Met
            435                 440                 445

Ala Asp Lys Gln Lys Asn Gly Ile Lys Val Asn Phe Lys Ile Arg His
        450                 455                 460

Asn Ile Glu Asp Gly Ser Val Gln Leu Ala Asp His Tyr Gln Gln Asn
465                 470                 475                 480

Thr Pro Ile Gly Asp Gly Pro Val Leu Leu Pro Asp Asn His Tyr Leu
                485                 490                 495

Ser Thr Gln Ser Ala Leu Ser Lys Asp Pro Asn Glu Met Ala Ser Thr
            500                 505                 510

Arg Val Leu Ala Ser Arg Leu Ala Ser Gln Met Ala Ala Ser Ala Lys
        515                 520                 525

Val Ala Arg Pro Ala Val Arg Val Ala Gln Val Ser Lys Arg Thr Ile
    530                 535                 540

Gln Thr Gly Ser Pro Leu Gln Thr Leu Lys Arg Thr Gln Met Thr Ser
545                 550                 555                 560

Ile Val Asn Ala Thr Thr Arg Gln Ala Phe Gln Lys Arg Ala
                565                 570

<210> SEQ ID NO 159
<211> LENGTH: 810
<212> TYPE: PRT
<213> ORGANISM: Artificial Sequence
<220> FEATURE:
<223> OTHER INFORMATION: ncATP9_zmLOC100282174_spilv1_lcSirt5_
      osP0644B06.24-2_hsATP5G2_ncATP9

<400> SEQUENCE: 159

Met Ala Ser Thr Arg Val Leu Ala Ser Arg Leu Ala Ser Gln Met Ala
1               5                   10                  15

Ala Ser Ala Lys Val Ala Arg Pro Ala Val Arg Val Ala Gln Val Ser
            20                  25                  30

Lys Arg Thr Ile Gln Thr Gly Ser Pro Leu Gln Thr Leu Lys Arg Thr
        35                  40                  45

Gln Met Thr Ser Ile Val Asn Ala Thr Thr Arg Gln Ala Phe Gln Lys
    50                  55                  60

Arg Ala Met Ala Leu Leu Arg Ala Ala Val Ser Glu Leu Arg Arg Arg
65                  70                  75                  80

Gly Arg Gly Ala Leu Thr Pro Leu Pro Ala Leu Ser Ser Leu Leu Ser
                85                  90                  95

Ser Leu Ser Pro Arg Ser Pro Ala Ser Thr Arg Pro Glu Pro Asn Asn
            100                 105                 110

Pro His Ala Asp Arg Arg His Val Ile Ala Leu Arg Arg Cys Pro Pro
        115                 120                 125

Leu Pro Ala Ser Ala Val Leu Ala Pro Glu Leu Leu His Ala Arg Gly
    130                 135                 140

Leu Leu Pro Arg His Trp Ser His Ala Ser Pro Leu Ser Thr Ser Ser
145                 150                 155                 160

Ser Ser Ser Arg Pro Ala Asp Lys Ala Gln Leu Thr Trp Val Asp Lys
                165                 170                 175

Trp Ile Pro Glu Ala Ala Arg Pro Tyr Met Thr Val Leu Ala Pro Leu
            180                 185                 190
```

```
Arg Arg Leu His Thr Arg Ala Ala Phe Ser Ser Tyr Gly Arg Glu Ile
            195                 200                 205

Ala Leu Gln Lys Arg Phe Leu Asn Leu Asn Ser Cys Ser Ala Val Arg
210                 215                 220

Arg Tyr Gly Thr Gly Phe Ser Asn Asn Leu Arg Ile Lys Lys Leu Lys
225                 230                 235                 240

Asn Ala Phe Gly Val Val Arg Ala Asn Ser Thr Lys Ser Thr Ser Thr
                245                 250                 255

Val Thr Thr Ala Ser Pro Ile Lys Tyr Asp Ser Ser Phe Val Gly Lys
            260                 265                 270

Thr Gly Gly Glu Ile Phe His Asp Met Met Leu Lys His Asn Val Lys
        275                 280                 285

His Val Phe Gly Tyr Pro Gly Gly Ala Ile Leu Pro Val Phe Asp Ala
    290                 295                 300

Ile Tyr Arg Ser Pro His Phe Glu Phe Ile Leu Pro Arg His Glu Gln
305                 310                 315                 320

Ala Ala Gly His Ala Met Arg Lys Arg Ser Leu Arg Cys His Leu Trp
                325                 330                 335

Ser Ala Asn Ala Ser Leu Ser Pro Arg Lys Asp Glu Val Thr Ser Arg
            340                 345                 350

Lys Glu Ser Glu Asn Leu Val Lys Gly Lys Lys Asn Lys Lys Ser His
        355                 360                 365

Leu His Leu Leu Leu Phe Thr Ala Ser Lys Ile Gly Thr Asp Ser Val
    370                 375                 380

Phe Asp Val Gln Lys Ser Lys Glu Cys Cys Lys Glu Leu Gly Leu Leu
385                 390                 395                 400

Phe Thr Ser Leu Ile His Ser Ile Gly Ser Phe Pro Phe Asp Glu Glu
                405                 410                 415

Pro Lys Ala Ala Ala Val Phe Leu Pro Gly Ser Leu Pro Gln Leu Thr
            420                 425                 430

Val Leu Val Leu Ala Pro Gly Ser Gly Ser Cys Pro Thr Gly Lys Ser
        435                 440                 445

Thr Pro His Leu Ala Ala Ser Gly Arg Asn Ala Glu Leu Leu Arg Pro
    450                 455                 460

Gln Asn Ser Met Ile Val Arg Gln Phe Thr Cys Arg Gly Thr Ile Ser
465                 470                 475                 480

Ser His Leu Cys Ala His Leu Arg Lys Pro His Asp Ser Arg Asn Met
                485                 490                 495

Ala Arg Pro Met Ala Leu Leu Arg His Ser Pro Lys Leu Arg Arg
            500                 505                 510

Ala His Ala Ile Leu Gly Cys Glu Arg Gly Thr Val Val Arg His Phe
        515                 520                 525

Ser Ser Ser Thr Cys Ser Ser Leu Val Lys Glu Asp Thr Val Ser Ser
    530                 535                 540

Ser Asn Leu His Pro Glu Tyr Ala Lys Lys Ile Gly Gly Ser Asp Phe
545                 550                 555                 560

Ser His Asp Arg Gln Ser Gly Lys Glu Leu Gln Asn Phe Lys Val Ser
                565                 570                 575

Pro Gln Glu Ala Ser Arg Ala Ser Asn Phe Met Arg Ala Ser Lys Tyr
            580                 585                 590

Gly Met Pro Ile Thr Ala Asn Gly Val His Ser Leu Phe Ser Cys Gly
        595                 600                 605

Gln Val Val Pro Ser Arg Cys Phe Met Pro Glu Leu Ile Leu Tyr Val
```

```
                610                 615                 620
Ala Ile Thr Leu Ser Val Ala Glu Arg Leu Val Gly Pro Gly His Ala
625                 630                 635                 640

Cys Ala Glu Pro Ser Phe Arg Ser Ser Arg Cys Ser Ala Pro Leu Cys
                645                 650                 655

Leu Leu Cys Ser Gly Ser Ser Ser Pro Ala Thr Ala Pro His Pro Leu
                660                 665                 670

Lys Met Phe Ala Cys Ser Lys Phe Val Ser Thr Pro Ser Leu Val Lys
                675                 680                 685

Ser Thr Ser Gln Leu Leu Ser Arg Pro Leu Ser Ala Val Val Leu Lys
                690                 695                 700

Arg Pro Glu Ile Leu Thr Asp Glu Ser Leu Ser Ser Leu Ala Val Ser
705                 710                 715                 720

Cys Pro Leu Thr Ser Leu Val Ser Ser Arg Ser Phe Gln Thr Ser Ala
                725                 730                 735

Ile Ser Arg Asp Ile Asp Thr Ala Met Ala Ser Thr Arg Val Leu Ala
                740                 745                 750

Ser Arg Leu Ala Ser Gln Met Ala Ala Ser Ala Lys Val Ala Arg Pro
                755                 760                 765

Ala Val Arg Val Ala Gln Val Ser Lys Arg Thr Ile Gln Thr Gly Ser
770                 775                 780

Pro Leu Gln Thr Leu Lys Arg Thr Gln Met Thr Ser Ile Val Asn Ala
785                 790                 795                 800

Thr Thr Arg Gln Ala Phe Gln Lys Arg Ala
                805                 810

<210> SEQ ID NO 160
<211> LENGTH: 459
<212> TYPE: PRT
<213> ORGANISM: Homo sapiens

<400> SEQUENCE: 160

Met Leu Lys Leu Ile Val Pro Thr Ile Met Leu Pro Leu Thr Trp
1               5                   10                  15

Leu Ser Lys Lys His Met Ile Trp Ile Asn Thr Thr Thr His Ser Leu
                20                  25                  30

Ile Ile Ser Ile Ile Pro Leu Leu Phe Phe Asn Gln Ile Asn Asn Asn
                35                  40                  45

Leu Phe Ser Cys Ser Pro Thr Phe Ser Ser Asp Pro Leu Thr Thr Pro
                50                  55                  60

Leu Leu Met Leu Thr Thr Trp Leu Leu Pro Leu Thr Ile Met Ala Ser
65                  70                  75                  80

Gln Arg His Leu Ser Ser Glu Pro Leu Ser Arg Lys Lys Leu Tyr Leu
                85                  90                  95

Ser Met Leu Ile Ser Leu Gln Ile Ser Leu Ile Met Thr Phe Thr Ala
                100                 105                 110

Thr Glu Leu Ile Met Phe Tyr Ile Phe Phe Glu Thr Thr Leu Ile Pro
                115                 120                 125

Thr Leu Ala Ile Ile Thr Arg Trp Gly Asn Gln Pro Glu Arg Leu Asn
                130                 135                 140

Ala Gly Thr Tyr Phe Leu Phe Tyr Thr Leu Val Gly Ser Leu Pro Leu
145                 150                 155                 160

Leu Ile Ala Leu Ile Tyr Thr His Asn Thr Leu Gly Ser Leu Asn Ile
                165                 170                 175
```

```
Leu Leu Leu Thr Leu Thr Ala Gln Glu Leu Ser Asn Ser Trp Ala Asn
            180                 185                 190

Asn Leu Met Trp Leu Ala Tyr Thr Met Ala Phe Met Val Lys Met Pro
        195                 200                 205

Leu Tyr Gly Leu His Leu Trp Leu Pro Lys Ala His Val Glu Ala Pro
210                 215                 220

Ile Ala Gly Ser Met Val Leu Ala Ala Val Leu Leu Lys Leu Gly Gly
225                 230                 235                 240

Tyr Gly Met Met Arg Leu Thr Leu Ile Leu Asn Pro Leu Thr Lys His
                245                 250                 255

Met Ala Tyr Pro Phe Leu Val Leu Ser Leu Trp Gly Met Ile Met Thr
            260                 265                 270

Ser Ser Ile Cys Leu Arg Gln Thr Asp Leu Lys Ser Leu Ile Ala Tyr
        275                 280                 285

Ser Ser Ile Ser His Met Ala Leu Val Val Thr Ala Ile Leu Ile Gln
    290                 295                 300

Thr Pro Trp Ser Phe Thr Gly Ala Val Ile Leu Met Ile Ala His Gly
305                 310                 315                 320

Leu Thr Ser Ser Leu Leu Phe Cys Leu Ala Asn Ser Asn Tyr Glu Arg
                325                 330                 335

Thr His Ser Arg Ile Met Ile Leu Ser Gln Gly Leu Gln Thr Leu Leu
            340                 345                 350

Pro Leu Met Ala Phe Trp Trp Leu Ala Ser Leu Ala Asn Leu Ala
        355                 360                 365

Leu Pro Pro Thr Ile Asn Leu Leu Gly Glu Leu Ser Val Leu Val Thr
370                 375                 380

Thr Phe Ser Trp Ser Asn Ile Thr Leu Leu Thr Gly Leu Asn Met
385                 390                 395                 400

Leu Val Thr Ala Leu Tyr Ser Leu Tyr Met Phe Thr Thr Gln Trp
                405                 410                 415

Gly Ser Leu Thr His His Ile Asn Asn Met Lys Pro Ser Phe Thr Arg
            420                 425                 430

Glu Asn Thr Leu Met Phe Met His Leu Ser Pro Ile Leu Leu Leu Ser
        435                 440                 445

Leu Asn Pro Asp Ile Ile Thr Gly Phe Ser Ser
    450                 455

<210> SEQ ID NO 161
<211> LENGTH: 174
<212> TYPE: PRT
<213> ORGANISM: Homo sapiens

<400> SEQUENCE: 161

Met Met Tyr Ala Leu Phe Leu Leu Ser Val Gly Leu Val Met Gly Phe
1               5                   10                  15

Val Gly Phe Ser Ser Lys Pro Ser Pro Ile Tyr Gly Gly Leu Val Leu
            20                  25                  30

Ile Val Ser Gly Val Val Gly Cys Val Ile Ile Leu Asn Phe Gly Gly
        35                  40                  45

Gly Tyr Met Gly Leu Met Val Phe Leu Ile Tyr Leu Gly Gly Met Met
    50                  55                  60

Val Val Phe Gly Tyr Thr Thr Ala Met Ala Ile Glu Glu Tyr Pro Glu
65                  70                  75                  80

Ala Trp Gly Ser Gly Val Glu Val Leu Val Ser Val Leu Val Gly Leu
                85                  90                  95
```

Ala Met Glu Val Gly Leu Val Leu Trp Val Lys Glu Tyr Asp Gly Val
            100                 105                 110

Val Val Val Val Asn Phe Asn Ser Val Gly Ser Trp Met Ile Tyr Glu
        115                 120                 125

Gly Glu Gly Ser Gly Leu Ile Arg Glu Asp Pro Ile Gly Ala Gly Ala
        130                 135                 140

Leu Tyr Asp Tyr Gly Arg Trp Leu Val Val Thr Gly Trp Thr Leu
145                 150                 155                 160

Phe Val Gly Val Tyr Ile Val Ile Glu Ile Ala Arg Gly Asn
                165                 170

<210> SEQ ID NO 162
<211> LENGTH: 316
<212> TYPE: PRT
<213> ORGANISM: Homo sapiens

<400> SEQUENCE: 162

Met Ala Asn Leu Leu Leu Ile Val Pro Ile Leu Ile Ala Met Ala
1               5                   10                  15

Phe Leu Met Leu Thr Glu Arg Lys Ile Leu Gly Tyr Met Gln Leu Arg
            20                  25                  30

Lys Gly Pro Asn Val Val Gly Pro Tyr Gly Leu Leu Gln Pro Phe Ala
        35                  40                  45

Asp Ala Ile Lys Leu Phe Thr Lys Glu Pro Leu Lys Pro Ala Thr Ser
    50                  55                  60

Thr Ile Thr Leu Tyr Ile Thr Ala Pro Thr Leu Ala Leu Thr Ile Ala
65                  70                  75                  80

Leu Leu Leu Trp Thr Pro Leu Pro Met Pro Asn Pro Leu Val Asn Leu
                85                  90                  95

Asn Leu Gly Leu Leu Phe Ile Leu Ala Thr Ser Ser Leu Ala Val Tyr
            100                 105                 110

Ser Ile Leu Trp Ser Gly Trp Ala Ser Asn Ser Asn Tyr Ala Leu Ile
        115                 120                 125

Gly Ala Leu Arg Ala Val Ala Gln Thr Ile Ser Tyr Glu Val Thr Leu
    130                 135                 140

Ala Ile Ile Leu Leu Ser Thr Leu Leu Met Ser Gly Ser Phe Asn Leu
145                 150                 155                 160

Ser Thr Leu Ile Thr Thr Gln Glu His Leu Trp Leu Leu Leu Pro Ser
                165                 170                 175

Trp Pro Leu Ala Met Met Trp Phe Ile Ser Thr Leu Ala Glu Thr Asn
            180                 185                 190

Arg Thr Pro Phe Asp Leu Ala Glu Gly Glu Ser Glu Leu Val Ser Gly
        195                 200                 205

Phe Asn Ile Glu Tyr Ala Ala Gly Pro Phe Ala Leu Phe Phe Met Ala
    210                 215                 220

Glu Tyr Thr Asn Ile Ile Met Met Asn Thr Leu Thr Thr Thr Ile Phe
225                 230                 235                 240

Leu Gly Thr Thr Tyr Asp Ala Leu Ser Pro Glu Leu Tyr Thr Thr Tyr
                245                 250                 255

Phe Val Thr Lys Thr Leu Leu Leu Thr Ser Leu Phe Leu Trp Ile Arg
            260                 265                 270

Thr Ala Tyr Pro Arg Phe Arg Tyr Asp Gln Leu Met His Leu Leu Trp
        275                 280                 285

```
Lys Asn Phe Leu Pro Leu Thr Leu Ala Leu Leu Met Trp Tyr Val Ser
    290                 295                 300

Met Pro Ile Thr Ile Ser Ser Ile Pro Pro Gln Thr
305                 310                 315

<210> SEQ ID NO 163
<211> LENGTH: 18
<212> TYPE: DNA
<213> ORGANISM: Artificial Sequence
<220> FEATURE:
<223> OTHER INFORMATION: GFP forward primer

<400> SEQUENCE: 163
acaagttcag cgtgtccg                                                 18

<210> SEQ ID NO 164
<211> LENGTH: 18
<212> TYPE: DNA
<213> ORGANISM: Artificial Sequence
<220> FEATURE:
<223> OTHER INFORMATION: GFP reverse primer

<400> SEQUENCE: 164
ctcgttgggg tctttgct                                                 18

<210> SEQ ID NO 165
<211> LENGTH: 22
<212> TYPE: DNA
<213> ORGANISM: Artificial Sequence
<220> FEATURE:
<223> OTHER INFORMATION: ND4-F primer

<400> SEQUENCE: 165
atctccgcac actctctcct ca                                            22

<210> SEQ ID NO 166
<211> LENGTH: 21
<212> TYPE: DNA
<213> ORGANISM: Artificial Sequence
<220> FEATURE:
<223> OTHER INFORMATION: ND4-R primer

<400> SEQUENCE: 166
taggttgttg ttgatttggt t                                             21

<210> SEQ ID NO 167
<211> LENGTH: 18
<212> TYPE: DNA
<213> ORGANISM: Artificial Sequence
<220> FEATURE:
<223> OTHER INFORMATION: B-actin F2 primer

<400> SEQUENCE: 167
cctagaagca tttgcggt                                                 18

<210> SEQ ID NO 168
<211> LENGTH: 18
<212> TYPE: DNA
<213> ORGANISM: Artificial Sequence
<220> FEATURE:
<223> OTHER INFORMATION: B-actin R2 primer

<400> SEQUENCE: 168
gagctacgag ctgcctga                                                 18
```